(12) United States Patent
Kanne et al.

(10) Patent No.: US 11,098,077 B2
(45) Date of Patent: Aug. 24, 2021

(54) LOCKED NUCLEIC ACID CYCLIC DINUCLEOTIDE COMPOUNDS AND USES THEREOF

(71) Applicants: CHINOOK THERAPEUTICS, INC., Seattle, WA (US); NOVARTIS AG, Basel (CH)

(72) Inventors: David Braun Kanne, Court Madera, CA (US); Chudi Obioma Ndubaku, Oakland, CA (US); Jacob Robert Bruml, San Francisco, CA (US); Thanh Ngoc Lan Le, Berkeley, CA (US); Jeffrey McKenna, Cambridge, MA (US); George Scott Tria, Cambridge, MA (US); Stephen Canham, Cambridge, MA (US)

(73) Assignees: CHINOOK THERAPEUTICS, INC., Seattle, WA (US); NOVARTIS AG, Basel (CH)

( * ) Notice: Subject to any disclaimer, the term of this patent is extended or adjusted under 35 U.S.C. 154(b) by 231 days.

(21) Appl. No.: 16/315,612

(22) PCT Filed: Jul. 1, 2017

(86) PCT No.: PCT/US2017/040535
§ 371 (c)(1),
(2) Date: Jan. 4, 2019

(87) PCT Pub. No.: WO2018/009466
PCT Pub. Date: Jan. 11, 2018

(65) Prior Publication Data
US 2019/0185511 A1   Jun. 20, 2019

Related U.S. Application Data

(60) Provisional application No. 62/358,425, filed on Jul. 5, 2016, provisional application No. 62/362,907, filed on Jul. 15, 2016.

(51) Int. Cl.
| | | |
|---|---|---|
| C07H 21/00 | (2006.01) |
| A61K 45/06 | (2006.01) |
| A61P 35/00 | (2006.01) |
| A61P 17/06 | (2006.01) |
| A61P 31/00 | (2006.01) |
| A61P 37/06 | (2006.01) |
| A61P 3/10 | (2006.01) |
| A61P 1/00 | (2006.01) |
| A61K 9/00 | (2006.01) |
| C12N 15/113 | (2010.01) |

(52) U.S. Cl.
CPC ........... *C07H 21/00* (2013.01); *A61K 9/0019* (2013.01); *A61K 45/06* (2013.01); *A61P 1/00* (2018.01); *A61P 3/10* (2018.01); *A61P 17/06* (2018.01); *A61P 31/00* (2018.01); *A61P 35/00* (2018.01); *A61P 37/06* (2018.01); *C12N 15/113* (2013.01)

(58) Field of Classification Search
CPC ...................................................... C07H 21/00
See application file for complete search history.

(56) References Cited

U.S. PATENT DOCUMENTS

| | | |
|---|---|---|
| 4,978,672 A | 12/1990 | Bowman et al. |
| 5,547,941 A | 8/1996 | Battistini et al. |
| 5,637,483 A | 6/1997 | Dranoff et al. |
| 5,698,432 A | 12/1997 | Oxford |
| 5,811,097 A | 9/1998 | Allison et al. |
| 5,904,920 A | 5/1999 | Dranoff et al. |
| 6,033,674 A | 3/2000 | Jaffee et al. |
| 6,111,090 A | 8/2000 | Gorman et al. |
| 6,277,368 B1 | 8/2001 | Hiserodt et al. |
| 6,464,973 B1 | 10/2002 | Levitsky et al. |
| 6,689,607 B2 | 2/2004 | Ni et al. |
| 6,833,361 B2 | 12/2004 | Hong et al. |
| 7,217,805 B2 | 5/2007 | Imanishi et al. |
| 7,335,765 B2 | 2/2008 | Kaneko et al. |
| 7,427,672 B2 | 9/2008 | Imanishi et al. |
| 7,569,555 B2 | 8/2009 | Karaolis |

(Continued)

FOREIGN PATENT DOCUMENTS

| | | |
|---|---|---|
| EP | 0296122 A2 | 12/1988 |
| EP | 2099447 B1 | 11/2012 |

(Continued)

OTHER PUBLICATIONS

Tang et al. (Cancer Res. "Agonist-Mediated Activation of STING Induces Apoptosis in Malignant B Cells". Apr. 15, 2016;76(8):2137-52. doi: 10.1158/0008-5472.CAN-15-1885. Epub Mar. 7, 2016.) (Year: 2016).*
International Search Report and Written Opinion dated Dec. 1, 2017 in PCT/US2017/040535 (11 pages).
Tang et al., "Agonist-Mediated Activation of STING Induces Apoptosis in Malignant B Cells", Cancer Res. Apr. 15, 2016;76(8)2137-52. doi: 10.1158/0008-5472.CAN-15-1885. Epub Mar. 7, 2016. Includes Supplementary Figures S1-S13.

(Continued)

*Primary Examiner* — Scott Long
(74) *Attorney, Agent, or Firm* — Acuity Law Group, PC; Michael A. Whittaker

(57) ABSTRACT

The present invention provides highly active locked nucleic acid cyclic-dinucleotide (LNA-CDN) immune stimulators that activate DCs via the cytoplasmic receptor known as STING (Stimulator of Interferon Genes). In particular, the LNA-CDNs of the present invention are provided in the form of a composition comprising one or more cyclic dinucleotides that induce human STING-dependent type I interferon production, wherein the cyclic dinucleotides present in the composition have at least one 2', 4' locked nucleic acids within the cyclic dinucleotide.

20 Claims, 17 Drawing Sheets

Specification includes a Sequence Listing.

(56) References Cited

U.S. PATENT DOCUMENTS

| | | |
|---|---|---|
| 7,569,686 B1 | 8/2009 | Brat et al. |
| 7,592,326 B2 | 9/2009 | Karaolis |
| 7,618,632 B2 | 11/2009 | Collins et al. |
| 7,709,458 B2 | 5/2010 | Karaolis et al. |
| 7,867,493 B2 | 1/2011 | Damiano et al. |
| 7,943,743 B2 | 5/2011 | Korman et al. |
| 8,008,449 B2 | 8/2011 | Korman et al. |
| 8,012,469 B2 | 9/2011 | Levitsky et al. |
| 8,022,193 B2 | 9/2011 | Seth et al. |
| 8,039,479 B2 | 10/2011 | Michellys et al. |
| 8,278,283 B2 | 10/2012 | Seth et al. |
| 8,278,425 B2 | 10/2012 | Prakash et al. |
| 8,278,426 B2 | 10/2012 | Seth et al. |
| 8,354,509 B2 | 1/2013 | Carven |
| 8,367,716 B2 | 2/2013 | Karaolis |
| 8,372,858 B2 | 2/2013 | Michellys et al. |
| 8,415,355 B2 | 4/2013 | Besong et al. |
| 8,420,645 B2 | 4/2013 | Weng et al. |
| 8,461,124 B2 * | 6/2013 | Chattopadhyaya ..... A61P 35/00 514/44 A |
| 8,541,562 B2 | 9/2013 | Obika et al. |
| 8,552,002 B2 | 10/2013 | Ding et al. |
| 8,552,003 B2 | 10/2013 | Chen et al. |
| 8,562,997 B2 | 10/2013 | Jaiswal et al. |
| 8,586,023 B2 | 11/2013 | Shiku et al. |
| 8,591,886 B2 | 11/2013 | Ponath et al. |
| 8,609,089 B2 | 12/2013 | Langermann et al. |
| 8,709,424 B2 | 4/2014 | Schebye et al. |
| 8,728,476 B2 | 5/2014 | Van Den Berg |
| 8,895,705 B2 | 11/2014 | Medema et al. |
| 9,005,906 B2 | 4/2015 | Swayze et al. |
| 9,090,646 B2 | 7/2015 | Jones et al. |
| 9,549,944 B2 | 1/2017 | Dubensky, Jr. et al. |
| 9,597,391 B2 | 3/2017 | Ebensen et al. |
| 9,695,212 B2 | 7/2017 | Dubensky, Jr. et al. |
| 9,718,848 B2 | 8/2017 | Adams et al. |
| 9,724,408 B2 | 8/2017 | Dubensky, Jr. et al. |
| 9,840,533 B2 | 12/2017 | Patel et al. |
| 10,047,115 B2 | 1/2018 | Biggadike et al. |
| 10,131,686 B2 | 5/2018 | Patel et al. |
| 9,994,607 B2 | 6/2018 | Adams et al. |
| 10,011,630 B2 | 7/2018 | Vernejoul et al. |
| 10,092,644 B2 | 10/2018 | Yan et al. |
| 10,106,574 B2 | 10/2018 | Altman et al. |
| 10,392,419 B2 | 8/2019 | Oost et al. |
| 10,537,590 B2 | 1/2020 | Oost et al. |
| 2010/0028330 A1 | 2/2010 | Collins et al. |
| 2010/0150946 A1 | 6/2010 | Jooss et al. |
| 2010/0310602 A1 | 12/2010 | Reed et al. |
| 2011/0150892 A1 | 6/2011 | Thudium et al. |
| 2012/0039906 A1 | 2/2012 | Olive |
| 2012/0053226 A1 * | 3/2012 | Iyer ................ C07H 21/04 514/44 A |
| 2012/0071646 A1 | 3/2012 | Umemoto et al. |
| 2012/0114649 A1 | 5/2012 | Langermann et al. |
| 2014/0072566 A1 | 3/2014 | Kwon |
| 2014/0242095 A1 | 8/2014 | Wang et al. |
| 2015/0152132 A1 | 6/2015 | Koizumi et al. |
| 2015/0210769 A1 | 7/2015 | Freeman et al. |
| 2015/0218274 A1 | 8/2015 | Sabatos-Peyton et al. |
| 2015/0259420 A1 | 9/2015 | Triebel et al. |
| 2015/0297645 A1 | 10/2015 | Portnoy et al. |
| 2015/0337002 A1 | 11/2015 | Obika et al. |
| 2016/0108123 A1 | 4/2016 | Freeman et al. |

FOREIGN PATENT DOCUMENTS

| | | |
|---|---|---|
| EP | 2581113 A1 | 4/2013 |
| EP | 1866339 B1 | 5/2013 |
| WO | 9749395 A1 | 12/1997 |
| WO | 9806842 A1 | 2/1998 |
| WO | 9835958 A1 | 8/1998 |
| WO | 9903854 A1 | 1/1999 |
| WO | 9920758 A1 | 4/1999 |
| WO | 9940196 A1 | 8/1999 |
| WO | 9960855 A1 | 12/1999 |
| WO | 0103720 A2 | 1/2001 |
| WO | 0210192 A2 | 2/2002 |
| WO | D222577 A2 | 3/2002 |
| WO | 03037347 A1 | 5/2003 |
| WO | 03077914 A1 | 9/2003 |
| WO | 2004005281 A1 | 1/2004 |
| WO | 2004045532 A2 | 6/2004 |
| WO | 2004060319 A2 | 7/2004 |
| WO | 2004072051 A1 | 8/2004 |
| WO | 2005007190 A1 | 1/2005 |
| WO | 2005039549 A1 | 5/2005 |
| WO | 2005055808 A2 | 6/2005 |
| WO | 2005073224 A2 | 8/2005 |
| WO | 2005115451 A2 | 12/2005 |
| WO | 2006083289 A2 | 8/2006 |
| WO | 2006121168 A1 | 11/2006 |
| WO | 2006122806 A2 | 11/2006 |
| WO | 2007005874 A2 | 1/2007 |
| WO | 2007024945 A1 | 3/2007 |
| WO | 2007030377 A1 | 3/2007 |
| WO | 2007070514 A1 | 6/2007 |
| WO | 2007084786 A1 | 7/2007 |
| WO | 2007131201 A2 | 11/2007 |
| WO | 2007133822 A1 | 11/2007 |
| WO | 2007145593 A1 | 12/2007 |
| WO | 2008016893 A1 | 2/2008 |
| WO | 2008073687 A2 | 6/2008 |
| WO | 2008106692 A1 | 9/2008 |
| WO | 2008154401 A2 | 12/2008 |
| WO | 2009006478 A2 | 1/2009 |
| WO | 2009101611 A1 | 8/2009 |
| WO | 2009114335 A2 | 9/2009 |
| WO | 2009115562 A2 | 9/2009 |
| WO | 2009141386 A1 | 11/2009 |
| WO | 2009143369 A2 | 11/2009 |
| WO | 2010002655 A2 | 1/2010 |
| WO | 2010003118 A1 | 1/2010 |
| WO | 2010007120 A1 | 1/2010 |
| WO | 2010019570 A2 | 2/2010 |
| WO | 2010026124 A1 | 3/2010 |
| WO | 2010027827 A2 | 3/2010 |
| WO | 2010029082 A1 | 3/2010 |
| WO | 2010060937 A2 | 6/2010 |
| WO | 2010077634 A1 | 7/2010 |
| WO | 2010091308 A2 | 8/2010 |
| WO | 2010101849 A1 | 9/2010 |
| WO | 2010104883 A1 | 9/2010 |
| WO | 2010149755 A1 | 12/2010 |
| WO | 2011003025 A1 | 1/2011 |
| WO | 2011025927 A1 | 3/2011 |
| WO | 2011028683 A1 | 3/2011 |
| WO | 2011051726 A2 | 5/2011 |
| WO | 2011066342 A2 | 6/2011 |
| WO | 2011076786 A1 | 6/2011 |
| WO | 2011085102 A1 | 7/2011 |
| WO | 2011090754 A1 | 7/2011 |
| WO | 2011101409 A1 | 8/2011 |
| WO | 2012004367 A1 | 1/2012 |
| WO | 2012022814 A1 | 2/2012 |
| WO | 2013036868 A1 | 3/2013 |
| WO | 2013039954 A1 | 3/2013 |
| WO | 2013079174 A1 | 6/2013 |
| WO | 2013111105 A1 | 8/2013 |
| WO | 2013124826 A1 | 8/2013 |
| WO | 2013166000 A1 | 11/2013 |
| WO | 2013171639 A1 | 11/2013 |
| WO | 2013171640 A1 | 11/2013 |
| WO | 2013171641 A1 | 11/2013 |
| WO | 2013171642 A1 | 11/2013 |
| WO | 2013184757 A1 | 12/2013 |
| WO | 2014008218 A1 | 1/2014 |
| WO | 2014012479 A1 | 1/2014 |
| WO | 2014018632 A1 | 1/2014 |
| WO | 2014072493 A1 | 5/2014 |
| WO | 2014085318 A1 | 6/2014 |
| WO | 2014093936 A1 | 6/2014 |
| WO | 2014141104 A1 | 9/2014 |

(56) References Cited

FOREIGN PATENT DOCUMENTS

| | | |
|---|---|---|
| WO | 2014145356 A1 | 9/2014 |
| WO | 2014151616 A1 | 9/2014 |
| WO | 2014160160 A2 | 10/2014 |
| WO | 2014179335 A1 | 11/2014 |
| WO | 2014179760 A1 | 11/2014 |
| WO | 2014189805 A1 | 11/2014 |
| WO | 2014189806 A1 | 11/2014 |
| WO | 2015017652 A1 | 2/2015 |
| WO | 2015026684 A1 | 2/2015 |
| WO | 2015066188 A1 | 5/2015 |
| WO | 2015074145 A1 | 5/2015 |
| WO | 2015077354 A1 | 5/2015 |
| WO | 2015125783 A1 | 8/2015 |
| WO | 2015138600 A2 | 9/2015 |
| WO | 2015142735 A1 | 9/2015 |
| WO | 2015185565 A1 | 12/2015 |
| WO | 2016017422 A1 | 2/2016 |
| WO | 2016096174 A1 | 6/2016 |
| WO | 2016096577 A1 | 6/2016 |
| WO | 2016120305 A1 | 8/2016 |
| WO | 2016145102 A1 | 9/2016 |
| WO | 2017027645 A1 | 2/2017 |
| WO | 2017027646 A1 | 2/2017 |
| WO | 2017075477 A1 | 5/2017 |
| WO | 2017093933 A1 | 6/2017 |
| WO | 2017123657 A1 | 7/2017 |
| WO | 2017123669 A1 | 7/2017 |
| WO | 2018098203 A1 | 5/2018 |

OTHER PUBLICATIONS

Ablasser et al., cGAS produces 2'-5'-linked cdn second messenger that activates STING. Nature. Jun. 20, 2013;498(7454):380-384.
Ahmed et al., Immunological mechanisms of vaccination. Nat Immunol. Jun. 2011;12(6):509-517.
Amman et al., A Simple Multinuclear NMR Thermometer. J Magn Reson. 1982;46:319-321.
Aslanidis and de Jong, Ligation-independent cloning of PCR products (LIC-PCR). Nucleic Acids Res. Oct. 25, 1990;18(20):6069-6074.
Bala et al., PLGA Nanoparticles in Drug Delivery: The State of the Art. Crit Rev Ther Drug Carrier Syst 2004;21(5):387-422.
Barber, Cytoplasmic DNA innate immune pathways. Immunol Rev. Sep. 2011;243(1):99-108.
Battistini et al., Stereoselective Synthesis of Cyclic Dinucleotide Phosphorothioates. Tetrahedron, 1993;49(5):1115-1132.
Brown, Variants of B19. Dev Biol (Basel). 2004;118:71-77.
Burdette and Vance, STING and the innate immune response to nucleic acids in the cytosol. Nat Immunol. Jan. 2013;14(1):19-26.
Burdette et al., STING is a direct innate immune sensor of cyclic di-GMP. Nature. Sep. 25, 2011;478(7370):515-518.
Caskey et al., Synthetic double-stranded RNA induces innate immune responses similar to a live viral vaccine in humans. J Exp Med. Nov. 2011;208(12): 2357-2366.
Civril et al., Structural mechanism of cytosolic DNA sensing by cGAS. Nature. Jun. 20, 2013;498(7454):332-337.
Coffman et al., Vaccine adjuvants: putting innate immunity to work. Immunity. Oct. 29, 2010;33(4):492-503.
Conlon et al., Mouse, but not Human STING, Binds and Signals in Response to the Vascular Disrupting Agent 5,6-Dimethylxanthenone-4-Acetic Acid. J Immunol. May 15, 2013;190(10):5216-5225.
Corrales et al., Direct Activation of STING in the Tumor Microenvironment Leads to Potent and Systemic Tumor Regression and Immunity. Cell Rep. May 19, 2015;11(7):1018-1030.
Crimmins et al., Listeria monocytogenes multidrug resistance transporters activate a cytosolic surveillance pathway of innate immunity. Proc Natl Acad Sci U S A. Jul. 22, 2008;105(29):10191-10196.
Danilchanka and Mekalanos, Cyclic Dinucleotides and the Innate Immune Response. Cell. Aug. 29, 2013;154(5):962-970.
Davies et al., Coordinated Regulation of Accessory Genetic Elements Produces Cyclic Di-Nucleotides for V. cholerae Virulence. Cell. Apr. 13, 2012;149(2):358-370.
Dessureault et al., A phase-I Trial Using a Universal GM-CSF-producing and CD40L-expressing Bystander Cell Line (GM.CD40L) in the Formulation of Autologous Tumor Cell-based Vaccines for Cancer Patients with Stage IV disease. Ann Surg Oncol. Feb. 2007;14(2):869-884.
Diner et al., The Innate Immune DNA Sensor cGAS Produces a Noncanonical Cyclic Dinucleotide that Activates Human STING. Cell Rep. May 30, 2013;3(5):1355-1361.
Dubensky et al., Abstract 4573: A novel tumor vaccine with cyclic dinucleotides—can induce potent anti-tumor responses in vivo. Cancer Res. Apr. 15, 2013;73(8 Suppl):4573-4573.
Dubensky et al., Rationale, progress, and development of vaccines utilizing STING-activating cyclic dinucleotide adjuvants. Ther Adv Vaccines. Nov. 2013;1(4):131-143.
Dubensky and Reed, Adjuvants for cancer vaccines. Semin Immunol. Jun. 2010;22(3):155-161.
Dubensky, oral slide presentation "Development of Cyclic Dinucleotides as STING-Targeted Molecular Adjuvants." Immunological Mechanisms of Vaccination seminar, Fairmont Chateau Laurier, Ottawa, Ontario Canada Dec. 14, 2012:13 pages.
Dubensky, Jr. et al., 2013 Annual Meeting of the Society for Immunotherapy of Cancer presented Nov. 9, 2013. "Modified STING-Activating Cyclic Dinucleotide Derivatives Significantly Enhance the Anti-Tumor Activity of Therapeutic Vaccines." (24 pages).
Dubensky, Jr. et al., 2014 Keystone Vaccines Symposia presented Oct. 9, 2014 "Development of Human STING-Activating Synthetic Cyclic Dinucleotide Derivatives as Adjuvants for Cancer Immunotherapy and Infectious Disease." (30 pages).
Eager and Nemunaitis, GM-CSF Gene-Transduced Tumor Vaccines. Mol Ther. Jul. 2005;12(1):18-27.
Ebensen et al., Bis-(3',5')-cyclic dimeric adenosine monophosphate: strong Th1/Th2/Th17 promoting mucosal adjuvant. Vaccine. Jul. 18, 2011;29(32):5210-5220.
Eckstein, Phosphorothioates, Essential Components of Therapeutic Oligonucleotides. Nucleic Acid Ther. Dec. 2014;24(6):374-387.
Einstein et al., Comparison of the immunogenicity and safety of Cervarix and Gardasil human papillomavirus (HPV) cervical cancer vaccines in healthy women aged 18-45 years. Hum Vaccin. Oct. 2009;5(10):705-719.
Fitzgerald et al., IKKepsilon and TBK1 are essential components of the IRF3 signaling pathway. Nat Immunol. May 2003;4(5):491-496.
Fu et al., STING agonist formulated cancer vaccines can cure established tumors resistant to PD-1 blockade. Sci Transl Med. Apr. 15, 2015;7(283):283ra52 (+ Supplementary materials, 25 pp total).
Gao et al., Cyclic [G(20,50)pA(30,50)p] is the Metazoan Second Messenger Produced by DNA-Activated Cyclic GMP-AMP Synthase. Cell. May 23, 2013;153(5)1094-1107.
Gao et al., Structure-Function Analysis of STING Activation by c[G(2',5')pA(3',5')p] and Targeting by Antiviral DMXAA. Cell. Aug. 15, 2013;154(4):748-762.
Hamid et al., Safety and Tumor Responses with Lambrolizumab (Anti-PD-1) in Melanoma. N Engl J Med. Jul. 11, 2013;369(2):134-144.
Hughes, Nanostructure-mediated drug delivery. Nanomedicine. Mar. 2005;1(1):22-30.
Ireton and Gale, RIG-I Like Receptors in Antiviral Immunity and Therapeutic Applications. Viruses Jun. 2011;3(6):906-919.
Ishikawa and Barber, STING an Endoplasmic Reticulum Adaptor that Facilitates Innate Immune Signaling. Nature. Oct. 2, 2008;455(7213):674-678.
Iwasaki and Medzhitov, Regulation of adaptive immunity by the innate immune system. Science. Jan. 15, 2010;327(5963):291-295.
Jin et al., Identification and characterization of a loss-of-function human MPYS variant. Genes Immun. Jun. 2011;12(4):263-269.
Karaolis et al., 3',5'-Cyclic Diguanylic Acid (c-di-GMP) Inhibits Basal and Growth Factor-Stimulated Human Colon Cancer Cell Proliferation. Biochem Biophys Res Commun. Apr. 2005;329(1):40-45.

(56) References Cited

OTHER PUBLICATIONS

Kastenmuller et al., Protective T cell immunity in mice following protein-TLR7/8 agonist-conjugate immunization requires aggregation, type I IFN, and multiple DC subsets. J Clin Invest. May 2011;121(5):1782-1796.
Kovács et al., Solid Phase Synthesis of 2', 5'-Oligoadenylates Containing 3'-Fluorinated Ribose. Nucleosides & Nucleotides, 1995;14(6):1259-1267.
Kranzusch et al., Structure of Human cGAS Reveals a Conserved Family of Second-Messenger Enzymes in Innate Immunity. Cell Rep. May 2013;3(5):1362-1368, 2013.
Leber et al., Distinct TLR- and NLR-Mediated Transcriptional Responses to an Intracellular Pathogen. PLoS Pathog. Jan. 2008;4(1):e6.
Li et al., Hydrolysis of 2'3'-cGAMP by ENPP1 and design of nonhydrolyzable analogs. Nat Chem Biol. Dec. 2014;10(12):1043-1048.
Lioux et al., Design, Synthesis, and Biological Evaluation of Novel Cyclic Adenosine-Inosine Monophosphate (cAIMP) Analogs That Activate Stimulator of Interferon Genes (STING). J Med Chem. Nov. 23, 2016;59(22):10253-10267.
Luo et al, Selective binding of 2'-F-c-di-GMP to Ct-E88 and Cb-E43, new class I riboswitches from Clostridium tetani and Clostridium botulinum respectively. Mol Biosyst. Jun. 2013;9(6):1535-1539.
McCune et al., Active specific immunotherapy with tumor cells and Corynebacterium parvum: A phase I study. Cancer. May 1979;43(5):1619-1623.
McWhirter et al., A host type I interferon response is induced by cytosolic sensing of the bacterial second messenger cyclic-di-GMP. J Exp Med. Aug. 31, 2009;206(9):1899-1911.
Meehan et al. Nuclease-Resistant c-di-AMP Derivatives That Differentially Recognize RNA and Protein Receptors. Biochemistry. Feb. 16, 2016;55(6):837-849.
Migawa et al., Synthesis and Biophysical Properties of Constrained D-Altritol Nucleic Acids (cANA). Org Lett. Sep. 2013;15(17):4316-4319.
Muderhwa et al., Oil-in-water liposomal emulsions: Characterization and potential use in vaccine delivery. J Pharm Sci. Dec. 1999;88(12):1332-1339.
Nelson and Griswold, A computer program for calculating antibody affinity constants. Comput Methods Programs Biomed. Jul.-Aug. 1988;27(1):65-68.
Pandey et. al., Microbial Sensing by Toll-like Receptors and Intracellular Nucleic Acid Sensors. Cold Spring Harb Perspect Biol. Oct. 2014;7(1): a016246 (19 pages).
Pulendran and Ahmed el al., Immunological mechanisms of vaccination. Nat Immunol. Jun. 2011;12(6):509-517.
Reed et al., New horizons in adjuvants for vaccine development. Trends Immunol. Jan. 2009;30(1):23-32.
Romling et al., Cyclic di-GMP: the First 25 Years of a Universal BacterialSecond Messenger. Microbiol Mol Biol Rev. Mar. 2013;77(1):1-52.
Sauer et al., The N-Ethyl-N-Nitrosourea-Induced Goldenticket Mouse Mutant Reveals an Essential Function of Sting in the In Vivo Interferon Response to Listeria monocytogenes and Cyclic Dinucleotides. Infect Immun. Feb. 2011;79(2):688-694.
Seth et al., Synthesis and Antisense Properties of Fluoro Cyclohexenyl Nucleic Acid (F-CeNA), a Nuclease Stable Mimic of 2'-fluoro RNA. J Org Chem. Jun. 2012;77(11):5074-5085.
Shanahan et al., Identification of c-di-GMP Derivatives Resistant to an EAL Domain Phosphodiesterase. Biochem. 2013;52:365-377.
Shanahan et al., Differential analogue binding by two classes of c-di-GMP riboswitches. J Am Chem Soc. Oct. 5, 2011;133(39):15578-15592.
Shu et al., Structure of STING bound to cyclic di-GMP reveals the mechanism of cyclic dinucleotide recognition by the Immune system. Nat Struct Mol Biol. Jun. 24, 2012;19(7):722-724.
Strbo et al., Secreted Heat Shock Protein gp96-Ig: Next-Generation Vaccines for Cancer and Infectious Diseases. Immunol Res. Dec. 2013;57(1-3):311-325.
Sun et al., Cyclic GMP-AMP Synthase is a Cytosolic DNA Sensor That Activates the Type I Interferon Pathway. Science. Feb. 15, 2013;339(6121):786-791.
Tchigvintsev et al., Structural Insight into the Mechanism of c-di-GMP Hydrolysis by EAL Domain Phosphodiesterases. J Mol Biol. Sep. 24, 2010;402(3):524-538.
Tezuka et al., Synthesis of 2'-Modified Cyclic Bis(3'-5')diadenylic Acids (c-di-AMPs) and Their Promotion of Cell Division in a Freshwater Green Alga. Chem Lett. 2012;41:1723-1725.
Van Erp et al., Application of a sol particle immunoassay to the determination of affinity constants of monoclonal antibodies. J Immunoassay. 1991;12(3):425-443.
Vance et al., Patterns of Pathogenesis: Discrimination of Pathogenic and Nonpathogenic Microbes by the Innate Immune System. Cell Host Microbe. Jul. 23, 2009;6(1):10-21.
Ward et al., Binding activities of a repertoire of single immunoglobulin variable domains secreted from *Escherichia coli*. Nature. Oct. 12, 1989;341(6242):544-546.
Wilson et al., Simplified conjugation chemistry for coupling peptides to F(ab') fragments: autologous red cell agglutination assay for HIV-1 antibodies. J Immunol Methods. Oct. 14, 1994;175(2):267-273.
Witte et al., Cyclic di-AMP is Critical for Listeria Monocytogenes Growth, Cell Wall Homeostasis, and Establishment of Infection. mBio May 2013;4(3):e00282-13 (10 pages).
Woodward et al., c-di-AMP secreted by intracellular Listeria monocytogenes activates a host type I interferon response. Science. Jun. 25, 2010;328(5986):1703-1705.
Woodward et al., Supporting online material May 27, 2010 on Science Express DOI: 10.1126/science.1189801 (15 pages).
Wu et al., Cyclic GMP-AMP is an Endogenous Second Messenger in Innate Immune Signaling by Cytosolic DNA. Science. Feb. 15, 2013;339(6121):826-830—plus Supplemental material (15 pages total).
Xiao and Fitzgerald, The cGAS-STING Pathway for DNA Sensing. Mol Cell. Jul. 25, 2013;51(2):135-139.
Xu et al., Synthesis of Conformationally Locked Carba-LNAs Through Intramolecular Free-Radical Addition to C=N. Electrostatic and Steric Implication of the carba-LNA Substituents in the Modified Oligos for Nuclease and Thermodynamic Stabilities. J Org Chem. Sep. 2009;74(17):6534-6554.
Yamazaki et al., Cutting Edge: Tumor Secreted Heat Shock-Fusion Protein Elicits CD8 Cells for Rejection. J Immunol. Nov. 1999;163(10):5178-5182.
Yan et al., Synthesis and immunostimulatory properties of the phosphorothioate analogues of cdiGMP. Bioorg Med Chem Lett. Oct. 15, 2008;18(20):5631-5634.
Yarmush et al., Coupling of antibody-binding fragments to solid-phase supports: site-directed binding of F(ab')2 fragments. J Biochem Biophys Methods. Dec. 1992;25(4):285-297.
Yi et al., Single Nucleotide Polymorphisms of Human STING Can Affect Innate Immune Response to Cyclic Dinucleotides. PLoS One. Oct. 21, 2013;8(10):e77846 (16 pages).
Zhang et al., Cyclic GMP-AMP Containing Mixed Phosphodiester Linkages is an Endogenous High-Affinity Ligand for STING. Mol Cell. Jul. 25, 2013;51(2):226-235.
Zhao et al., Thiophosphate Analogs of c-di-GMP: Impact on Polymorphism. Nucleosides Nucleotides Nucleic Acids. May 2009;28(5):352-378.
Zhou et al., Potent suppression of c-di-GMP synthesis via I-site allosteric inhibition of diguanylate cyclases with 2'-F-c-di-GMP. Bioorg Med Chem. Jul. 15, 2013;21(14):4396-4404.
Zhou et al., Endo-S-c-di-GMP analogues-polymorphism and binding studies with class I riboswitch. Molecules. Nov. 9, 2012;17(11):13376-13389.

\* cited by examiner

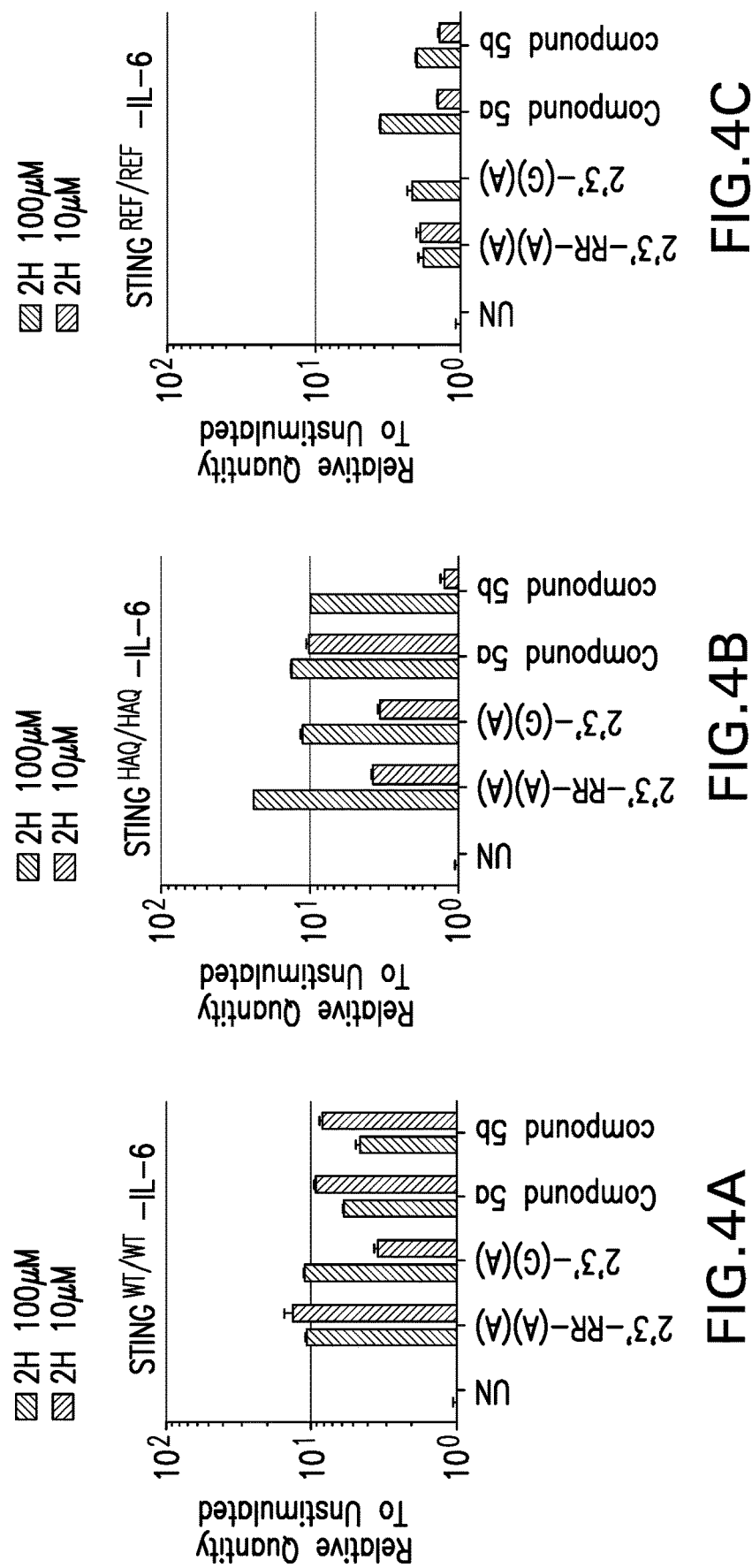

LOCKED NUCLEIC ACID CYCLIC DINUCLEOTIDE COMPOUNDS AND USES THEREOF

The present invention is filed under 35 U.S.C. § 371 as the U.S. national phase of International Application No. PCT/US2017/040535, filed Jul. 1, 2017, which designated the U.S. and claims priority to U.S. Provisional Patent Application 62/358,425, filed Jul. 5, 2016, and U.S. Provisional Patent Application 62/362,907, filed Jul. 15, 2016, each of which is hereby incorporated in its entirety including all tables, figures, and claims.

SEQUENCE LISTING

The instant application contains a Sequence Listing which has been submitted in ASCII format via EFS-Web and is hereby incorporated by reference in its entirety. Said ASCII copy, created on Oct. 2, 2019, is named ADR-1008-US_SeqListing.txt and is 16 kilobytes in size.

BACKGROUND OF THE INVENTION

The following discussion of the background of the invention is merely provided to aid the reader in understanding the invention and is not admitted to describe or constitute prior art to the present invention.

New insights into the mechanisms underlying immune-evasion, together with combination treatment regimens that potentiate the potency of therapeutic vaccination, either directly or indirectly, through combination with immune checkpoint inhibitors or other therapies, have served as a basis for the development of vaccines or immune modulators that can prime or boost an effective adaptive immune response. These modulators consist of tumor-specific CD4$^+$ and CD8$^+$ T cells specific for a targeted malignancy, resulting in an antitumor response and clinical benefit. How the innate immune system is engaged by targeted ligands shapes the development of an adaptive response and lends itself to the design of vaccines and immunomodulators (Reed et al., Trends Immunol., 30: 23-32, 2009; Dubensky and Reed, Semin. Immunol., 22: 155-61, 2010; Kastenmuller et al., J. Clin. Invest., 121: 1782-1796, 2011; Coffman et al., Immunity, 33: 492-503, 2010).

The cyclic-di-nucleotides (CDNs) cyclic-di-AMP (produced by *Listeria monocytogenes* and other bacteria) and its analogs cyclic-di-GMP and cyclic-GMP-AMP are recognized by the host cell as a pathogen associated molecular pattern (PAMP), which bind to the pathogen recognition receptor (PRR) known as Stimulator of INterferon Genes (STING). STING is an adaptor protein in the cytoplasm of host mammalian cells which activates the TANK binding kinase (TBK1)-IRF3 and the NF-κB signaling axis, resulting in the induction of IFN-β and other gene products that strongly activate innate immunity. It is now recognized that STING is a component of the host cytosolic surveillance pathway (Vance et al., Cell Host & Microbe, 6:10-21, 2009), that senses infection with intracellular pathogens and in response induces the production of IFN-β, leading to the development of an adaptive protective pathogen-specific immune response consisting of both antigen-specific CD4$^+$ and CD8$^+$ T cells as well as pathogen-specific antibodies. Other publications related to cyclic dinucleotides include, for example: U.S. Pat. Nos. 7,709,458 and 7,592,326; PCT Publication Nos. WO2007/054279, WO2014/093936, WO2014/179335, WO2014/189805, WO2015/185565, WO2016/096174, WO2016/145102, WO2017/027645, WO2017/027646, and WO2017/075477; and Yan et al., Bioorg. Med. Chem Lett. 18:5631-4, 2008.

An uncharacterized mouse gene with significant structural homology to the catalytic domain of human oligoadenylate synthase cyclic GMP-AMP synthase was reported to be the enzyme responsible for producing STING-binding CDNs in mammalian cells (Sun et al., Science 339(6121):786-91, 2013). Termed cyclic GMP-AMP Synthase (cGAS), this enzyme catalyzes the synthesis of cyclic GMP-AMP (cGAMP) from ATP and GTP in the presence of DNA. This cGAMP then functions as a second messenger that binds to and activates STING. These cGAS-produced CDNs differed structurally from the bacterially produced CDNs in that they possess an unusual phosphodiester linkage. Thus, while the bacterially produced CDNs contain a bis-3',5' linkage between the two nucleotides, mammalian CDNs contained one 2',5' linkage and one 3',5' linkage, or a so-called "mixed linkage" (ML) or non-canonical CDNs. These 2',5'-3',5' molecules bind STING with nM affinity, some 300-fold better than bacterial c-di-GMP.

Human STING (hSTING) also has known polymorphisms, including alleles encoding histidine at position 232, which are refractory to bis-3',5' (canonical) CDNs, but not 2',5'-3',5' (non-canonical, mixed linkage) CDNs (Diner et al., Cell Reports 3, 1355-61, 2013; Jin et al., Genes and Immunity, 12: 263-9, 2011). Single nucleotide polymorphisms in the hSTING gene have been reported to affect the responsiveness to bacterial-derived canonical CDNs (Diner et al., 2013; Gao et al., Cell 154, 748-762, 2013; Conlon et. al., J. Immunol. 190: 5216-5225, 2013). Five haplotypes of hSTING have been reported (WT, REF, HAQ, AQ and Q alleles), which vary at amino acid positions 71, 230, 232 and 293 (Jin et al., 2011; Yi et al., PLOS One 8: e77846, 2013). Cells expressing hSTING reportedly respond poorly to stimulation with bacterial CDNs cGAMP, c-di-AMP and c-di-GMP having bis-(3', 5') linkages, but are responsive to the endogenously produced cGAS product, ML cGAMP (Diner et al., 2013). Thus, it has been suggested that the 2',5'-3',5' molecules represent much more potent physiological ligands in terms of hSTING targeting (Zhang et al., Mol. Cell. 51:226-35, 2013; Xiao and Fitzgerald, Mol. Cell 51:135-39, 2013).

There are therapeutic applications for compounds that target hSTING as either an agonist (e.g. increasing the tumor-specific CD4$^+$ and CD8$^+$ T cells specific for a targeted malignancy, or improving a response to vaccination) or as an antagonist (e.g. decreasing a type I interferon response associated with autoimmune disease). Thus there is a desire for improved compounds for the modulation of hSTING.

SUMMARY OF THE INVENTION

It is an object of the present invention to provide compositions and methods which modulate immune responses to diseases. It is a further object of the invention to provide compositions and methods which provide locked nucleic acid cyclic dinucleotide analogs that exhibit improved characteristics when employed for modulation of mammalian, and preferably human, STING. It is yet a further object of the invention to provide locked nucleic acid cyclic dinucleotide analogs that activate hSTING, and compositions and methods thereof for the treatment of cancer.

In a first aspect, the present invention provides a locked nucleic acid cyclic dinucleotide ("LNA-CDN") compound of Formula I:

Formula I

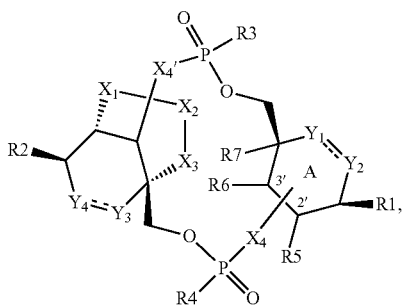

or a prodrug, pharmaceutically acceptable salt, pharmaceutically acceptable solvate or pharmaceutically acceptable hydrate thereof, wherein:

R1 and R2 are independently a pyrimidine or purine nucleic acid base or analog or derivative thereof;

R3 and R4 are independently —OH, —OR$^a$, —SH or —SR$^a$;

$Y_1$ is —O—, —S— or —CRR— and $Y_2$ is absent, wherein each R is independently —H or —C$_{1-6}$alkyl, or the two R together with the carbon to which they are attached form a 3-6 membered heterocycloalkyl or C$_{3-6}$ cycloalkyl spirocyclic ring; or $Y_1$ is —O—, —CH$_2$— or —CH═ and $Y_2$ is —CH$_2$— or ═CH—, selected to provide —Y$_1$—Y$_2$— as —O—CH$_2$—, —CH$_2$—CH$_2$— or —CH═CH—;

$Y_3$ is —O—, —S— or —CRR— and $Y_4$ is absent, wherein each R is independently —H or —C$_{1-6}$alkyl, or the two R together with the carbon to which they are attached form a 3-6 membered heterocycloalkyl or C$_{3-6}$ cycloalkyl spirocyclic ring; or $Y_3$ is —O—, —CH$_2$— or —CH═ and $Y_4$ is —CH$_2$— or ═CH—, selected to provide —Y$_3$—Y$_4$— as —O—CH$_2$—, —CH$_2$—CH$_2$— or —CH═CH—;

$X_1$, $X_2$, and $X_3$ are all present, $X_1$ and $X_2$ are —C(R$^b$R$^c$)—, —N(R$^d$), —O— or —S(═O)$_2$—, and $X_3$ is —C(R$^b$R$^c$)— or —O—, selected to provide —X$_1$—X$_2$—X$_3$— as —C(R$^b$R$^c$)—C(R$^b$R$^c$)—C(R$^b$R$^c$)—, —C(R$^b$R$^c$)—N(R$^d$)—C(R$^b$R$^c$)—, —C(R$^b$R$^c$)—O—C(R$^b$R$^c$)—, —C(R$^b$R$^c$)—C(R$^b$R$^c$)—O—, —O—C(R$^b$R$^c$)—C(R$^b$R$^c$)—, —O—N(R$^d$)—C(R$^b$R$^c$)—, —S(═O)$_2$—N(R$^d$)—C(R$^b$R$^c$)—, —N(R$^d$)—C(R$^b$R$^c$)—C(R$^b$R$^c$)—, —N(R$^d$)—O—C(R$^b$R$^c$)— or —N(R$^d$)—S(═O)$_2$—C(R$^b$R$^c$)—; or $X_2$ is absent, $X_1$ and $X_3$ are both present, $X_1$ is —C(R$^b$R$^c$)—, —N(R$^d$) or —O— and $X_3$ is —C(R$^b$R$^c$)— or —S(═O)$_2$—, selected to provide —X$_1$—X$_3$— as —C(R$^b$R$^c$)—C(R$^b$R$^c$)—, —O—C(R$^b$R$^c$)—, —N(R$^d$)—C(R$^b$R$^c$)— or —N(R$^d$)—S(═O)$_2$—;

$X_4'$ is —O— or —NH—;

$X_4$ is —O— or —NH— bonded to either the 2' or the 3' carbon atom of the indicated ring A;

wherein:

when $X_4$ is —O— or —NH— bonded to the 2' carbon atom of ring A:

R5 is absent, R6 is selected from the group consisting of —H, —OH, halogen and —OR$^e$, and R7 is —H;

when $X_4$ is —O— or —NH— bonded to the 3' carbon atom of ring A:

R6 is absent, R5 is selected from the group consisting of —H, —OH, halogen and —OR$^e$, and R7 is —H; or R6 is absent, and R5 and R7 join to form —X$_5$—X$_6$—X$_7$—, resulting in a fused ring system with X$_5$ bonded to the 2' carbon atom of ring A and X$_7$ bonded to the carbon atom of ring A to which R7 is attached, wherein:

$X_5$, $X_6$, and $X_7$ are all present, $X_5$ and $X_6$ are —C(R$^b$R$^c$)—, —N(R$^d$), —O— or —S(═O)$_2$—, and $X_7$ is —C(R$^b$R$^c$)— or —O—, selected to provide —X$_5$—X$_6$—X$_7$— as —C(R$^b$R$^c$)—C(R$^b$R$^c$)—C(R$^b$R$^c$)—, —C(R$^b$R$^c$)—N(R$^d$)—C(R$^b$R$^c$)—, —C(R$^b$R$^c$)—O—C(R$^b$R$^c$)—, —C(R$^b$R$^c$)—C(R$^b$R$^c$)—O—, —O—C(R$^b$R$^c$)—C(R$^b$R$^c$)—, —O—N(R$^d$)—C(R$^b$R$^c$)—, —S(═O)$_2$—N(R$^d$)—C(R$^b$R$^c$)—, —N(R$^d$)—C(R$^b$R$^c$)—C(R$^b$R$^c$)—, —N(R$^d$)—O—C(R$^b$R$^c$)— or —N(R$^d$)—S(═O)$_2$—C(R$^b$R$^c$)—; or $X_6$ is absent, $X_5$ and $X_7$ are both present, $X_5$ is —C(R$^b$R$^c$)—, —N(R$^d$) or —O— and $X_7$ is —C(R$^b$R$^c$)— or —S(═O)$_2$—, selected to provide —X$_5$—X$_7$— as —C(R$^b$R$^c$)—C(R$^b$R$^c$)—, —O—C(R$^b$R$^c$)—, —N(R$^d$)—C(R$^b$R$^c$)— or —N(R$^d$)—S(═O)$_2$—;

R$^a$ at each occurrence is independently selected from the group consisting of alkyl, alkenyl, alkynyl, heteroalkyl, carbocyclyl, heterocyclyl, aryl, heteroaryl and —C(═O)R$^f$; wherein alkyl, alkenyl, alkynyl or heteroalkyl are optionally independently substituted with one or more —R$^m$, and carbocyclyl, heterocyclyl, aryl or heteroaryl are optionally independently substituted with one or more —R$^n$;

R$^b$ and R$^c$, at each occurrence, are independently selected from the group consisting of —H, halogen, alkyl, alkenyl, alkynyl, heteroalkyl, carbocyclyl, heterocyclyl, aryl, heteroaryl, —R' and -L$_1$-R$^g$; or R$^b$ and R$^c$ together on a carbon are ═O, ═CR$^h$R$^h$, ═N—OR$^i$, ═N—R$^i$, or ═N—NR$^i$R$^i$; or R$^b$ and R$^c$ together with the carbon to which they are attached form a C$_{3-6}$ cycloalkyl or 3 to 6 membered heterocycloalkyl spirocyclic ring; wherein alkyl, alkenyl, alkynyl or heteroalkyl are optionally independently substituted with one or more —R$^m$, and carbocyclyl, heterocyclyl, aryl or heteroaryl are optionally independently substituted with one or more —R$^n$;

R$^d$ at each occurrence is independently selected from the group consisting of —H, alkyl, alkenyl, alkynyl, heteroalkyl, carbocyclyl, heterocyclyl, aryl, heteroaryl, —R" and -L$_2$-R$^j$; wherein alkyl, alkenyl, alkynyl or heteroalkyl are optionally independently substituted with one or more —R$^m$, and carbocyclyl, heterocyclyl, aryl or heteroaryl are optionally independently substituted with one or more —R$^n$; or R$^d$ is a suitable nitrogen protecting group.

R$^e$ is selected from the group consisting of alkyl, alkenyl, alkynyl, heteroalkyl, carbocyclyl, heterocyclyl, aryl, heteroaryl and —C(═O)R$^f$; wherein alkyl, alkenyl, alkynyl or heteroalkyl are optionally independently substituted with one or more —R$^m$, and carbocyclyl, heterocyclyl, aryl or heteroaryl are optionally independently substituted with one or more —R$^n$; or R$^e$ is a suitable oxygen protecting group;

R$^f$ at each occurrence is independently selected from the group consisting of alkyl, alkenyl, alkynyl, heteroalkyl, carbocyclyl, heterocyclyl, aryl, and heteroaryl; wherein alkyl, alkenyl, alkynyl or heteroalkyl are optionally independently substituted with one or more —R$^m$, and carbocyclyl, heterocyclyl, aryl or heteroaryl are optionally independently substituted with one or more —R$^n$;

R' at each occurrence is selected from the group consisting of —CN, —NO$_2$, —OH, —SH, —NH$_2$, —C(=W)—WH, —C(=W)—NH$_2$, —C(=W)—NH—WH, —C=N—OH, —C(=NH)—NH$_2$, —W—C(=W)—WH, —W—C(=W)—NH$_2$, —S(=O)$_2$—NH$_2$, —S(=O)$_2$—NH—W—, —NH—NH$_2$, —NH—WH, —NH—C(=W)—WH, —NH—C(=W)—NH$_2$, —NH—S(=O)$_2$—NH$_2$, and —NH—C(=NH)—NH$_2$;

R'' at each occurrence is selected from the group consisting of —OH, —SH, —NH$_2$, —C(=W)—WH, —C(=W)—NH$_2$, —C(=NH)—NH$_2$, and —S(=O)$_2$—NH$_2$;

L$_1$ is selected from the group consisting of —O—, —S—, —S(=O)—, —S(=O)$_2$—, —C(=W)—, —C(=W)—W—, —C(=W)—NR$^k$—, —C(=W)—NR$^k$—W—, —C(=NR$^k$)NR$^k$—, —C(NR$^k$R$^k$)=N—, —W—C(=W)—, —W—C(=W)—NR$^k$—, —S(=O)$_2$—NR$^k$—, —S(=O)$_2$—NR$^k$—W—, —NR$^k$—, —N=CR$^h$—, —NR$^k$—W—, —NR$^k$—NR$^k$—, —NR$^k$—C(=NR$^k$)NR$^k$—, —NR$^k$—C(NR$^k$R$^k$)=N—, —NR$^k$—C(=W)—, —NR$^k$—C(=W)—W—, —NR$^k$—C(=W)—NR$^k$—, —NR$^k$—S(=O)$_2$—NR$^k$— and —NR$^k$—S(=O)$_2$—;

L$_2$ is selected from the group consisting of —O—, —S—, —NR$^k$—, —C(=W)—, —C(=W)—W—, —C(=W)—NR$^k$—, —C(=NR$^k$)NR$^k$—, —C(NR$^k$R$^k$)=N—, —S(=O)$_2$—NR$^k$—, and —S(=O)$_2$—;

R$^g$ and R$^j$, at each occurrence, are independently selected from the group consisting of alkyl, alkenyl, alkynyl, heteroalkyl, carbocyclyl, heterocyclyl, aryl and heteroaryl; wherein alkyl, alkenyl, alkynyl or heteroalkyl are optionally independently substituted with one or more —R$^m$, and carbocyclyl, heterocyclyl, aryl or heteroaryl are optionally independently substituted with one or more —R$^n$;

R$^h$ at each occurrence is independently selected from the group consisting of —H, halogen, alkyl, alkenyl, alkynyl, heteroalkyl, carbocyclyl, heterocyclyl, aryl and heteroaryl; wherein alkyl, alkenyl, alkynyl or heteroalkyl are optionally independently substituted with one or more —R$^m$, and carbocyclyl, heterocyclyl, aryl or heteroaryl are optionally independently substituted with one or more —R$^n$;

R$^i$ and R$^k$, at each occurrence, are independently selected from the group consisting of —H, alkyl, alkenyl, alkynyl, heteroalkyl, carbocyclyl, heterocyclyl, aryl and heteroaryl; wherein alkyl, alkenyl, alkynyl or heteroalkyl are optionally independently substituted with one or more —R$^m$, and carbocyclyl, heterocyclyl, aryl or heteroaryl are optionally independently substituted with one or more —R$^n$;

R$^m$ at each occurrence is independently selected from the group consisting of =O, halogen, carbocyclyl, heterocyclyl, aryl, heteroaryl, —R' and -L$_3$-R$^o$, when substituted on an available carbon atom, and carbocyclyl, heterocyclyl, aryl, heteroaryl, —R'' and -L$_4$-R$^p$, when substituted on an available nitrogen atom; wherein carbocyclyl, heterocyclyl, aryl and heteroaryl are optionally independently substituted with one or more —R$^n$.

R$^n$ at each occurrence is independently selected from the group consisting of =O, halogen, alkyl, alkenyl, alkynyl, heteroalkyl, carbocyclyl, heterocyclyl, aryl, heteroaryl, —R' and -L$_3$-R$^o$, when substituted on an available carbon atom, and alkyl, alkenyl, alkynyl, heteroalkyl, carbocyclyl, heterocyclyl, aryl, heteroaryl, —R'' and -L$_4$-R$^p$, when substituted on an available nitrogen atom;

L$_3$ is selected from the group consisting of —O—, —S—, —S(=O)—, —S(=O)$_2$—, —C(=W)—, —C(=W)—W—, —C(=W)—NR$^q$—, —C(=W)—NR$^q$—W—, —C=N—O—, —C(=NR$^q$)NR$^q$—, —C(NR$^q$R$^q$)=N—, —W—C(=W)—, —W—C(=W)—W—, —W—C(=W)—NR$^q$—, —S(=O)$_2$—NR$^q$—, —S(=O)$_2$—NR$^q$—W—, —NR$^q$—, —N=CR$^r$—, —NR$^q$—W—, —NR$^q$—NR$^q$—, —NR$^q$—C(=NR$^q$)NR$^q$—, —NR$^q$—C(NR$^q$R$^q$)=N—, —NR$^q$—C(=W)—, —NR$^q$—C(=W)—W—, —NR$^q$—C(=W)—NR$^q$—, —NR$^q$—S(=O)$_2$—NR$^q$—, and —NR$^q$—S(=O)$_2$—;

L$_4$ is selected from the group consisting of —O—, —S—, —NR$^q$—, —C(=W)—, —C(=W)—W—, —C(=W)—NR$^q$—, —C(=NR$^q$)NR$^q$—, —C(NR$^q$R$^q$)=N—, —S(=O)$_2$—NR$^q$—, and —S(=O)$_2$—;

each W is independently O or S;

R$^o$ and R$^p$, at each occurrence, are independently selected from the group consisting of alkyl, alkenyl, alkynyl, heteroalkyl, carbocyclyl, heterocyclyl, aryl and heteroaryl; wherein alkyl, alkenyl, alkynyl and heteroalkyl, are optionally independently substituted with one or more —R$^s$; carbocyclyl or heterocyclyl are optionally independently substituted with one or more —R$^t$; and aryl or heteroaryl are optionally independently substituted with one or more —R$^u$;

R$^q$ at each occurrence is independently selected from the group consisting of —H, alkyl, alkenyl, alkynyl, heteroalkyl, carbocyclyl, heterocyclyl, aryl and heteroaryl; wherein alkyl, alkenyl, alkynyl and heteroalkyl, are optionally independently substituted with one or more —R$^s$; carbocyclyl or heterocyclyl are optionally independently substituted with one or more —R$^t$; and aryl or heteroaryl are optionally independently substituted with one or more —R$^u$;

R$^r$ at each occurrence is independently selected from the group consisting of —H, halogen, alkyl, alkenyl, alkynyl, heteroalkyl, carbocyclyl, heterocyclyl, aryl and heteroaryl; wherein alkyl, alkenyl, alkynyl and heteroalkyl, are optionally independently substituted with one or more —R$^s$; carbocyclyl or heterocyclyl are optionally independently substituted with one or more —R$^t$; and aryl or heteroaryl are optionally independently substituted with one or more —R$^u$;

R$^s$ at each occurrence is independently selected from the group consisting of halogen, =O, —OH, —SH, —NH$_2$, —CN, C$_{1-6}$alkoxy, C$_{1-6}$alkylthio, C$_{1-6}$alkylsulfinyl, C$_{1-6}$alkylsulfonyl, C$_{1-6}$alkylamino, C$_{1-6}$ dialkylamino, and N-linked-heterocycloalkyl; wherein C$_{1-6}$alkyl, alone or as part of C$_{1-6}$alkoxy, C$_{1-6}$alkylthio, C$_{1-6}$alkylsulfinyl, C$_{1-6}$alkylsulfonyl, C$_{1-6}$alkylamino, or C$_{1-6}$ dialkylamino, is optionally substituted with one or more substituents independently selected from the group consisting of —OH, —SH, —NH$_2$, halogen, C$_{1-6}$alkoxy, C$_{1-6}$haloalkoxy, C$_{1-6}$alkylthio, C$_{1-6}$haloalkylthio, C$_{1-6}$alkylsulfinyl, C$_{1-6}$haloalkylsulfinyl, C$_{1-6}$alkylsulfonyl, C$_{1-6}$haloalkylsulfonyl, C$_{1-6}$alkylamino, C$_{1-6}$ dialkylamino and N-linked-heterocycloalkyl;

R$^t$ at each occurrence is independently selected from the group consisting of halogen, =O, —OH, —SH, —NH$_2$, —CN, C$_{1-6}$alkyl, C$_{2-6}$alkenyl, C$_{2-6}$alkynyl, C$_{1-6}$alkoxy, C$_{1-6}$alkylthio, C$_{1-6}$alkylsulfinyl, C$_{1-6}$alkylsulfonyl, C$_{1-6}$alkylamino, C$_{1-6}$ dialkylamino and N-linked-heterocycloalkyl; wherein C$_{2-6}$alkenyl, C$_{2-6}$alkynyl, and C$_{1-6}$alkyl, alone or as part of C$_{1-6}$alkoxy, C$_{1-6}$alkylthio, C$_{1-6}$alkylsulfinyl, C$_{1-6}$alkylsulfonyl, C$_{1-6}$alkylamino, or C$_{1-6}$ dialkylamino, is optionally substituted with one or more substituents independently selected from the group consisting of —OH, —SH, —NH$_2$, halogen, C$_{1-6}$alkoxy, C$_{1-6}$haloalkoxy, C$_{1-6}$alkylthio, C$_{1-6}$haloalkylthio, C$_{1-6}$alkylsulfinyl, C$_{1-6}$haloalkylsulfinyl, C$_{1-6}$alkylsulfonyl, $C_{1-6}$haloalkylsulfonyl, $C_{1-6}$alkylamino, $C_{1-6}$ dialkylamino and N-linked-heterocycloalkyl; and $R^u$ at each occurrence is independently selected from the group consisting of halogen, —OH, —SH, —NH$_2$, —CN, —NO$_2$, $C_{1-6}$alkyl, $C_{2-6}$alkenyl, $C_{2-6}$alkynyl, $C_{1-6}$alkoxy, $C_{1-6}$alkylthio, $C_{1-6}$alkylsulfinyl, $C_{1-6}$alkylsulfonyl, $C_{1-6}$alkylamino, $C_{1-6}$ dialkylamino, and N-linked-heterocycloalkyl; wherein $C_{2-6}$alkenyl, $C_{2-6}$alkynyl, and $C_{1-6}$alkyl, alone or as part of $C_{1-6}$alkoxy, $C_{1-6}$alkylthio, $C_{1-6}$alkylsulfinyl, $C_{1-6}$alkylsulfonyl, $C_{1-6}$alkylamino, or $C_{1-6}$ dialkylamino, is optionally substituted with one or more substituents independently selected from the group consisting of —OH, —SH, —NH$_2$, halogen, $C_{1-6}$alkoxy, $C_{1-6}$haloalkoxy, $C_{1-6}$alkylthio, $C_{1-6}$haloalkylthio, $C_{1-6}$alkylsulfinyl, $C_{1-6}$haloalkylsulfinyl, $C_{1-6}$alkylsulfonyl, $C_{1-6}$haloalkylsulfonyl, $C_{1-6}$alkylamino, $C_{1-6}$ dialkylamino and N-linked-heterocycloalkyl.

In a first embodiment of the first aspect, R1 and R2 are independently selected from the group consisting of:

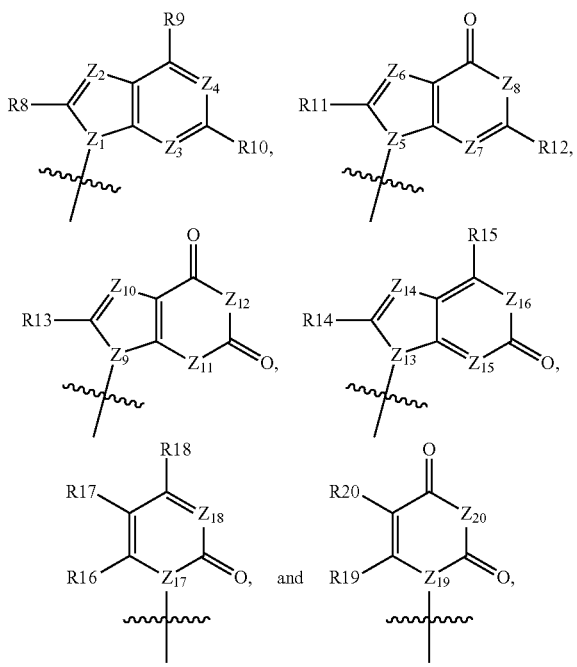

wherein:

indicates the bond of R1 or R2 to the ring as shown in Formula I;

$Z_1$, $Z_5$, $Z_9$, $Z_{13}$, $Z_{17}$ and $Z_{19}$ are independently

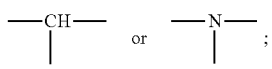

$Z_8$, $Z_{11}$, $Z_{12}$, $Z_{16}$ and $Z_{20}$ are independently —CR$^v$R$^w$—, —O— or —NR$^x$—;

$Z_2$, $Z_3$, $Z_4$, $Z_6$, $Z_7$, $Z_{10}$, $Z_{14}$, $Z_{15}$ and $Z_{18}$ are independently =CR$^v$— or =N—;

R$^v$ and R$^w$, at each occurrence, are independently selected from the group consisting of —H, halogen, alkyl, alkenyl, alkynyl, heteroalkyl, carbocyclyl, heterocyclyl, aryl, heteroaryl, —R' and -L$_1$-R$^g$; or R$^v$ and R$^w$ together are =O, =CR$^h$R$^h$, =N—OR$^i$, =N—R$^i$, or =N—NR$^i$R$^i$; wherein alkyl, alkenyl, alkynyl or heteroalkyl are optionally independently substituted with one or more —R$^m$, and carbocyclyl, heterocyclyl, aryl or heteroaryl are optionally independently substituted with one or more —R$^n$;

each R$^x$ is independently selected from the group consisting of —H, alkyl, alkenyl, alkynyl, heteroalkyl, carbocyclyl, heterocyclyl, aryl, heteroaryl, —R" and -L$_2$-R$^j$; wherein alkyl, alkenyl, alkynyl or heteroalkyl are optionally independently substituted with one or more —R$^m$, and carbocyclyl, heterocyclyl, aryl or heteroaryl are optionally independently substituted with one or more —R$^n$; and R8, R9, R10, R11, R12, R13, R14, R15, R16, R17, R18, R19 and R20 are independently selected from the group consisting of —H, halogen, alkyl, alkenyl, alkynyl, heteroalkyl, carbocyclyl, heterocyclyl, aryl, heteroaryl, —R' and -L$_1$-R$^{g'}$; wherein alkyl, alkenyl, alkynyl or heteroalkyl are optionally independently substituted with one or more —R$^m$, and carbocyclyl, heterocyclyl, aryl or heteroaryl are optionally independently substituted with one or more —R$^n$, wherein R', R", R$^g$, R$^h$, R$^i$, R$^j$, R$^m$, R$^n$, L$_1$ and L$_2$ are as defined for Formula I, and R$^{g'}$ is R$^g$ or a suitable nitrogen protecting group when L$_1$ is —NH—.

In a second embodiment of the first aspect and first embodiment thereof, when R5 or R6 are selected from the group consisting of —H, —OH, halogen and —OR$^e$, R5 or R6 are selected from the group consisting of —H, —OH optionally substituted with a suitable oxygen protecting group, halogen, —O—$C_{1-14}$alkyl and —O—(C=O)—$C_{1-14}$alkyl. In some embodiments, when R5 or R6 are selected from the group consisting of —H, —OH, halogen and —OR$^e$, R5 and R6 are selected from the group consisting of —H, —OH, —F and —O—(C=O)—$C_{1-14}$alkyl. In some embodiments, when R5 or R6 are selected from the group consisting of —H, —OH, halogen and —OR$^e$, R5 and R6 are —H, —OH or —F, in some embodiments —OH or —F.

In a third embodiment of the first aspect and any of the above embodiments thereof, the compound of Formula I is selected from the group consisting of a compound of Formula Ia, a compound of Formula Ib, a compound of Formula Ic and a compound of Formula Id:

Formula Ia

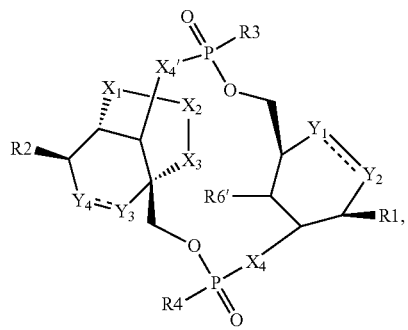

-continued

Formula Ib

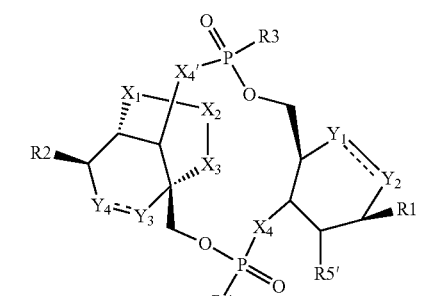

Formula Ic

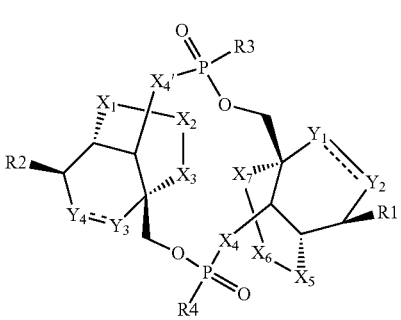
and

Formula Id

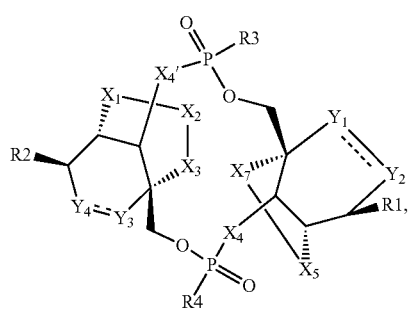

or a prodrug, pharmaceutically acceptable salt, pharmaceutically acceptable solvate or pharmaceutically acceptable hydrate thereof, wherein R5' and R6' are selected from the group consisting of —H, —OH, halogen and —OR$^e$, and R1, R2, R3, R4, R$^e$, $Y_1$, $Y_2$, $Y_3$, $Y_4$, $X_1$, $X_2$, $X_3$, $X_4$, $X_4'$, $X_5$, $X_6$ and $X_7$ are as defined for Formula I. In some embodiments, R5' and R6' are selected from the group consisting of —H, —OH optionally substituted with a suitable oxygen protecting group, halogen, —O—$C_{1-14}$alkyl and —O—(C=O)—$C_{1-14}$alkyl. In some embodiments, R5' and R6' are selected from the group consisting of —H, —OH, —F and —O—(C=O)—$C_{1-14}$alkyl. In some embodiments, R5' and R6' are —H, —OH or —F. In some embodiments, R5' and R6' are —OH or —F.

In a fourth embodiment of the first aspect and any of the above embodiments thereof, the compound of Formula I is selected from the group consisting of a compound of Formula Ia-A, a compound of Formula Ia-B, a compound of Formula Ia-C, a compound of Formula Ia-D, a compound of Formula Ia-E, a compound of Formula Ia-F, a compound of Formula Ia-G, a compound of Formula Ia-H, a compound of Formula Ia-I, a compound of Formula Ia-J, a compound of Formula Ia-K, a compound of Formula Ia-L, a compound of Formula Ia-M, a compound of Formula Ia-N, a compound of Formula Ib-A, a compound of Formula Ib-B, a compound of Formula Ib-C, a compound of Formula Ib-D, a compound of Formula Ib-E, a compound of Formula Ib-F, a compound of Formula Ib-G, a compound of Formula Ib-H, a compound of Formula Ib-I, a compound of Formula Ib-J, a compound of Formula Ib-K, a compound of Formula Ib-L, a compound of Formula Ib-M, a compound of Formula Ib-N, a compound of Formula Ic-A, a compound of Formula Ic-B, a compound of Formula Ic-C, a compound of Formula Ic-D, a compound of Formula Ic-E, a compound of Formula Ic-F, a compound of Formula Ic-G, a compound of Formula Ic-H, a compound of Formula Ic-I, a compound of Formula Ic-J, a compound of Formula Ic-K, a compound of Formula Ic-L, a compound of Formula Ic-M, a compound of Formula Ic-N, a compound of Formula Id-A, a compound of Formula Id-B, a compound of Formula Id-C, a compound of Formula Id-D, a compound of Formula Id-E, a compound of Formula Id-F, a compound of Formula Id-G, a compound of Formula Id-H, a compound of Formula Id-I, a compound of Formula Id-J, a compound of Formula Id-K, a compound of Formula Id-L, a compound of Formula Id-M and a compound of Formula Id-N:

Formula Ia-A

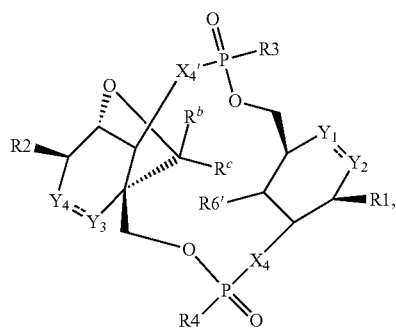

Formula Ia-B

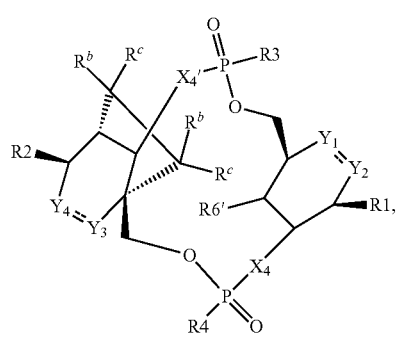

Formula Ia-C

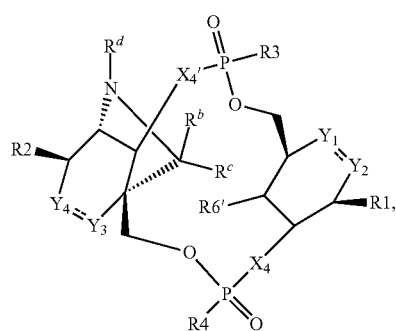

-continued
Formula Ia-D
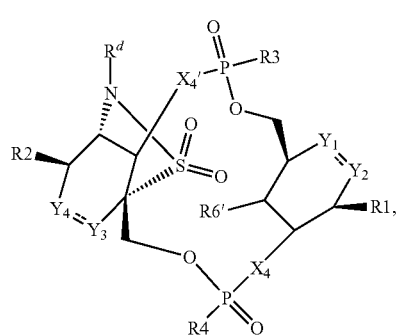
Formula Ia-E
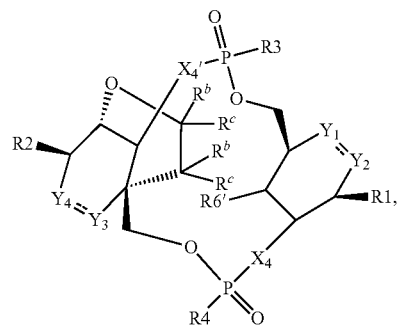
Formula Ia-F
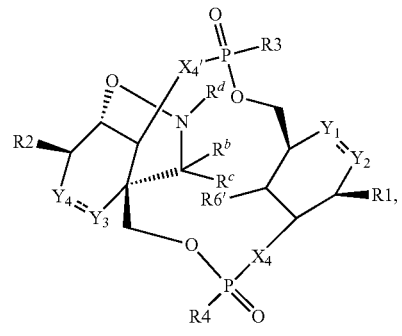
Formula Ia-G
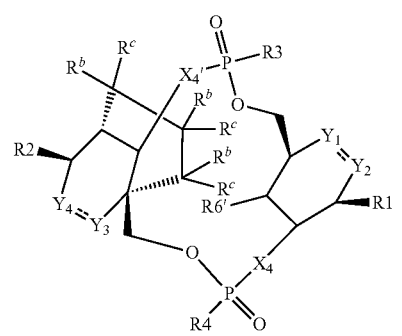
Formula Ia-H
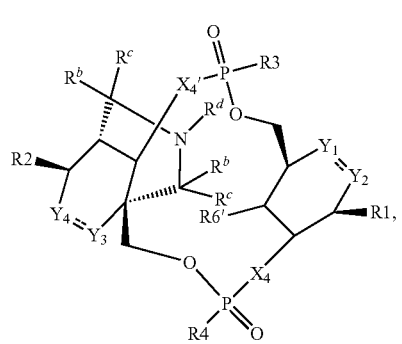
Formula Ia-I
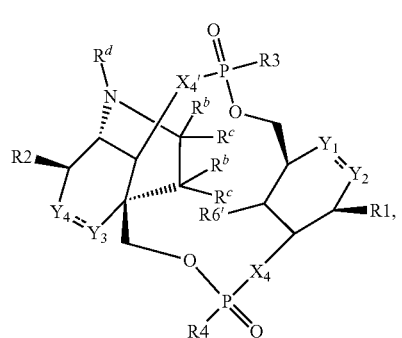
Formula Ia-J
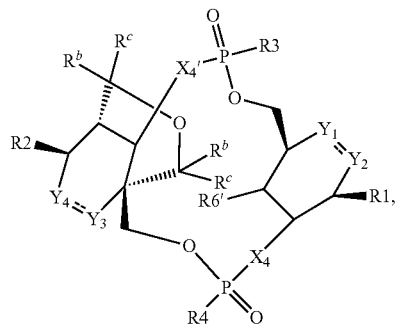
Formula Ia-K
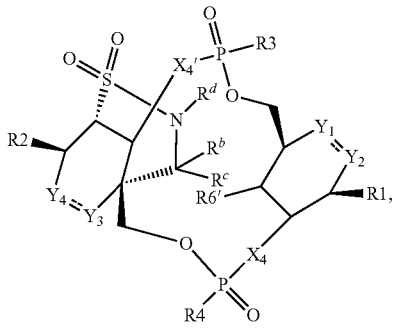
Formula Ia-L
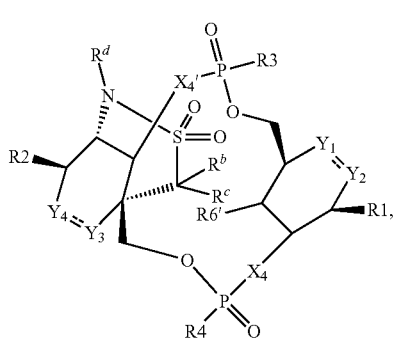
Formula Ia-M
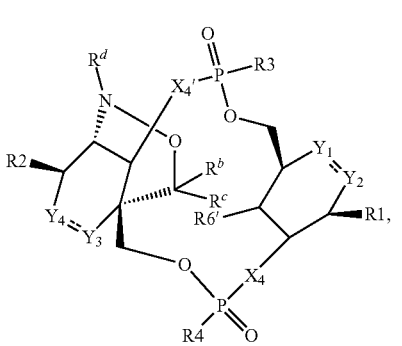

-continued
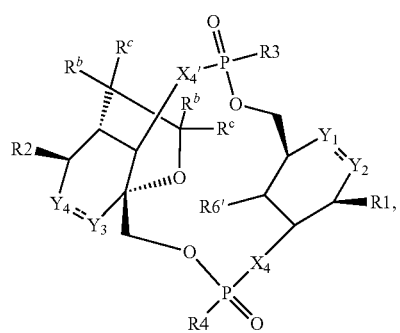
Formula Ia-N
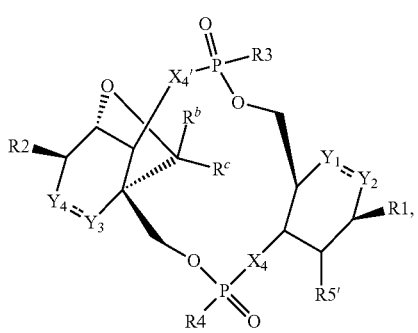
Formula Ib-A
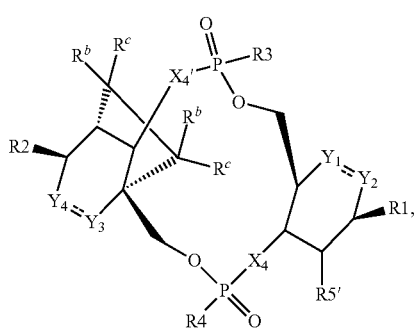
Formula Ib-B
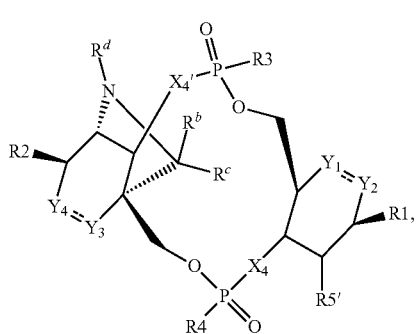
Formula Ib-C
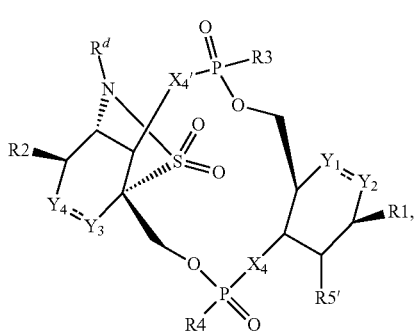
Formula Ib-D
-continued
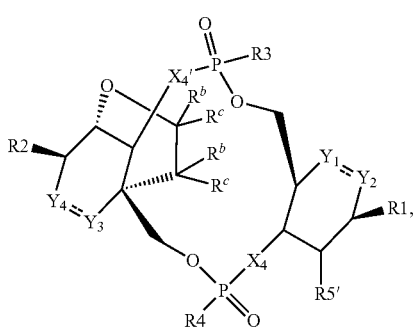
Formula Ib-E
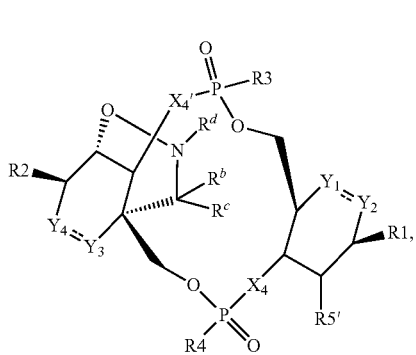
Formula Ib-F
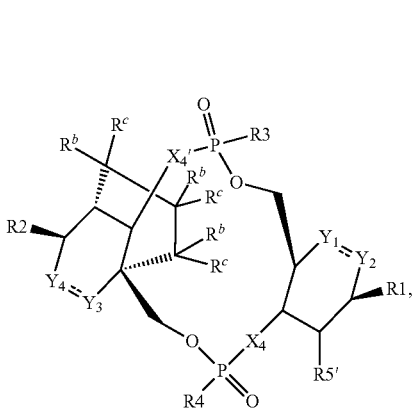
Formula Ib-G
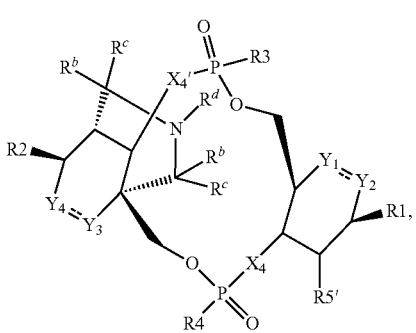
Formula Ib-H -continued
Formula Ib-I
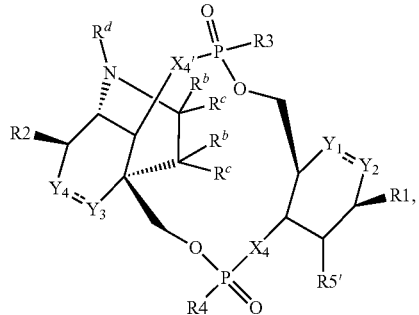
Formula Ib-J
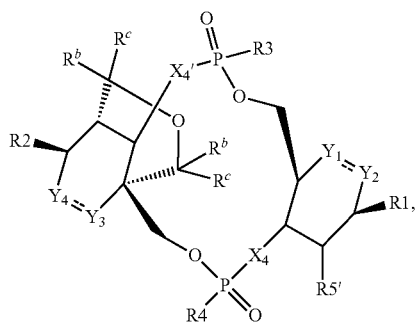
Formula Ib-K
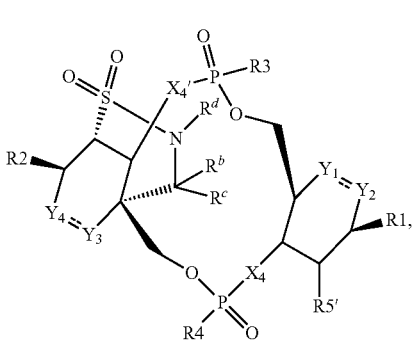
Formula Ib-L
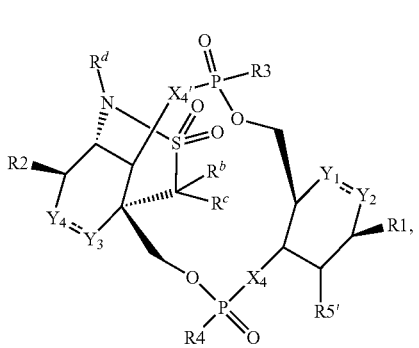
-continued
Formula Ib-M
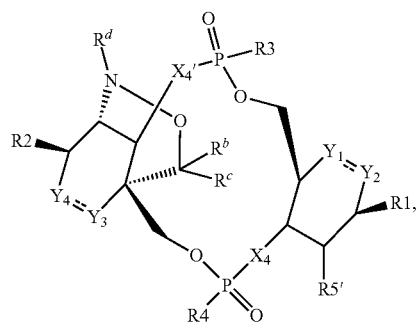
Formula Ib-N
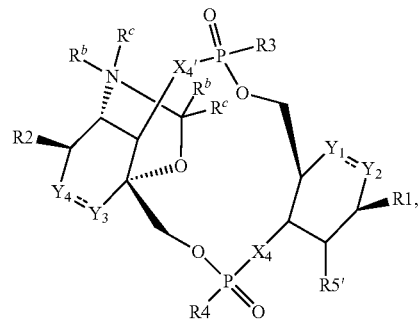
Formula Ic-A
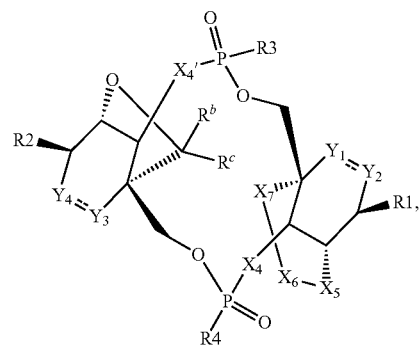
Formula Ic-B
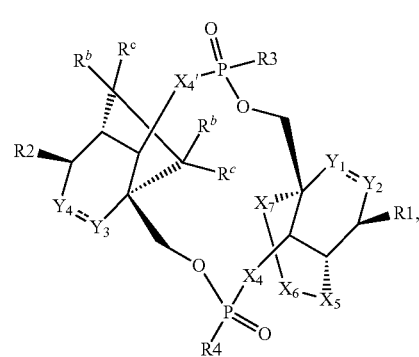

-continued
Formula Ic-C
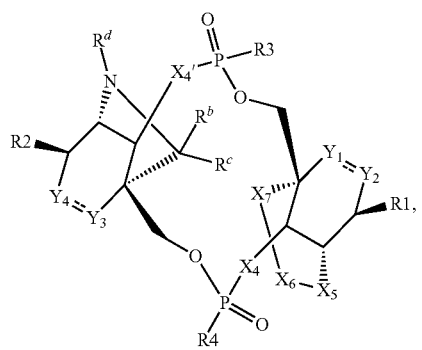
Formula Ic-D
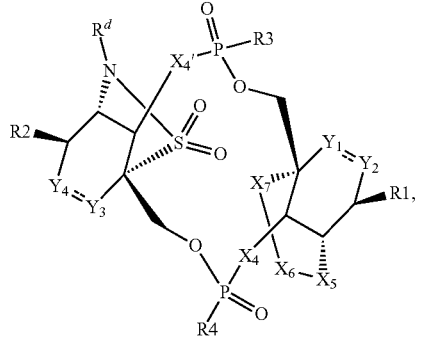
Formula Ic-E
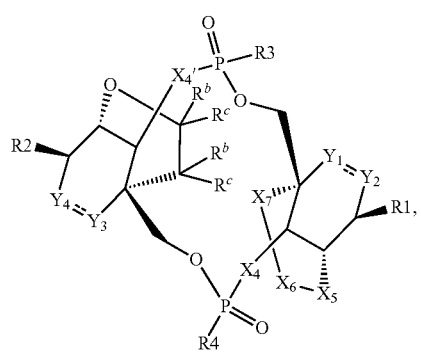
Formula Ic-F
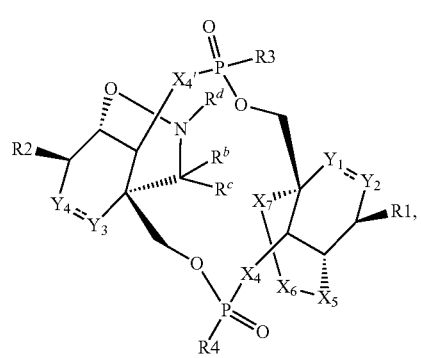
Formula Ic-G
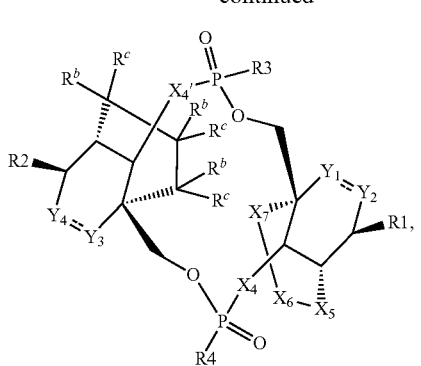
Formula Ic-H
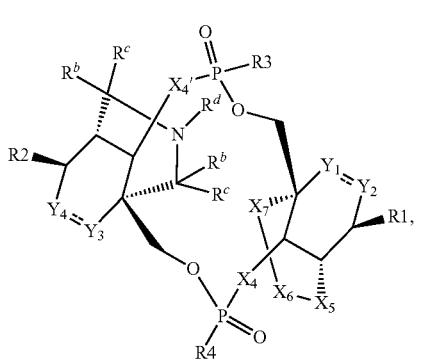
Formula Ic-I
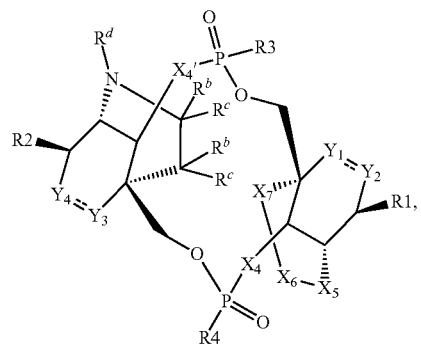
Formula Ic-J
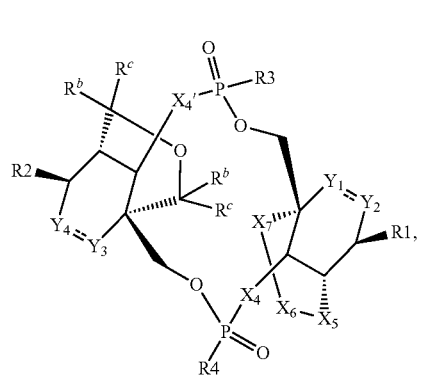

Formula Ic-K
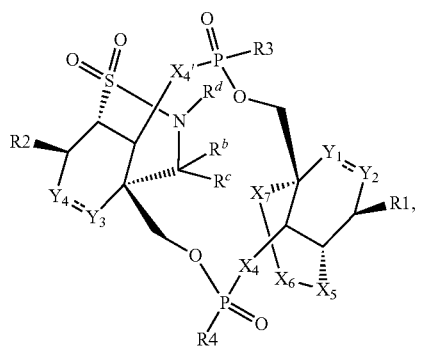
Formula Ic-L
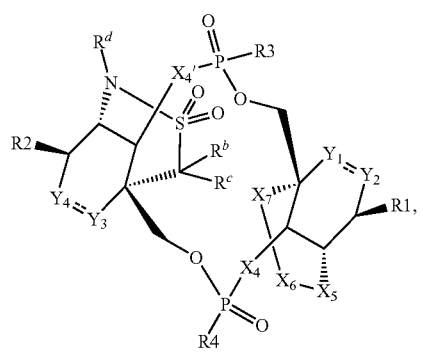
Formula Ic-M
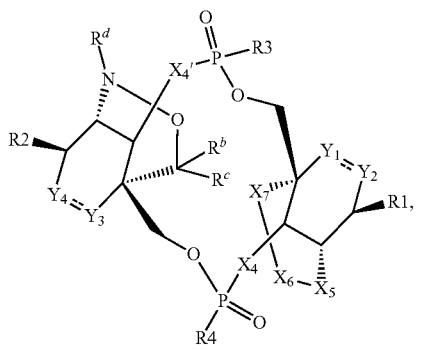
Formula Ic-N
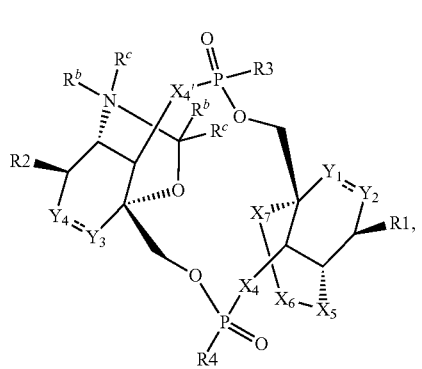
Formula Id-A
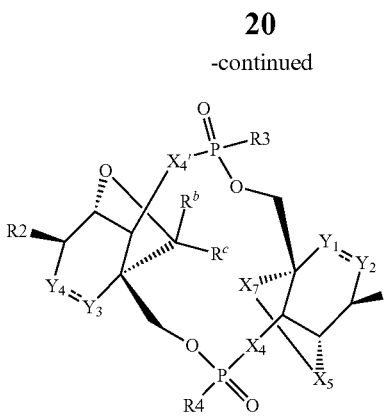
Formula Id-B
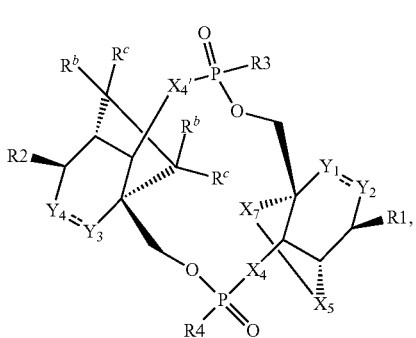
Formula Id-C
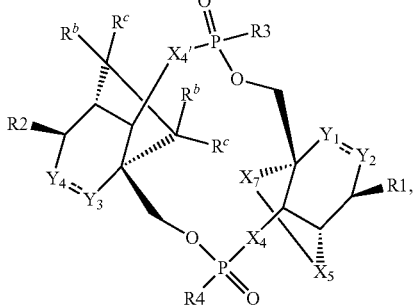
Formula Id-D
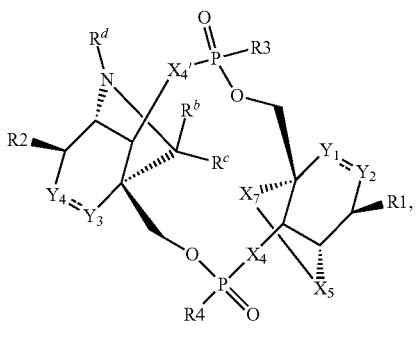
Formula Id-E
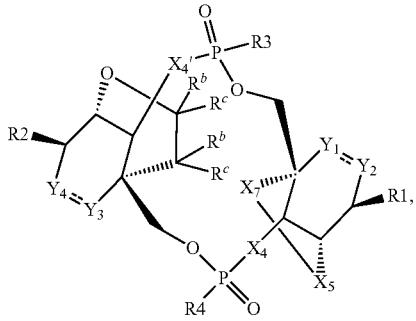

Formula Id-F

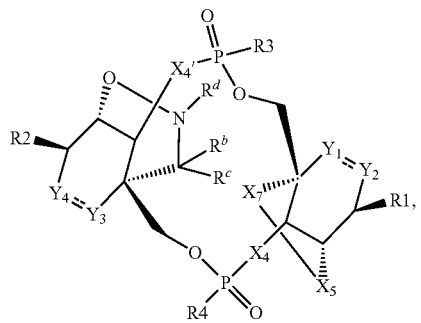

Formula Id-G

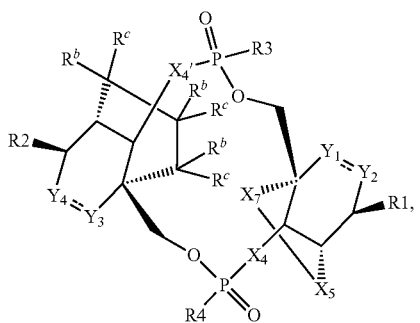

Formula Id-H

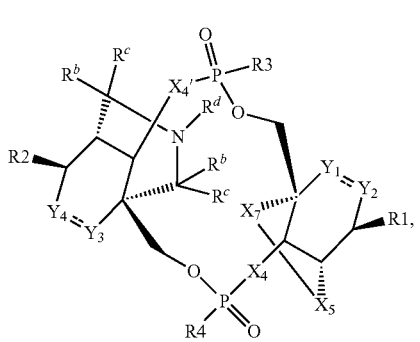

Formula Id-I

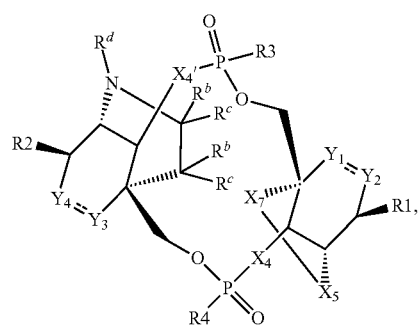

Formula Id-J

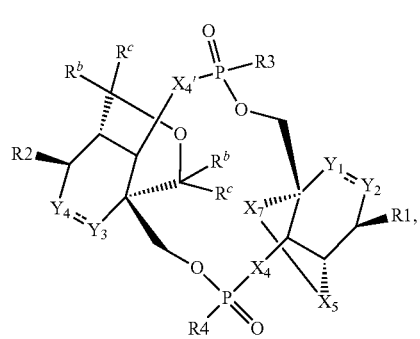

Formula Id-K

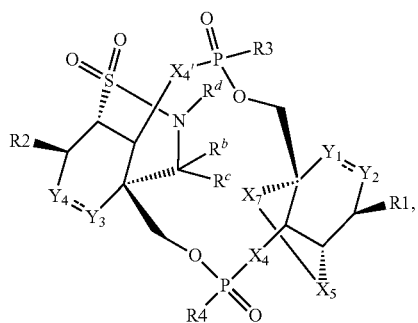

Formula Id-L

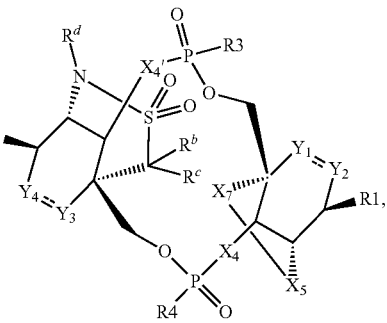

Formula Id-M

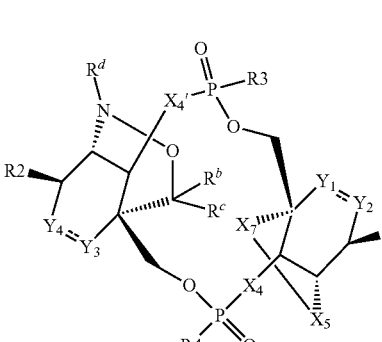

and

Formula Id-N

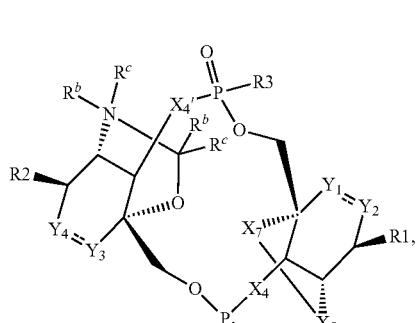

or a prodrug, pharmaceutically acceptable salt, pharmaceutically acceptable solvate or pharmaceutically acceptable hydrate thereof, wherein R5' and R6' are selected from the group consisting of —H, —OH, halogen and —$OR^e$, and R1, R2, R3, R4, $R^b$, $R^c$, $R^d$, $R^e$, $Y_1$, $Y_2$, $Y_3$, $Y_4$, $X_1$, $X_2$, $X_3$, $X_4$, $X_4'$, $X_5$, $X_6$ and $X_7$ are as defined for Formula I. In some embodiments, R5' and R6' are selected from the group consisting of —H, —OH optionally substituted with a suitable oxygen protecting group, halogen, —O—$C_{1-14}$alkyl and —O—(C═O)—$C_{1-14}$alkyl. In some embodiments, R5' and R6' are selected from the group consisting of —H, —OH, —F and —O—(C═O)—$C_{1-14}$alkyl. In some embodiments, R5' and R6' are —H, —OH or —F. In some embodiments, R5' and R6' are —OH or —F.

In some embodiments, the compound of Formula Ia-A is a compound of Formula Ia-A', the compound of Formula Ia-B is a compound of Formula Ia-B', the compound of Formula Ia-C is a compound of Formula Ia-C', the compound of Formula Ia-D is a compound of Formula Ia-D', the compound of Formula Ia-E is a compound of Formula Ia-E', the compound of Formula Ia-F is a compound of Formula Ia-F', the compound of Formula Ia-G is a compound of Formula Ia-G', the compound of Formula Ia-H is a compound of Formula Ia-H', the compound of Formula Ia-I is a compound of Formula Ia-I', the compound of Formula Ia-J is a compound of Formula Ia-J', the compound of Formula Ia-K is a compound of Formula Ia-K', the compound of Formula Ia-L is a compound of Formula Ia-L', the compound of Formula Ia-M is a compound of Formula Ia-M', the compound of Formula Ia-N is a compound of Formula Ia-N', the compound of Formula Ib-A is a compound of Formula Ib-A', the compound of Formula Ib-B is a compound of Formula Ib-B', the compound of Formula Ib-C is a compound of Formula Ib-C', the compound of Formula Ib-D is a compound of Formula Ib-D', the compound of Formula Ib-E is a compound of Formula Ib-E', the compound of Formula Ib-F is a compound of Formula Ib-F', the compound of Formula Ib-G is a compound of Formula Ib-G', the compound of Formula Ib-H is a compound of Formula Ib-H', the compound of Formula Ib-I is a compound of Formula Ib-I', the compound of Formula Ib-J is a compound of Formula Ib-J', the compound of Formula Ib-K is a compound of Formula Ib-K', the compound of Formula Ib-L is a compound of Formula Ib-U, the compound of Formula Ib-M is a compound of Formula Ib-M', the compound of Formula Ib-N is a compound of Formula Ib-N', the compound of Formula Ic-A is a compound of Formula Ic-A', the compound of Formula Ic-B is a compound of Formula Ic-B', the compound of Formula Ic-C is a compound of Formula Ic-C', the compound of Formula Ic-D is a compound of Formula Ic-D', the compound of Formula Ic-E is a compound of Formula Ic-E', the compound of Formula Ic-F is a compound of Formula Ic-F', the compound of Formula Ic-G is a compound of Formula Ic-G', the compound of Formula Ic-H is a compound of Formula Ic-H', the compound of Formula Ic-I is a compound of Formula Ic-I', the compound of Formula Ic-J is a compound of Formula Ic-J', the compound of Formula Ic-K is a compound of Formula Ic-K', the compound of Formula Ic-L is a compound of Formula Ic-L', the compound of Formula Ic-M is a compound of Formula Ic-M', the compound of Formula Ic-N is a compound of Formula Ic-N', the compound of Formula Id-A is a compound of Formula Id-A', the compound of Formula Id-B is a compound of Formula Id-B', the compound of Formula Id-C is a compound of Formula Id-C', the compound of Formula Id-D is a compound of Formula Id-D', the compound of Formula Id-E is a compound of Formula Id-E', the compound of Formula Id-F is a compound of Formula Id-F', the compound of Formula Id-G is a compound of Formula Id-G', the compound of Formula Id-H is a compound of Formula Id-H', the compound of Formula Id-I is a compound of Formula Id-I', the compound of Formula Id-J is a compound of Formula Id-J', the compound of Formula Id-K is a compound of Formula Id-K', the compound of Formula Id-L is a compound of Formula Id-L', the compound of Formula Id-M is a compound of Formula Id-M' and the compound of Formula Id-N is a compound of Formula Id-N':

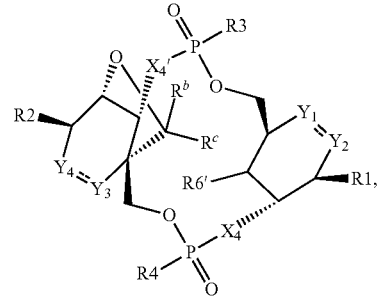

Formula Ia-A'

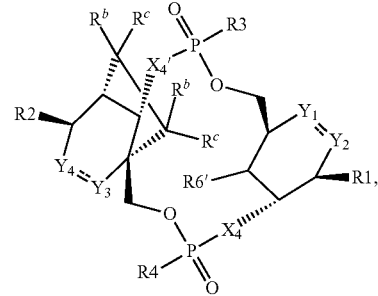

Formula Ia-B'

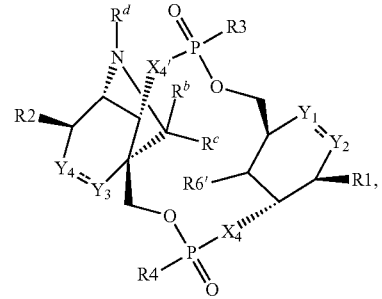

Formula Ia-C'

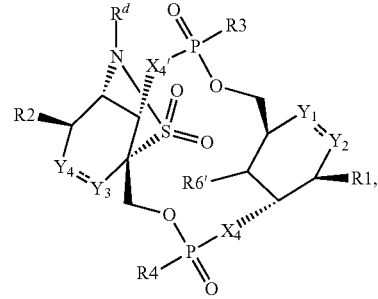

Formula Ia-D'

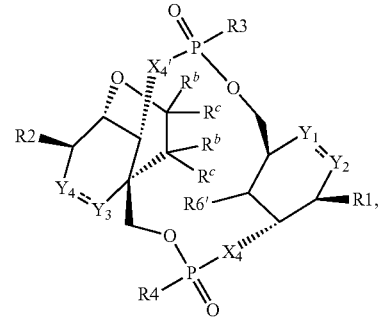

Formula Ia-E'

Formula Ia-F'
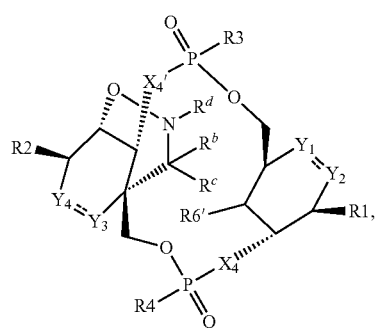
Formula Ia-G'
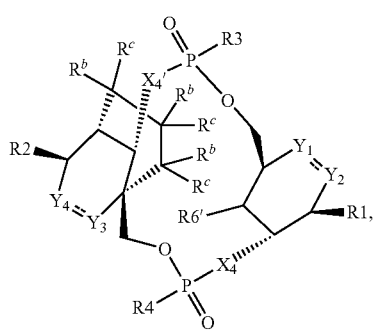
Formula Ia-H'
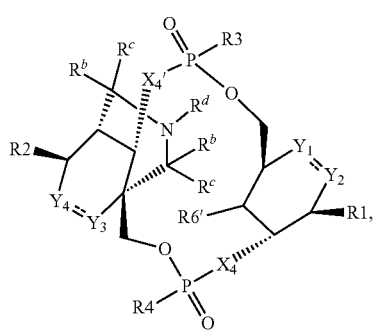
Formula Ia-I'
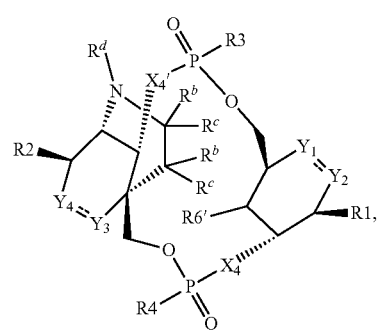
Formula Ia-J'
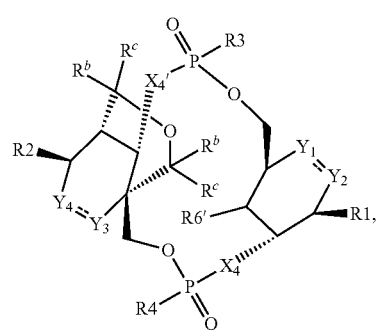
Formula Ia-K'
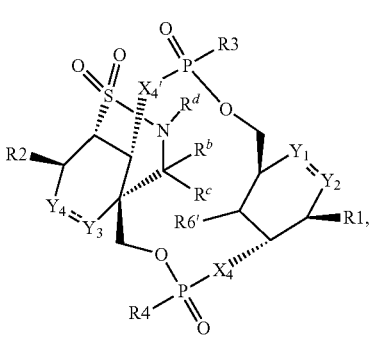
Formula Ia-L'
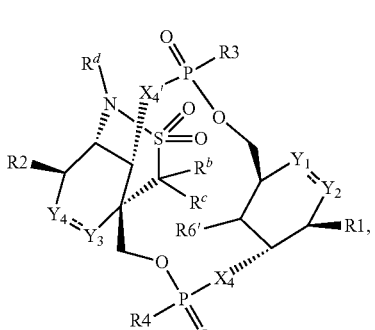
Formula Ia-M'
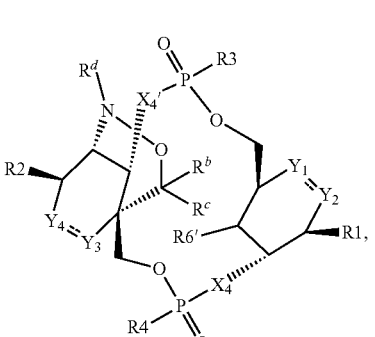
Formula Ia-N'
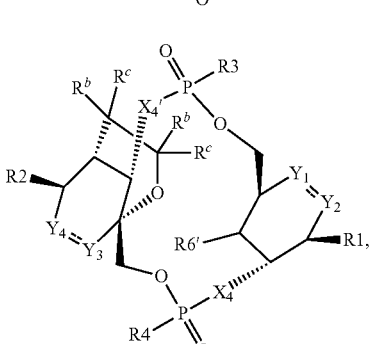
Formula Ib-A'
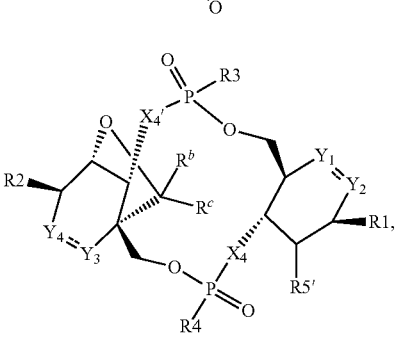

Formula Ib-B'
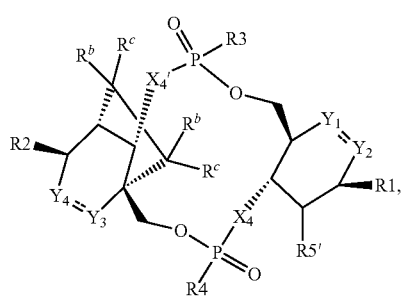
Formula Ib-C'
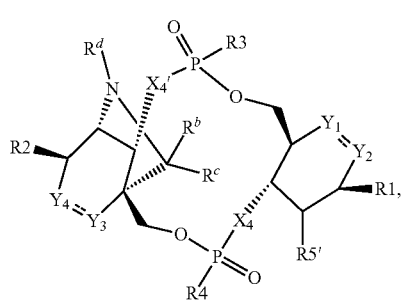
Formula Ib-D'
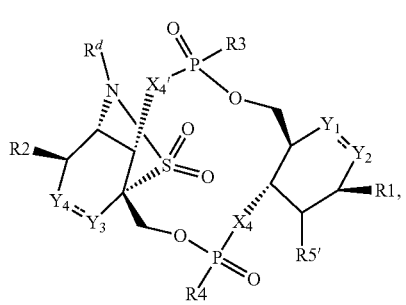
Formula Ib-E'
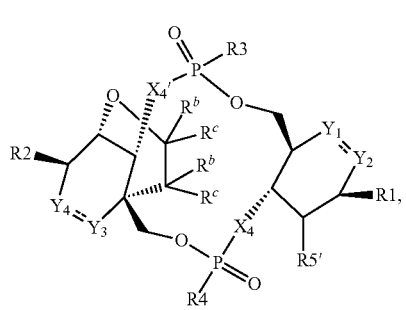
Formula Ib-F'
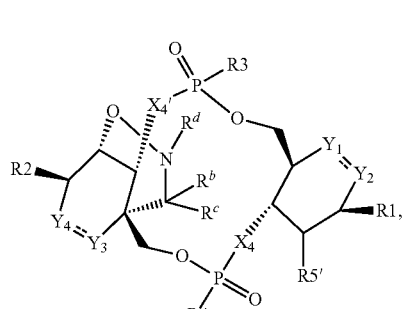
Formula Ib-G'
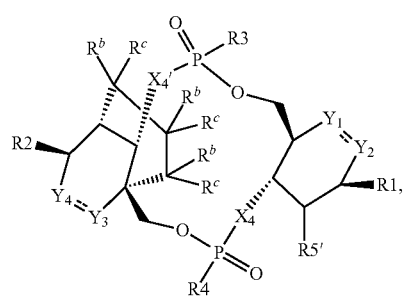
Formula Ib-H'
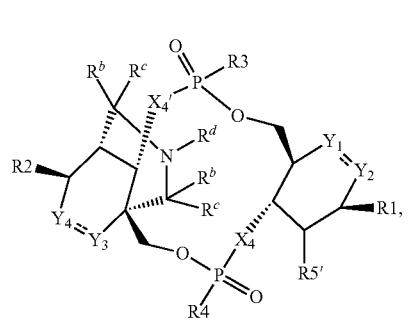
Formula Ib-I'
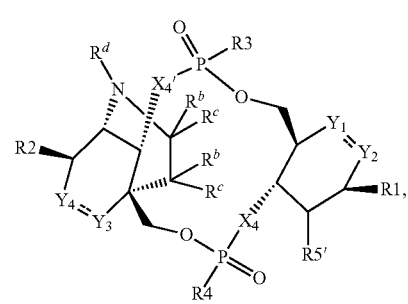
Formula Ib-J'
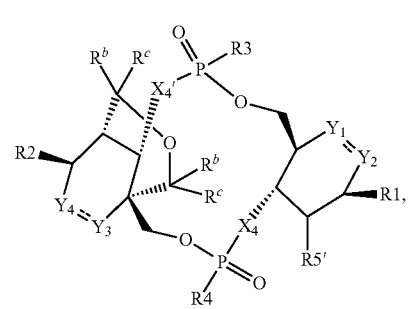
Formula Ib-K'
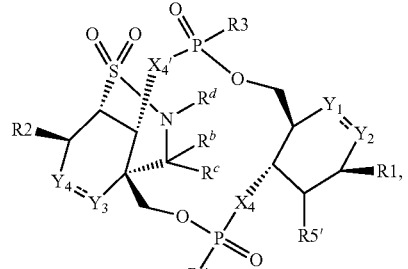

Formula Ib-L'
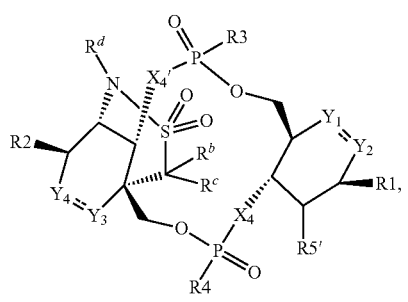
Formula Ib-M'
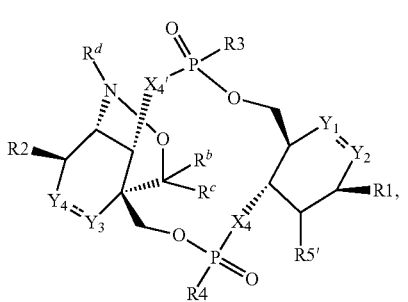
Formula Ib-N'
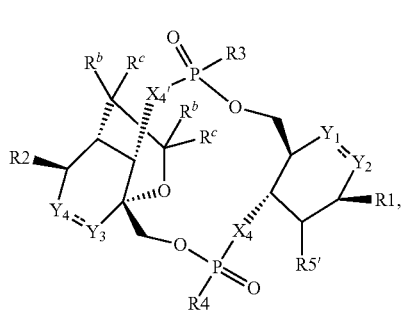
Formula Ic-A'
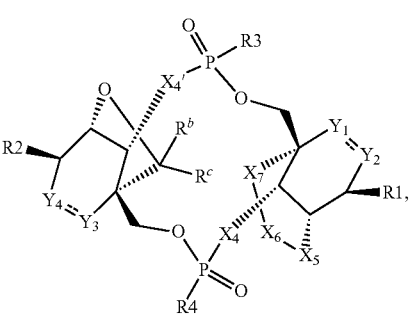
Formula Ic-B'
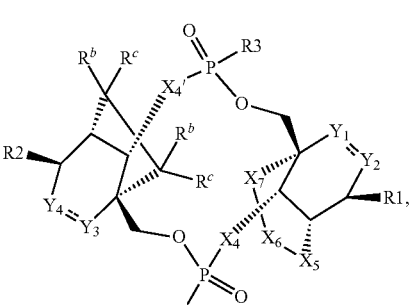
Formula Ic-C'
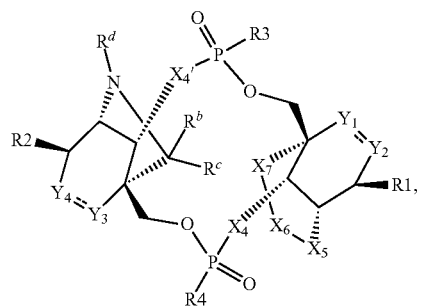
Formula Ic-D'
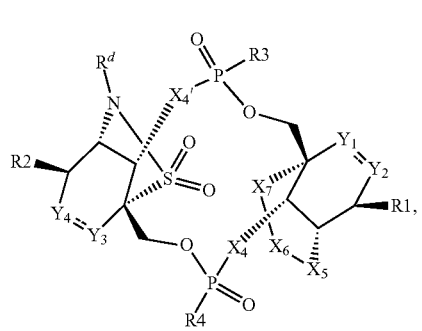
Formula Ic-E'
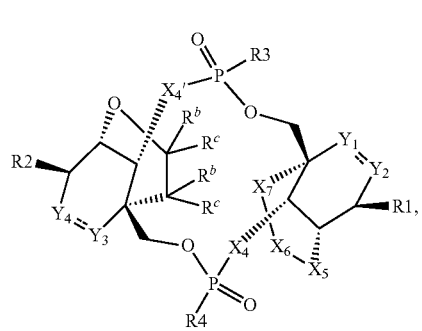
Formula Ic-F'
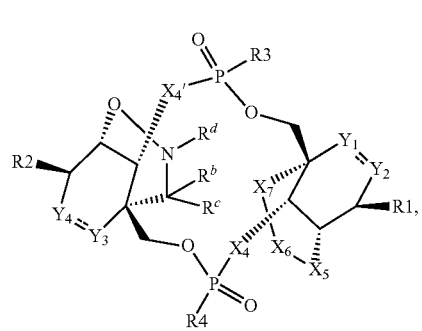
Formula Ic-G'
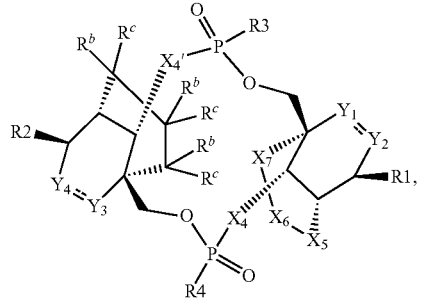

-continued
Formula Ic-H'
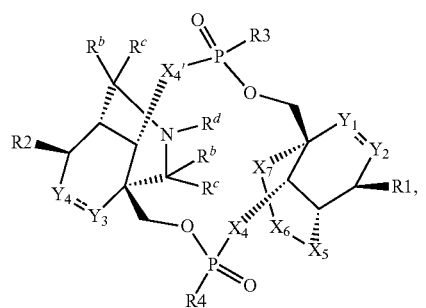
Formula Ic-I'
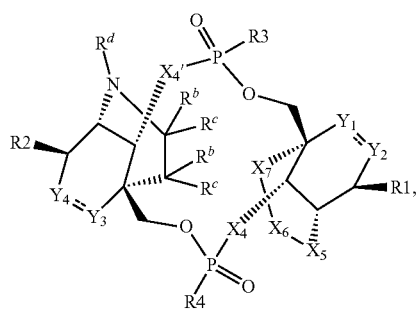
Formula Ic-J'
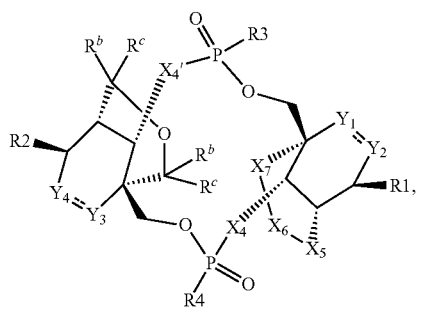
Formula Ic-K'
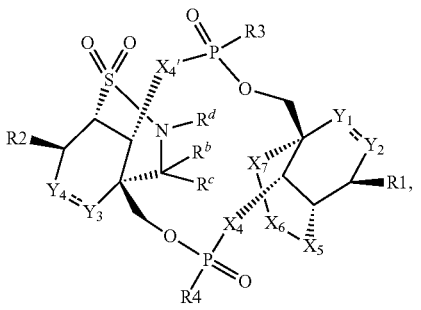
Formula Ic-L'
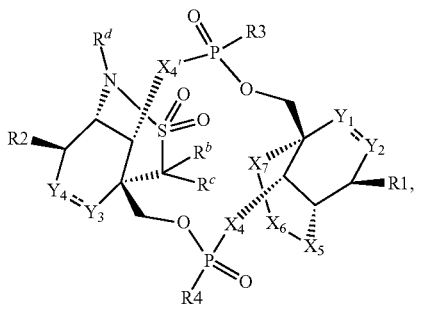
-continued
Formula Ic-M'
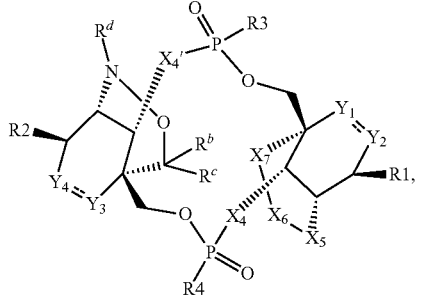
Formula Ic-N'
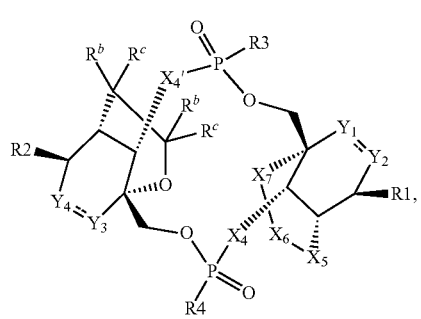
Formula Id-A'
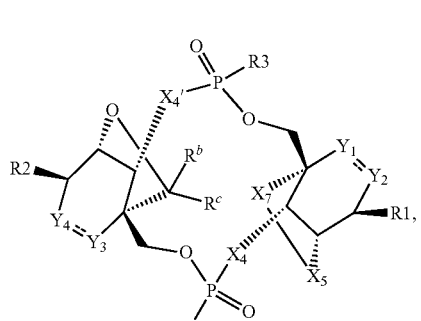
Formula Id-B'
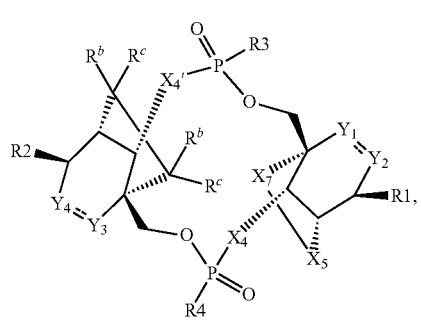
Formula Id-C'
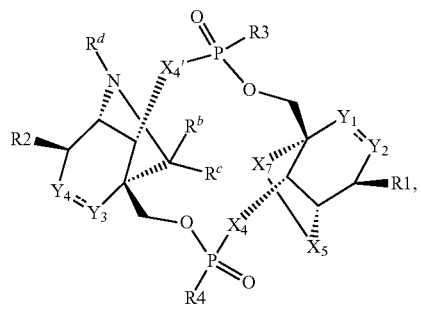

Formula Id-D'
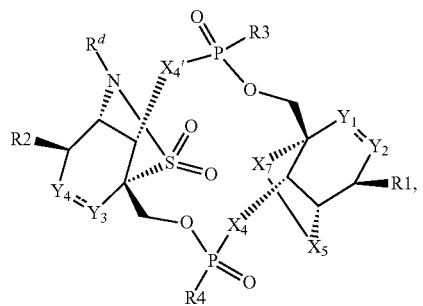
Formula Id-E'
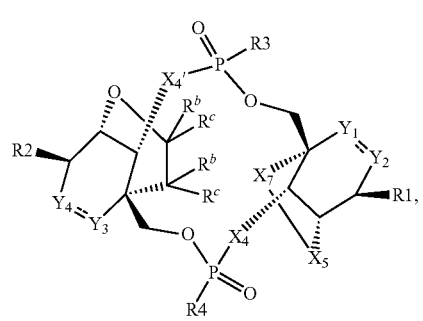
Formula Id-F'
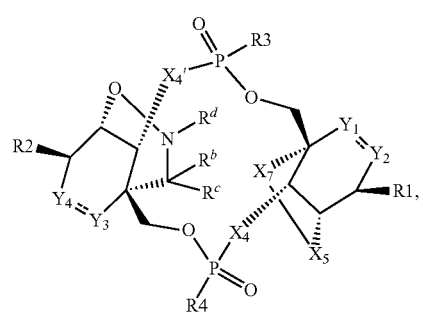
Formula Id-G'
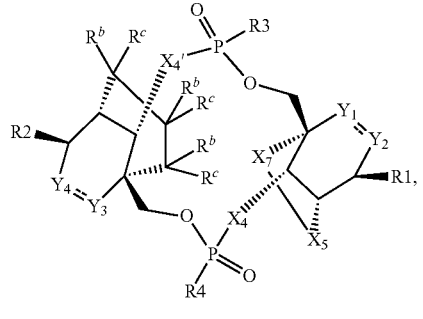
Formula Id-H'
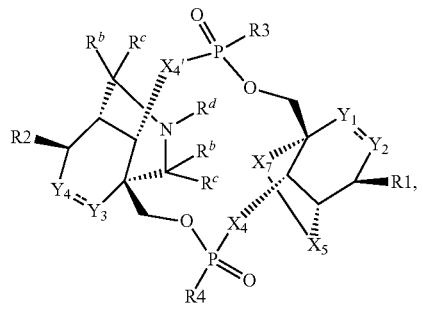
Formula Id-I'
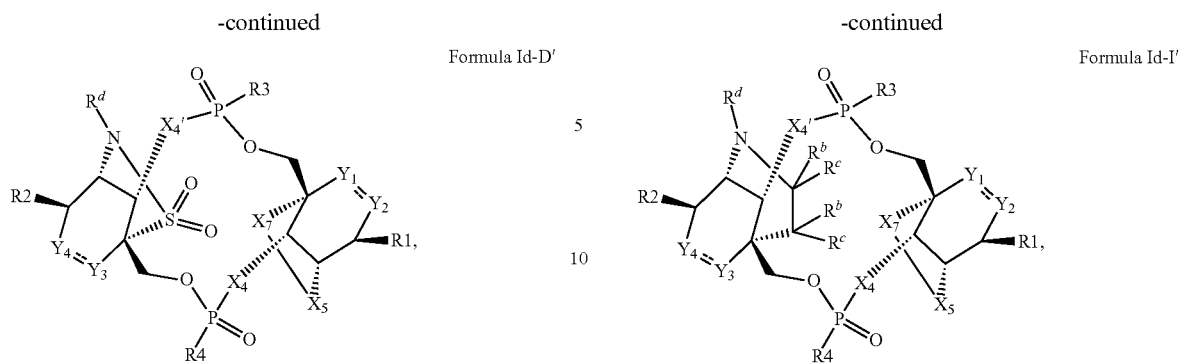
Formula Id-J'
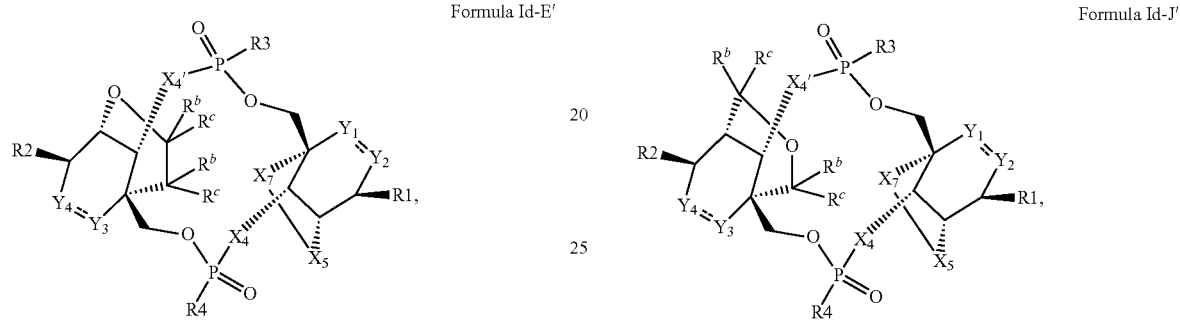
Formula Id-K'
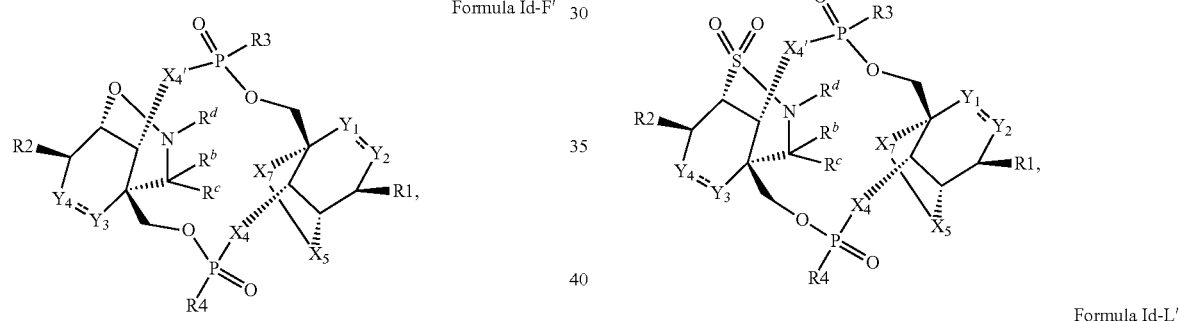
Formula Id-L'
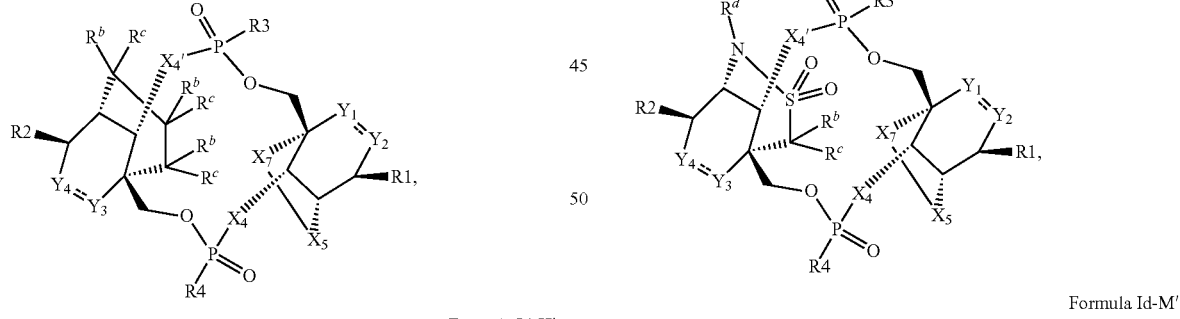
Formula Id-M'
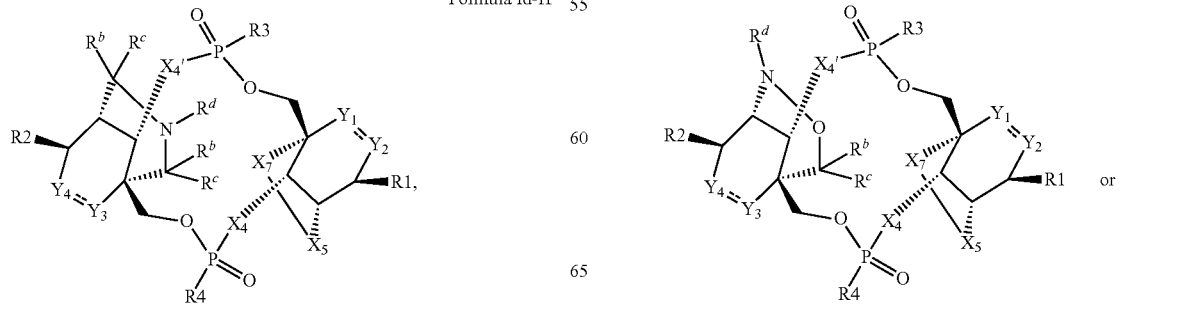
or -continued Formula Id-N'

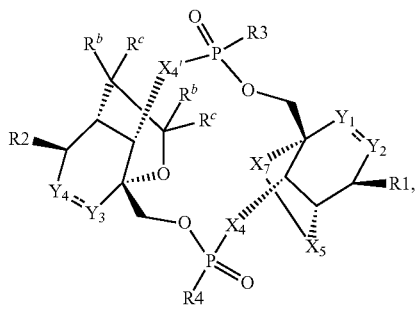

or a prodrug, pharmaceutically acceptable salt, pharmaceutically acceptable solvate or pharmaceutically acceptable hydrate thereof, wherein R5' and R6' are selected from the group consisting of —H, —OH, halogen and —OR$^e$, and R1, R2, R3, R4, R$^b$, R$^c$, R$^d$, R$^e$, Y$_1$, Y$_2$, Y$_3$, Y$_4$, X$_1$, X$_2$, X$_3$, X$_4$, X$_4'$, X$_5$, X$_6$ and X$_7$ are as defined for Formula I. In some embodiments, R5' and R6' are selected from the group consisting of —H, —OH optionally substituted with a suitable oxygen protecting group, halogen, —O—C$_{1-14}$alkyl and —O—(C=O)—C$_{1-14}$alkyl. In some embodiments, R5' and R6' are selected from the group consisting of —H, —OH, —F and —O—(C=O)—C$_{1-14}$alkyl. In some embodiments, R5' and R6' are —H, —OH or —F. In some embodiments, R5' and R6' are —OH or —F. In any of the above embodiments, the bond to R5' or R6' is preferably down into the paper, i.e. in the above structures is represented as e.g.  R5' where the * represents the bond to the core ring.

In a fifth embodiment of the first aspect, and any of the above embodiments thereof, R3 and R4 are independently —OH or —SH. In some embodiments, R3 and R4 are both —OH. In some embodiments, R3 and R4 are both —SH. In some embodiments, one of R3 and R4 is —OH and the other is —SH. In some embodiments, R3 and R4 are both —SH, wherein with reference to the stereochemistry at the phosphorus atoms, the compound is the substantially pure Rp,Rp isomer, the substantially pure the Rp,Sp isomer, the substantially pure Sp,Rp isomer, or the substantially pure Sp,Sp isomer.

In a sixth embodiment of the first aspect, and any of the above embodiments thereof, R1 and R2 are independently

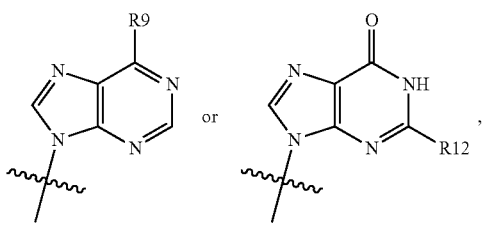

wherein indicates the bond of R1 or R2 to the ring as shown in Formula I and wherein R9 and R12 are independently —NH$_2$ or —NH—C$_{1-6}$alkyl, wherein —NH$_2$ is optionally substituted with a suitable nitrogen protecting group. In some embodiments, R9 and R12 are independently —NH$_2$, —NH—C$_{1-6}$alkyl, —N=CH—N(CH$_3$)$_2$, —NH—C(=O)—C$_{1-6}$-alkyl or —NH—C(=O)-phenyl. In some embodiments, R9 is —NH$_2$ or —NH—C(=O)-phenyl and R12 is —NH$_2$ or —NH—C(=O)-isopropyl. In some embodiments R9 and R12 are both —NH$_2$.

In a seventh embodiment of the first aspect, and any of the above embodiments thereof, R1 and R2 are independently

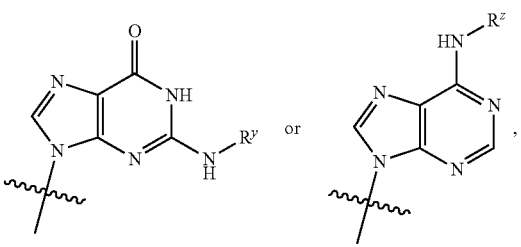

wherein

indicates the bond of R1 or R2 to the ring as shown in Formula I and wherein R$^y$ and R$^z$ are independently —H, —C(=O)—C$_{1-6}$alkyl, —C(=O)-phenyl or other suitable nitrogen protecting group. In some embodiments R$^y$ and R$^z$ are independently —H, —C(=O)—C$_{1-6}$alkyl or —C(=O)-phenyl. In some embodiments, R$^y$ is —H or —C(=O)-isopropyl and R$^z$ is —H or —C(=O)-phenyl. In some embodiments, R$^y$ and R$^z$ are both —H.

In an eighth embodiment of the first aspect, and any of the above embodiments thereof, Y$_1$ and Y$_2$, and Y$_3$ and Y$_4$, independently, are selected to provide —O—, —O—CH$_2$— or —CH=CH—. In some embodiments, Y$_1$ and Y$_2$, and Y$_3$ and Y$_4$, independently, are selected to provide —O— or —O—CH$_2$—. In some embodiments, Y$_1$ and Y$_3$ are O and Y$_2$ and Y$_4$ are absent.

In a ninth embodiment of the first aspect, and any of the above embodiments thereof, the bridging portion, i.e. —X$_1$—X$_2$—X$_3$— or —X$_1$—X$_3$—, and when present —X$_5$—X$_6$—X$_7$— or —X$_5$—X$_7$—, are independently selected from the group consisting of —CH$_2$—CH$_2$—CH$_2$—; —CH$_2$—N(R$^{d'}$)—CH$_2$—, where R$^{d'}$ at each occurrence is independently —H or a suitable nitrogen protecting group; —CH$_2$—O—CH$_2$—; —C(R$^{b'}$R$^{c'}$)—CH$_2$—O—, where R$^{b'}$ and R$^{c'}$ at each occurrence are independently —H, —CH$_3$, or together form =CH$_2$; —O—CH$_2$—CH$_2$—; —O—N(R$^{d'}$)—CH$_2$— or —O—N(R$^{d'}$)—C(=O)—, where R$^{d'}$ at each occurrence is independently —H, —CH$_3$ or a suitable nitrogen protecting group; —S(=O)$_2$—N(R$^{d'}$)—CH$_2$—, where R$^{d'}$ at each occurrence is independently —H or —C$_{1-3}$alkyl or a suitable nitrogen protecting group; —NH—CH$_2$—CH$_2$— or —N(R$^{d'}$)—C(=O)—CH$_2$—, where R$^{d'}$ at each occurrence is independently —H, —CH$_3$ or a suitable nitrogen protecting group; —N(R$^{d'}$)—O—CH$_2$— or —N(R$^{d'}$)—S(=O)$_2$—CH$_2$—, where R$^{d'}$ at each occurrence is independently —H or —C$_{1-3}$alkyl or a suitable nitrogen protecting group; —C(R$^{b'}$R$^{c'}$)—C(R$^{b''}$R$^{c''}$)—, where R$^{b'}$ and R$^{c'}$ at each occurrence are independently —H, —F, —NH$_2$, —CH$_3$, or together form =CH$_2$, =CHF or =O, and where R$^{b''}$ and R$^{c''}$ at each occurrence are independently —H, —F, —OH, —OCH$_3$, —CH$_3$, —CH$_2$F, —CHF$_2$, —CF$_3$, or together form =CH$_2$, =CHF or =O; —O—C(R$^{b'}$R$^{c'}$)—, where R$^{b'}$, R$^{c'}$ at each occurrence are independently —H, —CH$_3$, —CH$_2$F, —CHF$_2$, —CF$_3$, or —CH$_2$OCH$_3$, or together form =CH$_2$, or together with the carbon to which they are attached form a 3-6 membered heterocycloalkyl or C$_{3-6}$ cycloalkyl spirocyclic ring; —N(R$^{d'}$)—CH$_2$—, where R$^{d'}$ at each occurrence is independently —H or —C$_{1-6}$alkoxy or a suitable nitrogen protecting group, wherein the alkyl chain of C$_{1-6}$alkoxy is optionally substituted with 1, 2 or 3 —F or with —OCH$_3$; —N(R$^{d'}$)—C(=O)—, where R$^{d'}$ at each occurrence is independently —H, —CH$_3$ or a suitable nitrogen protecting group; or —N(R$^{d'}$)—S(=O)$_2$—, where R$^{d'}$ at each occurrence is independently —H or —C$_{1-3}$alkyl or a suitable nitrogen protecting group. In some embodiments, the bridging portion is —X$_1$—X$_3$— and when present —X$_5$—X$_7$—, wherein —X$_1$—X$_3$— and —X$_5$—X$_7$— are independently —O—C(R$^{b'}$R$^{c'}$)—, where R$^{b'}$, R$^{c'}$ at each occurrence are independently —H, —CH$_3$, —CH$_2$F, —CHF$_2$, —CF$_3$, or —CH$_2$OCH$_3$, or together form =CH$_2$, or together with the carbon to which they are attached form a cyclopropyl spirocyclic ring, preferably wherein —X$_1$—X$_3$— and when present —X$_5$—X$_7$— are —O—CH$_2$—.

In a tenth embodiment of the first aspect, and any of the above embodiments thereof, X$_4$' and X$_4$ are both —O—.

In an eleventh embodiment of the first aspect, and any of the above embodiments thereof, X$_4$ and X$_4$' are —O—, R3 and R4 are independently —OH or —SH, Y$_1$ and Y$_3$ are O and Y$_2$ and Y$_4$ are absent. In some embodiments, X$_4$ and X$_4$' are —O—, one of R3 and R4 is —OH and the other of R3 and R4 is —SH, Y$_1$ and Y$_3$ are O and Y$_2$ and Y$_4$ are absent. In some embodiments, X$_4$ and X$_4$' are —O—, R3 and R4 are both —OH, Y$_1$ and Y$_3$ are O and Y$_2$ and Y$_4$ are absent. In some embodiments, X$_4$ and X$_4$' are —O—, R3 and R4 are both —SH, Y$_1$ and Y$_3$ are O and Y$_2$ and Y$_4$ are absent. In some embodiments, X$_4$ and X$_4$' are —O—, R3 and R4 are both —SH, wherein with reference to the stereochemistry at the phosphorus atoms, the compound is the substantially pure Rp,Rp isomer, the substantially pure Rp,Sp isomer, the substantially pure Sp,Rp isomer, or the substantially pure Sp,Sp isomer, Y$_1$ and Y$_3$ are O and Y$_2$ and Y$_4$ are absent.

In a twelfth embodiment of the first aspect, and any of the above embodiments thereof, X$_4$ and X$_4$' are —O—, R3 and R4 are independently —OH or —SH, Y$_1$ and Y$_3$ are O, Y$_2$ and Y$_4$ are absent, and R1 and R2 are independently

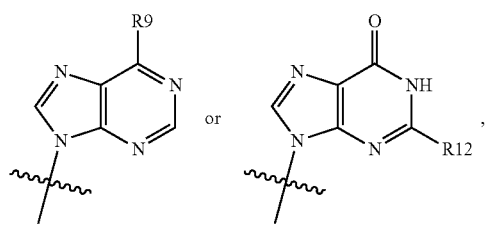

wherein

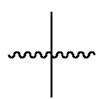

indicates the bond of R1 or R2 to the ring as shown in Formula I and wherein R9 and R12 are independently —NH$_2$, —NH—C$_{1-6}$alkyl, —N=CH—N(CH$_3$)$_2$, —NH—C(=O)—C$_{1-6}$alkyl or —NH—C(=O)-phenyl. In some embodiments, X$_4$ and X$_4$' are —O—, one of R3 and R4 is —OH and the other of R3 and R4 is —SH, Y$_1$ and Y$_3$ are O, Y$_2$ and Y$_4$ are absent, and R1 and R2 are independently

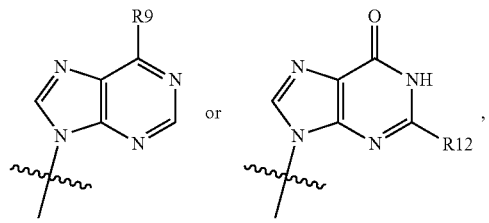

wherein

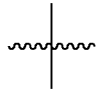

indicates the bond of R1 or R2 to the ring as shown in Formula I and wherein R9 and R12 are independently —NH$_2$, —NH—C$_{1-6}$alkyl, —N=CH—N(CH$_3$)$_2$, —NH—C(=O)—C$_{1-6}$alkyl or —NH—C(=O)-phenyl. In some embodiments, X$_4$ and X$_4$' are —O—, R3 and R4 are both —OH, Y$_1$ and Y$_3$ are O, Y$_2$ and Y$_4$ are absent, and R1 and R2 are independently

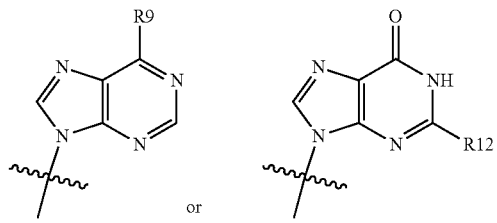

wherein

indicates the bond of R1 or R2 to the ring as shown in Formula I and wherein R9 and R12 are independently —NH$_2$, —NH—C$_{1-6}$alkyl, —N=CH—N(CH$_3$)$_2$, —NH—C(=O)—C$_{1-6}$alkyl or —NH—C(=O)-phenyl. In some embodiments, X$_4$ and X$_4$' are —O—, R3 and R4 are both —SH, Y$_1$ and Y$_3$ are O, Y$_2$ and Y$_4$ are absent, and R1 and R2 are independently

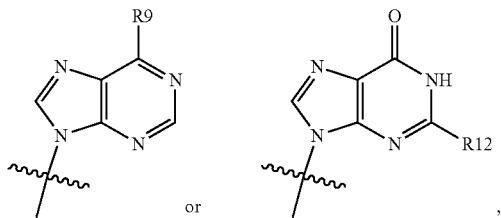

wherein

indicates the bond of R1 or R2 to the ring as shown in Formula I and wherein R9 and R12 are independently —NH$_2$, —NH—C$_{1-6}$alkyl, —N=CH—N(CH$_3$)$_2$, —NH—C(=O)—C$_{1-6}$alkyl or —NH—C(=O)-phenyl. In some embodiments, X$_4$ and X$_4$' are —O—, R3 and R4 are both —SH, wherein with reference to the stereochemistry at the phosphorus atoms, the compound is the substantially pure Rp,Rp isomer, the substantially pure Rp,Sp isomer, the substantially pure Sp,Rp isomer, or the substantially pure Sp,Sp isomer, Y$_1$ and Y$_3$ are O, Y$_2$ and Y$_4$ are absent, and R1 and R2 are independently

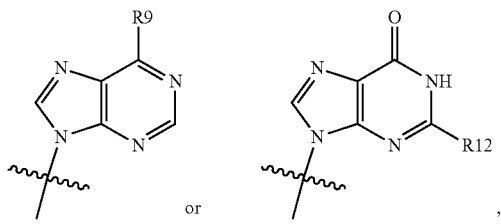

wherein

indicates the bond of R1 or R2 to the ring as shown in Formula I and wherein R9 and R12 are independently —NH$_2$, —NH—C$_{1-6}$alkyl, —N=CH—N(CH$_3$)$_2$, —NH—C(=O)—C$_{1-6}$alkyl or —NH—C(=O)-phenyl.

In any of the above embodiments of the first aspect, the bridging portions —X$_1$—X$_2$—X$_3$— or —X$_1$—X$_3$— are excluded wherein X$_2$ is absent and —X$_1$—X$_3$— provide —O—C(R$^b$R$^c$)—.

In any of the above embodiments of the first aspect, the bridging portions —X$_1$—X$_2$—X$_3$— or —X$_1$—X$_3$— are selected such that X$_1$, X$_2$, and X$_3$ are all present, X$_1$ and X$_2$ are —C(R$^b$R$^c$)—, —N(R$^d$)—, —O— or —S(=O)$_2$—, and X$_3$ is —C(R$^b$R$^c$)— or —O—, selected to provide —X$_1$—X$_2$—X$_3$— as —C(R$^b$R$^c$)—C(R$^b$R$^c$)—C(R$^b$R$^c$)—, —C(R$^b$R$^c$)—N(R$^d$)—C(R$^b$R$^c$)—, —C(R$^b$R$^c$)—O—C(R$^b$R$^c$)—, —C(R$^b$R$^c$)—C(R$^b$R$^c$)—O—, —O—C(R$^b$R$^c$)—C(R$^b$R$^c$)—, —O—N(R$^d$)—C(R$^b$R$^c$)—, —S(=O)$_2$—N(R$^d$)—C(R$^b$R$^c$)—, —N(R$^d$)—C(R$^b$R$^c$)—C(R$^b$R$^c$)—, —N(R$^d$)—O—C(R$^b$R$^c$)— or —N(R$^d$)—S(=O)$_2$—C(R$^b$R$^c$)—; or X$_2$ is absent, X$_1$ and X$_3$ are both present, X$_1$ is —C(R$^b$R$^c$)— or —N(R$^d$) and X$_3$ is —C(R$^b$R$^c$)— or —S(=O)$_2$—, selected to provide —X$_1$—X$_3$— as —C(R$^b$R$^c$)—C(R$^b$R$^c$)—, —N(R$^d$)—C(R$^b$R$^c$)— or —N(R$^d$)—S(=O)$_2$—.

In any of the above embodiments of the first aspect, when X$_2$ is absent and X$_1$ and X$_3$ are both present, then X$_1$ is —C(R$^b$R$^c$)— or —N(R$^d$) and X$_3$ is —C(R$^b$R$^c$)— or —S(=O)$_2$—, selected to provide —X$_1$—X$_3$— as —C(R$^b$R$^c$)—C(R$^b$R$^c$)—, —N(R$^d$)—C(R$^b$R$^c$)— or —N(R$^d$)—S(=O)$_2$—; and when X$_4$ is —O— or —NH— bonded to the 3' carbon atom of ring A, R6 is absent, and R5 and R7 join to form —X$_5$—X$_6$—X$_7$—, resulting in a fused ring system with X$_5$ bonded to the 2' carbon atom of ring A and X$_7$ bonded to the carbon atom of ring A to which R7 is attached, and X$_6$ is absent and X$_5$ and X$_7$ are both present, then X$_5$ is —C(R$^b$R$^c$)— or —N(R$^d$) and X$_7$ is —C(R$^b$R$^c$)— or —S(=O)$_2$—, selected to provide —X$_5$—X$_7$— as —C(R$^b$R$^c$)—C(R$^b$R$^c$)—, —N(R$^d$)—C(R$^b$R$^c$)— or —N(R$^d$)—S(=O)$_2$—.

In any of the eleventh or twelfth embodiments of the first aspect, X$_2$ is absent and X$_1$ and X$_3$ provide —O—C(R$^b$R$^c$)—; X$_4$ is —O— bonded to the 2' carbon atom of ring A, R5 is absent, R6 is selected from the group consisting of —H, —OH, halogen and —OR$^e$, and R7 is —H; or X$_4$ is —O— bonded to the 3' carbon atom of ring A, R6 is absent, and R5 is selected from the group consisting of —H, —OH, halogen and —OR$^e$, and R7 is —H; or X$_4$ is —O— bonded to the 3' carbon atom of ring A, R6 is absent, and R5 and R7 join to form —X$_5$—X$_7$— to provide —O—C(R$^a$R$^b$)—, resulting in a fused ring system with —O— bonded to the 2' carbon atom of ring A and —C(R$^a$R$^b$)— bonded to the carbon atom of ring A to which R7 is attached; R1 and R2 are independently

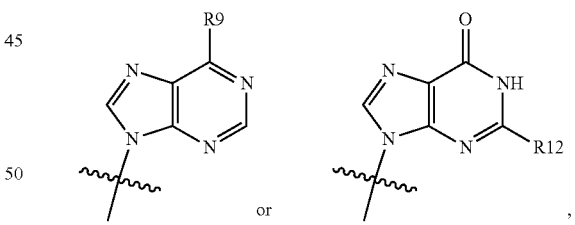

provided that when X$_4$ is —O— bonded to the 2' carbon atom of ring A, R1 is

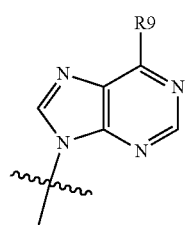

and R2 is

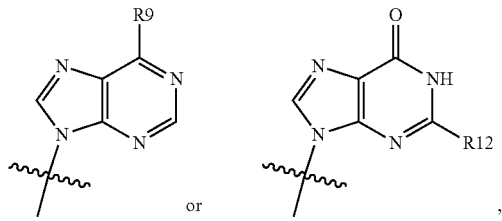

or

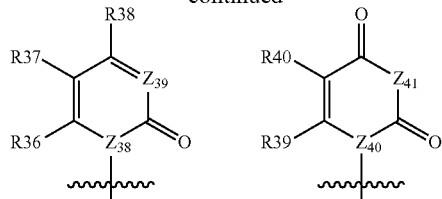

, and wherein R9 and R12 are independently —NH$_2$, —NH—C$_{1-6}$ alkyl, —N=CH—N(CH$_3$)$_2$, —NH—C(=O)—C$_{1-6}$alkyl or —NH—C(=O)-phenyl, preferably where R9 and R12 are both —NH$_2$.

In a second aspect, the present invention provides a locked nucleic acid cyclic dinucleotide ("LNA-CDN") compound of Formula II:

Formula II

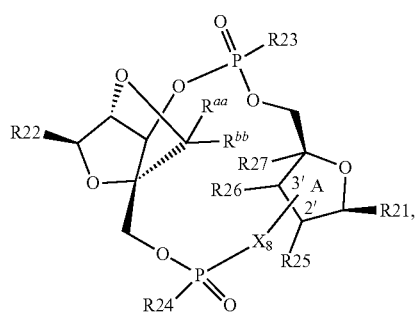

or a prodrug, pharmaceutically acceptable salt, pharmaceutically acceptable solvate or pharmaceutically acceptable hydrate thereof, wherein:

R21 and R22 are independently selected from the group consisting of:

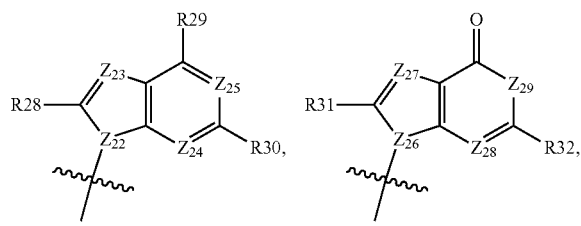

,

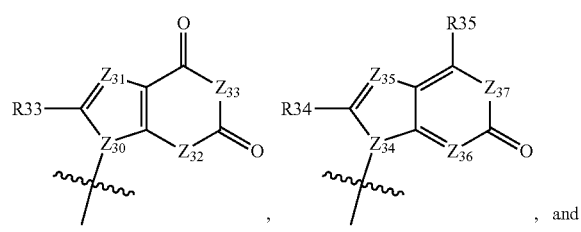

, and wherein

indicates the bond of R21 or R22 to the ring as shown in Formula II; R23 and R24 are independently —OH, —OR$^{cc}$, —SH or —SR$^{cc}$;

X$_8$ is —O— bonded to either the 2' or the 3' carbon atom of the indicated ring A;

wherein:
  when X$_8$ is —O— bonded to the 2' carbon atom of ring A:
    R25 is absent, R26 is selected from the group consisting of —H, —OH, halogen and —OR$^{dd}$, and R27 is —H;
  when X$_8$ is —O— bonded to the 3' carbon atom of ring A:
    R26 is absent, R25 is selected from the group consisting of —H, —OH, halogen and —OR$^{dd}$, and R27 is —H; or
    R26 is absent, and R25 and R27 join to form —O—C(R$^{aa}$R$^{bb}$)—, resulting in a) fused ring system with —O— bonded to the 2' carbon atom of ring A and —C(R$^{aa}$R$^{bb}$)— bonded to the carbon atom of ring A to which R27 is attached;

R$^{aa}$ and R$^{bb}$, at each occurrence, are independently selected from the group consisting of —H, halogen, alkyl, alkenyl, alkynyl, heteroalkyl, carbocyclyl, heterocyclyl, aryl, heteroaryl, —R' and -L$_5$-R$^{ee}$; or R$^{aa}$ and R$^{bb}$ together on a carbon are =O, =C$^{ff}$R$^{ff}$, =N—OR$^{gg}$, =N—R$^{gg}$, or =N—NR$^{gg}$R$^{gg}$; or R$^{aa}$ and R$^{bb}$ together with the carbon to which they are attached form a C$_{3-6}$ cycloalkyl or 3 to 6 membered heterocycloalkyl spirocyclic ring; wherein alkyl, alkenyl, alkynyl or heteroalkyl are optionally independently substituted with one or more —R$^{jj}$, and carbocyclyl, heterocyclyl, aryl or heteroaryl are optionally independently substituted with one or more —R$^{kk}$;

R$^{cc}$ at each occurrence are independently selected from the group consisting of alkyl, alkenyl, alkynyl, heteroalkyl, carbocyclyl, heterocyclyl, aryl, heteroaryl and —C(=O)R$^{hh}$; wherein alkyl, alkenyl, alkynyl or heteroalkyl are optionally independently substituted with one or more —R$^{jj}$, and carbocyclyl, heterocyclyl, aryl or heteroaryl are optionally independently substituted with one or more —R$^{kk}$;

R$^{dd}$ is selected from the group consisting of alkyl, alkenyl, alkynyl, heteroalkyl, carbocyclyl, heterocyclyl, aryl, heteroaryl and —C(=O)R$^{hh}$; wherein alkyl, alkenyl, alkynyl or heteroalkyl are optionally independently substituted with one or more —R$^{jj}$, and carbocyclyl, heterocyclyl, aryl or heteroaryl are optionally independently substituted with one or more —$R^{kk}$; or $R^{dd}$ is a suitable oxygen protecting group;

$R^{ee}$ at each occurrence is independently selected from the group consisting of alkyl, alkenyl, alkynyl, heteroalkyl, carbocyclyl, heterocyclyl, aryl and heteroaryl; wherein alkyl, alkenyl, alkynyl or heteroalkyl are optionally independently substituted with one or more —$R^{jj}$, and carbocyclyl, heterocyclyl, aryl or heteroaryl are optionally independently substituted with one or more —$R^{kk}$;

$R^{ff}$ at each occurrence is independently selected from the group consisting of —H, halogen, alkyl, alkenyl, alkynyl, heteroalkyl, carbocyclyl, heterocyclyl, aryl and heteroaryl; wherein alkyl, alkenyl, alkynyl or heteroalkyl are optionally independently substituted with one or more —$R^{jj}$, and carbocyclyl, heterocyclyl, aryl or heteroaryl are optionally independently substituted with one or more —$R^{kk}$;

$R^{gg}$ at each occurrence is independently selected from the group consisting of —H, alkyl, alkenyl, alkynyl, heteroalkyl, carbocyclyl, heterocyclyl, aryl and heteroaryl; wherein alkyl, alkenyl, alkynyl or heteroalkyl are optionally independently substituted with one or more —$R^{jj}$, and carbocyclyl, heterocyclyl, aryl or heteroaryl are optionally independently substituted with one or more —$R^{kk}$;

$R^{hh}$ at each occurrence is independently selected from the group consisting of alkyl, alkenyl, alkynyl, heteroalkyl, carbocyclyl, heterocyclyl, aryl, and heteroaryl; wherein alkyl, alkenyl, alkynyl or heteroalkyl are optionally independently substituted with one or more —$R^{jj}$, and carbocyclyl, heterocyclyl, aryl or heteroaryl are optionally independently substituted with one or more —$R^{kk}$;

R' at each occurrence is selected from the group consisting of —CN, —$NO_2$, —OH, —SH, —$NH_2$, —C(=W)—WH, —C(=W)—$NH_2$, —C(=W)—NH—WH, —C=N—OH, —C(=NH)—$NH_2$, —W—C(=W)—WH, —W—C(=W)—$NH_2$, —S(=O)$_2$—$NH_2$, —S(=O)$_2$—NH—W—, —NH—$NH_2$, —NH—WH, —NH—C(=W)—WH, —NH—C(=W)—$NH_2$, —NH—S(=O)$_2$—$NH_2$, and —NH—C(=NH)—$NH_2$;

$L_5$ is selected from the group consisting of —O—, —S—, —S(=O)—, —S(=O)$_2$—, —C(=W)—, —C(=W)—W—, —C(=W)—$NR^{ii}$—, —C(=W)—$NR^{ii}$—W—, —C=N—O—, —C(=$NR^{ii}$)$NR^{ii}$—, —C($NR^{ii}R^{ii}$)=N—, —W—C(=W)—, —W—C(=W)—W—, —W—C(=W)—$NR^{ii}$—, —S(=O)$_2$—$NR^{ii}$—, —S(=O)$_2$—$NR^{ii}$—W—, —$NR^{ii}$—, —N=$CR^{ff}$—, —$NR^{ii}$—W—, —$NR^{ii}$—$NR^{ii}$—, —$NR^{ii}$—C(=$NR^{ii}$)$NR^{ii}$—, —$NR^{ii}$—C($NR^{ii}R^{ii}$)=N—, —$NR^{ii}$—C(=W)—, —$NR^{ii}$—C(=W)—W—, —$NR^{ii}$—C(=W)—$NR^{ii}$—, —$NR^{ii}$—S(=O)$_2$—$NR^{ii}$— and —$NR^{ii}$—S(=O)$_2$—;

$R^{ii}$ at each occurrence is independently selected from the group consisting of —H, alkyl, alkenyl, alkynyl, heteroalkyl, carbocyclyl, heterocyclyl, aryl and heteroaryl; wherein alkyl, alkenyl, alkynyl or heteroalkyl are optionally independently substituted with one or more —$R^{jj}$, and carbocyclyl, heterocyclyl, aryl or heteroaryl are optionally independently substituted with one or more —$R^{kk}$;

$R^{jj}$ at each occurrence is independently selected from the group consisting of =O, halogen, carbocyclyl, heterocyclyl, aryl, heteroaryl, —R' and -$L_6$-$R^{mm}$, when substituted on an available carbon atom, and carbocyclyl, heterocyclyl, aryl, heteroaryl, —R" and -$L_7$-$R^{mm}$, when substituted on an available nitrogen atom; wherein carbocyclyl, heterocyclyl, aryl and heteroaryl are optionally independently substituted with one or more —$R^{kk}$.

$R^{kk}$ at each occurrence is independently selected from the group consisting of =O, halogen, alkyl, alkenyl, alkynyl, heteroalkyl, carbocyclyl, heterocyclyl, aryl, heteroaryl, —R' and -$L_6$-$R^{mm}$, when substituted on an available carbon atom, and alkyl, alkenyl, alkynyl, heteroalkyl, carbocyclyl, heterocyclyl, aryl, heteroaryl, —R" and -$L_7$-$R^{mm}$, when substituted on an available nitrogen atom;

R" at each occurrence is selected from the group consisting of —OH, —SH, —$NH_2$, —C(=W)—WH, —C(=W)—$NH_2$, —C(=NH)—$NH_2$, and —S(=O)$_2$—$NH_2$;

$L_6$ is selected from the group consisting of —O—, —S—, —S(=O)—, —S(=O)$_2$—, —C(=W)—, —C(=W)—W—, —C(=W)—$NR^{oo}$—, —C(=W)—$NR^{oo}$—W—, —C=N—O—, —C(=$NR^{oo}$)$NR^{oo}$—, —C($NR^{oo}R^{oo}$)=N—, —W—C(=W)—, —W—C(=W)—W—, —W—C(=W)—$NR^{oo}$—, —S(=O)$_2$—$NR^{oo}$—, —S(=O)$_2$—$NR^{oo}$—W—, —$NR^{oo}$—, —N=$CR^{pp}$—, —$NR^{oo}$—W—, —$NR^{oo}$—$NR^{oo}$—, —$NR^{oo}$—C(=$NR^{oo}$)$NR^{oo}$—, —$NR^{oo}$—C($NR^{oo}R^{oo}$)=N—, —$NR^{oo}$—C(=W)—, —$NR^{oo}$—C(=W)—W—, —$NR^{oo}$—C(=W)—$NR^{oo}$—, —$NR^{oo}$—S(=O)$_2$—$NR^{oo}$—, and —$NR^{oo}$—S(=O)$_2$—;

$L_7$ is selected from the group consisting of —O—, —S—, —$NR^{oo}$—, —C(=W)—, —C(=W)—W—, —C(=W)—$NR^{oo}$—, —C(=$NR^{oo}$)$NR^{oo}$—, —C($NR^{oo}R^{oo}$)=N—, —S(=O)$_2$—$NR^{oo}$—, and —S(=O)$_2$—;

each W is independently O or S;

$R^{mm}$ and $R^{nn}$, at each occurrence, are independently selected from the group consisting of alkyl, alkenyl, alkynyl, heteroalkyl, carbocyclyl, heterocyclyl, aryl and heteroaryl; wherein alkyl, alkenyl, alkynyl and heteroalkyl, are optionally independently substituted with one or more —$R^{qq}$; carbocyclyl or heterocyclyl are optionally independently substituted with one or more —$R^{rr}$; and aryl or heteroaryl are optionally independently substituted with one or more —$R^{ss}$;

$R^{oo}$ at each occurrence is independently selected from the group consisting of —H, alkyl, alkenyl, alkynyl, heteroalkyl, carbocyclyl, heterocyclyl, aryl and heteroaryl; wherein alkyl, alkenyl, alkynyl and heteroalkyl, are optionally independently substituted with one or more —$R^{qq}$; carbocyclyl or heterocyclyl are optionally independently substituted with one or more —$R^{rr}$; and aryl or heteroaryl are optionally independently substituted with one or more —$R^{ss}$;

$R^{pp}$ at each occurrence is independently selected from the group consisting of —H, halogen, alkyl, alkenyl, alkynyl, heteroalkyl, carbocyclyl, heterocyclyl, aryl and heteroaryl; wherein alkyl, alkenyl, alkynyl and heteroalkyl, are optionally independently substituted with one or more —$R^{qq}$; carbocyclyl or heterocyclyl are optionally independently substituted with one or more —$R^{rr}$; and aryl or heteroaryl are optionally independently substituted with one or more —$R^{ss}$;

$R^{qq}$ at each occurrence is independently selected from the group consisting of halogen, =O, —OH, —SH, —$NH_2$, —CN, $C_{1-6}$alkoxy, $C_{1-6}$alkylthio, $C_{1-6}$alkylsulfinyl, $C_{1-6}$alkylsulfonyl, $C_{1-6}$alkylamino, $C_{1-6}$ dialkylamino, and N-linked-heterocycloalkyl; wherein $C_{1-6}$alkyl, alone or as part of $C_{1-6}$alkoxy, $C_{1-6}$alkylthio, $C_{1-6}$alkylsulfinyl, $C_{1-6}$alkylsulfonyl, $C_{1-6}$alkylamino, or $C_{1-6}$ dialkylamino, is optionally substituted with one or more substituents independently selected from the group consisting of —OH, —SH, —$NH_2$, halogen, $C_{1-6}$alkoxy, $C_{1-6}$haloalkoxy, $C_{1-6}$alkylthio, $C_{1-6}$haloalkylthio, $C_{1-6}$alkylsulfinyl, $C_{1-6}$haloalkylsulfinyl, $C_{1-6}$alkylsulfonyl, $C_{1-6}$haloalkylsulfonyl, $C_{1-6}$alkylamino, $C_{1-6}$ dialkylamino and N-linked-heterocycloalkyl;

$R^{rr}$ at each occurrence is independently selected from the group consisting of halogen, =O, —OH, —SH, —NH$_2$, —CN, $C_{1-6}$alkyl, $C_{2-6}$alkenyl, $C_{2-6}$alkynyl, $C_{1-6}$alkoxy, $C_{1-6}$alkylthio, $C_{1-6}$alkylsulfinyl, $C_{1-6}$alkylsulfonyl, $C_{1-6}$alkylamino, $C_{1-6}$ dialkylamino and N-linked-heterocycloalkyl; wherein $C_{2-6}$alkenyl, $C_{2-6}$alkynyl, and $C_{1-6}$alkyl, alone or as part of $C_{1-6}$alkoxy, $C_{1-6}$alkylthio, $C_{1-6}$alkylsulfinyl, $C_{1-6}$alkylsulfonyl, $C_{1-6}$alkylamino, or $C_{1-6}$ dialkylamino, is optionally substituted with one or more substituents independently selected from the group consisting of —OH, —SH, —NH$_2$, halogen, $C_{1-6}$alkoxy, $C_{1-6}$haloalkoxy, $C_{1-6}$alkylthio, $C_{1-6}$haloalkylthio, $C_{1-6}$alkylsulfinyl, $C_{1-6}$haloalkylsulfinyl, $C_{1-6}$alkylsulfonyl, $C_{1-6}$haloalkylsulfonyl, $C_{1-6}$alkylamino, $C_{1-6}$ dialkylamino and N-linked-heterocycloalkyl; and $R^{ss}$ at each occurrence is independently selected from the group consisting of halogen, —OH, —SH, —NH$_2$, —CN, —NO$_2$, $C_{1-6}$alkyl, $C_{2-6}$alkenyl, $C_{2-6}$alkynyl, $C_{1-6}$alkoxy, $C_{1-6}$alkylthio, $C_{1-6}$alkylsulfinyl, $C_{1-6}$alkylsulfonyl, $C_{1-6}$alkylamino, $C_{1-6}$ dialkylamino, and N-linked-heterocycloalkyl; wherein $C_{2-6}$alkenyl, $C_{2-6}$alkynyl, and $C_{1-6}$alkyl, alone or as part of $C_{1-6}$alkoxy, $C_{1-6}$alkylthio, $C_{1-6}$alkylsulfinyl, $C_{1-6}$alkylsulfonyl, $C_{1-6}$alkylamino, or $C_{1-6}$ dialkylamino, is optionally substituted with one or more substituents independently selected from the group consisting of —OH, —SH, —NH$_2$, halogen, $C_{1-6}$alkoxy, $C_{1-6}$haloalkoxy, $C_{1-6}$alkylthio, $C_{1-6}$haloalkylthio, $C_{1-6}$alkylsulfinyl, $C_{1-6}$haloalkylsulfinyl, $C_{1-6}$alkylsulfonyl, $C_{1-6}$haloalkylsulfonyl, $C_{1-6}$alkylamino, $C_{1-6}$ dialkylamino and N-linked-heterocycloalkyl;

$Z_{22}$, $Z_{26}$, $Z_{30}$, $Z_{34}$, $Z_{38}$ and $Z_{40}$ are independently

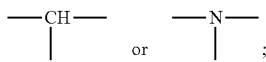

$Z_{29}$, $Z_{32}$, $Z_{33}$, $Z_{37}$ and $Z_{41}$ are independently —CR$^{tt}$R$^{uuu}$—, —O— or —NR$^{vv}$—;

$Z_{23}$, $Z_{24}$, $Z_{25}$, $Z_{27}$, $Z_{28}$, $Z_{31}$, $Z_{35}$, $Z_{36}$ and $Z_{39}$ are independently =CR$^{tt}$— or =N—;

$R^{tt}$ and $R^{uuu}$, at each occurrence, are independently selected from the group consisting of —H, halogen, alkyl, alkenyl, alkynyl, heteroalkyl, carbocyclyl, heterocyclyl, aryl, heteroaryl, —R' and -L$_5$-R$^{ee}$; or R$^{tt}$ and R$^{uuu}$ together are =O, =CR$^{ff}$R$^{ff}$, =N—OR$^{gg}$, =N—R$^{gg}$, or =N—NR$^{gg}$R$^{gg}$; wherein alkyl, alkenyl, alkynyl or heteroalkyl are optionally independently substituted with one or more —R$^{jj}$, and carbocyclyl, heterocyclyl, aryl or heteroaryl are optionally independently substituted with one or more —R$^{kk}$;

each R$^{vv}$ is independently selected from the group consisting of —H, alkyl, alkenyl, alkynyl, heteroalkyl, carbocyclyl, heterocyclyl, aryl, heteroaryl, —R'' and -L$_8$-R$^{ww}$; wherein alkyl, alkenyl, alkynyl or heteroalkyl are optionally independently substituted with one or more —R$^{jj}$, and carbocyclyl, heterocyclyl, aryl or heteroaryl are optionally independently substituted with one or more —R$^{kk}$;

L$_8$ is selected from the group consisting of —O—, —S—, —NR$^{xx}$—, —C(=W)—, —C(=W)—W—, —C(=W)—NR$^{xx}$—, —C(=NR$^{xx}$)NR$^{xx}$—, —C(NR$^{xx}$R$^{xx}$)=N—, —S(=O)$_2$—NR$^{xx}$—, and —S(=O)$_2$—;

R$^{ww}$ at each occurrence is independently selected from the group consisting of alkyl, alkenyl, alkynyl, heteroalkyl, carbocyclyl, heterocyclyl, aryl and heteroaryl; wherein alkyl, alkenyl, alkynyl or heteroalkyl are optionally independently substituted with one or more —R$^{jj}$, and carbocyclyl, heterocyclyl, aryl or heteroaryl are optionally independently substituted with one or more —R$^{kk}$;

R$^{xx}$ at each occurrence is independently selected from the group consisting of —H, alkyl, alkenyl, alkynyl, heteroalkyl, carbocyclyl, heterocyclyl, aryl and heteroaryl; wherein alkyl, alkenyl, alkynyl or heteroalkyl are optionally independently substituted with one or more —R$^{jj}$, and carbocyclyl, heterocyclyl, aryl or heteroaryl are optionally independently substituted with one or more —R$^{kk}$;

R28, R29, R30, R31, R32, R33, R34, R35, R36, R37, R38, R39 and R40 are independently selected from the group consisting of —H, halogen, alkyl, alkenyl, alkynyl, heteroalkyl, carbocyclyl, heterocyclyl, aryl, heteroaryl, —R' and -L$_5$-R$^{ee'}$; wherein alkyl, alkenyl, alkynyl or heteroalkyl are optionally independently substituted with one or more —R$^{jj}$, and carbocyclyl, heterocyclyl, aryl or heteroaryl are optionally independently substituted with one or more —R$^{kk}$, wherein R$^{ee'}$ is R$^{ee}$ or a suitable nitrogen protecting group when L$_5$ is —NH—;

provided that when X$_8$ is —O— bonded to the 2' carbon atom of ring A, R21 is

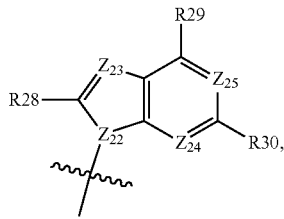

and R22 is

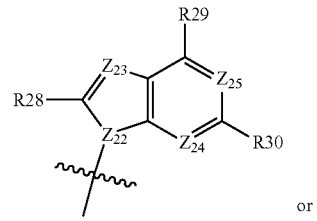

or

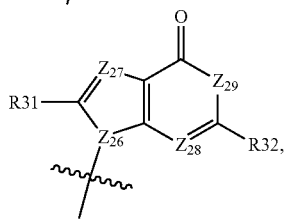

wherein Z$_{22}$ and Z$_{26}$ are

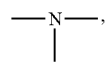

Z$_{23}$, Z$_{24}$, Z$_{25}$, Z$_{27}$ and Z$_{28}$ are =N—, Z$_{29}$ is —NH—, R28, R30 and R31 are —H, and R29 and R32 are independently -L$_5$-R$^{ee'}$, wherein L$_s$ is —NH— and R$^{ee'}$ is R$^{ee}$ or a suitable nitrogen protecting group.

In a first embodiment of the second aspect, the compound of Formula II is a compound selected from the group consisting of a compound of Formula IIa, a compound of Formula IIb, and a compound of Formula IIc:

Formula IIa

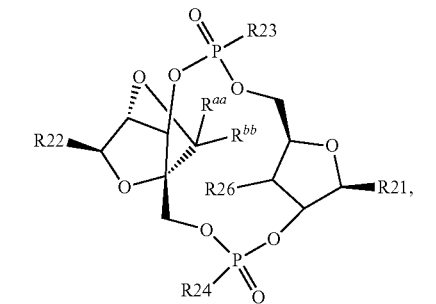

Formula IIb

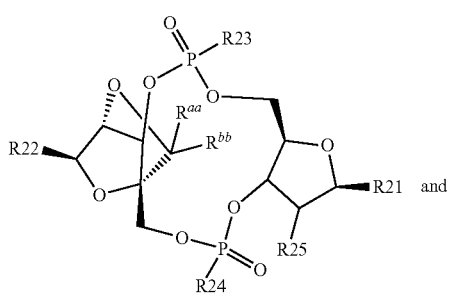
and

Formula IIc

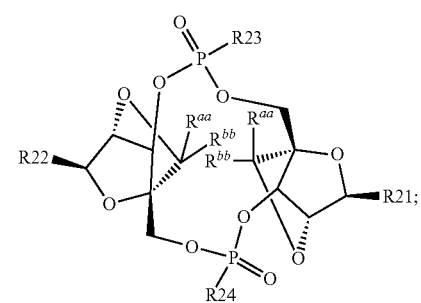

or a prodrug, pharmaceutically acceptable salt, pharmaceutically acceptable solvate or pharmaceutically acceptable hydrate thereof, wherein R21, R22, R23, R24, R25, R26, $R^{aa}$ and $R^{bb}$ are as defined for Formula II.

In a second embodiment of the second aspect, the compound of Formula II is a compound selected from the group consisting of a compound of Formula IIa-1, a compound of Formula IIa-2, a compound of Formula IIa-3, a compound of Formula IIa-4, a compound of Formula IIb-1, a compound of Formula IIb-2, a compound of Formula IIb-3, a compound of Formula IIb-4, a compound of Formula IIc-1, a compound of Formula IIc-2, a compound of Formula IIc-3, and a compound of Formula IIc-4:

Formula IIa-1

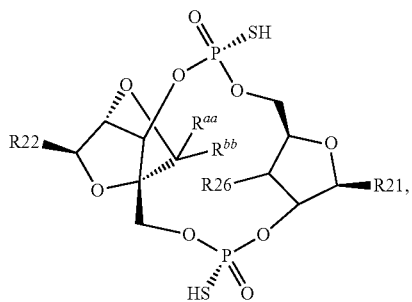

Formula IIa-2

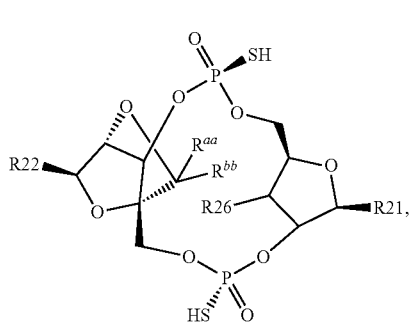

Formula IIa-3

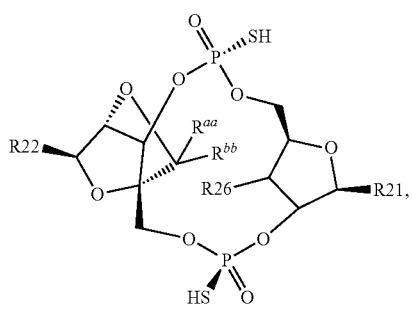

Formula IIa-4

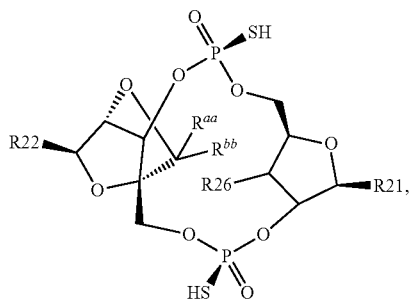

Formula IIb-1

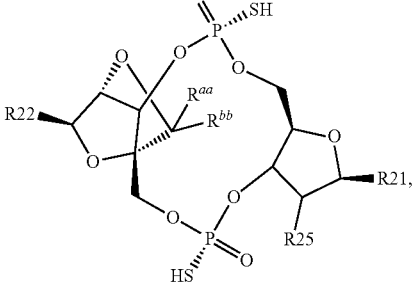

-continued

Formula IIb-2

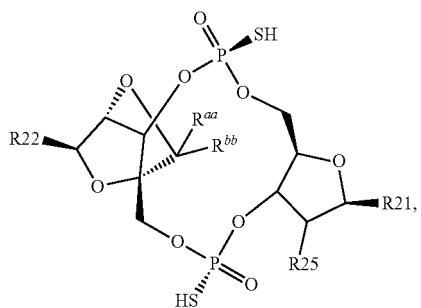

Formula IIb-3

Formula IIb-4

Formula IIc-1

Formula IIc-2

-continued

Formula IIc-3

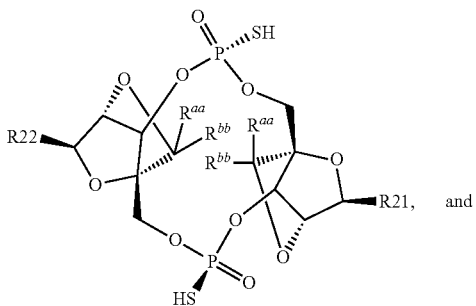

Formula IIc-4 or a prodrug, pharmaceutically acceptable salt, pharmaceutically acceptable solvate or pharmaceutically acceptable hydrate thereof, wherein R21, R22, R25, R26, $R^{aa}$ and $R^{bb}$ are as defined for Formula II.

In a third embodiment of the second aspect, the compound of Formula II is a compound of Formula II':

Formula II'

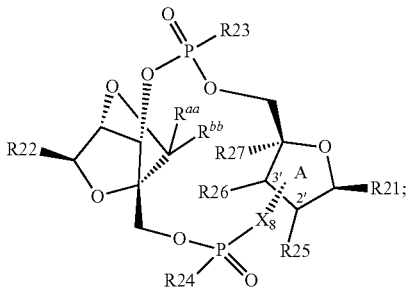

or a prodrug, pharmaceutically acceptable salt, pharmaceutically acceptable solvate or pharmaceutically acceptable hydrate thereof, wherein $X_8$, R21, R22, R23, R24, R25, R26, R27, $R^{aa}$ and $R^{bb}$ are as defined for Formula II.

In a fourth embodiment of the second aspect, the compound of Formula II is a compound selected from the group consisting of a compound of Formula IIa', a compound of Formula IIb', and a compound of Formula IIc':

Formula IIa'

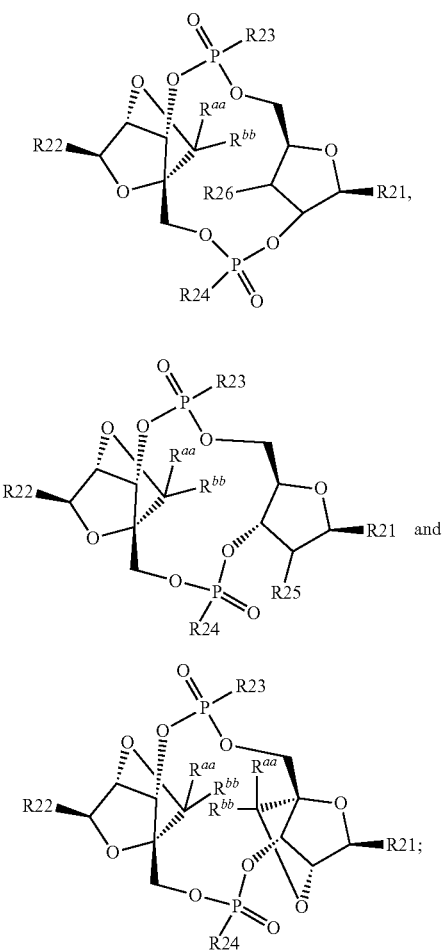

Formula IIb'

Formula IIc' or a prodrug, pharmaceutically acceptable salt, pharmaceutically acceptable solvate or pharmaceutically acceptable hydrate thereof, wherein R21, R22, R23, R24, R25, R26, $R^{aa}$ and $R^{bb}$ are as defined for Formula II.

In a fifth embodiment of the second aspect, the compound of Formula II is a compound selected from the group consisting of a compound of Formula IIa'-1, a compound of Formula IIa'-2, a compound of Formula IIa'-3, a compound of Formula IIa'-4, a compound of Formula IIb'-1, a compound of Formula IIb'-2, a compound of Formula IIb'-3, a compound of Formula IIb'-4, a compound of Formula IIc'-1, a compound of Formula IIc'-2, a compound of Formula IIc'-3, and a compound of Formula IIc'-4:

Formula IIa'-1

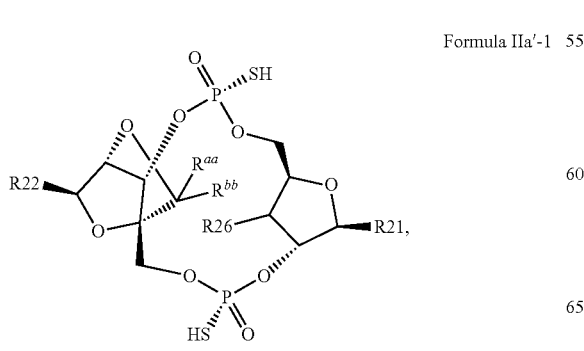

-continued

Formula IIa'-2

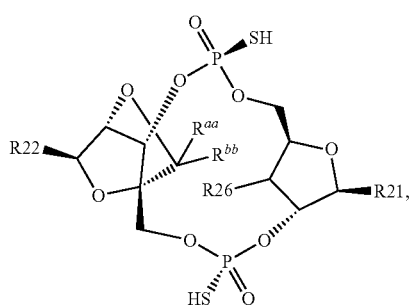

Formula IIa'-3

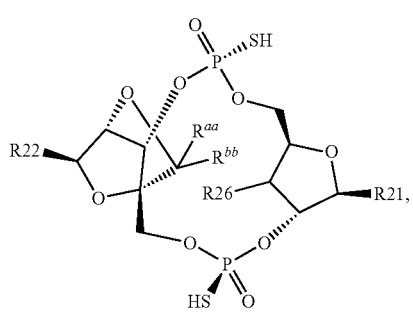

Formula IIa'-4

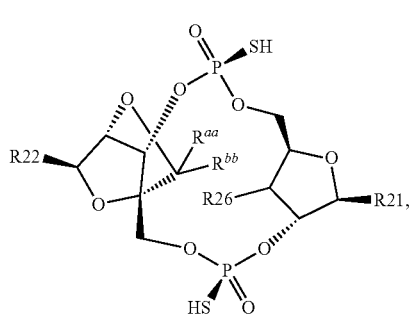

Formula IIb'-1

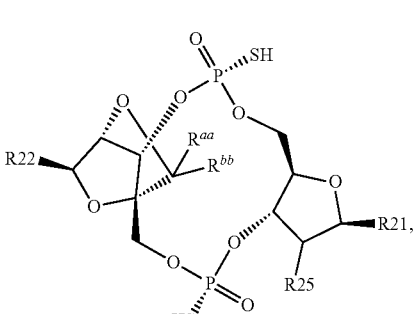

Formula IIb'-2

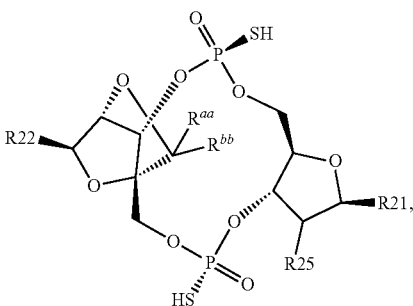

Formula IIb'-3

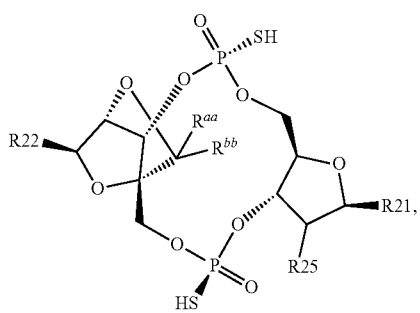

Formula IIb'-4

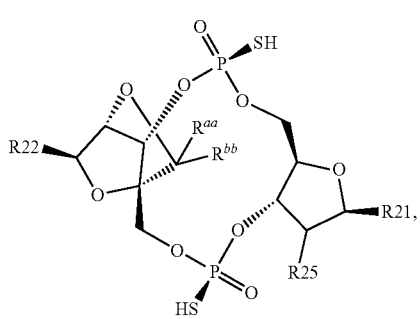

Formula IIc'-1

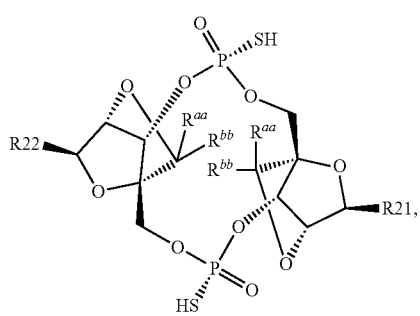

Formula IIc'-2

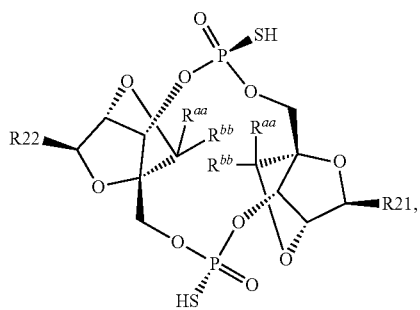

Formula IIc'-3

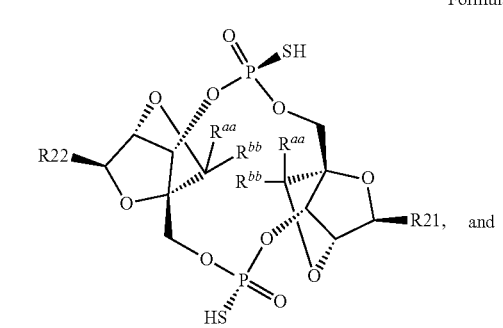 and

Formula IIc'-4

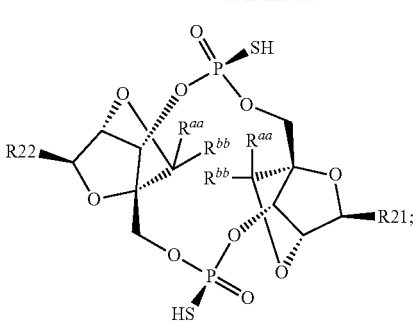

or a prodrug, pharmaceutically acceptable salt, pharmaceutically acceptable solvate or pharmaceutically acceptable hydrate thereof, wherein R21, R22, R25, R26, $R^{aa}$ and $R^{bb}$ are as defined for Formula II. In some embodiment of the compounds of Formula IIa'-1, Formula IIa'-2, Formula IIa'-3, Formula IIa'-4, Formula IIb'-1, Formula IIb'-2, Formula IIb'-3, or Formula IIb'-4, the bond to R25 or R26 is preferably down into the paper, i.e. in the above structures is

represented as e.g. ⳽R5' where the * represents the bond to the core ring.

In a sixth embodiment of the second aspect, and any of the above embodiments thereof, R23 and R24 are independently —OH or —SH. In some embodiments, R23 and R24 are both —OH. In some embodiments, one of R23 and R24 is —OH and the other is —SH. In some embodiments, R23 and R24 are both —SH. In some embodiments, R23 and R24 are both —SH, wherein with reference to the stereochemistry at the phosphorous atoms, the compound is the substantially pure Rp,Rp isomer, the substantially pure Rp,Sp isomer, the substantially pure Sp,Rp isomer, or the substantially pure Sp,Sp isomer.

In a seventh embodiment of the second aspect, and any of the above embodiments thereof, when $X_8$ is —O— bonded to the 3' carbon atom of ring A, R21 and R22 are independently

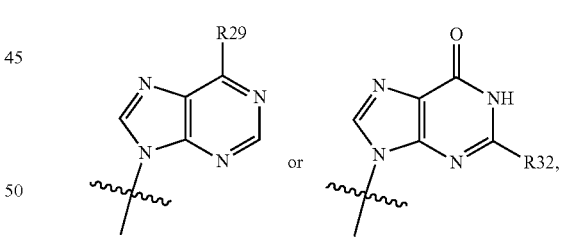

and when $X_8$ is —O— bonded to the 2' carbon atom of ring A, R21 is

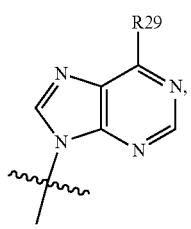

and R22 is

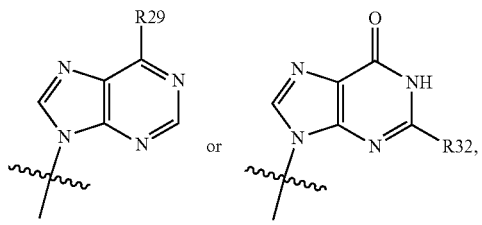

wherein R29 and R32 are independently —NH$_2$ or —NH—C$_{1-6}$alkyl, wherein —NH$_2$ is optionally substituted with a suitable nitrogen protecting group. In some embodiments, R29 and R32 are independently —NH$_2$, —NH—C$_{1-6}$alkyl, —N=CH—N(CH$_3$)$_2$, —NH—C(=O)—C$_{1-6}$-alkyl or —NH—C(=O)-phenyl. In some embodiments, R29 is —NH$_2$ or —NH—C(=O)-phenyl and R32 is —NH$_2$ or —NH—C(=O)-isopropyl. In some embodiments R29 and R32 are both —NH$_2$.

In an eighth embodiment of the second aspect, and any of the above embodiments thereof, when R25 or R26 are selected from the group consisting of —H, —OH, halogen and —OR$^{dd}$, R25 or R26 are selected from the group consisting of —H, —OH optionally substituted with a suitable oxygen protecting group, halogen, —O—C$_{1-14}$alkyl and —O—(C=O)—C$_{1-14}$alkyl. In some embodiments, when R25 or R26 are selected from the group consisting of —H, —OH, halogen and —OR$^{dd}$, R25 and R26 are selected from the group consisting of —H, —OH, —OTBS, —F and —O—(C=O)—C$_{1-14}$alkyl. In some embodiments, when R25 or R26 are selected from the group consisting of —H, —OH, halogen and —OR$^{dd}$, R25 and R26 are —H, —OH, —OTBS or —F, in some embodiments —H, —OH or —F, in some embodiments —OH or —F.

In a ninth embodiment of the second aspect, and any of the above embodiments thereof:
R$^{aa}$ and R$^{bb}$, at each occurrence, are independently selected from the group consisting of —H, —CN, —OH, —NH$_2$, halogen, alkyl, alkenyl, alkynyl, heteroalkyl, —O—R$^{a'}$, —OC(=O)—R$^{a'}$ and —NH—C(=O)—R$^{b'}$, wherein alkyl, alkenyl, alkynyl or heteroalkyl are optionally substituted with 1, 2 or 3 substituents independently selected from the group consisting of —OH, —NH$_2$, —CN, halogen, C$_{1-6}$alkoxy, C$_{1-6}$haloalkoxy, C$_{1-6}$alkylamino, C$_{1-6}$ dialkylamino and N-linked-heterocycloalkyl; or R$^{aa}$ and R$^{bb}$ together are =O, =CH$_2$ or with the carbon to which they are attached form a C$_{3-6}$ cycloalkyl or 3 to 6 membered heterocycloalkyl spirocyclic ring;
R$^{cc}$ at each occurrence is independently selected from the group consisting of alkyl, alkenyl, alkynyl, heteroalkyl, and —C(=O)—R$^{c'}$; wherein alkyl, alkenyl, alkynyl or heteroalkyl are optionally substituted with 1, 2 or 3 substituents independently selected from the group consisting of —OH, —NH$_2$, —CN, halogen, C$_{1-6}$alkoxy, C$_{1-6}$haloalkoxy, C$_{1-6}$alkylamino, C$_{1-6}$ dialkylamino and N-linked-heterocycloalkyl;
R$^{dd}$ is selected from the group consisting of alkyl, alkenyl, alkynyl, heteroalkyl, and —C(=O)—R$^{c'}$; wherein alkyl, alkenyl, alkynyl or heteroalkyl are optionally substituted with 1, 2 or 3 substituents independently selected from the group consisting of —OH, —NH$_2$, —CN, halogen, C$_{1-6}$alkoxy, C$_{1-6}$haloalkoxy, C$_{1-6}$alkylamino, C$_{1-6}$ dialkylamino and N-linked-heterocycloalkyl; or R$^{dd}$ is a suitable oxygen protecting group;

R$^{a'}$ at each occurrence is independently selected from the group consisting of phenyl, toluenyl, alkyl, alkenyl, alkynyl and heteroalkyl, wherein alkyl, alkenyl, alkynyl or heteroalkyl are optionally substituted with 1, 2 or 3 substituents independently selected from the group consisting of —OH, —NH$_2$, —CN, halogen, C$_{1-6}$alkoxy, C$_{1-6}$haloalkoxy, C$_{1-6}$alkylamino, C$_{1-6}$ dialkylamino and N-linked-heterocycloalkyl;
R$^{b'}$ at each occurrence is independently selected from the group consisting of alkyl, alkenyl, alkynyl and heteroalkyl, wherein alkyl, alkenyl, alkynyl or heteroalkyl are optionally substituted with 1, 2 or 3 substituents independently selected from the group consisting of —OH, —NH$_2$, —CN, —O-phenyl, halogen, C$_{1-6}$alkoxy, C$_{1-6}$haloalkoxy, C$_{1-6}$alkylamino, C$_{1-6}$ dialkylamino and N-linked-heterocycloalkyl; and
R$^{c'}$ at each occurrence is independently selected from the group consisting of alkyl, alkenyl, alkynyl and heteroalkyl, wherein alkyl, alkenyl, alkynyl or heteroalkyl are optionally substituted with 1, 2 or 3 substituents independently selected from the group consisting of —OH, —NH$_2$, —CN, halogen, C$_{1-6}$alkoxy, C$_{1-6}$haloalkoxy, C$_{1-6}$alkylamino, C$_{1-6}$ dialkylamino and N-linked-heterocycloalkyl.

In tenth embodiment of the second aspect, and any of of the above embodiments thereof, R$^{aa}$ and R$^{bb}$ at each occurrence are independent —H or —C$_{1-6}$alkyl, wherein alkyl is optionally substituted with 1, 2 or 3 —F or with —C$_{1-6}$alkoxy; or together form =CH$_2$, or together with the carbon to which they are attached form a 3-6 membered heterocycloalkyl or C$_{3-6}$ cycloalkyl spirocyclic ring. In some embodiments R$^{aa}$ and R$^{bb}$ at each occurrence are independently —H, —CH$_3$, —CH$_2$F, —CHF$_2$, —CF$_3$, or —CH$_2$OCH$_3$; or together form =CH$_2$; or together with the carbon to which they are attached form a cyclopropyl spirocyclic ring. In some embodiments, R$^{aa}$ and R$^{bb}$ at each occurrence are independently —H or —C$_{1-6}$alkyl. In some embodiment, R$^{aa}$ and R$^{bb}$ are both —H.

In an eleventh embodiment of the second aspect, and any of the above embodiments thereof:
R23 and R24 are independently selected from the group consisting of —OH, —SH, —O—C$_{1-14}$alkyl, —S—C$_{1-14}$alkyl, —O—(C=O)—C$_{1-14}$alkyl and —S—C(=O)—C$_{1-14}$alkyl;
X$_8$ is —O— bonded to either the 2' or the 3' carbon atom of the indicated ring A;
wherein:
when X$_1$ is —O— bonded to the 2' carbon atom of ring A:
R25 is absent, R26 is selected from the group consisting of —H, —OH, halogen, —O—C$_{1-14}$alkyl and —O—(C=O)—C$_{1-14}$alkyl, and R27 is —H;
when X$_8$ is —O— bonded to the 3' carbon atom of ring A:
R26 is absent, R25 is selected from the group consisting of —H, —OH, halogen, —O—C$_{1-14}$alkyl and —O—(C=O)—C$_{1-14}$alkyl, and R27 is —H; or R26 is absent, and R25 and R27 join to form —O—C(R$^{aa}$R$^{bb}$)—, resulting in a) fused ring system with —O— bonded to the 2' carbon atom of ring A and —C(R$^{aa}$R$^{bb}$)— bonded to the carbon atom of ring A to which R27 is attached;
R$^{aa}$ and R$^{bb}$, at each occurrence, are —H; and
when X$_8$ is —O— bonded to the 3' carbon atom of ring A, R21 and R22 are independently

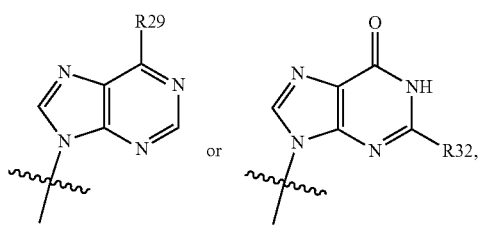

and
when $X_8$ is —O— bonded to the 2' carbon atom of ring A,
R21 is

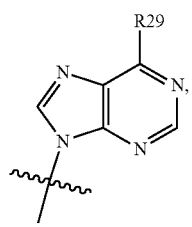

and R22 is

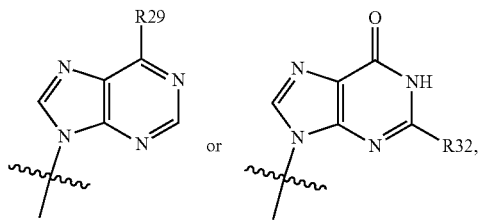

wherein R29 and R32 are independently —NH$_2$, —NH—C$_{1-6}$alkyl, —N=CH—N(CH$_3$)$_2$, —NH—C(=O)—C$_{1-6}$alkyl or —NH—C(=O)-phenyl.

In a third aspect, the present invention provides a locked nucleic acid cyclic dinucleotide ("LNA-CDN") compound of Formula III:

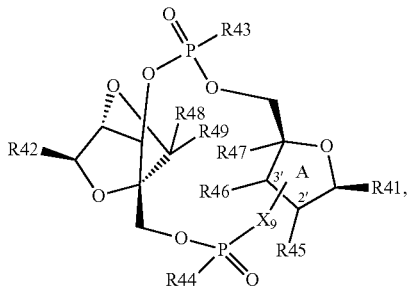

Formula III or a prodrug, pharmaceutically acceptable salt, pharmaceutically acceptable solvate or pharmaceutically acceptable hydrate thereof,
wherein:
R43 and R44 are independently selected from the group consisting of —OH, —SH, —O—C$_{1-14}$alkyl, —S—C$_{1-14}$alkyl, —O—(C=O)—C$_{1-14}$alkyl and —S—C(=O)—C$_{1-14}$alkyl;

$X_9$ is —O— bonded to either the 2' or the 3' carbon atom of the indicated ring A;
wherein:
when $X_9$ is —O— bonded to the 2' carbon atom of ring A:
R45 is absent, R46 is selected from the group consisting of —H, —OH optionally substituted with a suitable oxygen protecting group, halogen, —O—C$_{1-14}$alkyl and —O—(C=O)—C$_{1-14}$alkyl and R47 is —H;
when $X_9$ is —O— bonded to the 3' carbon atom of ring A:
R46 is absent, R45 is selected from the group consisting of —H, —OH optionally substituted with a suitable oxygen protecting group, halogen, —O—C$_{1-14}$alkyl and —O—(C=O)—C$_{1-14}$alkyl, and R47 is —H; or
R46 is absent, and R45 and R47 join to form —O—C(R48R49)-, resulting in a fused ring system with —O— bonded to the 2' carbon atom of ring A and —C(R48R49)- is bonded to the carbon atom of ring A to which R47 is attached;
R48 and R49 at each occurrence are independently —H or —C$_{1-6}$alkyl, wherein alkyl is optionally substituted with 1, 2 or 3 —F or with —C$_{1-6}$alkoxy; or R48 and R49 on the same carbon together form a C$_{3-6}$ cycloalkyl spirocyclic ring;
and
when $X_9$ is —O— bonded to the 3' carbon atom of ring A, R41 and R42 are independently

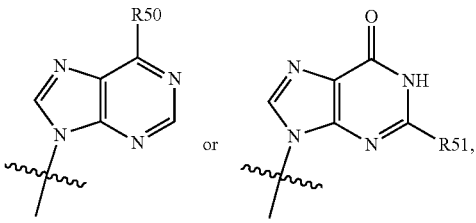

and
when $X_9$ is —O— bonded to the 2' carbon atom of ring A,
R41 is

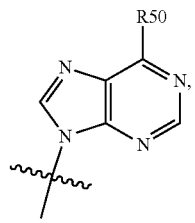

and R42 is

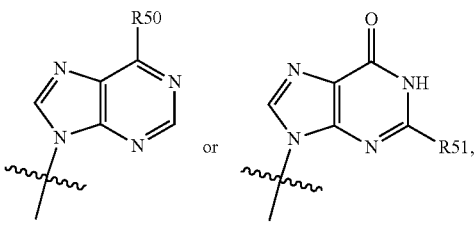

wherein

indicates the bond of R41 or R42 to the ring as shown in Formula III, and wherein R50 and R51 are independently —NH₂ or —NH—C₁₋₆alkyl, wherein —NH₂ is optionally substituted with a suitable nitrogen protecting group.

In a first embodiment of the third aspect, the compound of Formula III is a compound selected from the group consisting of a compound of Formula IIIa, a compound of Formula IIIb, and a compound of Formula IIIc:

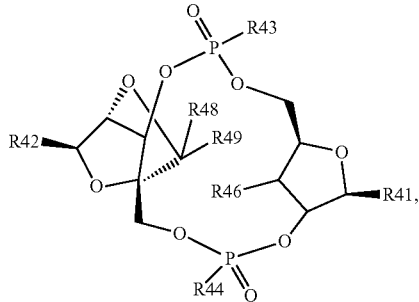

Formula IIIa

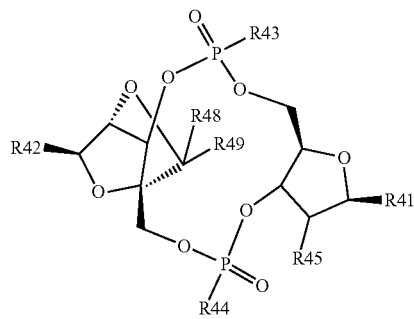

Formula IIIb and

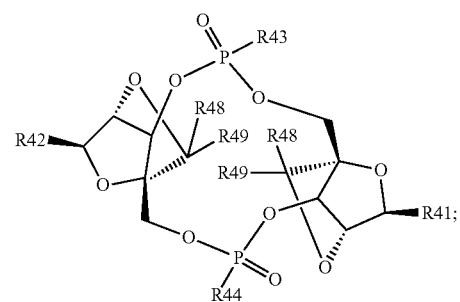

Formula IIIc or a prodrug, pharmaceutically acceptable salt, pharmaceutically acceptable solvate or pharmaceutically acceptable hydrate thereof, wherein R41, R42, R43, R44, R45, R46, R48 and R49 are as defined for Formula III.

In a second embodiment of the third aspect, the compound of Formula III is a compound selected from the group consisting of a compound of Formula IIIa-1, a compound of Formula IIIa-2, a compound of Formula IIIa-3, a compound of Formula IIIa-4, a compound of Formula IIIb-1, a compound of Formula IIIb-2, a compound of Formula IIIb-3, a compound of Formula IIIb-4, a compound of Formula IIIc-1, a compound of Formula IIIc-2, a compound of Formula IIIc-3, and a compound of Formula IIIc-4:

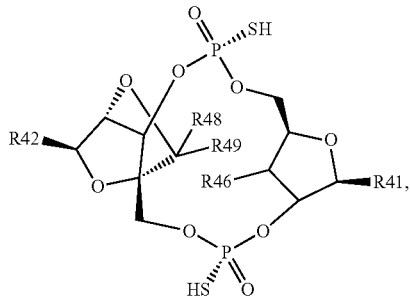

Formula IIIa-1

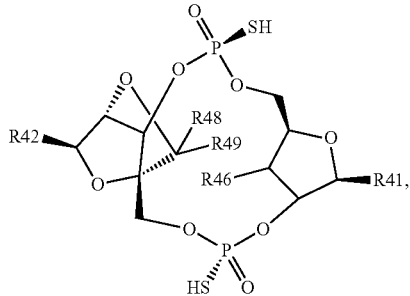

Formula IIIa-2

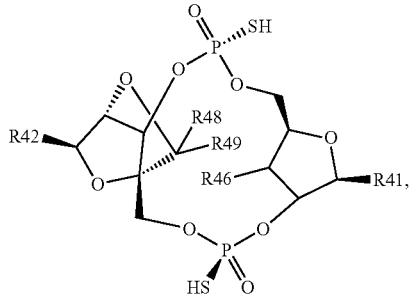

Formula IIIa-3

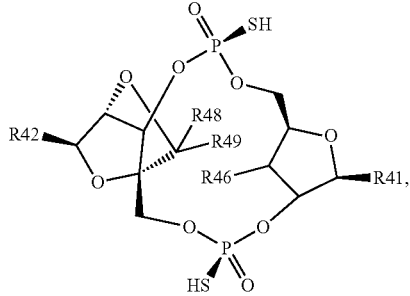

Formula IIIa-4

Formula IIIb-1
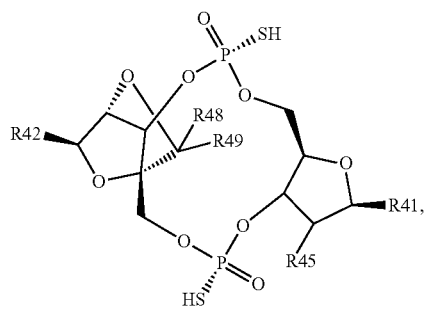

Formula IIIb-2
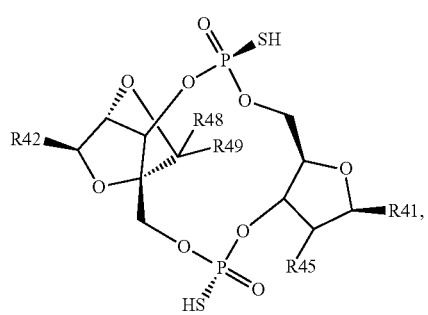

Formula IIIb-3
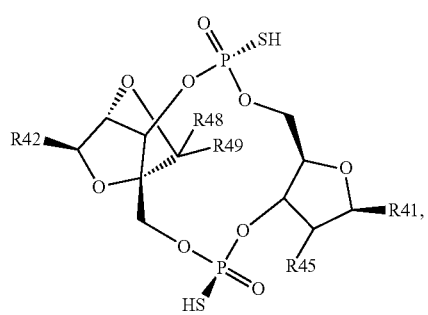

Formula IIIb-4
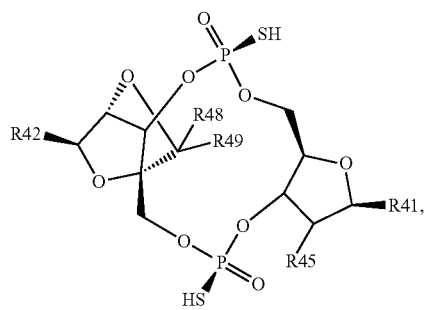

Formula IIIc-1
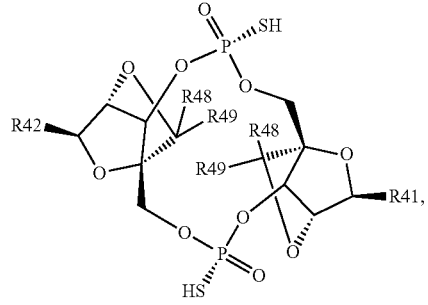

Formula IIIc-2
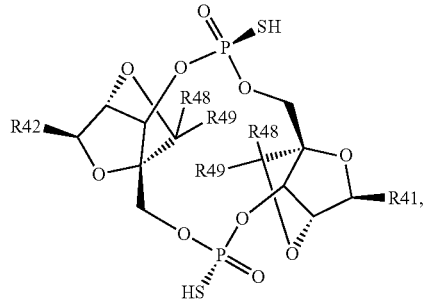

Formula IIIc-3
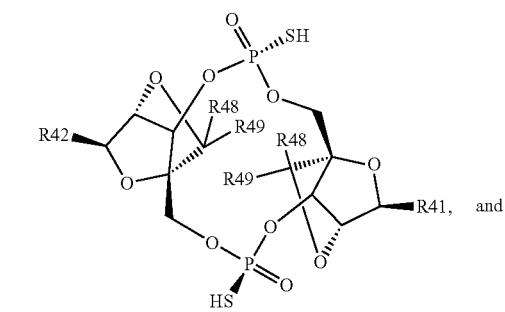

Formula IIIc-4
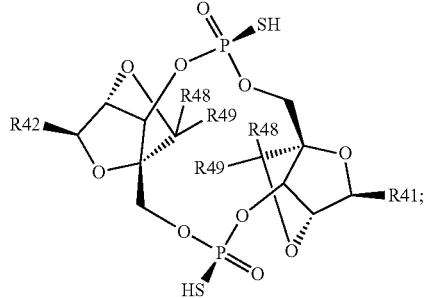

or a prodrug, pharmaceutically acceptable salt, pharmaceutically acceptable solvate or pharmaceutically acceptable hydrate thereof, wherein R41, R42, R45, R46, R48 and R49 are as defined for Formula III.

In a third embodiment of the third aspect, the compound of Formula III is a compound of Formula III':

Formula III'
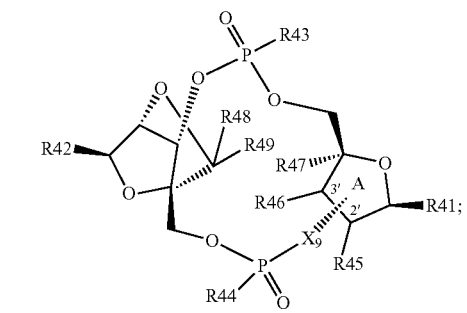

or a prodrug, pharmaceutically acceptable salt, pharmaceutically acceptable solvate or pharmaceutically acceptable hydrate thereof, wherein $X_9$, R41, R42, R43, R44, R45, R46, R47, R48 and R49 are as defined for Formula III.

In a fourth embodiment of the third aspect, the compound of Formula III is a compound selected from the group consisting of a compound of Formula IIIa', a compound of Formula IIIb' and a compound of Formula IIIc':

Formula IIIa'

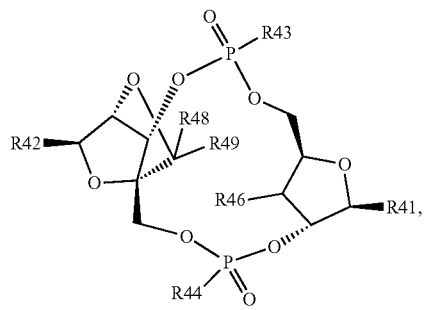

Formula IIIb'

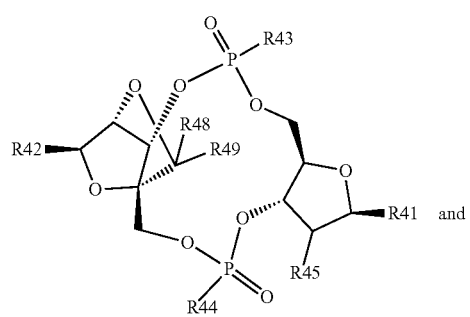

and

Formula IIIc'

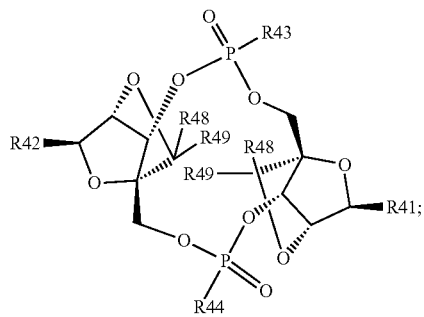

or a prodrug, pharmaceutically acceptable salt, pharmaceutically acceptable solvate or pharmaceutically acceptable hydrate thereof, wherein R41, R42, R43, R44, R45, R46, R48 and R49 are as defined for Formula III.

In a fifth embodiment of the third aspect, the compound of Formula III' is a compound selected from the group consisting of a compound of Formula IIIa'-1, a compound of Formula IIIa'-2, a compound of Formula IIIa'-3, a compound of Formula IIIa'-4, a compound of Formula IIIb'-1, a compound of Formula IIIb'-2, a compound of Formula IIIb'-3, a compound of Formula IIIb'-4, a compound of Formula IIIc'-1, a compound of Formula IIIc'-2, a compound of Formula IIIc'-3, and a compound of Formula IIIc'-4:

Formula IIIa'-1

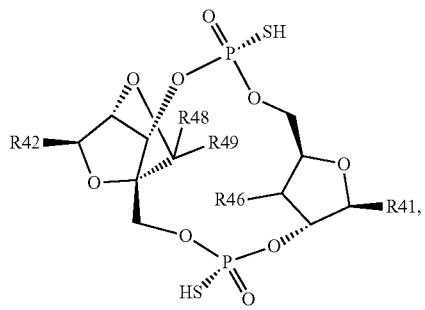

Formula IIIa'-2

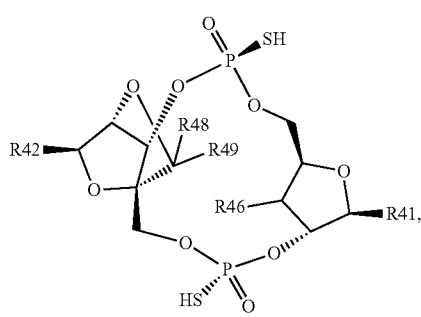

Formula IIIa'-3

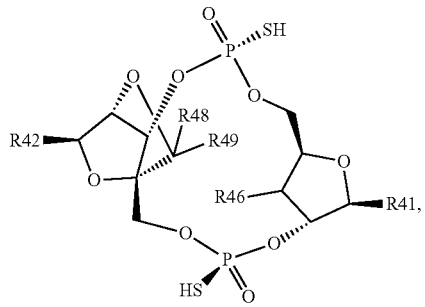

Formula IIIa'-4

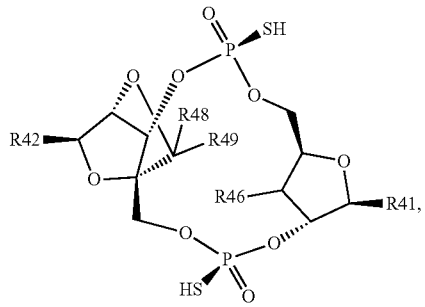

Formula IIIb'-1

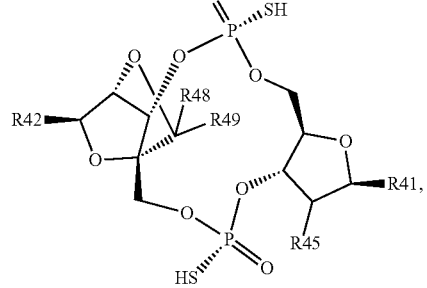

Formula IIIb'-2

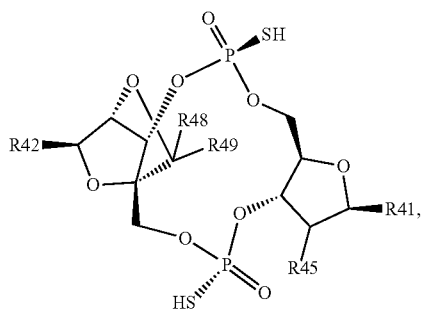

Formula IIIb'-3

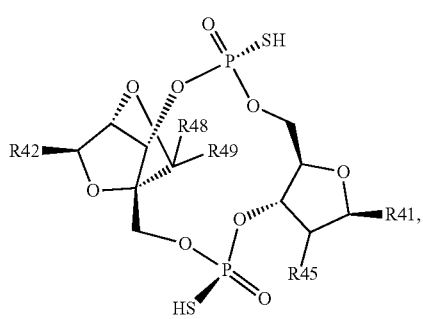

Formula IIIb'-4

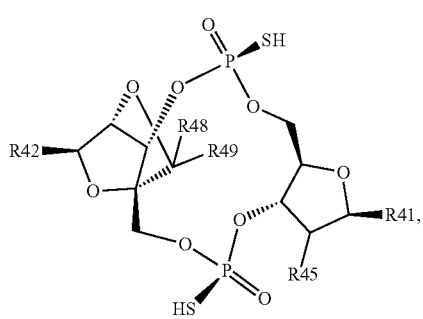

Formula IIIc'-1

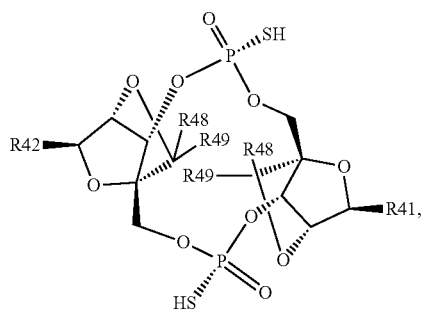

Formula IIIc'-2

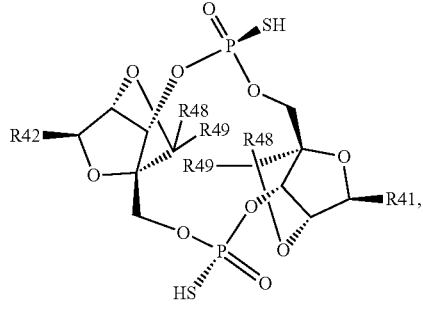

Formula IIIc'-3

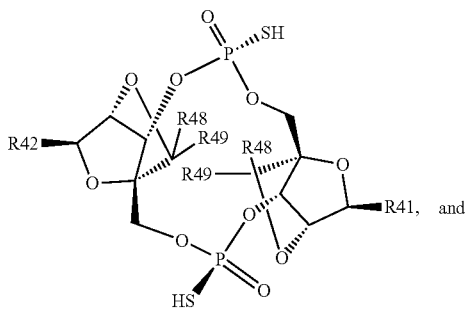

and

Formula IIIc'-4

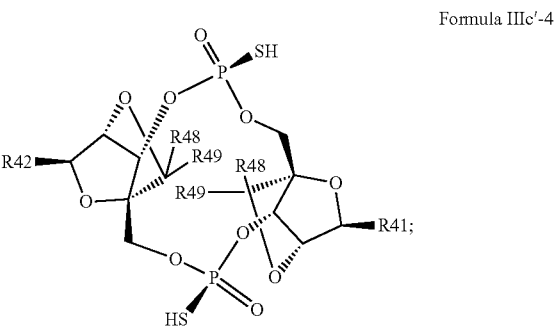

or a prodrug, pharmaceutically acceptable salt, pharmaceutically acceptable solvate or pharmaceutically acceptable hydrate thereof, wherein R41, R42, R45, R46, R48 and R49 are as defined for Formula III. In some embodiment of the compounds of Formula IIIa'-1, Formula IIIa'-2, Formula IIIa'-3, Formula IIIa'-4, Formula IIIb'-1, Formula IIIb'-2, Formula IIIb'-3, or Formula IIIb'-4, the bond to R45 or R46 is preferably down into the paper, i.e. in the above structures is represented as e.g.

*
⋮
R5' where the * represents the bond to the core ring.

In a sixth embodiment of the third aspect, and any of the above embodiments thereof, R43 and R44 are independently —OH or —SH. In some embodiments, R43 and R44 are both —OH. In some embodiments, R43 and R44 are both —SH. In some embodiments, one of R43 and R44 is —OH and the other is —SH. In some embodiments, R43 and R44 are both —SH. In some embodiments, R43 and R44 are both —SH, and the compound is substantially pure with respect to the Rp,Rp isomer, the Rp,Sp isomer, the Sp,Rp isomer, or the Sp,Sp isomer.

In a seventh embodiment of the third aspect, and any of the above embodiments thereof, when $X_9$ is —O— bonded to the 3' carbon atom of ring A, R41 and R42 are independently

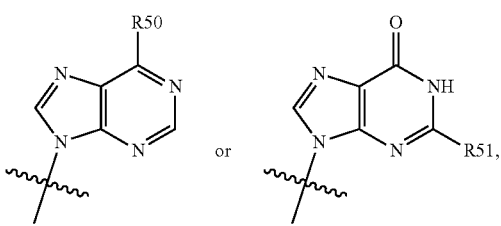

and
when $X_9$ is —O— bonded to the 2' carbon atom of ring A, R41 is

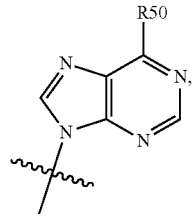

and R42 is

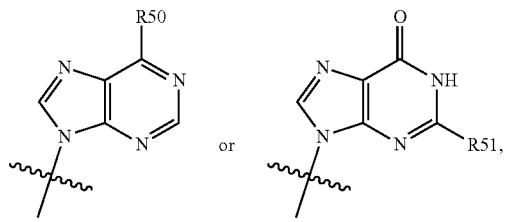

wherein R50 and R51 are independently —NH$_2$, —NH—C$_{1-6}$alkyl, —N=CH—N(CH$_3$)$_2$, —NH—C(=O)—C$_{1-6}$alkyl or —NH—C(=O)-phenyl. In some embodiments, R50 is —NH$_2$ or —NH—C(=O)-phenyl and R51 is —NH$_2$ or —NH—C(=O)-isopropyl. In some embodiments R50 and R51 are both —NH$_2$.

In an eighth embodiment of the third aspect, and any of the above embodiments thereof, when R45 or R46 are selected from the group consisting of —H, —OH optionally substituted with a suitable oxygen protecting group, halogen, —O—C$_{1-14}$alkyl and —O—(C=O)—C$_{1-14}$alkyl, R45 or R46 are selected from the group consisting of —H, —OH, —OTBS, —F and —O—(C=O)—C$_{1-14}$alkyl, or R45 and R46 are —H, —OH, —OTBS or —F, or R45 and R46 are —H, —OH or —F or R45 and R46 are —OH or —F.

In a ninth embodiment of the third aspect, and any of the above embodiments thereof, R48 and R49 at each occurrence are independently —H or —C$_{1-6}$alkyl. In some embodiments, R48 and R49 at each occurrence are —H.

In a tenth embodiment of the third aspect, R43 and R44 are both —SH; when $X_9$ is —O— bonded to the 3' carbon atom of ring A, R41 and R42 are independently

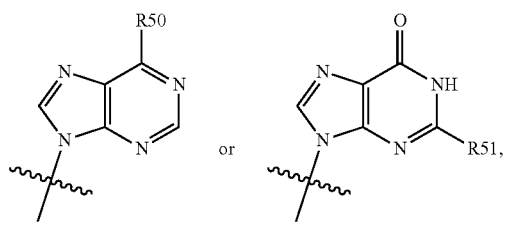

and
when $X_9$ is —O— bonded to the 2' carbon atom of ring A, R41 is

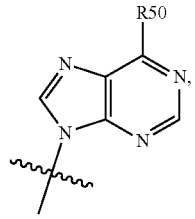

and R42 is

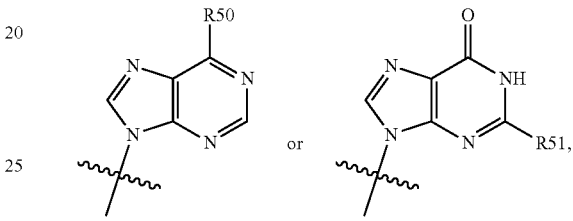

wherein each R50 is independently —NH$_2$ or —NH—C(=O)-phenyl and each R51 is independently —NH$_2$ or —NH—C(=O)-isopropyl, preferably where R50 and R52 are both —NH$_2$; when R45 or R46 are selected from the group consisting of —H, —OH optionally substituted with a suitable oxygen protecting group, halogen, —O—C$_{1-14}$alkyl and —O—(C=O)—C$_{1-14}$alkyl, R45 or R46 are selected from the group consisting of —H, —OH, —OTBS, —F and —O—(C=O)—C$_{1-14}$alkyl, or R45 and R46 are —H, —OH or —F, preferably where R45 or R46 are —OH or —F; and R48 and R49 at each occurrence are independently —H or —C$_{1-6}$alkyl, preferably where R48 and R49 are both —H.

In a fourth aspect, the present invention provides a locked nucleic acid cyclic dinucleotide ("LNA-CDN") compound of Formula IV:

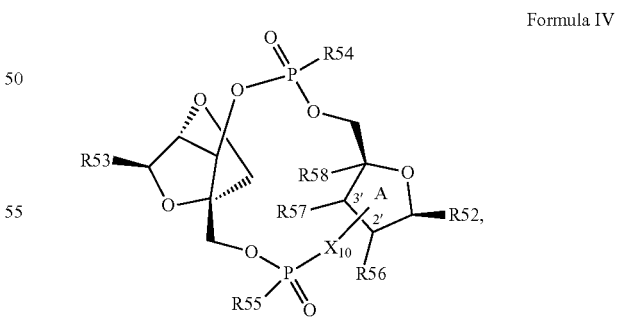

Formula IV or a prodrug, pharmaceutically acceptable salt, pharmaceutically acceptable solvate or pharmaceutically acceptable hydrate thereof, wherein:

R54 and R55 are independently —OH or —SH;

$X_{10}$ is —O— bonded to either the 2' or the 3' carbon atom of the indicated ring A;

wherein:
when $X_{10}$ is —O— bonded to the 2' carbon atom of ring A:
  R56 is absent, R57 is selected from the group consisting of —H, —OH optionally substituted with a suitable oxygen protecting group, and halogen, and R58 is —H;
when $X_{10}$ is —O— bonded to the 3' carbon atom of ring A:
  R57 is absent, R56 is selected from the group consisting of —H, —OH optionally substituted with a suitable oxygen protecting group, and halogen, and R58 is —H; or
  R57 is absent, and R56 and R58 join to form —O—CH$_2$—, resulting in a fused ring system with —O— bonded to the 2' carbon atom of ring A and —CH$_2$— bonded to the carbon atom of ring A to which R58 is attached; and
when $X_{10}$ is —O— bonded to the 3' carbon atom of ring A, R52 and R53 are independently

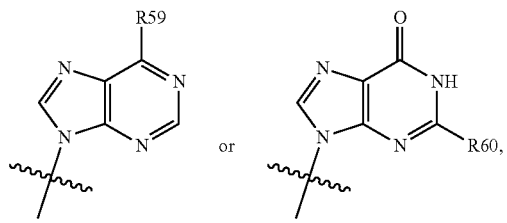

and
when $X_{10}$ is —O— bonded to the 2' carbon atom of ring A,
  R52 is

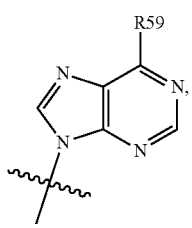

and R53 is

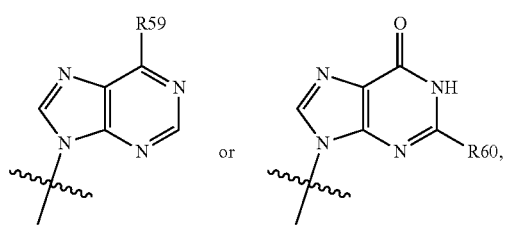

wherein

indicates the bond of R52 or R53 to the ring as shown in Formula IV, and wherein R59 and R60 are independently —NH$_2$ optionally substituted with a suitable nitrogen protecting group.

In a first embodiment of the fourth aspect, the compound of Formula IV is a compound selected from the group consisting of a compound of Formula IVa, a compound of Formula IVb and a compound of Formula IVc:

Formula IVa

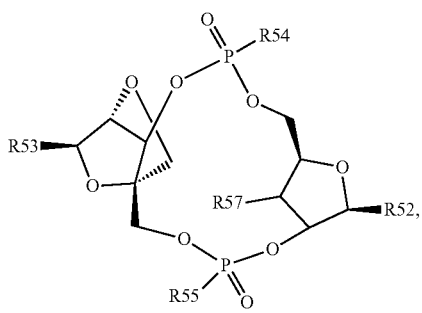

Formula IVb

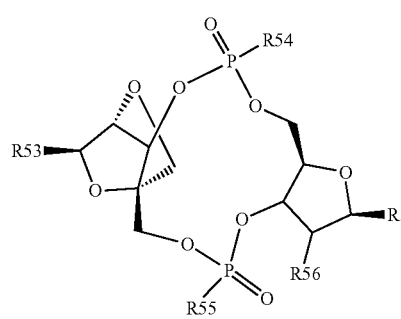

Formula IVc

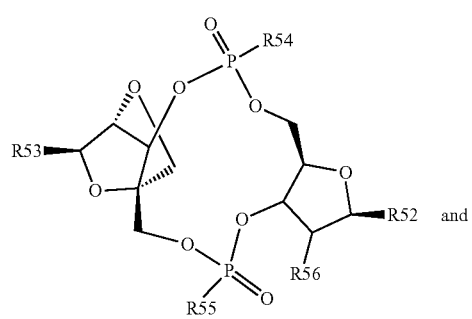

or a prodrug, pharmaceutically acceptable salt, pharmaceutically acceptable solvate or pharmaceutically acceptable hydrate thereof, wherein R52, R53, R54, R55, R56 and R57 are as defined for Formula IV.

In a second embodiment of the fourth aspect, the compound of Formula IV is a compound selected from the group consisting of a compound of Formula IVa-1, a compound of Formula IVa-2, a compound of Formula IVa-3, a compound of Formula IVa-4, a compound of Formula IVb-1, a compound of Formula IVb-2, a compound of Formula IVb-3, a compound of Formula IVb-4, a compound of Formula IVc-1, a compound of Formula IVc-2, a compound of Formula IVc-3, and a compound of Formula IVc-4:

Formula IVa-1
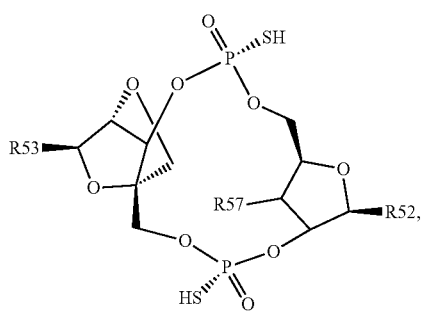
Formula IVa-2
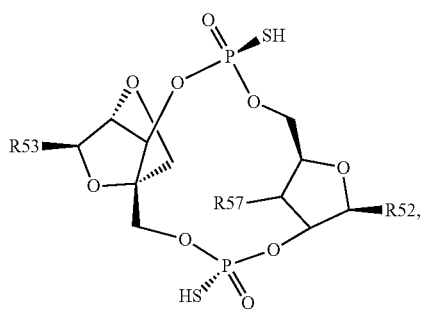
Formula IVa-3
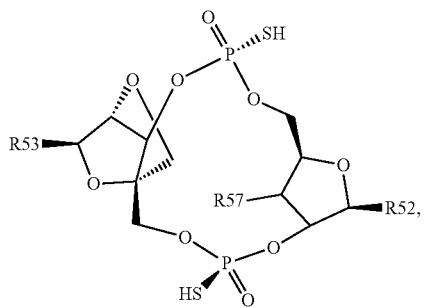
Formula IVa-4
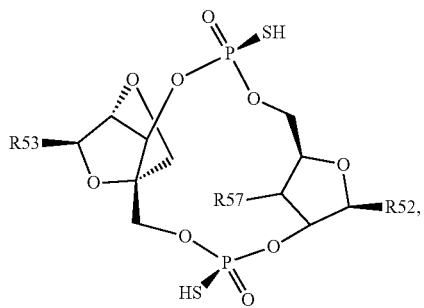
Formula IVb-1
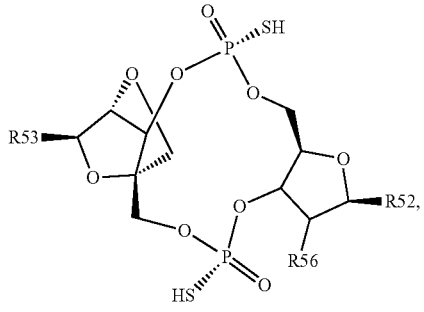
-continued
Formula IVb-2
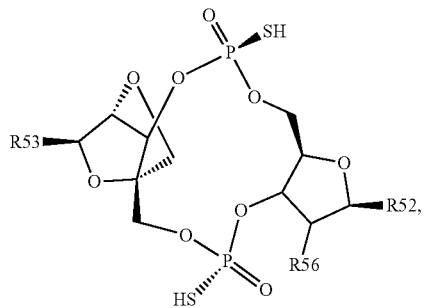
Formula IVb-3
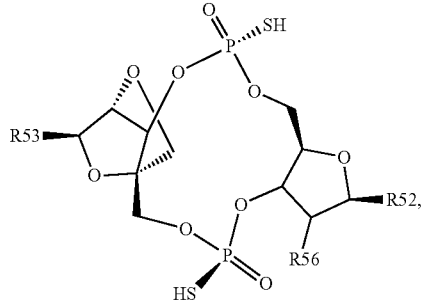
Formula IVb-4
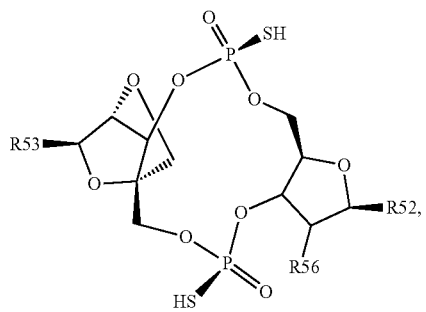
Formula IVc-1
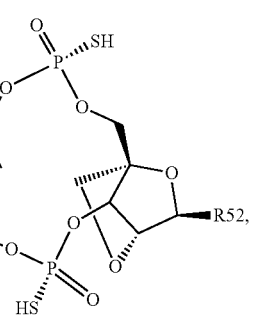

Formula IVc-2

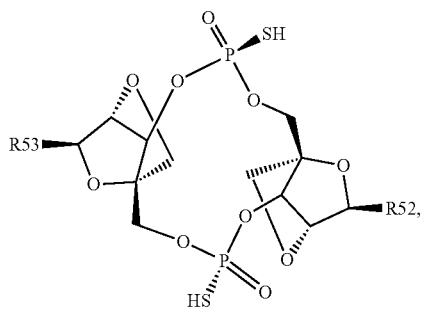

Formula IVc-3

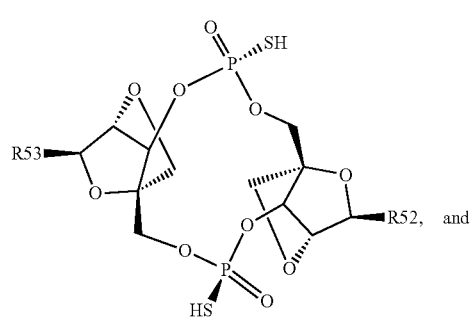

Formula IVc-4

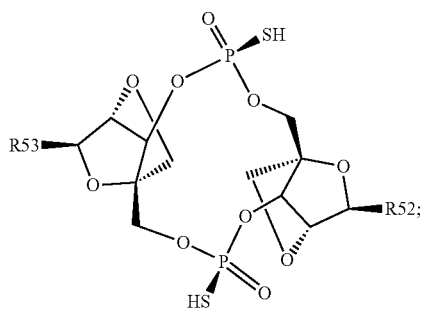

or a prodrug, pharmaceutically acceptable salt, pharmaceutically acceptable solvate or pharmaceutically acceptable hydrate thereof, wherein R52, R53, R56 and R57 are as defined for Formula IV.

In a third embodiment of the fourth aspect, the compound of Formula IV is a compound of formula IV':

Formula IV'

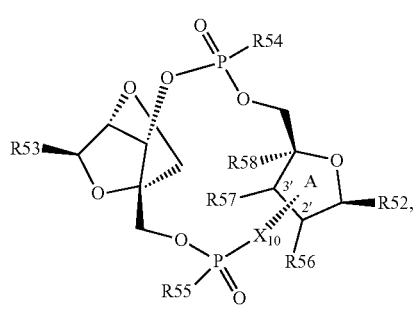

or a prodrug, pharmaceutically acceptable salt, pharmaceutically acceptable solvate or pharmaceutically acceptable hydrate thereof, wherein $X_{10}$, R52, R53, R54, R55, R56, R57 and R58 are as defined for Formula IV.

In a fourth embodiment of the fourth aspect, the compound of Formula IV is a compound selected from the group consisting of a compound of Formula IVa', a compound of Formula IVb' and a compound of Formula IVc':

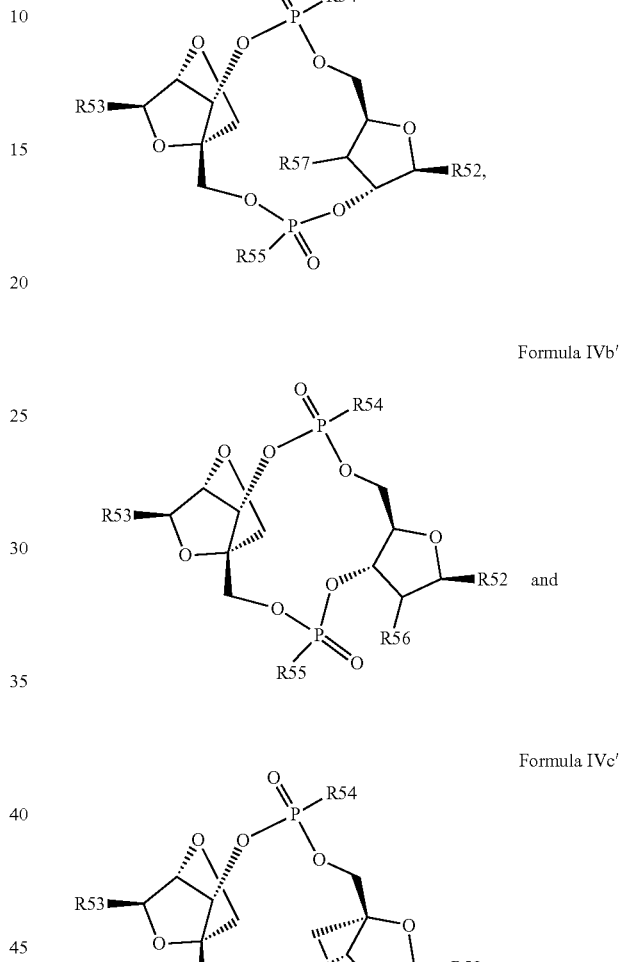

or a prodrug, pharmaceutically acceptable salt, pharmaceutically acceptable solvate or pharmaceutically acceptable hydrate thereof, wherein R52, R53, R54, R55, R56 and R57 are as defined for Formula IV.

In a fifth embodiment of the fourth aspect, the compound of Formula IV is a compound selected from the group consisting of a compound of Formula IVa'-1, a compound of Formula IVa'-2, a compound of Formula IVa'-3, a compound of Formula IVa'-4, a compound of Formula IVb'-1, a compound of Formula IVb'-2, a compound of Formula IVb'-3, a compound of Formula IVb'-4, a compound of Formula IVc'-1, a compound of Formula IVc'-2, a compound of Formula IVc'-3, and a compound of Formula IVc'-4:

Formula IVa′-1
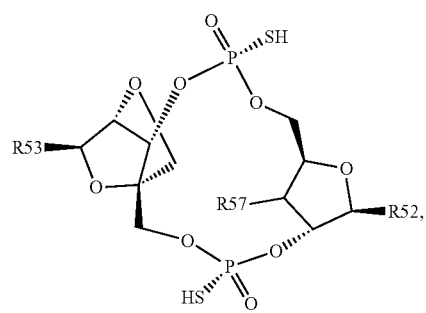
Formula IVa′-2
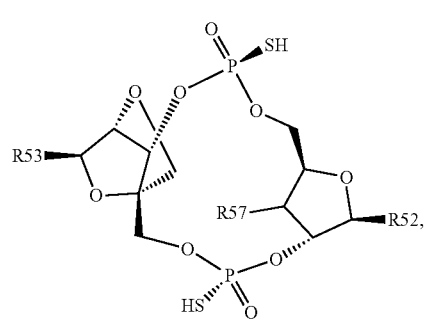
Formula IVa′-3
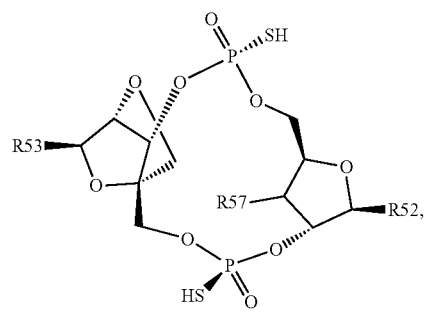
Formula IVa′-4
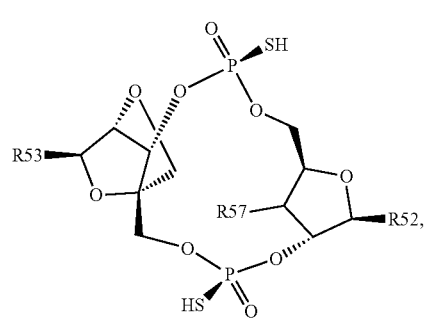
Formula IVb′-1
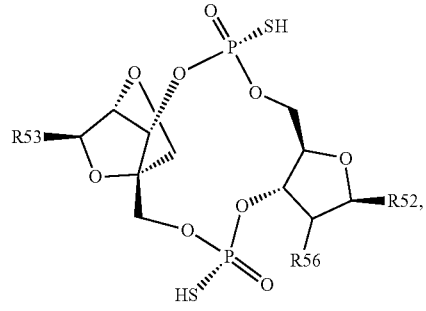
Formula IVb′-2
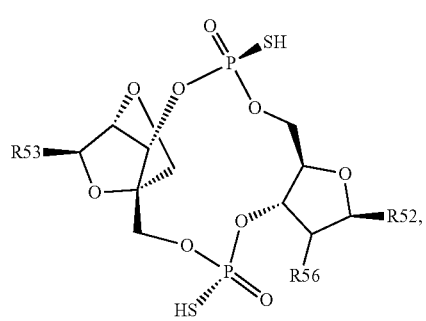
Formula IVb′-3
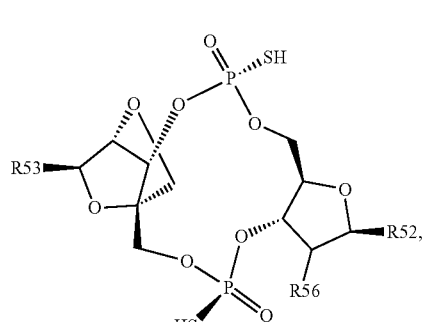
Formula IVb′-4
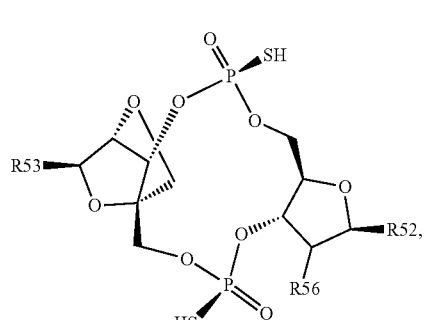
Formula IVc′-1
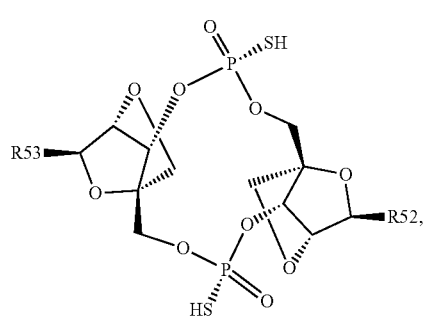
Formula IVc′-2
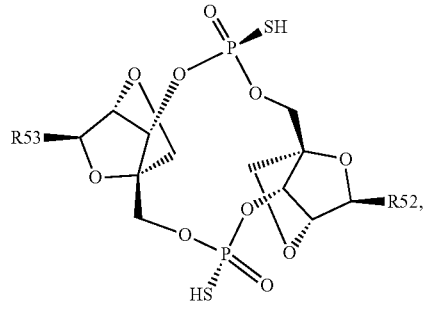

-continued

Formula IVc'-3

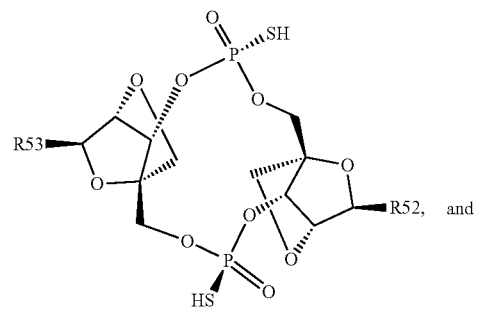

Formula IVc'-4

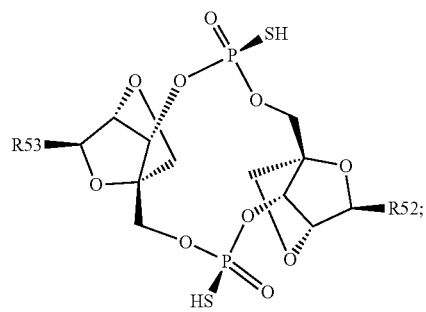

or a prodrug, pharmaceutically acceptable salt, pharmaceutically acceptable solvate or pharmaceutically acceptable hydrate thereof, wherein R52, R53, R56 and R57 are as defined for Formula IV. In some embodiment of the compounds of Formula IVa'-1, Formula IVa'-2, Formula IVa'-3, Formula IVa'-4, Formula IVb'-1, Formula IVb'-2, Formula IVb'-3, or Formula IVb'-4, the bond to R56 or R57 is preferably down into the paper, i.e. in the above structures is represented as e.g.  R5' where the * represents the bond to the core ring.

In a sixth embodiment of the fourth aspect, and any of the above embodiments thereof, R56 or R57 are —H, —OH, —OTBS or —F. In some embodiments R56 or R57 are —H, —OH or —F. In some embodiments R56 or R57 are —OH or —F.

In a seventh embodiment of the fourth aspect, and any of the above embodiments thereof, R54 and R55 are —SH, preferably wherein relative to the stereochemistry at each phosphorous atom the compound is the substantially pure Rp,Rp isomer, the substantially pure Rp,Sp isomer, the substantially pure Sp,Rp isomer, or the substantially pure Sp,Sp isomer.

In an eighth embodiment of the fourth aspect, and any of the above embodiments thereof, each R59 is independently —NH$_2$ or —NH—C(=O)-phenyl and each R60 is independently —NH$_2$ or —NH—C(=O)-isopropyl. In some embodiments, R59 and R60 are —NH$_2$.

In a sixth embodiment of the fourth aspect, and any of the above embodiments thereof, R56 or R57 are —H, —OH or —F. In some embodiments, R54 and R55 are —SH and R56 or R57 are —H, —OH or —F. In some embodiments, R54 and R55 are —SH, R56 or R57 are —H, —OH or —F, and each occurrence of R59 and R60 is —NH$_2$.

In a seventh embodiment of the fourth aspect, and any of the above embodiments thereof, when X$_{10}$ is —O— bonded to the 3' carbon atom of ring A, R52 and R53 are independently

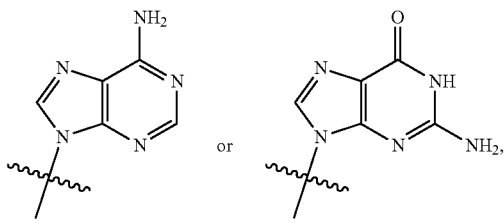 [SMILES: *n1cnc2c(N)ncnc21 ; *n1cnc2c(=O)[nH]c(N)nc21]

and when X$_{10}$ is —O— bonded to the 2' carbon atom of ring A, R52 is

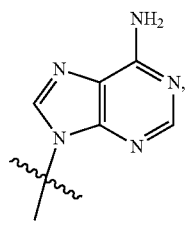 [SMILES: *n1cnc2c(N)ncnc21]

and R53 is

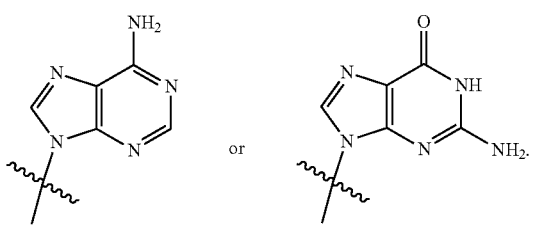 [SMILES: *n1cnc2c(N)ncnc21 ; "or" ; *n1cnc2c(=O)[nH]c(N)nc21]

In any of the above aspects and embodiments, an oxygen protecting group is selected from the group consisting of a silyl protecting group, an ester forming protecting group and an ether forming protecting group. In a preferred embodiment, the oxygen protecting group is selected from the group consisting of TBS (—Si(CH$_3$)$_2$C(CH$_3$)$_3$), TMS (—Si(CH$_3$)$_3$), TES (—Si(CH$_2$CH$_3$)$_3$), TIPS (—Si(CH(CH$_3$)$_2$)$_3$), TBDPS (—Si(C(CH$_3$)$_3$)(phenyl)$_2$), pivalyl (—C(=O)C(CH$_3$)$_3$), acetyl (—C(=O)CH$_3$), methyl (—CH$_3$), methoxymethyl (—CH$_2$—O—CH$_3$), t-butyl (—C(CH$_3$)$_3$), allyl (—CH$_2$—CH=CH$_2$), benzyl (—CH$_2$-phenyl) and p-methoxybenzyl (—CH$_2$-(4-methoxy-phenyl)). In some embodiments, the oxygen protecting group is TBS.

In any of the above aspects and embodiments, a nitrogen protecting group is selected from the group consisting of benzyl (—CH$_2$-phenyl), benzoyl (—C(=O)-phenyl), isobutyryl (—C(=O)—CH(CH$_3$)$_2$), acetyl (—C(=O)—CH$_3$), t-butyl formate (—C(=O)OC(CH$_3$)$_2$), and N'N'-dimethylformamidine (=CH—N(CH$_3$)$_2$, i.e. the protected nitrogen is —N=CH—N(CH$_3$)$_2$). In some embodiments the nitrogen protecting group is benzoyl or isobutyryl.

In some embodiments of any of the above aspects and embodiments, the LNA-CDN compound is selected from the group consisting of:

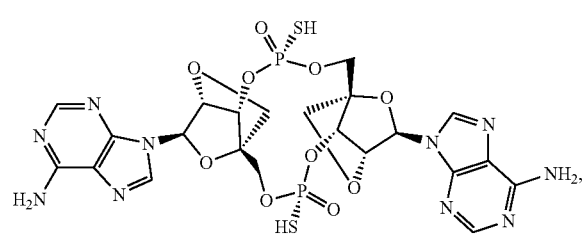
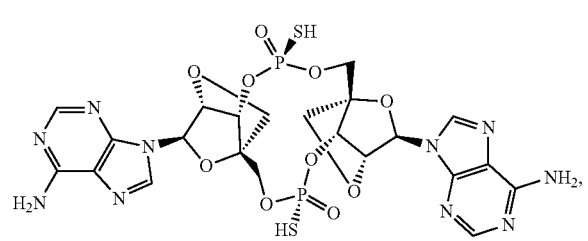
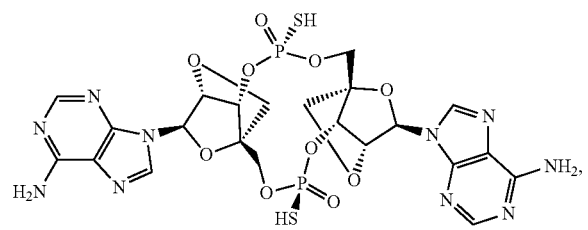
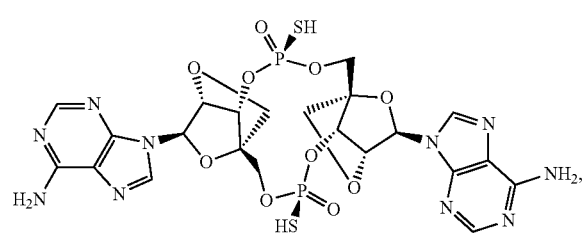
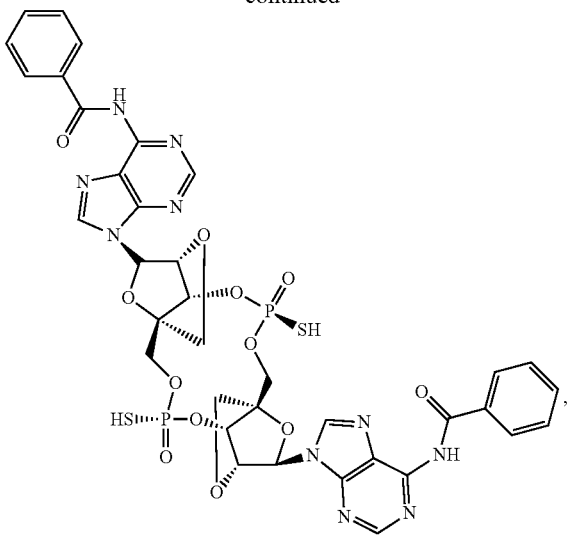
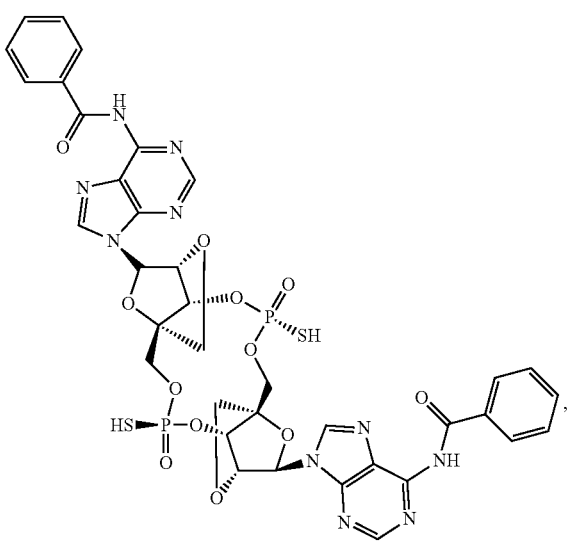
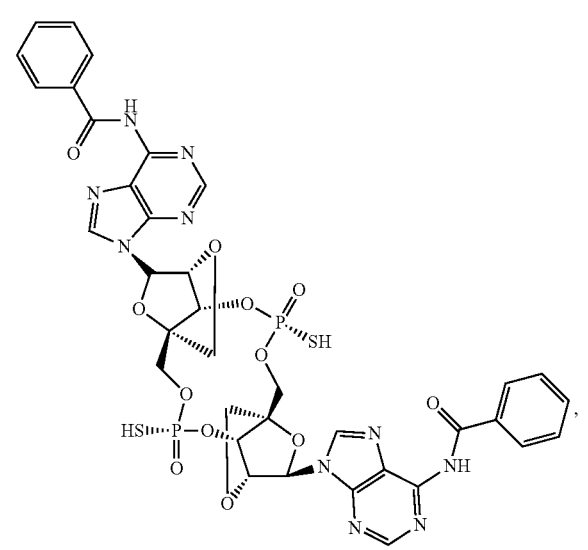
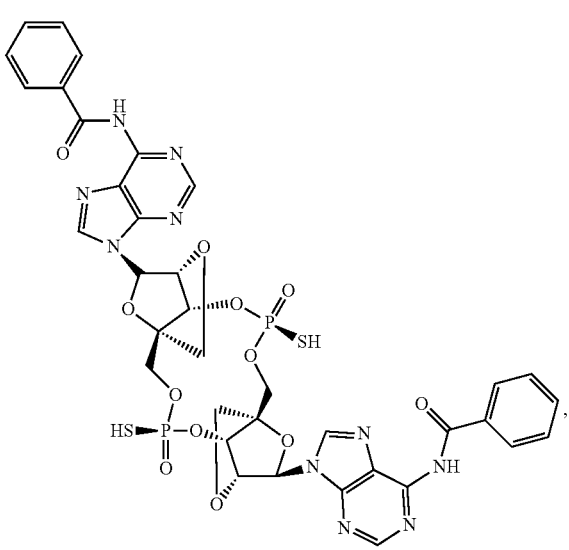

-continued
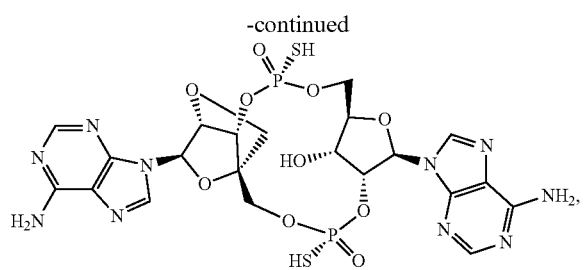
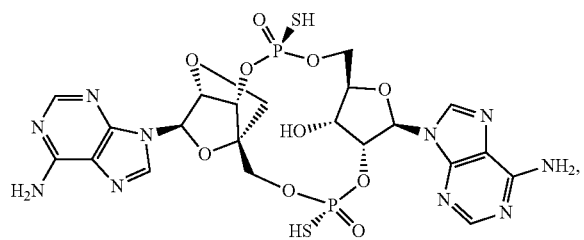
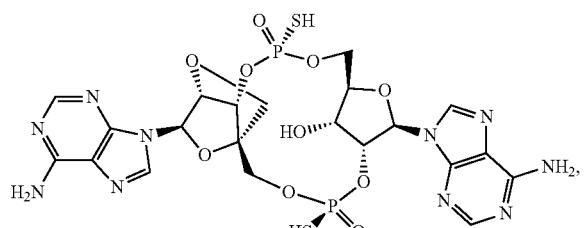
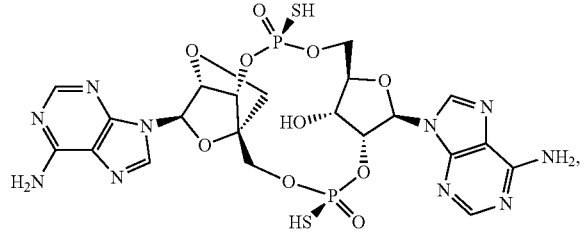
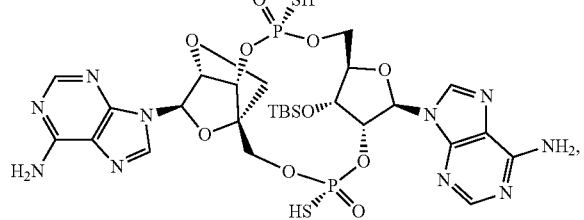
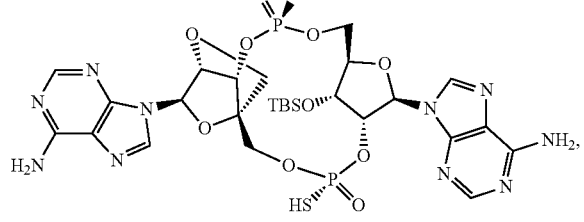
-continued
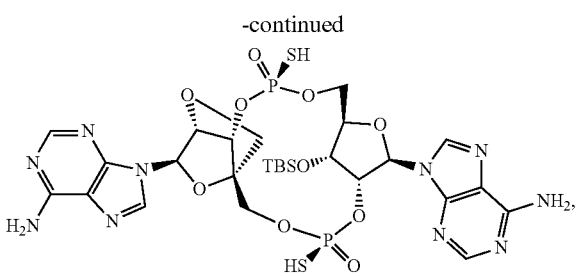
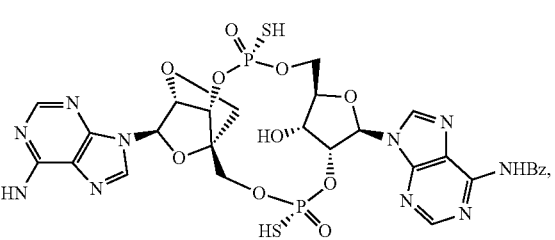
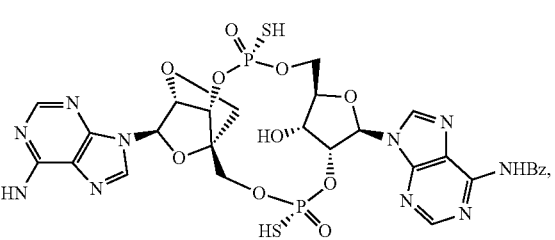
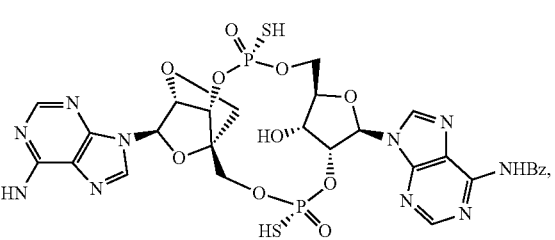
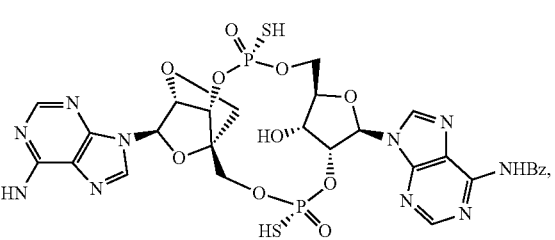
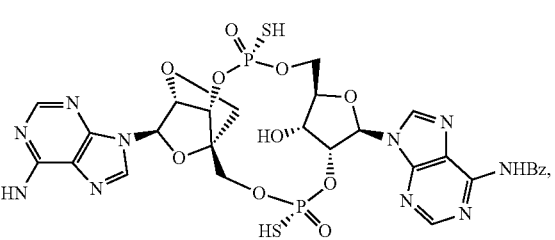

83
-continued
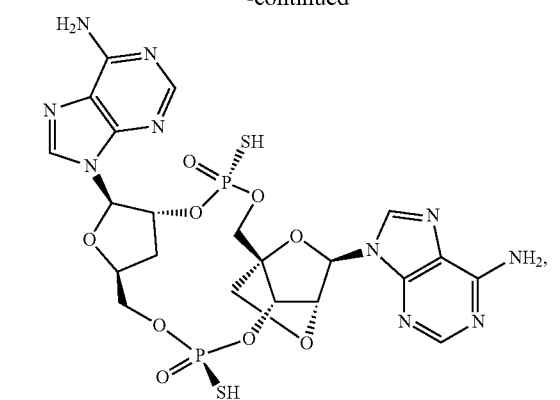
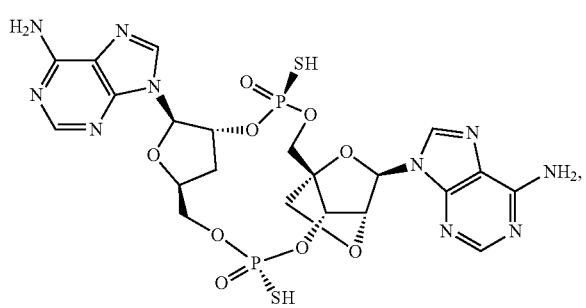
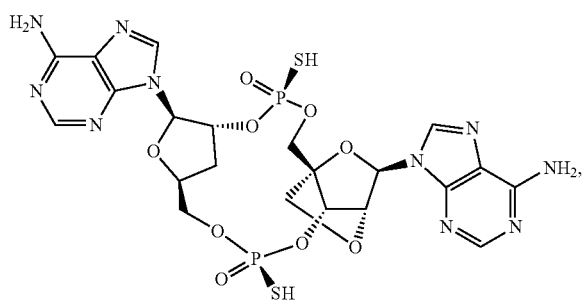
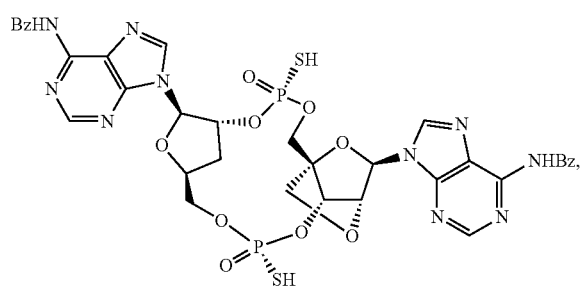
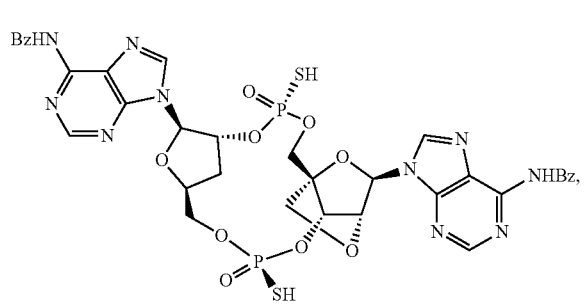
84
-continued

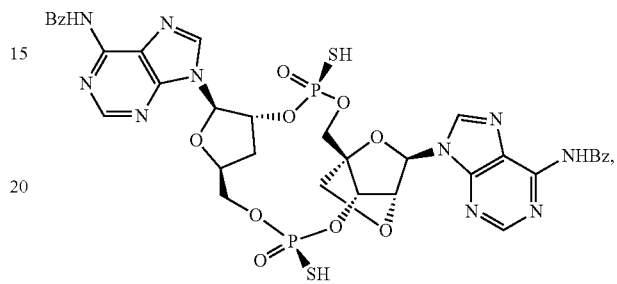
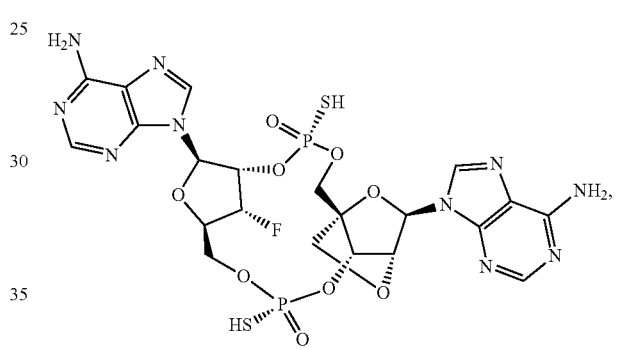
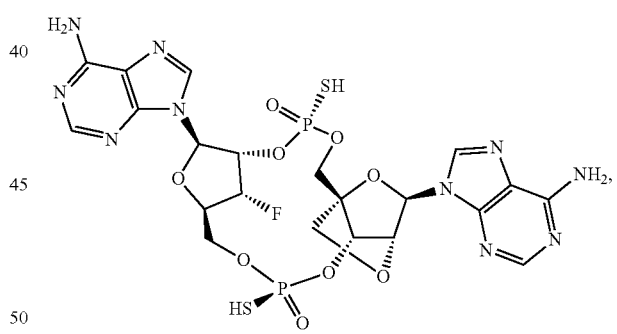
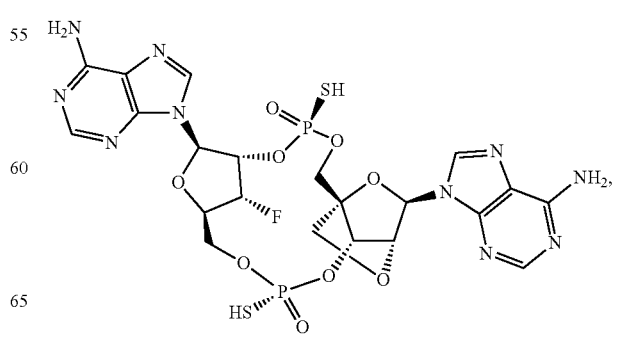

85
-continued
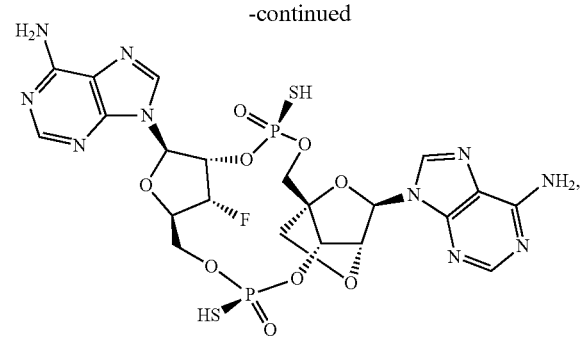
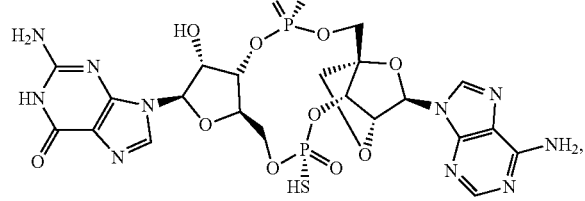
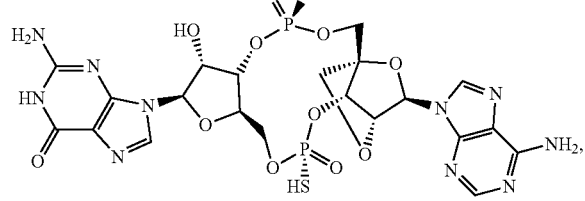
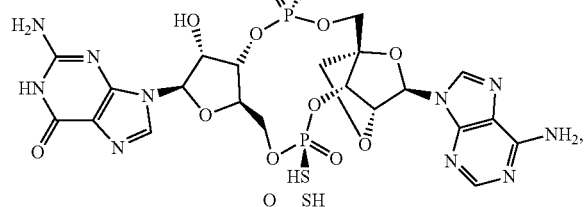
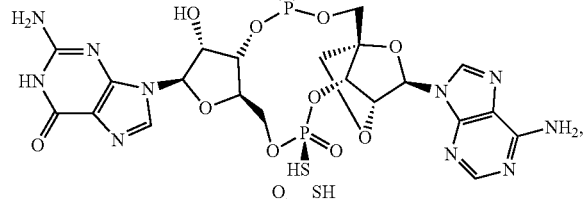
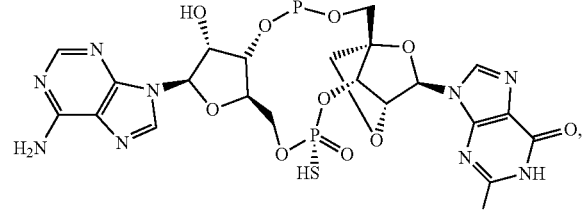
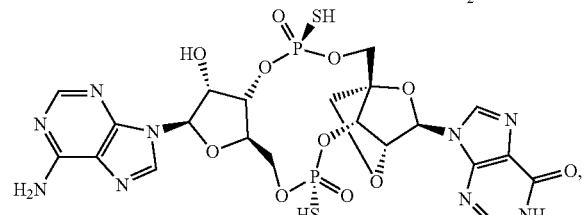
86
-continued
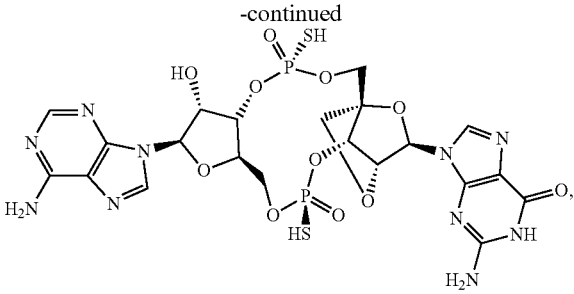
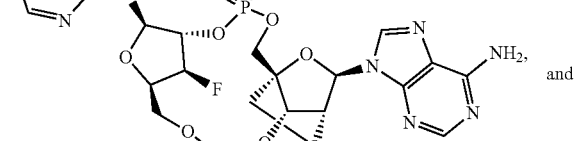
and

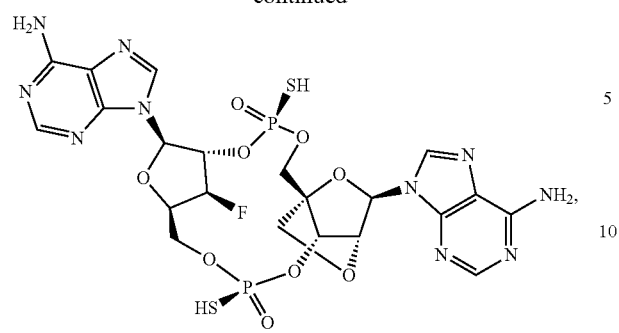
or a prodrug, pharmaceutically acceptable salt, pharmaceutically acceptable solvate or pharmaceutically acceptable hydrate thereof.
In some embodiments of any of the above aspects and embodiments, the LNA-CDN compound is selected from the group consisting of:
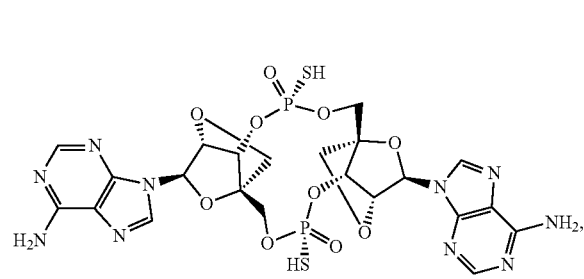
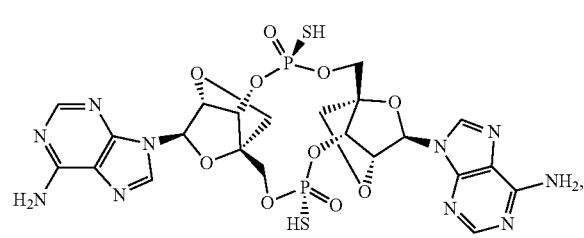
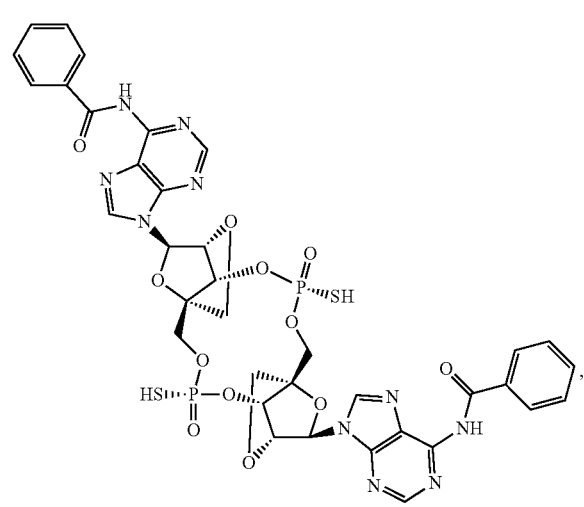
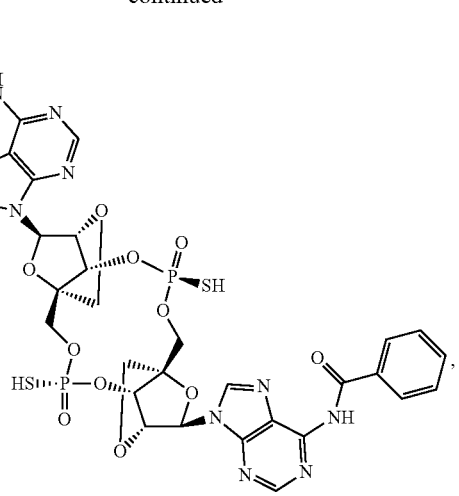
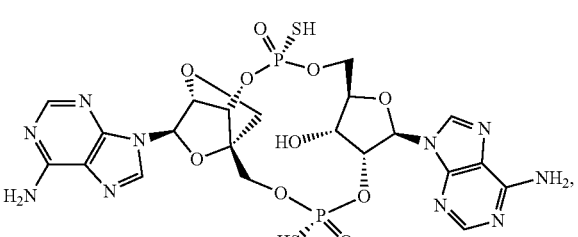
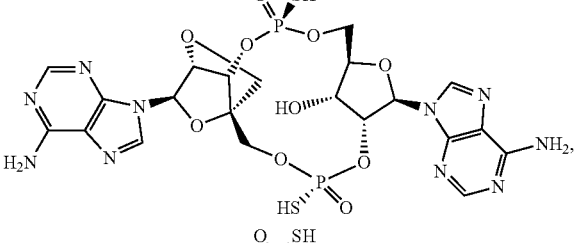
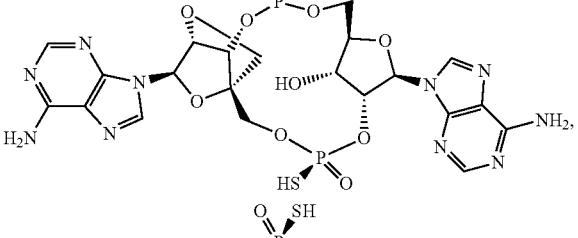
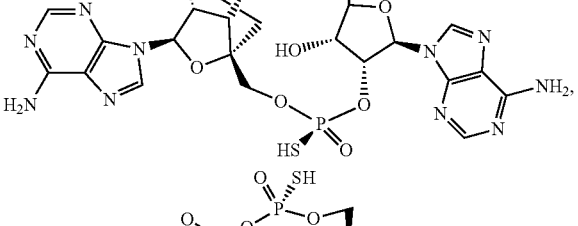
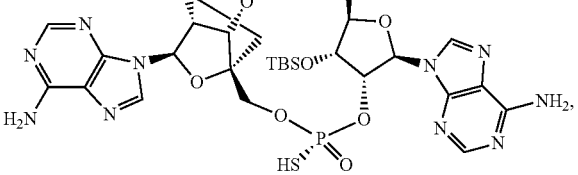

89
-continued
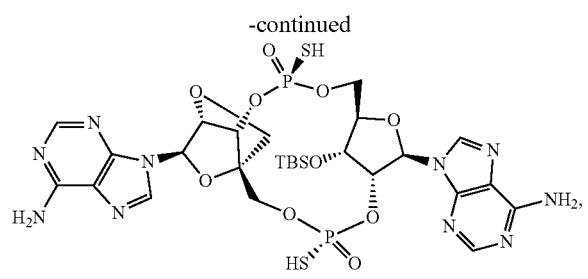
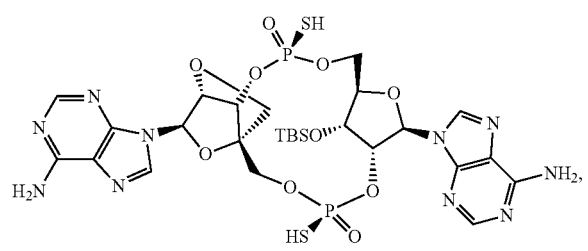
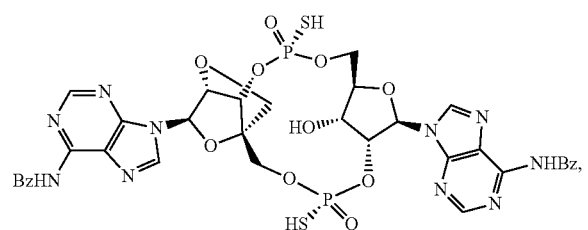
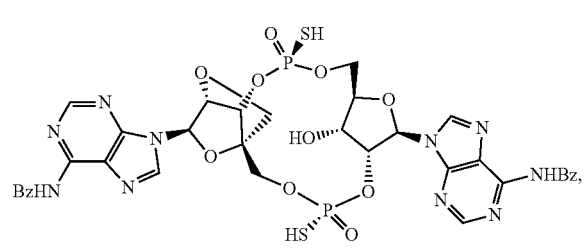
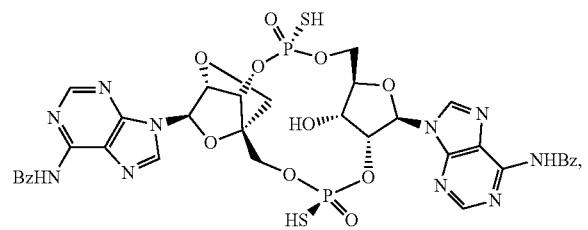
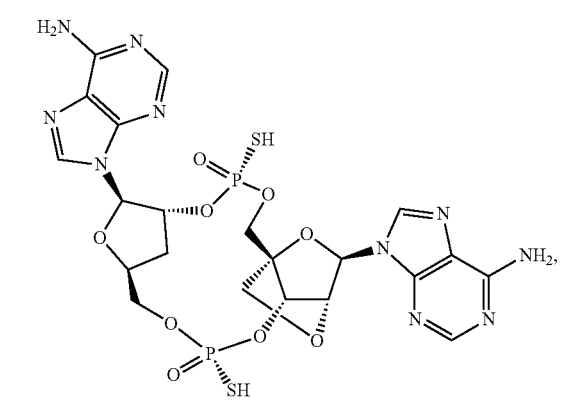
90
-continued
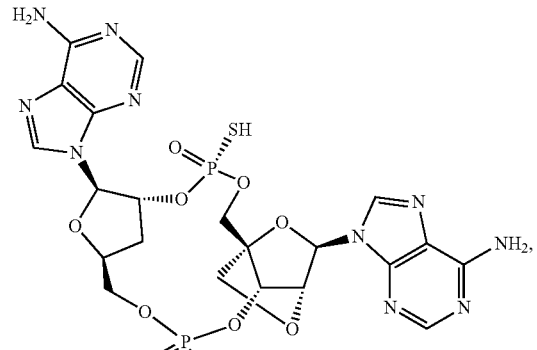
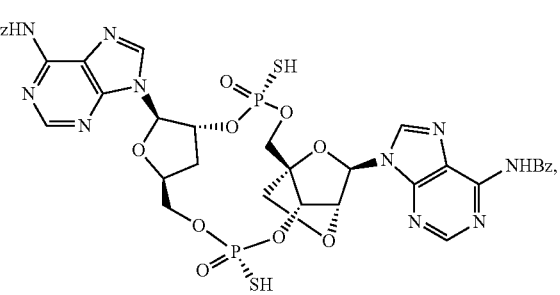
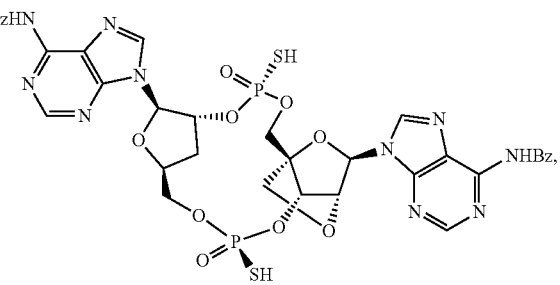
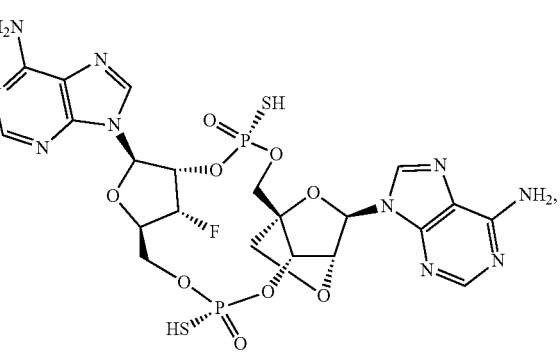
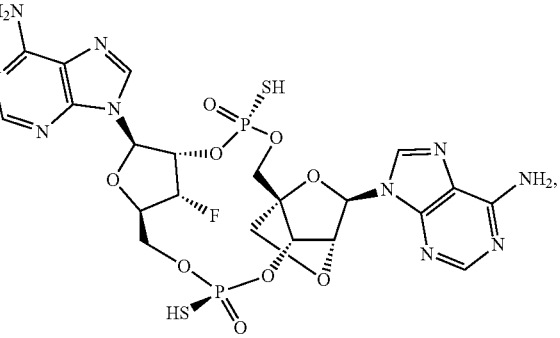

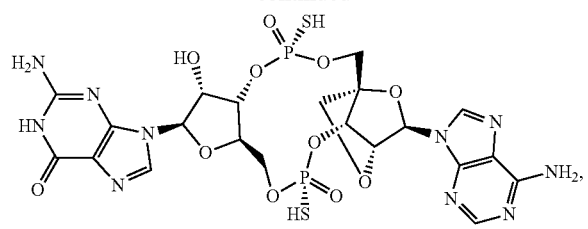
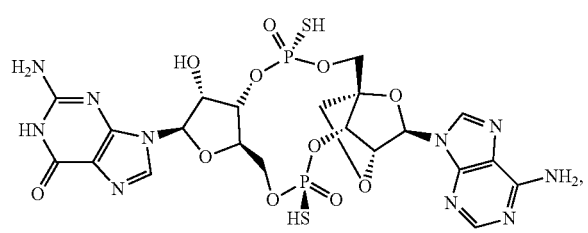
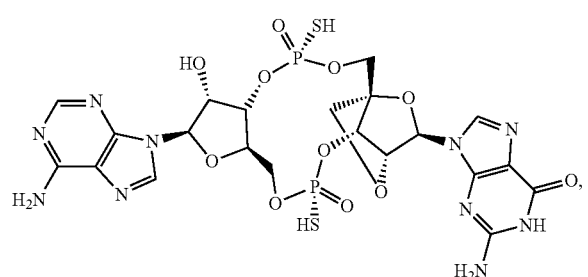
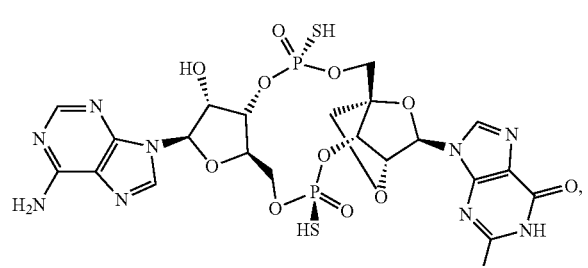
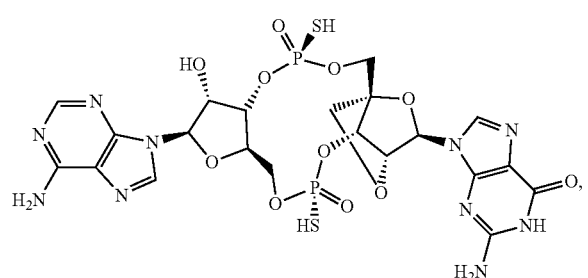
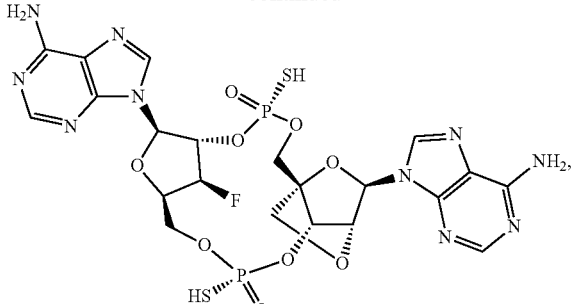
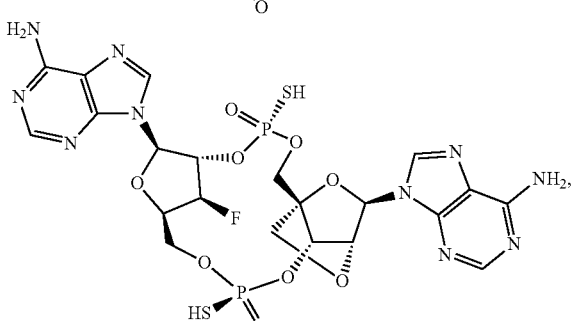
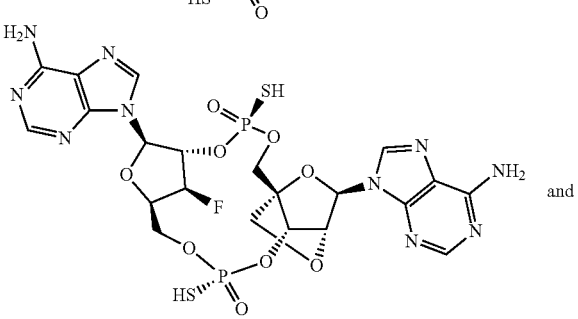 and
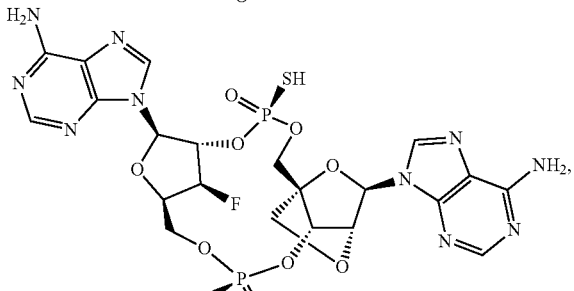
or a prodrug, pharmaceutically acceptable salt, pharmaceutically acceptable solvate or pharmaceutically acceptable hydrate thereof.
In some embodiments of any of the above aspects and embodiments, the LNA-CDN compound is selected from the group consisting of:
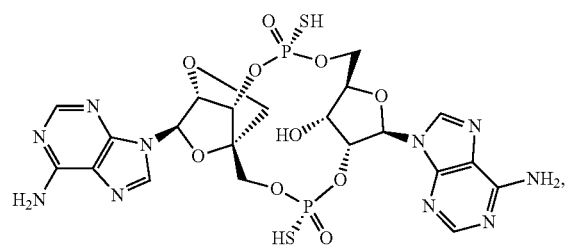

93
-continued
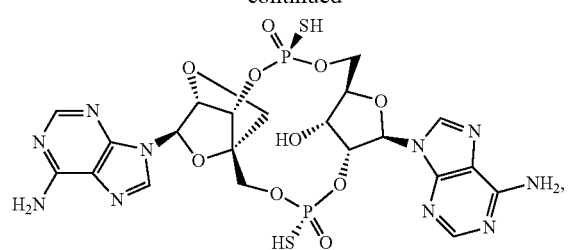
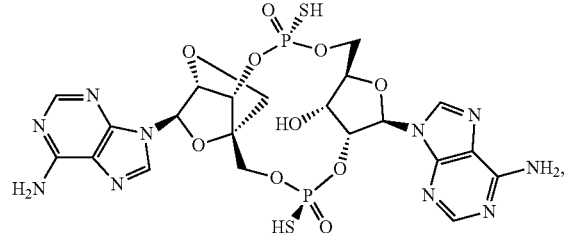
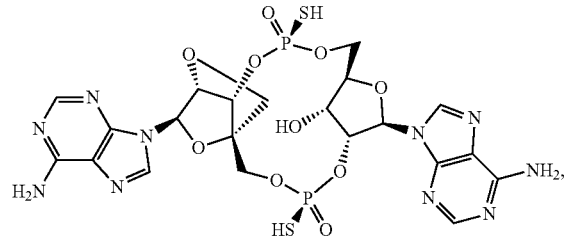
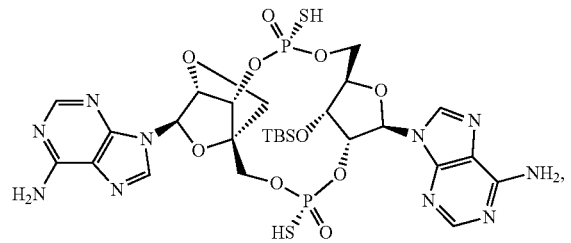
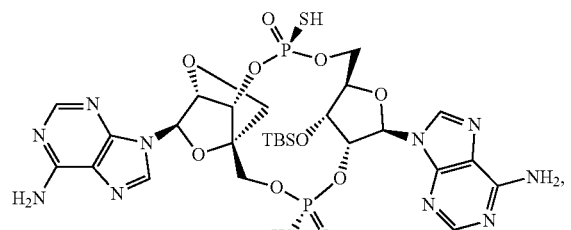
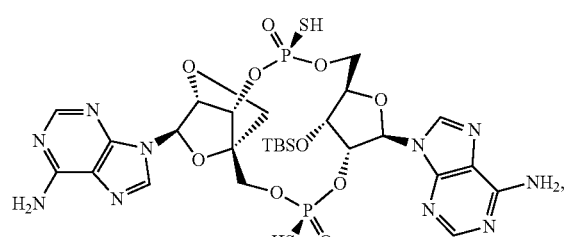
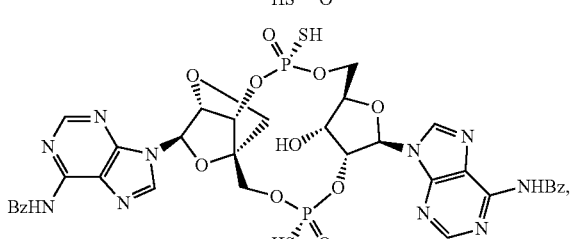
94
-continued
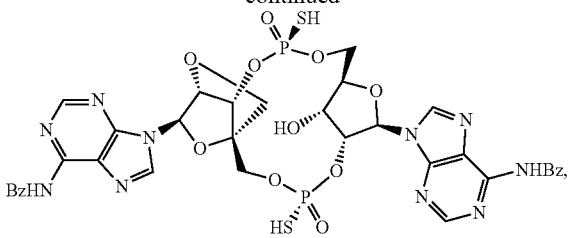
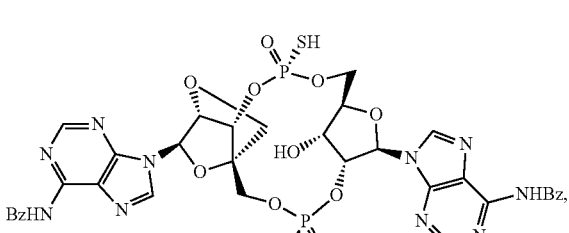
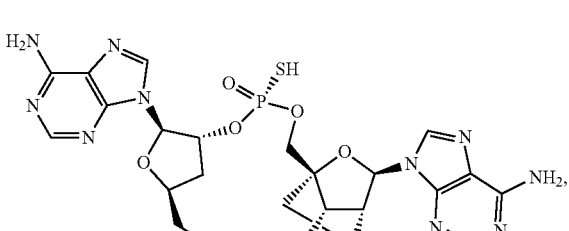
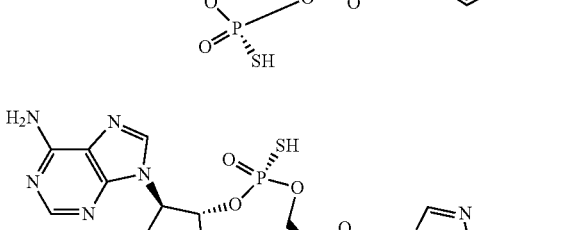
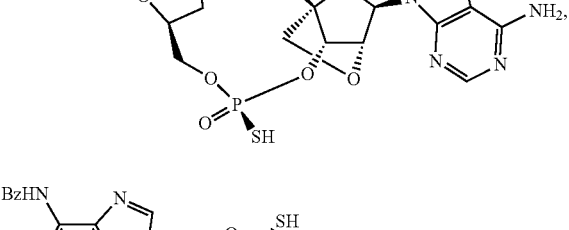
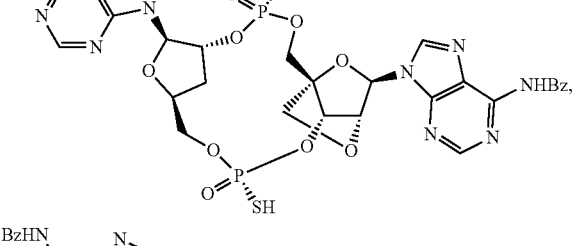
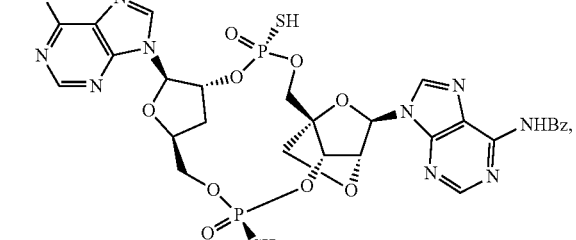

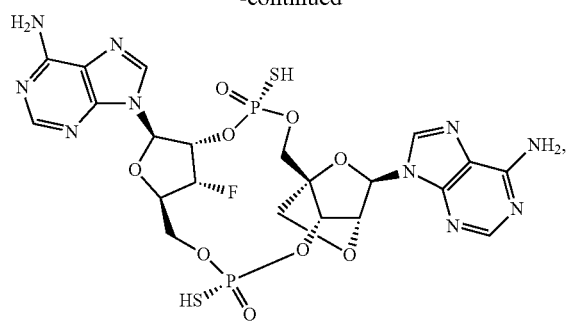
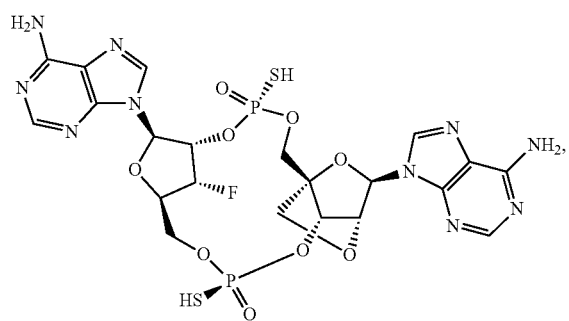
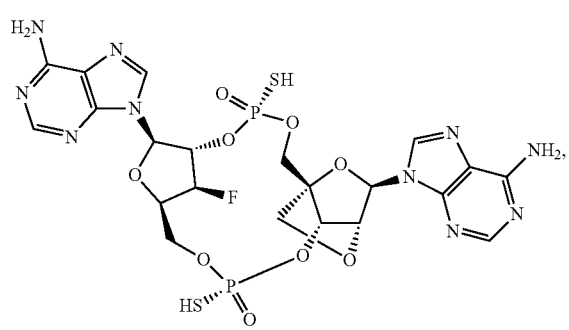
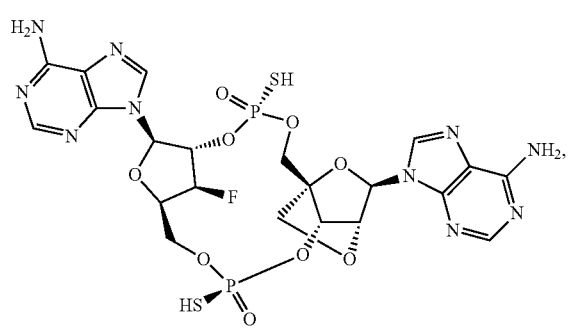
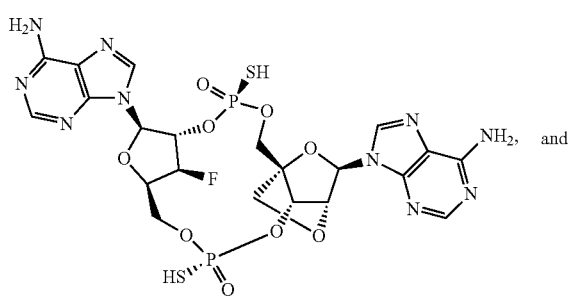
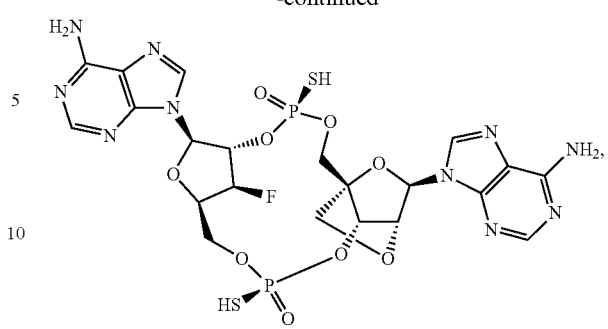
or a prodrug, pharmaceutically acceptable salt, pharmaceutically acceptable solvate or pharmaceutically acceptable hydrate thereof.
In some embodiments of any of the above aspects and embodiments, the LNA-CDN compound is selected from the group consisting of:
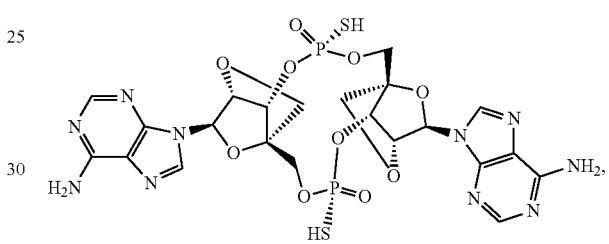
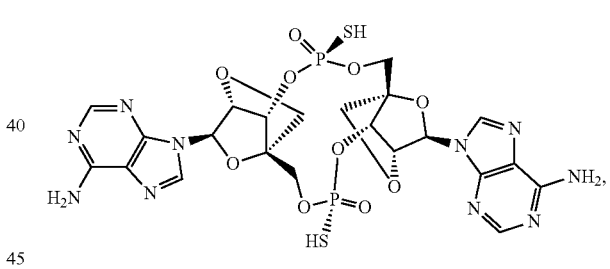
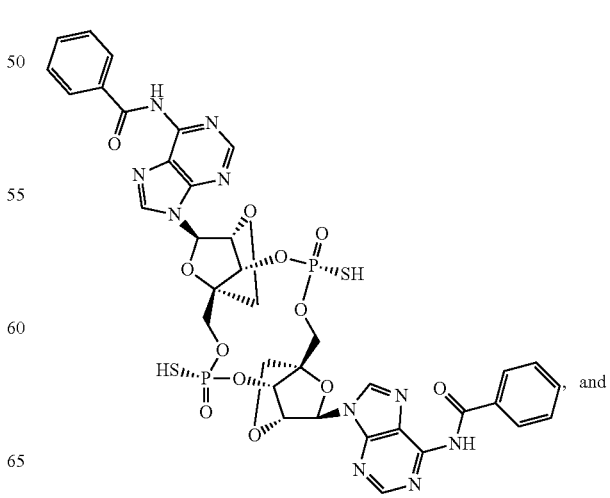
, and -continued

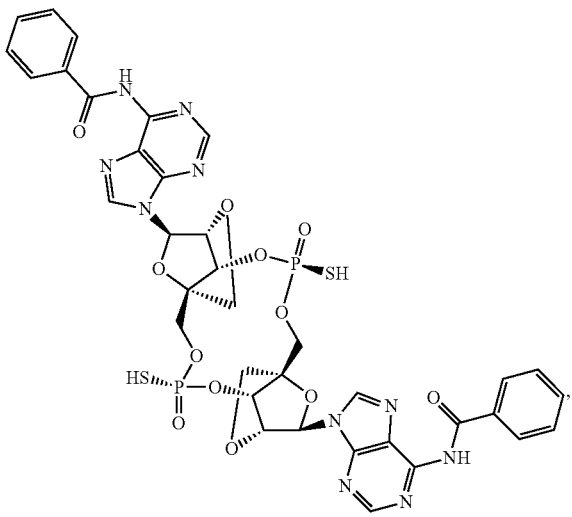

or a prodrug, pharmaceutically acceptable salt, pharmaceutically acceptable solvate or pharmaceutically acceptable hydrate thereof.

In some embodiments of any of the above aspects and embodiments, the LNA-CDN compound is selected from the group consisting of:

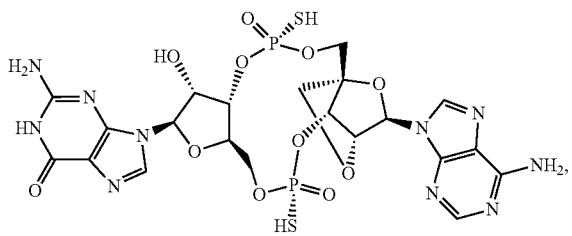

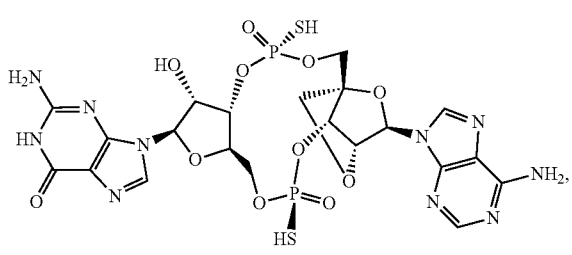

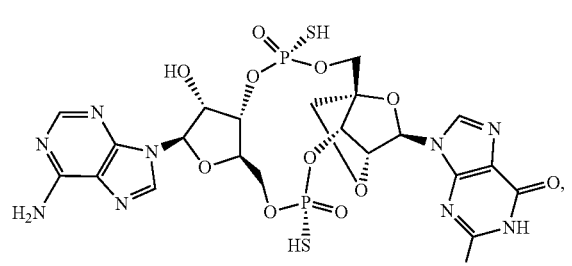

-continued

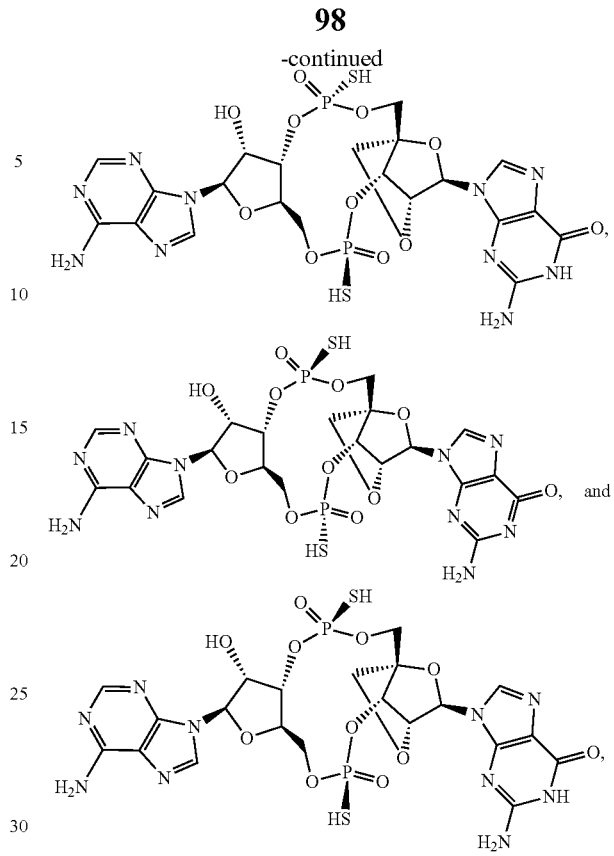

or a prodrug, pharmaceutically acceptable salt, pharmaceutically acceptable solvate or pharmaceutically acceptable hydrate thereof.

In a fifth aspect, a compound 3'3'-RR-(2'O,4'C-LNA-A)(2'O,4'C-LNA-A) is provided, having the structure:

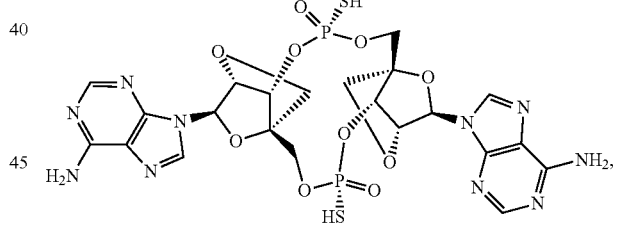

or a prodrug, pharmaceutically acceptable salt, pharmaceutically acceptable solvate or pharmaceutically acceptable hydrate thereof.

In a sixth aspect, a compound 3'3'-RS-(2'O,4'C-LNA-A)(2'O,4'C-LNA-A) is provided, having the structure:

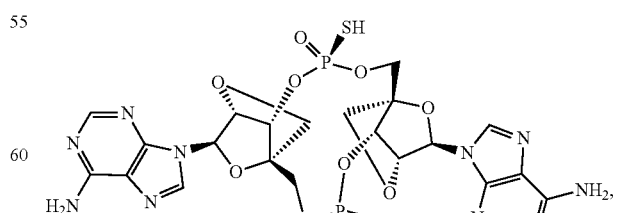

or a prodrug, pharmaceutically acceptable salt, pharmaceutically acceptable solvate or pharmaceutically acceptable hydrate thereof.

In a seventh aspect, a compound 3'3'-RR-(2'O,4'C-LNA-BzA)(2'O,4'C-LNA-BzA) is provided, having the structure:

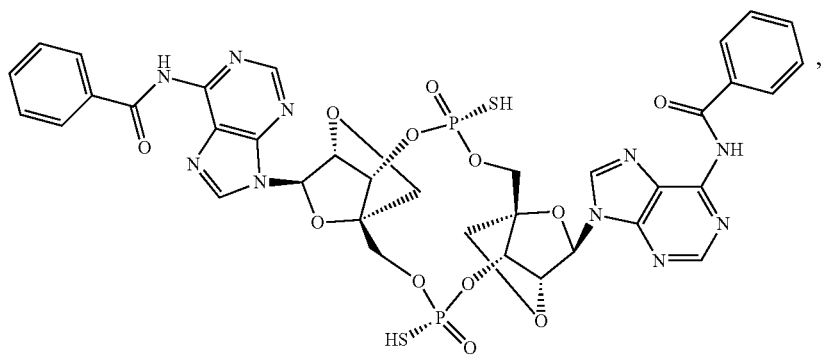 [SMILES: O=C(Nc1ncnc2c1ncn2[C@@H]1O[C@@]23CO[C@@H]1[C@@H]2O[P@](=O)(S)OC[C@@]12CO[C@@H]([C@H](n4cnc5c(NC(=O)c6ccccc6)ncnc54)O1)[C@@H]2O[P@](=O)(S)OC3)c1ccccc1]

or a prodrug, pharmaceutically acceptable salt, pharmaceutically acceptable solvate or pharmaceutically acceptable hydrate thereof.

In an eighth aspect, a compound 3'3'-RS-(2'O,4'C-LNA-BzA)(2'O,4'C-LNA-BzA) is provided, having the structure:

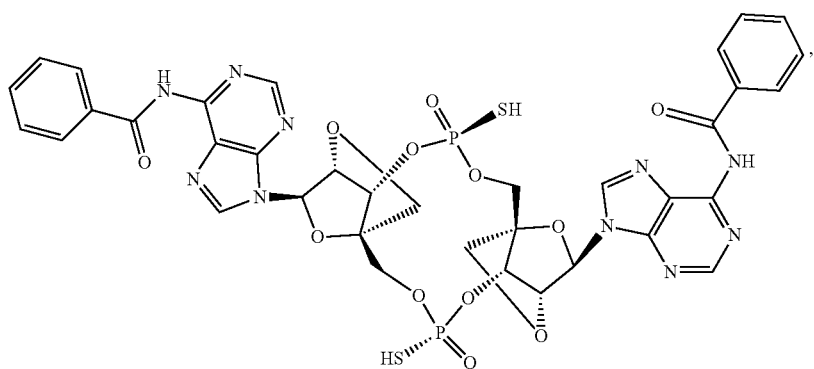 [SMILES: O=C(Nc1ncnc2c1ncn2[C@@H]1O[C@@]23CO[C@@H]1[C@@H]2O[P@@](=O)(S)OC[C@@]12CO[C@@H]([C@H](n4cnc5c(NC(=O)c6ccccc6)ncnc54)O1)[C@@H]2O[P@](=O)(S)OC3)c1ccccc1]

or a prodrug, pharmaceutically acceptable salt, pharmaceutically acceptable solvate or pharmaceutically acceptable hydrate thereof.

In a ninth aspect, a compound 2'3'-RR-(A)(2'O,4'C-LNA-A) is provided, having the structure:

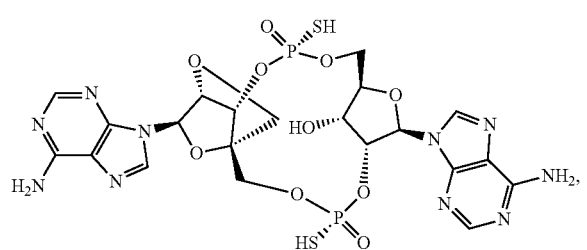 [SMILES: Nc1ncnc2c1ncn2[C@@H]1O[C@@H]2CO[P@@](=O)(S)O[C@H]3[C@H]4OC[C@]3(CO[P@@](=O)(S)O[C@@H]1[C@@H]2O)O[C@H]4n1cnc2c(N)ncnc21]

or a prodrug, pharmaceutically acceptable salt, pharmaceutically acceptable solvate or pharmaceutically acceptable hydrate thereof.

In a tenth aspect, a compound 2'3'-RS-(A)(2'O,4'C-LNA-A) is provided, having the structure:

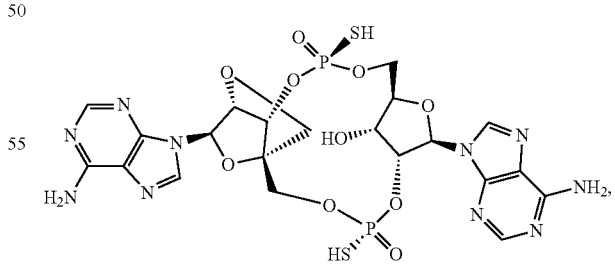

or a prodrug, pharmaceutically acceptable salt, pharmaceutically acceptable solvate or pharmaceutically acceptable hydrate thereof.

In an eleventh aspect, a compound 2'3'-SR-(A)(2'O,4'C-LNA-A) is provided, having the structure:

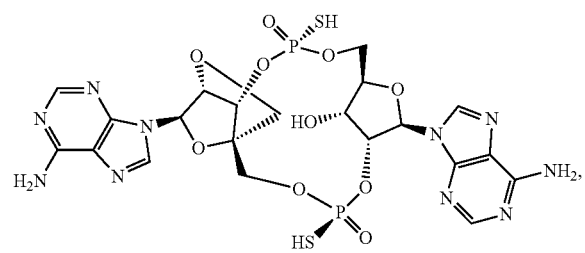 [SMILES: Nc1ncnc2c1ncn2[C@@H]1O[C@@H]2CO[P@@](=O)(S)O[C@H]3[C@H]4OC[C@]3(CO[P@](=O)(S)O[C@@H]1[C@@H]2O)O[C@H]4n1cnc2c(N)ncnc21]

or a prodrug, pharmaceutically acceptable salt, pharmaceutically acceptable solvate or pharmaceutically acceptable hydrate thereof.

In a twelfth aspect, a compound 2'3'-SS-(A)(2'O,4'C-LNA-A) is provided, having the structure:

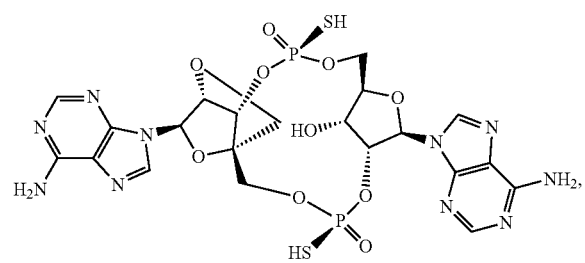 [SMILES: Nc1ncnc2c1ncn2[C@@H]1O[C@@H]2CO[P@](=O)(S)O[C@H]3[C@H]4OC[C@]3(CO[P@](=O)(S)O[C@@H]1[C@@H]2O)O[C@H]4n1cnc2c(N)ncnc21]

or a prodrug, pharmaceutically acceptable salt, pharmaceutically acceptable solvate or pharmaceutically acceptable hydrate thereof.

In a thirteenth aspect, a compound 2'3'-RR-(3'-OTBS-A)(2'O,4'C-LNA-A) is provided, having the structure:

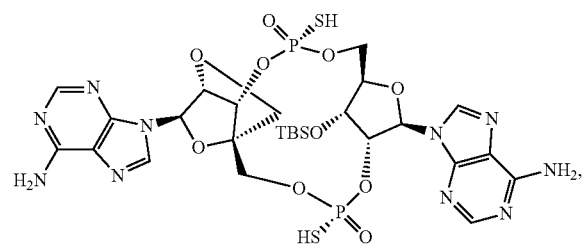 [SMILES: CC(C)(C)[Si](C)(C)O[C@H]1[C@H]2O[P@](=O)(S)OC[C@@]34CO[C@@H]([C@H](n5cnc6c(N)ncnc65)O3)[C@@H]4O[P@](=O)(S)OC[C@H]1O[C@H]2n1cnc2c(N)ncnc21]

or a prodrug, pharmaceutically acceptable salt, pharmaceutically acceptable solvate or pharmaceutically acceptable hydrate thereof.

In a fourteenth aspect, a compound 2'3'-RS-(3'-OTBS-A)(2'O,4'C-LNA-A) is provided, having the structure:

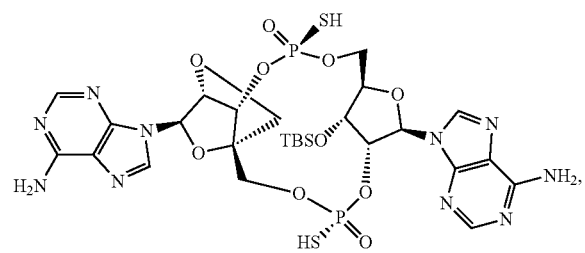 [SMILES: CC(C)(C)[Si](C)(C)O[C@H]1[C@H]2O[P@](=O)(S)OC[C@@]34CO[C@@H]([C@H](n5cnc6c(N)ncnc65)O3)[C@@H]4O[P@@](=O)(S)OC[C@H]1O[C@H]2n1cnc2c(N)ncnc21]

or a prodrug, pharmaceutically acceptable salt, pharmaceutically acceptable solvate or pharmaceutically acceptable hydrate thereof.

In a fifteenth aspect, a compound 2'3'-SS-(3'-OTBS-A)(2'O,4'C-LNA-A) is provided, having the structure:

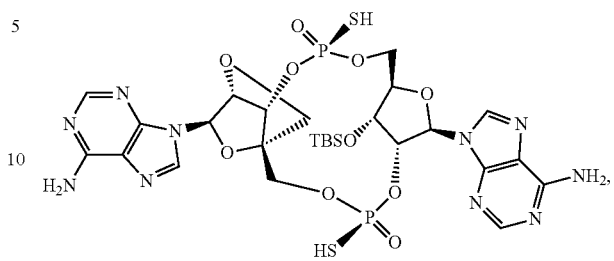

or a prodrug, pharmaceutically acceptable salt, pharmaceutically acceptable solvate or pharmaceutically acceptable hydrate thereof.

In a sixteenth aspect, a compound 2'3'-RR-(BzA)(2'O,4'C-LNA-BzA) is provided, having the structure:

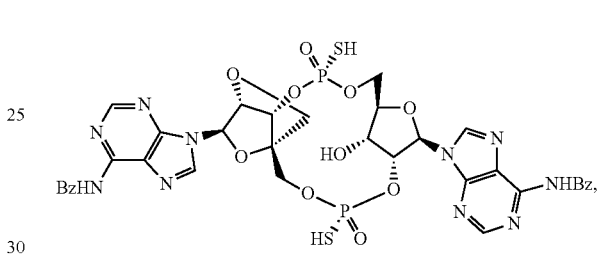

or a prodrug, pharmaceutically acceptable salt, pharmaceutically acceptable solvate or pharmaceutically acceptable hydrate thereof.

In a seventeenth aspect, a compound 2'3'-RS-(BzA)(2'O,4'C-LNA-BzA) is provided, having the structure:

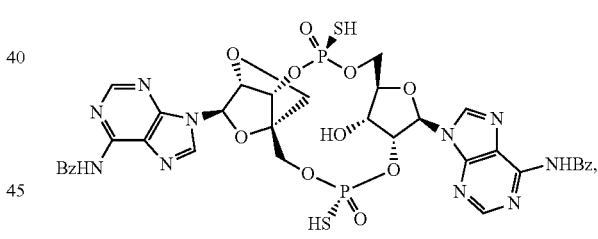

or a prodrug, pharmaceutically acceptable salt, pharmaceutically acceptable solvate or pharmaceutically acceptable hydrate thereof.

In an eighteenth aspect, a compound 2'3'-SR-(BzA)(2'O,4'C-LNA-BzA) is provided, having the structure:

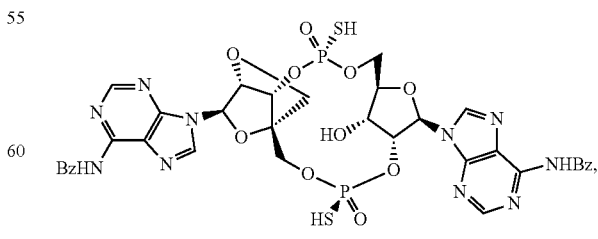

or a prodrug, pharmaceutically acceptable salt, pharmaceutically acceptable solvate or pharmaceutically acceptable hydrate thereof.

In a nineteenth aspect, a compound 2'3'-RR-(3'H-A)(2'O,4'C-LNA-A) is provided, having the structure:

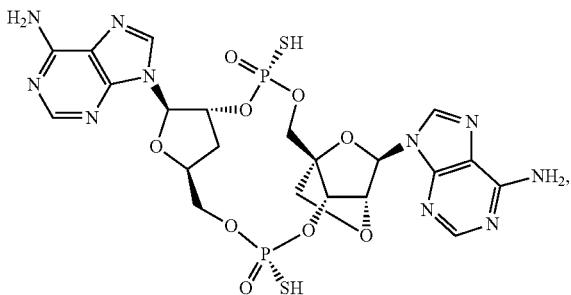 [SMILES: Nc1ncnc2c1ncn2[C@@H]1O[C@@]23CO[C@@H]1[C@@H]2O[P@](=O)(S)OC[C@@H]1C[C@@H](O[P@](=O)(S)OC3)[C@H](n2cnc3c(N)ncnc32)O1]

or a prodrug, pharmaceutically acceptable salt, pharmaceutically acceptable solvate or pharmaceutically acceptable hydrate thereof.

In a twentieth aspect, a compound 2'3'-RS-(3'H-A)(2'O,4'C-LNA-A) is provided, having the structure:

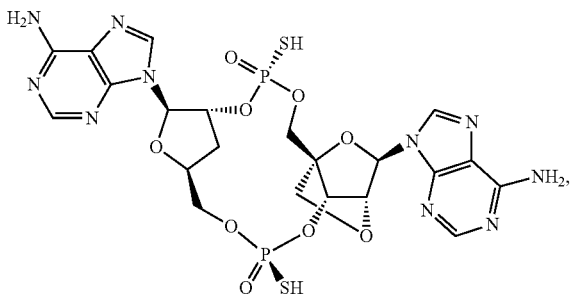 [SMILES: Nc1ncnc2c1ncn2[C@@H]1O[C@@]23CO[C@@H]1[C@@H]2O[P@@](=O)(S)OC[C@@H]1C[C@@H](O[P@](=O)(S)OC3)[C@H](n2cnc3c(N)ncnc32)O1]

or a prodrug, pharmaceutically acceptable salt, pharmaceutically acceptable solvate or pharmaceutically acceptable hydrate thereof.

In a twenty-first aspect, a compound 2'3'-RR-(3'H-BzA)(2'O,4'C-LNA-BzA) is provided, having the structure:

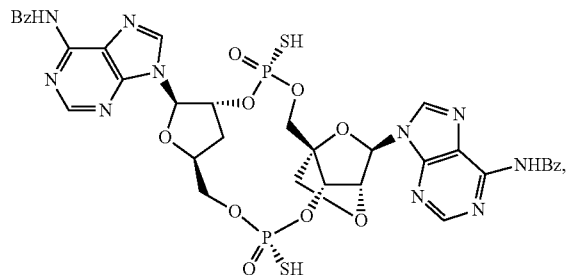

or a prodrug, pharmaceutically acceptable salt, pharmaceutically acceptable solvate or pharmaceutically acceptable hydrate thereof.

In a twenty-second aspect, a compound 2'3'-RS-(3'H-BzA)(2'O,4'C-LNA-BzA) is provided, having the structure:

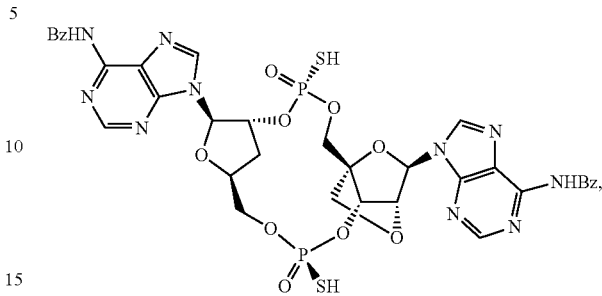

or a prodrug, pharmaceutically acceptable salt, pharmaceutically acceptable solvate or pharmaceutically acceptable hydrate thereof.

In a twenty-third aspect, a compound 2'3'-RR-(3'F-A)(2'O,4'C-LNA-A) is provided, having the structure:

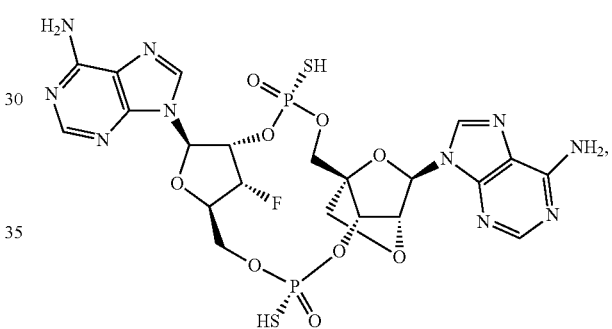

or a prodrug, pharmaceutically acceptable salt, pharmaceutically acceptable solvate or pharmaceutically acceptable hydrate thereof.

In a twenty-fourth aspect, a compound 2'3'-RS-(3'F-A)(2'O,4'C-LNA-A) is provided, having the structure:

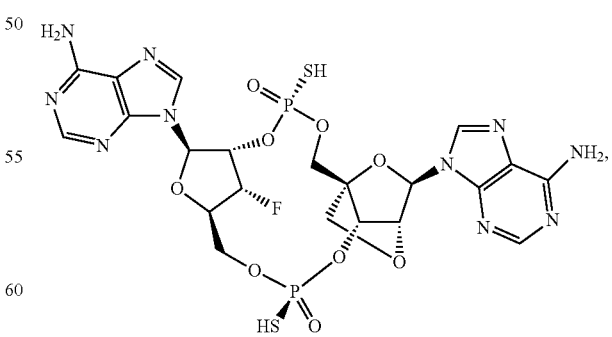

or a prodrug, pharmaceutically acceptable salt, pharmaceutically acceptable solvate or pharmaceutically acceptable hydrate thereof.

In a twenty-fifth aspect, a compound 3'3'-RR-(G)(2'O, 4'C-LNA-A) is provided, having the structure:

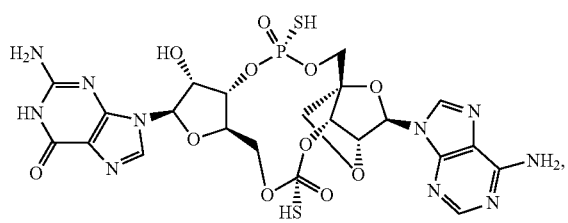

or a prodrug, pharmaceutically acceptable salt, pharmaceutically acceptable solvate or pharmaceutically acceptable hydrate thereof.

In a twenty-sixth aspect, a compound 3'3'-RS-(G)(2'O, 4'C-LNA-A) is provided, having the structure:

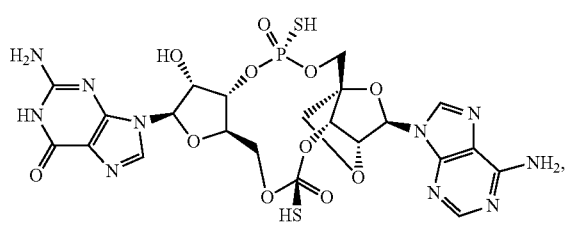

or a prodrug, pharmaceutically acceptable salt, pharmaceutically acceptable solvate or pharmaceutically acceptable hydrate thereof.

In a twenty-seventh aspect, a compound 3'3'-RR-(A)(2'O, 4'C-LNA-G) is provided, having the structure:

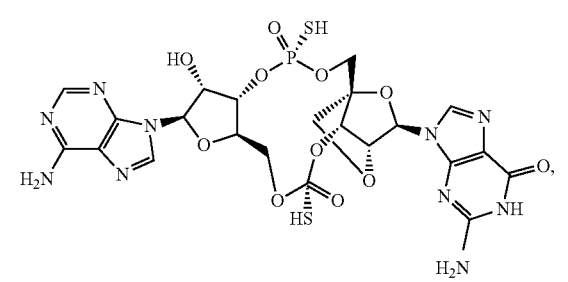

or a prodrug, pharmaceutically acceptable salt, pharmaceutically acceptable solvate or pharmaceutically acceptable hydrate thereof.

In a twenty-eighth aspect, a compound 3'3'-RS-(A)(2'O, 4'C-LNA-G) is provided, having the structure:

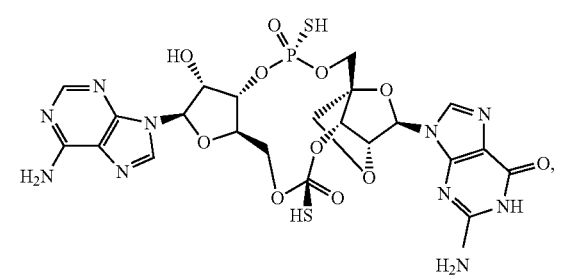

or a prodrug, pharmaceutically acceptable salt, pharmaceutically acceptable solvate or pharmaceutically acceptable hydrate thereof.

In a twenty-ninth aspect, a compound 3'3'-SR-(A)(2'O, 4'C-LNA-G) is provided, having the structure:

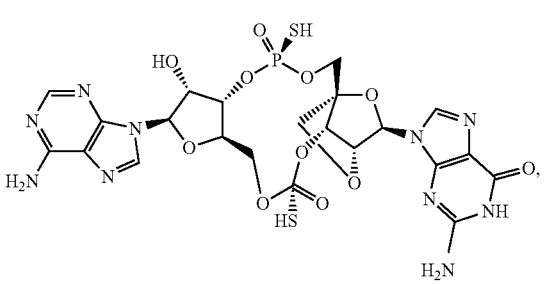

or a prodrug, pharmaceutically acceptable salt, pharmaceutically acceptable solvate or pharmaceutically acceptable hydrate thereof.

In a thirtieth aspect, a compound 3'3'-SS-(A)(2'O,4'C-LNA-G) is provided, having the structure:

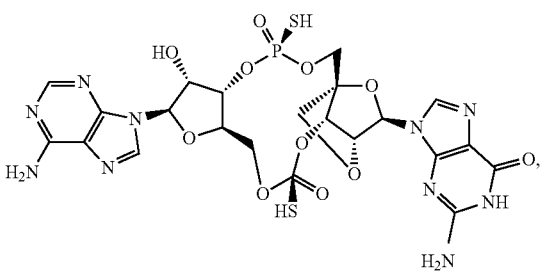

or a prodrug, pharmaceutically acceptable salt, pharmaceutically acceptable solvate or pharmaceutically acceptable hydrate thereof.

In a thirty-first aspect, a compound 2'3'-RR-(3'βF-A)(2'O, 4'LNA-A) is provided, having the structure:

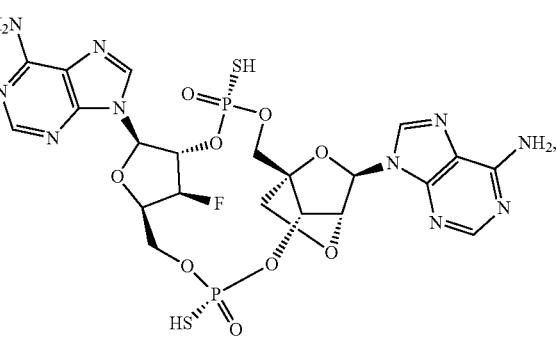

or a prodrug, pharmaceutically acceptable salt, pharmaceutically acceptable solvate or pharmaceutically acceptable hydrate thereof.

In a thirty-second aspect, a compound 2'3'-RS-(3'βF-A)(2'O,4'LNA-A) is provided, having the structure:

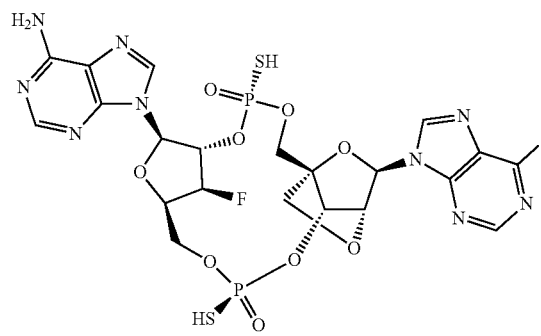

or a prodrug, pharmaceutically acceptable salt, pharmaceutically acceptable solvate or pharmaceutically acceptable hydrate thereof.

In a thirty-third aspect, a compound 2'3'-SR-(3'βF-A)(2'O,4'LNA-A) is provided, having the structure:

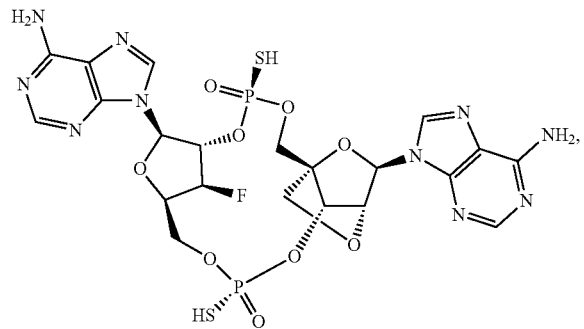 [SMILES: Nc1ncnc2c1ncn2[C@@H]1O[C@@H]2CO[P@@](=O)(S)O[C@H]3[C@H]4OC[C@]3(CO[P@](=O)(S)O[C@@H]1[C@H]2F)O[C@H]4n1cnc2c(N)ncnc21]

or a prodrug, pharmaceutically acceptable salt, pharmaceutically acceptable solvate or pharmaceutically acceptable hydrate thereof.

In a thirty-fourth aspect, a compound 2'3'-SS-(3'βF-A)(2'O,4'LNA-A) is provided, having the structure:

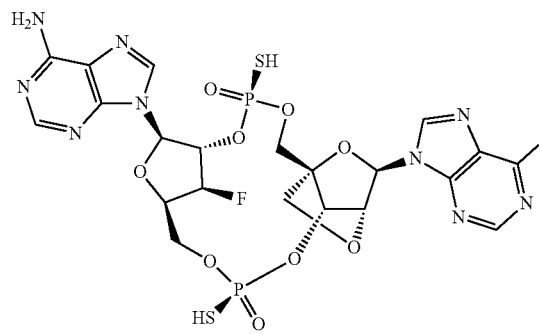

or a prodrug, pharmaceutically acceptable salt, pharmaceutically acceptable solvate or pharmaceutically acceptable hydrate thereof.

In a thirty-fifth aspect, a compound 2'3'-RR-(3'F-G)(2'O,4'C-LNA-A) is provided, having the structure:

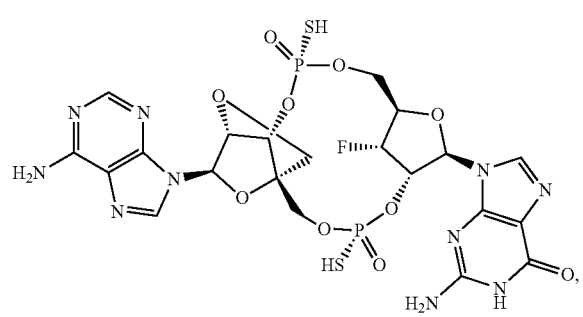 [SMILES: Nc1nc2c(ncn2[C@@H]2O[C@@H]3CO[P@@](=O)(S)O[C@H]4[C@H]5OC[C@]4(CO[P@@](=O)(S)O[C@@H]2[C@@H]3F)O[C@H]5n2cnc3c(N)ncnc32)c(=O)[nH]1]

or a prodrug, pharmaceutically acceptable salt, pharmaceutically acceptable solvate or pharmaceutically acceptable hydrate thereof.

In a thirty-sixth aspect, a compound 2'3'-RS-(3'F-G)(2'O,4'C-LNA-A) is provided, having the structure:

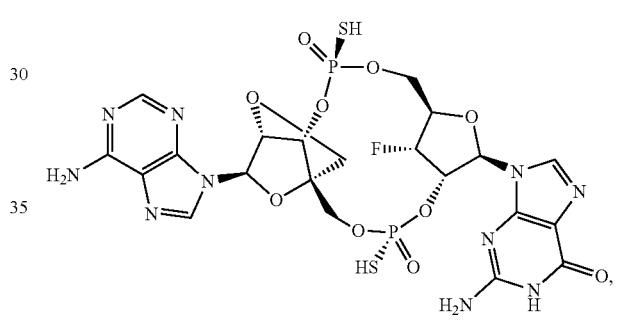

or a prodrug, pharmaceutically acceptable salt, pharmaceutically acceptable solvate or pharmaceutically acceptable hydrate thereof.

In a thirty-seventh aspect, a compound 2'3'-SR-(3'F-G)(2'O,4'C-LNA-A) is provided, having the structure:

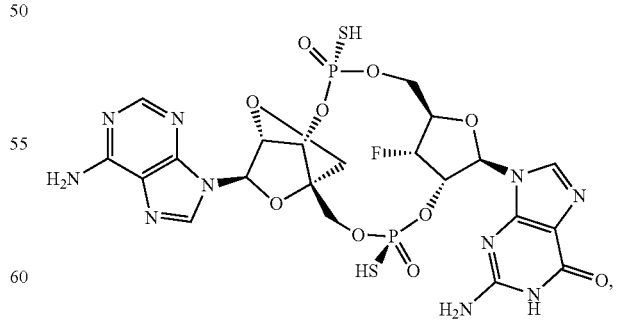

or a prodrug, pharmaceutically acceptable salt, pharmaceutically acceptable solvate or pharmaceutically acceptable hydrate thereof.

In a thirty-eighth aspect, a compound 2'3'-SS-(3'F-G)(2'O, 4'C-LNA-A) is provided, having the structure:

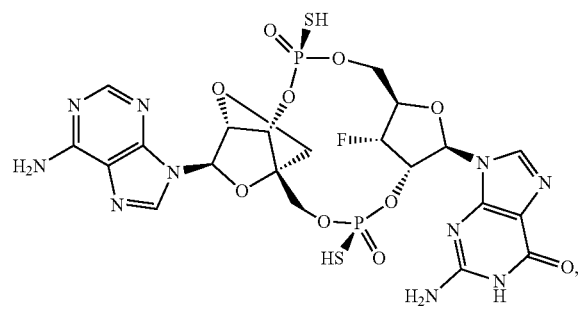 [SMILES: Nc1nc2c(ncn2[C@@H]2O[C@@H]3CO[P@](=O)(S)O[C@H]4[C@H]5OC[C@]4(CO[P@](=O)(S)O[C@@H]2[C@@H]3F)O[C@H]5n2cnc3c(N)ncnc32)c(=O)[nH]1]

or a prodrug, pharmaceutically acceptable salt, pharmaceutically acceptable solvate or pharmaceutically acceptable hydrate thereof.

In some embodiments of any of the above aspects and embodiments thereof, the LNA-CDN compounds include prodrugs, pharmaceutically acceptable salts, pharmaceutically acceptable solvates or pharmaceutically acceptable hydrates thereof, including pharmaceutically acceptable salts, pharmaceutically acceptable solvates or pharmaceutically acceptable hydrates of any prodrugs thereof, and including any pharmaceutically acceptable solvates or pharmaceutically acceptable hydrates of any pharmaceutically acceptable salts thereof. In some embodiments, the LNA-CDN compounds include pharmaceutically acceptable solvates, pharmaceutically acceptable hydrates or pharmaceutically acceptable salts thereof. In some embodiments, the LNA-CDN compound is a pharmaceutically acceptable salt, or a pharmaceutically acceptable solvate or pharmaceutically acceptable hydrate thereof. In some embodiments, the LNA-CDN compound is a pharmaceutically acceptable salt.

In some embodiments of any of the above aspects and embodiments thereof, the LNA-CDN compounds include pharmaceutically acceptable salts thereof. In some embodiments, the pharmaceutically acceptable salt is selected from the group consisting of the sodium, potassium, calcium, magnesium, zinc, aluminum, ammonium, diethylamine, isopropylamine, olamine, benzathine, benethamine, tromethamine (2-amino-2-(hydroxymethyl)propane-1,3-diol), morpholine, epolamine, piperidine, piperazine, picoline, dicyclohexylamine, N,N'-dibenzylethylenediamine, 2-hydroxyethylamine, tri-(2-hydroxyethyl)amine, chloroprocaine, choline, deanol, imidazole, diethanolamine, ethylenediamine, meglumine (N-methylglucamine), procaine, dibenzylpiperidine, dehydroabietylamine, glucamine, collidine, quinine, quinolone, erbumine, lysine and arginine salt.

In one embodiment of any of the above aspects or embodiments thereof, the LNA-CDN compounds are provided as the disodium salt thereof. In some embodiments, the LNA-CDN compounds are provided as the disodium salt thereof, or a pharmaceutically acceptable solvate or pharmaceutically acceptable hydrate thereof.

In some embodiments of any of the above aspects and embodiments thereof, the LNA-CDN compound is a STING agonist. In some embodiments, the LNA-CDN compound is more active in a cellular assay that measures the induction of human STING dependent IFN-β production as compared to one or more STING agonist reference compounds. In some embodiments, the one or more reference compounds are selected from the group consisting of 2'3'-(A)(A), 2'3'-(G)(A), 3'2'-(G)(A), 2'3'-RR-(A)(A) and 2'3'-RR-(G)(A). In some embodiments, the LNA-CDN compound is a LNA-RR-CDN compound and the one or more reference compounds are selected from the group consisting of 2'3'-RR-(A)(A) and 2'3'-(G)(A). In some embodiments, the cellular assay is an hPBMC assay, for example the assay as described in Example 11. In some embodiments, the cellular assay is a THP1 assay, for example the assay as described in Example 12. In a preferred embodiment, the cellular assay is performed without the addition of an agent that enhances uptake of the LNA-CDN compound or reference compound by the assay cells or an agent that enhances the permeability of the LNA-CDN compound or reference compound to the assay cells. In some embodiments, the cellular assay is a THP1 cellular assay performed without the addition of an agent that enhances uptake of the LNA-CDN compound or reference compound by the assay cells or an agent that enhances the permeability of the LNA-CDN compound or reference compound to the assay cells, in which the LNA-CDN compound has an EC50 of less than 40 µM, less than 30 µM, less than 20 µM, less than 15 µM, less than 10 µM or less than 5 µM. In some embodiments the LNA-CDN compound has an EC50 of less than 40 µM, less than 30 µM, less than 20 µM, less than 15 µM, less than 10 µM or less than 5 µM in a cellular assay that measures induction of human STING dependent IFN-β production, wherein the cellular assay is performed without the addition of an agent that enhances uptake of the LNA-CDN compound by the assay cells or an agent that enhances the permeability of the LNA-CDN compound to the assay cells. In one embodiment the cellular assay is a THP1 cellular assay as described in Example 12, wherein the assay is performed without addition of digitonin. In some embodiments, the LNA-CDN compound has an EC50 that is less than the EC50 of one or more reference compounds selected from the group consisting of 2'3'-(A)(A), 2'3'-(G)(A), 3'2'-(G)(A), 2'3'-RR-(A)(A), and 2'3'-RR-(G)(A) in a cellular assay that measures induction of human STING dependent IFN-β production, preferably wherein the cellular assay is performed without the addition of an agent that enhances uptake of the LNA-CDN compound or reference compound by the assay cells or an agent that enhances the permeability of the LNA-CDN compound or reference compound to the assay cells. In some embodiments, the LNA-CDN compound has an EC50 that is less than the EC50 of a reference compound in a THP1 cellular assay as described in Example 12, preferably wherein the assay is performed without addition of digitonin. In some embodiments, the LNA-CDN compound has an EC50 that is at least 2-fold, at least 3-fold, at least 4-fold, at least 5-fold, at least 6-fold, at least 7-fold, or at least 8-fold lower than the EC50 of the reference compound in the THP1 cellular assay as described in Example 12, wherein the assay is performed without addition of digitonin.

In some embodiments of any of the above aspects and embodiments thereof, the LNA-CDN compound binds at least one human STING allelic protein product (including any one of WT, REF, HAQ, AQ and Q alleles) with a greater affinity than one or more reference compounds selected from the group consisting of 2'3'-(A)(A), 2'3'-(G)(A), 3'2'-(G)(A), 2'3'-RR-(A)(A), and 2'3'-RR-(G)(A) when measured using at least one human STING protein. Preferably, this is measured using the isolated protein encoded by the hSTING (WT), hSTING (HAQ) or hSTING (REF) allele (Ishikawa, H., and Barber, G. N. (2008). *Nature* 455, 674-678; Y₁ et al., 2013, PLos One 2013 Oct. 21, 8(10):e77846; the protein sequence of the REF allele is NCBI Reference Sequence NP_938023) using a method such as differential scanning fluorometry (DSF) as described hereinafter and in Example 10.

In a thirty-ninth aspect, the present invention provides pharmaceutical compositions comprising one or more LNA-CDN compounds, as described in the first through thirty-eighth aspects and any embodiments thereof as described herein above, including any prodrugs, pharmaceutically acceptable salts, pharmaceutically acceptable solvates, or pharmaceutically acceptable hydrates thereof, and a delivery vehicle which enhances cellular uptake and/or stability of the compound. In some embodiments, the delivery vehicle comprises one or more agents selected from the group consisting of adjuvants, lipids, liposomes, interbilayer cross-linked multilamellar vesicles, biodegradable poly(D,L-lactic-co-glycolic acid) [PLGA]-based or poly anhydride-based nanoparticles or microparticles, and nanoporous particle-supported lipid bilayers.

In a fortieth aspect, the present invention provides pharmaceutical compositions comprising one or more LNA-CDN compounds, as described in the first through thirty-eighth aspects and any embodiments thereof as described herein above, including any prodrugs, pharmaceutically acceptable salts, pharmaceutically acceptable solvates, or pharmaceutically acceptable hydrates thereof, and a pharmaceutically acceptable excipient.

In a first embodiment of the fortieth aspect, the pharmaceutical composition does not include an agent that enhances cellular permeability of the one or more LNA-CDN compounds.

In a second embodiment of the fortieth aspect, the pharmaceutical composition does not include an agent that enhances cellular uptake of the one or more LNA-CDN compounds.

In a third embodiment of the fortieth aspect, the pharmaceutical composition further comprises a delivery vehicle which enhances cellular uptake and/or stability of the compound. In some embodiments, the delivery vehicle comprises one or more agents selected from the group consisting of adjuvants, lipids, liposomes, interbilayer crosslinked multilamellar vesicles, biodegradable poly(D,L-lactic-co-glycolic acid) [PLGA]-based or poly anhydride-based nanoparticles or microparticles, and nanoporous particle-supported lipid bilayers.

In some embodiments of the thirty-ninth aspect or fortieth aspect and any of the above embodiments thereof, the pharmaceutical composition further comprises one or more additional pharmaceutically active components selected from the group consisting of an immune checkpoint inhibitor (e.g. CTLA-4, PD-1, Tim-3, Vista, BTLA, LAG-3 and TIGIT pathway antagonists; PD-1 pathway blocking agents; PD-L1 inhibitors; including without limitation anti-PD-1 antibodies nivolumab, pembrolizumab or pidilizumab; PD-1 inhibitor AMP-224; anti-CTLA-4 antibody ipilimumab; and anti-PD-L1 antibodies BMS-936559, MPDL$_{3280}$A, MEDI4736, or avelumab); a TLR agonist (e.g. CpG or monophosphoryl lipid A); an inactivated or attenuated bacteria which induce innate immunity (e.g., inactivated or attenuated *Listeria monocytogenes*); a composition that mediates innate immune activation via Toll-like Receptors (TLRs), via (NOD)-like receptors (NLRs), via Retinoic acid inducible gene-based (RIG)-I-like receptors (RLRs), via C-type lectin receptors (CLRs), or via pathogen-associated molecular patterns (PAMPs); and a chemotherapeutic agent. In some embodiments, the immune checkpoint inhibitor is selected from the group consisting of a CTLA-4 pathway antagonist, a PD-1 pathway antagonist, a Tim-3 pathway antagonist, a Vista pathway antagonist, a BTLA pathway antagonist, a LAG-3 pathway antagonist, and a TIGIT pathway antagonist. In some embodiments, the immune checkpoint inhibitor is an anti-PD-1 antibody, an anti-PD-L1 antibody, an anti-CTLA-4 antibody, an anti-TIM-3 antibody, an anti-BTLA antibody, an anti-B7-H3 antibody, an anti-CD70 antibody, an anti-CD40 antibody, an anti-CD137 antibody, an anti-GITR antibody, an anti-OX40 antibody, an anti-KIR antibody or an anti-LAG-3 antibody. In some embodiments, the immune checkpoint inhibitor is selected from the group consisting of nivolumab, pembrolizumab, pidilizumab, PDR001, MEDI0680, REGN2810, AMP-224, ipilimumab, BMS-936559, MPDL$_{3280}$A, MEDI4736, and avelumab. In some embodiments, the TLR agonist is CpG or monophosphoryl lipid A.

In some embodiments of the thirty-ninth aspect or fortieth aspect and any of the above embodiments thereof, the pharmaceutical composition further comprises an inactivated tumor cell which expresses and secretes one or more cytokines which stimulate dendritic cell induction, recruitment and/or maturation, or which expresses and secretes one or more heat shock proteins, including gp96-Ig fusion proteins. In some embodiments, the one or more cytokines is selected from the group consisting of GM-CSF, CCL20, CCL3, IL-12p70 and FLT-3 ligand. In some embodiments, the tumor cell is inactivated by treatment with radiation. In some embodiments, the one or more cytokines is selected from the group consisting of GM-CSF, CCL20, CCL3, IL-12p70 and FLT-3 ligand, and the tumor cell is inactivated by treatment with radiation. In some embodiments, the inactivated tumor cell expresses and secretes a gp96-Ig fusion protein.

In some embodiments of the thirty-ninth aspect or fortieth aspect and any of the above embodiments thereof, the pharmaceutical composition further comprises one or more antigens selected for the purposes of inducing an immune response against said one or more antigen(s) when the composition is administered to an individual. In some embodiments, the antigen is a recombinant protein antigen. In some embodiments, the antigen is a recombinant protein antigen related to an infectious disease, a malignancy, or an allergen. In some embodiments, the one or more antigens is one or more antigens in Table 1.

In some embodiments of the thirty-ninth aspect or fortieth aspect and any of the above embodiments thereof, the pharmaceutical compositions are formulated as aqueous or oil-in-water emulsions.

In a forty-first aspect, the invention provides a method for treating an individual suffering from a cancer, wherein the method comprises administering to the individual in need thereof an effective amount of one or more LNA-CDN compounds, as described in the first through thirty-eighth aspects and any embodiments thereof as described herein above, including any prodrugs, pharmaceutically acceptable salts, pharmaceutically acceptable solvates, or pharmaceutically acceptable hydrates thereof, or compositions thereof as described in the thirty-ninth and fortieth aspects and any embodiments thereof as described herein above. In some embodiments, the one or more LNA-CDN compounds or composition thereof is administered non-parenterally or parenterally. In some embodiments, the administration is subcutaneous, intramuscular, intradermal, mucosal, vaginal, cervical, peri-tumoral, intra-tumoral, or directly into the tumor-draining lymph node(s). In some embodiments, the administration is mucosal, preferably oral.

In a first embodiment of the forty-first aspect, the individual receiving such treatment may be suffering from a cancer selected from the group consisting of a colorectal cancer, an aero-digestive squamous cancer, a lung cancer (small cell lung cancer, non-small cell lung cancer), a brain cancer, a liver cancer (e.g. hepatocellular carcinoma), a stomach cancer, a bladder cancer, a thyroid cancer, an adrenal cancer, a gastrointestinal cancer, an oropharyngeal cancer, an esophageal cancer, a head and neck cancer, an ovarian cancer, a uterine cancer, a cervical cancer, an endometrial cancer, a breast cancer, a melanoma, a prostate cancer, a pancreatic carcinoma, a renal carcinoma, a sarcoma, a leukemia, a Merkel-cell carcinoma, a lymphoma (e.g. Hodgkin lymphoma, non-Hodgkin lymphoma), and a multiple myeloma.

In a second embodiment of the forty-first aspect and of the first embodiment thereof, the method for treating an individual suffering from a cancer further comprises administering one or more additional cancer therapies. In some embodiments, the one or more additional cancer therapies comprises radiation therapy, surgery, a chemotherapy, or an immunotherapy (for example, without limitation, an immunomodulator, an immune checkpoint inhibitor, a cellular immunotherapy, or a cancer vaccine). In some embodiments, the one or more additional cancer therapies comprises an inactivated tumor cell that expresses and secretes one or more cytokines or one or more heat shock proteins. In some embodiments, the cytokine is selected from the group consisting of GM-CSF, CCL20, CCL3, IL-12p70, and FLT-3 ligand. In some embodiments the heat shock protein is a gp96-Ig protein. In some embodiments, the method comprises administering one or more additional cancer therapies selected from the group consisting of a chemotherapeutic agent; an immune checkpoint inhibitor; a TLR agonist; a vaccine selected to stimulate an immune response to one or more cancer antigens, a therapeutic antibody that induces antibody-dependent cellular cytotoxicity; an immunomodulatory cell line; an inactivated or attenuated bacteria that induces innate immunity; an antigen selected for the purpose of inducing an immune response, and a composition that mediates innate immune activation via Toll-like Receptors (TLRs), (NOD)-like receptors (NLRs), Retinoic acid inducible gene-based (RIG)-I-like receptors (RLRs), C-type lectin receptors (CLRs) or pathogen-associated molecular patterns ("PAMPs"). In some embodiments, the immune checkpoint inhibitor is an anti-PD-1 antibody, an anti-PD-L1 antibody, an anti-CTLA-4 antibody, an anti-TIM-3 antibody, an anti-BTLA antibody or an anti-LAG-3 antibody. In some embodiments, the TLR agonist is CpG or monophosphoryl lipid A. In some embodiments, the therapeutic antibody that induces antibody-dependent cellular cytotoxicity is rituximab, ibritumomab, tositumomab, cetuximab, trastuzumab, brentuximab vedotin, alemtuzumab, oncolym, ibilimumab, vitaxin, or bevacizumab.

In some embodiments of the forty-first aspect and first and second embodiments thereof, the individual suffers from a cancer expressing a cancer antigen, and the method for treating said individual further comprises administering to the individual a primary therapy to remove or kill cancer cells expressing the cancer antigen, wherein the administration of the primary therapy is simultaneously with, prior to or following administration of the LNA-CDN compound or composition thereof. In some embodiments, the LNA-CDN compound or composition thereof is administered as a neoadjuvant therapy to the primary therapy. In preferred embodiments, the LNA-CDN compound or composition thereof is administered following the primary therapy. In some embodiments, the primary therapy comprises surgery to remove the cancer cells from the mammal, radiation therapy to kill the cancer cells in the mammal, or both surgery and radiation therapy.

In a forty-second aspect, the invention provides a method of treating a disease in an individual, comprising administering to the individual in need thereof i) an effective amount of one or more LNA-CDN compounds, as described in the first through thirty-eighth aspects and any embodiments thereof as described herein above, including any prodrugs, pharmaceutically acceptable salts, pharmaceutically acceptable solvates, or pharmaceutically acceptable hydrates thereof, or compositions thereof as described in the thirty-ninth and fortieth aspects and any embodiments thereof as described herein above; and ii) an effective amount of one or more therapeutic antibodies that induce antibody-dependent cellular cytotoxicity, wherein the disease is selected from the group consisting of a cancer, acute rejection of an organ transplant, Type I diabetes mellitus, rheumatoid arthritis, psoriasis, Crohn's disease, restenosis and allergic asthma. In some embodiments, the cancer is selected from the group consisting of lymphoma (e.g. B-cell lymphoma), breasts cancer, chronic lymphocytic leukemia, colorectal cancer, melanoma, non-small cell lung carcinoma, small cell lung cancer, bladder cancer, prostate cancer and other solid tumors. In some embodiments, the therapeutic antibody is selected from the group consisting of muromonab-CD3, infliximab, daclizumab, omalizumab, abciximab, rituximab, ibritumomab, tositumomab, cetuximab, trastuzumab, brentuximab vedotin, alemtuzumab, oncolym, ibilimumab, vitaxin, and bevacizumab.

In a forty-third aspect, the invention provides a method for the treatment of disorders in which shifting of Th1 to Th2 immunity confers clinical benefit, wherein the method comprises administering to the individual in need thereof one or more LNA-CDN compounds, as described in the first through thirty-eighth aspects and any embodiments thereof as described herein above, including any prodrugs, pharmaceutically acceptable salts, pharmaceutically acceptable solvates, or pharmaceutically acceptable hydrates thereof, or compositions thereof as described in the thirty-ninth and fortieth aspects and any embodiments thereof as described herein above. Cell-mediated immunity (CMI) is associated with TH1 CD4+ T lymphocytes producing cytokines IL-2, interferon (IFN)-γ and tumor necrosis factor (TNF)-α. In contrast, humoral immunity is associated with TH2 CD4+ T lymphocytes producing IL-4, IL-6 and IL-10. Immune deviation towards TH1 responses typically produces activation of cytotoxic T-cell lymphocytes (CTL), natural killer (NK) cells, macrophages and monocytes. Generally, Th1 responses are more effective against intracellular pathogens (viruses and bacteria that are inside host cells) and tumors, while Th2 responses are more effective against extracellular bacteria, parasites including helminths and toxins. In addition, the activation of innate immunity is expected to normalize the T-helper type 1 and 2 (Th1/Th2) immune system balance and to suppress the excessive reaction of Th2 type responses that cause immunoglobulin (Ig) E-dependent allergies and allergic asthma.

In a forty-fourth aspect, the invention provides a method for treating an individual suffering from a chronic infectious disease, wherein the method comprises administering to the individual in need thereof an effective amount of one or more LNA-CDN compounds, as described in the first through thirty-eighth aspects and any embodiments thereof as described herein above, including any prodrugs, pharmaceutically acceptable salts, pharmaceutically acceptable solvates, or pharmaceutically acceptable hydrates thereof, or compositions thereof as described in the thirty-ninth and fortieth aspects and any embodiments thereof as described herein above. In some embodiments, the one or more LNA-CDN compounds or composition thereof is administered in combination with another agent for use in treating the chronic infectious disease. In some embodiments, the chronic infectious disease is selected from the group consisting of HBV infection, HCV infection, HPV infection, HSV infection and hepatocellular cancer.

The LNA-CDN compounds, as described in the first through thirty-eighth aspects and any embodiments thereof as described herein above, including any prodrugs, pharmaceutically acceptable salts, pharmaceutically acceptable solvates, or pharmaceutically acceptable hydrates thereof, or compositions thereof as described in the thirty-ninth and fortieth aspects and any embodiments thereof as described herein above, may be administered to individuals in need thereof, as described in the methods of the forty-first through forty-fourth aspects and any embodiments thereof as described herein above, by a variety of parenteral and non-parenteral routes in formulations containing pharmaceutically acceptable excipients (e.g. carriers, adjuvants, vehicles and the like). Preferred non-parenteral routes include mucosal (e.g., oral, vaginal, nasal, cervical, etc.) routes. Preferred parenteral routes include but, are not limited to, one or more of subcutaneous, intravenous, intramuscular, intraarterial, intradermal, intrathecal and epidural administrations. Preferably administration is by subcutaneous, intra-tumoral or peri-tumoral routes.

The LNA-CDN compounds, as described in the first through thirty-eighth aspects and any embodiments thereof as described herein above, including any prodrugs, pharmaceutically acceptable salts, pharmaceutically acceptable solvates, or pharmaceutically acceptable hydrates thereof, or compositions thereof as described in the thirty-ninth and fortieth aspects and any embodiments thereof as described herein may be co-administered to individuals in need thereof, as described in the methods of the forty-first through forty-fourth aspects and any embodiments thereof as described herein above, with one or more additional pharmaceutically active components such as adjuvants, lipids, interbilayer crosslinked multilamellar vesicles, biodegradeable poly(D,L-lactic-co-glycolic acid) [PLGA]-based or poly anhydride-based nanoparticles or microparticles, and nanoporous particle-supported lipid bilayers, immune checkpoint inhibitors (e.g. CTLA-4, PD-1, Tim-3, Vista, BTLA, LAG-3 and TIGIT pathway antagonists; PD-1 pathway blocking agents; PD-L1 inhibitors; including without limitation anti-PD-1 antibodies nivolumab, pembrolizumab or pidilizumab; PD-1 inhibitor AMP-224; anti-CTLA-4 antibody ipilimumab; and anti-PD-L1 antibodies BMS-936559, MPDL$_{3280}$A, MEDI4736, or avelumab), inactivated or attenuated bacteria which induce innate immunity (e.g., inactivated or attenuated *Listeria monocytogenes*), compositions which mediate innate immune activation via Toll-like Receptors (TLRs), (NOD)-like receptors (NLRs), Retinoic acid inducible gene-based (RIG)-I-like receptors (RLRs), C-type lectin receptors (CLRs), or pathogen-associated molecular patterns ("PAMPs"), or chemotherapeutic agents.

In a forty-fifth aspect, the invention provides one or more LNA-CDN compounds, as described in the first through thirty-eighth aspects and any embodiments thereof as described herein above, including any prodrugs, pharmaceutically acceptable salts, pharmaceutically acceptable solvates, or pharmaceutically acceptable hydrates thereof, or compositions thereof as described in the thirty-ninth and fortieth aspects and any embodiments thereof as described herein above, for use as adjuvants in combination with a therapeutic or prophylactic vaccine. In some embodiments, the vaccine is selected to stimulate an immune response to one or more predetermined antigens. In some embodiments, the vaccine comprises one or more antigens, including a recombinant protein antigen related to an infectious disease, a malignancy, or an allergen. In some embodiments, the one or more LNA-CDN compound or composition thereof is used simultaneously with, prior to or following the vaccine. In some embodiments, the one or more LNA-CDN compound or composition thereof is formulated in the same composition as the vaccine.

In a first embodiment of the forty-fifth aspect, the vaccine comprises an inactivated or attenuated bacteria or virus comprising the one or more antigens of interest, one or more purified antigens, live viral or bacterial delivery vectors recombinantly engineered to express and/or secrete the one or more antigens, antigen presenting cell (APC) vectors comprising cells that are loaded with the one or more antigens or transfected with a composition comprising a nucleic acid encoding the one or more antigens, liposomal antigen delivery vehicles, or naked nucleic acid vectors encoding the one or more antigens. In some embodiments, the vaccine is an anti-bacterial, anti-viral, or anti-cancer therapeutic or prophylactic vaccine. In some embodiments, the one or more antigens is one or more antigens selected from the group consisting of a viral antigen, a bacterial antigen and a cancer antigen.

In some embodiments of the forty-fifth aspect and first embodiment thereof, the vaccine comprises an inactivated tumor cell that expresses and secretes one or more cytokines. In some embodiments, the cytokine is selected from the group consisting of GM-CSF, CCL20, CCL3, IL-12p70, and FLT-3 ligand.

In some embodiments of the forty-fifth aspect and first embodiment thereof, the vaccine comprises an inactivated tumor cell that expresses and secretes one or more heat shock proteins. In some embodiments, the heat shock protein is gp96-Ig fusion protein.

In a forty-sixth aspect, the invention provides one or more LNA-CDN compounds, as described in the first through thirty-eighth aspects and any embodiments thereof as described herein above, including any prodrugs, pharmaceutically acceptable salts, pharmaceutically acceptable solvates, or pharmaceutically acceptable hydrates thereof, or compositions thereof as described in the thirty-ninth through fortieth aspects and any embodiments thereof as described herein above, for use in treating a disease or indication as described in any of the forty-first through forty-fifth aspects and any embodiments thereof as described herein above. In a preferred embodiment, the one or more LNA-CDN compounds are for use in treating a cancer. In some embodiments, the cancer is selected from the group consisting of a colorectal cancer, an aero-digestive squamous cancer, a lung cancer, a brain cancer, a liver cancer, a stomach cancer, a bladder cancer, a thyroid cancer, an adrenal cancer, a gastrointestinal cancer, an oropharyngeal cancer, an esophageal cancer, a head and neck cancer, an ovarian cancer, a uterine cancer, a cervical cancer, an endometrial cancer, a breast cancer, a melanoma, a prostate cancer, a pancreatic carcinoma, a renal carcinoma, a sarcoma, a leukemia, a Merkelcell carcinoma, a lymphoma and a multiple myeloma.

In a forty-seventh aspect, the invention provides one or more LNA-CDN compounds, as described in the first through thirty-eighth aspects and any embodiments thereof as described herein above, including any prodrugs, pharmaceutically acceptable salts, pharmaceutically acceptable solvates, or pharmaceutically acceptable hydrates thereof, or compositions thereof as described in the thirty-ninth and fortieth aspects and any embodiments thereof as described herein above, for use the preparation of a medicament for the treatment of a disease or indication as described in any of the forty-first through forty-fifth aspects and any embodiments thereof as described herein above. In a preferred embodiment, the one or more LNA-CDN compounds are for use in preparation of a medicament for the treatment of a cancer. In some embodiments, the cancer is selected from the group consisting of a colorectal cancer, an aero-digestive squamous cancer, a lung cancer, a brain cancer, a liver cancer, a stomach cancer, a bladder cancer, a thyroid cancer, an adrenal cancer, a gastrointestinal cancer, an oropharyngeal cancer, an esophageal cancer, a head and neck cancer, an ovarian cancer, a uterine cancer, a cervical cancer, an endometrial cancer, a breast cancer, a melanoma, a prostate cancer, a pancreatic carcinoma, a renal carcinoma, a sarcoma, a leukemia, a Merkel-cell carcinoma, a lymphoma and a multiple myeloma.

In a forty-eighth aspect, the invention provides a kit that includes one or more LNA-CDN compounds, as described in the first through thirty-eighth aspects and any embodiments thereof as described herein above, including any prodrugs, pharmaceutically acceptable salts, pharmaceutically acceptable solvates, or pharmaceutically acceptable hydrates thereof, or compositions thereof as described in the thirty-ninth and fortieth aspects and any embodiments thereof as described herein above. In some embodiments, one or more LNA-CDN compounds or compositions thereof is packaged, e.g., in a vial, bottle or similar container, which may be further packaged, e.g., within a box, envelope, or similar container. In some embodiments, one or more LNA-CDN compounds or compositions thereof is approved by the U.S. Food and Drug Administration or similar regulatory agency for administration to a mammal, e.g., a human. In one embodiment, such a kit includes written instructions for use and/or other indication that the one or more LNA-CDN compounds or compositions thereof is suitable or approved for administration to a mammal, e.g., a human, for a suitable disease or condition. In some embodiments, the compound or composition is packaged in unit dose or single dose form, e.g., single dose pills, capsules, or the like.

BRIEF DESCRIPTION OF THE FIGURES

FIG. 4A-C depicts relative expression of IL-6 by $STING^{WT/WT}$ (4A), $STING^{HAQ/HAQ}$ (4B), and $STING^{REF/REF}$ (4C) in human PBMCs at 2 hours following stimulation with 10 μM or 100 μM of LNA-CDN Compounds 5a and 5b.

FIG. 6A-C depicts relative expression of IFNβ by $STING^{WT/WT}$ (6A), $STING^{HAQ/HAQ}$ (6B), and $STING^{REF/REF}$ (6C) in human PBMCs at 2 and 6 hours following stimulation with 10 μM or 100 μM of LNA-CDN Compounds 5a and 15a.

FIG. 7A-C depicts relative expression of TNFα by $STING^{WT/WT}$ (7A), $STING^{HAQ/HAQ}$ (7B), and $STING^{REF/REF}$ (7C) in human PBMCs at 2 and 6 hours following stimulation with 10 μM or 100 μM of LNA-CDN Compounds 5a and 15a.

FIG. 8A-C depicts relative expression of IFNγ by $STING^{WT/WT}$ (8A), $STING^{HAQ/HAQ}$ (8B), and $STING^{REF/REF}$ (8C) in human PBMCs at 2 and 6 hours following stimulation with 10 μM or 100 μM of LNA-CDN Compounds 5a and 15a.

FIG. 9A-C depicts relative expression of IL-6 by $STING^{WT/WT}$ (9A), $STING^{HAQ/HAQ}$ (9B), and $STING^{REF/REF}$ (9C) in human PBMCs at 2 and 6 hours following stimulation with 10 μM or 100 μM of LNA-CDN Compounds 5a and 15a.

FIG. 10A-C depicts relative expression of IL-12p35 by $STING^{WT/WT}$ (10A), $STING^{HAQ/HAQ}$ (10B), and $STING^{REF/REF}$ (10C) in human PBMCs at 2 and 6 hours following stimulation with 10 μM or 100 μM of LNA-CDN Compounds 5a and 15a.

DETAILED DESCRIPTION OF THE INVENTION

Figure 1C:
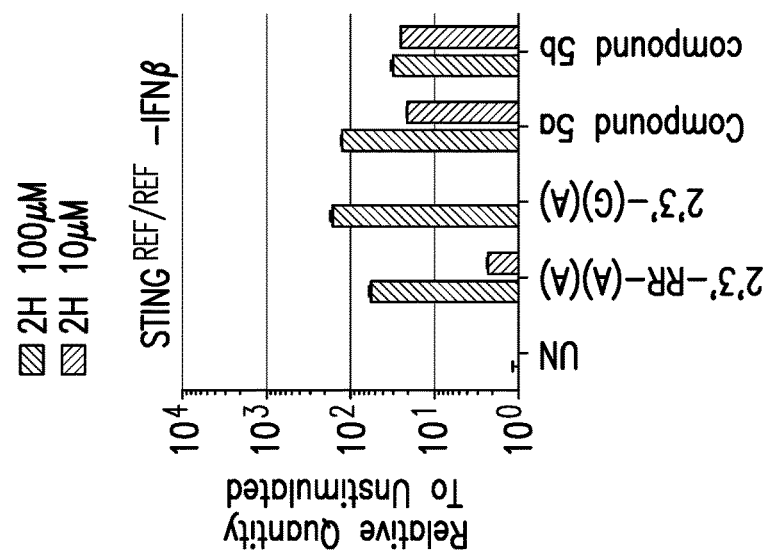
FIG. 1A-C depicts relative expression of IFNβ by $STING^{WT/WT}$ (1A), $STING^{HAQ/HAQ}$ (1B), and $STING^{REF/REF}$ (1C) in human PBMCs at 2 hours following stimulation with 10 μM or 100 μM of LNA-CDN Compounds 5a and 5b.

The present invention relates to the production and use of locked nucleic acid cyclic-di-nucleotide (LNA-CDN) immune stimulators that activate DCs via a cytoplasmic receptor known as STING (Stimulator of Interferon Genes).

Conserved microbial structures known as Pathogen-Associated Molecular Patterns (PAMPs) are sensed by host cell Pattern Recognition Receptors (PRRs with germ-line encoded specificity), triggering a downstream signaling cascade resulting in the induction of cytokines and chemokines, and initiation of a specific adaptive immune response (Iwasaki and Medzhitov, Science 327, 291-5, 2010). How the innate immune system is engaged by PAMPs presented from an infectious agent shapes the development of an adaptive response appropriate to combat the invading pathogen from causing disease.

One objective in the design of immune modulators and adjuvants is to select defined PAMPs or synthetic molecules which activate designated PRRs and initiate a desired response. Adjuvants such as monophosphoryl lipid A (MPL) and CpG are microbial-derived PAMPs recognized by Toll-like receptors (TLRs), a class of PRRs that signal through MyD88 and TRIF adaptor molecules and mediate induction of NF-kB dependent proinflammatory cytokines (Pandey et. al., Cold Spring Harb Perspect Biol 2015; 7: a016246). MPL (TLR-4 agonist) and CpG (TLR-9 agonist) are the most clinically advanced adjuvants, and are components of vaccines that are approved or pending approval by the FDA (Einstein et al., Human Vaccines, 5: 705-19, 2009; Ahmed et al., Nature Immunol. 12: 509-17, 2011). While TLRs present on the cell surface (e.g., TLR-4) and endosomes (e.g., TLR-9) sense extracellular and vacuolar pathogens, the productive growth cycle of multiple pathogens including viruses and intracellular bacteria occurs in the cytosol. The compartmentalization of extracellular, vacuolar, and cytosolic PRRs has led to the hypothesis that the innate immune system can sense productively replicating pathogenic microbes by monitoring the cytosol (Vance et al., Cell Host & Microbe 6: 10-21, 2009). This provides a rationale for the use of agonists that activate PRRs comprising the cytosolic surveillance pathway and may be an effective strategy for the design of effective vaccines for eliciting cellular immunity, an immune correlate of protection against intracellular pathogens and therapeutic benefit in cancer.

Type I interferons (IFN-$\alpha$, IFN-($\beta$) are the signature cytokines induced by two distinct TLR-independent cytosolic signaling pathways. In the first pathway, various forms of single-stranded and double-stranded (ds) RNA are sensed by RNA helicases, including retinoic acid-inducible gene I (RIG-I) and melanoma differentiation-associated gene 5 (MDA-5), and through the IFN-$\beta$ promoter stimulator 1 (IPS-1) adaptor protein mediate phosphorylation of the IRF-3 transcription factor, leading to induction of IFN-$\beta$ (Ireton and Gale, Viruses 3: 906-19, 2011). IPS-1$^{-/-}$ deficient mice have increased susceptibility to infection with RNA viruses. Sensors that signal through the IPS-1 pathway are directly targeted for inactivation by various viral proteins, demonstrating a requirement of this cytosolic host defense pathway to control productive virus infection. Synthetic dsRNA, such as polyinosinic:polycytidylic acid (poly (I:C) and poly ICLC, an analog that is formulated with poly L lysine to resist RNase digestion, is an agonist for both TLR3 and MDAS pathways, is a powerful inducer of IFN-$\beta$, and is currently being evaluated in several diverse clinical settings (Caskey et al., J. Exp. Med. 208: 2357-77, 2011).

STING (Stimulator of Interferon Genes) is a central mediator for the second cytosolic pathway that triggers type 1 interferon, in response to sensing cytosolic double-stranded (ds) DNA from infectious pathogens or aberrant host cells (Danger Associated Molecular Patterns, DAMPS) (Barber, Immunol. Rev 243: 99-108, 2011). Alternatively known as TMEM173, MITA, ERIS, and MPYS, STING was discovered using cDNA expression cloning methods as a MyD88-independent host cell defense factor expressed in macrophages, dendritic cells (DCs) and fibroblasts was found to induce expression of IFN-$\beta$ and NF-$\kappa$B dependent pro-inflammatory cytokines in response to sensing cytoplasmic DNA, in response to infection with herpes simplex virus (Ishikawa and Barber, Nature 455: 674-79, 2008).

Cyclic dinucleotides (CDNs) have been studied as ubiquitous small molecule second messengers synthesized by bacteria which regulate diverse processes including motility and formation of biofilms (Romling et al., Micrb. Mol. Biol. Rev., 77: 1-52, 2013). CDNs are also a ligand for STING (Burdette et al., Nature 478: 515-18, 2011). In response to binding CDNs, STING activates signaling through the TBK-1/IRF-3 axis and NF-$\kappa$B axis and induces the expression of IFN-$\beta$ and other co-regulated genes (Burdette and Vance, Nat Immunol. 14: 19-26, 2013; McWhirter et al., J. Exp. Med. 206: 1899-1911, 2009). Cyclic (c)-di-AMP is secreted by multidrug resistance efflux pumps from the intracellular bacterium *Listeria monocytogenes* into the cytosol of infected host antigen presenting cells, and is correlated with $CD4^+$ and $CD8^+$ T cell-mediated protection in the mouse listeriosis model (Woodward et al., Science 328, 1703-05, 2010; Crimmins et al., Proc. Natl. Acad. Sci. USA 105: 10191-10196, 2008). Induction of IFN-$\beta$ in Lm-infected macrophages is dependent upon activation of the STING signaling pathway, and the level of type I IFN induced by c-di-AMP in macrophages from $MyD88^{-/-}$ $Trif^{-/-}$ or C57BL/6 parental mice is indistinguishable (Leber et al., PLoS Pathog 4(1): e6. doi:10.1371, 2008; Witte et al., mBio 4: e00282-13, 2012). In contrast, IFN-$\beta$ is not induced by CDNs in macrophages derived from goldenticket (gt) mice encoding a nonfunctional mutant STING protein (Sauer et al., Infect. Immun. 79: 688-94, 2011). The extracellular bacterium, *Vibrio cholera*, produces a hybrid c-GMP-AMP (cGAMP) molecule, which also induces the STING pathway (Davies et al., Cell 149: 358-70, 2012). The activation of innate immunity with these ubiquitous second messengers suggests that sensing CDNs may be integral to host defense against bacterial infection.

While STING was discovered as being the critical sensor for inducing the production of IFN-$\beta$ in response to infection with herpes simplex virus, how the DNA from this viral pathogen was detected in the cytoplasm initially remained elusive. This conundrum was solved with the discovery of cyclic GMP-AMP synthase (cGAS), a host cell nucleotidyl transferase that directly binds dsDNA, and in response synthesizes a second messenger, cyclic GMP-AMP (cGAMP), which activates the STING pathway and induces IFN-$\beta$ expression (Sun et al., Science 339: 786-91, 2013; Wu et al., Science 339: 826-30, 2013). Cells without a functional cGAS are unable to express IFN-$\beta$ in response to stimulation with cytosolic DNA. It was later shown that cells expressing a particular STING allele were non-responsive to stimulation by CDNs, but responsive to stimulation with dsDNA in a cGAS-dependent and TLR9 (MyD88)-independent manner (Diner et. al., 2013). This observation was incompatible with a mechanism defined by cGAS synthesizing STING-activating CDN ligands in response to sensing cytosolic dsDNA. This apparent paradox was resolved by several independent investigators, who demonstrated that cGAS produces a non-canonical CDN (c-GMP-AMP; cGAMP) that activates STING alleles that are non-responsive to canonical CDNs (Civril et al., Nature 498: 332-37, 2013, Diner et al., 2013, Gao et al., 2013, Ablasser et al., Nature 498: 380-84, 2013, Kranzusch et al., Cell Reports 3: 1362-68, 2013, Zhang et al., Mol. Cell. 51: 226-35, 2013). cGAMP thus functions as a second messenger that binds to and activates STING. Unlike the CDN second messengers produced by bacteria, in which the two purine nucleosides are joined by a phosphate bridge with bis-(3', 5') linkages, the internucleotide phosphate bridge in the cyclic-GMP-AMP synthesized by cGAS is joined by non-canonical 2',5' and 3',5' linkages (alternatively termed "mixed" linkages or ML), represented c[G(2',5')pA(3',5')p]. These 2',5'-3',5' molecules bind STING with nM affinity, some 300-fold better than bacterial c-di-GMP. Thus, it has been suggested that the 2',5'-3',5' molecules represent much more potent physiological ligands in terms of STING targeting. Zhang et al., 2013; see also, Xiao and Fitzgerald, Mol. Cell 51: 135-39, 2013. The differences in internucleotide phosphate bridge structures between CDNs produced by bacteria [canonical bis-(3', 5') linkages] and by host cell cGAS (non-canonical 2',5' and 3',5' linkages) indicates that the STING receptor evolved to distinguish between CDNs produced by bacteria or by host cell cGAS. The LNA-CDN compounds as described herein demonstrate high potency, in some instances even more potent than the natural 2'5'-3'5' cGAMP ligand, or other known mixed linkage CDNs such as 2'3'-RR-(A)(A), and provide STING activating compounds for therapeutic use.

Human STING has known polymorphisms, including alleles encoding histidine at position 232, which are refractory to canonical CDNs, but not non-canonical CDNs (Diner et al., 2013, Jin et al., 2011). Single nucleotide polymorphisms in the hSTING gene have been shown to affect the responsiveness to bacterial-derived canonical CDNs (Diner et al., 2013; Gao et al., 2013; Conlon et. al., 2013). Five haplotypes of hSTING have been identified (WT, REF, HAQ, AQ and Q alleles), which vary at amino acid positions 71, 230, 232 and 293 (Jin et al., 2011; $Y_1$ et al., 2013). Cells expressing hSTING reportedly respond poorly to stimulation with bacterial CDNs cGAMP, c-di-AMP and c-di-GMP having bis-(3', 5') linkages, but are responsive to the endogenously produced cGAS product, ML cGAMP (Diner et al., 2013). Therefore, the published literature indicates that for broad activation of all human STING alleles it is desirable that the CDN internucleotide phosphate bridge have a non-canonical, mixed linkage c[G(2',5')pA(3',5')p] structure. Examples of cyclic purine dinucleotides are described in some detail in, e.g., U.S. Pat. Nos. 7,709,458 and 7,592,326; WO2007/054279, WO2014/093936, and WO2014/189805; and Yan et al., Bioorg. Med. Chem Lett. 18: 5631 (2008).

Native CDN molecules are sensitive to degradation by phosphodiesterases that are present in host cells, for example in antigen presenting cells, which take up vaccine formulations that contain said native CDN molecules. The potency of a defined adjuvant may be diminished by such degradation, as the adjuvant would be unable to bind and activate its defined PRR target. Lower adjuvant potency could be measured, for example by a lower amount of induced expression of a signature molecule of innate immunity (e.g., IFN-(3), correlated with weaker vaccine potency, as defined by the magnitude of a measured antigen-specific immune response.

Definitions

Compounds of this invention include those described generally above, and are further illustrated by the classes, subclasses, and species disclosed herein. As used herein, the following definitions shall apply unless otherwise indicated. The abbreviations used herein have their conventional meaning within the chemical and biological arts. The chemical structures and formulae set forth herein are constructed according to the standard rules of chemical valency known in the chemical arts.

Unless otherwise stated or depicted, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C— or $^{14}$C-enriched carbon are within the scope of this invention. Such compounds are useful, for example, as analytical tools, as probes in biological assays, or as therapeutic agents in accordance with the present invention.

The term "alkyl" as used herein, by itself or as part of another substituent, refers to, unless otherwise indicated, a saturated straight or branched chain hydrocarbon radical having from 1 to 24 carbon atoms (i.e. $C_{1-24}$alkyl), from 1 to 20 carbon atoms (i.e. $C_{1-20}$alkyl), from 1 to 14 carbon atoms (i.e. $C_{1-14}$alkyl), from 1 to 12 carbon atoms (i.e. $C_{1-12}$alkyl), from 1 to 10 carbon atoms (i.e. $C_{1-10}$alkyl), from 1 to 8 carbon atoms (i.e. $C_{1-8}$alkyl), from 1 to 6 carbon atoms (i.e. $C_{1-6}$alkyl), or from 1 to 4 carbon atoms (i.e. $C_{1-4}$alkyl). Unless indicated otherwise, more preferred alkyl groups are $C_{1-6}$alkyl. Examples of alkyl radicals include, but are not limited to, methyl, ethyl, n-propyl, isopropyl, n-butyl, tert-butyl, iso-butyl, sec-butyl, n-pentyl, n-hexyl, n-heptyl, n-octyl, n-nonyl, n-decyl, n-undecyl, n-dodecyl, and the like, including any isomers thereof. Where it is indicated that alkyl is optionally substituted with one or more substituents, one or more is typically 1, 2, 3, 4, or 5; 1, 2, 3, or 4; 1, 2, or 3; 1 or 2; or 1, where multiple substituents are independently selected unless indicated otherwise. It is understood that any substitutions of alkyl, or alkyl substituted on another moiety, are attached at any available atom to provide a stable compound.

The term "alkenyl" as used herein, by itself or as part of another substituent, refers to a straight or branched chain hydrocarbon radical that is unsaturated or polyunsaturated so as to have at least one double bond, for example one, two, three or more double bonds, and having from 2 to 24 carbon atoms (i.e. $C_{2-24}$alkenyl). In some embodiments, alkenyl includes from 2 to 24 carbon atoms ($C_{2-24}$alkenyl), from 2 to 20 carbon atoms (i.e. $C_{2-20}$alkenyl), from 2 to 14 carbon atoms (i.e. $C_{2-14}$alkenyl), from 2 to 12 carbon atoms (i.e. $C_{2-12}$alkenyl), from 2 to 10 carbon atoms (i.e. $C_{2-10}$alkenyl), from 2 to 8 carbon atoms (i.e. $C_{2-8}$alkenyl), or from 2 to 6 carbon atoms (i.e. $C_{2-6}$alkenyl) having 1 to 3 double bonds, or from 2 to 4 carbon atoms (i.e. $C_{2-4}$alkenyl) having 1 or 2 double bonds. Unless indicated otherwise, more preferred alkenyl groups are $C_{2-6}$alkenyl, and having 1 to 3 double bonds, 1 to 2 double bonds, or preferably 1 double bond. Exemplary "alkenyl" groups include vinyl, propenyl, (E)- but-1-enyl, (Z)-but-1-enyl, (E)-but-2-enyl, but-3-enyl, (E)-buta-1,3-dienyl, (E)-penta-2,4-dienyl, (2E,4E,6E)-octa-2,4,6-trienyl and the like, including any isomers thereof. Where it is indicated that alkenyl is optionally substituted with one or more substituents, one or more is typically 1, 2, 3, 4, or 5; 1, 2, 3, or 4; 1, 2, or 3; 1 or 2; or 1, where multiple substituents are independently selected unless indicated otherwise. It is understood that any substitutions of alkenyl, or alkenyl substituted on another moiety, are attached at any available atom to provide a stable compound.

The term "alkynyl" as used herein, by itself or as part of another substituent, refers to a straight or branched chain hydrocarbon radical that is unsaturated or polyunsaturated so as to have at least one triple bond, for example one, two, three or more triple bonds, and having from 2 to 24 carbon atoms (i.e. $C_{2-24}$alkynyl). In some embodiments, alkynyl includes from 2 to 24 carbon atoms ($C_{2-24}$alkynyl), from 2 to 20 carbon atoms (i.e. $C_{2-20}$alkynyl), from 2 to 14 carbon atoms (i.e. $C_{2-14}$alkynyl), from 2 to 12 carbon atoms (i.e. $C_{2-12}$alkynyl), from 2 to 10 carbon atoms (i.e. $C_{2-10}$alkynyl), from 2 to 8 carbon atoms (i.e. $C_{2-8}$alkynyl), or from 2 to 6 carbon atoms (i.e. $C_{2-6}$alkynyl) having 1 to 3 triple bonds, or from 2 to 4 carbon atoms (i.e. $C_{2-4}$alkynyl) having 1 or 2 triple bonds. Unless indicated otherwise, more preferred alkynyl groups are $C_{2-6}$alkynyl, and having 1 to 3 triple bonds, 1 to 2 triple bonds, or preferably 1 triple bond. Exemplary "alkynyl" groups include prop-1-ynyl, prop-2-ynyl (propargyl), ethynyl and 3-butynyl and the like, including any isomers thereof. Where it is indicated that alkynyl is optionally substituted with one or more substituents, one or more is typically 1, 2, 3, 4, or 5; 1, 2, 3, or 4; 1, 2, or 3; 1 or 2; or 1, where multiple substituents are independently selected unless indicated otherwise. It is understood that any substitutions of alkynyl, or alkynyl substituted on another moiety, are attached at any available atom to provide a stable compound.

The term "$C_{1-6}$alkoxy" represents a substituent —O—$C_{1-6}$alkyl, wherein $C_{1-6}$alkyl is as defined herein, and is optionally substituted where indicated. Where it is indicated that the $C_{1-6}$alkyl group within $C_{1-6}$alkoxy is optionally substituted with one or more substituents, one or more is typically 1, 2, 3, 4, or 5, also 1, 2, 3, or 4, also 1, 2, or 3, also 1 or 2, or one, where multiple substituents are independently selected unless indicated otherwise. It is understood that any substitutions of $C_{1-6}$alkoxy, or any $C_{1-6}$alkoxy substituted on another moiety, are attached at any available atom to provide a stable compound.

The terms "$C_{1-6}$alkylthio", "$C_{1-6}$alkylsulfinyl" or "$C_{1-6}$alkylsulfonyl" represent a substituent —S—$C_{1-6}$alkyl, —S(=O)—$C_{1-6}$alkyl or —S(=O)$_2$—$C_{1-6}$alkyl, respectively, wherein $C_{1-6}$alkyl is as defined herein, and is optionally substituted where indicated. Where it is indicated that the $C_{1-6}$alkyl group within $C_{1-6}$alkylthio, $C_{1-6}$alkylsulfinyl or $C_{1-6}$alkylsulfonyl is optionally substituted with one or more substituents, one or more is typically 1, 2, 3, 4, or 5, also 1, 2, 3, or 4, also 1, 2, or 3, also 1 or 2, or one, where multiple substituents are independently selected unless indicated otherwise. It is understood that any substitutions of $C_{1-6}$alkylthio, $C_{1-6}$alkylsulfinyl or $C_{1-6}$alkylsulfonyl, or any $C_{1-6}$alkylthio, $C_{1-6}$alkylsulfinyl or $C_{1-6}$alkylsulfonyl substituted on another moiety, are attached at any available atom to provide a stable compound.

The terms "$C_{1-6}$alkylamino" or "$C_{1-6}$ dialkylamino" represent a substituent —NH—$C_{1-6}$alkyl or —N—($C_{1-6}$alkyl)($C_{1-6}$alkyl), respectively, wherein $C_{1-6}$alkyl is as defined herein, and is optionally substituted where indicated. The two $C_{1-6}$alkyl groups of $C_{1-6}$ dialkylamino may be the same or different. Where it is indicated that the $C_{1-6}$alkyl group within $C_{1-6}$alkylamino or $C_{1-6}$ dialkylamino is optionally substituted with one or more substituents, one or more is typically 1, 2, 3, 4, or 5, also 1, 2, 3, or 4, also 1, 2, or 3, also 1 or 2, or one, where multiple substituents are independently selected unless indicated otherwise. It is understood that any substitutions of $C_{1-6}$alkylamino or $C_{1-6}$ dialkylamino, or any $C_{1-6}$alkylamino or $C_{1-6}$ dialkylamino substituted on another moiety, are attached at any available atom to provide a stable compound.

The terms "halo" or "halogen," by themselves or as part of another substituent, mean at least one of fluorine, chlorine, bromine and iodine. For example the terms "$C_{1-6}$haloalkoxy", "$C_{1-6}$haloalkylthio", "$C_{1-6}$haloalkylsulfinyl", and "$C_{1-6}$haloalkylsulfonyl", mean that the alkyl portion of these substituents is substituted with at least one halogen, such as 1, 2 or 3 halogen. For example, $C_{1-6}$haloalkoxy includes —OCH$_2$CH$_2$F, —OCH$_2$CH$_2$Cl, —OCF$_3$, and the like.

The term "N-linked heterocycloalkyl" by itself or as part of another substituent, means the group —NR$_1$'R$_1$", where R$_1$' and R$_1$" combine with the nitrogen to form a nitrogen linked 5-7 membered heterocycloalkyl monocycle, where the heterocycloalkyl may contain an additional heteroatom within the ring, such as O, N, or S, and is optionally substituted with $C_{1-6}$alkyl. The ring is bound to the group it is a substituent of via the nitrogen. Examples of N-linked-heterocycloalkyl include, but are not limited to, piperidine, piperazine, 4-methylpiperazine, morpholine, and thiomorpholine. Where it is indicated that N-linked-heterocycloalkyl is optionally substituted with one or more substituents, one or more is typically 1, 2, 3, 4 or 5, also 1, 2, 3, or 4, also 1, 2, or 3, also 1 or 2, or one, where multiple substituents are independently selected unless indicated otherwise. It is understood that any substitutions of N-linked-heterocycloalkyl, or N-linked-heterocycloalkyl substituted on another moiety, are attached at any available atom to provide a stable compound.

The term "heteroalkyl" as used herein, by itself or as part of another substituent, refers to a stable, straight or branched chain radical consisting of a number of carbon atoms (e.g., $C_{2-24}$, $C_{2-20}$, $C_{2-14}$, $C_{2-12}$, $C_{2-10}$, $C_{2-8}$, $C_{2-6}$ or $C_{2-4}$) and at least one heteroatom, e.g. 1-7, 1-6, 1-5, 1-4, 1-3, 1-2, or 1 heteroatom independently selected from the group consisting of N, O, S, Si, B and P (preferably N, O and S), wherein the nitrogen, sulfur and phosphorus atoms are optionally oxidized, and the nitrogen atom(s) are optionally quaternized. Typically, a heteroalkyl group will have from 3 to 24 carbon and heteroatoms in a straight or branched chain, excluding hydrogen (3- to 24-membered heteroalkyl), 3 to 12 carbon and heteroatoms (3- to 12-membered heteroalkyl), 3 to 10 carbon and heteroatoms (3- to 10-membered heteroalkyl) or from 3 to 8 carbon and heteroatoms (3- to 8-membered heteroalkyl). The heteroatom(s) is/are placed at any position of the heteroalkyl group. In some embodiments, where more than one heteroatoms are in the heteroalkyl group, the more than one heteroatoms are the same. The heteroalkyl group can be unsaturated or poly unsaturated, i.e. can include at least one, e.g. one, two or three, carbon carbon or carbon nitrogen double bond, or a carbon carbon triple bond. Examples of heteroalkyl groups include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$—S(=O)—CH$_3$, —CH$_2$—CH$_2$—S(=O)$_2$—CH$_3$, —CH=CH—O—CH$_3$, —CH$_2$—Si(CH$_3$)$_3$, —CH$_2$—CH=N—OCH$_3$, and —CH=CH—N(CH$_3$)—CH$_3$. Up to two heteroatoms within heteroalkyl can be consecutive, such as, for example, —CH$_2$—NH—OCH$_3$ and —CH$_2$—O—Si(CH$_3$)$_3$. Heteroalkyl also includes, without limitation, a group comprising polyalkoxy (e.g. polyalkylene glycols), polyamines or polyimines, for example —C$_{0-4}$alkyl-O—(C$_{2-3}$alkyl-O)$_a$—H, —C$_{0-4}$alkyl-O—(C$_{2-3}$alkyl-O)$_a$—C$_{1-4}$alkyl, —C$_{0-4}$alkyl-NH—(C$_{2-3}$alkyl-NH)$_a$—H or —C$_{0-4}$alkyl-NH—(C$_{2-3}$alkyl-NH)$_a$—C$_{1-4}$alkyl, where a is e.g. 2-7, such as —O—(CH$_2$CH(CH$_3$)O)$_a$—H, —O—(CH$_2$CH(CH$_3$)O)$_a$—CH$_3$, —O—(CH$_2$CH(CH$_3$)O)$_a$—CH$_2$CH$_3$, —O—(CH$_2$CH$_2$O)$_a$—H, —O—(CH$_2$CH$_2$O)$_a$—CH$_3$, —O—(CH$_2$CH$_2$O)$_a$—CH$_2$CH$_3$ or the like, —NH—(CH$_2$CH$_2$NH)$_a$—H, —NH—(CH$_2$CH$_2$NH)$_a$—CH$_3$, —NH—(CH$_2$CH$_2$NH)$_a$—CH$_2$CH$_3$ or the like, wherein a is 2-7, 2-6, 2-5, 2-4 or 2-3. Where it is indicated that heteroalkyl is optionally substituted with one or more substituents, one or more is typically 1, 2, 3, 4, or 5; 1, 2, 3, or 4; 1, 2, or 3; 1 or 2; or 1, where multiple substituents are independently selected unless indicated otherwise. Substituents may be bound to any substitutable atom, i.e. carbon or heteroatom. It is understood that any substitutions of heteroalkyl, or heteroalkyl substituted on another moiety, are attached at any available atom to provide a stable compound.

The term "aryl" as used herein, by itself or as part of another substituent, refers to a fully aromatic monocyclic (i.e. phenyl) or polycyclic (e.g. naphthalene, anthracene) carbocyclic ring system having 6 to 14 carbon atoms (C$_{6-14}$ aryl), or 6 to 10 carbon atoms (C$_{6-10}$ aryl), or includes a polycyclic ring system wherein at least one ring is aromatic, e.g. aryl fused to 1 or 2 additional rings. Exemplary polycyclic aryl having at least one aromatic ring include a phenyl ring fused to a carbocyclyl, heterocycloalkyl or heteroaryl ring (e.g., 1 or 2 other rings), wherein such polycyclic aryl ring system is attached to the group it is a substituent of via the aryl (e.g. phenyl) ring portion. In a preferred embodiment, aryl is phenyl. Where it is indicated that aryl is optionally substituted with one or more substituents, one or more is typically 1, 2, 3, 4, or 5; 1, 2, 3, or 4; 1, 2, or 3; 1 or 2; or 1, where multiple substituents are independently selected unless indicated otherwise. Non-limiting examples of aryl groups include phenyl, 1-naphthyl, 2-naphthyl, indanyl, indenyl, dihydronaphthyl, fluorenyl, tetralinyl, chromanyl, isochromanyl, benzo[d][1,3]dioxolyl, 2,3-dihydrobenzo[b][1,4]dioxinyl, and the like. Where it is indicated that aryl is optionally substituted with one or more substituents, one or more is typically 1, 2, 3, 4 or 5, also 1, 2, 3, or 4, also 1, 2, or 3, also 1 or 2, or one, where multiple substituents are independently selected unless indicated otherwise. It is understood that any substitutions of aryl, or aryl substituted on another moiety, are attached at any available atom to provide a stable compound.

The term "carbocyclyl" as used herein, by itself or as part of another substituent, refers to a mono- or polycyclic saturated or unsaturated, non-aromatic carbocyclic radical having from 3 to 24 carbon atoms (i.e. C$_{3-24}$carbocyclyl), also 3 to 12 carbon atoms (i.e., C$_{3-12}$carbocyclyl), 3 to 10 carbon atoms (i.e. C$_{3-10}$carbocyclyl), 3 to 8 carbon atoms (i.e. C$_{3-8}$carbocyclyl) or 3 to 6 carbon atoms (i.e. C$_{3-6}$carbocyclyl). Included within carbocyclyl are fully saturated mono- or polycyclic ring systems referred to as "cycloalkyl", including bridged or spirocyclic polycyclics, for example cycloalkyl includes cyclopropyl, cyclobutyl, cyclopentyl, cyclohexyl, cycloheptyl, bicyclo[2.2.1]heptyl, adamantly, and spiro[4.4]nonanyl, and the like. Also included within carbocyclyl are partially unsaturated mono- or polycyclic non-aromatic ring systems having at least one double bond referred to as "cycloalkenyl", for example 1-cyclohexenyl, 3-cyclohexenyl, and the like. In some instances of the compounds described herein, two substituents on the same carbon atom can form a C$_{3-6}$ cycloalkyl spirocyclic ring (e.g. CRR portion of a ring, where the two R along with the carbon forms a spirocyclic ring). A polycyclic carbocyclyl group includes a cycloalkyl or cycloalkenyl group fused to 1 or 2 other aryl, heterocycloalkyl or heteroaryl rings, wherein such polycyclic carbocyclyl ring system is attached to the group it is a substituent of via the cycloalkyl or cycloalkenyl ring portion. Preferred carbocyclyl groups include monocyclic C$_{3-8}$ cycloalkyl, preferably C$_{3-6}$ cycloalkyl. Where it is indicated that carbocyclyl is optionally substituted with one or more substituents, one or more is typically 1, 2, 3, 4 or 5, also 1, 2, 3, or 4, also 1, 2, or 3, also 1 or 2, or one, where multiple substituents are independently selected unless indicated otherwise. It is understood that any substitutions of carbocyclyl, or carbocyclyl substituted on another moiety, are attached at any available atom to provide a stable compound.

The term "heterocyclyl" as used herein, by itself or as part of another substituent, refers to a mono- or polycyclic saturated or unsaturated, non-aromatic ring having, for example, 3- to 24-members, 3- to 12 members, 3- to 10-members, 3- to 8-members, also 4-, 5-, 6- or 7-members, where 1 to 5 members, 1-4 members, 1-3 members, 1-2 members, or one member of the ring are heteroatoms, e.g., N, O, S, Si, B or P, preferably N, O or S, where the remaining ring atoms are carbon atoms, in stable combinations known to those of skill in the art. The heterocyclyl ring nitrogen, sulfur or phosphorus atoms are optionally oxidized, and the nitrogen atom(s) are optionally quaternized. Included within heterocyclyl are "3-7 membered heterocycloalkyl", "3-6 membered heterocycloalkyl", "4-7 membered heterocycloalkyl", "5-7 membered heterocycloalkyl" or the like which refer to a monocyclic heterocyclic ring having the indicated number of ring atoms (e.g. 3-7 members has 3-, 4-, 5-, 6-, or 7-ring atoms), where 1, 2, or 3 members, 1 or 2 members, or one member is N, O or S, and the remaining ring atoms are carbon atoms. In some instances of the compounds described herein, two substituents on the same carbon atom can form a 3-6 membered heteroycloalkyl spirocyclic ring (e.g. CRR portion of a ring, where the two R along with the carbon forms a spirocyclic ring containing e.g. O or NH). In some preferred embodiments, heterocyclyl is monocyclic 4-7 or 5-7 membered heterocycloalkyl. Heterocyclyl group includes a heterocycloalkyl fused to 1 or 2 other aryl, heteroaryl or cycloalkyl rings, wherein such polycyclic heterocyclyl ring system is attached to the group it is a substituent of via the heterocycloalkyl portion. The point of attachment of heterocycloalkyl to the group it is a substituent of can be via a carbon atom or via a heteroatom. Exemplary heterocycloalkyl groups for compounds described herein (e.g. compounds of Formula I) include morpholinyl, thiomorpholinyl, thiomorpholinyl S-oxide, thiomorpholinyl S,S-dioxide, piperazinyl, homopiperazinyl, pyrrolidinyl, pyrrolinyl, imidazolidinyl, tetrahydropyranyl, piperidinyl, tetrahydrofuranyl, tetrahydrothienyl, homopiperidinyl, homomorpholinyl, homothiomorpholinyl, homothiomorpholinyl S,S-di oxide, oxazolidinonyl, dihydropyrazolyl, dihydropyrrolyl, dihydropyrazolyl, dihydropyridyl, dihydropyrimidinyl, dihydrofuryl, dihydropyranyl, tetrahydrothienyl S-oxide, tetrahydrothienyl S,S-dioxide, homothiomorpholinyl S-oxide, and the like. In one example, heterocycloalkyl is N-linked heterocycloalkyl as defined herein above. Where it is indicated that heterocycloalkyl is optionally substituted with one or more substituents, one or more is typically 1, 2, 3, 4 or 5, also 1, 2, 3, or 4, also 1, 2, or 3, also 1 or 2, or one, where multiple substituents are independently selected unless indicated otherwise. It is understood that any substitutions of heterocycloalkyl, or heterocycloalkyl substituted on another moiety, are attached at any available atom to provide a stable compound.

The term "heteroaryl", by itself or as part of another substituent means, unless otherwise stated, a monocyclic polyunsaturated, 5-, 6- or 7-membered aromatic ring containing at least one heteroatom (e.g., 1 to 5, 1 to 4, 1 to 3, 1 to 2 or 1 heteroatoms) selected from N, O, S, Si and B (in one example N, O and S), and the remaining ring atoms are carbon atoms, in stable combinations known to those of skill in the art; or such 5-, 6- or 7-membered aromatic ring fused to 1 or 2 other aryl, heteroaryl, cycloalkyl or heterocycloalkyl rings. Where heteroaryl includes additional fused rings, the heteroaryl is attached to the group it is a substituent of via the 5-, 6-, or 7-membered heteroaryl portion. Heteroaryl ring nitrogen and sulfur atoms are optionally oxidized, and the nitrogen atom(s) are optionally quatern/zed. The point of attachment of heteroaryl to the group it is a substituent of can be via a carbon atom or a heteroatom (e.g. nitrogen). In one example, the heteroaryl group has from 1 to 10 carbon atoms and from 1 to 5 heteroatoms selected from O, S and N. In some preferred embodiments, the heteroaryl is a "5 or 6 membered heteroaryl", meaning a monocyclic heteroaryl ring having 5- or 6-members, where 1, 2, 3, or 4, also 1, 2 or 3, also 1 or 2, also 1 member(s) is N, O or S. Non-limiting examples of heteroaryl groups include pyridyl, pyrimidinyl, quinolinyl, benzothienyl, indolyl, pryidazinyl, pyrazinyl, isoindolyl, isoquinolinyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, triazolyl, tetrazolyl, isothiazolyl, naphthyridinyl, tetrahydroisoquinolinyl, isoindolinyl, isobenzothienyl, benzoxazolyl, pyridopyridyl, purinyl, benzodioxolyl, triazinyl, pteridinyl, benzothiazolyl, imidazopyridyl, imidazothiazolyl, dihydrobenzisoxazinyl, benzisoxazinyl, benzoxazinyl, dihydrobenzisothiazinyl, benzopyranyl, benzothiopyranyl, chromonyl, tetrahydroquinolinyl, dihydroquinolinyl, and the like. In one example, heteroaryl groups include pyrrolyl, furanyl, thienyl, imidazolyl, pyrazolyl, thiadiazolyl, triazolyl, isoxazolyl, oxazolyl, isothiazolyl, thiazolyl, oxadiazolyl, pyridazinyl, pyrazinyl, pyrimidinyl, and pyridyl. Where it is indicated that heteroaryl is optionally substituted with one or more substituents, one or more is typically 1, 2, 3, 4 or 5, also 1, 2, 3, or 4, also 1, 2, or 3, also 1 or 2, or one, where multiple substituents are independently selected unless indicated otherwise. It is understood that any substitutions of heteroaryl, or heteroaryl substituted on another moiety, are attached at any available atom to provide a stable compound.

As described herein, compounds of the invention may contain "optionally substituted" or "substituted" moieties. Unless indicated otherwise, the "optionally substituted" or "substituted" moiety may be substituted with one or more substituents, such as 1, 2, 3, 4 or 5 substituents, 1, 2, 3 or 4 substituents, 1, 2 or 3 substituents, 1 or 2 substituents, or 1 substituent. Any substitutable position within a moiety can be substituted with a suitable substituent, for example, a substitutable carbon or nitrogen atom within a moiety. When the moiety has more than one substitution, each substituent may be the same or different, i.e. substituents are independently selected from a group of options. More than one substituent may be at the same position within the moiety, for example, where a carbon atom can be substituted by more than one substituent. It is understood that all such substitutions result in a stable or chemically feasible compound.

The terms "suitable oxygen protecting group" or "suitable nitrogen protecting group" refer to protecting groups used during organic synthesis and are known to one skilled in the art, e.g. as described in *Greene's Protective Groups in Organic Synthesis, 4th Edition*, (John Wiley & Sons, Inc.), the disclosure of which is incorporated herein by reference as it relates to nitrogen and oxygen protecting groups. Without limitation, a suitable oxygen protecting group includes silyl protecting groups such as TBS (—Si(CH$_3$)$_2$C(CH$_3$)$_3$), TMS (—Si(CH$_3$)$_3$), TES (—Si(CH$_2$CH$_3$)$_3$), TIPS (—Si(CH(CH$_3$)$_2$)$_3$), TBDPS (—Si(C(CH$_3$)$_3$)(phenyl)$_2$), ester forming protecting groups such as pivalyl (—C(=O)C(CH$_3$)$_3$) and acetyl (—C(=O)CH$_3$), or ether forming protecting groups, such as methyl (—CH$_3$), methoxymethyl (—CH$_2$—O—CH$_3$), t-butyl (—C(CH$_3$)$_3$), allyl (—CH$_2$—CH=CH$_2$), benzyl (—CH$_2$-phenyl) and p-methoxybenzyl (—CH$_2$-(4-methoxy-phenyl)). Without limitation, suitable nitrogen protecting groups include benzyl (—CH$_2$-phenyl), benzoyl (—C(=O)-phenyl), isobutyryl (—C(=O)—CH(CH$_3$)$_2$), acetyl (—C(=O)—CH$_3$), t-butyl formate (—C(=O)OC(CH$_3$)$_2$), and N'N'-dimethylformamidine (=CH—N(CH$_3$)$_2$, i.e. the protected nitrogen is —N=CH—N(CH$_3$)$_2$).

"Administration" as it is used herein with regard to a human, mammal, mammalian subject, animal, veterinary subject, placebo subject, research subject, experimental subject, cell, tissue, organ, or biological fluid, refers without limitation to contact of an exogenous ligand, reagent, placebo, small molecule, pharmaceutical agent, therapeutic agent, diagnostic agent, or composition to the subject, cell, tissue, organ, or biological fluid, and the like. "Administration" can refer, e.g., to therapeutic, pharmacokinetic, diagnostic, research, placebo, and experimental methods. Treatment of a cell encompasses contact of a reagent to the cell, as well as contact of a reagent to a fluid, where the fluid is in contact with the cell. "Administration" also encompasses in vitro and ex vivo treatments, e.g., of a cell, by a reagent, diagnostic, binding composition, or by another cell. By "administered together" or "co-administered" it is not meant to be implied that two or more agents be administered as a single composition. Although administration as a single composition is contemplated by the present invention, such agents may be delivered to a single subject as separate administrations, which may be at the same or different time, and which may be by the same route or different routes of administration. By "administered simultaneously" it is meant to be implied that two or more agents be administered at essentially the same time, although not necessarily administered as a single composition or by the same route of administration.

An "agonist," as it relates to a ligand and receptor, comprises a molecule, combination of molecules, a complex, or a combination of reagents, that stimulates the receptor. For example, an agonist of granulocyte-macrophage colony stimulating factor (GM-CSF) receptor can encompass GM-CSF, a mutant or derivative of GM-CSF, a peptide mimetic of GM-CSF, a small molecule that mimics the biological function of GM-CSF, or an antibody that stimulates GM-CSF receptor.

An "antagonist," as it relates to a ligand and receptor, comprises a molecule, combination of molecules, or a complex, that inhibits, counteracts, downregulates, and/or desensitizes the receptor. "Antagonist" encompasses any reagent that inhibits a constitutive activity of the receptor. A constitutive activity is one that is manifest in the absence of a ligand/receptor interaction. "Antagonist" also encompasses any reagent that inhibits or prevents a stimulated (or regulated) activity of a receptor. By way of example, an antagonist of GM-CSF receptor includes, without implying any limitation, an antibody that binds to the ligand (GM-CSF) and prevents it from binding to the receptor, or an antibody that binds to the receptor and prevents the ligand from binding to the receptor, or where the antibody locks the receptor in an inactive conformation.

The term "antibody" as used herein refers to a peptide or polypeptide derived from, modeled after or substantially encoded by an immunoglobulin gene or immunoglobulin genes, or fragments thereof, capable of specifically binding an antigen or epitope. See, e.g. Fundamental Immunology, 3rd Edition, W. E. Paul, ed., Raven Press, N.Y. (1993); Wilson (1994; J. Immunol. Methods 175:267-273; Yarmush (1992) J. Biochem. Biophys. Methods 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and $CH_1$ domains; (ii) a F(ab')$_2$ fragment, a bivalent fragment comprising two Fab fragments linked by a disulfide bridge at the hinge region; (iii) a Fd fragment consisting of the VH and $CH_1$ domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

By "an agent that enhances permeability" or "an agent that enhances uptake" as used herein as it relates to cell permeability or uptake of compound by cells, is an agent that enhances the permeability of a cell to a compound or enhances the uptake of a compound by the cell, either in vitro, or in vivo. The LNA-CDN compounds as described herein can be compared to a reference compound in an in vitro cell based assay, wherein the assay may be performed with or without an agent, such as digitonin, or by electroporation, that allows for the compound to be taken up by the cell. The LNA-CDN compounds as described herein are surprisingly active in such cell based assays without the need for such an agent that enhances permeability of the cell or enhances uptake of the compound by the cell, for example in the THP-1 cell assay as described herein. Compositions comprising the LNA-CDN compounds as described herein can be formulated without an agent that enhances permeability of the cell or enhances uptake of the compound by the cell, for example without a delivery vehicle that enhances permeability of the cell or enhances cellular uptake. Such additives or delivery vehicles include, without limitation, lipid or lipid-like adjuvants, liposomes, interbilayer cross-linked multilamellar vesicles, nanocarriers, nanoparticles and the like, such as nanoparticles comprising Poly(lactic acid) (PLA), Poly(glycolic acid) (PGA), and/or their copolymers such as biodegradable poly(D,L-lactic-co-glycolic acid) [PLGA]-based or poly anhydride-based nanoparticles or microparticles.

By "substantially purified" with regard to LNA-CDNs of the invention is meant that a specified species accounts for at least 50%, more often accounts for at least 60%, typically accounts for at least 70%, more typically accounts for at least 75%, most typically accounts for at least 80%, usually accounts for at least 85%, more usually accounts for at least 90%, most usually accounts for at least 95%, and conventionally accounts for at least 98% by weight, or greater, of the CDN activity present in a composition. The weights of water, buffers, salts, detergents, reductants, protease inhibitors, stabilizers (including an added protein such as albumin), and excipients are generally not used in the determination of purity.

"Specifically" or "selectively" binds, when referring to a ligand/receptor, nucleic acid/complementary nucleic acid, antibody/antigen, or other binding pair (e.g., a cytokine to a cytokine receptor) (each generally referred to herein as a "target biomolecule" or a "target") indicates a binding reaction which is related to the presence of the target in a heterogeneous population of proteins and other biologics. Specific binding can mean, e.g., that the binding compound, nucleic acid ligand, antibody, or binding composition derived from the antigen-binding site of an antibody, of the contemplated method binds to its target with an affinity that is often at least 25% greater, more often at least 50% greater, most often at least 100% (2-fold) greater, normally at least ten times greater, more normally at least 20-times greater, and most normally at least 100-times greater than the affinity with a non-target molecule.

"Ligand" refers to a small molecule, nucleic acid, peptide, polypeptide, saccharide, polysaccharide, glycan, glycoprotein, glycolipid, or combinations thereof that binds to a target biomolecule. While such ligands may be agonists or antagonists of a receptor, a ligand also encompasses a binding agent that is not an agonist or antagonist, and has no agonist or antagonist properties. Specific binding of a ligand for its cognate target is often expressed in terms of an "Affinity." In preferred embodiments, the ligands of the present invention bind with affinities of between about $10^4$ $M^{-1}$ and about $10^8$ $M^{-1}$. Affinity is calculated as $K_d = k_{off}/k_{on}$ ($k_{off}$ is the dissociation rate constant, $K_{on}$ is the association rate constant and $K_d$ is the equilibrium constant).

Affinity can be determined at equilibrium by measuring the fraction bound (r) of labeled ligand at various concentrations (c). The data are graphed using the Scatchard equation: r/c=K(n−r): where r=moles of bound ligand/mole of receptor at equilibrium; c=free ligand concentration at equilibrium; K=equilibrium association constant; and n=number of ligand binding sites per receptor molecule. By graphical analysis, r/c is plotted on the Y-axis versus r on the X-axis, thus producing a Scatchard plot. Affinity measurement by Scatchard analysis is well known in the art. See, e.g., van Erp et al., J. Immunoassay 12: 425-43, 1991; Nelson and Griswold, Comput. Methods Programs Biomed. 27: 65-8, 1988. In an alternative, affinity can be measured by isothermal titration calorimetry (ITC). In a typical ITC experiment, a solution of ligand is titrated into a solution of its cognate target. The heat released upon their interaction (AH) is monitored over time. As successive amounts of the ligand are titrated into the ITC cell, the quantity of heat absorbed or released is in direct proportion to the amount of binding. As the system reaches saturation, the heat signal diminishes until only heats of dilution are observed. A binding curve is then obtained from a plot of the heats from each injection against the ratio of ligand and binding partner in the cell. The binding curve is analyzed with the appropriate binding model to determine $K_B$, n and AH. Note that $K_B=1/K_d$.

The term "prodrug" as used herein refers to a modification of contemplated compounds, wherein the modified compound exhibits less pharmacological activity (as compared to the modified compound) and wherein the modified compound is converted within the body (e.g., in a target cell or target organ) back into the unmodified form through enzymatic or non-enzymatic reactions. In certain embodiments, the hydroxyl on one ribose comprises a prodrug leaving group. Prodrugs can modify the physicochemical, biopharmaceutic, and pharmacokinetic properties of drugs. Traditional prodrugs are classified as drugs that are activated by undergoing transformation in vivo to form the active drug. Reasons for prodrug development are typically poor aqueous solubility, chemical instability, low oral bioavailability, lack of blood brain barrier penetration, and high first pass metabolism associated with the parent drug. Suitable prodrug moieties are described in, for example, "Prodrugs and Targeted Delivery," J. Rautico, Ed., John Wiley & Sons, 2011. Examples include, but are not limited to, leaving groups removed by cellular esterases, a C6 to C18 fatty acid ester, a myristoyl ester, a pentanoyl ester, a hexanoyl ester, and a heptanoyl ester. For example, the LNA-CDN compounds as described herein wherein one of the nucleotides does not include a locked portion, but has either a 2' hydroxyl or 3'hydroxyl substitutent on the ribose ring can include derivatives at the 2' hydroxyl or 3' hydroxyl, respectively, to form such esters.

The term "subject" or "individual" as used herein refers to a human or non-human organism. Thus, the methods and compositions described herein are applicable to both human and veterinary disease. In certain embodiments, subjects are "patients," i.e., living humans that are receiving medical care for a disease or condition. This includes persons with no defined illness who are being investigated for signs of pathology. Preferred are subjects who have an existing diagnosis of a particular cancer which is being targeted by the compositions and methods of the present invention. Preferred cancers for treatment with the compositions described herein include, but are not limited to prostate cancer, renal carcinoma, melanoma, pancreatic cancer, cervical cancer, ovarian cancer, colon cancer, head & neck cancer, lung cancer and breast cancer.

"Therapeutically effective amount" is defined as an amount of a reagent or pharmaceutical composition that is sufficient to show a patient benefit, i.e., to cause a decrease, prevention, or amelioration of the symptoms of the condition being treated. When the agent or pharmaceutical composition comprises a diagnostic agent, a "diagnostically effective amount" is defined as an amount that is sufficient to produce a signal, image, or other diagnostic parameter. Effective amounts of the pharmaceutical formulation will vary according to factors such as the degree of susceptibility of the individual, the age, gender, and weight of the individual, and idiosyncratic responses of the individual. "Effective amount" encompasses, without limitation, an amount that can ameliorate, reverse, mitigate, prevent, or diagnose a symptom or sign of a medical condition or disorder or a causative process thereof. Unless dictated otherwise, explicitly or by context, an "effective amount" is not limited to a minimal amount sufficient to ameliorate a condition.

"Treatment" or "treating" (with respect to a condition or a disease) is an approach for obtaining beneficial or desired results including and preferably clinical results. For purposes of this invention, beneficial or desired results with respect to a disease include, but are not limited to, one or more of the following: improving a condition associated with a disease, curing a disease, lessening severity of a disease, delaying progression of a disease, alleviating one or more symptoms associated with a disease, increasing the quality of life of one suffering from a disease, and/or prolonging survival. Likewise, for purposes of this invention, beneficial or desired results with respect to a condition include, but are not limited to, one or more of the following: improving a condition, curing a condition, lessening severity of a condition, delaying progression of a condition, alleviating one or more symptoms associated with a condition, increasing the quality of life of one suffering from a condition, and/or prolonging survival. For instance, in embodiments where the compositions described herein are used for treatment of cancer, the beneficial or desired results include, but are not limited to, one or more of the following: reducing the proliferation of (or destroying) neoplastic or cancerous cells, reducing metastasis of neoplastic cells found in cancers, shrinking the size of a tumor, decreasing symptoms resulting from the cancer, increasing the quality of life of those suffering from the cancer, decreasing the dose of other medications required to treat the disease, delaying the progression of the cancer, and/or prolonging survival of patients having cancer. Depending on the context, "treatment" of a subject can imply that the subject is in need of treatment, e.g., in the situation where the subject comprises a disorder expected to be ameliorated by administration of a reagent.

"Vaccine" encompasses preventative vaccines. Vaccine also encompasses therapeutic vaccines, e.g., a vaccine administered to a mammal that comprises a condition or disorder associated with the antigen or epitope provided by the vaccine.

Locked Nucleic Acid Cyclic Dinucleotides

Prokaryotic as well as eukaryotic cells use various small molecules for cell signaling and intra- and intercellular communication. Cyclic purine nucleotides like cGMP, cAMP, etc. are known to have regulatory and initiating activity in pro- and eukaryotic cells. Unlike eukaryotic cells, prokaryotic cells also use cyclic purine dinucleotides as regulatory molecules. In prokaryotes, the condensation of two GTP molecules is catalyzed by the enzyme diguanylate cyclase (DGC) to give c-diGMP, which represents an important regulator in bacteria.

Recent work suggests that cyclic diGMP or analogs thereof can also stimulate or enhance immune or inflammatory response in a patient or can enhance the immune response to a vaccine by serving as an adjuvant in mammals. Cytosolic detection of pathogen-derived DNA requires signaling through TANK binding kinase 1 (TBK1) and its downstream transcription factor, IFN-regulatory factor 3 (IRF3). A transmembrane protein called STING (stimulator of IFN genes; also known as MITA, ERIS, MPYS and TMEM173) functions as the signaling receptor for these cyclic purine dinucleotides, causing stimulation of the TBK1-IRF3 signalling axis and a STING-dependent type I interferon response. Burdette et al., Nature 478: 515-18, 2011 demonstrated that STING binds directly to cyclic diguanylate monophosphate, but not to other unrelated nucleotides or nucleic acids.

The Locked Nucleic Acid Cyclic dinucleotides as described herein can be readily derived from nucleotides known in the art, using the synthetic methods as described herein and as known in the art. Such Locked Nucleic Acids for use as nucleotide precursors to derive the LNA-CDNs of the present invention are described in some detail in the literature and patents, including, but not limited to, PCT Publication Nos. WO 99/60855; WO 2007/145593; WO 2008/154401; WO 2009/006478; WO 2009/143369; WO 2010/091308; WO 2011/085102; WO 2013/036868; WO 2014/145356; WO 2015/125783; WO 2015/142735; WO 2015/185565; and WO 2016/017422; U.S. Pat. Nos. 6,403,556; 6,833,361; 7,217,805; 7,335,765; 7,427,672; 7,569,686; 8,022,193; 8,278,283; 8,278,425; 8,278,426; 8,461,124; 8,541,562; and 9,005,906; US Patent Publication Nos. 2003/0028013; 2012/071646; 2015/0337002; 2015/

0152132; and Seth et al., J. Org. Chem., 2012, 77: 5074-5085; Migawa et al., Org. Letters, 2013, 15(17): 4316-4319; Xu et al., J. Org. Chem. 2009, 74, 6534-6554; and Kovacs et al., 1995, Nucleosides & Nucleotides, 14(6): 1259-1267. Synthesis of cyclic dinucleotides, and additional nucleotide precursors useful in preparing the LNA-CDNs of the present invention are also described, for example, in Gao et al., Cell (2013) 153: doi: 10.1016/j.cell.2013.04.046; U.S. Pat. Nos. 7,709,458 and 7,592,326; PCT Publication Nos. WO2007/054279, WO2014/093936, WO2014/179335, WO2014/189805, WO2015/185565, WO2016/096174, WO2016/145102, WO2017/027645, WO2017/027646, and WO2017/075477; and Yan et al., Bioorg. Med. Chem Lett. 18:5631-4, 2008. The disclosure of the references in this paragraph are hereby incorporated by reference as it relates to compounds for use in synthetic methods as described herein for the synthesis of compounds of the invention as described herein. Such nucleotides may be modified using standard organic chemistry techniques in order to produce the LNA-CDNs of the present invention.

In some embodiments, the LNA-CDN compounds of the present invention as described herein are potent STING agonists, and are compared to known CDN STING agonists as a reference compound, such as the natural ligand 2'3'-(G)(G), and 2'3'-RR-(A)(A), a STING agonist which has been shown to be efficacious in mouse tumor models (Corrales et al., Cell Reports 2015, 11:1018-1031). The properties of the LNA-CDN compounds are demonstrated in Examples 7-12 below, where the compounds demonstrate an improvement over the reference compound as having one or more of i) a higher $T_m$ shift in a DSF assay as described in Example 10 for one or more of hSTING (WT), hSTING (HAQ) or hSTING (REF); ii) a higher relative expression of IFN-β transcript in an hPBMC assay as described in Example 11 for one or more of hSTING (WT), hSTING (HAQ) or hSTING (REF); or iii) a lower EC50 in a THP1 cell assay as described in Example 12, where preferably the THP1 assay is performed in the absence of digitonin. In some embodiments, the LNA-CDN demonstrates an improvement over the reference compound as having two or more of i) a higher $T_m$ shift in a DSF assay as described in Example 10 for one or more of hSTING (WT), hSTING (HAQ) or hSTING (REF); ii) a higher relative expression of IFN-β transcript in an hPBMC assay as described in Example 11 for one or more of hSTING (WT), hSTING (HAQ) or hSTING (REF); or iii) a lower EC50 in a THP1 cell assay as described in Example 12, where preferably the THP1 assay is performed in the absence of digitonin. In some embodiments, the LNA-CDN demonstrates an improvement over the reference compound as having each of i) a higher $T_m$ shift in a DSF assay as described in Example 10 for one or more of hSTING (WT), hSTING (HAQ) or hSTING (REF); ii) a higher relative expression of IFN-β transcript in an hPBMC assay as described in Example 11 for one or more of hSTING (WT), hSTING (HAQ) or hSTING (REF); or iii) a lower EC50 in a THP1 cell assay as described in Example 12, where preferably the THP1 assay is performed in the absence of digitonin. In some embodiments of the LNA-CDN compounds as described herein, the LNA-CDN compound has at least a 2-fold, at least a 5-fold, at least a 10-fold, at least a 50-fold, at least a 100-fold, at least a 500-fold, or at least a 1000-fold higher relative expression of IFN-β transcript in an hPBMC assay as described in Example 11 for hSTING REF allele as compared to 2'3'-RR-(A)(A). In some embodiments, the LNA-CDN compound has an EC50 in the THP1 assay described in Example 12 without addition of digitonin that is at least 2-fold, at least 3-fold, at least 4-fold, at least 5-fold, at least 6-fold, at least 7-fold, or at least 8-fold lower than the EC50 of a reference compound. In some embodiments, the LNA-CDN compound has an EC50 in the THP1 cell assay without addition of an agent that enhances the permeability of the compound to the cell or an agent that enhances the uptake of the compound by the cell that is less than 40 µM, less than 30 µM, less than 20 µM, less than 15 µM, less than 10 µM or less than 5 µM. In some embodiments, the LNA-CDN compound has an EC50 in the THP1 assay described in Example 12 without addition of digitonin or other cell permeabilizing agent that is less than 40 µM, less than 30 µM, less than 20 µM, less than 15 µM, less than 10 µM or less than 5 µM.

The LNA-CDN compounds of the present invention as described herein can be phosphorothioate analogues, referred to herein as "thiophosphates". Phosphorothioates are a variant of normal nucleotides in which one of the nonbridging oxygens is replaced by a sulfur. The sulfurization of the internucleotide bond dramatically reduces the action of endo- and exonucleases, including 5' to 3' and 3' to 5' DNA POL 1 exonuclease, nucleases Si and P1, RNases, serum nucleases and snake venom phosphodiesterase. In addition, the potential for crossing the lipid bilayer increases.

A phosphorothioate linkage is inherently chiral. The skilled artisan will recognize that the phosphates in this structure may each exist in R or S forms. Thus, Rp,Rp, Sp,Sp, Sp,Rp, and Rp,Sp forms are possible. The dithio LNA-CDN compounds of the present invention are preferably of the Rp,Rp form.

As noted above, the LNA-CDN compounds also include prodrug forms of the LNA-CDNs. Prodrugs can modify the physicochemical, biopharmaceutic, and pharmacokinetic properties of drugs. Traditional prodrugs are classified as drugs that are activated by undergoing transformation in vivo to form the active drug. Reasons for prodrug development are typically poor aqueous solubility, chemical instability, low oral bioavailability, lack of blood brain barrier penetration, and high first pass metabolism associated with the parent drug. Suitable prodrug moieties are described in, for example, "Prodrugs and Targeted Delivery," J. Rautico, Ed., John Wiley & Sons, 2011.

The term "substantially pure" as used herein with regard to dithio-diphosphate cyclic dinucleotides refers to an Rp,Rp form which is at least 75% pure relative to other possible stereochemistries at the chiral phosphorus centers indicated in the dithio LNA-CDN compounds as described herein. By way of example, a "substantially pure 2'3'-RR-LNA-CDN" would be at least 75% pure with regard to the Rp,Sp, Sp,Rp and Sp,Sp, i.e. with respect to 2'3'-RS-LNA-CDN, 2'3'-SR-LNA-CDN, and 2'3'-SS-LNA-CDN. In preferred embodiments, a substantially pure cyclic dinucleotide is at least 85% pure, at least 90% pure, at least 95% pure, at least 97% pure, and at least 99% pure. Similarly, any of the other isomers can be substantially pure with respect to the other three isomers, e.g. substantially pure Rp,Sp form relative to the Rp,Rp, Sp,Sp and Sp,Rp forms. While a substantially pure cyclic dinucleotide preparation of the invention is "stereochemically pure," this is not meant to indicate that all CDNs within the preparation having a particular stereochemistry at these chiral centers are otherwise identical. For example, a substantially pure cyclic dinucleotide preparation may contain a combination of 2'3'-RR-(G)(G)(2'O,4'C-LNA-A) thiophosphate and 2'3'-RR-(A)(A)(2'O,4'C-LNA-A) thiophosphate and still be a substantially pure cyclic dinucleotide preparation. Such a preparation may also include other components as described hereinafter that are advantageous for patient treatment, provided that all CDNs within the preparation having a particular stereochemistry at these chiral centers.

The LNA-CDN compounds and compositions thereof described herein can be administered to a host, either alone or in combination with a pharmaceutically acceptable excipient, in an amount sufficient to induce, modify, or stimulate an appropriate immune response. The immune response can comprise, without limitation, specific immune response, non-specific immune response, both specific and non-specific response, innate response, primary immune response, adaptive immunity, secondary immune response, memory immune response, immune cell activation, immune cell proliferation, immune cell differentiation, and cytokine expression. In certain embodiments, the LNA-CDN and compositions thereof described herein are administered in conjunction with one or more additional compositions including vaccines intended to stimulate an immune response to one or more predetermined antigens; adjuvants; CTLA-4 and PD-1 pathway antagonists, lipids, liposomes, chemotherapeutic agents, immunomodulatory cell lines, etc.

The LNA-CDN compounds and compositions thereof described herein may be administered before, after, and/or simultaneously with an additional therapeutic or prophylactic composition or modality. These include, without limitation, B7 costimulatory molecule, interleukin-2, interferon-γ, GM-CSF, CTLA-4 antagonists, OX-40/OX-40 ligand, CD40/CD40 ligand, sargramostim, levamisol, vaccinia virus, Bacille Calmette-Guerin (BCG), liposomes, alum, Freund's complete or incomplete adjuvant, detoxified endotoxins, mineral oils, surface active substances such as lipolecithin, pluronic polyols, polyanions, peptides, and oil or hydrocarbon emulsions. Carriers for inducing a T cell immune response which preferentially stimulate a cytolytic T cell response versus an antibody response are preferred, although those that stimulate both types of response can be used as well. In cases where the agent is a polypeptide, the polypeptide itself or a polynucleotide encoding the polypeptide can be administered. The carrier can be a cell, such as an antigen presenting cell (APC) or a dendritic cell. Antigen presenting cells include such cell types as macrophages, dendritic cells and B cells. Other professional antigen-presenting cells include monocytes, marginal zone Kupffer cells, microglia, Langerhans' cells, interdigitating dendritic cells, follicular dendritic cells, and T cells. Facultative antigen-presenting cells can also be used. Examples of facultative antigen-presenting cells include astrocytes, follicular cells, endothelium and fibroblasts. The carrier can be a bacterial cell that is transformed to express the polypeptide or to deliver a polynucleotide which is subsequently expressed in cells of the vaccinated individual. Adjuvants, such as aluminum hydroxide or aluminum phosphate, can be added to increase the ability of the vaccine to trigger, enhance, or prolong an immune response. Additional materials, such as cytokines, chemokines, and bacterial nucleic acid sequences, like CpG, a toll-like receptor (TLR) 9 agonist as well as additional agonists for TLR 2, TLR 4, TLR 5, TLR 7, TLR 8, TLR9, including lipoprotein, LPS, monophosphoryl lipid A, lipoteichoic acid, imiquimod, resiquimod, and in addition retinoic acid-inducible gene I (RIG-I) agonists such as poly I:C, used separately or in combination with the described compositions are also potential adjuvants. Other representative examples of adjuvants include the synthetic adjuvant QS-21 comprising a homogeneous saponin purified from the bark of *Quillaja saponaria* and *Corynebacterium parvum* (McCune et al., Cancer, 1979; 43:1619). It will be understood that the adjuvant is subject to optimization. In other words, the skilled artisan can engage in routine experimentation to determine the best adjuvant to use.

Methods for co-administration with an additional therapeutic agent are well known in the art (Hardman, et al. (eds.) (2001) Goodman and Gilman's The Pharmacological Basis of Therapeutics, 10th ed., McGraw-Hill, New York, N.Y.; Poole and Peterson (eds.) (2001) Pharmacotherapeutics for Advanced Practice: A Practical Approach, Lippincott, Williams & Wilkins, Phila., Pa.; Chabner and Longo (eds.) (2001) Cancer Chemotherapy and Biotherapy, Lippincott, Williams & Wilkins, Phila., Pa.). Generally, co-administration or administration together indicates treating a subject with two or more agents, where the agents can be administered simultaneously or at different times. For example, such agents may be delivered to a single subject as separate administrations, which may be at essentially the same time or different times, and which may be by the same route or different routes of administration. Such agents may be delivered to a single subject in the same administration (e.g. same formulation) such that they are administered at the same time by the same route of administration.

Because of the adjuvant properties of the compounds of the present invention, their use may also be combined with other therapeutic modalities including other vaccines, adjuvants, antigen, antibodies, and immune modulators. Examples are provided below.

Adjuvants

In addition to the LNA-CDN compounds and compositions thereof described herein described above, the compositions or methods of the present invention may further comprise one or more additional substances which, because of their nature, can act to stimulate or otherwise utilize the immune system to respond to the cancer antigens present on the targeted tumor cell(s). Such adjuvants include, but are not limited to, lipids, liposomes, inactivated bacteria which induce innate immunity (e.g., inactivated or attenuated *Listeria monocytogenes*), compositions which mediate innate immune activation via Toll-like Receptors (TLRs), (NOD)-like receptors (NLRs), Retinoic acid inducible gene-based (RIG)-I-like receptors (RLRs), C-type lectin receptors (CLRs), and/or pathogen-associated molecular patterns ("PAMPs"). Examples of PAMPs include lipoproteins, lipopolypeptides, peptidoglycans, zymosan, lipopolysaccharide, neis serial porins, flagellin, profillin, galactoceramide, muramyl dipeptide. Peptidoglycans, lipoproteins, and lipoteichoic acids are cell wall components of Gram-positive. Lipopolysaccharides are expressed by most bacteria, with MPL being one example. Flagellin refers to the structural component of bacterial flagella that is secreted by pathogenic and commensal bacterial. α-Galactosylceramide (α-GalCer) is an activator of natural killer T (NKT) cells. Muramyl dipeptide is a bioactive peptidoglycan motif common to all bacteria. This list is not meant to be limiting. Preferred adjuvant compositions are described below.

Immune Checkpoint Inhibitors

The LNA-CDN compounds as described herein can be used in combination with an immune checkpoint inhibitor, such as an immune checkpoint inhibitor selected from the group consisting of a CTLA-4 pathway antagonist, a PD-1 pathway antagonist, a Tim-3 pathway antagonist, a Vista pathway antagonist, a BTLA pathway antagonist, a LAG-3 pathway antagonist, or a TIGIT pathway antagonist. In some embodiments, the immune checkpoint inhibitor is selected from the group consisting of an anti-CTLA-4 antibody, an anti-PD-1 antibody, an anti-Tim-3 antibody, an anti-Vista antibody, an anti-BTLA antibody, an anti-LAG-3 antibody, or an anti-TIGIT antibody.

The LNA-CDN compounds as described herein can be used in combination with CTLA-4 pathway antagonists. In some embodiments, the combination is used to treat a solid tumor or a hematologic malignancy. CTLA-4 is thought to be an important negative regulator of the adaptive immune response. Activated T cells upregulate CTLA-4, which binds CD80 and CD86 on antigen-presenting cells with higher affinity than CD28, thus inhibiting T-cell stimulation, IL-2 gene expression and T-cell proliferation. Anti-tumor effects of CTLA4 blockade have been observed in murine models of colon carcinoma, metastatic prostate cancer, and metastatic melanoma. In some embodiments, the CTLA-4 pathway antagonist is an anti-CTLA-4 antibody molecule selected from the group consisting of tremelimumab and ipilimumab. In some embodiments, the anti-CTLA-4 antibody is an anti-CTLA-4 antibody as disclosed in e.g., U.S. Pat. No. 5,811,097.

Ipilimumab (Yervoy™, a CTLA-4 antibody, also known as MDX-010, CAS No. 477202-00-9) and tremelimumab (IgG2 monoclonal antibody available from Pfizer, formerly known as ticilimumab, CP-675,206) are humanized monoclonal antibodies that bind to human CTLA4 and prevent its interaction with CD80 and CD86. Phase I and II studies using ipilimumab and tremelimumab have demonstrated clinical activity in cancer patients. Other negative immune regulators which may be targeted by a similar strategy include programmed cell death 1 (PD-1), B and T lymphocyte attenuator, transforming growth factor beta β, interleukin-10, and vascular endothelial growth factor.

In some embodiments, the LNA-CDN compounds as described herein can be used in combination with an anti-CTLA-4 antibody and an anti-PD-1 antibody. In one embodiment, the combination includes an anti-PD-1 antibody molecule, e.g., as described herein, and an anti-CTLA-4 antibody, e.g., ipilimumab. Exemplary doses that can be use include a dose of anti-PD-1 antibody molecule of about 1 to 10 mg/kg, e.g., 3 mg/kg, and a dose of an anti-CTLA-4 antibody, e.g., ipilimumab, of about 3 mg/kg.

The LNA-CDN compounds as described herein can be used in combination with PD-1 pathway antagonists. In some embodiments, the combination is used to treat a solid tumor or a hematologic malignancy. PD-1 is another negative regulator of adaptive immune response that is expressed on activated T-cells. PD-1 binds to B7-H1 and B7-DC, and the engagement of PD-1 suppresses T-cell activation. Anti-tumor effects have been demonstrated with PD-1 pathway blockade. Anti-PD-1 antibody molecules (e.g. Nivolumab (Opdivo™), pembrolizumab (Keytruda™), and pidilizumab), and AMP-224 have been reported in the literature to be examples of PD-1 pathway blockers which may find use in the present invention. In some embodiments, the PD-1 pathway antagonist is an anti-PD-1 antibody molecule selected from the group consisting of nivolumab, pembrolizumab or pidilizumab.

In some embodiments, the anti-PD-1 antibody is nivolumab. Alternative names for nivolumab include MDX-1106, MDX-1106-04, ONO-4538, or BMS-936558. In some embodiments, the anti-PD-1 antibody is nivolumab (CAS Registry Number: 946414-94-4). Nivolumab is a fully human IgG4 monoclonal antibody which specifically blocks PD1. Nivolumab (clone 5C4) and other human monoclonal antibodies that specifically bind to PD1 are disclosed in U.S. Pat. No. 8,008,449 and WO2006/121168. In one embodiment, the inhibitor of PD-1 is nivolumab, and having a sequence disclosed herein (or a sequence substantially identical or similar thereto, e.g., a sequence at least 85%, 90%, 95% identical or higher to the sequence specified).

The heavy chain amino acid sequence of nivolumab is as follows:

(SEQ ID NO: 1)
QVQLVESGGGVVQPGRSLRLDCKASGITFSNSGMHWVRQAPGKGLEWVAV

IWYDGSKRYYADSVKGRFTISRDNSKNTLFLQMNSLRAEDTAVYYCATND

DYWGQGTLVTVSSASTKGPSVFPLAPCSRSTSESTAALGCLVKDYFPEPV

TVSWNSGALTSGVHTFPAVLQSSGLYSLSSVVTVPSSSLGTKTYTCNVDH

KPSNTKVDKRVESKYGPPCPPCPAPEFLGGPSVFLFPPKPKDTLMISRTP

EVTCVVVDVSQEDPEVQFNWYVDGVEVHNAKTKPREEQFNSTYRVVSVLT

VLHQDWLNGKEYKCKVSNKGLPSSIEKTISKAKGQPREPQVYTLPPSQEE

MTKNQVSLTCLVKGFYPSDIAVEWESNGQPENNYKTTPPVLDSDGSFFLY

SRLTVDKSRWQEGNVFSCSVMHEALHNHYTQKSLSLSLGK

The light chain amino acid sequence of nivolumab is as follows:

(SEQ ID NO: 2)
EIVLTQSPATLSLSPGERATLSCRASQSVSSYLAWYQQKPGQAPRLLIYD

ASNRATGIPARFSGSGSGTDFTLTISSLEPEDFAVYYCQQSSNWPRTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

In some embodiments, the anti-PD-1 antibody is pembrolizumab. Pembrolizumab (also referred to as lambrolizumab, MK-3475, MK03475, SCH-900475 or KEYTRUDA®; Merck) is a humanized IgG4 monoclonal antibody that binds to PD-1. Pembrolizumab and other humanized anti-PD-1 antibodies are disclosed in Hamid, O. et al. (2013) *New England Journal of Medicine* 369 (2): 134-44, U.S. Pat. No. 8,354,509 and WO2009/114335. In one embodiment, the inhibitor of PD-1 is pembrolizumab, and having a sequence disclosed herein (or a sequence substantially identical or similar thereto, e.g., a sequence at least 85%, 90%, 95% identical or higher to the sequence specified).

The heavy chain amino acid sequences of pembrolizumab is as follows:

(SEQ ID NO: 3)
QVQLVQSGVE VKKPGASVKV SCKASGYTFT NYYMYWVRQA PGQGLEWMGG  50

INPSNGGTNF NEKFKNRVTL TTDSSTTTAY MELKSLQFDD TAVYYCARRD  100

YRFDMGFDYW GQGTTVTVSS ASTKGPSVFP LAPCSRSTSE STAALGCLVK  150

```
DYFPEPVTVS WNSGALTSGV HTFPAVLQSS GLYSLSSVVT VPSSSLGTKT  200

YTCNVDHKPS NTKVDKRVES KYGPPCPPCP APEFLGGPSV FLFPPKPKDT  250

LMISRTPEVT CVVVDVSQED PEVQFNWYVD GVEVHNAKTK PREEQFNSTY  300

RVVSVLTVLH QDWLNGKEYK CKVSNKGLPS SIEKTISKAK GQPREPQVYT  350

LPPSQEEMTK NQVSLTCLVK GFYPSDIAVE WESNGQPENN YKTTPPVLDS  400

DGSFFLYSRL TVDKSRWQEG NVFSCSVMHE ALHNHYTQKS LSLSLGK     447
```

The light chain amino acid sequences of pembrolizumab is as follows:

```
                                            (SEQ ID NO: 4)
EIVLTQSPAT LSLSPGERAT LSCRASKGVS TSGYSYLHWY QQKPGQAPRL     50

LIYLASYLES GVPARFSGSG SGTDFTLTIS SLEPEDFAVY YCQHSRDLPL    100

TFGGGTKVEI KRTVAAPSVF IFPPSDEQLK SGTASVVCLL NNFYPREAKV    150

QWKVDNALQS GNSQESVTEQ DSKDSTYSLS STLTLSKADY EKHKVYACEV    200

THQGLSSPVT KSFNRGEC                                       218
```

In some embodiments, the anti-PD-1 antibody is pidilizumab. Pidilizumab (CT-011; Cure Tech) is a humanized IgG1k monoclonal antibody that binds to PD-1. Pidilizumab and other humanized anti-PD-1 monoclonal antibodies are disclosed in WO2009/101611.

In some embodiments, the anti-PD-1 antibody is AMP 514 (Amplimmune), or an anti-PD-1 antibody as disclosed in U.S. Pat. No. 8,609,089, US 2010028330, and/or US 20120114649.

In some embodiments the PD-1 pathway antagonist is an anti-PD-1 antibody molecule disclosed in US 2015/0210769, published on Jul. 30, 2015, entitled "Antibody Molecules to PD-1 and Uses Thereof".

In one embodiment, the anti-PD-1 antibody molecule includes at least one or two heavy chain variable domain (optionally including a constant region), at least one or two light chain variable domain (optionally including a constant region), or both, comprising the amino acid sequence of BAP049-Clone-A, BAP049-Clone-B, BAP049-Clone-C, BAP049-Clone-D, or BAP049-Clone-E; or as described in Table 1 of US 2015/0210769, or encoded by the nucleotide sequence in Table 1 therein; or a sequence substantially identical (e.g., at least 80%, 85%, 90%, 92%, 95%, 97%, 98%, 99% or higher identical) to any of the aforesaid sequences. The anti-PD-1 antibody molecule, optionally, comprises a leader sequence from a heavy chain, a light chain, or both, as shown in Table 4 of US 2015/0210769; or a sequence substantially identical thereto.

In yet another embodiment, the anti-PD-1 antibody molecule includes at least one, two, or three complementarity determining regions (CDRs) from a heavy chain variable region and/or a light chain variable region of an antibody described in US 2015/0210769, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table 1 therein, or encoded by the nucleotide sequence in Table 1 therein; or a sequence substantially identical (e.g., at least 80%, 85%, 90%, 92%, 95%, 97%, 98%, 99% or higher identical) to any of the aforesaid sequences.

In yet another embodiment, the anti-PD-1 antibody molecule includes at least one, two, or three CDRs (or collectively all of the CDRs) from a heavy chain variable region comprising an amino acid sequence shown in Table 1 of US 2015/0210769, or encoded by a nucleotide sequence shown in Table 1 therein. In one embodiment, one or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1 therein.

In yet another embodiment, the anti-PD-1 antibody molecule includes at least one, two, or three CDRs (or collectively all of the CDRs) from a light chain variable region comprising an amino acid sequence shown in Table 1 of US 2015/0210769, or encoded by a nucleotide sequence shown in Table 1 therein. In one embodiment, one or more of the CDRs (or collectively all of the CDRs) have one, two, three, four, five, six or more changes, e.g., amino acid substitutions or deletions, relative to the amino acid sequence shown in Table 1 therein, or encoded by a nucleotide sequence shown in Table 1 therein. In certain embodiments, the anti-PD-1 antibody molecule includes a substitution in a light chain CDR, e.g., one or more substitutions in a CDR1, CDR2 and/or CDR3 of the light chain. In one embodiment, the anti-PD-1 antibody molecule includes a substitution in the light chain CDR3 at position 102 of the light variable region, e.g., a substitution of a cysteine to tyrosine, or a cysteine to serine residue, at position 102 of the light variable region according to Table 1 (e.g., SEQ ID NO: 16 or 24 for murine or chimeric, unmodified; or any of SEQ ID NOs: 34, 42, 46, 54, 58, 62, 66, 70, 74, or 78 for a modified sequence).

In another embodiment, the anti-PD-1 antibody molecule includes at least one, two, three, four, five or six CDRs (or collectively all of the CDRs) from a heavy and light chain variable region comprising an amino acid sequence shown in Table 1 of US 2015/0210769, or encoded by a nucleotide sequence shown in Table 1 therein. In one embodiment, one or more of the CDRs (or collectively all of the CDRs) have one, two, three, four, five, six or more changes, e.g., amino acid substitutions or deletions, relative to the amino acid sequence shown in Table 1 therein, or encoded by a nucleotide sequence shown in Table 1 therein.

In one embodiment, the anti-PD-1 antibody molecule includes: (a) a heavy chain variable region (VH) comprising a VHCDR1 amino acid sequence of SEQ ID NO: 4, a VHCDR2 amino acid sequence of SEQ ID NO: 5, and a VHCDR3 amino acid sequence of SEQ ID NO: 3; and a light chain variable region (VL) comprising a VLCDR1 amino acid sequence of SEQ ID NO: 13, a VLCDR2 amino acid sequence of SEQ ID NO: 14, and a VLCDR3 amino acid sequence of SEQ ID NO: 33, each as disclosed in Table 1 of US 2015/0210769; (b) a VH comprising a VHCDR1 amino acid sequence chosen from SEQ ID NO: 1; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 32, each as disclosed in Table 1 of US 2015/0210769; (c) a VH comprising a VHCDR1 amino acid sequence of SEQ ID NO: 224, a VHCDR2 amino acid sequence of SEQ ID NO: 5, and a VHCDR3 amino acid sequence of SEQ ID NO: 3; and a VL comprising a VLCDR1 amino acid sequence of SEQ ID NO: 13, a VLCDR2 amino acid sequence of SEQ ID NO: 14, and a VLCDR3 amino acid sequence of SEQ ID NO: 33, each as disclosed in Table 1 of US 2015/0210769; or (d) a VH comprising a VHCDR1 amino acid sequence of SEQ ID NO: 224; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 32, each as disclosed in Table 1 of US 2015/0210769.

In another embodiment, the anti-PD-1 antibody molecule comprises (i) a heavy chain variable region (VH) comprising a VHCDR1 amino acid sequence chosen from SEQ ID NO: 1, SEQ ID NO: 4, or SEQ ID NO: 224; a VHCDR2 amino acid sequence of SEQ ID NO: 2 or SEQ ID NO: 5; and a VHCDR3 amino acid sequence of SEQ ID NO: 3; and (ii) a light chain variable region (VL) comprising a VLCDR1 amino acid sequence of SEQ ID NO: 10 or SEQ ID NO: 13, a VLCDR2 amino acid sequence of SEQ ID NO: 11 or SEQ ID NO: 14, and a VLCDR3 amino acid sequence of SEQ ID NO: 32 or SEQ ID NO: 33, each as disclosed in Table 1 of US 2015/0210769.

In some embodiments the PD-1 pathway antagonist is an immunoadhesin (e.g., an immunoadhesin comprising an extracellular or PD-1 binding portion of PD-L1 or PD-L$_2$ fused to a constant region (e.g., an Fc region of an immunoglobulin sequence). In some embodiments, the PD-1 inhibitor is AMP-224 (B7-DCIg; Amplimmune; e.g., disclosed in WO2010/027827 and WO2011/066342) is a PD-L$_2$ Fc fusion soluble receptor that blocks the interaction between PD-1 and B7-H1.

In some embodiments the PD-1 pathway antagonist is a PD-L1 or PD-L$_2$ inhibitor. In some embodiments the PD-L1 or PD-L$_2$ inhibitor is an anti-PD-L1 antibody or an anti-PD-L$_2$ antibody.

In some embodiments, the PD-L1 inhibitor is an anti-PD-L1 antibody. Exemplary non-limiting combinations and uses of the anti-PD-L1 antibody molecules are disclosed in US 2016/0108123, published Apr. 21, 2016, entitled "Antibody Molecules to PD-L1 and Uses Thereof".

In one embodiment, the anti-PD-L1 antibody molecule includes at least one or two heavy chain variable domain (optionally including a constant region), at least one or two light chain variable domain (optionally including a constant region), or both, comprising the amino acid sequence of any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O; or as described in Table 1 of US 2016/0108123, or encoded by the nucleotide sequence in Table 1 therein; or a sequence substantially identical (e.g., at least 80%, 85%, 90%, 92%, 95%, 97%, 98%, 99% or higher identical) to any of the aforesaid sequences.

In yet another embodiment, the anti-PD-L1 antibody molecule includes at least one, two, or three complementarity determining regions (CDRs) from a heavy chain variable region and/or a light chain variable region of an antibody described herein, e.g., an antibody chosen from any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O; or as described in Table 1 of US 2016/0108123, or encoded by the nucleotide sequence in Table 1 therein; or a sequence substantially identical (e.g., at least 80%, 85%, 90%, 92%, 95%, 97%, 98%, 99% or higher identical) to any of the aforesaid sequences.

In yet another embodiment, the anti-PD-L1 antibody molecule includes at least one, two, or three CDRs (or collectively all of the CDRs) from a heavy chain variable region comprising an amino acid sequence shown in Table 1 of US 2016/0108123, or encoded by a nucleotide sequence shown in Table 1 therein. In one embodiment, one or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1.

In yet another embodiment, the anti-PD-L1 antibody molecule includes at least one, two, or three CDRs (or collectively all of the CDRs) from a light chain variable region comprising an amino acid sequence shown in Table 1 of US 2016/0108123, or encoded by a nucleotide sequence shown in Table 1 therein. In one embodiment, one or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1. In certain embodiments, the anti-PD-L1 antibody molecule includes a substitution in a light chain CDR, e.g., one or more substitutions in a CDR1, CDR2 and/or CDR3 of the light chain.

In another embodiment, the anti-PD-L1 antibody molecule includes at least one, two, three, four, five or six CDRs (or collectively all of the CDRs) from a heavy and light chain variable region comprising an amino acid sequence shown in Table 1 of US 2016/0108123, or encoded by a nucleotide sequence shown in Table 1 therein. In one embodiment, one or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1.

In one embodiment, the anti-PD-L1 antibody molecule includes: (i) a heavy chain variable region (VH) including a VHCDR1 amino acid sequence chosen from SEQ ID NO: 1, SEQ ID NO: 4 or SEQ ID NO: 195; a VHCDR2 amino acid sequence of SEQ ID NO: 2; and a VHCDR3 amino acid sequence of SEQ ID NO: 3, each disclosed in Table 1 of US 2016/0108123; and (ii) a light chain variable region (VL) including a VLCDR1 amino acid sequence of SEQ ID NO: 9, a VLCDR2 amino acid sequence of SEQ ID NO: 10, and a VLCDR3 amino acid sequence of SEQ ID NO: 11, each disclosed in Table 1 of US 2016/0108123.

In one embodiment, the anti-PD-L1 antibody molecule includes: (i) a heavy chain variable region (VH) including a VHCDR1 amino acid sequence chosen from SEQ ID NO: 1, SEQ ID NO: 4 or SEQ ID NO: 195; a VHCDR2 amino acid sequence of SEQ ID NO: 5, and a VHCDR3 amino acid sequence of SEQ ID NO: 3, each disclosed in Table 1 of US 2016/0108123; and (ii) a light chain variable region (VL) including a VLCDR1 amino acid sequence of SEQ ID NO: 12, a VLCDR2 amino acid sequence of SEQ ID NO: 13, and a VLCDR3 amino acid sequence of SEQ ID NO: 14, each disclosed in Table 1 of US 2016/0108123.

In one embodiment, the anti-PD-L1 antibody molecule comprises the VHCDR1 amino acid sequence of SEQ ID NO: 1. In another embodiment, the anti-PD-L$_1$ antibody molecule comprises the VHCDR1 amino acid sequence of SEQ ID NO: 4. In yet another embodiment, the anti-PD-L1 antibody molecule comprises the VHCDR1 amino acid sequence of SEQ ID NO: 195, each disclosed in Table 1 of US 2016/0108123.

In some embodiments, the anti-PD-L1 inhibitor is chosen from YW243.55.570, MPDL$_{3280}$A, MEDI-4736, MSB-0010718C, or MDX-1105. In some embodiments, the PD-L1 inhibitor is an anti-PD-L1 antibody MSB0010718C. MSB0010718C (also referred to as A09-246-2; Merck Serono) is a monoclonal antibody that binds to PD-L1. MSB0010718C and other humanized anti-PD-L1 antibodies are disclosed in WO2013/079174, and having a sequence disclosed therein (or a sequence substantially identical or similar thereto, e.g., a sequence at least 85%, 90%, 95% identical or higher to the sequence specified).

The heavy chain amino acid sequence (SEQ ID NO: 24 as disclosed in WO2013/079174) of MSB0010718C includes at least the following:

```
                                            (SEQ ID NO: 5)
EVQLLESGGGLVQPGGSLRLSCAASGFTFSSYIMMWVRQAPGKGLEWVSS
IYPSGGITFYADKGRFTISRDNSKNTLYLQMNSLRAEDTAVYYCARIKLG
TVTTVDYWGQGTLVTVSS
```

The light chain amino acid sequence (SEQ ID NO: 25 as disclosed in WO2013/079174) of MSB0010718C includes at least the following:

```
                                            (SEQ ID NO: 6)
QSALTQPASVSGSPGQSITISCTGTSSDVGGYNYVSWYQQHPGKAPKLMI
YDVSNRPSGVSNRFSGSKSGNTASLTISGLQAEDEADYYCSSYTSSSTRV
EGTGTKVTVL
```

In one embodiment, the PD-L1 inhibitor is YW243.55.570. The YW243.55.570 antibody is an anti-PD-L1 antibody as described in WO 2010/077634 (heavy and light chain variable region sequences shown in SEQ ID Nos. 20 and 21, respectively), and having a sequence disclosed therein (or a sequence substantially identical or similar thereto, e.g., a sequence at least 85%, 90%, 95% identical or higher to the sequence specified).

In one embodiment, the PD-L1 inhibitor is MDX-1105. MDX-1105, also known as BMS-936559, is an anti-PD-L1 antibody described in WO2007/005874, and having a sequence disclosed therein (or a sequence substantially identical or similar thereto, e.g., a sequence at least 85%, 90%, 95% identical or higher to the sequence specified).

In one embodiment, the PD-L1 inhibitor is MDPL3280A (Genentech/Roche). MDPL3280A is a human Fc optimized IgG1 monoclonal antibody that binds to PD-L1. MDPL3280A and other human monoclonal antibodies to PD-L1 are disclosed in U.S. Pat. No. 7,943,743 and U.S Publication No.: 20120039906.

In other embodiments, the PD-L$_2$ inhibitor is AMP-224. AMP-224 is a PD-L$_2$ Fc fusion soluble receptor that blocks the interaction between PD1 and B7-H1 (B7-DCIg; Amplimmune; e.g., disclosed in WO2010/027827 and WO2011/066342

The LNA-CDN compounds as described herein can be used in combination with TIM-3 pathway antagonists. In some embodiments, the combination is used to treat a solid tumor or a hematologic malignancy. In some embodiments, the TIM-3 pathway antagonist is an anti-TIM-3 antibody. In some embodiments, anti-TIM-3 antibody molecules are disclosed in US 2015/0218274, published on Aug. 6, 2015, entitled "Antibody Molecules to TIM-3 and Uses Thereof".

In one embodiment, the anti-TIM-3 antibody molecule includes at least one or two heavy chain variable domain (optionally including a constant region), at least one or two light chain variable domain (optionally including a constant region), or both, comprising the amino acid sequence of ABTIM3, ABTIM3-hum01, ABTIM3-hum02, ABTIM3-hum03, ABTIM3-hum04, ABTIM3-hum05, ABTIM3-hum06, ABTIM3-hum07, ABTIM3-hum08, ABTIM3-hum09, ABTIM3-hum10, ABTIM3-hum11, ABTIM3-hum12, ABTIM3-hum13, ABTIM3-hum14, ABTIM3-hum15, ABTIM3-hum16, ABTIM3-hum17, ABTIM3-hum18, ABTIM3-hum19, ABTIM3-hum20, ABTIM3-hum21, ABTIM3-hum22, ABTIM3-hum23; or as described in Tables 1-4 of US 2015/0218274; or encoded by the nucleotide sequence in Tables 1-4 therein; or a sequence substantially identical (e.g., at least 80%, 85%, 90%, 92%, 95%, 97%, 98%, 99% or higher identical) to any of the aforesaid sequences. The anti-TIM-3 antibody molecule, optionally, comprises a leader sequence from a heavy chain, a light chain, or both, as shown in US 2015/0218274; or a sequence substantially identical thereto.

In yet another embodiment, the anti-TIM-3 antibody molecule includes at least one, two, or three complementarity determining regions (CDRs) from a heavy chain variable region and/or a light chain variable region of an antibody described in US 2015/0218274, e.g., an antibody chosen from any of ABTIM3, ABTIM3-hum01, ABTIM3-hum02, ABTIM3-hum03, ABTIM3-hum04, ABTIM3-hum05, ABTIM3-hum06, ABTIM3-hum07, ABTIM3-hum08, ABTIM3-hum09, ABTIM3-hum10, ABTIM3-hum11, ABTIM3-hum12, ABTIM3-hum13, ABTIM3-hum14, ABTIM3-hum15, ABTIM3-hum16, ABTIM3-hum17, ABTIM3-hum18, ABTIM3-hum19, ABTIM3-hum20, ABTIM3-hum21, ABTIM3-hum22, ABTIM3-hum23; or as described in Tables 1-4 of US 2015/0218274; or encoded by the nucleotide sequence in Tables 1-4 therein;

or a sequence substantially identical (e.g., at least 80%, 85%, 90%, 92%, 95%, 97%, 98%, 99% or higher identical) to any of the aforesaid sequences.

In yet another embodiment, the anti-TIM-3 antibody molecule includes at least one, two, or three CDRs (or collectively all of the CDRs) from a heavy chain variable region comprising an amino acid sequence shown in Tables 1-4 of US 2015/0218274, or encoded by a nucleotide sequence shown in Tables 1-4 therein. In one embodiment, one or more of the CDRs (or collectively all of the CDRs) have one, two, three, four, five, six or more changes, e.g., amino acid substitutions or deletions, relative to the amino acid sequence shown in Tables 1-4 therein, or encoded by a nucleotide sequence shown in Table 1-4 therein.

In yet another embodiment, the anti-TIM-3 antibody molecule includes at least one, two, or three CDRs (or collectively all of the CDRs) from a light chain variable region comprising an amino acid sequence shown in Tables 1-4 of US 2015/0218274, or encoded by a nucleotide sequence shown in Tables 1-4 therein. In one embodiment, one or more of the CDRs (or collectively all of the CDRs) have one, two, three, four, five, six or more changes, e.g., amino acid substitutions or deletions, relative to the amino acid sequence shown in Tables 1-4 therein, or encoded by a nucleotide sequence shown in Tables 1-4 therein. In certain embodiments, the anti-TIM-3 antibody molecule includes a substitution in a light chain CDR, e.g., one or more substitutions in a CDR1, CDR2 and/or CDR3 of the light chain.

In another embodiment, the anti-TIM-3 antibody molecule includes at least one, two, three, four, five or six CDRs (or collectively all of the CDRs) from a heavy and light chain variable region comprising an amino acid sequence shown in Tables 1-4 of US 2015/0218274, or encoded by a nucleotide sequence shown in Tables 1-4 therein. In one embodiment, one or more of the CDRs (or collectively all of the CDRs) have one, two, three, four, five, six or more changes, e.g., amino acid substitutions or deletions, relative to the amino acid sequence shown in Tables 1-4 therein, or encoded by a nucleotide sequence shown in Tables 1-4 therein.

In one embodiment, the anti-TIM-3 antibody molecule includes: (a) a heavy chain variable region (VH) comprising a VHCDR1 amino acid sequence chosen from SEQ ID NO: 9; a VHCDR2 amino acid sequence of SEQ ID NO: 10; and a VHCDR3 amino acid sequence of SEQ ID NO: 5; and a light chain variable region (VL) comprising a VLCDR1 amino acid sequence of SEQ ID NO: 12, a VLCDR2 amino acid sequence of SEQ ID NO: 13, and a VLCDR3 amino acid sequence of SEQ ID NO: 14, each as disclosed in Tables 1-4 of US 2015/0218274; (b) a VH comprising a VHCDR1 amino acid sequence chosen from SEQ ID NO: 3; a VHCDR2 amino acid sequence of SEQ ID NO: 4; and a VHCDR3 amino acid sequence of SEQ ID NO: 5; and a VL comprising a VLCDR1 amino acid sequence of SEQ ID NO: 6, a VLCDR2 amino acid sequence of SEQ ID NO: 7, and a VLCDR3 amino acid sequence of SEQ ID NO: 8, each as disclosed in Tables 1-4 of US 2015/0218274; (c) a VH comprising a VHCDR1 amino acid sequence chosen from SEQ ID NO: 9; a VHCDR2 amino acid sequence of SEQ ID NO: 25; and a VHCDR3 amino acid sequence of SEQ ID NO: 5; and a VL comprising a VLCDR1 amino acid sequence of SEQ ID NO: 12, a VLCDR2 amino acid sequence of SEQ ID NO: 13, and a VLCDR3 amino acid sequence of SEQ ID NO: 14, each as disclosed in Tables 1-4 of US 2015/0218274; (d) a VH comprising a VHCDR1 amino acid sequence chosen from SEQ ID NO: 3; a VHCDR2 amino acid sequence of SEQ ID NO: 24; and a VHCDR3 amino acid sequence of SEQ ID NO: 5; and a VL comprising a VLCDR1 amino acid sequence of SEQ ID NO: 6, a VLCDR2 amino acid sequence of SEQ ID NO: 7, and a VLCDR3 amino acid sequence of SEQ ID NO: 8, each as disclosed in Tables 1-4 of US 2015/0218274; (e) a VH comprising a VHCDR1 amino acid sequence chosen from SEQ ID NO: 9; a VHCDR2 amino acid sequence of SEQ ID NO: 31; and a VHCDR3 amino acid sequence of SEQ ID NO: 5; and a VL comprising a VLCDR1 amino acid sequence of SEQ ID NO: 12, a VLCDR2 amino acid sequence of SEQ ID NO: 13, and a VLCDR3 amino acid sequence of SEQ ID NO: 14, each as disclosed in Tables 1-4 of US 2015/0218274; or (f) a VH comprising a VHCDR1 amino acid sequence chosen from SEQ ID NO: 3; a VHCDR2 amino acid sequence of SEQ ID NO: 30; and a VHCDR3 amino acid sequence of SEQ ID NO: 5; and a VL comprising a VLCDR1 amino acid sequence of SEQ ID NO: 6, a VLCDR2 amino acid sequence of SEQ ID NO: 7, and a VLCDR3 amino acid sequence of SEQ ID NO: 8, each as disclosed in Tables 1-4 of US 2015/0218274.

In some embodiments, the TIM-3 pathway antagonist is an anti-TIM-3 antibody as disclosed in U.S. Pat. No. 8,552,156, WO 2011/155607, EP 2581113 or U.S Publication No.: 2014/044728.

The LNA-CDN compounds as described herein can be used in combination with LAG-3 pathway antagonists. In some embodiments, the combination is used to treat a solid tumor or a hematologic malignancy. In some embodiments, the LAG-3 pathway antagonist is an anti-LAG-3 antibody. In some embodiments the anti-LAG-3 antibody molecules are disclosed in US 2015/0259420, filed Mar. 13, 2015, entitled "Antibody Molecules to LAG-3 and Uses Thereof".

In one embodiment, the anti-LAG-3 antibody molecule includes at least one or two heavy chain variable domain (optionally including a constant region), at least one or two light chain variable domain (optionally including a constant region), or both, comprising the amino acid sequence of any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J; or as described in Table 1 of US 2015/0259420, or encoded by the nucleotide sequence in Table 1 therein; or a sequence substantially identical (e.g., at least 80%, 85%, 90%, 92%, 95%, 97%, 98%, 99% or higher identical) to any of the aforesaid sequences.

In yet another embodiment, the anti-LAG-3 antibody molecule includes at least one, two, or three complementarity determining regions (CDRs) from a heavy chain variable region and/or a light chain variable region of an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J; or as described in Table 1 of US 2015/0259420, or encoded by the nucleotide sequence in Table 1 therein; or a sequence substantially identical (e.g., at least 80%, 85%, 90%, 92%, 95%, 97%, 98%, 99% or higher identical) to any of the aforesaid sequences.

In yet another embodiment, the anti-LAG-3 antibody molecule includes at least one, two, or three CDRs (or collectively all of the CDRs) from a heavy chain variable region comprising an amino acid sequence shown in Table 1 of US 2015/0259420, or encoded by a nucleotide sequence shown in Table 1 therein. In one embodiment, one or more of the CDRs (or collectively all of the CDRs) have one, two, three, four, five, six or more changes, e.g., amino acid substitutions or deletions, relative to the amino acid sequence shown in Table 1 therein, or encoded by a nucleotide sequence shown in Table 1 therein.

In yet another embodiment, the anti-LAG-3 antibody molecule includes at least one, two, or three CDRs (or collectively all of the CDRs) from a light chain variable region comprising an amino acid sequence shown in Table 1 of US 2015/0259420, or encoded by a nucleotide sequence shown in Table 1 therein. In one embodiment, one or more of the CDRs (or collectively all of the CDRs) have one, two, three, four, five, six or more changes, e.g., amino acid substitutions or deletions, relative to the amino acid sequence shown in Table 1 therein, or encoded by a nucleotide sequence shown in Table 1 therein. In certain embodiments, the anti-PD-L1 antibody molecule includes a substitution in a light chain CDR, e.g., one or more substitutions in a CDR1, CDR2 and/or CDR3 of the light chain.

In another embodiment, the anti-LAG-3 antibody molecule includes at least one, two, three, four, five or six CDRs (or collectively all of the CDRs) from a heavy and light chain variable region comprising an amino acid sequence shown in Table 1 of US 2015/0259420, or encoded by a nucleotide sequence shown in Table 1 therein. In one embodiment, one or more of the CDRs (or collectively all of the CDRs) have one, two, three, four, five, six or more changes, e.g., amino acid substitutions or deletions, relative to the amino acid sequence shown in Table 1 therein, or encoded by a nucleotide sequence shown in Table 1 therein.

In one embodiment, the anti-LAG-3 antibody molecule includes: (i) a heavy chain variable region (VH) including a VHCDR1 amino acid sequence chosen from SEQ ID NO: 1, SEQ ID NO: 4 or SEQ ID NO: 286; a VHCDR2 amino acid sequence of SEQ ID NO: 2; and a VHCDR3 amino acid sequence of SEQ ID NO: 3, each as disclosed in Table 1 of US 2015/0259420; and (ii) a light chain variable region (VL) including a VLCDR1 amino acid sequence of SEQ ID NO: 10, a VLCDR2 amino acid sequence of SEQ ID NO: 11, and a VLCDR3 amino acid sequence of SEQ ID NO: 12, each as disclosed in Table 1 of US 2015/0259420.

In another embodiment, the anti-LAG-3 antibody molecule includes: (i) a heavy chain variable region (VH) including a VHCDR1 amino acid sequence chosen from SEQ ID NO: 1, SEQ ID NO: 4 or SEQ ID NO: 286; a VHCDR2 amino acid sequence of SEQ ID NO: 5, and a VHCDR3 amino acid sequence of SEQ ID NO: 3, each as disclosed in Table 1 of US 2015/0259420; and (ii) a light chain variable region (VL) including a VLCDR1 amino acid sequence of SEQ ID NO: 13, a VLCDR2 amino acid sequence of SEQ ID NO: 14, and a VLCDR3 amino acid sequence of SEQ ID NO: 15, each as disclosed in Table 1 of US 2015/0259420.

In one embodiment, the anti-LAG-3 antibody molecule comprises the VHCDR1 amino acid sequence of SEQ ID NO: 1 as disclosed in Table 1 of US 2015/0259420. In another embodiment, the anti-LAG-3 antibody molecule comprises the VHCDR1 amino acid sequence of SEQ ID NO: 4 as disclosed in Table 1 of US 2015/0259420. In yet another embodiment, the anti-LAG-3 antibody molecule comprises the VHCDR1 amino acid sequence of SEQ ID NO: 286, as disclosed in Table 1 of US 2015/0259420.

In some embodiments, the anti-LAG-3 antibody is BMS-986016. BMS-986016 (also referred to as BMS986016; Bristol-Myers Squibb) is a monoclonal antibody that binds to LAG-3. BMS-986016 and other humanized anti-LAG-3 antibodies are disclosed in US 2011/0150892, WO2010/019570, and WO2014/008218.

T-Cell Receptor Agonists

The LNA-CDN compounds as described herein can be used in combination with a T-cell receptor agonist, such as a CD28 agonist, an OX40 agonist, a GITR agonist, a CD137 agonist, a CD27 agonist or an HVEM agonist.

The LNA-CDN compounds as described herein can be used in combination with a CD27 agonist. Exemplary CD27 agonists include an anti-CD27 agonistic antibody, e.g. as described in PCT Publication No. WO 2012/004367.

The LNA-CDN compounds as described herein can be used in combination with a GITR agonist. In some embodiments, the combination is used to treat a solid tumor or a hematologic malignancy. Exemplary GITR agonists include, e.g., GITR fusion proteins and anti-GITR antibodies (e.g., bivalent anti-GITR antibodies), such as, a GITR fusion protein described in U.S. Pat. No. 6,111,090, European Patent No.: 0920505B1, U.S. Pat. No. 8,586,023, PCT Publication Nos.: WO 2010/003118 and 2011/090754, or an anti-GITR antibody described, e.g., in U.S. Pat. No. 7,025,962, European Patent No.: 1947183B1, U.S. Pat. Nos. 7,812,135, 8,388,967, 8,591,886, European Patent No.: EP 1866339, PCT Publication No.: WO 2011/028683, U.S. Pat. No. 8,709,424, PCT Publication No.: WO 2013/039954, International Publication No.: WO2013/039954, U.S. Publication No.: US2014/0072566, International Publication NO.: WO2015/026684, PCT Publication No.: WO2005/007190, PCT Publication No.: WO 2007/133822, PCT Publication No.: WO2005/055808, PCT Publication No.: WO 99/40196, PCT Publication No.: WO 2001/03720, PCT Publication No.: WO99/20758, U.S. Pat. No. 6,689,607, PCT Publication No.: WO2006/083289, PCT Publication No.: WO 2005/115451, U.S. Pat. No. 7,618,632, PCT Publication No.: WO 2011/051726, International Publication No.: WO2004060319, and International Publication No.: WO2014012479.

In one embodiment, the LNA-CDN compounds as described herein is used in combination with a GITR agonist used in combination with a PD-1 inhibitor, e.g., as described in WO2015/026684.

In another embodiment, the LNA-CDN compounds as described herein is used in combination with a GITR agonist used in combination with a TLR agonist, e.g., as described in WO2004060319, and International Publication No.: WO2014012479.

TLR Agonists

The LNA-CDN compounds as described herein can be used in combination with a Toll like receptor agonist. The term "Toll like receptor" (or "TLR") as used herein refers to a member of the Toll-like receptor family of proteins or a fragment thereof that senses a microbial product and/or initiates an adaptive immune response. In one embodiment, a TLR activates a dendritic cell (DC). Toll like receptors (TLRs) are a family of pattern recognition receptors that were initially identified as sensors of the innate immune system that recognize microbial pathogens. TLRs comprise a family of conserved membrane spanning molecules containing an ectodomain of leucine-rich repeats, a transmembrane domain and an intracellular TIR (Toll/IL-1R) domain. TLRs recognize distinct structures in microbes, often referred to as "PAMPs" (pathogen associated molecular patterns). Ligand binding to TLRs invokes a cascade of intracellular signaling pathways that induce the production of factors involved in inflammation and immunity.

In humans, ten TLR have been identified. TLRs that are expressed on the surface of cells include TLR-1, -2, -4, -5, and -6, while TLR-3, -7/8, and -9 are expressed with the ER compartment. Human dendritic cell subsets can be identified on the basis of distinct TLR expression patterns. By way of example, the myeloid or "conventional" subset of DC (mDC) expresses TLRs 1-8 when stimulated, and a cascade of activation markers (e.g. CD80, CD86, MHC class I and II, CCR7), pro-inflammatory cytokines, and chemokines are produced. A result of this stimulation and resulting expression is antigen-specific CD4$^+$ and CD8$^+$ T cell priming. These DCs acquire an enhanced capacity to take up antigens and present them in an appropriate form to T cells. In contrast, the plasmacytoid subset of DC (pDC) expresses only TLR7 and TLR9 upon activation, with a resulting activation of NK cells as well as T-cells. As dying tumor cells may adversely affect DC function, it has been suggested that activating DC with TLR agonists may be beneficial for priming anti-tumor immunity in an immunotherapy approach to the treatment of cancer. It has also been suggested that successful treatment of breast cancer using radiation and chemotherapy requires TLR4 activation.

TLR agonists known in the art and finding use in the present invention include, but are not limited to, the following:

Pam3Cys, a TLR-1/2 agonist;
CFA, a TLR-2 agonist;
MALP2, a TLR-2 agonist;
Pam2Cys, a TLR-2 agonist;
FSL-1, a TLR-2 agonist;
Hib-OMPC, a TLR-2 agonist;
polyribosinic:polyribocytidic acid (Poly I:C), a TLR-3 agonist;
polyadenosine-polyuridylic acid (poly AU), a TLR-3 agonist;
Polyinosinic-Polycytidylic acid stabilized with poly-L-lysine and carboxymethylcellulose (Hiltonol®), a TLR-3 agonist;
monophosphoryl lipid A (MPL), a TLR-4 agonist;
LPS, a TLR-4 agonist;
bacterial flagellin, a TLR-5 agonist;
sialyl-Tn (STn), a carbohydrate associated with the MUC1 mucin on a number of human cancer cells and a TLR-4 agonist;
imiquimod, a TLR-7 agonist;
resiquimod, a TLR-7/8 agonist;
loxoribine, a TLR-7/8 agonist; and
unmethylated CpG dinucleotide (CpG-ODN), a TLR-9 agonist.

Because of their adjuvant qualities, TLR agonists are preferably used in combinations with other vaccines, adjuvants and/or immune modulators, and may be combined in various combinations. Thus, in certain embodiments, the LNA-CDN compounds that bind to STING and induce STING-dependent TBK1 activation and an inactivated tumor cell which expresses and secretes one or more cytokines which stimulate dendritic cell induction, recruitment and/or maturation, as described herein can be administered together with one or more TLR agonists for therapeutic purposes.

Antibody Therapeutics

The LNA-CDN compounds as described herein can be used in combination with therapeutic antibodies. In some embodiments, the mechanism of action of the therapeutic antibody is Antibody-Dependent Cell-Mediated Cytotoxicity (ADCC)/phagocytosis (ADCP). ADCC is a mechanism of cell-mediated immune defense whereby an effector cell of the immune system actively lyses a target cell, whose membrane-surface antigens have been bound by specific antibodies. It is one of the mechanisms through which antibodies, as part of the humoral immune response, can act to limit and contain infection. Classical ADCC is mediated by natural killer (NK) cells; macrophages, neutrophils and eosinophils can also mediate ADCC. ADCC is an important mechanism of action of therapeutic monoclonal antibodies, including trastuzumab and rituximab, against tumors. Compounds of the present invention may act to potentiate ADCC.

The following are an exemplary list of antibodies which may be used together with the LNA-CDN compounds of the present invention.

Muromonab-CD3: Used to prevent acute rejection of organ, e.g., kidney, transplants. The humanized versions show promise in inhibiting the autoimmune destruction of beta cells in Type 1 diabetes mellitus.

Infliximab (Remicade®) and adalimumab (Humira®): Bind to tumor necrosis factor-alpha (TNF-α). Used in some inflammatory diseases such as rheumatoid arthritis, psoriasis, Crohn's disease.

Omalizumab (Xolair®). Binds to IgE thus preventing IgE from binding to mast cells. Used against allergic asthma.

Daclizumab (Zenapax®). Binds to part of the IL-2 receptor exposed at the surface of activated T cells. Used to prevent acute rejection of transplanted kidneys.

Rituximab (trade name=Rituxan®). Binds to the CD20 molecule found on most B-cells and is used to treat B-cell lymphomas.

Ibritumomab (trade name=Zevalin®). This is a monoclonal antibody against the CD20 molecule on B cells (and lymphomas) conjugated to isotopes. Given to the lymphoma patient supplemented with Rituxan.

Tositumomab (Bexxar®). This is a conjugate of a monoclonal antibody against CD20 and the radioactive isotope iodine-131 (131I).

Cetuximab (Erbitux®). Blocks HER1, a receptor for epidermal growth factor (EGF) that is found on some tumor cells (some breast cancers, lymphomas).

Trastuzumab (Herceptin®). Blocks HER2, a growth factor receptor over-expressed in some 20% of breast cancers.

Brentuximab Vedotin (Adcetris®). A conjugate of a monoclonal antibody that binds CD30, a cell-surface molecule expressed by the cells of some lymphomas but not found on the normal stem cells needed to repopulate the bone marrow.

Alemtuzumab (Campath-1H®). Binds to CD52, a molecule found on lymphocytes and depletes both T cells and B cells. Has produced complete remission of chronic lymphocytic leukemia and shows promise in preventing rejection of kidney transplants.

Lym-1 (Oncolym®). Binds to the HLA-DR-encoded histocompatibility antigen that can be expressed at high levels on lymphoma cells.

Ipilimumab (Yervoy®) that acts to enhance the body's own immune response to tumors.

Vitaxin. Binds to a vascular integrin (alpha-v/beta-3) found on the blood vessels of tumors but not on the blood vessels supplying normal tissues. In Phase II clinical trials, Vitaxin has shown some promise in shrinking solid tumors without harmful side effects.

Bevacizumab (Avastin®). Binds to vascular endothelial growth factor (VEGF) preventing it from binding to its receptor. Used for the treatment of colorectal cancers.

Abciximab (ReoPro®). Inhibits the clumping of platelets by binding the receptors on their surface that normally are linked by fibrinogen. Helpful in preventing reclogging of the coronary arteries in patients who have undergone angioplasty.

Additional therapeutic antibodies that may be used in combination with the LNA-CDN compounds as described herein include a prolactin receptor (PRLR) inhibitor, e.g. as disclosed in U.S. Pat. No. 7,867,493, a HER3 inhibitor, e.g. as disclosed in PCT Publication No. WO 2012/022814, an EGFR2 and/or EGFR4 inhibitor, e.g. as disclosed in PCT Publication No. WO 2014/160160, an M-CSF inhibitor, e.g. as disclosed in PCT Publication No. WO 2004/045532, an anti-APRIL antibody, e.g. as disclosed in U.S. Pat. No. 8,895,705, or an anti-SIRPα antibody e.g., as disclosed in U.S. Pat. No. 8,728,476, WO2015138600 and US20140242095, an anti-CD47 antibody, e.g. as disclosed in U.S. Pat. No. 8,562,997.

In one embodiment, the combination, e.g., a combination comprising a LNA-CDN compound as described herein, is used in combination a prolactin receptor (PRLR) inhibitor, a human monoclonal antibody molecule (Compound A26) as disclosed in U.S. Pat. No. 7,867,493), to treat a disorder, e.g., a disorder described herein. In one embodiment, the PRLR inhibitor is a human monoclonal antibody (Compound A26) disclosed in U.S. Pat. No. 7,867,493. In one embodiment, the LNA-CDN compound is used in combination with human monoclonal antibody molecule (Compound A26) described in U.S. Pat. No. 7,867,493 to treat a disorder such as, a cancer, a prostate cancer, or a breast cancer.

In another embodiment, the combination, e.g., a combination comprising a LNA-CDN compound as described herein, is used in combination with a HER3 inhibitor, Compound A31, or a compound disclosed in PCT Publication No. WO 2012/022814, to treat a disorder, e.g., a disorder described herein. In one embodiment, the HER3 inhibitor is Compound A31 or a compound disclosed in PCT Publication WO 2012/022814. In one embodiment, the LNA-CDN compound is used in combination with Compound A31, or a compound disclosed in PCT Publication WO 2012/022814, to treat a disorder such as a gastric cancer, an esophageal cancer, a head and neck cancer, a squamous cell carcinoma, a stomach cancer, a breast cancer (e.g., metastatic breast cancer), or a digestive/gastrointestinal cancer. In some embodiments, Compound A31 is a human monoclonal antibody molecule. In one embodiment, the HER3 inhibitor or Compound A31 is administered at a dose of about 3, 10, 20, or 40 mg/kg, e.g., once weekly (QW). In one embodiment, the compound is administered at a dose of about 3-10, 10-20, or 20-40 mg/kg.

In another embodiment, the combination, e.g., a combination comprising a LNA-CDN compound as described herein, is used in combination an FGFR2 and/or FGFR4 inhibitor, Compound A32, or a compound disclosed in a publication PCT Publication No. WO 2014/160160 (e.g., an antibody molecule drug conjugate against an FGFR2 and/or FGFR4, e.g., mAb 12425 as described therein), to treat a disorder, e.g., a disorder described herein. In one embodiment, the FGFR2 and/or FGFR4 inhibitor is Compound A32 or a compound disclosed in a publication PCT Publication No. WO 2014/160160. In one embodiment, the LNA-CDN compound is used in combination with Compound A32, or in further combination with a compound as described in Table 2, to treat a disorder such as a cancer, a gastric cancer, a breast cancer, a rhabdomyosarcoma, a liver cancer, an adrenal cancer, a lung cancer, an esophageal cancer, a colon cancer, or an endometrial cancer. In some embodiments, Compound A32 is an antibody molecule drug conjugate against an FGFR2 and/or FGFR4, e.g., mAb 12425.

In another embodiment, the combination, e.g., a combination comprising a LNA-CDN compound described herein, is used in combination an M-CSF inhibitor, Compound A33, or a compound disclosed in PCT Publication No. WO 2004/045532 (e.g., an antibody molecule or Fab fragment against M-CSF), to treat a disorder, e.g., a disorder described herein. In one embodiment, the M-CSF inhibitor is Compound A33 or a compound disclosed in PCT Publication No. WO 2004/045532. In one embodiment, the LNA-CDN compound is used in combination with Compound A33, or a compound as described in PCT Publication No. WO 2004/045532, to treat a disorder such as a cancer, a prostate cancer, a breast cancer, or pigmented villonodular synovitis (PVNS). In embodiments, Compound A33 is a monoclonal antibody molecule against M-CSF or a fragment (e.g., Fab fragment) thereof. In embodiments, the M-CSF inhibitor or Compound A33 is administered at an average dose of about 10 mg/kg.

Delivery Agents

Liposomes are vesicles formed from one ("unilamellar") or more ("multilamellar") layers of phospholipid. Because of the amphipathic character of the phospholipid building blocks, liposomes typically comprise a hydrophilic layer presenting a hydrophilic external face and enclosing a hydrophilic core. The versatility of liposomes in the incorporation of hydrophilic/hydrophobic components, their nontoxic nature, biodegradability, biocompatibility, adjuvanticity, induction of cellular immunity, property of sustained release and prompt uptake by macrophages, makes them attractive candidates for the delivery of antigens.

WO2010/104833 describes suitable liposomal preparations. Such liposomal formulations, referred to herein as VesiVax® (Molecular Express, Inc.), with our without the "immunogenic polypeptide(s) or carbohydrate(s)" referred to above, can contain one or more additional components such as peptidoglycan, lipopeptide, lipopolysaccharide, monophosphoryl lipid A, lipoteichoic acid, resiquimod, imiquimod, flagellin, oligonucleotides containing unmethylated CpG motifs, beta-galactosylceramide, muramyl dipeptide, all-trans retinoic acid, double-stranded viral RNA, heat shock proteins, dioctadecyldimethylammonium bromide, cationic surfactants, toll-like receptor agonists, dimyristoyltrimethylammoniumpropane, and nod-like receptor agonists.

Advantageously, these liposomal formulations can be used to deliver one or more LNA-CDN compounds and compositions thereof described herein in accordance with the present invention.

Moreover, while the liposomal formulations discussed above employ a "steroid derivative" as an anchor for attaching an immunogenic polypeptide or carbohydrate to a liposome, the steroid may simply be provided as an unconjugated steroid such as cholesterol.

Suitable methods for preparing liposomes from lipid mixtures are well known in the art. See, e.g., Basu & Basu, Liposome Methods and Protocols (Methods in Molecular Biology), Humana Press, 2002; Gregoriadis, Liposome Technology, 3rd Edition, Informa HealthCare, 2006. Preferred methods include extrusion, homogenization, and sonication methods described therein. An exemplary method for preparing liposomes for use in the present invention, which comprises drying a lipid mixture, followed by hydration in an aqueous vehicle and sonication to form liposomes, is described in WO2010/104833.

In certain embodiments, the liposomes are provided within a particular average size range. Liposome size can be selected, for example, by extrusion of an aqueous vehicle comprising liposomes through membranes having a preselected pore size and collecting the material flowing through the membrane. In preferred embodiments, the liposomes are selected to be substantially between 50 and 500 nm in diameter, more preferably substantially between 50 and 200 nm in diameter, and most preferably substantially between 50 and 150 nm in diameter. The term "substantially" as used herein in this context means that at least 75%, more preferably 80%, and most preferably at least 90% of the liposomes are within the designated range.

Other lipid and lipid-like adjuvants which may find use in the present invention include oil-in-water (o/w) emulsions (see, e.g., Muderhwa et al., J. Pharmaceut. Sci. 88: 1332-9, 1999)), VesiVax® TLR (Molecular Express, Inc.), digitonin (see, e.g., U.S. Pat. No. 5,698,432), and glucopyranosyl lipids (see, e.g., United States Patent Application 20100310602).

Nanoparticles also represent drug delivery systems suitable for most administration routes. Over the years, a variety of natural and synthetic polymers have been explored for the preparation of nanoparticles, of which Poly(lactic acid) (PLA), Poly(glycolic acid) (PGA), and their copolymers (PLGA) have been extensively investigated because of their biocompatibility and biodegradability. Nanoparticles and other nanocarriers act as potential carries for several classes of drugs such as anticancer agents, antihypertensive agents, immunomodulators, and hormones; and macromolecules such as nucleic acids, proteins, peptides, and antibodies. See, e.g., Crit. Rev. Ther. Drug Carrier Syst. 21:387-422, 2004; Nanomedicine: Nanotechnology, Biology and Medicine 1:22-30, 2005.

Chemotherapeutic Agents

In additional embodiments the methods described herein, the LNA-CDN compounds as described herein are used in combination with chemotherapeutic agents (e.g. small molecule pharmaceutical compounds). Thus the methods further involve administering to the subject an effective amount of one or more chemotherapeutic agents as an additional treatment or a combination treatment. In certain embodiments the one or more chemotherapeutic agents is selected from the group consisting of abiraterone acetate, altretamine, anhydrovinblastine, auristatin, bexarotene, bicalutamide, BMS 184476, 2,3,4,5,6-pentafluoro-N-(3-fluoro-4-methoxyphenyl)benzene sulfonamide, bleomycin, N,N-di-methyl-L-valyl-L-valyl-N-methyl-L-valyl-L-proly-1-Lproline-t-butylamide, cachectin, cemadotin, chlorambucil, cyclophosphamide, 3',4'-didehydro-4'-deoxy-8'-norvincaleukoblastine, docetaxol, doxetaxel, cyclophosphamide, carboplatin, carmustine, cisplatin, cryptophycin, cyclophosphamide, cytarabine, dacarbazine (DTIC), dactinomycin, daunorubicin, decitabine dolastatin, doxorubicin (adriamycin), etoposide, 5-fluorouracil, finasteride, flutamide, hydroxyurea and hydroxyureataxanes, ifosfamide, liarozole, lonidamine, lomustine (CCNU), enzalutamide, mechlorethamine (nitrogen mustard), melphalan, mivobulin isethionate, rhizoxin, sertenef, streptozocin, mitomycin, methotrexate, taxanes, nilutamide, onapristone, paclitaxel, prednimustine, procarbazine, RPR109881, stramustine phosphate, tamoxifen, tasonermin, taxol, tretinoin, vinblastine, vincristine, vindesine sulfate, and vinflunine.

In additional embodiments the methods described herein, the LNA-CDN compounds as described herein are used in combination with chemotherapeutic agents and/or additional agents for treating the indications as described in the methods herein. In some embodiments, the LNA-CDN compounds as described herein are used in combination with one or more agents selected from the group consisting of sotrastaurin, nilotinib, 5-(2,4-dihydroxy-5-isopropylphenyl)-N-ethyl-4-(4-(morpholinomethyl)phenyl)isoxazole-3-carboxamide, dactolisib, 8-(6-Methoxy-pyridin-3-yl)-3-methyl-1-(4-piperazin-1-yl-3-trifluoromethyl-phenyl)-1,3-dihydro-imidazo[4,5-c]quinolin-2-one, 3-(2,6-dichloro-3,5-dimethoxyphenyl)-1-(6-((4-(4-ethylpiperazin-1-yl)phenyl) amino)pyrimidin-4-yl)-1-methylurea, buparlisib, 8-(2,6-difluoro-3,5-dimethoxyphenyl)-N-(4-((dimethylamino) methyl)-1H-imidazol-2-yl)quinoxaline-5-carboxamide, (S)—N1-(4-methyl-5-(2-(1,1,1-trifluoro-2-methylpropan-2-yl)pyridin-4-yl)thiazol-2-yl)pyrrolidine-1,2-dicarboxamide, (S)-1-(4-chlorophenyl)-7-isopropoxy-6-methoxy-2-(4-(methyl(((1R,4S)-4-(4-methyl-3-oxopiperazin-1-yl)cyclohexyl)methyl)amino)phenyl)-1,2-dihydroisoquinolin-3 (4H)-one, deferasirox, letrozole, (4S,5R)-3-(2'-amino-2-morpholino-4'-(trifluoromethyl)-[4,5'-bipyrimidin]-6-yl)-4-(hydroxymethyl)-5-methyloxazolidin-2-one, (S)-5-(5-chloro-1-methyl-2-oxo-1,2-dihydropyridin-3-yl)-6-(4-chlorophenyl)-2-(2,4-dimethoxypyrimidin-5-yl)-1-isopropyl-5,6-dihydropyrrolo[3,4-d]imidazol-4(1H)-one, 4-((2-(((1R,2R)-2-hydroxycyclohexyl)amino)benzo[d]thiazol-6-yl)oxy)-N-methylpicolinamide, imatinib mesylate, 2-fluoro-N-methyl-4-(7-(quinolin-6-ylmethyl)imidazo[1,2-b][1,2,4]triazin-2-yl)benzamide, ruxolitinib, panobinostat, osilodrostat, (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide, (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide, sonidegib phosphate, ceritinib, 7-cyclopentyl-N,N-dimethyl-2-((5-(piperazin-1-yl)pyridin-2-yl)amino)-7H-pyrrolo[2,3-d]pyrimidine-6-carboxamide, N-(4-((1R,3S,5S)-3-amino-5-methylcyclohexyl)pyridin-3-yl)-6-(2,6-difluorophenyl)-5-fluoropicolinamide, 2-(2',3-dimethyl-[2,4'-bipyridin]-5-yl)-N-(5-(pyrazin-2-yl)pyridin-2-yl)acetamide, encorafenib, 7-cyclopentyl-N,N-dimethyl-2-((5-((1R,6S)-9-methyl-4-oxo-3,9-diazabicyclo[4.2.1]nonan-3-yl)pyridin-2-yl) amino)-7H-pyrrolo[2,3-d]pyrimidine-6-carboxamide, binimetinib, midostaurin, everolimus, 1-methyl-5-((2-(5-(trifluoromethyl)-1H-imidazol-2-yl)pyridin-4-yl)oxy)-N-(4-(trifluoromethyl)phenyl)-1H-benzo[d]imidazol-2-amine, pasireotide diaspartate, dovitinib, (R,E)-N-(7-chloro-1-(1-(4-(dimethylamino)but-2-enoyl)azepan-3-yl)-1H-benzo[d] imidazol-2-yl)-2-methylisonicotinamide, $N^6$-(2-isopropoxy- 5-methyl-4-(1-methylpiperidin-4-yl)phenyl)-N$^4$-(2-(isopropylsulfonyl)phenyl)-1H-pyrazolo[3,4-d]pyrimidine-4,6-diamine, 3-(4-(4-((5-chloro-4-((5-methyl-1H-pyrazol-3-yl)amino)pyrimidin-2-yl)amino)-5-fluoro-2-methylphenyl)piperidin-1-yl)thietane 1,1-dioxide, 5-chloro-N$^2$-(2-fluoro-5-methyl-4-(1-(tetrahydro-2H-pyran-4-yl)piperidin-4-yl)phenyl)-N$^4$-(5-methyl-1H-pyrazol-3-yl)pyrimidine-2,4-diamine, 5-chloro-N2-(4-(1-ethylpiperidin-4-yl)-2-fluoro-5-methylphenyl)-N$^4$-(5-methyl-1H-pyrazol-3-yl)pyrimidine-2,4-diamine, valspodar, and vatalanib succinate.

In one embodiment, the combination, e.g., a combination comprising a LNA-CDN compound as described herein, is used in combination with a PKC inhibitor, Sotrastaurin (Compound A1), or a compound disclosed in PCT Publication No. WO 2005/039549, to treat a disorder, e.g., a disorder described herein. In one embodiment, the PKC inhibitor is Sotrastaurin (Compound A1) or a compound disclosed in PCT Publication No. WO 2005/039549. In one embodiment, the LNA-CDN compound is used in combination with Sotrastaurin (Compound A1), or a compound as described in PCT Publication No. WO 2005/039549, to treat a disorder such as a cancer, a melanoma, a non-Hodgkin lymphoma, an inflammatory bowel disease, transplant rejection, an ophthalmic disorder, or psoriasis. In certain embodiments, Sotrastaurin (Compound A1) is administered at a dose of about 20 to 600 mg, e.g., about 200 to about 600 mg, about 50 mg to about 450 mg, about 100 mg to 400 mg, about 150 mg to 350 mg, or about 200 mg to 300 mg, e.g., about 50 mg, 100 mg, 150 mg, 200 mg, 300 mg, 400 mg, 500 mg, or 600 mg. The dosing schedule can vary from e.g., every other day to daily, twice or three times a day.

In one embodiment, the combination, e.g., a combination comprising a LNA-CDN compound as described herein, is used in combination with a BCR-ABL inhibitor, TASIGNA (Compound A2, nilotinib), or a compound disclosed in PCT Publication No. WO 2004/005281, to treat a disorder, e.g., a disorder described herein. In one embodiment, the BCR-ABL inhibitor is TASIGNA, or a compound disclosed in PCT Publication No. WO 2004/005281. In one embodiment, the LNA-CDN compound is used in combination with TASIGNA (Compound A2), or a compound as described in PCT Publication No. WO 2004/005281, to treat a disorder such as a lymphocytic leukemia, Parkinson's Disease, a neurologic cancer, a melanoma, a digestive/gastrointestinal cancer, a colorectal cancer, a myeloid leukemia, a head and neck cancer, or pulmonary hypertension. In one embodiment, the BCR-ABL inhibitor or TASIGNA is administered at a dose of about 300 mg (e.g., twice daily, e.g., for newly diagnosed Ph+ CML-CP), or about 400 mg, e.g., twice daily, e.g., for resistant or intolerant Ph+ CML-CP and CML-AP). BCR-ABL inhibitor or a Compound A2 is administered at a dose of about 300-400 mg.

In another embodiment, the combination, e.g., a combination comprising a LNA-CDN compound as described herein, is used in combination with an HSP90 inhibitor, such as 5-(2,4-dihydroxy-5-isopropylphenyl)-N-ethyl-4-(4-(morpholinomethyl)phenyl)isoxazole-3-carboxamide (Compound A3), or a compound disclosed in PCT Publication No. WO 2010/060937 or WO 2004/072051, to treat a disorder, e.g., a disorder described herein. In one embodiment, the HSP90 inhibitor is 5-(2,4-dihydroxy-5-isopropylphenyl)-N-ethyl-4-(4-(morpholinomethyl)phenyl)isoxazole-3-carboxamide (Compound A3), or a compound disclosed in PCT Publication No. WO 2010/060937 or WO 2004/072051. In one embodiment, the LNA-CDN compound is used in combination with 5-(2,4-dihydroxy-5-isopropylphenyl)-N-ethyl-4-(4-(morpholinomethyl)phenyl)isoxazole-3-carboxamide (Compound A3), or a compound as described in PCT Publication No. WO 2010/060937 or WO 2004/072051, to treat a disorder such as a cancer, a multiple myeloma, a non-small cell lung cancer, a lymphoma, a gastric cancer, a breast cancer, a digestive/gastrointestinal cancer, a pancreatic cancer, a colorectal cancer, a solid tumor, or a hematopoiesis disorder.

In another embodiment, the combination, e.g., a combination comprising a LNA-CDN compound as described herein, is used in combination with an inhibitor of PI3K and/or mTOR, Dactolisib (Compound A4) or 8-(6-Methoxy-pyridin-3-yl)-3-methyl-1-(4-piperazin-1-yl-3-trifluoromethyl-phenyl)-1,3-dihydro-imidazo[4,5-c]quinolin-2-one (Compound A41), or a compound disclosed in PCT Publication No. WO 2006/122806, to treat a disorder, e.g., a disorder described herein. In one embodiment, the PI3K and/or mTOR inhibitor is Dactolisib (Compound A4), 8-(6-Methoxy-pyridin-3-yl)-3-methyl-1-(4-piperazin-1-yl-3-trifluoromethyl-phenyl)-1,3-dihydro-imidazo[4,5-c]quinolin-2-one (Compound A41), or a compound disclosed in PCT Publication No. WO 2006/122806. In one embodiment, the LNA-CDN compound is used in combination with Dactolisib (Compound A4), 8-(6-Methoxy-pyridin-3-yl)-3-methyl-1-(4-piperazin-1-yl-3-trifluoromethyl-phenyl)-1,3-dihydro-imidazo[4,5-c]quinolin-2-one (Compound A41), or a compound described in PCT Publication No. WO 2006/122806, to treat a disorder such as a cancer, a prostate cancer, a leukemia (e.g., lymphocytic leukemia), a breast cancer, a brain cancer, a bladder cancer, a pancreatic cancer, a renal cancer, a solid tumor, or a liver cancer.

In another embodiment, the combination, e.g., a combination comprising a LNA-CDN compound as described herein, is used in combination with an FGFR inhibitor, 3-(2,6-dichloro-3,5-dimethoxyphenyl)-1-(6-((4-(4-ethylpiperazin-1-yl)phenyl)amino)pyrimidin-4-yl)-1-methylurea (Compound A5) or a compound disclosed in U.S. Pat. No. 8,552,002, to treat a disorder, e.g., a disorder described herein. In one embodiment, the FGFR inhibitor is 3-(2,6-dichloro-3,5-dimethoxyphenyl)-1-(6-((4-(4-ethylpiperazin-1-yl)phenyl)amino)pyrimidin-4-yl)-1-methylurea (Compound A5) or a compound disclosed in U.S. Pat. No. 8,552,002. In one embodiment, the LNA-CDN compound is used in combination with Compound A5, or a compound as described in U.S. Pat. No. 8,552,002, to treat a disorder such as a digestive/gastrointestinal cancer, a hematological cancer, or a solid tumor. In one embodiment, the FGFR inhibitor or 3-(2,6-dichloro-3,5-dimethoxyphenyl)-1-(6-((4-(4-ethylpiperazin-1-yl)phenyl)amino)pyrimidin-4-yl)-1-methylurea (Compound A5) is administered at a dose of about 100-125 mg (e.g., per day), e.g., about 100 mg or about 125 mg.

In another embodiment, the combination, e.g., a combination comprising a LNA-CDN compound as described herein, is used in combination with a PI3K inhibitor, Buparlisib (Compound A6), or a compound disclosed in PCT Publication No. WO 2007/084786, to treat a disorder, e.g., a disorder described herein. In one embodiment, the PI3K inhibitor is Buparlisib (Compound A6) or a compound disclosed in PCT Publication No. WO 2007/084786. In one embodiment, the LNA-CDN compound is used in combination with Buparlisib (Compound A6), or a compound disclosed in PCT Publication No. WO 2007/084786, to treat a disorder such as, a prostate cancer, a non-small cell lung cancer, an endocrine cancer, a leukemia, an ovarian cancer, a melanoma, a bladder cancer, a breast cancer, a female reproductive system cancer, a digestive/gastrointestinal cancer, a colorectal cancer, a glioblastoma multiforme, a solid tumor, a non-Hodgkin lymphoma, a hematopoiesis disorder, or a head and neck cancer. In one embodiment, the PI3K inhibitor or Buparlisib (Compound A6) is administered at a dose of about 100 mg (e.g., per day).

In another embodiment, the combination, e.g., a combination comprising a LNA-CDN compound as described herein, is used in combination with an FGFR inhibitor, 8-(2,6-difluoro-3,5-dimethoxyphenyl)-N-(4-((dimethylamino)methyl)-1H-imidazol-2-yl)quinoxaline-5-carboxamide (Compound A7) or a compound disclosed in PCT Publication No. WO 2009/141386, to treat a disorder, e.g., a disorder described herein. In one embodiment, the FGFR inhibitor is 8-(2,6-difluoro-3,5-dimethoxyphenyl)-N-(4-((dimethylamino)methyl)-1H-imidazol-2-yl)quinoxaline-5-carboxamide (Compound A7) or a compound disclosed in PCT Publication No. WO 2009/141386. In one embodiment, the FGFR inhibitor is 8-(2,6-difluoro-3,5-dimethoxyphenyl)-N-(4-((dimethylamino)methyl)-1H-imidazol-2-yl)quinoxaline-5-carboxamide (Compound A7). In one embodiment, the LNA-CDN compound is used in combination with 8-(2,6-difluoro-3,5-dimethoxyphenyl)-N-(4-((dimethylamino)methyl)-1H-imidazol-2-yl)quinoxaline-5-carboxamide (Compound A7), or a compound disclosed in PCT Publication No. WO 2009/141386, to treat a disorder such as a cancer characterized by angiogenesis. In one embodiment, the FGFR inhibitor or 8-(2,6-difluoro-3,5-dimethoxyphenyl)-N-(4-((dimethylamino)methyl)-1H-imidazol-2-yl)quinoxaline-5-carboxamide (Compound A7) is administered at a dose of e.g., from approximately 3 mg to approximately 5 g, more preferably from approximately 10 mg to approximately 1.5 g per person per day, optionally divided into 1 to 3 single doses which may, for example, be of the same size.

In another embodiment the combination, e.g., a combination comprising a LNA-CDN compound as described herein, is used in combination with a PI3K inhibitor, (S)—N1-(4-methyl-5-(2-(1,1,1-trifluoro-2-methylpropan-2-yl)pyridin-4-yl)thiazol-2-yl)pyrrolidine-1,2-dicarboxamide (Compound A8) or a compound disclosed PCT Publication No. WO 2010/029082, to treat a disorder, e.g., a disorder described herein. In one embodiment, the PI3K inhibitor is (S)—N1-(4-methyl-5-(2-(1,1,1-trifluoro-2-methylpropan-2-yl)pyridin-4-yl)thiazol-2-yl)pyrrolidine-1,2-dicarboxamide (Compound A8) or a compound disclosed PCT Publication No. WO 2010/029082. In one embodiment, the LNA-CDN compound is used in combination with (S)—N1-(4-methyl-5-(2-(1,1,1-trifluoro-2-methylpropan-2-yl)pyridin-4-yl)thiazol-2-yl)pyrrolidine-1,2-dicarboxamide (Compound A8), or a compound disclosed PCT Publication No. WO 2010/029082, to treat a disorder such as a gastric cancer, a breast cancer, a pancreatic cancer, a digestive/gastrointestinal cancer, a solid tumor, and a head and neck cancer. In one embodiment, the PI3K inhibitor or (S)—N1-(4-methyl-5-(2-(1,1,1-trifluoro-2-methylpropan-2-yl)pyridin-4-yl)thiazol-2-yl)pyrrolidine-1,2-dicarboxamide (Compound A8) is administered at a dose of about 150-300, 200-300, 200-400, or 300-400 mg (e.g., per day), e.g., about 200, 300, or 400 mg.

In another embodiment, the combination, e.g., a combination comprising a LNA-CDN compound as described herein, is used in combination with an inhibitor of cytochrome P450 (e.g., a CYP17 inhibitor) or a compound disclosed in PCT Publication No. WO 2010/149755, to treat a disorder, e.g., a disorder described herein. In one embodiment, the cytochrome P450 inhibitor (e.g., the CYP17 inhibitor) is a compound disclosed in PCT Publication No. WO 2010/149755. In one embodiment, the LNA-CDN compound is used in combination with a compound disclosed in PCT Publication No. WO 2010/149755, to treat prostate cancer.

In another embodiment, the combination, e.g., a combination comprising a LNA-CDN compound as described herein, is used in combination with an HDM2 inhibitor, (S)-1-(4-chlorophenyl)-7-isopropoxy-6-methoxy-2-(4-(methyl(((1R,4S)-4-(4-methyl-3-oxopiperazin-1-yl)cyclohexyl)methyl)amino)phenyl)-1,2-dihydroisoquinolin-3 (4H)-one (Compound A10) or a compound disclosed in PCT Publication No. WO 2011/076786, to treat a disorder, e.g., a disorder described herein). In one embodiment, the HDM2 inhibitor is (S)-1-(4-chlorophenyl)-7-isopropoxy-6-methoxy-2-(4-(methyl(((1R,4S)-4-(4-methyl-3-oxopiperazin-1-yl)cyclohexyl)methyl)amino)phenyl)-1,2-dihydroisoquinolin-3(4H)-one (Compound A10) or a compound disclosed in PCT Publication No. WO 2011/076786. In one embodiment, the LNA-CDN compound is used in combination with (S)-1-(4-chlorophenyl)-7-isopropoxy-6-methoxy-2-(4-(methyl(((1R,4S)-4-(4-methyl-3-oxopiperazin-1-yl)cyclohexyl)methyl)amino)phenyl)-1,2-dihydroisoquinolin-3(4H)-one (Compound A10), or a compound disclosed in PCT Publication No. WO 2011/076786, to treat a disorder such as a solid tumor. In one embodiment, the HDM2 inhibitor or (S)-1-(4-chlorophenyl)-7-isopropoxy-6-methoxy-2-(4-(methyl(((1R,4S)-4-(4-methyl-3-oxopiperazin-1-yl)cyclohexyl)methyl)amino)phenyl)-1,2-dihydroisoquinolin-3(4H)-one (Compound A10) is administered at a dose of about 400 to 700 mg, e.g., administered three times weekly, 2 weeks on and one week off. In some embodiments, the dose is about 400, 500, 600, or 700 mg; about 400-500, 500-600, or 600-700 mg, e.g., administered three times weekly.

In another embodiment, the combination, e.g., a combination comprising a LNA-CDN compound as described herein, is used in combination with an iron chelating agent, Deferasirox (also known as EXJADE; Compound A11), or a compound disclosed in PCT Publication No. WO 1997/049395, to treat a disorder, e.g., a disorder described herein. In one embodiment, the iron chelating agent is Deferasirox or a compound disclosed in PCT Publication No. WO 1997/049395. In one embodiment, the iron chelating agent is Deferasirox (Compound A11). In one embodiment, the LNA-CDN compound is used in combination with Deferasirox (Compound A11), or a compound disclosed in PCT Publication No. WO 1997/049395, to treat iron overload, hemochromatosis, or myelodysplasia.

In another embodiment, the combination, e.g., a combination comprising a LNA-CDN compound as described herein, is used in combination with an aromatase inhibitor, Letrozole (also known as FEMARA; Compound A12), or a compound disclosed in U.S. Pat. No. 4,978,672, to treat a disorder, e.g., a disorder described herein. In one embodiment, the aromatase inhibitor is Letrozole (Compound A12) or a compound disclosed in U.S. Pat. No. 4,978,672. In one embodiment, the LNA-CDN compound is used in combination with Letrozole (Compound A12), or a compound disclosed in U.S. Pat. No. 4,978,672, to treat a disorder such as a cancer, a leiomyosarcoma, an endometrium cancer, a breast cancer, a female reproductive system cancer, or a hormone deficiency.

In another embodiment, the combination, e.g., a combination comprising a LNA-CDN compound as described herein, is used in combination with a PI3K inhibitor, e.g., a pan-PI3K inhibitor, (4S,5R)-3-(2'-amino-2-morpholino-4'-(trifluoromethyl)-[4,5'-bipyrimidin]-6-yl)-4-(hydroxymethyl)-5-methyloxazolidin-2-one (Compound A13) or a compound disclosed in PCT Publication No. WO2013/124826, to treat a disorder, e.g., a disorder described herein. In one embodiment, the PI3K inhibitor is (4S,5R)-3-(2'-amino-2-morpholino-4'-(trifluoromethyl)-[4,5'-bipyrimidin]-6-yl)-4-(hydroxymethyl)-5-methyloxazolidin-2-one (Compound A13) or a compound disclosed in PCT Publication No. WO2013/124826. In one embodiment, the LNA-CDN compound is used in combination with (4S,5R)-3-(2'-amino-2-morpholino-4'-(trifluoromethyl)-[4,5'-bipyrimidin]-6-yl)-4-(hydroxymethyl)-5-methyloxazolidin-2-one (Compound A13), or a compound disclosed in PCT Publication No. WO2013/124826, to treat a disorder such as a cancer or an advanced solid tumor.

In another embodiment, the combination, e.g., a combination comprising a LNA-CDN compound as described herein, is used in combination with an inhibitor of p53 and/or a p53/Mdm2 interaction, (S)-5-(5-chloro-1-methyl-2-oxo-1,2-dihydropyridin-3-yl)-6-(4-chlorophenyl)-2-(2,4-dimethoxypyrimidin-5-yl)-1-isopropyl-5,6-dihydropyrrolo[3,4-d]imidazol-4(1H)-one (Compound A14), or a compound disclosed in PCT Publication No. WO2013/111105, to treat a disorder, e.g., a disorder described herein. In one embodiment, the p53 and/or a p53/Mdm2 interaction inhibitor is (S)-5-(5-chloro-1-methyl-2-oxo-1,2-dihydropyridin-3-yl)-6-(4-chlorophenyl)-2-(2,4-dimethoxypyrimidin-5-yl)-1-isopropyl-5,6-dihydropyrrolo[3,4-d]imidazol-4(1H)-one (Compound A14) or a compound disclosed in PCT Publication No. WO2013/111105. In one embodiment, the LNA-CDN compound is used in combination with (S)-5-(5-chloro-1-methyl-2-oxo-1,2-dihydropyridin-3-yl)-6-(4-chlorophenyl)-2-(2,4-dimethoxypyrimidin-5-yl)-1-isopropyl-5,6-dihydropyrrolo[3,4-d]imidazol-4(1H)-one (Compound A14), or a compound disclosed in PCT Publication No. WO2013/111105, to treat a disorder such as a cancer or a soft tissue sarcoma.

In another embodiment, the combination, e.g., a combination comprising a LNA-CDN compound as described herein, is used in combination with a CSF-1R tyrosine kinase inhibitor, 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224, to treat a disorder, e.g., a disorder described herein. In one embodiment, the CSF-1R tyrosine kinase inhibitor is 4-((2-(((1R,2R)-2-hydroxycyclohexyl)amino)benzo[d]thiazol-6-yl)oxy)-N-methylpicolinamide (Compound A15) or a compound disclosed in PCT Publication No. WO 2005/073224. In one embodiment, the LNA-CDN compound is used in combination with 4-((2-(((1R,2R)-2-hydroxycyclohexyl)amino)benzo[d]thiazol-6-yl)oxy)-N-methylpicolinamide (Compound A15) or a compound disclosed in PCT Publication No. WO 2005/073224, to treat a disorder such as cancer.

In another embodiment, the combination, e.g., a combination comprising a LNA-CDN compound as described herein, is used in combination with an apoptosis inducer and/or an angiogenesis inhibitor, such as Imatinib mesylate (also known as GLEEVEC; Compound A16) or a compound disclosed in PCT Publication No. WO1999/003854, to treat a disorder, e.g., a disorder described. In one embodiment, the apoptosis inducer and/or an angiogenesis inhibitor is Imatinib mesylate (Compound A16) or a compound disclosed in PCT Publication No. WO1999/003854. In one embodiment, the LNA-CDN compound is used in combination with Imatinib mesylate (Compound A16), or a compound disclosed in PCT Publication No. WO1999/003854, to treat a disorder such as a cancer, a multiple myeloma, a prostate cancer, a non-small cell lung cancer, a lymphoma, a gastric cancer, a melanoma, a breast cancer, a pancreatic cancer, a digestive/gastrointestinal cancer, a colorectal cancer, a glioblastoma multiforme, a liver cancer, a head and neck cancer, asthma, multiple sclerosis, allergy, Alzheimer's dementia, amyotrophic lateral sclerosis, or rheumatoid arthritis. In certain embodiments, Imatinib mesylate (Compound A16) is administered at a dose of about 100 to 1000 mg, e.g., about 200 mg to 800 mg, about 300 mg to 700 mg, or about 400 mg to 600 mg, e.g., about 200 mg, 300 mg, 400 mg, 500 mg, 600 mg, or 700 mg. The dosing schedule can vary from e.g., every other day to daily, twice or three times a day. In one embodiment, Imatinib mesylate is administered at an oral dose from about 100 mg to 600 mg daily, e.g., about 100 mg, 200 mg, 260 mg, 300 mg, 400 mg, or 600 mg daily.

In another embodiment, the combination, e.g., a combination comprising a LNA-CDN compound as described herein, is used in combination with a JAK inhibitor, 2-fluoro-N-methyl-4-(7-(quinolin-6-ylmethyl)imidazo[1,2-b][1,2,4]triazin-2-yl)benzamide (Compound A17), or a dihydrochloric salt thereof, or a compound disclosed in PCT Publication No. WO 2007/070514, to treat a disorder, e.g., a disorder described herein. In one embodiment, the JAK inhibitor is 2-fluoro-N-methyl-4-(7-(quinolin-6-ylmethyl)imidazo[1,2-b][1,2,4]triazin-2-yl)benzamide (Compound A17), or a dihydrochloric salt thereof, or a compound disclosed in PCT Publication No. WO 2007/070514. In one embodiment, the LNA-CDN compound is used in combination with 2-fluoro-N-methyl-4-(7-(quinolin-6-ylmethyl)imidazo[1,2-b][1,2,4]triazin-2-yl)benzamide (Compound A17), or a dihydrochloric salt thereof, or a compound disclosed in PCT Publication No. WO 2007/070514, to treat a disorder such as colorectal cancer, myeloid leukemia, hematological cancer, autoimmune disease, non-Hodgkin lymphoma, or thrombocythemia. In one embodiment, the JAK inhibitor or a 2-fluoro-N-methyl-4-(7-(quinolin-6-ylmethyl)imidazo[1,2-b][1,2,4]triazin-2-yl)benzamide (Compound A17), or a dihydrochloric salt thereof is administered at a dose of about 400-600 mg (e.g., per day), e.g., about 400, 500, or 600 mg, or about 400-500 or 500-600 mg.

In another embodiment, the combination, e.g., a combination comprising a LNA-CDN compound as described herein, is used in combination with a JAK inhibitor, Ruxolitinib Phosphate (also known as JAKAFI; Compound A18) or a compound disclosed in PCT Publication No. WO 2007/070514 to treat a disorder, e.g., a disorder described herein. In one embodiment, the JAK inhibitor is Ruxolitinib Phosphate (Compound A18) or a compound disclosed in PCT Publication No. WO 2007/070514. In one embodiment, the LNA-CDN compound is used in combination with Ruxolitinib Phosphate (Compound A18), or a compound disclosed in PCT Publication No. WO 2007/070514, to treat a disorder such as a prostate cancer, a lymphocytic leukemia, a multiple myeloma, a lymphoma, a lung cancer, a leukemia, cachexia, a breast cancer, a pancreatic cancer, rheumatoid arthritis, psoriasis, a colorectal cancer, a myeloid leukemia, a hematological cancer, an autoimmune disease, a non-Hodgkin lymphoma, or thrombocythemia. In one embodiment, the JAK inhibitor or Ruxolitinib Phosphate (Compound A18) is administered at a dose of about 15-25 mg, e.g., twice daily. In some embodiments, the dose is about 15, 20, or 25 mg, or about 15-20 or 20-25 mg.

In another embodiment, the combination, e.g., a combination comprising a LNA-CDN compound as described herein, is used in combination with a histone deacetylase (HDAC) inhibitor. In some embodiments, the HDAC inhibitor is selected from the group consisting of panobinostat, vorinostat, romidepsin, chidamide, valproic acid, belinostat, pyroxamide, mocetinostat, abexinostat, entinostat, pracinostat, resminostat, givinostat, quisinostat, ricolinostat, CUDC-101, AR-42, CHR-2845, CHR-3996, 4SC-202, and CG200745. In some embodiments, the combination comprising a LNA-CDN compound as described herein, is used in combination with a histone deacetylase (HDAC) inhibitor, Panobinostat (Compound A19), or a compound disclosed in PCT Publication No. WO 2014/072493, to treat a disorder, e.g., a disorder described herein. In one embodiment, the HDAC inhibitor is Panobinostat (Compound A19) or a compound disclosed in PCT Publication No. WO 2014/072493. In one embodiment, the LNA-CDN compound is used in combination with Panobinostat (Compound A19), a compound disclosed in PCT Publication No. WO 2014/072493, to treat a disorder such as a small cell lung cancer, a respiratory/thoracic cancer, a prostate cancer, a multiple myeloma, myelodysplastic syndrome, a bone cancer, a non-small cell lung cancer, an endocrine cancer, a lymphoma, a neurologic cancer, a leukemia, HIV/AIDS, an immune disorder, transplant rejection, a gastric cancer, a melanoma, a breast cancer, a pancreatic cancer, a colorectal cancer, a glioblastoma multiforme, a myeloid leukemia, a hematological cancer, a renal cancer, a non-Hodgkin lymphoma, a head and neck cancer, a hematopoiesis disorders, or a liver cancer. In one embodiment, the HDAC inhibitor or Panobinostat (Compound A19) is administered at a dose of about 20 mg (e.g., per day).

In another embodiment, the combination, e.g., a combination comprising a LNA-CDN compound as described herein, is used in combination with an inhibitor of one or more of cytochrome P450 (e.g., 11B2), aldosterone or angiogenesis, Osilodrostat (Compound A20), or a compound disclosed in PCT Publication No. WO2007/024945, to treat a disorder, e.g., a disorder described herein. In one embodiment, the inhibitor of one or more of cytochrome P450 (e.g., 11B2), aldosterone or angiogenesis is Osilodrostat (Compound A20) or a compound disclosed in PCT Publication No. WO2007/024945. In one embodiment, the LNA-CDN compound is used in combination with Osilodrostat (Compound A20), or a compound disclosed in PCT Publication No. WO2007/024945, to treat a disorder such as Cushing's syndrome, hypertension, or heart failure therapy.

In another embodiment, the combination, e.g., a combination comprising a LNA-CDN compound as described herein, is used in combination with a IAP inhibitor, (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21) or a compound disclosed in U.S. Pat. No. 8,552,003, to treat a disorder, e.g., a disorder described herein. In one embodiment, the IAP inhibitor is (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21) or a compound disclosed in U.S. Pat. No. 8,552,003. In one embodiment, the LNA-CDN compound is used in combination with (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21), or a compound disclosed in U.S. Pat. No. 8,552,003, to treat a disorder such as a multiple myeloma, a breast cancer, an ovarian cancer, a pancreatic cancer, or a hematopoiesis disorder. In one embodiment, the IAP inhibitor or (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21) or a compound disclosed in U.S. Pat. No. 8,552,003 is administered at a dose of approximately 1800 mg, e.g., once weekly.

In another embodiment, the combination, e.g., a combination comprising a LNA-CDN compound as described herein, is used in combination a Smoothened (SMO) inhibitor, Sonidegib phosphate (Compound A22), (R)-2-(5-(4-(6-benzyl-4,5-dimethylpyridazin-3-yl)-2-methylpiperazin-1-yl)pyrazin-2-yl)propan-2-ol (Compound A25), or a compound disclosed in PCT Publication No. WO 2007/131201 or WO 2010/007120, to treat a disorder, e.g., a disorder described herein. In one embodiment, the SMO inhibitor is Sonidegib phosphate (Compound A22), (R)-2-(5-(4-(6-benzyl-4,5-dimethylpyridazin-3-yl)-2-methylpiperazin-1-yl)pyrazin-2-yl)propan-2-ol (Compound A25), or a compound disclosed in PCT Publication No. WO 2007/131201 or WO 2010/007120. In one embodiment, the LNA-CDN compound is used in combination with Sonidegib phosphate (Compound A22), (R)-2-(5-(4-(6-benzyl-4,5-dimethylpyridazin-3-yl)-2-methylpiperazin-1-yl)pyrazin-2-yl)propan-2-ol (Compound A25), or a compound disclosed in PCT Publication No. WO 2007/131201 or WO 2010/007120 to treat a disorder such as a cancer, a medulloblastoma, a small cell lung cancer, a prostate cancer, a basal cell carcinoma, a pancreatic cancer, or an inflammation. In certain embodiments, Sonidegib phosphate (Compound A22) is administered at a dose of about 20 to 500 mg, e.g., about 40 mg to 400 mg, about 50 mg to 300 mg, or about 100 mg to 200 mg, e.g., about 50 mg, 100 mg, 150 mg, 200 mg, 250 mg, or 300 mg. The dosing schedule can vary from e.g., every other day to daily, twice or three times a day.

In another embodiment, the combination, e.g., a combination comprising a LNA-CDN compound as described herein, is used in combination with an Alk inhibitor, ceritinib (also known as ZYKADIA; Compound A23) or a compound disclosed in PCT Publication No. WO 2007/131201, to treat a disorder, e.g., a disorder described herein. In one embodiment, the Alk inhibitor is ceritinib (Compound A23) or a compound disclosed in PCT Publication No. WO 2007/131201. In one embodiment, the LNA-CDN compound is used in combination with ceritinib (Compound A23), or a compound disclosed in PCT Publication No. WO 2007/131201, to treat a disorder such as non-small cell lung cancer or solid tumors. In one embodiment, the Alk inhibitor or ceritinib (Compound A23) is administered at a dose of approximately 750 mg, e.g., once daily.

In another embodiment, the combination, e.g., a combination comprising a LNA-CDN compound as described herein, is used in combination with a JAK and/or CDK4/6 inhibitor, 7-cyclopentyl-N,N-dimethyl-2-((5-(piperazin-1-yl)pyridin-2-yl)amino)-7H-pyrrolo[2,3-d]pyrimidine-6-carboxamide (Compound A24), or a compound disclosed in U.S. Pat. No. 8,415,355 or 8,685,980, to treat a disorder, e.g., a disorder described herein. In one embodiment, the JAK and/or CDK4/6 inhibitor is 7-cyclopentyl-N,N-dimethyl-2-((5-(piperazin-1-yl)pyridin-2-yl)amino)-7H-pyrrolo[2,3-d]pyrimidine-6-carboxamide (Compound A24) or a compound disclosed in U.S. Pat. No. 8,415,355 or 8,685,980. In one embodiment, the LNA-CDN compound is used in combination with 7-cyclopentyl-N,N-dimethyl-2-((5-(piperazin-1-yl)pyridin-2-yl)amino)-7H-pyrrolo[2,3-d]pyrimidine-6-carboxamide (Compound A24), or a compound disclosed in U.S. Pat. No. 8,415,355 or 8,685,980, to treat a disorder such as a lymphoma, a neurologic cancer, a melanoma, a breast cancer, or a solid tumor. In one embodiment, the JAK and/or CDK4/6 inhibitor or 7-cyclopentyl-N,N-dimethyl-2-((5-(piperazin-1-yl)pyridin-2-yl)amino)-7H-pyrrolo[2,3-d]pyrimidine-6-carboxamide (Compound A24) is administered at a dose of approximately 200-600 mg, e.g., per day. In one embodiment, the compound is administered at a dose of about 200, 300, 400, 500, or 600 mg, or about 200-300, 300-400, 400-500, or 500-600 mg.

In another embodiment, the combination, e.g., a combination comprising a LNA-CDN compound as described herein, is used in combination with a PIM Kinase inhibitor, N-(4-((1R,3S,5S)-3-amino-5-methylcyclohexyl)pyridin-3-yl)-6-(2,6-difluorophenyl)-5-fluoropicolinamide (Compound A27) or a compound disclosed in PCT Publication No. WO 2010/026124, to treat a disorder, e.g., a disorder described herein. In one embodiment, the PIM Kinase inhibitor is N-(4-((1R,3S,5S)-3-amino-5-methylcyclohexyl) pyridin-3-yl)-6-(2,6-difluorophenyl)-5-fluoropicolinamide (Compound A27) or a compound disclosed in PCT Publication No. WO 2010/026124. In one embodiment, the LNA-CDN compound is used in combination with N-(4-((1R,3S,5S)-3-amino-5-methylcyclohexyl)pyridin-3-yl)-6-(2,6-difluorophenyl)-5-fluoropicolinamide (Compound A27), or a compound disclosed in PCT Publication No. WO 2010/026124, to treat a disorder such as a multiple myeloma, myelodysplastic syndrome, a myeloid leukemia, or a non-Hodgkin lymphoma.

In another embodiment, the combination, e.g., a combination comprising a LNA-CDN compound as described herein, is used in combination a Wnt signaling inhibitor, 2-(2',3-dimethyl-[2,4'-bipyridin]-5-yl)-N-(5-(pyrazin-2-yl) pyridin-2-yl)acetamide (Compound A28) or a compound disclosed in PCT publication No. WO 2010/101849, to treat a disorder, e.g., a disorder described herein. In one embodiment, the Wnt signaling inhibitor is 2-(2',3-dimethyl-[2,4'-bipyridin]-5-yl)-N-(5-(pyrazin-2-yl)pyridin-2-yl)acetamide (Compound A28) or a compound disclosed in PCT publication No. WO 2010/101849. In one embodiment, the Wnt signaling inhibitor is 2-(2',3-dimethyl-[2,4'-bipyridin]-5-yl)-N-(5-(pyrazin-2-yl)pyridin-2-yl)acetamide (Compound A28). In one embodiment, the LNA-CDN compound is used in combination with 2-(2',3-dimethyl-[2,4'-bipyridin]-5-yl)-N-(5-(pyrazin-2-yl)pyridin-2-yl)acetamide (Compound A28), or a compound disclosed in PCT publication No. WO 2010/101849, to treat a disorder such as a solid tumor (e.g., a head and neck cancer, a squamous cell carcinoma, a breast cancer, a pancreatic cancer, or a colon cancer). In certain embodiments, 2-(2',3-dimethyl-[2,4'-bipyridin]-5-yl)-N-(5-(pyrazin-2-yl)pyridin-2-yl)acetamide (Compound A28) is administered at a dose of about 1 to 50 mg, e.g., about 2 mg to 45 mg, about 3 mg to 40 mg, about 5 mg to 35 mg, 5 mg to 10 mg, or about 10 mg to 30 mg, e.g., about 2 mg, 5 mg, 10 mg, 20 mg, 30 mg, or 40 mg. The dosing schedule can vary from e.g., every other day to daily, twice or three times a day.

In another embodiment, the combination, e.g., a combination comprising a LNA-CDN compound as described herein, is used in combination with a BRAF inhibitor, Encorafenib (Compound A29), or a compound disclosed in PCT Publication No. WO 2011/025927, to treat a disorder, e.g., a disorder described herein. In one embodiment, the BRAF inhibitor is Encorafenib (Compound A29) or a compound disclosed in PCT Publication No. WO 2011/025927. In one embodiment, the LNA-CDN compound is used in combination with Encorafenib (Compound A29), or a compound disclosed in PCT Publication No. WO 2011/025927, to treat a disorder such as a non-small cell lung cancer, a melanoma, or a colorectal cancer. In one embodiment, the BRAF inhibitor or Encorafenib (Compound A29) is administered at a dose of about 200-300, 200-400, or 300-400 mg, e.g., per day. In one embodiment, the compound is administered at a dose of about 200, about 300 or about 400 mg.

In another embodiment, the combination, e.g., a combination comprising a LNA-CDN compound as described herein, is used in combination a CDK4/6 inhibitor, 7-cyclopentyl-N,N-dimethyl-2-((5-((1R,6S)-9-methyl-4-oxo-3,9-diazabicyclo[4.2.1]nonan-3-yl)pyridin-2-yl)amino)-7H-pyrrolo[2,3-d]pyrimidine-6-carboxamide (Compound A30), or a compound disclosed in PCT publication No. WO 2011/101409, to treat a disorder, e.g., a disorder described herein. In one embodiment, the CDK4/6 inhibitor is 7-cyclopentyl-N,N-dimethyl-2-((5-((1R,6S)-9-methyl-4-oxo-3,9-diazabicyclo[4.2.1]nonan-3-yl)pyridin-2-yl)amino)-7H-pyrrolo[2,3-d]pyrimidine-6-carboxamide (Compound A30) or a compound disclosed in PCT publication No. WO 2011/101409. In one embodiment, the LNA-CDN compound is used in combination with 7-cyclopentyl-N,N-dimethyl-2-((5-((1R,6S)-9-methyl-4-oxo-3,9-diazabicyclo[4.2.1]nonan-3-yl)pyridin-2-yl)amino)-7H-pyrrolo[2,3-d]pyrimidine-6-carboxamide (Compound A30), or a compound disclosed in PCT publication No. WO 2011/101409, to treat a disorder such as a cancer, a mantle cell lymphoma, a liposarcoma, a non-small cell lung cancer, a melanoma, a squamous cell esophageal cancer, or a breast cancer.

In another embodiment, the combination, e.g., a combination comprising a LNA-CDN compound as described herein, is used in combination with a MEK inhibitor, Binimetinib (Compound A34), or a compound disclosed in PCT Publication No. WO 2003/077914, to treat a disorder, e.g., a disorder described herein. In one embodiment, the MEK inhibitor is Binimetinib (Compound A34), or a compound disclosed in PCT Publication No. WO 2003/077914. In one embodiment, the LNA-CDN compound is used in combination with Binimetinib (Compound A34), or a compound disclosed in PCT Publication No. WO 2003/077914, to treat a disorder such as a non-small cell lung cancer, a multisystem genetic disorder, a melanoma, an ovarian cancer, a digestive/gastrointestinal cancer, a rheumatoid arthritis, or a colorectal cancer. In one embodiment, the MEK inhibitor or Binimetinib (Compound A34) is administered at a dose of about 45 mg, e.g., twice daily.

In another embodiment, the combination, e.g., a combination comprising a LNA-CDN compound as described herein, is used in combination an inhibitor of one or more of c-KIT, histamine release, Flt3 (e.g., FLK2/STK1) or PKC, Midostaurin (Compound A35) or a compound disclosed in PCT Publication No. WO 2003/037347, to treat a disorder, e.g., a disorder described herein. In one embodiment, the inhibitor is Midostaurin (Compound A35) or compound disclosed in PCT Publication No. WO 2003/037347. In one embodiment, the inhibitor of one or more of c-KIT, histamine release, Flt3 (e.g., FLK2/STK1) or PKC is Midostaurin. In one embodiment, the LNA-CDN compound is used in combination with Midostaurin (Compound A35), or compound disclosed in PCT Publication No. WO 2003/037347, to treat a disorder such as a cancer, a colorectal cancer, a myeloid leukemia, myelodysplastic syndrome, an age-related mascular degeneration, a diabetic complication, or a dermatologic disorder.

In another embodiment, the combination, e.g., a combination comprising a LNA-CDN compound as described herein, is used in combination with a TOR inhibitor (e.g., mTOR inhibitor), Everolimus (also known as AFINITOR; Compound A36) or a Compound disclosed in PCT Publication No. WO 2014/085318, to treat a disorder, e.g., a disorder described herein). In one embodiment, the TOR inhibitor is Everolimus (Compound A36) or a Compound disclosed in PCT Publication No. WO 2014/085318. In one embodiment, the LNA-CDN compound is used in combination with Everolimus (Compound A36) to treat a disorder such as an interstitial lung disease, a small cell lung cancer, a respiratory/thoracic cancer, a prostate cancer, a multiple myeloma, a sarcoma, an age-related macular degeneration, a bone cancer, tuberous sclerosis, a non-small cell lung cancer, an endocrine cancer, a lymphoma, a neurologic disorders, an astrocytoma, a cervical cancer, a neurologic cancer, a leukemia, an immune disorders, transplant rejection, a gastric cancer, a melanoma, epilepsy, a breast cancer, or a bladder cancer. In one embodiment, the TOR inhibitor or Everolimus is (Compound A36) administered at a dose of about 2.5-20 mg/day. In one embodiment, the compound is administered at a dose of about 2.5, 5, 10, or 20 mg/day, e.g., about 2.5-5, 5-10, or 10-20 mg/day.

In another embodiment, the combination, e.g., a combination comprising a LNA-CDN compound as described herein, is used in combination an inhibitor of one or more of VEGFR-2, PDGFRbeta, KIT or Raf kinase C, 1-methyl-5-((2-(5-(trifluoromethyl)-1H-imidazol-2-yl)pyridin-4-yl)oxy)-N-(4-(trifluoromethyl)phenyl)-1H-benzo[d]imidazol-2-amine (Compound A37) or a compound disclosed in PCT Publication No. WO 2007/030377, to treat a disorder, e.g., a disorder described herein. In one embodiment, the inhibitor of one or more of VEGFR-2, PDGFRbeta, KIT or Raf kinase C is 1-methyl-5-((2-(5-(trifluoromethyl)-1H-imidazol-2-yl)pyridin-4-yl)oxy)-N-(4-(trifluoromethyl)phenyl)-1H-benzo[d]imidazol-2-amine (Compound A37) or a compound disclosed in PCT Publication No. WO 2007/030377. In one embodiment, the LNA-CDN compound is used in combination with 1-methyl-5-((2-(5-(trifluoromethyl)-1H-imidazol-2-yl)pyridin-4-yl)oxy)-N-(4-(trifluoromethyl)phenyl)-1H-benzo[d]imidazol-2-amine (Compound A37), or a compound disclosed in PCT Publication No. WO 2007/030377, to treat a disorder such as a cancer, a melanoma, or a solid tumor.

In another embodiment, the combination, e.g., a combination comprising a LNA-CDN compound as described herein, is used in combination a somatostatin agonist and/or growth hormone release inhibitor, Pasireotide diaspartate (also known as SIGNIFOR; Compound A38) or a compound disclosed in PCT Publication No. WO2002/010192 or U.S. Pat. No. 7,473,761, to treat a disorder, e.g., a disorder described herein. In one embodiment, the somatostatin agonist and/or growth hormone release inhibitor is Pasireotide diaspartate (Compound A38) or a compound disclosed in PCT Publication No. WO2002/010192 or U.S. Pat. No. 7,473,761. In one embodiment, the LNA-CDN compound is used in combination with Pasireotide diaspartate (Compound A38), or a compound disclosed in PCT Publication No. WO2002/010192 or U.S. Pat. No. 7,473,761, to treat a disorder such as a prostate cancer, an endocrine cancer, a neurologic cancer, a skin cancer (e.g., a melanoma), a pancreatic cancer, a liver cancer, Cushing's syndrome, a gastrointestinal disorder, acromegaly, a liver and biliary tract disorder, or liver cirrhosis.

In another embodiment, the combination, e.g., a combination comprising a LNA-CDN compound as described herein, is used in combination a signal transduction modulator and/or angiogenesis inhibitor, Dovitinib (Compound A39) or a compound disclosed in PCT Publication No. WO 2009/115562, to treat a disorder, e.g., a disorder described herein. In one embodiment, the signal transduction modulator and/or angiogenesis inhibitor is Dovitinib (Compound A39) or a compound disclosed in PCT Publication No. WO 2009/115562. In one embodiment, the LNA-CDN compound is used in combination with Dovitinib (Compound A39), or a compound disclosed in PCT Publication No. WO 2009/115562, to treat a disorder such as a cancer, a respiratory/thoracic cancer, a multiple myeloma, a prostate cancer, a non-small cell lung cancer, an endocrine cancer, or a neurological genetic disorder.

In another embodiment, the combination, e.g., a combination comprising a LNA-CDN compound as described herein, is used in combination with an EGFR inhibitor, (R,E)-N-(7-chloro-1-(1-(4-(dimethylamino)but-2-enoyl)azepan-3-yl)-1H-benzo[d]imidazol-2-yl)-2-methylisonicotinamide (Compound A40) or a compound disclosed in PCT Publication No. WO 2013/184757, to treat a disorder, e.g., a disorder described herein. In one embodiment, the EGFR inhibitor is (R,E)-N-(7-chloro-1-(1-(4-(dimethylamino) but-2-enoyl)azepan-3-yl)-1H-benzo[d]imidazol-2-yl)-2-methylisonicotinamide (Compound A40) or a compound disclosed in PCT Publication No. WO 2013/184757. In one embodiment, the LNA-CDN compound is used in combination with (R,E)-N-(7-chloro-1-(1-(4-(dimethylamino)but-2-enoyl)azepan-3-yl)-1H-benzo[d]imidazol-2-yl)-2-methylisonicotinamide (Compound A40), or a compound disclosed in PCT Publication No. WO 2013/184757, to treat a disorder such as a cancer, e.g., a solid tumor. In one embodiment, the EGFR inhibitor or (R,E)-N-(7-chloro-1-(1-(4-(dimethylamino)but-2-enoyl)azepan-3-yl)-1H-benzo[d]imidazol-2-yl)-2-methylisonicotinamide (Compound A40) is administered at a dose of 150-250 mg, e.g., per day. In one embodiment, the compound is administered at a dose of about 150, 200, or 250 mg, or about 150-200 or 200-250 mg.

In another embodiment, the combination, e.g., a combination comprising a LNA-CDN compound as described herein, is used in combination an ALK inhibitor, $N^6$-(2-isopropoxy-5-methyl-4-(1-methylpiperidin-4-yl)phenyl)-$N^4$-(2-(isopropylsulfonyl)phenyl)-1H-pyrazolo[3,4-d]pyrimidine-4,6-diamine (Compound A42) or a compound disclosed in PCT Publication No. WO 2008/073687, to treat a disorder, e.g., a disorder described herein. In one embodiment, the ALK inhibitor is $N^6$-(2-isopropoxy-5-methyl-4-(1-methylpiperidin-4-yl)phenyl)-$N^4$-(2-(isopropylsulfonyl)phenyl)-1H-pyrazolo[3,4-d]pyrimidine-4,6-diamine (Compound A42) or a compound disclosed in PCT Publication No. WO 2008/073687. In one embodiment, the LNA-CDN compound is used in combination with $N^6$-(2-isopropoxy-5-methyl-4-(1-methylpiperidin-4-yl)phenyl)-$N^4$-(2-(isopropylsulfonyl)phenyl)-1H-pyrazolo[3,4-d]pyrimidine-4,6-diamine (Compound A42), or a compound disclosed in PCT Publication No. WO 2008/073687, to treat a disorder such as a cancer, an anaplastic large-cell lymphoma (ALCL), a non-small cell lung carcinoma (NSCLC), or a neuroblastoma.

In another embodiment, the combination, e.g., a combination comprising a LNA-CDN compound as described herein, is used in combination an IGF-1R inhibitor, 3-(4-(4-((5-chloro-4-((5-methyl-1H-pyrazol-3-yl)amino)pyrimidin-2-yl)amino)-5-fluoro-2-methylphenyl)piperidin-1-yl)thietane 1,1-dioxide (Compound A43), 5-chloro-$N^2$-(2-fluoro-5-methyl-4-(1-(tetrahydro-2H-pyran-4-yl)piperidin-4-yl)phenyl)-$N^4$-(5-methyl-1H-pyrazol-3-yl)pyrimidine-2,4-diamine (Compound A44), or 5-chloro-N2-(4-(1-ethylpiperidin-4-yl)-2-fluoro-5-methylphenyl)-$N^4$-(5-methyl-1H-pyrazol-3-yl)pyrimidine-2,4-diamine (Compound A45) or a compound disclosed in PCT Publication No. WO 2010/002655, to treat a disorder, e.g., a disorder described. In one embodiment, the IGF-1R inhibitor is 3-(4-(4-((5-chloro-4-((5-methyl-1H-pyrazol-3-yl)amino)pyrimidin-2-yl)amino)-5-fluoro-2-methylphenyl)piperidin-1-yl)thietane 1,1-dioxide (Compound A43), 5-chloro-N²-(2-fluoro-5-methyl-4-(1-(tetrahydro-2H-pyran-4-yl)piperidin-4-yl)phenyl)-N⁴-(5-methyl-1H-pyrazol-3-yl)pyrimidine-2,4-diamine (Compound A44), 5-chloro-N2-(4-(1-ethylpiperidin-4-yl)-2-fluoro-5-methylphenyl)-N⁴-(5-methyl-1H-pyrazol-3-yl)pyrimidine-2,4-diamine (Compound A45), or a compound disclosed in PCT Publication No. WO 2010/002655. In one embodiment, the LNA-CDN compound is used in combination with 3-(4-(4-((5-chloro-4-((5-methyl-1H-pyrazol-3-yl)amino)pyrimidin-2-yl)amino)-5-fluoro-2-methylphenyl)piperidin-1-yl)thietane 1,1-dioxide (Compound A43), 5-chloro-N²-(2-fluoro-5-methyl-4-(1-(tetrahydro-2H-pyran-4-yl)piperidin-4-yl)phenyl)-N⁴-(5-methyl-1H-pyrazol-3-yl)pyrimidine-2,4-diamine (Compound A44), 5-chloro-N2-(4-(1-ethylpiperidin-4-yl)-2-fluoro-5-methylphenyl)-N⁴-(5-methyl-1H-pyrazol-3-yl)pyrimidine-2,4-diamine (Compound A45), or a compound disclosed in PCT Publication No. WO 2010/002655, to treat a disorder such as a cancer or a sarcoma.

In another embodiment, the combination, e.g., a combination comprising a LNA-CDN compound as described herein, is used in combination a P-Glycoprotein 1 inhibitor, Valspodar (also known as AMDRAY; Compound A46) or a compound disclosed in EP 296122, to treat a disorder, e.g., a disorder described herein. In one embodiment, the P-Glycoprotein 1 inhibitor is Valspodar (Compound A46) or a compound disclosed in EP 296122. In one embodiment, the LNA-CDN compound is used in combination with Valspodar (Compound A46), or a compound disclosed in EP 296122, to treat a disorder such as a cancer or a drug-resistant tumor.

In another embodiment, the combination, e.g., a combination comprising a LNA-CDN compound as described herein, is used in combination one or more of a VEGFR inhibitor, Vatalanib succinate (Compound A47) or a compound disclosed in WO 98/35958, to treat a disorder, e.g., a disorder described herein. In one embodiment, the VEGFR inhibitor is Vatalanib succinate (Compound A47) or a compound disclosed in WO 98/35958. In one embodiment, the LNA-CDN compound is used in combination with Vatalanib succinate (Compound A47), or a compound disclosed in EP 296122, to treat cancer.

In another embodiment, the combination, e.g., a combination comprising a LNA-CDN compound as described herein, is used in combination with an IDH inhibitor or a compound disclosed in WO2014/141104, to treat a disorder, e.g., a disorder described herein. In one embodiment, the IDH inhibitor is a compound disclosed in PCT Publication No. WO2014/141104. In one embodiment, the LNA-CDN compound is used in combination with a compound disclosed in WO2014/141104 to treat a disorder such as a cancer.

In another embodiment, the combination, e.g., a combination comprising a LNA-CDN compound as described herein, is used in combination with a BCL-ABL inhibitor or a compound disclosed in PCT Publication No. WO2013/171639, WO2013/171640, WO2013/171641, or WO2013/171642, to treat a disorder, e.g., a disorder described herein. In one embodiment, the BCL-ABL inhibitor is a compound disclosed in PCT Publication No. WO2013/171639, WO2013/171640, WO2013/171641, or WO2013/171642. In one embodiment, the LNA-CDN compound is used in combination with a compound disclosed in PCT Publication No. WO2013/171639, WO2013/171640, WO2013/171641, or WO2013/171642 to treat a disorder such as a cancer.

In another embodiment, the combination, e.g., a combination comprising a LNA-CDN compound as described herein, is used in combination with a c-RAF inhibitor or a compound disclosed in PCT Publication No. WO2014/151616, to treat a disorder, e.g., a disorder described herein. In one embodiment, the c-RAF inhibitor is Compound A50 or a compound disclosed in PCT Publication No. WO2014/151616. In one embodiment, the LNA-CDN compound is used in combination with a compound disclosed in PCT Publication No. WO2014/151616 to treat a disorder such as a cancer.

In another embodiment, the combination, e.g., a combination comprising a LNA-CDN compound as described herein, is used in combination with an ERK1/2 ATP competitive inhibitor or a compound disclosed in PCT Publication No. WO2015/066188, to treat a disorder, e.g., a disorder described herein. In one embodiment, the ERK1/2 ATP competitive inhibitor is a compound disclosed in PCT Publication No. WO2015/066188. In one embodiment, the LNA-CDN compound is used in combination with Compound A51 or a compound disclosed in PCT Publication No. WO2015/066188 to treat a disorder such as a cancer. In some embodiments, the combination, e.g., a combination comprising a LNA-CDN compound described herein, and Compound A51 or a compound disclosed in PCT Publication No. WO2015/066188, is administered in combination with one or more agents selected from, Compound A8, Compound A17, Compound A23, Compound A24, Compound A27, Compound A29, and Compound A33.

In some embodiments, the combination, e.g., a combination comprising a LNA-CDN compound as described herein, is administered in combination with an anti-cancer agent having a known activity in an immune cell assay, e.g., in one or more of a huMLR assay, a T cell proliferation assay, and a B-cell proliferation assay, where such assays are known in the art, and can be used to demonstrate the compounds will not inhibit an immune response (i.e. demonstrate little or no inhibition in such assays). An IC50 in such assays can be determined for the compounds to be used in combination with the LNA-CDN compound. In embodiments, the anti-cancer agent has an IC50 of, e.g., >1 µM, 1-4 µM, or greater than 4 µM, e.g., 4-10 µM or 4-20 µM, or greater than 20 µM. In embodiments, the second therapeutic agent is chosen from one or more of: Compound A9, Compound A16, Compound A17, Compound A21, Compound A22, Compound A25, Compound A28, Compound A48, and Compound A49.

In some embodiments, the Compound A28 (or a compound related to Compound A28) is administered at a dose of approximately 5-10 or 10-30 mg. In some embodiments, the Compound A22 (or compound related to Compound A22) is administered at a dose of about 200 mg. In some embodiments, the Compound A17 (or compound related to Compound A17) is administered at a dose of approximately 400-600 mg. In some embodiments, the Compound A16 (or compound related to Compound A16) is administered at a dose of approximately 400-600 mg PO qDay. In some embodiments, the Compound A29 (or compound related to Compound A29) is administered at a dose of approximately 200-400 or 300-400 mg. In some embodiments, the Compound A24 (or compound related to Compound A24) is administered at a dose of approximately 200-600 mg. In some embodiments, the Compound A23 (ceritinib) (or compound related to ceritinib) is administered at a dose of approximately 750 mg once daily. In some embodiments, the Compound A8 (or compound related to Compound A8) is administered at a dose of approximately 200-400 or 300-400 mg. In some embodiments, the Compound A5 (or compound related to Compound A5) is administered at a dose of approximately 100-125 mg. In some embodiments, the Compound A6 (or compound related to Compound A6) is administered at a dose of about 100 mg. In some embodiments, the Compound A1 (or compound related to Compound A1) is administered at a dose of approximately 200-300 or 200-600 mg. In some embodiments, the Compound A40 (or compound related to Compound A40) is administered at a dose of approximately 150-250 mg. In embodiments, the Compound A10 (or compound related to Compound A10) is administered at a dose of approximately 400 to 700 mg, e.g., administered three times weekly, 2 weeks on and one week off. In embodiments, the BCR-ABL inhibitor is administered at a dose of approximately 20 mg bid-80 mg bid.

TABLE 2

Therapeutic agents that can be administered in combination with the LNA-CDN compounds as described herein.

| Compound designation/ generic name | Patent/Reference | Compound Structure |
| --- | --- | --- |
| A1 Sotrastaurin | EP 1682103 US 2007/142401 WO 2005/039549 | 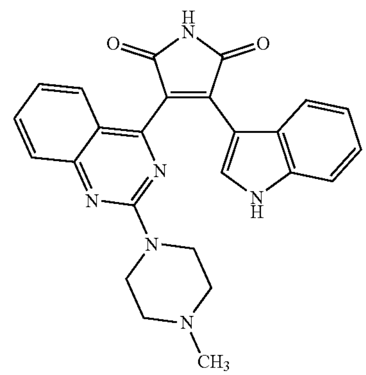 [SMILES: CN1CCN(c2nc(C3=C(c4c[nH]c5ccccc45)C(=O)NC3=O)c3ccccc3n2)CC1] |
| A2 Nilotinib HCl monohydrate TASIGNA ® | WO 2004/005281 U.S. Pat. No. 7,169,791 | HCl·H$_2$0 |
| A3 | WO 2010/060937 WO 2004/072051 EP 1611112 U.S. Pat. No. 8,450,310 | 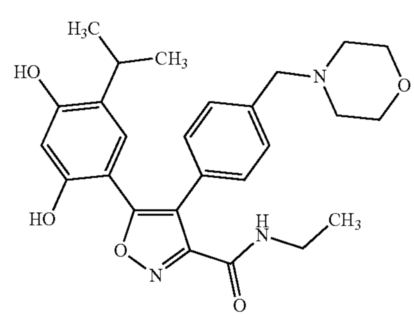 [SMILES: CCNC(=O)c1noc(-c2cc(C(C)C)c(O)cc2O)c1-c1ccc(CN2CCOCC2)cc1] |

TABLE 2-continued
Therapeutic agents that can be administered in combination with the LNA-CDN compounds as described herein.
| Compound designation/ generic name | Patent/Reference | Compound Structure |
|---|---|---|
| A4 Dactolisib | WO 2006/122806 | 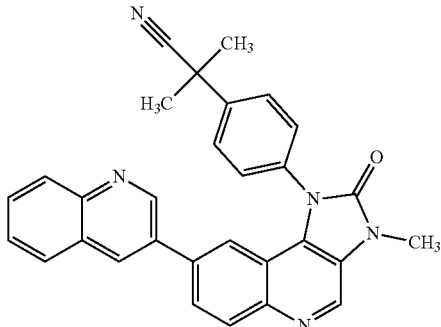 |
| A5 | U.S. Pat. No. 8,552,002 | 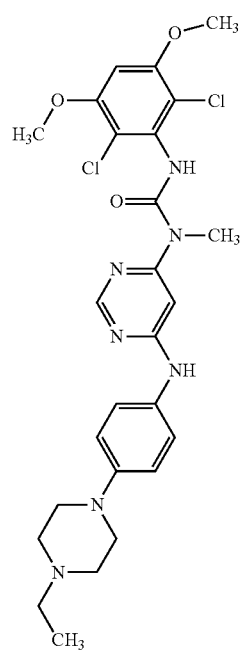 |
| A6 Buparlisib | WO 2007/084786 | 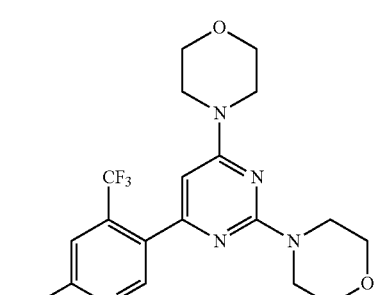 |

TABLE 2-continued

Therapeutic agents that can be administered in combination with the LNA-CDN compounds as described herein.

| Compound designation/ generic name | Patent/Reference | Compound Structure |
|---|---|---|
| A7 | WO 2009/141386<br>US 2010/0105667 | 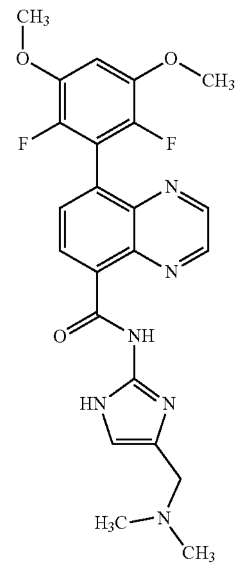 [SMILES: COc1cc(OC)c(F)c(-c2ccc(C(=O)Nc3nc(CN(C)C)c[nH]3)c3nccnc23)c1F] |
| A8 | WO 2010/029082 | 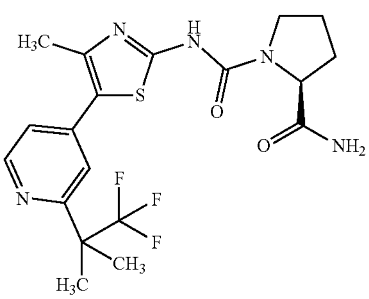 [SMILES: Cc1nc(NC(=O)N2CCC[C@H]2C(N)=O)sc1-c1ccnc(C(C)(C)C(F)(F)F)c1] |
| A9<br>CYP17 inhibitor | WO 2010/149755<br>U.S. Pat. No. 8,263,635 B2<br>EP 2445903 B1 | |
| A10 | WO 2011/076786 | 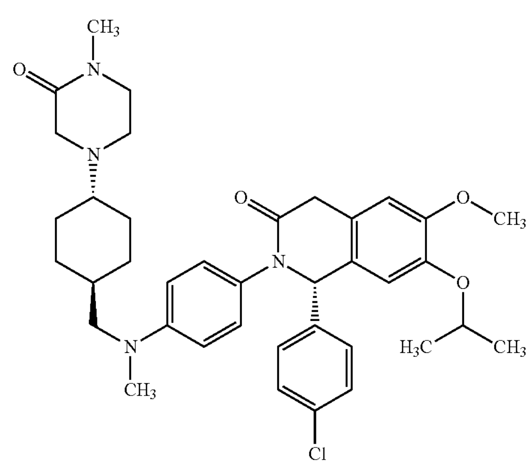 [SMILES: COc1cc2c(cc1OC(C)C)[C@H](c1ccc(Cl)cc1)N(c1ccc(N(C)C[C@H]3CC[C@H](N4CCN(C)C(=O)C4)CC3)cc1)C(=O)C2] |

TABLE 2-continued

Therapeutic agents that can be administered in combination with the LNA-CDN compounds as described herein.

| Compound designation/ generic name | Patent/Reference | Compound Structure |
|---|---|---|
| A11 Deferasirox EXJADE ® | WO 1997/049395 | 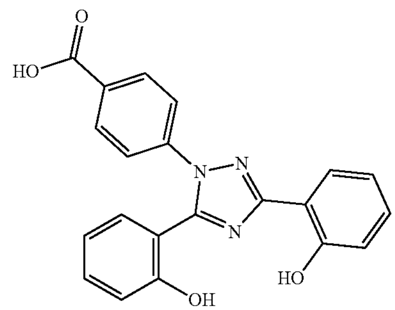 [SMILES: O=C(O)c1ccc(-n2nc(-c3ccccc3O)nc2-c2ccccc2O)cc1] |
| A12 Letrozole FEMARA ® | U.S. Pat. No. 4,978,672 | 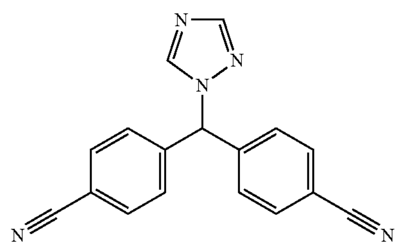 [SMILES: N#Cc1ccc(C(c2ccc(C#N)cc2)n2cncn2)cc1] |
| A13 | WO 2013/124826 US 2013/0225574 | 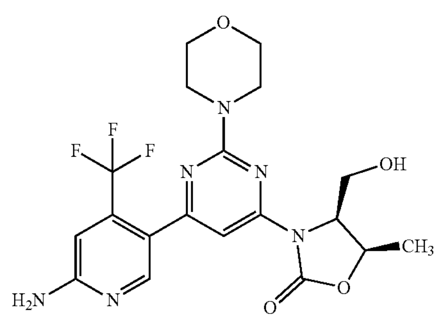 [SMILES: C[C@H]1OC(=O)N(c2cc(-c3cnc(N)cc3C(F)(F)F)nc(N3CCOCC3)n2)[C@H]1CO] |
| A14 | WO 2013/111105 | 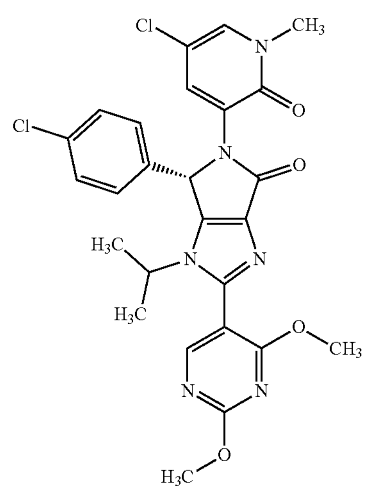 [SMILES: COc1ncc(-c2nc3c(n2C(C)C)[C@H](c2ccc(Cl)cc2)N(c2cc(Cl)cn(C)c2=O)C3=O)c(OC)n1] |

TABLE 2-continued
Therapeutic agents that can be administered in combination with the LNA-CDN compounds as described herein.
| Compound designation/ generic name | Patent/Reference | Compound Structure |
|---|---|---|
| A15 | WO 2005/073224 | 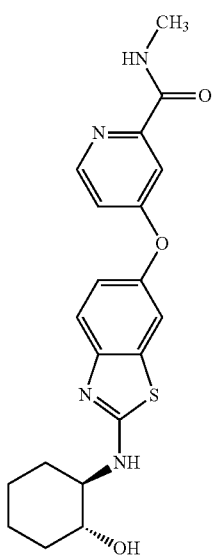 [SMILES: CNC(=O)c1cc(Oc2ccc3nc(N[C@@H]4CCCC[C@H]4O)sc3c2)ccn1] |
| A16<br>Imatinib mesylate<br>GLEEVEC ® | WO 1999/003854 | 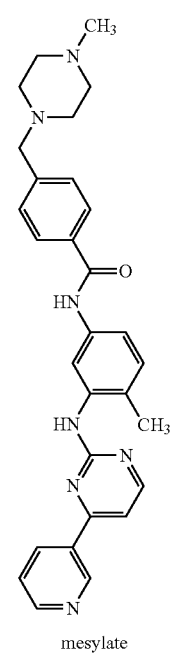 [SMILES: Cc1ccc(NC(=O)c2ccc(CN3CCN(C)CC3)cc2)cc1Nc1nccc(-c2cccnc2)n1]<br>mesylate |

TABLE 2-continued

Therapeutic agents that can be administered in combination with the LNA-CDN compounds as described herein.

| Compound designation/ generic name | Patent/Reference | Compound Structure |
|---|---|---|
| A17 | EP 2099447<br>U.S. Pat. No. 7,767,675<br>U.S. Pat. No. 8,420,645 | 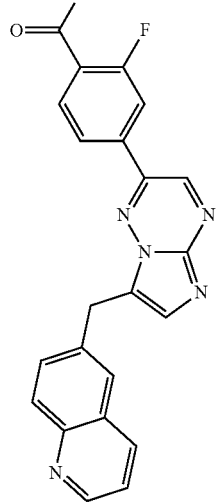<br>dihydrochloric salt |
| A18<br>Ruxolitinib phosphate<br>JAKAFI ® | WO 2007/070514<br>EP 2474545<br>U.S. Pat. No. 7,598,257<br>WO 2014/018632 | 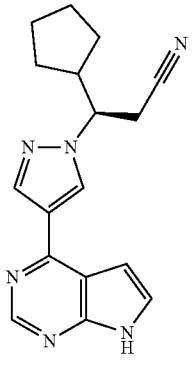<br>$H_3PO_4$ |
| A19<br>Panobinostat | WO 2014/072493<br>WO 2002/022577<br>EP 1870399 | 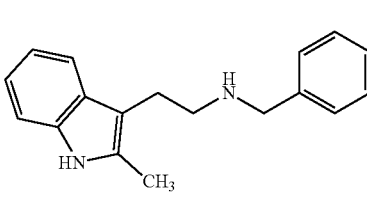 |
| A20<br>Osilodrostat | WO 2007/024945 | 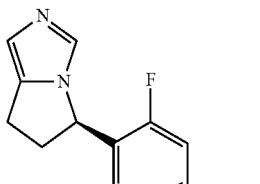 |

TABLE 2-continued

Therapeutic agents that can be administered in combination with the LNA-CDN compounds as described herein.

| Compound designation/ generic name | Patent/Reference | Compound Structure |
|---|---|---|
| A21 | WO 2008/016893<br>EP 2051990<br>U.S. Pat. No. 8,546,336 | 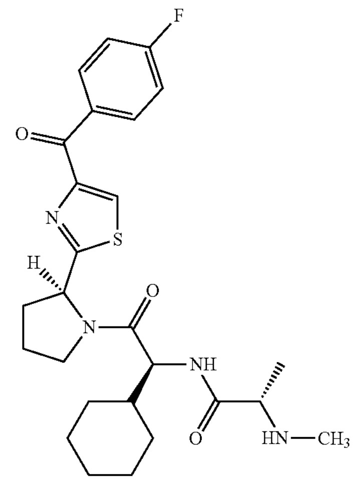 [SMILES: CN[C@@H](C)C(=O)N[C@H](C(=O)N1CCC[C@H]1c1nc(C(=O)c2ccc(F)cc2)cs1)C1CCCCC1] |
| A22<br>Sonidegib phosphate | WO 2007/131201<br>EP 2021328<br>U.S. Pat. No. 8,178,563 | 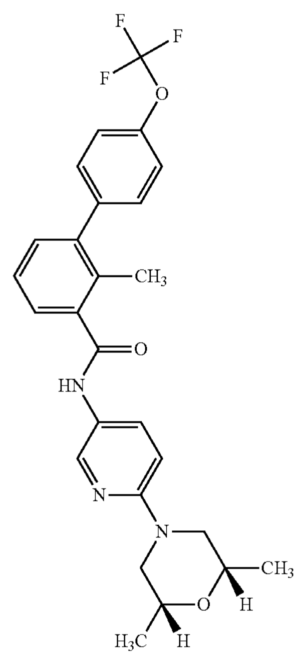 [SMILES: Cc1c(C(=O)Nc2ccc(N3C[C@@H](C)O[C@@H](C)C3)nc2)cccc1-c1ccc(OC(F)(F)F)cc1] |
| A23<br>Ceritinib<br>ZYKADIA ™ | WO 2008/073687<br>U.S. Pat. No. 8,039,479 | 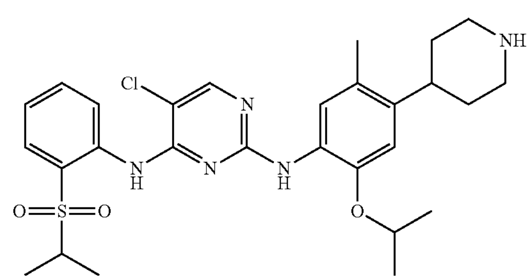 [SMILES: Cc1cc(Nc2ncc(Cl)c(Nc3ccccc3S(=O)(=O)C(C)C)n2)c(OC(C)C)cc1C1CCNCC1] |

TABLE 2-continued

Therapeutic agents that can be administered in combination with the LNA-CDN compounds as described herein.

| Compound designation/ generic name | Patent/Reference | Compound Structure |
| --- | --- | --- |
| A24 | U.S. Pat. No. 8,415,355<br>U.S. Pat. No. 8,685,980 | 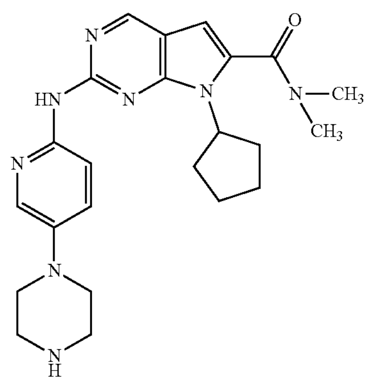 [SMILES: CN(C)C(=O)c1cc2cnc(Nc3ccc(N4CCNCC4)cn3)nc2n1C1CCCC1] |
| A25 | WO 2010/007120 | 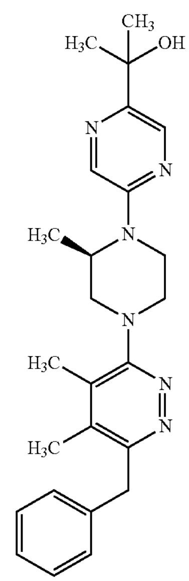 [SMILES: Cc1c(Cc2ccccc2)nnc(N2CCN(c3cnc(C(C)(C)O)cn3)[C@H](C)C2)c1C] |
| A26 | U.S. Pat. No. 7,867,493 | Human monoclonal antibody to PRLR |
| A27 | WO 2010/026124<br>EP 2344474<br>US 2010/0056576<br>WO2008/106692 | 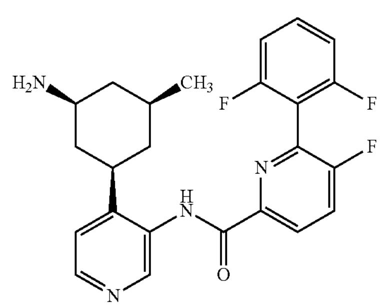 [SMILES: C[C@@H]1C[C@H](N)C[C@H](c2ccncc2NC(=O)c2ccc(F)c(-c3c(F)cccc3F)n2)C1] |

TABLE 2-continued
Therapeutic agents that can be administered in combination with the LNA-CDN compounds as described herein.
| Compound designation/ generic name | Patent/Reference | Compound Structure |
|---|---|---|
| A28 | WO 2010/101849 | 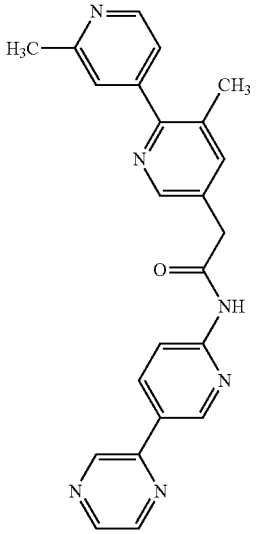 |
| A29 Encorafenib | WO 2011/025927 | 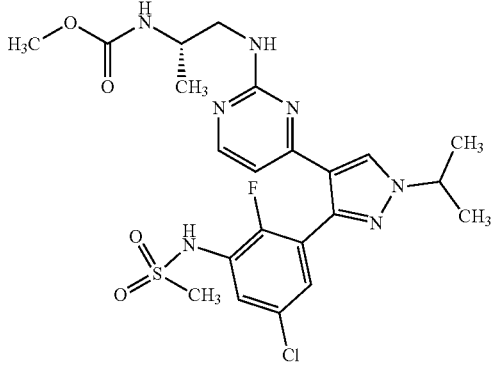 [SMILES: COC(=O)N[C@@H](C)CNc1nccc(-c2cn(C(C)C)nc2-c2cc(Cl)cc(NS(C)(=O)=O)c2F)n1] |
| A30 | WO 2011/101409 | 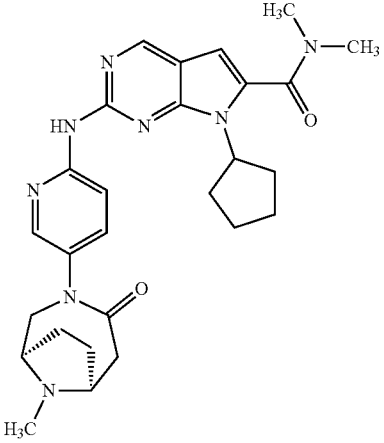 [SMILES: CN(C)C(=O)c1cc2cnc(Nc3ccc(N4C[C@H]5CC[C@@H](CC4=O)N5C)cn3)nc2n1C1CCCC1] |

TABLE 2-continued

Therapeutic agents that can be administered in combination with the LNA-CDN compounds as described herein.

| Compound designation/ generic name | Patent/Reference | Compound Structure |
|---|---|---|
| A31 | WO 2012/022814<br>EP 2606070<br>U.S. Pat. No. 8,735,551 | Human monoclonal antibody to HER 3 |
| A32 | WO 2014/160160<br>Ab: 12425 (see Table 1, paragraph [00191])<br>Linker: SMCC (see paragraph [00117]<br>Payload: DM1 (see paragraph [00111]<br>See also Claim 29 | Antibody Drug Conjugate (ADC) |
| A33 | WO 2004/045532 | Monoclonal antibody or Fab to M-CSF |
| A34<br>Binimetinib | WO 2003/077914 | 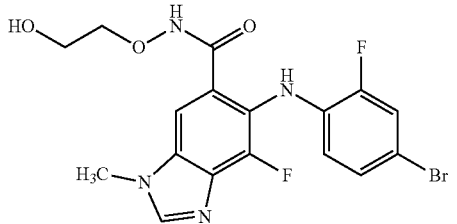 [SMILES: Cn1cnc2c(F)c(Nc3ccc(Br)cc3F)c(C(=O)NOCCO)cc21] |
| A35<br>Midostaurin | WO 2003/037347<br>EP 1441737<br>US 2012/252785 | 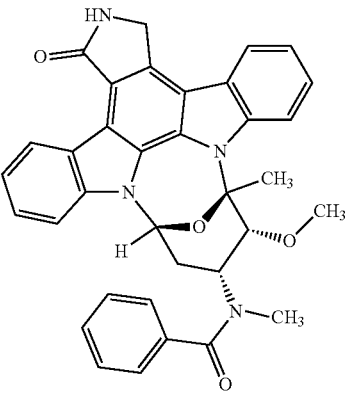 [SMILES: CO[C@@H]1[C@H](N(C)C(=O)c2ccccc2)C[C@H]2O[C@]1(C)n1c3ccccc3c3c4c(c5c6ccccc6n2c5c31)C(=O)NC4] |

TABLE 2-continued

Therapeutic agents that can be administered in combination with the
LNA-CDN compounds as described herein.

| Compound designation/ generic name | Patent/Reference | Compound Structure |
|---|---|---|
| A36 Everolimus AFINITOR ® | WO 2014/085318 | 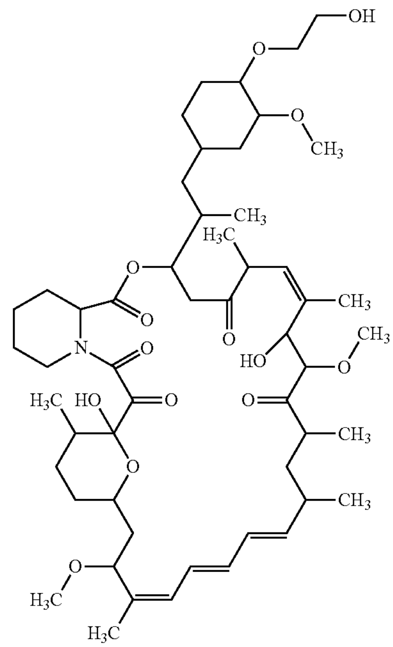 [SMILES: COC1CC2CCC(C)C(O)(O2)C(=O)C(=O)N2CCCCC2C(=O)OC(C(C)CC2CCC(OCCO)C(OC)C2)CC(=O)C(C)/C=C(/C)C(O)C(OC)C(=O)C(C)CC(C)/C=C/C=C/C=C\1C] |
| A37 | WO 2007/030377 U.S. Pat. No. 7,482,367 | 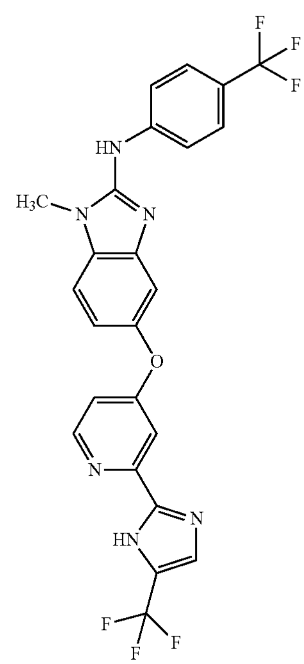 [SMILES: Cn1c(Nc2ccc(C(F)(F)F)cc2)nc2cc(Oc3ccnc(-c4ncc(C(F)(F)F)[nH]4)c3)ccc21] |

TABLE 2-continued

Therapeutic agents that can be administered in combination with the LNA-CDN compounds as described herein.

| Compound designation/ generic name | Patent/Reference | Compound Structure |
| --- | --- | --- |
| A38 Pasireotide diaspartate SIGNIFOR ® | WO2002/010192 U.S. Pat. No. 7,473,761 | 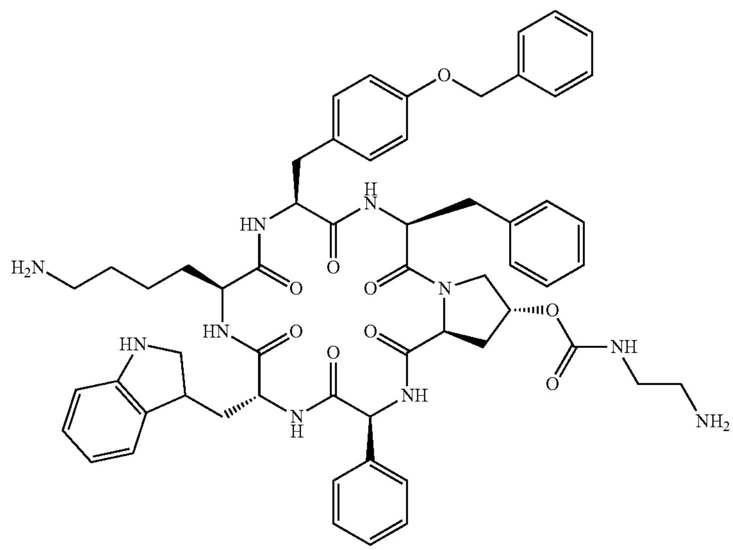 [SMILES: NCCCC[C@@H]1NC(=O)[C@@H](CC2CNc3ccccc32)NC(=O)[C@H](c2ccccc2)NC(=O)[C@@H]2C[C@@H](OC(=O)NCCN)CN2C(=O)[C@H](Cc2ccccc2)NC(=O)[C@H](Cc2ccc(OCc3ccccc3)cc2)NC1=O] |
| A39 Dovitinib | WO 2009/115562 U.S. Pat. No. 8,563,556 | 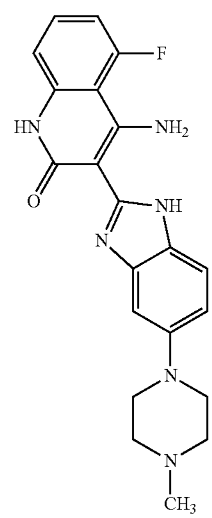 [SMILES: CN1CCN(c2ccc3[nH]c(-c4c(N)c5c(F)cccc5[nH]c4=O)nc3c2)CC1] |
| A40 | WO 2013/184757 | 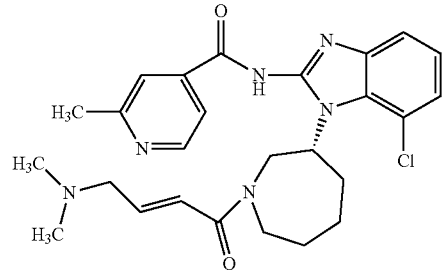 [SMILES: Cc1cc(C(=O)Nc2nc3cccc(Cl)c3n2[C@@H]2CCCCN(C(=O)/C=C/CN(C)C)C2)ccn1] |

TABLE 2-continued

Therapeutic agents that can be administered in combination with the LNA-CDN compounds as described herein.

| Compound designation/ generic name | Patent/Reference | Compound Structure |
|---|---|---|
| A41 | WO 2006/122806 | 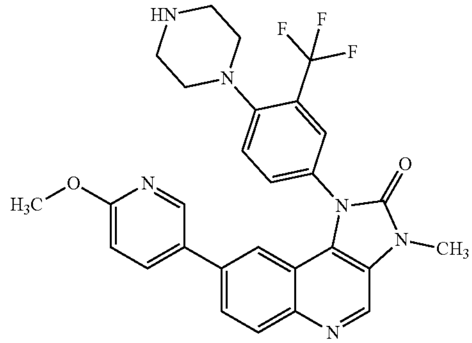 |
| A42 | WO 2008/073687<br>U.S. Pat. No. 8,372,858 | 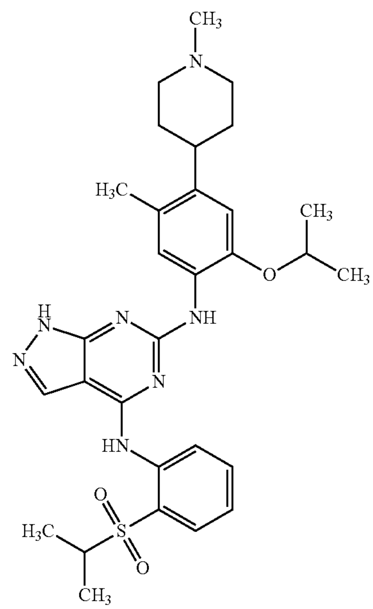 [SMILES: Cc1cc(Nc2nc(Nc3ccccc3S(=O)(=O)C(C)C)c3cn[nH]c3n2)c(OC(C)C)cc1C1CCN(C)CC1] |
| A43 | WO 2010/002655<br>U.S. Pat. No. 8,519,129 | 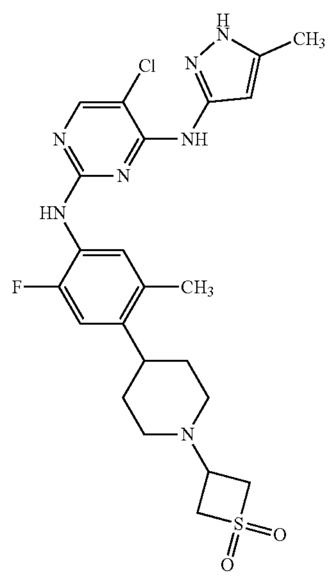 [SMILES: Cc1cc(Nc2nc(Nc3cc(C)c(C4CCN(C5CS(=O)(=O)C5)CC4)cc3F)ncc2Cl)n[nH]1] |

TABLE 2-continued
Therapeutic agents that can be administered in combination with the LNA-CDN compounds as described herein.
| Compound designation/ generic name | Patent/Reference | Compound Structure |
|---|---|---|
| A44 | WO 2010/002655<br>U.S. Pat. No. 8,519,129 | 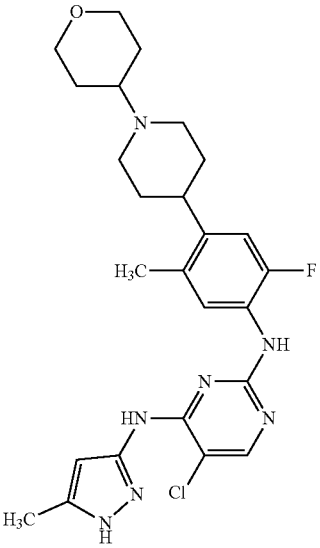 [SMILES: Cc1cc(Nc2nc(Nc3cc(C)c(C4CCN(C5CCOCC5)CC4)cc3F)ncc2Cl)n[nH]1] |
| A45 | WO 2010/002655 | 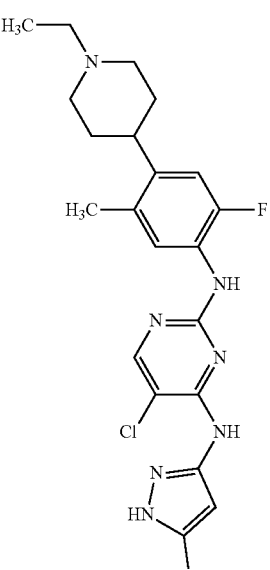 |

TABLE 2-continued

Therapeutic agents that can be administered in combination with the LNA-CDN compounds as described herein.

| Compound designation/ generic name | Patent/Reference | Compound Structure |
|---|---|---|
| A46 Valspodar AMDRAY ™ | EP 296122 | 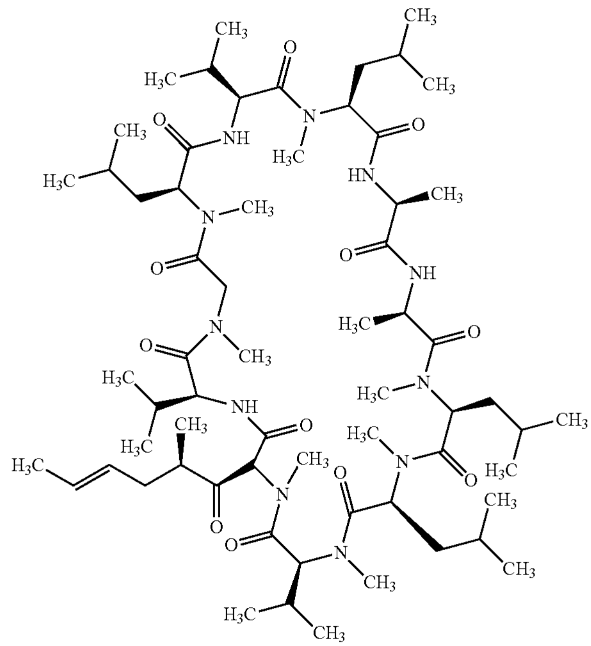 |
| A47 Vatalanib succinate | WO 98/35958 | succinate |
| A48 | WO2014/141104 | IDH inhibitor |
| A49 | WO2013/171639<br>WO2013/171640<br>WO2013/171641<br>WO2013/171642 | BCR-ABL inhibitor |
| A50 | WO2014/151616 | cRAF inhibitor |
| A51 | WO2015/066188 | ERK1/2 ATP competitive inhibitor |

Immunomodulatory Cell Lines

By "inactivated tumor cell" is meant a tumor cell (either "autologous" or "allogeneic" to the patient) which has been treated to prevent division of the cells. For purposes of the present invention, such cells preserve their immunogenicity and their metabolic activity. Such tumor cells are genetically modified to express a transgene which is expressed within a patient as part of cancer therapy. Thus, a composition or vaccine of the invention comprises neoplastic (e.g., tumor) cells that are autologous or allogeneic to the patient undergoing treatment and is most preferably the same general type of tumor cell as is afflicting the patient. For example, a patient suffering from melanoma will typically be administered a genetically modified cell derived from a melanoma. Methods for inactivating tumor cells for use in the present invention, such as the use of irradiation, are well known in the art.

In some embodiments, the inactivated tumor cells of the present invention are modified to express and secrete one or more heat shock proteins. For example, gp96-Ig fusion proteins can be expressed and secreted to stimulate an immune response (Yamazaki et al., The Journal of Immunology, 1999, 163:5178-5182; Strbo et al., Immunol Res. 2013 December; 57(1-3):311-25). In some embodiments the inactivated tumor cells are modified to express and secrete a gp96-Ig fusion protein.

The inactivated tumor cells of the present invention are administered to the patient together with one or more costimulatory molecules or agents. A preferred costimulatory agent comprises one or more cytokines which stimulate dendritic cell induction, recruitment, and/or maturation. Methods for assessing such costimulatory agents are well known in the literature. Induction and maturation of DCs is typically assessed by increased expression of certain membrane molecules such as CD80 and CD86, and/or secretion of pro-inflammatory cytokines, such as IL-12 and type I interferons following stimulation.

In preferred embodiments, the inactivated tumor cells themselves are modified to express and secrete one or more cytokines which stimulate dendritic cell induction, recruitment, and/or maturation. The present invention is described in exemplary terms with regard to the use of GM-CSF. Thus, by way of example, the tumor cell may express a transgene encoding GM-CSF as described in U.S. Pat. Nos. 5,637,483, 5,904,920, 6,277,368 and 6,350,445, as well as in US Patent Publication No. 20100150946. A form of GM-CSF-expressing genetically modified cancer cells or a "cytokine-expressing cellular vaccine" for the treatment of pancreatic cancer is described in U.S. Pat. Nos. 6,033,674 and 5,985,290.

Other suitable cytokines which may be expressed by such inactivated tumor cells and/or bystander cells instead of, or together with, GM-CSF include, but are not limited to, one or more of CD40 ligand, FLT-3 ligand, IL-12, CCL3, CCL20, and CCL21. This list is not meant to be limiting.

While it is preferred that the inactivated tumor cells administered to the subject express one or more cytokines of interest, the tumor cell line may be accompanied by an inactivated bystander cell line which expresses and secretes one or more cytokines which stimulate dendritic cell induction, recruitment, and/or maturation. The bystander cell line may provide all of the cytokines which stimulate dendritic cell induction, recruitment, and/or maturation, or may supplement cytokines which stimulate dendritic cell induction, recruitment, and/or maturation expressed and secreted by the inactivated tumor cells. By way of example, immunomodulatory cytokine-expressing bystander cell lines are disclosed in U.S. Pat. Nos. 6,464,973, and 8,012,469, Dessureault et al., Ann. Surg. Oncol. 14: 869-84, 2007, and Eager and Nemunaitis, Mol. Ther. 12: 18-27, 2005.

By "Granulocyte-macrophage colony stimulating factor (GM-CSF) polypeptide" is meant a cytokine or fragment thereof having immunomodulatory activity and having at least about 85% amino acid sequence identity to GenBank Accession No. AAA52122.1.

Vaccines

In certain embodiments, the CDN compositions are administered in conjunction with one or more vaccines intended to stimulate an immune response to one or more predetermined antigens. Examples of target antigens that may find use in the invention are listed in the following table. The target antigen may also be a fragment or fusion polypeptide comprising an immunologically active portion of the antigens listed in the table. This list is not meant to be limiting.

TABLE 1

List of antigens for use in combination with the LNA-CDN compounds as described herein.

| Antigen | Reference |
| --- | --- |
| Tumor antigens | |
| Mesothelin | GenBank Acc. No. NM_005823; U40434; NM_013404; BC003512 (see also, e.g., Hassan, et al. (2004) Clin. Cancer Res. 10: 3937-3942; Muminova, et al. (2004) BMC Cancer 4: 19; Iacobuzio-Donahue, et al. (2003) Cancer Res. 63: 8614-8622). |
| Wilms' tumor-1 associated protein (Wt-1), including isoform A; isoform B; isoform C; isoform D. | WT-1 isoform A (GenBank Acc. Nos. NM_000378; NP_000369). WT-1 isoform B (GenBank Acc. Nos. NM_024424; NP_077742). WT-1 isoform C (GenBank Acc. Nos. NM_024425; NP_077743). WT-1 isoform D (GenBank Acc. Nos. NM_024426; NP_077744). |
| Stratum corneum chymotryptic enzyme (SCCE), and variants thereof. | GenBank Acc. No. NM_005046; NM_139277; AF332583. See also, e.g., Bondurant, et al. (2005) Clin. Cancer Res. 11: 3446-3454; Santin, et al. (2004) Gynecol. Oncol. 94: 283-288; Shigemasa, et al. (2001) Int. J. Gynecol. Cancer 11: 454-461; Sepehr, et al. (2001) Oncogene 20: 7368-7374. |
| MHC class I chain-related protein A (MICA); MHC class I chain-related protein B (MICB). | See, e.g., Groh, et al. (2005) Proc. Natl. Acad. Sci. USA 102: 6461-6466; GenBank Acc. Nos. NM_000247; BC_016929; AY750850; NM_005931. |
| Gastrin and peptides derived from gastrin; gastrin/CCK-2 receptor (also known as CCK-B). | Harris, et al. (2004) Cancer Res. 64: 5624-5631; Gilliam, et al. (2004) Eur. J. Surg. Oncol. 30: 536-543; Laheru and Jaffee (2005) Nature Reviews Cancer 5: 459-467. |
| Glypican-3 (an antigen of, e.g., hepatocellular carcinoma and melanoma). | GenBank Acc. No. NM_004484. Nakatsura, et al. (2003) Biochem. Biophys. Res. Commun. 306: 16-25; Capurro, et al. (2003) Gasteroenterol. 125: 89-97; Nakatsura, et al. (2004) Clin. Cancer Res. 10: 6612-6621). |
| Coactosin-like protein. | Nakatsura, et al. (2002) Eur. J. Immunol. 32: 826-836; Laheru and Jaffee (2005) Nature Reviews Cancer 5: 459-467. |
| Prostate stem cell antigen (PSCA). | GenBank Acc. No. AF043498; AR026974; AR302232 (see also, e.g., Argani, et al. (2001) Cancer Res. 61: 4320-4324; Christiansen, et al. (2003) Prostate 55: 9-19; Fuessel, et al. (2003) 23: 221-228). |

TABLE 1-continued

List of antigens for use in combination with the LNA-CDN compounds as described herein.

| Antigen | Reference |
|---|---|
| Prostate acid phosphatase (PAP); prostate-specific antigen (PSA); PSM; PSMA. | Small, et al. (2000) J. Clin. Oncol. 18: 3894-3903; Altwein and Luboldt (1999) Urol. Int. 63: 62-71; Chan, et al. (1999) Prostate 41: 99-109; Ito, et al. (2005) Cancer 103: 242-250; Schmittgen, et al. (2003) Int. J. Cancer 107: 323-329; Millon, et al. (1999) Eur. Urol. 36: 278-285. |
| Six-transmembrane epithelial antigen of prostate (STEAP). | See, e.g., Machlenkin, et al. (2005) Cancer Res. 65: 6435-6442; GenBank Acc. No. NM_018234; NM_001008410; NM_182915; NM_024636; NM_012449; BC011802. |
| Prostate carcinoma tumor antigen-1 (PCTA-1). | See, e.g., Machlenkin, et al. (2005) Cancer Res. 65: 6435-6442; GenBank Acc. No. L78132. |
| Prostate tumor-inducing gene-1 (PTI-1). | See, e.g., Machlenkin, et al. (2005) Cancer Res. 65: 6435-6442). |
| Prostate-specific gene with homology to G protein-coupled receptor. | See, e.g., Machlenkin, et al. (2005) Cancer Res. 65: 6435-6442). |
| Prostase (an antrogen regulated serine protease). | See, e.g., Machlenkin, et al. (2005) Cancer Res. 65: 6435-6442; GenBank Acc. No. BC096178; BC096176; BC096175. |
| Proteinase 3. | GenBank Acc. No. X55668. |
| Cancer-testis antigens, e.g., NY-ESO-1; SCP-1; SSX-1; SSX-2; SSX-4; GAGE, CT7; CT8; CT10; MAGE-1; MAGE-2; MAGE-3; MAGE-4; MAGE-6; LAGE-1. MAGE-A1, MAGE-A2; MAGE-A3; MAGE-A4; MAGE-A6; MAGE-A9; MAGE-A10; MAGE-A12; GAGE-3/6; NT-SAR-35; BAGE; CA125. | GenBank Acc. No. NM_001327 (NY-ESO-1) (see also, e.g., Li, et al. (2005) Clin. Cancer Res. 11: 1809-1814; Chen, et al. (2004) Proc. Natl. Acad. Sci. USA. 101(25): 9363-9368; Kubuschok, et al. (2004) Int. J. Cancer. 109: 568-575; Scanlan, et al. (2004) Cancer Immun. 4: 1; Scanlan, et al. (2002) Cancer Res. 62: 4041-4047; Scanlan, et al. (2000) Cancer Lett. 150: 155-164; Dalerba, et al. (2001) Int. J. Cancer 93: 85-90; Ries, et al. (2005) Int. J. Oncol. 26: 817-824. Otte, et al. (2001) Cancer Res. 61: 6682-6687; Lee, et al. (2003) Proc. Natl. Acad. Sci. USA 100: 2651-2656; Sarcevic, et al. (2003) Oncology 64: 443-449; Lin, et al. (2004) Clin. Cancer Res. 10: 5708-5716. |
| GAGE-1; GAGE-2; GAGE-3; GAGE-4; GAGE-5; GAGE-6; GAGE-7; GAGE-8; GAGE-65; GAGE-11; GAGE-13; GAGE-7B. | De Backer, et al. (1999) Cancer Res. 59: 3157-3165; Scarcella, et al. (1999) Clin. Cancer Res. 5: 335-341. |
| HIP1R; LMNA; KIAA1416; Seb4D; KNSL6; TRIP4; MBD2; HCAC5; MAGEA3. | Scanlan, et al. (2002) Cancer Res. 62: 4041-4047. |
| DAM family of genes, e.g., DAM-1; DAM-6. | Fleishhauer, et al. (1998) Cancer Res. 58: 2969-2972. |
| RCAS1. | Enjoji, et al. (2004) Dig. Dis. Sci. 49: 1654-1656. |
| RU2. | Van Den Eynde, et al. (1999) J. Exp. Med. 190: 1793-1800. |
| CAMEL. | Slager, et al. (2004) J. Immunol. 172: 5095-5102; Slager, et al. (2004) Cancer Gene Ther. 11: 227-236. |
| Colon cancer associated antigens, e.g., NY-CO-8; NY-CO-9; NY-CO-13; NY-CO-16; NY-CO-20; NY-CO-38; NY-CO-45; NY-CO-9/HDAC5; NY-CO-41/MBD2; NY-CO-42/TRIP4; NY-CO-95/KIAA1416; KNSL6; seb4D. | Scanlan, et al. (2002) Cancer Res. 62: 4041-4047. |
| N-Acetylglucosaminyl-tranferase V (GnT-V). | Dosaka-Akita, et al. (2004) Clin. Cancer Res. 10: 1773-1779. |
| Elongation factor 2 mutated (ELF2M). | Renkvist, et al. (2001) Cancer Immunol Immunother. 50: 3-15. |
| HOM-MEL-40/SSX2 | Neumann, et al. (2004) Int. J. Cancer 112: 661-668; Scanlan, et al. (2000) Cancer Lett. 150: 155-164. |
| BRDT. | Scanlan, et al. (2000) Cancer Lett. 150: 155-164. |
| SAGE; HAGE. | Sasaki, et al. (2003) Eur. J. Surg. Oncol. 29: 900-903. |
| RAGE. | See, e.g., Li, et al. (2004) Am. J. Pathol. 164: 1389-1397; Shirasawa, et al. (2004) Genes to Cells 9: 165-174. |
| MUM-1 (melanoma ubiquitous mutated); MUM-2; MUM-2 Arg-Gly mutation; MUM-3. | Gueguen, et al. (1998) J. Immunol. 160: 6188-6194; Hirose, et al. (2005) Int. J. Hematol. 81: 48-57; Baurain, et al. (2000) J. Immunol. 164: 6057-6066; Chiari, et al. (1999) Cancer Res. 59: 5785-5792. |
| LDLR/FUT fusion protein antigen of melanoma. | Wang, et al. (1999) J. Exp. Med. 189: 1659-1667. |

TABLE 1-continued

List of antigens for use in combination with the LNA-CDN compounds as described herein.

| Antigen | Reference |
|---|---|
| NY-REN series of renal cancer antigens. | Scanlan, et al. (2002) Cancer Res. 62: 4041-4047; Scanlan, et al. (1999) Cancer Res. 83: 456-464. |
| NY-BR series of breast cancer antigens, e.g., NY-BR-62; NY-BR-75; NY-BR-85; NY-BR-62; NY-BR-85. | Scanlan, et al. (2002) Cancer Res. 62: 4041-4047; Scanlan, et al. (2001) Cancer Immunity 1: 4. |
| BRCA-1; BRCA-2. | Stolier, et al. (2004) Breast J. 10: 475-480; Nicoletto, et al. (2001) Cancer Treat Rev. 27: 295-304. |
| DEK/CAN fusion protein. | Von Lindern, et al. (1992) Mol. Cell. Biol. 12: 1687-1697. |
| Ras, e.g., wild type ras, ras with mutations at codon 12, 13, 59, or 61, e.g., mutations G12C; G12D; G12R; G12S; G12V; G13D; A59T; Q61H. K-RAS; H-RAS; N-RAS. | GenBank Acc. Nos. P01112; P01116; M54969; M54968; P01111; P01112; K00654. See also, e.g., GenBank Acc. Nos. M26261; M34904; K01519; K01520; BC006499; NM_006270; NM_002890; NM_004985; NM_033360; NM_176795; NM_005343. |
| BRAF (an isoform of RAF). | Tannapfel, et al. (2005) Am. J. Clin. Pathol. 123: 256-2601; Tsao and Sober (2005) Dermatol. Clin. 23: 323-333. |
| Melanoma antigens, including HST-2 melanoma cell antigens. | GenBank Acc. No. NM_206956; NM_206955; NM_206954; NM_206953; NM_006115; NM_005367; NM_004988; AY148486; U10340; U10339; M77481. See, eg., Suzuki, et al. (1999) J. Immunol. 163: 2783-2791. |
| Survivin | GenBank Acc. No. AB028869; U75285 (see also, e.g., Tsuruma, et al. (2004) J. Translational Med. 2: 19 (11 pages); Pisarev, et al. (2003) Clin. Cancer Res. 9: 6523-6533; Siegel, et al. (2003) Br. J. Haematol. 122: 911-914; Andersen, et al. (2002) Histol. Histopathol. 17: 669-675). |
| MDM-2 | NM_002392; NM_006878 (see also, e.g., Mayo, et al. (1997) Cancer Res. 57: 5013-5016; Demidenko and Blagosklonny (2004) Cancer Res. 64: 3653-3660). |
| Methyl-CpG-binding proteins (MeCP2; MBD2). | Muller, et al. (2003) Br. J. Cancer 89: 1934-1939; Fang, et al. (2004) World J. Gastreenterol. 10: 3394-3398. |
| NA88-A. | Moreau-Aubry, et al. (2000) J. Exp. Med. 191: 1617-1624. |
| Histone deacetylases (HDAC), e.g., HDAC5. | Waltregny, et al. (2004) Eur. J. Histochem. 48: 273-290; Scanlan, et al. (2002) Cancer Res. 62: 4041-4047. |
| Cyclophilin B (Cyp-B). | Tamura, et al. (2001) Jpn. J. Cancer Res. 92: 762-767. |
| CA 15-3; CA 27.29. | Clinton, et al. (2003) Biomed. Sci. Instrum. 39: 408-414. |
| Heat shock protein Hsp70. | Faure, et al. (2004) Int. J. Cancer 108: 863-870. |
| GAGE/PAGE family, e.g., PAGE-1; PAGE-2; PAGE-3; PAGE-4; XAGE-1; XAGE-2; XAGE-3. | Brinkmann, et al. (1999) Cancer Res. 59: 1445-1448. |
| MAGE-A, B, C, and D families. MAGE-B5; MAGE-B6; MAGE-C2; MAGE-C3; MAGE-3; MAGE-6. | Lucas, et al. (2000) Int. J. Cancer 87: 55-60; Scanlan, et al. (2001) Cancer Immun. 1: 4. |
| Kinesin 2; TATA element modulatory factor 1; tumor protein D53; NY | Scanlan, et al. (2001) Cancer Immun. 30: 1-4. |
| Alpha-fetoprotein (AFP) | Grimm, et al. (2000) Gastroenterol. 119: 1104-1112. |
| SART1; SART2; SART3; ART4. | Kumamuru, et al. (2004) Int. J. Cancer 108: 686-695; Sasatomi, et al. (2002) Cancer 94: 1636-1641; Matsumoto, et al. (1998) Jpn. J. Cancer Res. 89: 1292-1295; Tanaka, et al. (2000) Jpn. J. Cancer Res. 91: 1177-1184. |
| Preferentially expressed antigen of melanoma (PRAME). | Matsushita, et al. (2003) Leuk. Lymphoma 44: 439-444; Oberthuer, et al. (2004) Clin. Cancer Res. 10: 4307-4313. |
| Carcinoembryonic antigen (CEA), CAP1-6D enhancer agonist peptide. | GenBank Acc. No. M29540; E03352; X98311; M17303 (see also, e.g., Zaremba (1997) Cancer Res. 57: 4570-4577; Sarobe, et al. (2004) Curr. Cancer Drug Targets 4: 443-454; Tsang, et al. (1997) Clin. Cancer Res. 3: 2439-2449; Fong, et al. (2001) Proc. Natl. Acad. Sci. USA 98: 8809-8814). |
| HER-2/neu. | Disis, et al. (2004) J. Clin. Immunol. 24: 571-578; Disis and Cheever (1997) Adv. Cancer Res. 71: 343-371. |
| Cdk4; cdk6; p16 (INK4); Rb protein. | Ghazizadeh, et al. (2005) Respiration 72: 68-73; Ericson, et al. (2003) Mol. Cancer Res. 1: 654-664. |
| TEL; AML1; TEL/AML1. | Stams, et al. (2005) Clin. Cancer Res. 11: 2974-2980. |
| Telomerase (TERT). | Nair, et al. (2000) Nat. Med. 6: 1011-1017. |
| 707-AP. | Takahashi, et al. (1997) Clin. Cancer Res. 3: 1363-1370. |

TABLE 1-continued

List of antigens for use in combination with the LNA-CDN compounds as described herein.

| Antigen | Reference |
|---|---|
| Annexin, e.g., Annexin II. | Zimmerman, et al. (2004) Virchows Arch. 445: 368-374. |
| BCR/ABL; BCR/ABL p210; BCR/ABL p190; CML-66; CML-28. | Cobaldda, et al. (2000) Blood 95: 1007-1013; Hakansson, et al. (2004) Leukemia 18: 538-547; Schwartz, et al. (2003) Semin. Hematol. 40: 87-96; Lim, et al. (1999) Int. J. Mol. Med. 4: 665-667. |
| BCL2; BLC6; CD10 protein. | Iqbal, et al. (2004) Am. J. Pathol. 165: 159-166. |
| CDC27 (this is a melanoma antigen). | Wang, et al. (1999) Science 284: 1351-1354. |
| Sperm protein 17 (SP17); 14-3-3-zeta; MEMD; KIAA0471; TC21. | Arora, et al. (2005) Mol. Carcinog. 42: 97-108. |
| Tyrosinase-related proteins 1 and 2 (TRP-1 and TRP-2). | GenBank Acc. No. NM_001922. (see also, e.g., Bronte, et al. (2000) Cancer Res. 60: 253-258). |
| Gp100/pmel-17. | GenBank Acc. Nos. AH003567; U31798; U31799; U31807; U31799 (see also, e.g., Bronte, et al. (2000) Cancer Res. 60: 253-258). |
| TARP. | See, e.g., Clifton, et al. (2004) Proc. Natl. Acad. Sci. USA 101: 10166-10171; Virok, et al. (2005) Infection Immunity 73: 1939-1946. |
| Tyrosinase-related proteins 1 and 2 (TRP-1 and TRP-2). | GenBank Acc. No. NM_001922. (see also, e.g., Bronte, et al. (2000) Cancer Res. 60: 253-258). |
| Melanocortin 1 receptor (MC1R); MAGE-3; gp100; tyrosinase; dopachrome tautomerase (TRP-2); MART-1. | Salazar-Onfray, et al. (1997) Cancer Res. 57: 4348-4355; Reynolds, et al. (1998) J. Immunol. 161: 6970-6976; Chang, et al. (2002) Clin. Cancer Res. 8: 1021-1032. |
| MUC-1; MUC-2. | See, e.g., Davies, et al. (1994) Cancer Lett. 82: 179-184; Gambus, et al. (1995) Int. J. Cancer 60: 146-148; McCool, et al. (1999) Biochem. J. 341: 593-600. |
| Spas-1. | U.S. Published Pat. Appl. No. 20020150588 of Allison, et al. |
| CASP-8; FLICE; MACH. | Mandruzzato, et al. (1997) J. Exp. Med. 186: 785-793. |
| CEACAM6; CAP-1. | Duxbury, et al. (2004) Biochem. Biophys. Res. Commun. 317: 837-843; Morse, et al. (1999) Clin. Cancer Res. 5: 1331-1338. |
| HMGB1 (a DNA binding protein and cytokine). | Brezniceanu, et al. (2003) FASEB J. 17: 1295-1297. |
| ETV6/AML1. | Codrington, et al. (2000) Br. J. Haematol. 111: 1071-1079. |
| Mutant and wild type forms of adenomatous polyposis coli (APC); beta-catenin; c-met; p53; E-cadherin; cyclooxygenase-2 (COX-2). | Clements, et al. (2003) Clin. Colorectal Cancer 3: 113-120; Gulmann, et al. (2003) Appl. Immunohistochem. Mol. Morphol. 11: 230-237; Jungck, et al. (2004) Int. J. Colorectal. Dis. 19: 438-445; Wang, et al. (2004) J. Surg. Res. 120: 242-248; Abutaily, et al. (2003) J. Pathol. 201: 355-362; Liang, et al. (2004) Br. J. Surg. 91: 355-361; Shirakawa, et al. (2004) Clin. Cancer Res. 10: 4342-4348. |
| Renal cell carcinoma antigen bound by mAB G250. | Mulders, et al. (2003) Urol. Clin. North Am. 30: 455-465; Steffens, et al. (1999) Anticancer Res. 19: 1197-1200. |
| EphA2 | See. e.g., U.S. Patent Publication No. 2005/0281783 A1; Genbank Accession No. NM_004431 (human); Genbank Accession No. NM_010139 (Mouse); Genbank Accession No. AB038986 (Chicken, partial sequence); GenBank Accession Nos. NP_004422, AAH37166, and AAA53375 (human); GenBank Accession Nos. NP_034269 (mouse), AAH06954 (mouse), XP_345597 (rat), and BAB63910 (chicken). |
| EGFRvIII | See, e.g., WO/2012/068360 |
| | *Francisella tularensis* antigens |
| *Francisella tularensis* A and B. | Complete genome of subspecies Schu S4 (GenBank Acc. No. AJ749949); of subspecies Schu 4 (GenBank Acc. No. NC_006570). Outer membrane protein (43 kDa) Bevanger, et al. (1988) J. Clin. Microbiol. 27: 922-926; Porsch-Ozcurumez, et al. (2004) Clin. Diagnostic. Lab. Immunol. 11: 1008-1015). Antigenic components of *F. tularensis* include, e.g., 80 antigens, including 10 kDa and 60 kDa chaperonins (Havlasova, et al. (2002) Proteomics 2: 857-86), nucleoside diphosphate kinase, isocitrate dehydrogenase, RNA-binding protein Hfq, the chaperone ClpB (Havlasova, et al. (2005) Proteomics 5: 2090-2103). See also, e.g., Oyston and Quarry (2005) Antonie Van Leeuwenhoek 87: 277-281; Isherwood, et al. (2005) Adv. Drug Deliv. Rev. 57: 1403-1414; Biagini, et al. (2005) Anal. Bioanal. Chem. 382: 1027-1034. |
| | Malarial antigens |
| Circumsporozoite protein (CSP); SSP2; HEP17; Exp-1 orthologs found in *P. falciparum*; and LSA-1. | See, e.g., Haddad, et al. (2004) Infection Immunity 72: 1594-1602; Hoffman, et al. (1997) Vaccine 15: 842-845; Oliveira-Ferreira and Daniel-Ribeiro (2001) Mem. Inst. Oswaldo Cruz, Rio de Janeiro 96: 221-227. CSP (see, e.g., GenBank Acc. No. AB121024). SSP2 (see, e.g., GenBank Acc. No. AF249739). LSA-1 (see, e.g., GenBank Acc. No. Z30319). |

TABLE 1-continued

List of antigens for use in combination with the LNA-CDN compounds as described herein.

| Antigen | Reference |
|---|---|
| Ring-infected erythrocyte survace protein (RESA); merozoite surface protein 2 (MSP2); Spf66; merozoite surface protein 1(MSP1); 195A; BVp42. | See, e.g., Stirnadel, et al. (2000) Int. J. Epidemiol. 29: 579-586; Krzych, et al. (1995) J. Immunol. 155: 4072-4077. See also, Good, et al. (2004) Immunol. Rev. 201: 254-267; Good, et al. (2004) Ann. Rev. Immunol. 23: 69-99. MSP2 (see, e.g., GenBank Acc. No. X96399; X96397). MSP1 (see, e.g., GenBank Acc. No. X03371). RESA (see, e.g., GenBank Acc. No. X05181; X05182). |
| Apical membrane antigen 1 (AMA1). | See, e.g., Gupta, et al. (2005) Protein Expr. Purif. 41: 186-198. AMA1 (see, e.g., GenBank Acc. No. A`13; AJ494905; AJ490565). |
| Viruses and viral antigens | |
| Hepatitis A | GenBank Acc. Nos., e.g., NC_001489; AY644670; X83302; K02990; M14707. |
| Hepatitis B | Complete genome (see, e.g., GenBank Acc. Nos. AB214516; NC_003977; AB205192; AB205191; AB205190; AJ748098; AB198079; AB198078; AB198076; AB074756). |
| Hepatitis C | Complete genome (see, e.g., GenBank Acc. Nos. NC_004102; AJ238800; AJ238799; AJ132997; AJ132996; AJ000009; D84263). |
| Hepatitis D | GenBank Acc. Nos, e.g. NC_001653; AB118847; AY261457. |
| Human papillomavirus, including all 200+ subtypes (classed in 16 groups), such as the high risk subtypes 16, 18, 30, 31, 33, 45. | See, e.g., Trimble, et al. (2003) Vaccine 21: 4036-4042; Kim, et al. (2004) Gene Ther. 11: 1011-1018; Simon, et al. (2003) Eur. J. Obstet. Gynecol. Reprod. Biol. 109: 219-223; Jung, et al. (2004) J. Microbiol. 42: 255-266; Damasus-Awatai and Freeman-Wang (2003) Curr. Opin. Obstet. Gynecol. 15: 473-477; Jansen and Shaw (2004) Annu. Rev. Med. 55: 319-331; Roden and Wu (2003) Expert Rev. Vaccines 2: 495-516; de Villiers, et al. (2004) Virology 324: 17-24; Hussain and Paterson (2005) Cancer Immunol. Immunother. 54: 577-586; Molijn, et al. (2005) J. Clin. Virol. 32 (Suppl. 1) S43-S51. GenBank Acc. Nos. AY686584; AY686583; AY686582; NC_006169; NC_006168; NC_006164; NC_001355; NC_001349; NC_005351; NC_001596). |
| Human T-cell lymphotropic virus (HTLV) types I and II, including the HTLV type I subtypes Cosmopolitan, Central African, and Austro-Melanesian, and the HTLV type II subtypes Iia, Iib, Iic, and Iid. | See, e.g., Capdepont, et al. (2005) AIDS Res. Hum. Retrovirus 21: 28-42; Bhigjee, et al. (1999) AIDS Res. Hum. Restrovirus 15: 1229-1233; Vandamme, et al. (1998) J. Virol. 72: 4327-4340; Vallejo, et al. (1996) J. Acquir. Immune Defic. Syndr. Hum. Retrovirol. 13: 384-391. HTLV type I (see, e.g., GenBank Acc. Nos. AY563954; AY563953. HTLV type II (see, e.g., GenBank Acc. Nos. L03561; Y13051; AF139382). |
| Coronaviridae, including Coronaviruses, such as SARS-coronavirus (SARS-CoV), and Toroviruses. | See, e.g., Brian and Baric (2005) Curr. Top. Microbiol. Immunol. 287: 1-30; Gonzalez, et al. (2003) Arch. Virol. 148: 2207-2235; Smits, et al. (2003) J. Virol. 77: 9567-9577; Jamieson, et al. (1998) J. Infect. Dis. 178: 1263-1269 (GenBank Acc. Nos. AY348314; NC_004718; AY394850). |
| Rubella virus. | GenBank Acc. Nos. NC_001545; AF435866. |
| Mumps virus, including the genotypes A, C, D, G, H, and I. | See, e.g., Orvell, eta 1. (2002) J. Gen. Virol. 83: 2489-2496. See, e.g., GenBank Acc. Nos. AY681495; NC_002200; AY685921; AF201473. |
| Coxsackie virus A including the serotypes 1, 11, 13, 15, 17, 18, 19, 20, 21, 22, and 24 (also known as Human enterovirus C; HEV-C). | See, e.g., Brown, et al. (2003) J. Virol. 77: 8973-8984. GenBank Acc. Nos. AY421768; AY790926: X67706. |
| Coxsackie virus B, including subtypes 1-6. | See, e.g., Ahn, et al. (2005) J. Med. Virol. 75: 290-294; Patel, et al. (2004) J. Virol. Methods 120: 167-172; Rezig, et al. (2004) J. Med. Virol. 72: 268-274. GenBank Acc. No. X05690. |
| Human enteroviruses including, e.g., human enterovirus A (HEV-A, CAV2 to CAV8, CAV10, CAV12, CAV14, CAV16, and EV71) and also including HEV-B (CAV9, CBV1 to CBV6, E1 to E7, E9, E11 to E21, E24 to E27, E29 to E33, and EV69 and E73), as well as HEV. | See, e.g., Oberste, et al. (2004) J. Virol. 78: 855-867. Human enterovirus A (GenBank Acc. Nos. NC_001612); human enterovirus B (NC_001472); human enterovirus C (NC_001428); human enterovirus D (NC_001430). Simian enterovirus A (GenBank Acc. No. NC_003988). |

TABLE 1-continued

List of antigens for use in combination with the LNA-CDN compounds as described herein.

| Antigen | Reference |
| --- | --- |
| Polioviruses including PV1, PV2, and PV3. | See, e.g., He, et al. (2003) J. Virol. 77: 4827-4835; Hahsido, et al. (1999) Microbiol. Immunol. 43: 73-77. GenBank Acc. No. AJ132961 (type 1); AY278550 (type 2); X04468 (type 3). |
| Viral encephalitides viruses, including equine encephalitis, Venezuelan equine encephalitis (VEE) (including subtypes IA, IB, IC, ID, IIIC, IIID), Eastern equine encephalitis (EEE), Western equine encephalitis (WEE), St. Louis encephalitis, Murray Valley (Australian) encephalitis, Japanese encephalitis, and tick-born encephalitis. | See, e.g., Hoke (2005) Mil. Med. 170: 92-105; Estrada-Franco, et al. (2004) Emerg. Infect. Dis. 10: 2113-2121; Das, et al. (2004) Antiviral Res. 64: 85-92; Aguilar, et al. (2004) Emerg. Infect. Dis. 10: 880-888; Weaver, et al. (2004) Arch. Virol. Suppl. 18: 43-64; Weaver, et al. (2004) Annu. Rev. Entomol. 49: 141-174. Eastern equine encephalitis (GenBank Acc. No. NC_003899; AY722102); Western equine encephalitis (NC_003908). |
| Human herpesviruses, including cytomegalovirus (CMV), Epstein-Barr virus (EBV), human herpesvirus-1 (HHV-1), HHV-2, HHV-3, HHV-4, HHV-5, HHV-6, HHV-7, HHV-8, herpes B virus, herpes simplex virus types 1 and 2 (HSV-1, HSV-2), and varicella zoster virus (VZV). | See, e.g., Studahl, et al. (2000) Scand. J. Infect. Dis. 32: 237-248; Padilla, et al. (2003) J. Med. Virol. 70 (Suppl. 1) S103-S110; Jainkittivong and Langlais (1998) Oral Surg. Oral Med. 85: 399-403. GenBank Nos. NC_001806 (herpesvirus 1); NC_001798 (herpesvirus 2); X04370 and NC_001348 (herpesvirus 3); NC_001345 (herpesvirus 4); NC_001347 (herpesvirus 5); X83413 and NC_000898 (herpesvirus 6); NC_001716 (herpesvirus 7). Human herpesviruses types 6 and 7 (HHV-6; HHV-7) are disclosed by, e.g., Padilla, et al. (2003) J. Med. Virol. 70 (Suppl. 1)S103-S110. Human herpesvirus 8 (HHV-8), including subtypes A-E, are disclosed in, e.g., Treurnicht, et al. (2002) J. Med. Virol. 66: 235-240. |
| HIV-1 including group M (including subtypes A to J) and group O (including any distinguishable subtypes) (HIV-2, including subtypes A-E. | See, e.g., Smith, et al. (1998) J. Med. Virol. 56: 264-268. See also, e.g., GenBank Acc. Nos. DQ054367; NC_001802; AY968312; DQ011180; DQ011179; DQ011178; DQ011177; AY588971; AY588970; AY781127; AY781126; AY970950; AY970949; AY970948; X61240; AJ006287; AJ508597; and AJ508596. |
| Epstein-Barr virus (EBV), including subtypes A and B. | See, e.g., Peh, et al. (2002) Pathology 34: 446-450. Epstein-Barr virus strain B95-8 (GenBank Acc. No. V01555). |
| Reovirus, including serotypes and strains 1, 2, and 3, type 1 Lang, type 2 Jones, and type 3 Dearing. | See, e.g., Barthold, et al. (1993) Lab. Anim. Sci. 43: 425-430; Roner, et al. (1995) Proc. Natl. Acad. Sci. USA 92: 12362-12366; Kedl, et al. (1995) J. Virol. 69: 552-559. GenBank Acc. No. K02739 (sigma-3 gene surface protein). |
| Cytomegalovirus (CMV) subtypes include CMV subtypes I-VII. | See, e.g., Chern, et al. (1998) J. Infect. Dis. 178: 1149-1153; Vilas Boas, et al. (2003) J. Med. Virol. 71: 404-407; Trincado, et al. (2000) J. Med. Virol. 61: 481-487. GenBank Acc. No. X17403. |
| Rhinovirus, including all serotypes. | Human rhinovirus 2 (GenBank Acc. No. X02316); Human rhinovirus B (GenBank Acc. No. NC_001490); Human rhinovirus 89 (GenBank Acc. No. NC_001617); Human rhinovirus 39 (GenBank Acc. No. AY751783). |
| Adenovirus, including all serotypes. | AY803294; NC_004001; AC_000019; AC_000018; AC_000017; AC_000015; AC_000008; AC_000007; AC_000006; AC_000005; AY737798; AY737797; NC_003266; NC_002067; AY594256; AY594254; AY875648; AJ854486; AY163756; AY594255; AY594253; NC_001460; NC_001405; AY598970; AY458656; AY487947; NC_001454; AF534906; AY45969; AY128640; L19443; AY339865; AF532578. |
| Filoviruses, including Marburg virus and Ebola virus, and strains such as Ebola-Sudan (EBO-S), Ebola-Zaire (EBO-Z), and Ebola-Reston (EBO-R). | See, e.g., Geisbert and Jahrling (1995) Virus Res. 39: 129-150; Hutchinson, et al. (2001) J. Med. Virol. 65: 561-566. Marburg virus (see, e.g., GenBank Acc. No. NC_001608). Ebola virus (see, e.g., GenBank Acc. Nos. NC_006432; AY769362; NC_002549; AF272001; AF086833). |

TABLE 1-continued

List of antigens for use in combination with the LNA-CDN compounds as described herein.

| Antigen | Reference |
| --- | --- |
| Arenaviruses, including lymphocytic choriomeningitis (LCM) virus, Lassa virus, Junin virus, and Machupo virus. | Junin virus, segment S (GenBank Acc. No. NC_005081); Junin virus, segment L (GenBank Acc. No. NC_005080). |
| Rabies virus. | See, e.g., GenBank Acc. Nos. NC_001542; AY956319; AY705373; AF499686; AB128149; AB085828; AB009663. |
| Arboviruses, including West Nile virus, Dengue viruses 1 to 4, Colorado tick fever virus, Sindbis virus, Togaviraidae, Flaviviridae, Bunyaviridae, Reoviridae, Rhabdoviridae, Orthomyxoviridae, and the like. | Dengue virus type 1 (see, e.g., GenBank Acc. Nos. AB195673; AY762084). Dengue virus type 2 (see, e.g., GenBank Acc. Nos. NC_001474; AY702040; AY702039; AY702037). Dengue virus type 3 (see, e.g., GenBank Acc. Nos. AY923865; AT858043). Dengue virus type 4 (see, e.g., GenBank Acc. Nos. AY947539; AY947539; AF326573). Sindbis virus (see, e.g., GenBank Acc. Nos. NC_001547; AF429428; J02363; AF103728). West Nile virus (see, e.g., GenBank Acc. Nos. NC_001563; AY603654). |
| Poxvirus including orthopoxvirus (variola virus, monkeypox virus, vaccinia virus, cowpox virus), yatapoxvirus (tanapox virus, Yaba monkey tumor virus), parapoxvirus, and molluscipoxvirus. | Viriola virus (see, e.g., GenBank Acc. Nos. NC_001611; Y16780; X72086; X69198). |
| Yellow fever. | See, e.g., GenBank Acc. No. NC_002031; AY640589; X03700. |
| Hantaviruses, including serotypes Hantaan (HTN), Seoul (SEO), Dobrava (DOB), Sin Nombre (SN), Puumala (PUU), and Dobrava-like Saaremaa (SAAV). | See, e.g., Elgh, et al. (1997) J. Clin. Microbiol. 35: 1122-1130; Sjolander, et al. (2002) Epidemiol. Infect. 128: 99-103; Zeier, et al. (2005) Virus Genes 30: 157-180. GenBank Acc. No. NC_005222 and NC_005219 (Hantavirus). See also, e.g., GenBank Acc. Nos. NC_005218; NC_005222; NC_005219. |
| Flaviviruses, including Dengue virus, Japanese encephalitis virus, West Nile virus, and yellow fever virus. | See, e.g., Mukhopadhyay, et al. (2005) Nature Rev. Microbiol. 3: 13-22. GenBank Acc. Nos NC_001474 and AY702040 (Dengue). GenBank Acc. Nos. NC_001563 and AY603654. |
| Measles virus. | See, e.g., GenBank Acc. Nos. AB040874 and AY486084. |
| Human parainfluenzaviruses (HPV), including HPV types 1-56. | Human parainfluenza virus 2 (see, e.g., GenBank Acc. Nos. AB176531; NC003443). Human parainfluenza virus 3 (see, e.g., GenBank Acc. No. NC_001796). |
| Influenza virus, including influenza virus types A, B, and C. | Influenza nucleocapsid (see, e.g., GenBank Acc. No. AY626145). Influenza hemagglutinin (see, e.g., GenBank Acc. Nos. AY627885; AY555153). Influenza neuraminidase (see, e.g., GenBank Acc. Nos. AY555151; AY577316). Influenza matrix protein 2 (see, e.g., GenBank Acc. Nos. AY626144(.Influenza basic protein 1 (see, e.g., GenBank Acc. No. AY627897). Influenza polymerase acid protein (see, e.g., GenBank Acc. No. AY627896). Influenza nucleoprotein (see, e.g., GenBank Acc. Nno. AY627895). |
| Influenza A virus subtypes, e.g., swine viruses (SIV): H1N1 influenzaA and swine influenza virus. | Hemagglutinin of H1N1 (GenBank Acc. No. S67220). Influenza A virus matrix protein (GenBank Acc. No. AY700216). Influenza virus A H5H1 nucleoprotein (GenBank Acc. No. AY646426). H1N1 haemagglutinin (GenBank Acc. No. D00837). See also, GenBank Acc. Nos. BD006058; BD006055; BD006052. See also, e.g., Wentworth, et al. (1994) J. Virol. 68: 2051-2058; Wells, et al. (1991) J.A.M.A. 265: 478-481. |
| Respiratory syncytial virus (RSV), including subgroup A and subgroup B. | Respiratory syncytial virus (RSV) (see, e.g., GenBank Acc. Nos. AY353550; NC_001803; NC001781). |
| Rotaviruses, including human rotaviruses A to E, bovine rotavirus, rhesus monkey rotavirus, and human-RVV reassortments. | Human rotavirus C segment 8 (GenBank Acc. No. AJ549087); Human rotavirus G9 strain outer capsid protein (see, e.g., GenBank Acc. No. DQ056300); Human rotavirus B strain non-structural protein 4 (see, e.g., GenBank Acc. No. AY548957); human rotavirus A strain major inner capsid protein (see, e.g., GenBank Acc. No. AY601554). |

TABLE 1-continued

List of antigens for use in combination with the LNA-CDN compounds as described herein.

| Antigen | Reference |
|---|---|
| Polyomavirus, including simian virus 40 (SV40), JC virus (JCV) and BK virus (BKV). | See, e.g., Engels, et al. (2004) J. Infect. Dis. 190: 2065-2069; Vilchez and Butel (2004) Clin. Microbiol. Rev. 17: 495-508; Shivapurkar, et al. (2004) Cancer Res. 64: 3757-3760; Carbone, et al. (2003) Oncogene 2: 5173-5180; Barbanti-Brodano, et al. (2004) Virology 318: 1-9) (SV40 complete genome in, e.g., GenBank Acc. Nos. NC_001669; AF168994; AY271817; AY271816; AY120890; AF345344; AF332562). |
| Coltiviruses, including Colorado tick fever virus, Eyach virus. | Attoui, et al. (1998) J. Gen. Virol. 79: 2481-2489. Segments of Eyach virus (see, e.g., GenBank Acc. Nos. AF282475; AF282472; AF282473; AF282478; AF282476; NC_003707; NC_003702; NC_003703; NC_003704; NC_003705; NC_003696; NC_003697; NC_003698; NC_003699; NC_003701; NC_003706; NC_003700; AF282471; AF282477). |
| Caliciviruses, including the genogroups Norwalk, Snow Mountain group (SMA), and Saaporo. | Snow Mountain virus (see, e.g., GenBank Acc. No. AY134748). |
| Parvoviridae, including dependovirus, parvovirus (including parvovirus B19), and erythrovirus. | See, e.g., Brown (2004) Dev. Biol. (Basel) 118: 71-77; Alvarez-Lafuente, et al. (2005) Ann. Rheum. Dis. 64: 780-782; Ziyaeyan, et al. (2005) Jpn. J. Infect. Dis. 58: 95-97; Kaufman, et al. (2005) Virology 332: 189-198. |

Other organisms for which suitable antigens are known in the art include, but are not limited to, *Chlamydia trachomatis*, *Streptococcus pyogenes* (Group A Strep), *Streptococcus agalactia* (Group B Strep), *Streptococcus pneumonia*, *Staphylococcus aureus*, *Escherichia coli*, *Haemophilus influenzae*, *Neisseria meningitidis*, *Neisseria gonorrheae*, *Vibrio cholerae*, *Salmonella* species (including *typhi*, *typhimurium*), *enterica* (including *Helicobactor pylori Shigella flexneri* and other Group D *shigella* species), *Burkholderia mallei*, *Burkholderia pseudomallei*, *Klebsiella pneumonia*, *Clostridium* species (including *C. difficile*), *Vibrio parahaemolyticus* and *V. vulnificus*. This list is not meant to be limiting.

Pharmaceutical Compositions

The term "pharmaceutical" as used herein refers to a chemical substance intended for use in the cure, treatment, or prevention of disease and which is subject to an approval process by the U.S. Food and Drug Administration (or a non-U.S. equivalent thereof) as a prescription or over-the-counter drug product. Details on techniques for formulation and administration of such compositions may be found in *Remington, The Science and Practice of Pharmacy* $21^{st}$ *Edition* (Mack Publishing Co., Easton, Pa.) and Nielloud and Marti-Mestres, Pharmaceutical Emulsions and Suspensions: $2^{nd}$ Edition (Marcel Dekker, Inc, New York).

For the purposes of this disclosure, the pharmaceutical compositions may be administered by a variety of means including non-parenterally, parenterally, by inhalation spray, topically, or rectally in formulations containing pharmaceutically acceptable carriers, adjuvants and vehicles. "Non-parenteral administration" encompasses oral, buccal, sublingual, topical, transdermal, ophthalmic, otic, nasal, rectal, cervical, pulmonary, mucosal, and vaginal routes. The term parenteral as used here includes but is not limited to subcutaneous, intravenous, intramuscular, intraarterial, intradermal, intrathecal and epidural injections with a variety of infusion techniques. Intraarterial and intravenous injection as used herein includes administration through catheters. Administration via intracoronary stents and intracoronary reservoirs is also contemplated. Intra-tumoral (directly into the tumor mass) or peri-tumoral (around the tumor mass) administration of the compounds of the present invention may directly activate locally infiltrating DC, directly promote tumor cell apoptosis or sensitize tumor cells to cytotoxic agents. The term oral as used herein includes, but is not limited to oral ingestion, or delivery by a sublingual or buccal route. Oral administration includes fluid drinks, energy bars, as well as pill formulations.

Pharmaceutical compositions may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing a drug compound in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents; such as magnesium stearate, stearic acid or talc. Tablets may be uncoated, or may be coated by known techniques including enteric coating, colonic coating, or microencapsulation to delay disintegration and adsorption in the gastrointestinal tract and/or provide a sustained action over a longer period. For example, a time delay material such as glyceryl monostearate or glyceryl distearate alone or with a wax may be employed.

Formulations for oral use may be also presented as hard gelatin capsules where the drug compound is mixed with an inert solid diluent, for example calcium phosphate or kaolin, or as soft gelatin capsules wherein the active ingredient is mixed with water or an oil medium, such as peanut oil, liquid paraffin or olive oil.

Pharmaceutical compositions may be formulated as aqueous suspensions in admixture with excipients suitable for the manufacture of aqueous-suspensions. Such excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the disclosure suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the disclosure may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the disclosure may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 20 to 500 mg of active material compounded with an appropriate and convenient amount of carrier material which may vary from about 5 to about 95% of the total compositions. It is preferred that the pharmaceutical composition be prepared which provides easily measurable amounts for administration. Typically, an effective amount to be administered systemically is about 0.1 mg/kg to about 100 mg/kg and depends upon a number of factors including, for example, the age and weight of the subject (e.g., a mammal such as a human), the precise condition requiring treatment and its severity, the route of administration, and will ultimately be at the discretion of the attendant physician or veterinarian. It will be understood, however, that the specific dose level for any particular patient will depend on a variety of factors including the activity of the specific compound employed, the age, body weight, general health, sex and diet of the individual being treated; the time and route of administration; the rate of excretion; other drugs which have previously been administered; and the severity of the particular condition undergoing therapy, as is well understood by those skilled in the art.

As noted above, formulations of the disclosure suitable for oral administration may be presented as discrete units such as capsules, cachets or tablets each containing a predetermined amount of the active ingredient, as a powder or granules; as a solution or a suspension in an aqueous or non-aqueous liquid, or as an oil-in-water liquid emulsion or a water-in-oil liquid emulsion. The pharmaceutical compositions may also be administered as a bolus, electuary or paste.

A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropyl ethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made in a suitable machine using a mixture of the powdered compound moistened with an inert liquid diluent. The tablets may optionally be coated or scored and may be formulated so as to provide slow or controlled release of the active ingredient therein using, for example, hydroxypropyl methylcellulose in varying proportions to provide the desired release profile. Tablets may optionally be provided with an enteric or colonic coating to provide release in parts of the gut other than the stomach. This is particularly advantageous with the LNA-CDN compounds as described herein when such compounds are susceptible to acid hydrolysis.

Formulations suitable for topical administration in the mouth include lozenges comprising the active ingredient in a flavored base, usually sucrose and acacia or tragacanth; pastilles comprising the active ingredient in an inert base such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Injection solutions and suspensions may be prepared from sterile powders, granules and tablets of the kind previously described.

When a disclosed compound or its salt is named or depicted by structure, it is to be understood that the compound or salt, including solvates (particularly, hydrates) thereof, may exist in crystalline forms, non-crystalline forms or a mixture thereof. The compound or salt, or solvates (particularly, hydrates) thereof, may also exhibit polymorphism (i.e. the capacity to occur in different crystalline forms). These different crystalline forms are typically known as "polymorphs." It is to be understood that when named or depicted by structure, the disclosed compound, or solvates (particularly, hydrates) thereof, also include all polymorphs thereof. Polymorphs have the same chemical composition but differ in packing, geometrical arrangement, and other descriptive properties of the crystalline solid state. Polymorphs may have different physical properties such as density, shape, hardness, stability, and dissolution properties. Polymorphs typically exhibit different melting points, IR spectra, and X-ray powder diffraction patterns, which may be used for identification. One of ordinary skill in the art will appreciate that different polymorphs may be produced, for example, by changing or adjust the conditions used during the crystallization or recrystallization of the compound.

For solvates of compounds of this invention, or salts thereof, that are in crystalline form, the skilled artisan will appreciate that pharmaceutically acceptable solvates may be formed wherein solvent molecules are incorporated into the crystalline lattice during crystallization. Solvates may involve nonaqueous solvents such as ethanol, isopropanol, dimethyl sulfoxide, acetic acid, ethanolamine, and ethyl acetate, or they may involve water as the solvent that is incorporated into the crystalline lattice. Solvates wherein water is the solvent that is incorporated into the crystalline lattice are typically referred to as "hydrates." Hydrates include stoichiometric hydrates as well as compositions containing variable amounts of water. The invention includes all such solvates.

Because of their potential use in medicine, the salts of the compounds of this invention are preferably pharmaceutically acceptable. Suitable pharmaceutically acceptable salts include those described by P. Heinrich Stahl and Camille G. Wermuth in *Handbook of Pharmaceutical Salts: Properties, Selection, and Use*, 2$^{nd}$ ed. (Wiley-VCH: 2011) and also *Remington's Pharmaceutical Sciences*, 18$^{th}$ ed. (Mack Publishing, Easton Pa.: 1990) and also *Remington: The Science and Practice of Pharmacy*, 19$^{th}$ ed. (Mack Publishing, Easton Pa.: 1995). Salt encompassed within the term "pharmaceutically acceptable salts" refer to non-toxic salts of the compounds in this invention.

Salts of the compounds of this invention containing a basic amine or other basic functional group may be prepared by any suitable method known in the art, including treatment of the free bases with an inorganic acid, such as hydrochloric acid, hydrobromic acid, sulfuric acid, nitric acid, phosphoric acid, and the like, or with an organic acid, such as acetic acid, trifluoroacetic acid, maleic acid, succinic acid, mandelic acid, fumaric acid, malonic acid, formic acid, alginic acid, pyruvic acid, oxalic acid, glycolic acid, salicylic acid, pyranosildyl acid, such as glucuronic acid or galacturonic acid, alphahydroxy acid, such as citric acid or tartaric acid, amino acid, such as aspartic acid or glutamic acid, aromatic acid, such as benzoic acid or cinnamic acid, sulfonic acid, such as p-toluenesulfonic acid, methanesulfonic acid, ethanesulfonic acid or the like. Examples of pharmaceutically acceptable salts include sulfates, pyrosulfates, bisulfates, sulfites, bisulfites, phosphates, chlorides, bromides, iodides, acetates, propionates, decanoates, caprylates, acrylates, formates, isobutyrates, caproates, heptanoates, propiolates, oxalates, malonates succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, phenylacetates, phenylpropionates, phenylbutrates, citrates, lactates, glycolate, resinate, lactates, camsylates, tartrates, mandelates, and sulfonates, such as xylenesulfonates, methanesulfonates, propanesulfonates, naphthalene-1-sulfonates and naphthalene-2-sulfonates.

Salts of the compounds of this invention containing a phosphate diester, phosphorothioate diester or other acidic functional group can be prepared by reacting with a suitable base. Pharmaceutically acceptable salts include, but are not limited to: pyridine, ammonium, piperazine, diethylamine, nicotinamide, formic, urea, sodium, potassium, calcium, magnesium, zinc, lithium, cinnamic, methylamino, methanesulfonic, picric, tartaric, triethylamino, dimethylamino, and tris(hydoxymethyl)aminomethane. Additional pharmaceutically acceptable salts are known to those skilled in the art.

Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, zinc, as well as salts made from physiologically acceptable organic bases such as diethylamine, isopropylamine, olamine, benzathine, benethamine, tromethamine (2-amino-2-(hydroxymethyl)propane-1,3-diol), morpholine, epolamine, piperidine, piperazine, picoline, dicyclohexylamine, N,N'-dibenzylethylenediamine, 2-hydroxyethylamine, tri-(2-hydroxyethyl)amine, chloroprocaine, choline, deanol, imidazole, diethanolamine, ethylenediamine, meglumine (N-methylglucamine), procaine, dibenzylpiperidine, dehydroabietylamine, glucamine, collidine, quinine, quinolone, erbumine and basic amino acids such as lysine and arginine.

The LNA-CDN compounds as described herein that include salts thereof can be described by structures wherein the —SH or —OH in the phosphate or thiophosphate bond (i.e. R3 or R4 of the compounds of Formula I as described herein) are represented as —S$^-$ or —O$^-$ with a corresponding cation to form salts of the compounds as described herein. For example, salts of compounds of Formula IVa as described herein where R54 and R55 are —OH or —SH can be represented by the following structures:

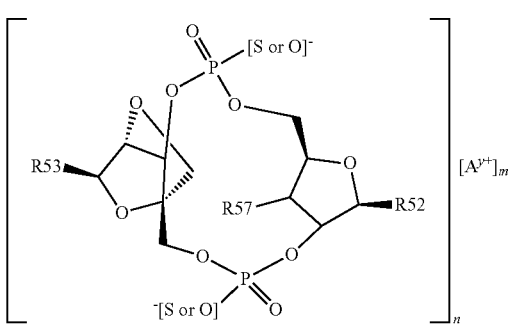

wherein $A^{y+}$ represents a mono or polyvalent salt cation, and n and m are the lowest possible whole number for a given y. For example when $A^{y+}$ is monovalent, i.e. when y is 1, such as $Na^+$, $K^+$, $NH_4^+$, $TEAH^+$ or the like, n is 1 and m is 2; when y is 2, such as $Ca^{2+}$, $Mg^{2+}$ and the like, n is 1 and m is 1; when y is 3, e.g. $Al^{3+}$ or the like, n is 3 and m is 2. For example, salts of a monovalent or divalent salt cation can be represented as

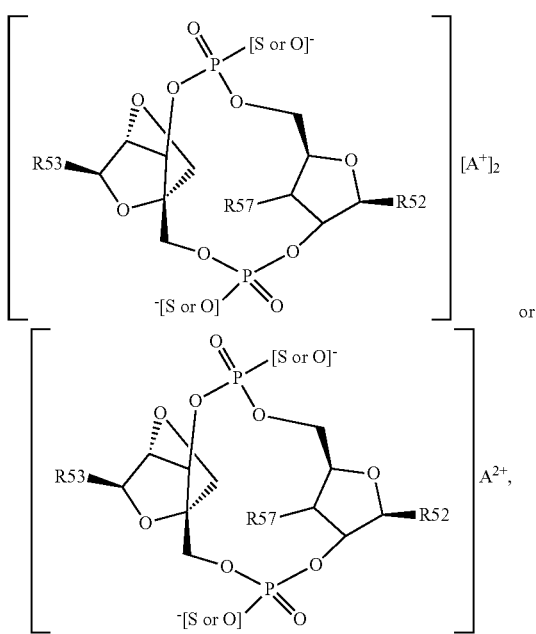

respectively, or in cases where n=1, these can be represented without brackets, e.g. as

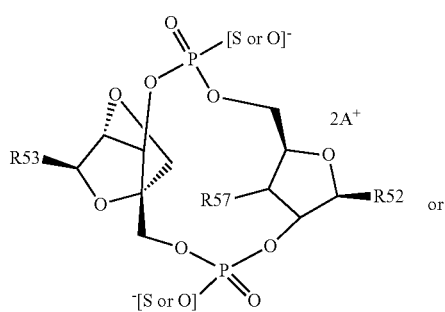

Alternatively, monovalent salts can be depicted with $A^+$ adjacent each of the —$S^-$ or —$O^-$.

For example, the sodium salt of above compounds of Formula IVa can be depicted as

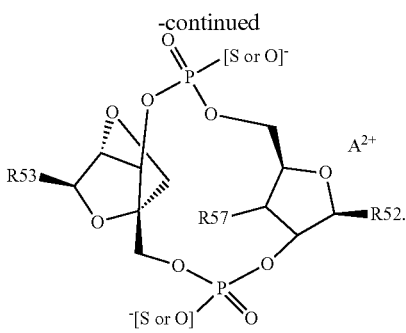

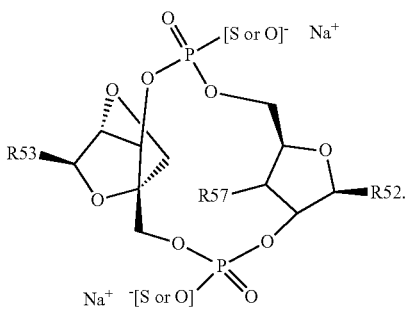

Other non-pharmaceutically acceptable salts, e.g. trifluoroacetate or triethylammonium may be used, for example in the isolation of compounds of the invention, and are included within the scope of this invention.

The invention includes within its scope all possible stoichiometric and non-stoichiometric forms of the salts of the compounds of this invention.

If a compound of this invention containing a basic amine or other basic functional group is isolated as a salt, the corresponding free base form of that compound may be prepared by any suitable method known to the art, including treatment of the salt with an inorganic or organic base, suitably an inorganic or organic base having a higher $pK_a$ than the free base form of the compound. Similarly, if a compound of this invention containing a phosphate diester, phosphorothioate diester or other acidic functional group is isolated as a salt, the corresponding free acid form of that compound may be prepared by any suitable method known to the art, including treatment of the salt with an inorganic or organic acid, suitably an inorganic or organic acid having a lower $pK_a$ than the free acid form of the compound.

An effective amount of a LNA-CDN compound, or a pharmaceutically acceptable salt, pharmaceutically acceptable solvate or pharmaceutically acceptable hydrate thereof as described herein, for a particular patient may vary depending on factors such as the condition being treated, the overall health of the patient, the route and dose of administration and the severity of side effects. Guidance for methods of treatment and diagnosis is available (see, e.g., Maynard, et al. (1996) A Handbook of SOPs for Good Clinical Practice, Interpharm Press, Boca Raton, Fla.; Dent (2001) Good Laboratory and Good Clinical Practice, Urch Publ., London, UK).

An effective amount may be given in one dose, but is not restricted to one dose. Thus, the administration can be two, three, four, five, six, seven, eight, nine, ten, eleven, twelve, thirteen, fourteen, fifteen, sixteen, seventeen, eighteen, nineteen, twenty, or more, administrations of a pharmaceutical composition comprising the LNA-CDN compound, or a pharmaceutically acceptable salt, pharmaceutically acceptable solvate or pharmaceutically acceptable hydrate thereof as described herein. Where there is more than one administration of a pharmaceutical composition in the present methods, the administrations can be spaced by time intervals of one minute, two minutes, three, four, five, six, seven, eight, nine, ten, or more minutes, by intervals of about one hour, two hours, three, four, five, six, seven, eight, nine, ten, 11, 12, 13, 14, 15, 16, 17, 18, 19, 20, 21, 22, 23, 24 hours, and so on. In the context of hours, the term "about" means plus or minus any time interval within 30 minutes. The administrations can also be spaced by time intervals of one day, two days, three days, four days, five days, six days, seven days, eight days, nine days, ten days, 11 days, 12 days, 13 days, 14 days, 15 days, 16 days, 17 days, 18 days, 19 days, 20 days, 21 days, and combinations thereof. The invention is not limited to dosing intervals that are spaced equally in time, but encompass doses at non-equal intervals. A dosing schedule of, for example, once/week, twice/week, three times/week, four times/week, five times/week, six times/week, seven times/week, once every two weeks, once every three weeks, once every four weeks, once every five weeks, and the like, is available for the invention. The dosing schedules encompass dosing for a total period of time of, for example, one week, two weeks, three weeks, four weeks, five weeks, six weeks, two months, three months, four months, five months, six months, seven months, eight months, nine months, ten months, eleven months, and twelve months.

Provided are cycles of the above dosing schedules. The cycle can be repeated about, e.g., every seven days; every 14 days; every 21 days; every 28 days; every 35 days; 42 days; every 49 days; every 56 days; every 63 days; every 70 days; and the like. An interval of non dosing can occur between a cycle, where the interval can be about, e.g., seven days; 14 days; 21 days; 28 days; 35 days; 42 days; 49 days; 56 days; 63 days; 70 days; and the like. In this context, the term "about" means plus or minus one day, plus or minus two days, plus or minus three days, plus or minus four days, plus or minus five days, plus or minus six days, or plus or minus seven days.

Methods for co-administration with an additional therapeutic agent are well known in the art (Hardman, et al. (eds.) (2001) Goodman and Gilman's The Pharmacological Basis of Therapeutics, 10th ed., McGraw-Hill, New York, N.Y.; Poole and Peterson (eds.) (2001) Pharmacotherapeutics for Advanced Practice: A Practical Approach, Lippincott, Williams & Wilkins, Phila., Pa.; Chabner and Longo (eds.) (2001) Cancer Chemotherapy and Biotherapy, Lippincott, Williams & Wilkins, Phila., Pa.). Generally, co-administration or administration together indicates treating a subject with two or more agents, where the agents can be administered simultaneously or at different times. For example, such agents may be delivered to a single subject as separate administrations, which may be at essentially the same time or different times, and which may be by the same route or different routes of administration. Such agents may be delivered to a single subject in the same administration (e.g. same formulation) such that they are administered at the same time by the same route of administration.

As noted, the compositions of the present invention are preferably formulated as pharmaceutical compositions for parenteral or enteral delivery. A typical pharmaceutical composition for administration to an animal subject comprises a pharmaceutically acceptable vehicle such as aqueous solutions, non-toxic excipients, including salts, preservatives, buffers and the like. See, e.g., *Remington's Pharmaceutical Sciences*, 15*th Ed*., Easton ed., Mack Publishing Co., pp 1405-1412 and 1461-1487 (1975); *The National Formulary XIV,* 14*th Ed*., American Pharmaceutical Association, Washington, D.C. (1975). Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to routine skills in the art.

Repeated administrations of a particular vaccine (homologous boosting) have proven effective for boosting humoral responses. Such an approach may not be effective at boosting cellular immunity because prior immunity to the vector tends to impair robust antigen presentation and the generation of appropriate inflammatory signals. One approach to circumvent this problem has been the sequential administration of vaccines that use different antigen-delivery systems (heterologous boosting). In a heterologous boosting regimen, at least one prime or boost delivery comprises delivery of the inactivated tumor cell/LNA-CDN compound or compositions thereof described herein. The heterologous arm of the regimen may comprise delivery of antigen using one or more of the following strategies:

inactivated or attenuated bacteria or viruses comprising the antigen of interest, which are particles that have been treated with some denaturing condition to render them ineffective or inefficient in mounting a pathogenic invasion;

purified antigens, which are typically naturally-produced antigens purified from a cell culture of the pathogen or a tissue sample containing the pathogen, or a recombinant version thereof;

live viral or bacterial delivery vectors recombinantly engineered to express and/or secrete antigens in the host cells of the subject. These strategies rely on attenuating (e.g., via genetic engineering) the viral or bacterial vectors to be non-pathogenic and non-toxic;

antigen presenting cell (APC) vectors, such as a dendritic cell (DC) vector, which comprise cells that are loaded with an antigen, or transfected with a composition comprising a nucleic acid encoding the antigen (e.g., Provenge® (Dendreon Corporation) for the treatment of castration-resistant metastatic prostate cancer);

liposomal antigen delivery vehicles; and naked DNA vectors and naked RNA vectors which may be administered by a gene gun, electroporation, bacterial ghosts, microspheres, microparticles, liposomes, polycationic nanoparticles, and the like.

A prime vaccine and a boost vaccine can be administered by any one or combination of the following routes. In one aspect, the prime vaccine and boost vaccine are administered by the same route. In another aspect, the prime vaccine and boost vaccine are administered by different routes. The term "different routes" encompasses, but is not limited to, different sites on the body, for example, a site that is oral, non-oral, enteral, parenteral, rectal, intranode (lymph node), intravenous, arterial, subcutaneous, intramuscular, intratumor, peritumor, intratumor, infusion, mucosal, nasal, in the cerebrospinal space or cerebrospinal fluid, and so on, as well as by different modes, for example, oral, intravenous, and intramuscular.

An effective amount of a prime or boost vaccine may be given in one dose, but is not restricted to one dose. Thus, the administration can be two, three, four, five, six, seven, eight, nine, ten, eleven, twelve, thirteen, fourteen, fifteen, sixteen, seventeen, eighteen, nineteen, twenty, or more, administrations of the vaccine. Where there is more than one administration of a vaccine the administrations can be spaced by time intervals of one minute, two minutes, three, four, five, six, seven, eight, nine, ten, or more minutes, by intervals of about one hour, two hours, three, four, five, six, seven, eight, nine, ten, 11, 12, 13, 14, 15, 16, 17, 18, 19, 20, 21, 22, 23, 24 hours, and so on. In the context of hours, the term "about" means plus or minus any time interval within 30 minutes. The administrations can also be spaced by time intervals of one day, two days, three days, four days, five days, six days, seven days, eight days, nine days, ten days, 11 days, 12 days, 13 days, 14 days, 15 days, 16 days, 17 days, 18 days, 19 days, 20 days, 21 days, and combinations thereof. The invention is not limited to dosing intervals that are spaced equally in time, but encompass doses at non-equal intervals, such as a priming schedule consisting of administration at 1 day, 4 days, 7 days, and 25 days, just to provide a non-limiting example.

Synthesis of Compounds of Formula I

The compounds of Formula I, and sub-generic formulae thereof, can be prepared by methods readily available to those of skill in the chemical arts, for example, without limitation, as described in the following generic synthetic Scheme I, and for the specific compounds as described in Examples 1-6 below.

The following Scheme I provides methods for the synthesis of compounds of Formula I wherein R3 and R4 are SH, and $X_4$ is O, represented by compounds Fa, Fb, Fc and Fd in Scheme I, wherein ring A, $Y_1$, $Y_2$, $Y_3$, $Y_4$, $X_1$, $X_2$, $X_3$, R1, R2, R5, R6, and R7 are as defined for Compounds of Formula I, and $R_f$ is a suitable oxygen protecting group (e.g. dimethoxytrityl). It is understood that the compounds represented in Scheme I have suitable protecting groups as needed, e.g. R1 and R2 include suitably protected bases (e.g. adenine with a nitrogen protecting group on the 6-position amine, guanine with a nitrogen protecting group on the 2-position amine, and the like), or R5 and R6 as OH is a suitably protected (e.g. OTBS).

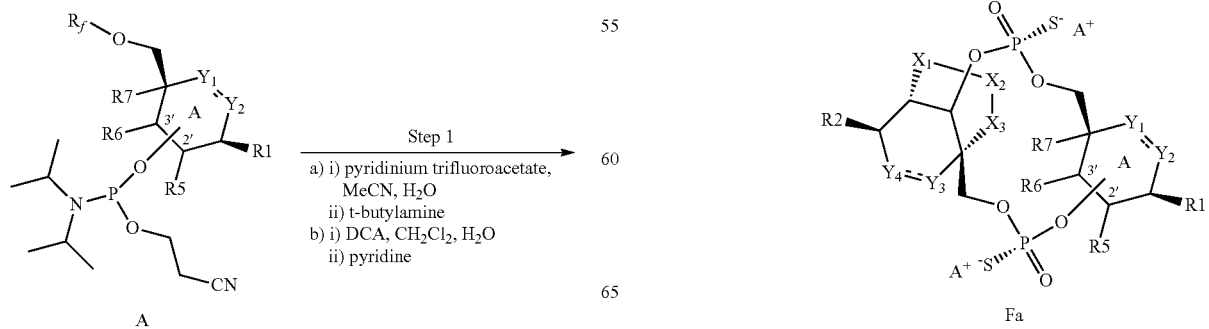

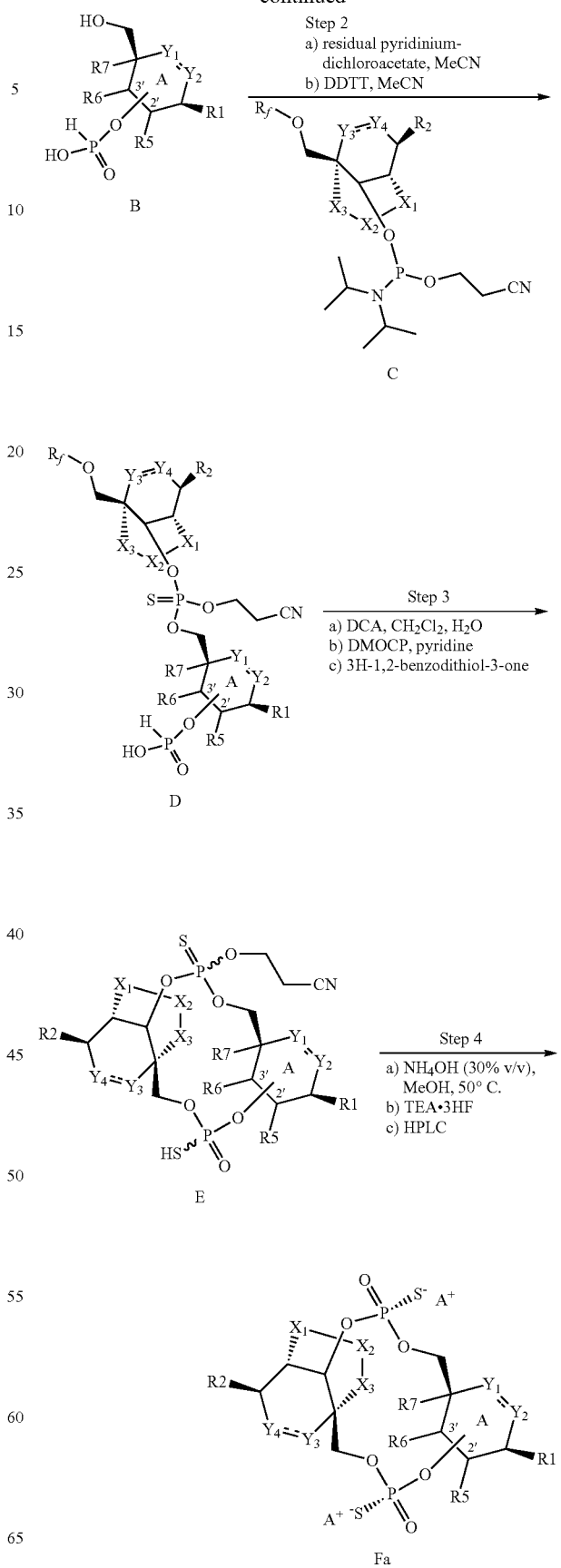

-continued

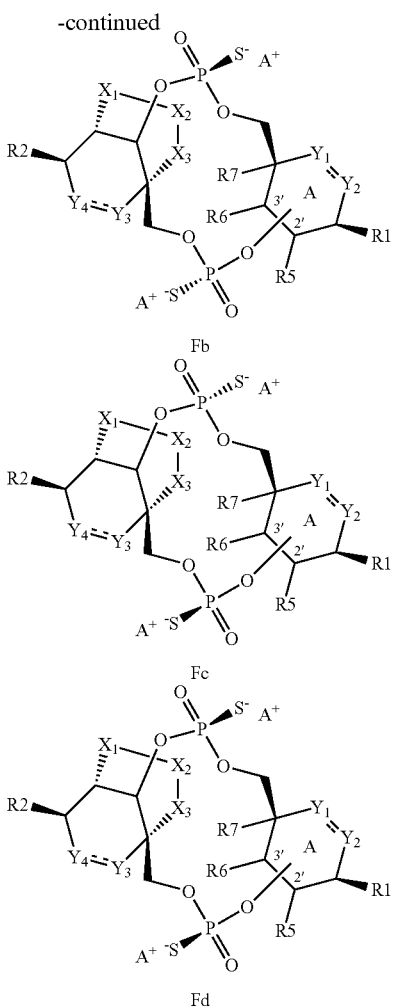

Scheme I, Step 1: Compound B: Compound A (where the oxygen can be bound to either the 2' or 3' carbon of ring A) is dissolved in e.g. MeCN with H$_2$O (e.g. 0.6% v/v) and pyridinium trifluoroacetate is added. The reaction mixture is stirred for e.g. 15 min at room temperature and tert-butyl amine is added. After e.g. 15 min, the reaction solution is concentrated in vacuo and water is removed as an azeotrope after concentration in vacuo 3× with MeCN. The resulting material is dissolved in e.g CH$_2$Cl$_2$ and to the resulting solution is added water (e.g. ~1% v/v) and 8% (v/v) solution of DCA in solvent CH$_2$Cl$_2$. After e.g. 10 min of stirring at room temperature, the solution is charged with pyridine. The resulting solution is concentrated in vacuo and water is removed as an azeotrope after concentration in vacuo with 3× MeCN to provide Compound B, which can be left in MeCN for the next step.

Scheme I, Step 2: Compound D: A solution of compound C in e.g. MeCN is dried through concentration in vacuo. This process is repeated two more times to remove water as an azeotrope. On the last azeotrope, to this solution of compound C in MeCN is introduced 3A molecular sieves and the solution is stored under an atmosphere of nitrogen. To a stirred mixture of compound B with residual pyridinium dichloroacetate in MeCN is added the solution of compound C in MeCN. After e.g. 1 h, to the stirred mixture is added DDTT, and after e.g. 2 h, the mixture is concentrated in vacuo to give compound D.

Scheme I, Step 3: Compound E: To a solution of compound D in e.g. CH$_2$Cl$_2$ is added water (e.g. ~0.6% v/v) and 15% (v/v) solution of DCA in CH$_2$Cl$_2$. After e.g. 10 min at room temperature pyridine is added to the solution, and the resulting solution is concentrated in vacuo to a volume of approximately 20 mL. Pyridine is added and the solution is concentrated 2× in vacuo, leaving the mixture in approximately 10 mL. To the stirred mixture is added pyridine and DMOCP. After e.g. 20 min, to the solution is added water (e.g. ~1.25% v/v), followed immediately by the introduction of 3H-1,2-benzodithiol-3-one. After e.g. 45 min, the solution is poured into a 1N aqueous NaHCO$_3$ solution. After e.g. 30 min, the biphasic mixture is extracted with EtOAc. After separation, the aqueous layer is back extracted 2× with EtOAc. The organic extracts are combined and concentrated in vacuo. To the concentrated material is added toluene and the mixture is evaporated in vacuo to remove residual pyridine, and repeated 2×. The resulting material is purified by silica gel chromatography (e.g. 0% to 60% MeOH in CH$_2$Cl$_2$) to provide compound E as a mixture of stereoisomers. The newly formed phosphorothioate bond is shown as a mixture of stereoisomers on the phosphorus, while in some instances, this reaction may result in primarily the R isomer at this phosphorus.

Scheme I, Step 4: Compound F (including Fa, Fb, Fc, Fd): To a stirred solution of compound E in e.g. EtOH is added AMA and the resulting solution is heated at 50° C. After e.g. 2 h, the solution is allowed to cool and concentrated in vacuo. To the residual solid is introduced triethylamine trihydrofluoride and the yellow solution is heated to 40° C. After e.g. 3 h, the solution is allowed to cool to room temperature, and the solution is slowly added to a cooled solution of 1M TEAB and triethylamine. The mixture is allowed to stir for e.g. 1 h. The resulting residue is purified by reverse phase silica gel chromatography (e.g. 0% to 50% MeCN in 10 mM aqueous TEAA) to isolate the RR, RS, SR and SS isomers (at the two phosphorous atoms) Compound Fa, Compound Fb, Compound Fc, and Compound Fd as a white bis-triethylammonium salt after lyophilization. In instances where the phosphorothioate bond formed in Step 3 is primarily the R isomer, primarily compounds Fa and Fb will be isolated.

The methods of Scheme I can be modified as necessary by one skilled in the chemical arts, e.g. in terms of relative amounts of compounds and solvents, temperatures, reaction conditions, and the like. Similar methods as described in Examples 1-6 below may also be used to provide the LNA-CDN compounds as described herein.

The starting materials, i.e. compounds A and C, are readily available to one of skill in the chemical arts, including modifications that are readily available to one of skill in the chemical arts to prepare compounds of Formula I. For example, compounds as described in Examples 1-6 below, or suitable modifications thereof, can be used as compound A or C. In addition, compounds of Formula A or C, or compounds that can be readily converted to a compound of Formula A or C are described in, for example, PCT Publication Number WO 2010/091308 and WO 2009/143369, and U.S. Pat. Nos. 8,022,193, 8,278,283 and 9,005,906, and Seth et al., J. Org. Chem., 2012, 77: 5074-5085, or Migawa et al., Org. Letters, 2013, 15(17): 4316-4319 (Y$_1$—Y$_2$ is —O—CH$_2$— or —CH=CH—, R5 is F and the phosphoramidite in A is linked to the 3' carbon, or where R5 and R7 and/or —X$_1$—X$_2$—X$_3$— form —O—CH$_2$—; or Y$_1$ is O, Y$_2$ is absent, and R5 and R7 and/or —X$_1$—X$_2$—X$_3$— form —O—CRR— or —O—C(=CH$_2$)—, where each R is independently e.g. H or CH$_3$, wherein the methyl is optionally substituted with one F or one methoxy); U.S. Pat. Nos. 7,569,686, 7,427,672 and US Patent Publication No. 2012/071646 ($Y_1$ is O, $Y_2$ is absent, and R5 and R7 and/or —$X_1$—$X_2$—$X_3$— form —O—NR—$CH_2$—, R is e.g. H, $CH_3$, or a nitrogen protecting group such as —C(=O)—$CH_2$—O-phenyl); U.S. Pat. No. 8,541,562 ($Y_1$ is O, $Y_2$ is absent, and R5 and R7 and/or —$X_1$—$X_2$—$X_3$— form —O—NR—C(=O)—, —NR—C(=O)— or —NR—C(=O)—$CH_2$—, R is e.g. H, Me or a nitrogen protecting group); PCT Publication Number WO 2015/142735 and WO 2014/145356 ($Y_1$ is O, $Y_2$ is absent, and R5 and R7 and/or —$X_1$—$X_2$—$X_3$— form —$CH_2$—NR—$CH_2$—, R is e.g. H or a nitrogen protecting group such as —C(=O)—$CF_3$); PCT Publication Number WO 99/60855, WO 2013/036868, US Patent Publication No. 2003/0028013, and U.S. Pat. Nos. 6,403,556 and 6,833,361 ($Y_1$ is O, $Y_2$ is absent, and R5 and R7 and/or —$X_1$—$X_2$—$X_3$— form —$CH_2$—O—$CH_2$—); PCT Publication No. WO 2008/154401, U.S. Pat. Nos. 8,461,124, 8,278,426, and Xu et al., J. Org. Chem. 2009, 74, 6534-6554 ($Y_1$ is O, $Y_2$ is absent, and R5 and R7 and/or —$X_1$—$X_2$—$X_3$— form —CRR—CR'R'—, each R is independently e.g. H, F, $NH_2$ or $CH_3$ or forms =$CH_2$ optionally substituted with F, or forms =O and each R' is independently e.g. H, F, OH, $OCH_3$, $CH_3$ optionally substituted with F, forms =$CH_2$ optionally substituted with F, or forms =O; or R5 and R7 and/or —$X_1$—$X_2$—$X_3$— form —CRR—$CH_2$—$CH_2$—, R is e.g. H, $CH_3$); PCT Publication No. WO 2016/017422 ($Y_1$ is O, $Y_2$ is absent, and R5 and R7 and/or —$X_1$—$X_2$—$X_3$— form —CRR—$CH_2$—O—, each R is independently e.g. H, $CH_3$ or forms =$CH_2$); U.S. Pat. No. 8,278,425, PCT Publication No. WO 2007/145593 ($Y_1$ is O, $Y_2$ is absent, and R5 and R7 and/or —$X_1$—$X_2$—$X_3$— form —NR—$CH_2$—, R is e.g. OR', R' is e.g. $C_{1-6}$alkyl (e.g. methyl, ethyl) optionally substituted with e.g. F or $OCH_3$), or R5 and R7 and/or —$X_1$—$X_2$—$X_3$— form —NH—$CH_2$—$CH_2$—); US Patent Publication No. US 2015/0337002 ($Y_1$ is O, $Y_2$ is absent, and R5 and R7 and/or —$X_1$—$X_2$—$X_3$— form —NR—S(=O)$_2$—, —NR—S(=O)$_2$—$CH_2$— or —S(=O)$_2$—NR—$CH_2$—, R is e.g. H or $C_{1-3}$alkyl); and PCT Publication No. WO 2015/125783, WO 2011/085102, WO 2009/006478, U.S. Pat. Nos. 7,217,805, 7,335,765, 8,278,283, and US Patent Publication No. 2015/0152132 ($Y_1$ is O, $Y_2$ is absent, and R5 and R7 and/or —$X_1$—$X_2$—$X_3$— form —O—$CH_2$—$CH_2$— or —O—CRR—, each R is independently e.g. H, $CH_3$, forms =$CH_2$, or together with the carbon atom to which they are bound form a 3-6 membered heterocyclyl or $C_{3-6}$ cycloalkyl (e.g. cyclopropyl), U.S. Pat. No. 7,217,805 includes compounds where $X_4$' and/or $X_4$ are NH). Additional references describing non-LNA starting materials and synthesis of cyclic dinucleotides include, for example, PCT Publication No. WO 2015/185565 (including compounds where e.g. $Y_1$ is —$CH_2$— and $Y_2$ is absent), WO2007/054279, WO2014/093936, WO2014/189805, U.S. Pat. Nos. 7,709,458 and 7,592,326; Yan et al., Bioorg. Med. Chem Lett. 2008, 18: 5631; and Kovacs et al., 1995, Nucleosides & Nucleotides, 14(6): 1259-1267 (including compounds where $Y_1$ is O, $Y_2$ is absent, R6 is F and the phosphoramidite is linked to the 2' carbon). It is understood in discussing these references, where $Y_1$, $Y_2$, R5 and R7 of Compound A are discussed, this also applies to Compound C, i.e. to $Y_3$, $Y_4$, $X_1$, $X_2$ and $X_3$ of Compound C. These references are incorporated by reference herein as it relates to the compounds and methods described herein, e.g. compounds of Formula A or C.

Examples

The following examples serve to illustrate the present invention. These examples are in no way intended to limit the scope of the invention.

General Methods

Anhydrous solvents and reagents suitable for solution phase oligonucleotide synthesis were purchased from commercial suppliers (Aldrich, ChemGenes Corporation, Wilmington, Mass., USA) and handled under dry argon or nitrogen using anhydrous technique. Phosphoramidite coupling reactions and H-phosphonate cyclizations were carried out in anhydrous acetonitrile or pyridine under dry argon or nitrogen. The starting materials for all reactions in dry pyridine were dried by concentration (three times) from pyridine, unless indicated otherwise. Chromatography conditions were as follows unless indicated otherwise in the examples below. Preparative silica gel flash chromatography was carried out under medium pressure chromatography (MPLC) using RediSep Rf silica columns (Teledyne Isco, Lincoln, Nebr.) on a Combiflash Rf+ UV-Vis (Teledyne Isco) using gradients of methanol in dichloromethane. Reverse phase preparative chromatography was executed under MPLC conditions using RediSep Rf C18 Aq columns (Teledyne Isco) on a Combiflash Rf+ UV-Vis using gradients of acetonitrile in aqueous 10 mM TEAA solution. Analytical high pressure liquid chromatography (HPLC) was performed on a Shimadzu Prominence HPLC system with two LC-20AD pumps and a SPD-M30A photodiode array detector monitoring at 254 nm. Gradients of 10 mM TEAA in acetonitrile or 20 mM $NH_4OAc$ in acetonitrile were used with either a 5 micron (Thermo Scientific Acclaim 120)C-18 column (4.6×250 mm) or a 10 micron (Thermo Scientific Hypersil)C-18 column (4.0×250 mm) at room temperature. Ultra-Performance analytical high pressure liquid chromatography (UPLC) was performed on a Shimadzu Nexera $X_2$ LCMS system with two LC-30AD pumps and a SPD-M30A photodiode array detector monitoring at 254 nm. Gradients of 20 mM $NH_4OAc$ in acetonitrile were used with a 1.7 micron (Acquity UPLC® BEH) C-18 column (2.1×30 mm) at room temperature. Preparative HPLC was carried out on a Shimadzu preparative LC20-AP HPLC system, equipped with a SPD-20A UV/Vis detector monitoring at 254 nm on a Varian Microsorb 60-8 C-18 41.6×250 mm column using gradients of 10 mM TEAA and acetonitrile at a flow rate of 50 ml/min. Solid phase extractions using C-18 Sep-Pak (Waters) were carried out at loadings of 3% (wt/wt). Analytical LCMS were recorded using a Shimadzu LCMS system featuring a Prominence HPLC coupled to a Shimadzu LCMS-2020 single quadrupole mass spectrometer, using an electrospray ionization source (ESI). Additional or alternative instrumentation and methods may also be provided in the examples that follow.

$^1$H NMR, $^{19}$F NMR, $^{31}$P NMR and $^{13}$C NMR spectra were recorded in $CDCl_3$, d6-DMSO, $CD_3OD$ or $D_2O$ as solvent, using a Bruker 400 MHz spectrometer with a broad band channel and variable temperature probe. The operating frequency for 1H was 400 MHz, $^{19}$F was 376 MHz, $^{31}$P was 162 MHz, and $^{13}$C was 100 MHz. All spectra were recorded at ambient temperature (20-25° C.) unless otherwise noted. The temperature for variable-temperature experiments was calibrated monthly or bimonthly using the ethylene glycol method described in C. Amman, P. Meier and A. E. Merbach, J. Magn. Reson. 1982, 46, 319-321.

The final compounds may exist as the triethylammonium (TEAH$^+$ or $Et_3NH^+$) salt, which can be converted to other salt forms (including but not limited to sodium (Nat) or ammonium ($NH_4^+$)) using standard ion exchange techniques or other well known methods.

Assignments of Stereochemistry at the phosphorus were made in analogy to literature methods (Zhao et al. Nucleosides, Nucleotides, and Nucleic Acid 289:352-378, 2009) or as discussed in the examples below.

Compound names were generated using the software program ChemBioDraw Ultra V 14.0 available from CambridgeSoft Corporation, 100 CambridgePark Drive, Cambridge, Mass. 02140 USA (www.cambridgesoft.com). Abridged names of compounds for which a name could not be generated by ChemBioDraw, or reference compounds used in the examples, are provided in the following Table 3. Reference compounds 2'3'-RR-(G)(A) and 2'3'-RR-(A)(A) were prepared as described in PCT Publication No. WO2014/189805, incorporated by reference with respect to such syntheses. Structures in the examples may also be represented as salts, e.g. —O⁻ A⁺ or —S⁻ A⁺, where A⁺ is the salt cation.

TABLE 3

Abridged compound names and structures.

| Example number and abridged Compound names | Structure |
| --- | --- |
| Example 2 Compound 5a 3'3'-RR-(2'O,4'C-LNA-A)(2'O,4'C-LNA-A) dithio-(Rp,Rp)-cyclic-[2'O,4'C-LNA-A(3',5')p-2'O,4'C-LNA-A(3',5')p] (2R,3R,3aS,5R,7aR,9S,10R,10aS,12R,14aR)-2,9-bis(6-amino-9H-purin-9-yl)-5,12-dimercaptotetrahydro-2H,7H,9H,14H-3,14a:10,7a-bis(epoxymethano)difuro[3,2-d:3',2'-j][1,3,7,9]tetraoxa[2,8]diphosphacyclododecine 5,12-dioxide | 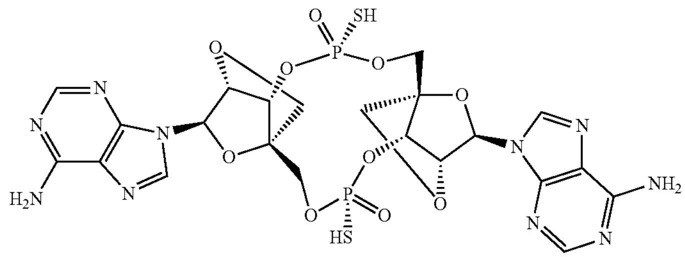 [SMILES: Nc1ncnc2c1ncn2[C@@H]1O[C@@]23CO[C@@H]1[C@@H]2O[P@](=O)(S)OC[C@@]12CO[C@@H]([C@H](n4cnc5c(N)ncnc54)O1)[C@@H]2O[P@](=O)(S)OC3] |
| Example 2 Compound 5b 3'3'-RS-(2'O,4'C-LNA-A)(2'O,4'C-LNA-A) dithio-(Rp,Sp)-cyclic-[2'O,4'C-LNA-A(3',5')p-2'O,4'C-LNA-A(3',5')p] (2R,3R,3aS,5R,7aR,9S,10R,10aS,12S,14aR)-2,9-bis(6-amino-9H-purin-9-yl)-5,12-dimercaptotetrahydro-2H,7H,9H,14H-3,14a:10,7a-bis(epoxymethano)difuro[3,2-d:3',2'-j][1,3,7,9]tetraoxa[2,8]diphosphacyclododecine 5,12-dioxide | 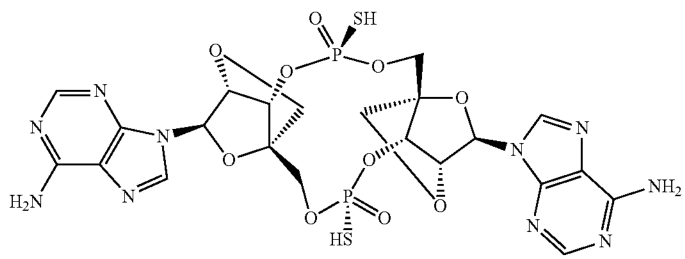 [SMILES: Nc1ncnc2c1ncn2[C@@H]1O[C@@]23CO[C@@H]1[C@@H]2O[P@@](=O)(S)OC[C@@]12CO[C@@H]([C@H](n4cnc5c(N)ncnc54)O1)[C@@H]2O[P@](=O)(S)OC3] |
| Example 2 Compound 4a 3'3'-RR-(2'O,4'C-LNA-BzA)(2'O,4'C-LNA-BzA) dithio-(Rp,Rp)-cyclic-[2'O,4'C-LNA-BzA(3',5')p-2'O,4'C-LNA-BzA(3',5')p] N,N'-(((2R,3R,3aS,5R,7aR,9R,10R,10aS,12R,14aR)-5,12-dimercapto-5,12-dioxidotetrahydro-2H,7H,9H,14H-3,14a:10,7a-bis(epoxymethano)difuro[3,2-d:3',2'-j][1,3,7,9]tetraoxa[2,8]diphosphacyclododecine-2,9-diyl)bis(9H-purine-9,6-diyl))dibenzamide | 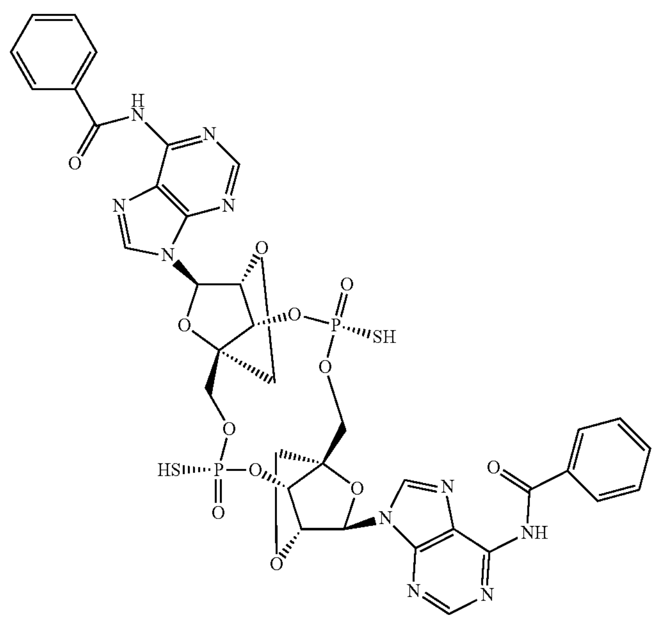 [SMILES: O=C(Nc1ncnc2c1ncn2[C@@H]1O[C@@]23CO[C@@H]1[C@@H]2O[P@](=O)(S)OC[C@@]12CO[C@@H]([C@H](n4cnc5c(NC(=O)c6ccccc6)ncnc54)O1)[C@@H]2O[P@](=O)(S)OC3)c1ccccc1] |

TABLE 3-continued

Abridged compound names and structures.

Example number and abridged Compound names | Structure

Example 2 Compound 4b
3'3'-RS-(2'O,4'C-LNA-BzA)(2'O,4'C-LNA-BzA)
dithio-(Rp,Sp)-cyclic-[2'O,4'C-LNA-BzA(3',5')p-2'O,4'C-LNA-BzA(3',5')p]
N,N'-(((2R,3R,3aS,5R,7aR,9R,10R,10aS,12S,14aR)-5,12-dimercapto-5,12-dioxidotetrahydro-2H,7H,9H,14H-3,14a:10,7a-bis(epoxymethano)difuro[3,2-d:3',2'-j][1,3,7,9]tetraoxa[2,8]diphosphacyclododecine-2,9-diyl)bis(9H-purine-9,6-diyl))dibenzamide

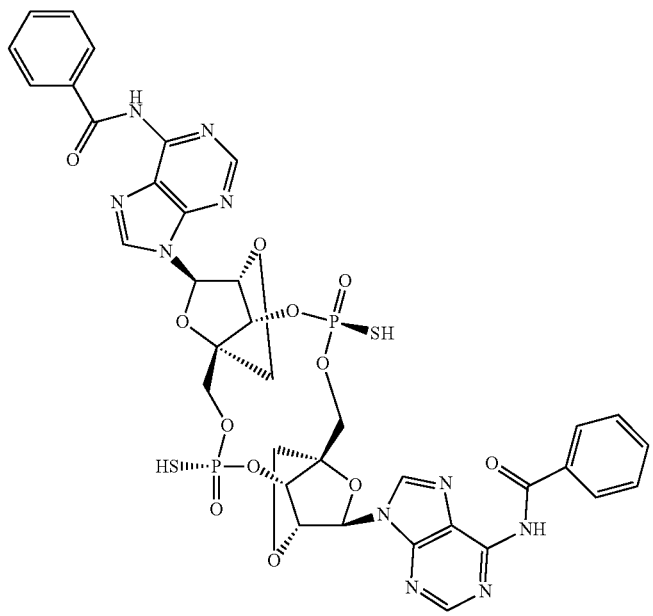 [SMILES: O=C(Nc1ncnc2c1ncn2[C@@H]1O[C@@]23CO[C@@H]1[C@@H]2O[P@@](=O)(S)OC[C@@]12CO[C@@H]([C@H](n4cnc5c(NC(=O)c6ccccc6)ncnc54)O1)[C@@H]2O[P@](=O)(S)OC3)c1ccccc1]

Example 3 Compound 10a
2'3'-RR-(A)(2'O,4'C-LNA-A)
dithio-(Rp,Rp)-cyclic-[A(2',5')p-2'O,4'C-LNA-A(3',5')p]

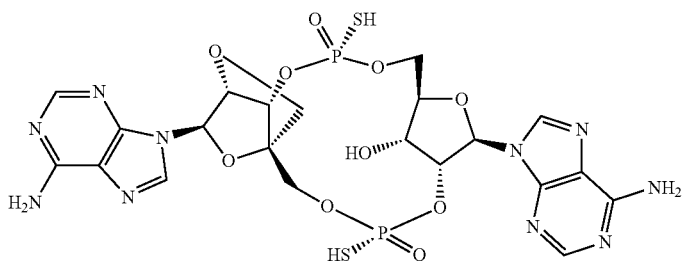 [SMILES: Nc1ncnc2c1ncn2[C@@H]1O[C@@H]2CO[P@@](=O)(S)O[C@H]3[C@H]4OC[C@]3(CO[P@@](=O)(S)O[C@@H]1[C@@H]2O)O[C@H]4n1cnc2c(N)ncnc21]

Example 3 Compound 10b
2'3'-RS-(A)(2'O,4'C-LNA-A)
dithio-(Rp,Sp)-cyclic-[A(2',5')p-2'O,4'C-LNA-A(3',5')p]

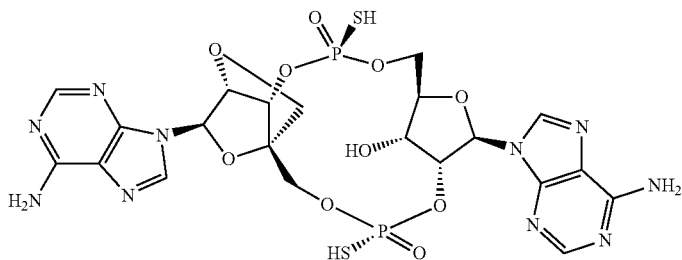 [SMILES: Nc1ncnc2c1ncn2[C@@H]1O[C@@H]2CO[P@](=O)(S)O[C@H]3[C@H]4OC[C@]3(CO[P@@](=O)(S)O[C@@H]1[C@@H]2O)O[C@H]4n1cnc2c(N)ncnc21]

Example 3 Compound 10c
2'3'-SR-(A)(2'O,4'C-LNA-A)
dithio-(Sp,Rp)-cyclic-[A(2',5')p-2'O,4'C-LNA-A(3',5')p]

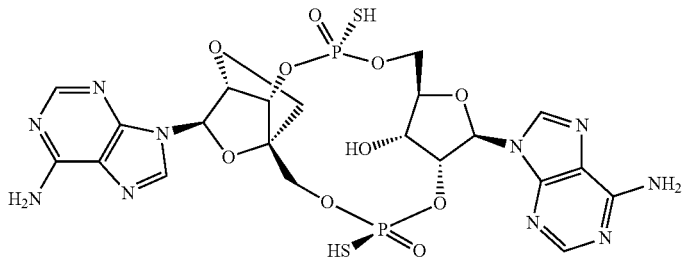 [SMILES: Nc1ncnc2c1ncn2[C@@H]1O[C@@H]2CO[P@@](=O)(S)O[C@H]3[C@H]4OC[C@]3(CO[P@](=O)(S)O[C@@H]1[C@@H]2O)O[C@H]4n1cnc2c(N)ncnc21]

TABLE 3-continued

Abridged compound names and structures.

| Example number and abridged Compound names | Structure |
|---|---|
| Example 3 Compound 10d<br>2'3'-SS-(A)(2'O,4'C-LNA-A)<br>dithio-(Sp,Sp)-cyclic-[A(2',5')p-<br>2'O,4'C-LNA-A(3',5')p] | 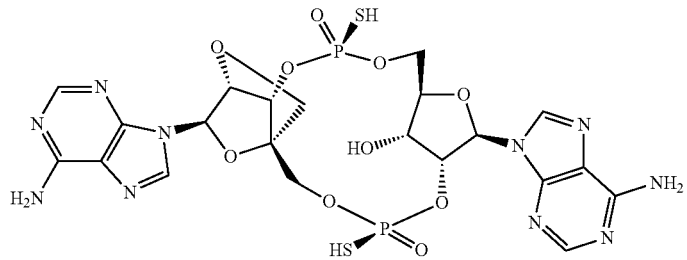 [SMILES: Nc1ncnc2c1ncn2[C@@H]1O[C@@H]2CO[P@](=O)(S)O[C@H]3[C@H]4OC[C@]3(CO[P@](=O)(S)O[C@@H]1[C@@H]2O)O[C@H]4n1cnc2c(N)ncnc21] |
| Example 3 Compound 11a<br>2'3'-RR-(3'-OTBS-A)(2'O,4'C-LNA-A)<br>dithio-(Rp,Rp)-cyclic-[3'-OTBS-A(2',5')p-2'O,4'C-LNA-A(3',5')p] | 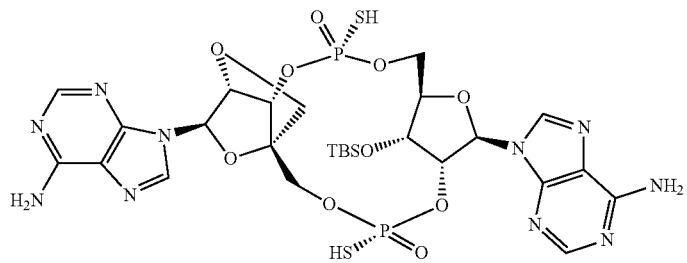 [SMILES: CC(C)(C)[Si](C)(C)O[C@H]1[C@H]2O[P@](=O)(S)OC[C@@]34CO[C@@H]([C@H](n5cnc6c(N)ncnc65)O3)[C@@H]4O[P@](=O)(S)OC[C@H]1O[C@H]2n1cnc2c(N)ncnc21] |
| Example 3 Compound 11b<br>2'3'-RS-(3'-OTBS-A)(2'O,4'C-LNA-A)<br>dithio-(Rp,Sp)-cyclic-[3'-OTBS-A(2',5')p-2'O,4'C-LNA-A(3',5')p] | 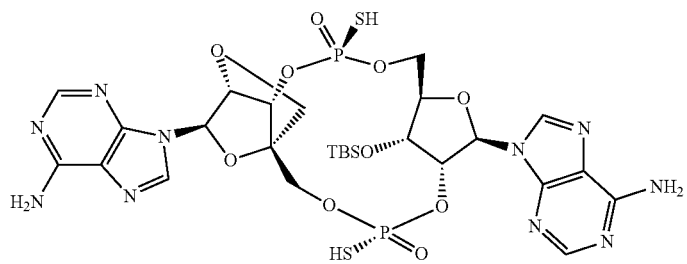 [SMILES: CC(C)(C)[Si](C)(C)O[C@H]1[C@H]2O[P@](=O)(S)OC[C@@]34CO[C@@H]([C@H](n5cnc6c(N)ncnc65)O3)[C@@H]4O[P@@](=O)(S)OC[C@H]1O[C@H]2n1cnc2c(N)ncnc21] |
| Example 3 Compound 11c<br>2'3'-SS-(3'-OTBS-A)(2'O,4'C-LNA-A)<br>dithio-(Sp,Sp)-cyclic-[3'-OTBS-A(2',5')p-2'O,4'C-LNA-A(3',5')p] | 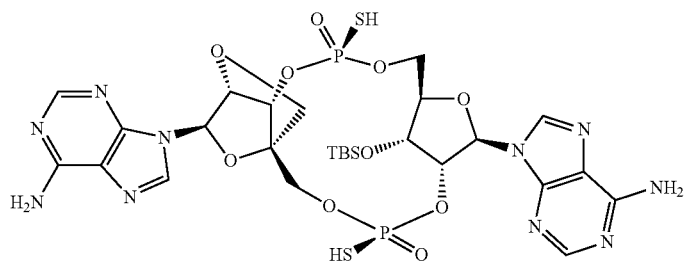 [SMILES: CC(C)(C)[Si](C)(C)O[C@H]1[C@H]2O[P@@](=O)(S)OC[C@@]34CO[C@@H]([C@H](n5cnc6c(N)ncnc65)O3)[C@@H]4O[P@@](=O)(S)OC[C@H]1O[C@H]2n1cnc2c(N)ncnc21] |
| Example 3 Compound 11d<br>2'3'-RR-(BzA)(2'O,4'C-LNA-BzA)<br>dithio-(Rp,Rp)-cyclic-[3'-BzA(2',5')p-2'O,4'C-LNA-BzA(3',5')p] | 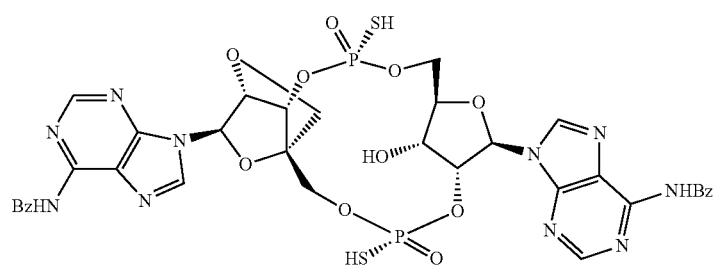 |

TABLE 3-continued

Abridged compound names and structures.

| Example number and abridged Compound names | Structure |
|---|---|
| Example 3 Compound 11e<br>2'3'-RS-(BzA)(2'O,4'C-LNA-BzA) dithio-(Rp,Sp)-cyclic-[3'-BzA(2',5')p-2'O,4'C-LNA-BzA(3',5')p] | 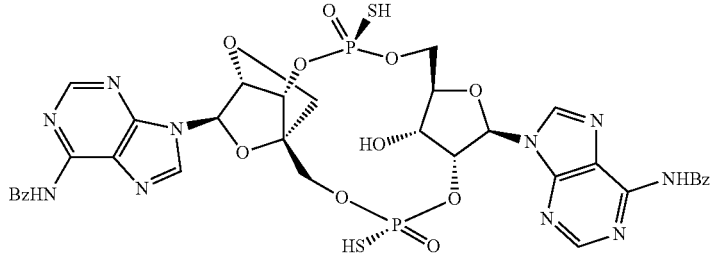 |
| Example 3 Compound 11f<br>2'3'-SR-(BzA)(2'O,4'C-LNA-BzA) dithio-(Sp,Rp)-cyclic-[3'-BzA(2',5')p-2'O,4'C-LNA-BzA(3',5')p] | 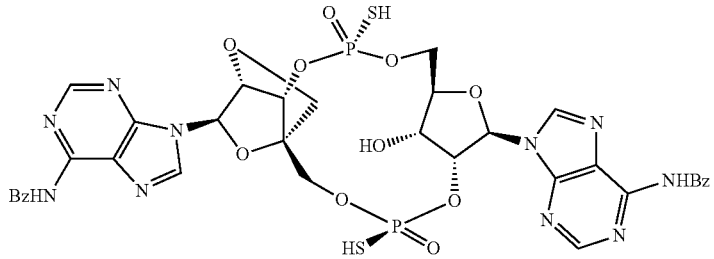 |
| Example 4 Compound 15a<br>2'3'-RR-(3'F-G)(2'O,4'C-LNA-A) dithio-(Rp,Rp)-cyclic-[3'F-G(2',5')p-2'O,4'C-LNA-A(3',5')p] | 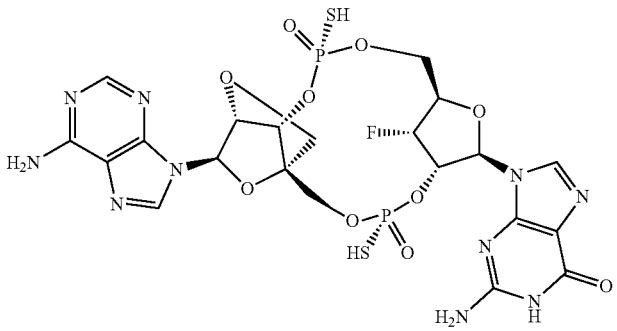 [SMILES: Nc1nc2c(ncn2[C@@H]2O[C@@H]3CO[P@@](=O)(S)O[C@H]4[C@H]5OC[C@]4(CO[P@@](=O)(S)O[C@@H]2[C@@H]3F)O[C@H]5n2cnc3c(N)ncnc32)c(=O)[nH]1] |
| Example 4 Compound 15b<br>2'3'-RS-(3'F-G)(2'O,4'C-LNA-A) dithio-Rp,Sp)-cyclic-[3'F-G(2',5')p-2'O,4'C-LNA-A(3',5')p] | 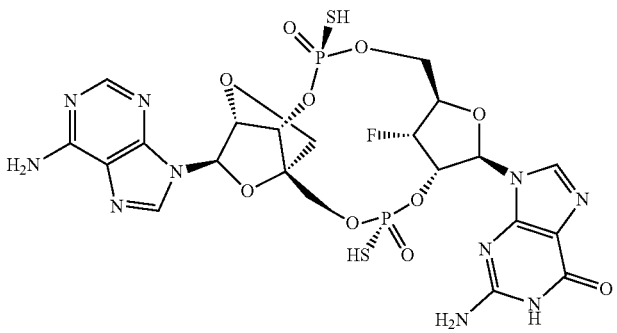 [SMILES: Nc1nc2c(ncn2[C@@H]2O[C@@H]3CO[P@](=O)(S)O[C@H]4[C@H]5OC[C@]4(CO[P@@](=O)(S)O[C@@H]2[C@@H]3F)O[C@H]5n2cnc3c(N)ncnc32)c(=O)[nH]1] |
| Example 4 Compound 15c<br>2'3'-SR-(3'F-G)(2'O,4'C-LNA-A) dithio-(Sp,Rp)-cyclic-[3'F-G(2',5')p-2'O,4'C-LNA-A(3',5')p] | 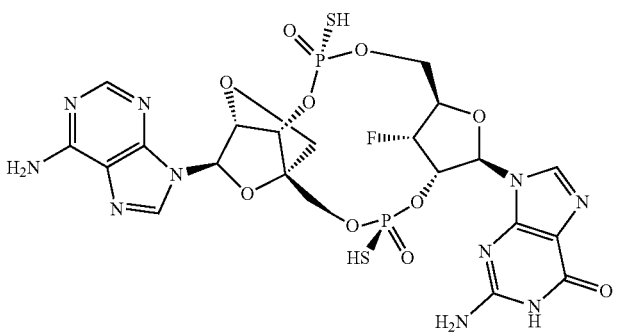 [SMILES: Nc1nc2c(ncn2[C@@H]2O[C@@H]3CO[P@@](=O)(S)O[C@H]4[C@H]5OC[C@]4(CO[P@](=O)(S)O[C@@H]2[C@@H]3F)O[C@H]5n2cnc3c(N)ncnc32)c(=O)[nH]1] |

TABLE 3-continued

Abridged compound names and structures.

| Example number and abridged Compound names | Structure |
|---|---|
| Example 4 Compound 15d<br>2'3'-SS-(3'F-G)(2'O,4'C-LNA-A)<br>dithio-(Sp,Sp)-cyclic-[3'F-G(2',5')p-<br>2'O,4'C-LNA-A(3',5')p] | 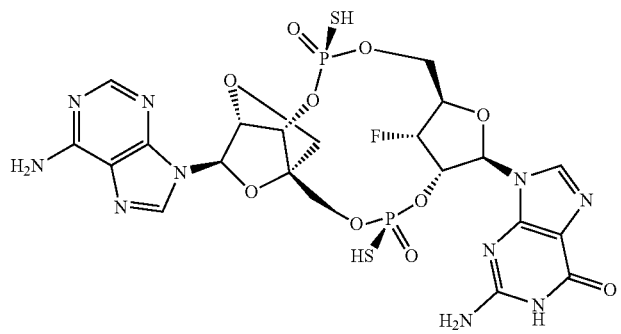 [SMILES: Nc1nc2c(ncn2[C@@H]2O[C@@H]3CO[P@](=O)(S)O[C@H]4[C@H]5OC[C@]4(CO[P@](=O)(S)O[C@@H]2[C@@H]3F)O[C@H]5n2cnc3c(N)ncnc32)c(=O)[nH]1] |
| Example 5 Compound 21a<br>2'3'-RR-(3'H-A)(2'O,4'C-LNA-A)<br>dithio-($R_p,R_p$)-cyclic-[3'H-A(2',5')p-<br>2'O,4'C-LNA-A(3',5')p] | 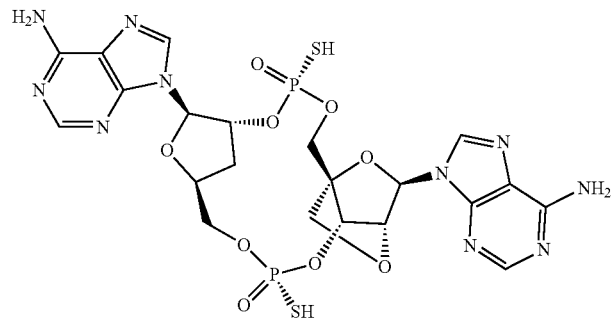 [SMILES: Nc1ncnc2c1ncn2[C@@H]1O[C@@]23CO[C@@H]1[C@@H]2O[P@](=O)(S)OC[C@@H]1C[C@@H](O[P@](=O)(S)OC3)[C@H](n2cnc3c(N)ncnc32)O1] |
| Example 5 Compound 21b<br>2'3'-RS-(3'H-A)(2'O,4'C-LNA-A)<br>dithio-($R_p,S_p$)-cyclic-[3'H-A(2',5')p-<br>2'O,4'C-LNA-A(3',5')p] | 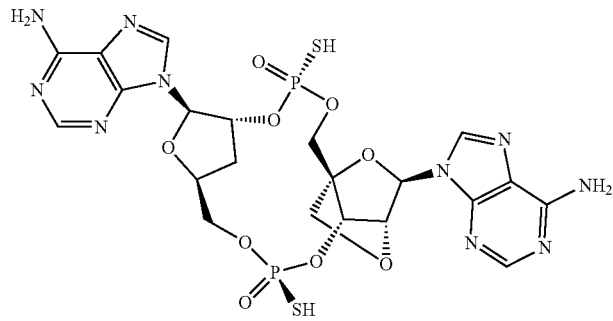 [SMILES: Nc1ncnc2c1ncn2[C@@H]1O[C@@]23CO[C@@H]1[C@@H]2O[P@@](=O)(S)OC[C@@H]1C[C@@H](O[P@](=O)(S)OC3)[C@H](n2cnc3c(N)ncnc32)O1] |
| Example 5 Compound 22a<br>2'3'-RR-(3'H-BzA)(2'O,4'C-LNA-BzA)<br>dithio-($R_p,R_p$)-cyclic-[3'H-BzA(2',5')p-<br>2'O,4'C-LNA-BzA(3',5')p] | 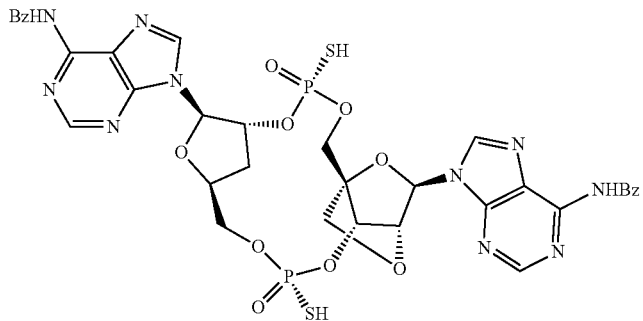 |

TABLE 3-continued

Abridged compound names and structures.

| Example number and abridged Compound names | Structure |
|---|---|
| Example 5 Compound 22b<br>2'3'-RS-(3'H-BzA)(2'O,4'C-LNA-BzA)<br>dithio-(Rp,Sp)-cyclic-[3'H-BzA(2',5')p-2'O,4'C-LNA-BzA(3',5')p] | 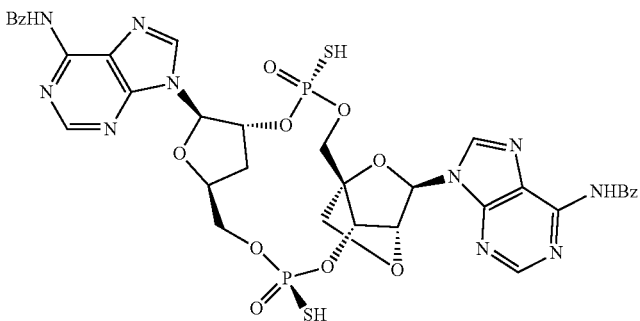 |
| Example 6 Compound 27a<br>2'3'-RR-(3'F-A)(2'O,4'C-LNA-A)<br>dithio-($R_p$,$R_p$)-cyclic-[3'F-A(2',5')p-2'O,4'C-LNA-A(3',5')p] | 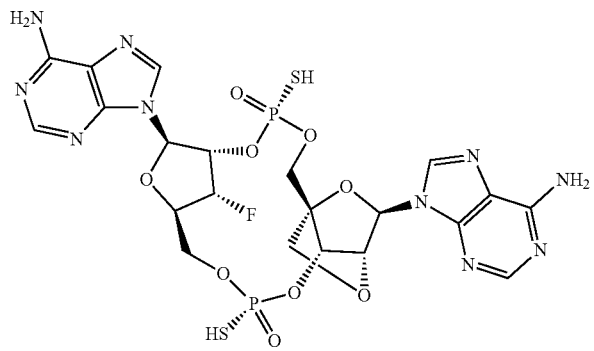 [SMILES: Nc1ncnc2c1ncn2[C@@H]1O[C@@H]2CO[P@@](=O)(S)O[C@H]3[C@H]4OC[C@]3(CO[P@@](=O)(S)O[C@@H]1[C@@H]2F)O[C@H]4n1cnc2c(N)ncnc21] |
| Example 6 Compound 27b<br>2'3'-RS-(3'F-A)(2'O,4'C-LNA-A)<br>dithio-($R_p$,$S_p$)-cyclic-[3'F-A(2',5')p-2'O,4'C-LNA-A(3',5')p] | 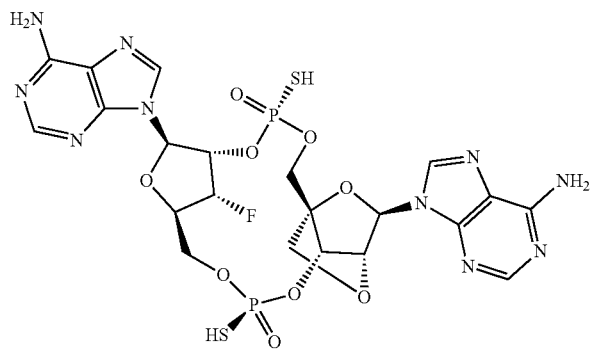 [SMILES: Nc1ncnc2c1ncn2[C@@H]1O[C@@H]2CO[P@](=O)(S)O[C@H]3[C@H]4OC[C@]3(CO[P@@](=O)(S)O[C@@H]1[C@@H]2F)O[C@H]4n1cnc2c(N)ncnc21] |
| Example 7 Compound 33a<br>3'3'-RR-(A)(2'O,4'C-LNA-G)<br>dithio-($R_p$,$R_p$)-cyclic-[A(3',5')p-2'O,4'C-LNA-G(3',5')p]<br>2-amino-9-((2R,3R,3aS,5R,7aR,9R,10R,10aS,12R,14aR)-9-(6-amino-9H-purin-9-yl)-10-hydroxy-5,12-dimercapto-5,12-dioxidohexahydro-2H,7H,14H-3,14a-(epoxymethano)difuro[3,2-d:3',2'-j][1,3,7,9]tetraoxa[2,8]diphosphacyclododecin-2-yl)-1,9-dihydro-6H-purin-6-one | 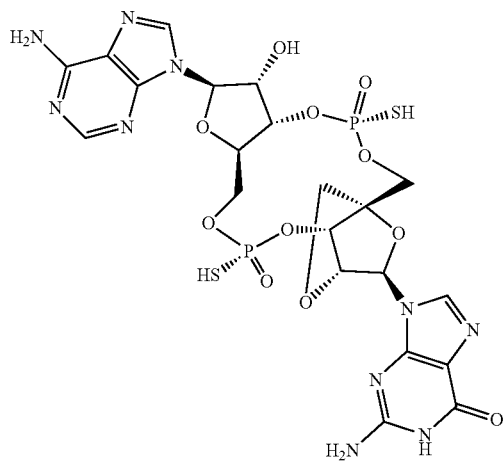 [SMILES: Nc1nc2c(ncn2[C@@H]2O[C@@]34CO[C@@H]2[C@@H]3O[P@](=O)(S)OC[C@H]2O[C@@H](n3cnc5c(N)ncnc53)[C@H](O)[C@@H]2O[P@](=O)(S)OC4)c(=O)[nH]1] |

TABLE 3-continued

Abridged compound names and structures.

Example number and abridged Compound names | Structure
---|---

Example 7 Compound 33b
3'3'-RS-(A)(2'O,4'C-LNA-G)
dithio-($R_p$,$S_p$)-cyclic-[A(3',5')p-
2'O,4'C-LNA-G(3',5')p]
2-amino-9-
((2R,3R,3aS,5S,7aR,9R,10R,10aS,12R,
14aR)-9-(6-amino-9H-purin-9-yl)-10-
hydroxy-5,12-dimercapto-5,12-
dioxidohexahydro-2H,7H,14H-3,14a-
(epoxymethano)difuro[3,2-d:3',2'-
j][1,3,7,9]tetraoxa[2,8]
diphosphacyclododecin-2-yl)-
1,9-dihydro-6H-purin-6-one

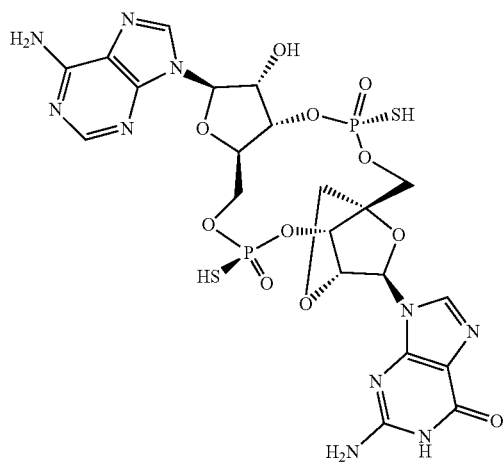 [SMILES: Nc1nc2c(ncn2[C@@H]2O[C@@]34CO[C@@H]2[C@@H]3O[P@@](=O)(S)OC[C@H]2O[C@@H](n3cnc5c(N)ncnc53)[C@H](O)[C@@H]2O[P@](=O)(S)OC4)c(=O)[nH]1]

Example 7 Compound 33c
3'3'-SR-(A)(2'O,4'C-LNA-G)
dithio-($S_p$,$R_p$)-cyclic-[A(3',5')p-
2'O,4'C-LNA-G(3',5')p]
2-amino-9-
((2R,3R,3aS,5R,7aR,9R,10R,10aS,12S,
14aR)-9-(6-amino-9H-purin-9-yl)-10-
hydroxy-5,12-dimercapto-5,12-
dioxidohexahydro-2H,7H,14H-3,14a-
(epoxymethano)difuro[3,2-d:3',2'-
j][1,3,7,9]tetraoxa[2,8]
diphosphacyclododecin-2-yl)-1,9-
dihydro-6H-purin-6-one

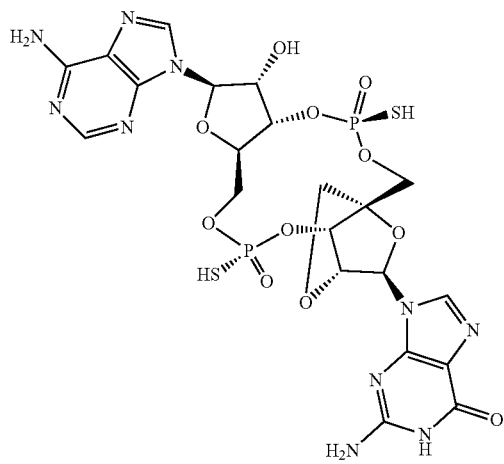 [SMILES: Nc1nc2c(ncn2[C@@H]2O[C@@]34CO[C@@H]2[C@@H]3O[P@](=O)(S)OC[C@H]2O[C@@H](n3cnc5c(N)ncnc53)[C@H](O)[C@@H]2O[P@@](=O)(S)OC4)c(=O)[nH]1]

Example 7 Compound 33d
3'3'-SS-(A)(2'O,4'C-LNA-G)
dithio-($S_p$,$S_p$)-cyclic-[A(3',5')p-
2'O,4'C-LNA-G(3',5')p]
2-amino-9-
((2R,3R,3aS,5S,7aR,9R,10R,10aS,12S,
14aR)-9-(6-amino-9H-purin-9-yl)-10-
hydroxy-5,12-dimercapto-5,12-
dioxidohexahydro-2H,7H,14H-3,14a-
(epoxymethano)difuro[3,2-d:3',2'-
j][1,3,7,9]tetraoxa[2,8]
diphosphacyclododecin-2-yl)-1,9-
dihydro-6H-purin-6-one

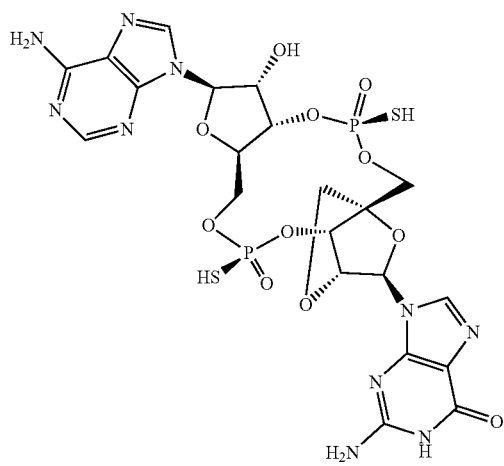 [SMILES: Nc1nc2c(ncn2[C@@H]2O[C@@]34CO[C@@H]2[C@@H]3O[P@@](=O)(S)OC[C@H]2O[C@@H](n3cnc5c(N)ncnc53)[C@H](O)[C@@H]2O[P@@](=O)(S)OC4)c(=O)[nH]1]

TABLE 3-continued

Abridged compound names and structures.

| Example number and abridged Compound names | Structure |
|---|---|
| Example 8 Compound 37a<br>2'3'-RR-(3'βF-A)(2'O,4'LNA-A)<br>dithio-($R_p$,$R_p$)-cyclic-[3'βF-A(2',5')p-<br>2'O,4'C-LNA-A(3',5')p] | 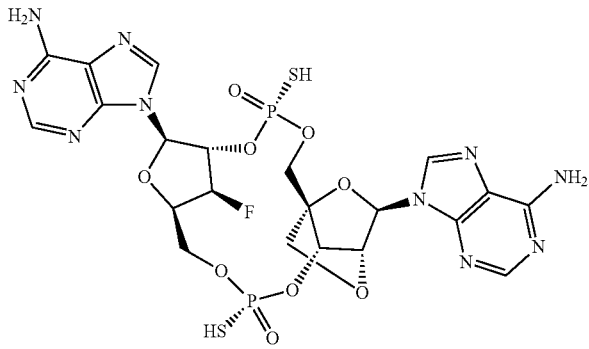 [SMILES: Nc1ncnc2c1ncn2[C@@H]1O[C@@H]2CO[P@@](=O)(S)O[C@H]3[C@H]4OC[C@]3(CO[P@@](=O)(S)O[C@@H]1[C@H]2F)O[C@H]4n1cnc2c(N)ncnc21] |
| Example 8 Compound 37b<br>2'3'-RS-(3'βF-A)(2'O,4'LNA-A)<br>dithio-($R_p$,$S_p$)-cyclic-[3'βF- A(2',5')p-<br>2'O,4'C-LNA-A(3',5')p] | 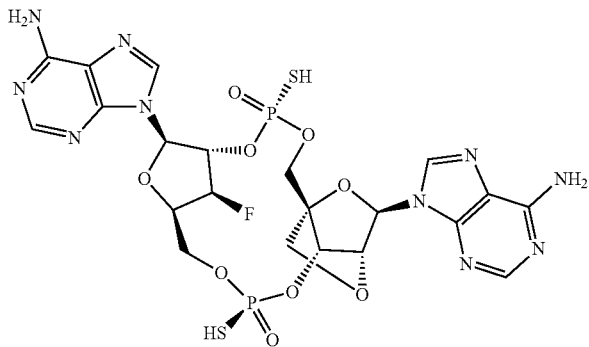 [SMILES: Nc1ncnc2c1ncn2[C@@H]1O[C@@H]2CO[P@](=O)(S)O[C@H]3[C@H]4OC[C@]3(CO[P@@](=O)(S)O[C@@H]1[C@H]2F)O[C@H]4n1cnc2c(N)ncnc21] |
| Example 8 Compound 37c<br>2'3'-SR-(3'βF-A)(2'O,4'LNA-A)<br>dithio-($S_p$,$R_p$)-cyclic-[3'βF-A(2',5')p-<br>2'O,4'C-LNA-A(3',5')p] | 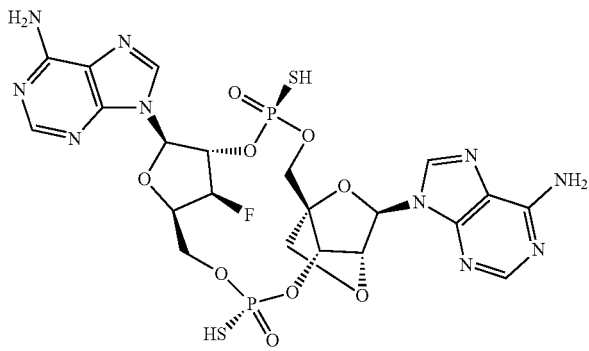 [SMILES: Nc1ncnc2c1ncn2[C@@H]1O[C@@H]2CO[P@@](=O)(S)O[C@H]3[C@H]4OC[C@]3(CO[P@](=O)(S)O[C@@H]1[C@H]2F)O[C@H]4n1cnc2c(N)ncnc21] |
| Example 8 Compound 37d<br>2'3'-SS-(3'βF-A)(2'O,4'LNA-A)<br>dithio-($S_p$,$S_p$)-cyclic-[3'βF-A(2',5')p-<br>2'O,4'C-LNA-A(3',5')p] | 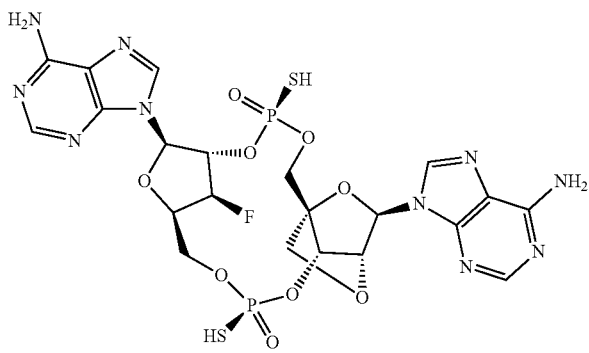 [SMILES: Nc1ncnc2c1ncn2[C@@H]1O[C@@H]2CO[P@](=O)(S)O[C@H]3[C@H]4OC[C@]3(CO[P@](=O)(S)O[C@@H]1[C@H]2F)O[C@H]4n1cnc2c(N)ncnc21] |

TABLE 3-continued

Abridged compound names and structures.

| Example number and abridged Compound names | Structure |
|---|---|
| Example 9 Compound 45a<br>3'3'-RR-(G)(2'O,4'C-LNA-A)<br>dithio-($R_p$,$R_p$)-cyclic-[G(3',5')p-<br>2'O,4'C-LNA-A(3',5')p]<br>2-amino-9-<br>((2R,3R,3aS,5R,7aR,9R,10R,10aS,12R,<br>14aR)-2-(6-amino-9H-purin-9-yl)-10-<br>hydroxy-5,12-dimercapto-5,12-<br>dioxidohexahydro-2H,7H,14H-3,14a-<br>(epoxymethano)difuro[3,2-d:3',2'-<br>j][1,3,7,9]tetraoxa[2,8]<br>diphosphacyclododecin-9-yl)-1,9-<br>dihydro-6H-purin-6-one | 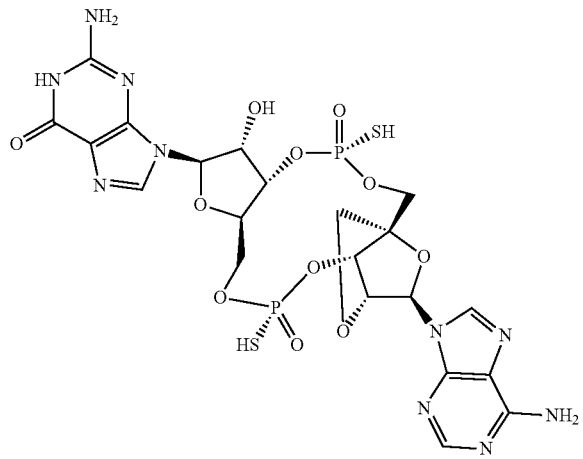 [SMILES: Nc1nc2c(ncn2[C@@H]2O[C@@H]3CO[P@@](=O)(S)O[C@H]4[C@H]5OC[C@]4(CO[P@@](=O)(S)O[C@H]3[C@H]2O)O[C@H]5n2cnc3c(N)ncnc32)c(=O)[nH]1] |
| Example 9 Compound 45b<br>3'3'-RS-(G)(2'O,4'C-LNA-A)<br>dithio-($R_p$,$S_p$)-cyclic-[G(3',5')p-<br>2'O,4'C-LNA-A(3',5')p]<br>2-amino-9-<br>((2R,3R,3aS,5S,7aR,9R,10R,10aS,12R,<br>14aR)-2-(6-amino-9H-purin-9-yl)-10-<br>hydroxy-5,12-dimercapto-5,12-<br>dioxidohexahydro-2H,7H,14H-3,14a-<br>(epoxymethano)difuro[3,2-d:3',2'-<br>j][1,3,7,9]tetraoxa[2,8]<br>diphosphacyclododecin-9-yl)-1,9-<br>dihydro-6H-purin-6-one | 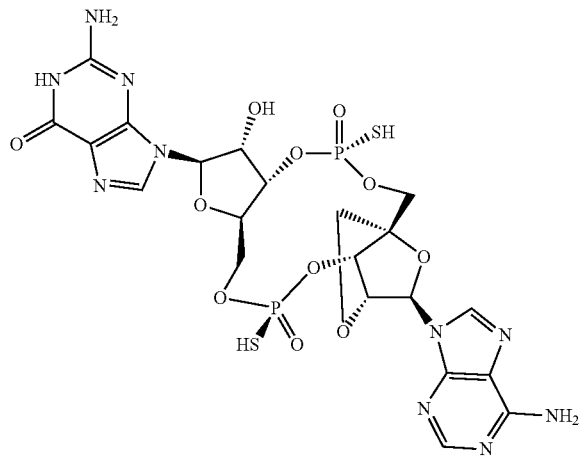 [SMILES: Nc1nc2c(ncn2[C@@H]2O[C@@H]3CO[P@](=O)(S)O[C@H]4[C@H]5OC[C@]4(CO[P@@](=O)(S)O[C@H]3[C@H]2O)O[C@H]5n2cnc3c(N)ncnc32)c(=O)[nH]1] |
| 2'3'-RR-(A)(A);<br>dithio-[$R_p$,$R_p$]-cyclic-<br>[A(2',5')pA(3',5')p] | 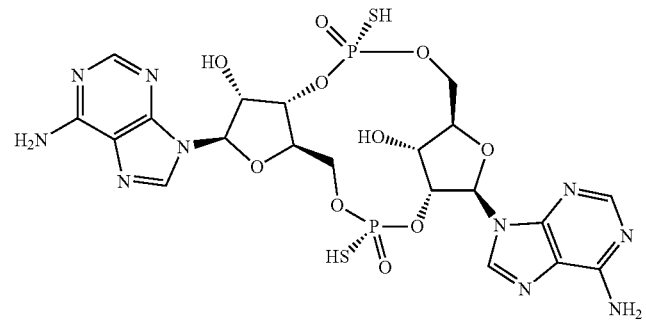 [SMILES: Nc1ncnc2c1ncn2[C@@H]1O[C@@H]2CO[P@@](=O)(S)O[C@@H]3[C@H](O)[C@@H](CO[P@@](=O)(S)O[C@H]2[C@H]1O)O[C@H]3n1cnc2c(N)ncnc21] |

TABLE 3-continued

Abridged compound names and structures.

| Example number and abridged Compound names | Structure |
|---|---|
| 2'3'-RR-(G)(A); dithio-[R$_p$,R$_p$]-cyclic- [G(2',5')pA(3',5')p] | 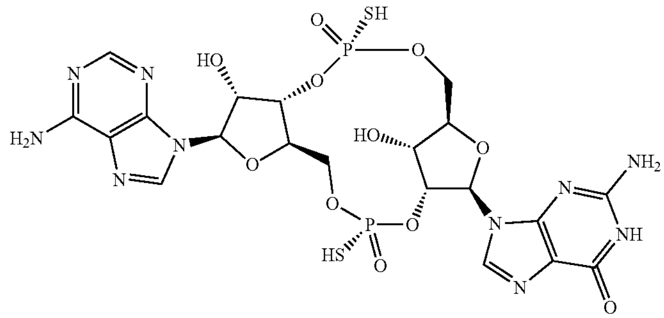 |
| 2'3'-(G)(A); cyclic-[G(2',5')pA(3',5')p] | 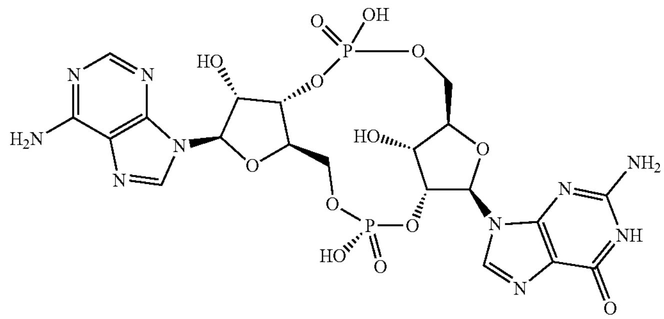 |

Abbreviations and Acronyms. SalPCl=Salicyl chlorophosphite. DCA=dichloroacetic acid. DDTT=((Dimethylamino-methylidene)amino)-3H-1,2,4-dithiazaoline-3-thione. DMP=Dess-Martin Periodinane. DAST=diethylaminosulfur trifluoride. NaHCO$_3$=sodium bicarbonate. DCM=CH$_2$Cl$_2$=dichloromethane. IPA=isopropyl alcohol. EtOH=ethanol. EtOAc=ethyl acetate. AcOH=acetic acid. KOAc=potassium acetate. MeCN=acetonitrile. MeOH=methanol. NH$_4$OAc=ammonium acetate. NH$_4$OH=ammonium hydroxide. DMAP=N,N-dimethylpyridin-4-amine. DMOCP=2-chloro-5,5-dimethyl-1,3,2-dioxaphosphinane-2-oxide. DMTCl=4,4'-dimethoxytrityl chloride. DMT=4,4-dimethoxytrityl. N-phenyltriflamide=1,1,1-trifluoro-N-phenyl-N-((trifluoromethyl)sulfonyl)methanesulfonamide. TBAF=tetrabutylammonium fluoride. TBS=tert-butyldimethylsilyl. TEAA=Triethylammonium acetate. TEA=triethylamine. TEAH$^+$=triethylammonium. TEAB=treithylammonium bicarbonate. TFA=trifluoroacetic acid. TMSCl=trimethylsilyl chloride. HF=hydrofluoric acid. THF=tetrahydrofuran. Me-THF=2-Methyltetrahydrofuran. G=Guanine. G$^{ib}$=isobutyryl guanine. A=adenine. A$^{Bz}$=benzoyl adenine. AMA= ammonium hydroxide/40% methylamine solution in water. Rt= retention time. rt=room temperature. min=minute(s). h= hour(s).

Example 1: Synthesis of Intermediate Compounds

The LCMS or HRMS data in this example, and where indicated in the following examples, were recorded using the indicated methods as follows. In all instances, masses reported are those of the protonated parent ions unless indicated otherwise.

Method A: LCMS data were recorded using a Waters System: Micromass ZQ mass spectrometer; Column: Sunfire C18 3.5 micron, 3.0×30 mm; gradient: 40-98% MeCN in water with 0.05% TFA over a 2.0 min period; flow rate 2 mL/min; column temperature 40° C.).

Method B: LCMS were recorded using a Waters System: Micromass SQ mass spectrometer; Column: Acquity UPLC BEH C18 1.7 micron, 2.1×30 mm; gradient 1% to 30% MeCN to 3.20 min then gradient: 30-98% MeCN in water with 5 mM NH$_4$OH over a 1.55 min period before returning to 1% MeCN at 5.19 min—total run time 5.2 min; flow rate 1 mL/min; column temperature 50° C.

Method C: LCMS were recorded using a Waters System: Micromass SQ mass spectrometer; Column: Acquity UPLC BEH C18 1.7 micron, 2.1×50 mm; gradient: 2-98% MeCN in water+5 mM NH$_4$OH over a 4.40 min period isocratic for 0.65 min before returning to 2% MeCN at 5.19 min—total run time 5.2 min; flow rate 1 mL/min; column temperature 50° C.

Method E: HRMS data were recorded using a Waters System: Acquity G2 Xevo QT of mass spectrometer; Column: Acquity BEH 1.7 micron, 2.1×50 mm; gradient: 40-98% MeCN in water with 0.1% Formic acid over a 3.4 min period, isocratic 98% MeCN for 1.75 mins returning to 40% at 5.2 mins; flow rate 1 mL/min; column temperature 50° C.

Method G: LCMS data were recorded using a Waters System: Micromass SQ mass spectrometer; Column: Acquity UPLC BEH C18 1.7 micron, 2.1×30 mm; gradient 1% to 30% MeCN to 1.20 mins then gradient: 30-98% MeCN in water with 5 mM NH$_4$OAc over a 0.55 min period before returning to 1% MeCN at 2.19 mins—total run time 2.2 mins; flow rate 1 mL/min; column temperature 50° C.

Method H: LCMS data were recorded using a Waters System: Micromass SQ mass spectrometer; Column: Acquity UPLC BEH C18 1.7 micron, 2.1×30 mm; gradient 2% to 98% MeCN to 1.76 mins then isocratic to 2.00 mins and then returning to 2% MeCN using gradient to 2.20 mins in water with 0.1% Formic acid; flow rate 1 mL/min; column temperature 50° C.

Method I: LCMS data were recorded using a Waters System: Micromass SQ mass spectrometer; Column: Acquity UPLC BEH C18 1.7 micron, 2.1×30 mm; gradient 40% to 98% MeCN to 1.40 mins then isocratic to 2.05 mins and then returning to 40% MeCN using gradient to 2.20 mins in water with 0.1% Formic acid; flow rate 1 mL/min; column temperature 50° C.

Intermediate i6 (used in Example 6) was prepared according to the following Scheme 1A:

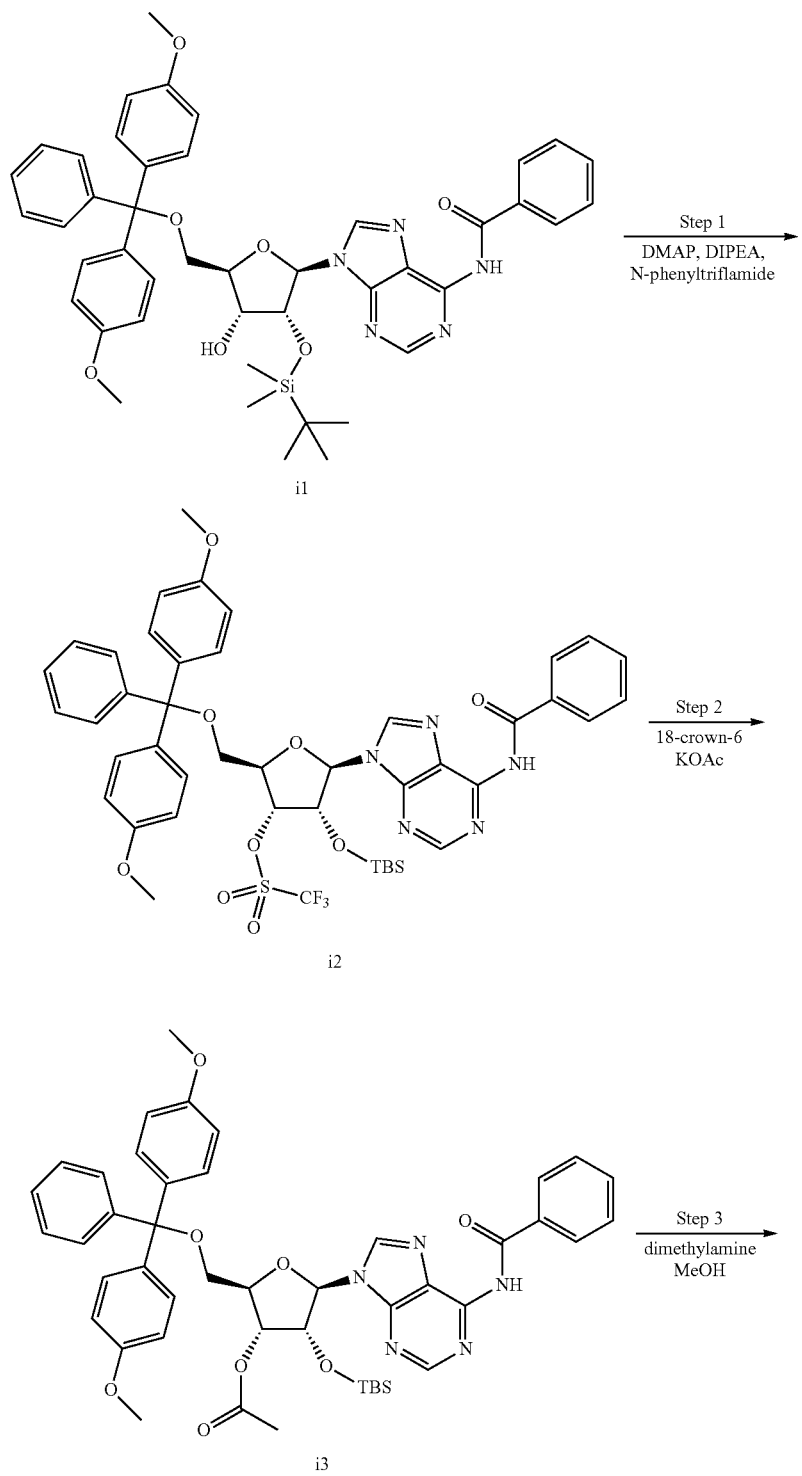

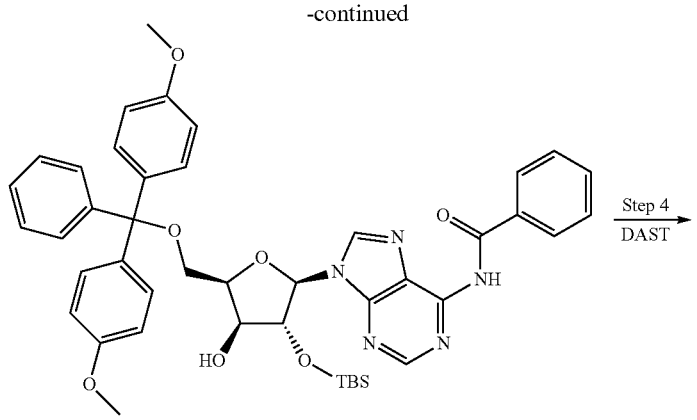

i4

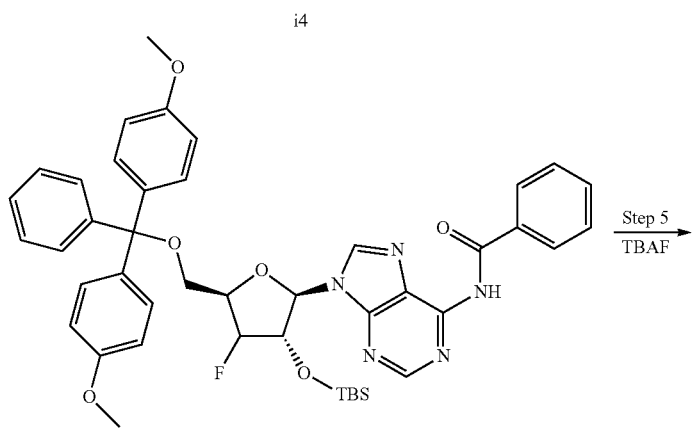

i5a = (2R, 3S, 4S, 5R)
i5b = (2R, 3S, 4R, 5R)

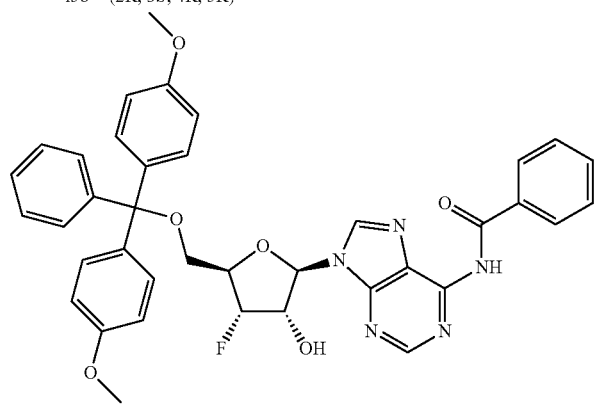

i6

Step 1:

Preparation of (2R,3R,4R,5R)-5-(6-benzamido-9H-purin-9-yl)-2-((bis(4-methoxyphenyl) (phenyl)methoxy)methyl)-4-((tert-butyldimethylsilyl)oxy)tetrahydrofuran-3-yl trifluoromethane-sulfonate (i2): A mixture of N-(9-((2R,3R,4R,5R)-5-((bis(4-methoxyphenyl)(phenyl)methoxy)methyl)-3-((tert-butyldimethylsilyl)oxy)-4-hydroxytetrahydrofuran-2-yl)-9H-purin-6-yl)benzamide (i1, 5.6 g, 7.11 mmol, ChemGenes) and DMAP (0.174 g, 1.42 mmol) was suspended in anhydrous THF (35 mL), addition of DIPEA (6.21 mL, 35.5 mmol) created a solution to which N-phenyltriflamide (5.08 g, 14.21 mmol), was added. The mixture was stirred for 3.5 h at rt, at which point it was poured into 5% brine (100 mL) and extracted with EtOAc (2×100 mL). The combined organic phases were dried ($Na_2SO_4$) the drying agent filtered-off and concentrated on silica gel (10 g) in vacuo. The crude material was purified by chromatography on silica gel (gradient elution 25-100% EtOAc/heptane) to give the desired compound i2 as a tan solid; 5.53 g; $^1$H NMR (400 MHz, $CDCl_3$) δ 9.05 (s, 1H), 8.68 (s, 1H), 8.18 (s, 1H), 8.06 (d, J=7.5 Hz, 2H), 7.66 (t, J=7.4 Hz, 1H), 7.61-7.48 (m, 4H), 7.48-7.25 (m, 7H), 6.88 (d, J=8.8 Hz, 4H), 6.04 (d, J=7.6 Hz, 1H), 5.50 (dd, J=7.5, 4.7 Hz, 1H), 5.32 (d, J=4.5 Hz, 1H), 4.50 (t, J=4.1 Hz, 1H), 3.82 (s, 6H), 3.77 (dt, J=10.8, 5.2 Hz, 1H), 3.41 (dd, J=10.8, 3.7 Hz, 1H), 0.77 (s, 9H), −0.01 (s, 3H), −0.46 (s, 3H); LCMS (Method A) $R_t$=1.65 min; m/z 920.5 [M+H]$^+$.

Step 2:

Preparation of (2R,3S,4R,5R)-5-(6-benzamido-9H-purin-9-yl)-2-((bis(4-methoxyphenyl)(phenyl)methoxy)methyl)-4-((tert-butyldimethylsilyl)oxy)tetrahydrofuran-3-yl acetate (i3): A mixture of compound i2 (5.5 g, 5.98 mmol), KOAc (2.93 g, 29.9 mmol), and 18-crown-6 (1,4,7,10,13,16-hexaoxacyclooctadecane, 0.79 g, 2.99 mmol) in toluene (40 mL) was heated at 110° C. for 4 h. The reaction mixture was then cooled to rt and silica gel (10 g) added and the solvent was removed in vacuo. The crude material was purified by chromatography on silica gel (gradient elution 25-100% EtOAc/heptane) to give the desired compound i3 as a tan solid: 3.3 g; $^1$H NMR (400 MHz, CDCl$_3$) δ 8.70 (s, 1H), 8.58 (s, 1H), 7.93 (s, 1H), 7.84 (d, J=7.5 Hz, 2H), 7.44 (t, J=7.4 Hz, 1H), 7.35 (t, J=7.6 Hz, 2H), 7.28 (d, J=7.2 Hz, 2H), 7.21-7.02 (m, 7H), 6.67 (dd, J=8.9, 2.1 Hz, 4H), 5.98 (s, 1H), 4.97 (dd, J=3.6, 1.4 Hz, 1H), 4.61-4.52 (m, 1H), 4.35 (s, 1H), 3.62 (s, 6H), 3.41 (dd, J=9.8, 6.2 Hz, 1H), 3.18 (dd, J=9.8, 5.6 Hz, 1H), 1.53 (s, 3H), 0.77 (s, 9H), 0.03 (s, 3H), 0.0 (s, 3H). LCMS (Method A) R$_t$ 1.68 min; m/z 830.2 [M+H]$^+$.

Step 3:

Preparation of N-(9-((2R,3R,4S,5R)-5-((bis(4-methoxyphenyl)(phenyl)methoxy)methyl)-3-((tert-butyldimethylsilyl)oxy)-4-hydroxytetrahydrofuran-2-yl)-9H-purin-6-yl) benzamide (i4): Compound i3 (6.78 g, 8.17 mmol) was dissolved in MeOH (120 mL) and a 2.0 M dimethylamine solution in MeOH (20.4 mL, 40.8 mmol) was added. The reaction mixture was stirred for 17 h at rt. Silica gel (12 g) was added and the solvent was removed in vacuo. The crude material was purified by chromatography on silica gel (gradient elution 25-75% EtOAc/heptane) to give the desired compound i4 as a tan solid: 3.9 g; $^1$H NMR (400 MHz, CDCl$_3$) δ 8.94 (s, 1H), 8.65 (s, 1H), 8.16 (s, 1H), 7.97-7.90 (m, 2H), 7.58-7.38 (m, 3H), 7.38-7.32 (m, 2H), 7.32-7.00 (m, 7H), 6.80-6.65 (m, 4H), 5.83 (d, J=1.2 Hz, 1H), 5.38 (d, J=8.0 Hz, 1H), 4.42 (s, 1H), 4.29 (t, J=4.6 Hz, 1H), 4.02-3.95 (m, 1H), 3.75-3.61 (m, 6H), 3.53 (d, J=5.0 Hz, 2H), 0.81 (s, 9H), 0.0 (s, 6H). LCMS (Method A) R$_t$ 1.57 min; m/z 788.2 [M+H]$^+$.

Step 4:

Preparation of N-(9-((2R,3S,4S,5R)-5-((bis(4-methoxyphenyl)(phenyl)methoxy)methyl)-3-((tert-butyldimethylsilyl)oxy)-4-fluorotetrahydrofuran-2-yl)-9H-purin-6-yl)benzamide (i5a) and N-(9-((2R,3S,4R,5R)-5-((bis(4-methoxyphenyl)(phenyl)methoxy)methyl)-3-((tert-butyldimethylsilyl)oxy)-4-fluorotetrahydrofuran-2-yl)-9H-purin-6-yl) benzamide (i5b): Compound i4 (750 mg, 0.952 mmol) was dissolved in anhydrous DCM (7 mL) under an inert nitrogen atmosphere and the solution was cooled to 0° C. A 1.0 M solution of DAST (1.90 mL, 1.90 mmol) was added and the reaction subsequently stirred at −5° C. for 17 h using a cryo-cool to control the reaction temperature. The vessel was warmed to 0° C. and saturated NaHCO$_3$(2 mL) was added. After 30 minutes of stirring the mixture was diluted with 5% brine (20 mL) and extracted with EtOAc (2×20 mL). The combined organics were dried (Na$_2$SO$_4$) with the drying agent filtered off, silica gel (2 g) added to the filtrate and the solvent removed in vacuo. The crude material was purified by chromatography on silica gel (gradient elution 10-75% EtOAc/heptane) to give a mixture of diastereoisomers i5a and i5b as a tan solid: 193 mg; Major (2R,3S,4S, 5R) diastereoisomer LCMS (Method A) R$_t$ 1.53 min; m/z 790.4 (M+H)+; Minor (2R,3S,4R,5R) diastereoisomer R$_t$ 1.58 min; m/z 790.4 [M+H]$^+$.

Step 5:

Preparation of N-(9-((2R,3S,4S,5R)-5-((bis(4-methoxyphenyl)(phenyl)methoxy)methyl)-4-fluoro-3-hydroxytetrahydrofuran-2-yl)-9H-purin-6-yl)benzamide (i6): The diastereomeric mixture of i5a and i5b (2.0 g, 2.53 mmol) was dissolved in anhydrous THF (100 mL) and cooled to −42° C. under an inert nitrogen atmosphere before 1.0 M TBAF (3.80 mL, 3.80 mmol) was added. The reaction was stirred for 2.5 h, then quenched with saturated NaHCO$_3$(20 mL). The cold bath was removed, and the slurry was stirred for 10 minutes before the mixture was diluted with 5% brine (150 mL) and extracted with DCM (2×100 mL). The combined organic phases were dried (Na$_2$SO$_4$), with the drying agent filtered off, silica gel (4 g) added to the filtrate and the solvent removed in vacuo. The crude material was purified by chromatography on silica gel (gradient elution 25-100% EtOAc/heptane) to give the desired compound i6 as a white solid: 355 mg; $^1$H NMR (400 MHz, CDCl$_3$) δ 9.16 (s, 1H), 8.64 (s, 1H), 8.23 (s, 1H), 7.99 (d, J=7.5 Hz, 2H), 7.59 (t, J=7.4 Hz, 1H), 7.48 (t, J=7.6 Hz, 2H), 7.41-7.31 (m, 3H), 7.31-7.11 (m, 7H), 6.79 (d, J=8.9 Hz, 4H), 6.16 (d, J=7.3 Hz, 1H), 5.77 (br s, 1H), 5.27-5.10 (m, 2H), 4.53 (dt, J=28.0 Hz, 3.4 Hz, 1H), 3.77 (s, 6H), 3.51 (dd, J=10.7, 3.7 Hz, 1H), 3.34 (dd, J=10.7, 3.3 Hz, 1H); $^{19}$F NMR (376.4 MHz, CDCl$_3$) δ −197.5; $^{13}$C NMR (101 MHz, CDCl$_3$) δ 164.66, 158.64, 158.62, 152.60, 151.43, 149.34, 144.22, 141.66, 135.29, 135.13, 133.40, 132.93, 129.96, 128.87, 127.99, 127.93, 127.86, 127.07, 122.65, 113.26, 93.85, 92.02, 87.56 (d, J=144 Hz), 83.56 (d, J=23 Hz), 77.30, 74.63 (d, J=16 Hz), 62.82 (d, J=11 Hz), 55.26; LCMS (Method A) R$_t$ 0.89 min; m/z 676.3 [M+H]$^+$.

Alternatively, Intermediate i6 was also prepared according to the following Scheme 1A':

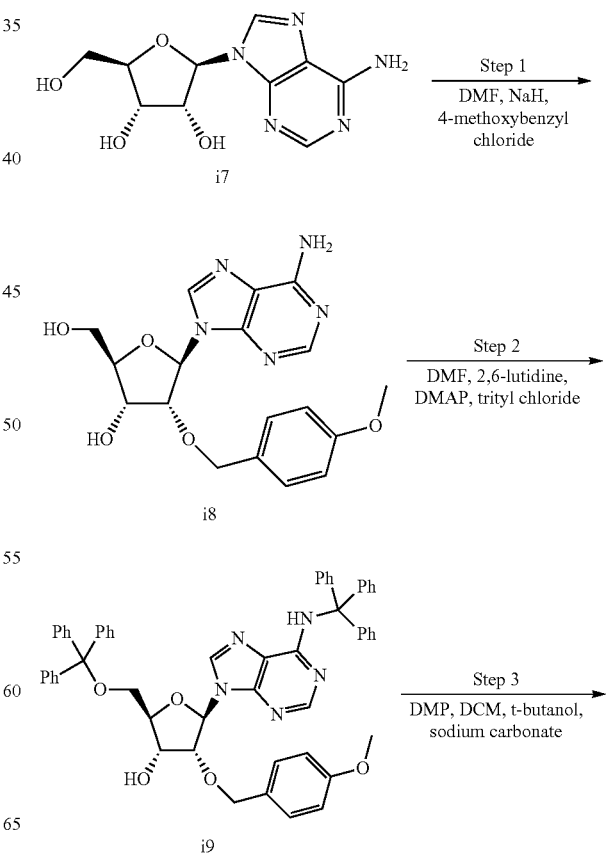

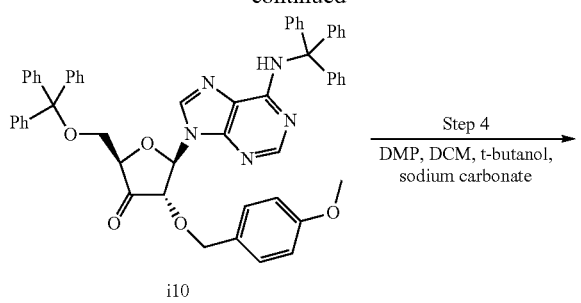

i10

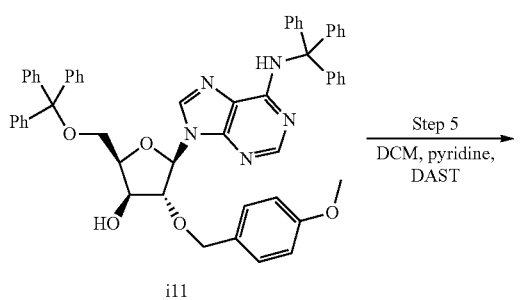

i11

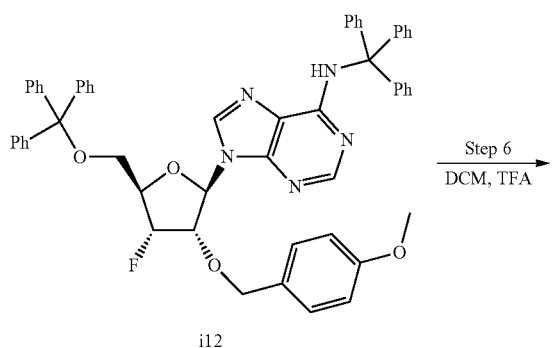

i12

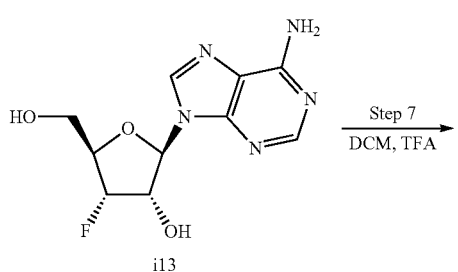

i13

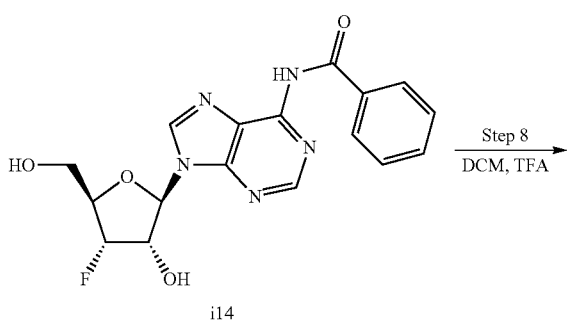

i14

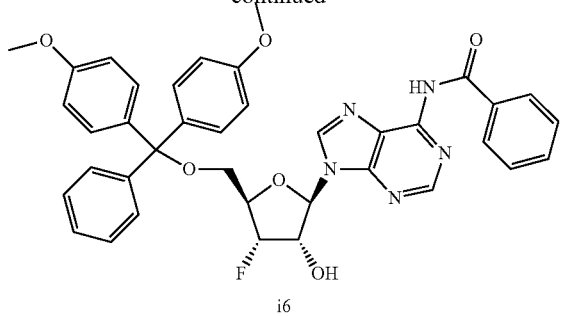

i6

Step 1:

Preparation of (2R,3R,4R,5R)-5-(6-amino-9H-purin-9-yl)-2-(hydroxymethyl)-4-((4-methoxybenzyl) oxy)tetrahydrofuran-3-ol (i8): To a suspension of adenosine (i7, 100 g, 374 mmol) in DMF (2.64 L) at 4° C. under nitrogen was added 60% sodium hydride (19.46 g, 486 mmol) in one portion and the reaction mixture stirred under nitrogen for 60 min. 4-Methoxybenzyl chloride (60.9 ml, 449 mmol) was added dropwise over a 10 min period and the suspension stirred and warmed to rt for 16 h. The reaction was quenched with water (50 mL), a short path condenser then fitted and the pale yellow mixture was heated (115° C.) in vacuo to remove the DMF (60-90° C.). The reaction volume was reduced to ~300 mL and then partitioned between water (2.5 L) and EtOAc (2×500 mL) with the pH of the aqueous phase ~8. The aqueous phase was separated and then extracted with 4:1 DCM-IPA (8×500 mL). The combined DCM-IPA phase was dried (Na$_2$SO$_4$), the drying agent filtered off and the filtrate concentrated in vacuo to yield a semi-solid residue. The crude residue was stirred in EtOH (130 mL) at 55° C. for 1 h, filtered off, the solid washed with EtOH and dried in vacuo to afford a white solid (55.7 g, 38%, regioisomer ratio 86:14). This material was re-subjected to a hot slurry in EtOH (100 mL at 55° C.), hot filtered, the solid washed with cold EtOH to give the desired compound i8 as a white crystalline solid (47.22 g): $^1$H NMR (400 MHz, DMSO-d$_6$) δ 8.30 (s, 1H), 8.08 (s, 1H), 7.33 (br s, 2H), 7.06 (d, J=8.6 Hz, 2H), 6.73 (d, J=8.6 Hz, 2H), 6.03 (d, J=6.3 Hz, 1H), 5.46 (dd, J=7.3, 4.4 Hz, 1H), 5.28 (d, J=5.1 Hz, 1H), 4.57 (d, J=11.6 Hz, 1H), 4.53 (dd, J=6.4, 5.0 Hz, 1H), 4.37 (d, J=11.6 Hz, 1H), 4.33 (dd, J=5.0, 2.9 Hz, 1H), 4.02 (q, J=3.3 Hz, 1H), 3.69 (s, 3H), 3.67 (m, 1H), 3.56 (m, 1H); LCMS (Method B) Rt 1.86 mins; m/z 388.0 (M+H$^+$).

Step 2:

Preparation of (2R,3R,4R,5R)-4-((4-methoxybenzyl) oxy)-5-(6-(tritylamino)-9H-purin-9-yl)-2-((trityloxy) methyl)tetrahydrofuran-3-ol (i9): To compound i8 (45.5 g, 117 mmol) in DMF (310 mL) was added 2,6-lutidine (68.4 mL, 587 mmol), DMAP (3.59 g, 29.4 mmol) and trityl chloride (82 g, 294 mmol). The reaction mixture was slowly heated to 80° C. The reaction mixture was stirred for 15 h at 80° C. and then cooled to rt. The reaction was poured into aq. sat. NH$_4$Cl (1500 mL) and extracted with EtOAc (3×1 L). The combined organic phases were dried (Na$_2$SO$_4$), the drying agent filtered off and the filtrate concentrated in vacuo. The crude product was purified by chromatography on silica gel (gradient elution EtOAc-Heptane 0-100%) to yield the desired compound i9 as an off white solid (85.79 g): $^1$H NMR (400 MHz, CDCl$_3$) δ 8.01 (s, 1H), 7.87 (s, 1H), 7.41 (m, 12H), 7.28 (m, 18H), 7.18 (d, J=8.6 Hz, 2H), 6.95 (s, 1H), 6.80 (d, J=8.6 Hz, 2H), 6.11 (d, J=4.4 Hz, 1H), 4.77-4.67 (m, 2H), 4.62 (d, J=11.6 Hz, 1H), 4.32 (q, J=5.3

Hz, 1H), 4.21 (m, 1H), 3.79 (s, 3H), 3.49 (dd, J=10.5, 3.3 Hz, 1H), 3.36 (dd, J=10.5, 4.5 Hz, 1H), 2.66 (d, J=5.7 Hz, 1H); LCMS (Method G) Rt 1.53 mins; m/z 872.0 (M+H$^+$).

Step 3:

Preparation of (2R,4S,5R)-4-((4-methoxybenzyl)oxy)-5-(6-(tritylamino)-9H-purin-9-yl)-2-((trityloxy) methyl)dihydrofuran-3(2H)-one (i10): To a solution of Dess-Martin Periodinane (DMP, 3.04 g, 7.17 mmol) in DCM (72 mL) at rt was added tert-butanol (0.713 mL, 7.45 mmol) and sodium carbonate (0.134 g, 1.261 mmol), followed by a dropwise addition over 1 h of a solution of compound i9 (5.00 g, 5.73 mmol) in DCM (72 mL). The resulting reaction mixture was stirred at rt for 4 hours before additional DCM (110 mL) was added. After a further 3 h additional DMP (0.63 g) and DCM (50 mL) were added. The reaction stirred for 13 h and then quenched by addition of sat. Na$_2$S$_2$O$_5$ (40 mL), sat. NaHCO$_3$(150 mL) and brine (50 mL). The organic phase was separated and the aqueous phase then re-extracted with DCM (2×150 mL). The combined DCM was dried (Na$_2$SO$_4$), the drying agent filtered off and the filtrate concentrated in vacuo. The crude material was purified by chromatography on silica gel (gradient elution EtOAc/heptane (0-80%) to afford compound i10 as a white foam (4.36 g): $^1$H NMR (400 MHz, CDCl$_3$) δ 7.95 (s, 1H), 7.78 (s, 1H), 7.46-7.15 (m, 30H), 7.05 (d, J=8.6 Hz, 2H), 6.98 (s, 1H), 6.73 (d, J=8.6 Hz, 2H), 6.13 (d, J=7.8 Hz, 1H), 5.23 (dd, J=7.9, 0.8 Hz, 1H), 4.80 (d, J=11.8 Hz, 1H), 4.72 (d, J=11.8 Hz, 1H), 4.35 (ddd, J=4.0, 2.4, 0.8 Hz, 1H), 3.76 (s, 3H), 3.52 (dd, J=10.5, 4.0 Hz, 1H), 3.43 (dd, J=10.5, 2.4 Hz, 1H); LCMS (Method C) Rt 1.53 mins; m/z 870.0 (M+H$^+$).

Step 4:

Preparation of (2R,3S,4R,5R)-4-((4-methoxybenzyl)oxy)-5-(6-(tritylamino)-9H-purin-9-yl)-2-((trityloxy) methyl)tetrahydrofuran-3-ol (i11): To a solution of compound i10 (98 mg, 0.113 mmol) in DCM (3 mL) at –20° C. was added glacial AcOH (0.15 mL) followed by NaBH$_4$ (13 mg, 0.34 mmol). After 1 h the reaction mixture was quenched with 5% brine (20 mL) and extracted with EtOAc (25 mL). The organic phase was separated and dried (Na$_2$SO$_4$), the drying agent filtered off and the filtrate concentrated in vacuo to a white solid. The crude solid (3S:3R ratio 7:1) was slurried in hot MeOH (3 mL, warmed to 50° C.) with DCM (~0.5 mL) added dropwise and the suspension cooled. The mother liquor was decanted off and the solid was dried in vacuo (63 mg, 3S:3R ratio 13:1). Recrystallization from MeOH:DCM (4 mL, v/v 5:1) gave compound i11 as a single diastereomer (ratio 50:1): $^1$H NMR (400 MHz, CDCl$_3$) δ 7.90 (s, 1H), 7.74 (s, 1H), 7.48-7.13 (m, 32H), 6.95-6.84 (m, 2H), 5.80 (s, 1H), 4.68 (d, J 11.3 Hz, 1H), 4.49 (d, J 11.3 Hz, 1H), 4.36 (s, 1H), 4.33-4.27 (m, 1H), 4.23 (d, J 3 Hz, 1H), 3.83 (s, 3H), 3.59-3.52 (m, 2H); LCMS (Method H) Rt 1.76 mins; m/z 872.2 (M+H$^+$).

Step 5:

Preparation of 9-((2R,3S,4R,5R)-4-fluoro-3-((4-methoxybenzyl)oxy)-5-((trityloxy)methyl)tetrahydro-furan-2-yl)-N-trityl-9H-purin-6-amine (i12): To a solution of compound i11 (240 mg, 0.275 mmol) in anhydrous DCM (15 mL) at 0° C. was added anhydrous pyridine (0.223 mL, 2.75 mmol). After 5 min, diethylaminosulfur trifluoride (DAST, 0.182 mL, 1.38 mmol) was added dropwise. After 5 min, the cooling bath was removed and the reaction stirred for 4.5 h. The reaction mixture was diluted with chloroform (20 mL), dry silica gel was added, and the mixture concentrated in vacuo before adding toluene (20 mL) and concentrating to dryness in vacuo. The crude material was purified by chromatography on silica gel (gradient elution 10-50% EtOAc/heptane) to give the desired compound i12 as a white solid (121 mg): $^1$H NMR (400 MHz, CDCl$_3$) δ 7.93 (s, 1H), 7.82 (s, 1H), 7.42-7.20 (m, 30H), 7.13-7.05 (m, 3H), 6.74 (d, J 8.3 Hz, 2H), 6.09-6.05 (m, 1H), 5.15-5.06 (m, 1H), 5.00 (dd, J 54.4, and 4.4 Hz, 1H), 4.60-4.50 (m, 2H), 4.49-4.39 (m, 1H), 3.77 (s, 3H), 3.51-3.38 (m, 1H), 3.32 (dd, J=10.6, 4.0 Hz, 1H); $^{19}$F NMR (376.4 MHz, CDCl$_3$) δ –198.09; LCMS (Method I) Rt 1.27 mins; m/z 874.5 (M+H)$^+$.

Step 6:

Preparation of (2R,3S,4S,5R)-2-(6-amino-9H-purin-9-yl)-4-fluoro-5-(hydroxymethyl)tetrahydrofuran-3-ol (i13): To a solution of compound i12 (70 mg, 0.080 mmol) in DCM (1 mL) was added TFA (0.5 mL, 6.49 mmol). After 45 min the reaction mixture was diluted with MeOH (10 mL) and concentrated in vacuo. The crude material was dissolved in MeOH (10 mL) and TEA (0.1 mL) was added before silica gel was added and the suspension concentrated in vacuo. The crude material was purified by chromatography on silica gel (gradient elution 0-10% MeOH/DCM) to give the desired compound i13 as a white solid (21 mg) containing TEA. TFA salt and used as is: $^1$H NMR (400 MHz, Methanol-d$_4$) δ 8.33 (s, 1H), 8.21 (s, 1H), 6.02 (d, J 7.9 Hz, 1H), 5.12 (dd, J 54.5, 4.3 Hz, 1H), 4.96 (ddd, J 25.1, 8.0, 4.3 Hz, 1H), 4.44 (dt, J 27.6, 2.5 Hz, 1H), 3.94-3.69 (m, 2H); $^{19}$F NMR (376.4 MHz, Methanol-d$_4$) δ –200.02; LCMS (Method G) Rt 0.51 mins; m/z 270.1 (M+H)$^+$.

Step 7:

Preparation of N-(9-((2R,3S,4S,5R)-4-fluoro-3-hydroxy-5-(hydroxymethyl)tetrahydrofuran-2-yl)-9H-purin-6-yl) benzamide (i14): To compound i13 (3.88 g, 14.41 mmol) in pyridine (65 mL) at 0° C. was added benzoyl chloride (8.36 mL, 72.1 mmol) slowly followed by TMSCl (9.21 mL, 72.1 mmol). The reaction mixture was stirred while warming to rt for 4 h. After another 1 h the solution was quenched with water (35 mL), followed by conc. NH$_4$OH (17 mL) after 5 min resulting in a pale tan solid. The mixture was diluted with water (100 mL) and extracted with MeTHF (3×75 mL). The combined organic phases were dried (Na$_2$SO$_4$), the drying agent filtered off and the filtrate concentrated in vacuo to a tan semi-solid crude material, which was purified by chromatography on silica gel (gradient elution 0-20% MeOH/DCM) to give the desired compound i14 (2.75 g): $^1$H NMR (400 MHz, CDCl$_3$) δ 8.78 (s, 1H), 8.09 (s, 1H), 8.08-8.01 (m, 2H), 7.66 (t, J=7.4 Hz, 1H), 7.57 (t, J=7.5 Hz, 2H), 6.13 (br s, 1H), 5.92 (d, J=7.9 Hz, 1H), 5.41-5.11 (m, 2H), 4.60 (d, J=28.4 Hz, 1H), 4.13-3.98 (m, 2H), 3.86 (d, J=13.0 Hz, 1H). $^{19}$F NMR (376.4 MHz, CDCl$_3$) δ –199.36; LCMS (Method G) Rt 0.72 mins; m/z 374.2 (M+H)$^+$.

Step 8:

Preparation of N-(9-((2R,3S,4S,5R)-5-((bis(4-methoxyphenyl)(phenyl)methoxy)methyl)-4-fluoro-3-hydroxytetrahydrofuran-2-yl)-9H-purin-6-yl)benzamide (i6): To compound i14 (2.73 g, 10.14 mmol) in pyridine (55 mL) was added DMTCl (4.12 g, 12.17 mmol) in one portion. The reaction was stirred at rt for 72 h before the yellowish solution was quenched by addition of MeOH (20 mL) and then concentrated in vacuo to a semi-solid following addition of toluene (2×50 mL) to azeotrope residual pyridine. The resulting material was dissolved in DCM (100 mL), washed with sat. NaHCO$_3$(100 mL), brine then dried (Na$_2$SO$_4$). The drying agent was filtered off and the filtrate evaporated in vacuo. The resulting residue was purified by chromatography on silica gel (gradient elution 0-10% MeOH/DCM with 0.04% TEA) to give compound i6 as a white solid (3.70 g): $^1$H NMR (400 MHz, CDCl$_3$) δ 9.16 (s, 1H), 8.64 (s, 1H), 8.23 (s, 1H), 7.99 (d, J 7.5 Hz, 2H), 7.59 (t, J 7.4 Hz, 1H), 7.48 (t, J 7.6 Hz, 2H), 7.41-7.31 (m, 3H), 7.31-7.11 (m, 7H), 6.79 (d, J 8.9 Hz, 4H), 6.16 (d, J 7.3 Hz, 1H), 5.77 (br s, 1H), 5.27-5.10 (m, 2H), 4.53 (dt, J 28.0 Hz, 3.4 Hz, 1H), 3.77 (s, 6H), 3.51 (dd, J 10.7, 3.7 Hz, 1H), 3.34 (dd, J 10.7, 3.3 Hz, 1H); $^{19}$F NMR (376.4 MHz, CDCl$_3$) δ −197.5; $^{13}$C NMR (101 MHz, CDCl$_3$) δ 164.66, 158.64, 158.62, 152.60, 151.43, 149.34, 144.22, 141.66, 135.29, 135.13, 133.40, 132.93, 129.96, 128.87, 127.99, 127.93, 127.86, 127.07, 122.65, 113.26, 93.85, 92.02, 87.56 (d, J 144 Hz), 83.56 (d, J 23 Hz), 77.30, 74.63 (d, J 16 Hz), 62.82 (d, J 11 Hz), 55.26; LCMS (Method C) Rt 2.72 mins; m/z 676.3 (M+H)$^+$.

Intermediate i17 N-(9-((2R,3S,4S,5R)-5-((bis(4-methoxyphenyl)(phenyl)methoxy)methyl)-4-fluoro-3-hydroxytetrahydrofuran-2-yl)-6-oxo-6,9-dihydro-1H-purin-2-yl)isobutyramide (used in Example 4) was prepared according to the following Scheme 1B:

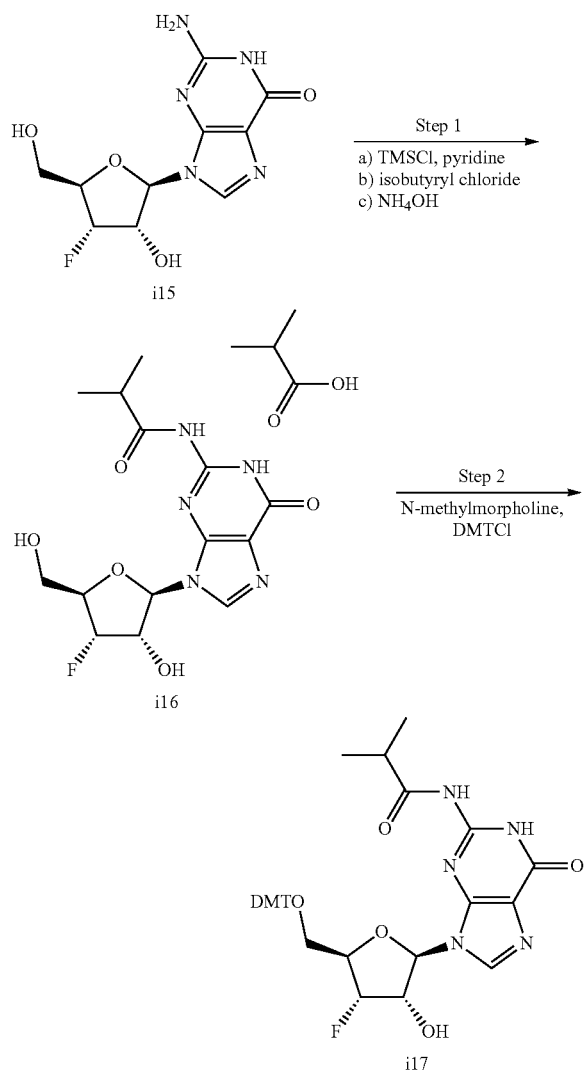

Step 1:
Preparation of N-(9-((2R,3S,4S,5R)-4-fluoro-3-hydroxy-5-(hydroxymethyl)tetrahydrofuran-2-yl)-6-oxo-6,9-dihydro-1H-purin-2-yl)isobutyramide isobutyric acid salt (i16): To a solution of 2-amino-9-((2R,3S,4S,5R)-4-fluoro-3-hydroxy-5-(hydroxymethyl)tetrahydrofuran-2-yl)-1,9-dihydro-6H-purin-6-one (i15, 1.69 g, 5.91 mmol, Carbosynth, San Diego, Calif.) in pyridine (27.0, 334 mmol) at rt was added chlorotrimethylsilane (5.67 mL, 44.4 mmol) dropwise over 5 min. The reaction was stirred at rt for 2 h after which time the solution was cooled to 0° C. and isobutyryl chloride (1.86 mL, 17.74 mmol) was added dropwise over 10 min. The mixture was allowed to stir at 0° C. for 5 min and then warmed to rt for 3.5 h. The reaction was then cooled to 0° C. and quenched by addition of water (9.0 mL), stirred for 10 min at 0° C. and then warmed to rt. After stirring for 5 min, concentrated ammonia (28% aq. NH$_4$OH solution, 18 mL) was added and the mixture was stirred for 35 min, the mixture was then diluted with water (80 mL) and washed with DCM (40 mL). The aqueous layer was separated and concentrated in vacuo with the resulting crude material then purified by chromatography on silica gel (gradient elution 0-50% MeOH/DCM) to afford the compound i16 (1.32 g): $^1$H NMR (400 MHz, CD$_3$OD) δ 8.27 (s, 1H), 6.01 (d, J 7.6 Hz, 1H), 5.02-5.20 (m, 1H), 4.76-4.84 (m, 1H), 4.29-4.41 (m, 1H), 3.79 (d, J=3.3 Hz, 2H), 2.72 (hept, J 6.8 Hz, 1H), 2.47 (hept, J 6.8 Hz, 1H), 1.23 (d, J 6.8 Hz, 6H), 1.12 (d, J 6.8 Hz, 6H); $^{19}$F NMR (376 MHz, CD$_3$OD) δ −200.84; LCMS (Method B) Rt 0.66 min; m/z 356.2 (M+H$^+$).

Step 2:
Preparation of N-(9-((2R,3S,4S,5R)-5-((bis(4-methoxyphenyl)(phenyl)methoxy)methyl)-4-fluoro-3-hydroxytetrahydrofuran-2-yl)-6-oxo-6,9-dihydro-1H-purin-2-yl)isobutyramide (i17): To a suspension of compound i16 (2.18 g, 6.14 mmol) in 1:1 THF:CHCl$_3$ (400 mL) at rt was added N-methylmorpholine (2.70 mL, 24.54 mmol) followed by 4,4'-dimethoxytrityl chloride (8.32 g, 24.54 mmol) in a single portion. The mixture was stirred at rt for 35 min after which time the reaction was quenched by addition of sat. aq. NaHCO$_3$ solution (250 mL). The organic layer was separated layers and the aqueous layer further extracted with DCM (2×150 mL). The combined organic layers were dried (MgSO$_4$) the drying agent then filtered off and the filtrate concentrated in vacuo to give an oil. The resulting crude material was purified by chromatography on silica gel (gradient 0-60% EtOAc to remove N-methylmorpholine, followed by 0-60% MeOH/DCM) to afford to the compound i17 (3.57 g): $^1$H NMR (400 MHz, CD$_3$OD) δ 8.04 (s, 1H), 7.36-7.42 (m, 2H), 7.17-7.31 (m, 7H), 6.78-6.85 (m, 4H), 6.00 (d, J 7.1 Hz, 1H), 5.00-5.25 (m, 2H), 4.41 (m, 1H), 3.76 (s, 6H), 3.46 (dd, J 10.6, 4.3 Hz, 1H), 3.37 (dd, J 10.6, 3.0 Hz, 1H), 2.57 (hept, J 6.8 Hz, 1H), 1.19 (d, J 6.8 Hz, 3H), 1.16 (d, J 6.8 Hz, 3H); $^{19}$F NMR (376 MHz, CD$_3$OD) δ −200.35; LCMS (Method C) Rt 2.16 min; m/z 658.3 (M+H$^+$).

Intermediate i25 (used in Example 8) was prepared according to the following Scheme 1C:

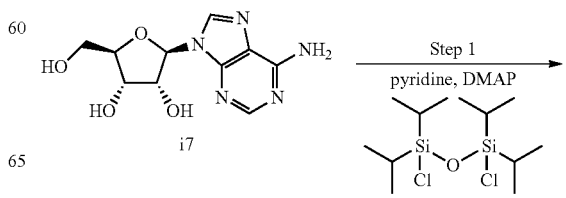

-continued

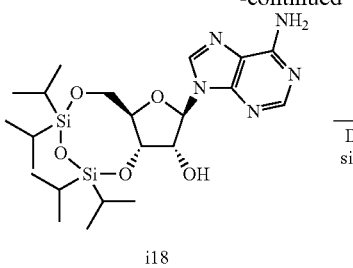

i18

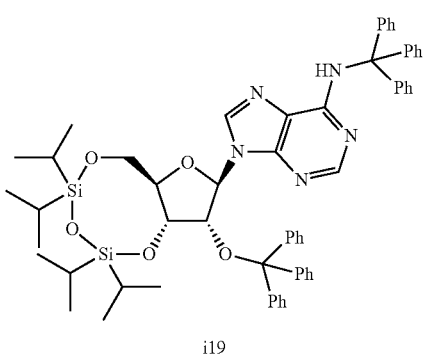

i19

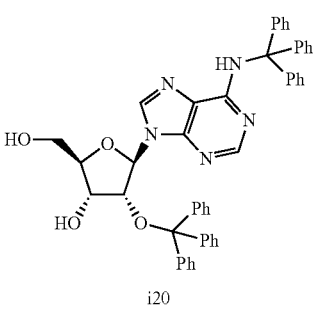

i20

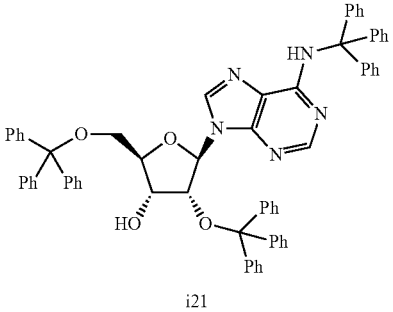

i21

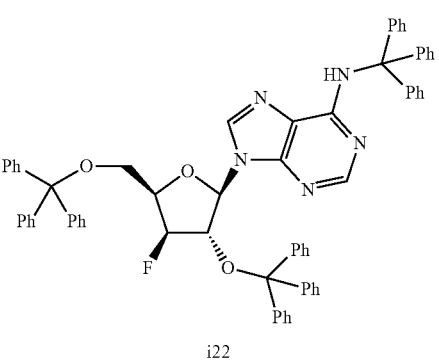

i22

Step 2
DMF, 2,6-di-tBu-pyridine,
silver triflate, trityl chloride

Step 3
THF, TBAF

Step 4
DMF, 2,6-di-tBu-pyridine,
silver triflate, trityl chloride

Step 5
CHCl₃, pyridine, DAST

Step 6
DCM, TFA

-continued

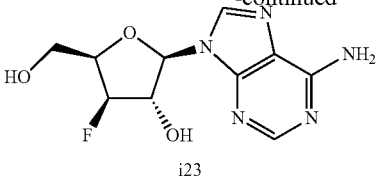

i23

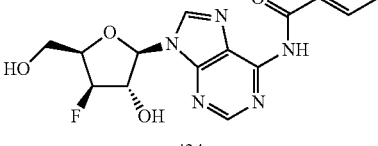

i24

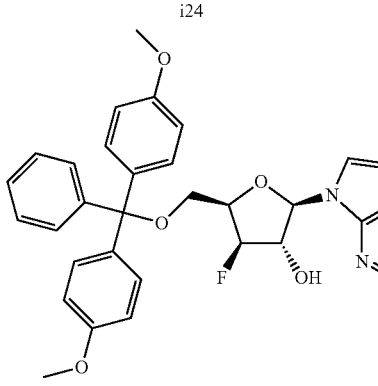

i25

Step 7
pyridine, TMSCl,
benzoyl chloride,

Step 8
pyridine, DMTCl

Step 1

Preparation of (6aR,8R,9R,9aS)-8-(6-amino-9H-purin-9-yl)-2,2,4,4-tetraisopropyltetrahydro-6H-furo[3,2-f][1,3,5,2,4]trioxadisilocin-9-ol (i18): To a suspension of adenosine (i7, 5.80 g, 21.70 mmol) in pyridine (40 mL) at 0° C. was added DMAP (1.33 g, 10.85 mmol) followed by 1,3-dichloro-1,1,3,3-tetraisopropyldisiloxane (7.64 mL, 23.87 mmol). The resulting mixture was warmed to rt and allowed to stir 5 h after which time the mixture was concentrated in vacuo to give a yellow oil. A mixture of MeCN and diethyl ether were added to the oil resulting in the formation of a white precipitate. The resulting precipitate was filtered off and collected to give compound i18 as a white solid (8.61 g): $^1$H (400 MHz, CD$_3$OD) δ 8.28 (s, 1H), 8.16 (s, 1H), 5.97 (d, J 0.8 Hz, 1H), 4.83 (dd, J 8.4, 4.9 Hz, 1H), 4.57 (d, J=4.8 Hz, 1H), 4.22-4.13 (m, 2H), 4.06 (dd, J 12.8, 2.5 Hz, 1H), 1.15-1.05 (m, 28H); LCMS (Method C) Rt 3.20 mins; m/z 510.1 (M+H$^+$).

Step 2:

Preparation of 9-(((6aR,8R,9R,9aR)-2,2,4,4-tetraisopropyl-9-(trityloxy)tetrahydro-6H-furo[3,2-f][1,3,5,2,4]trioxadisilocin-8-yl)-N-trityl-9H-purin-6-amine (i19): To a suspension of compound i18 (15.52 g, 30.4 mmol) in DCM (200 mL) at rt was added 2,6-di-tert-butylpyridine (23.94 mL, 107 mmol) followed by silver triflate (22.69, 88 mmol), the resulting mixture was sonicated to dissolve most of the silver triflate and then cooled to 0° C. Triphenylmethyl chloride (25.4 g, 88 mmol) was then added portion wise and the solution turned dark yellow in color and a precipitate was observed, after 5 min the reaction was allowed to warm to rt. The reaction was allowed to stir for 18 h after which time the mixture was filtered through Celite™ and washed with DCM. The filtrate was washed with sat. aq. NaHCO₃ solution, brine, and the combined organic phases were dried (MgSO$_4$), the drying agent filtered off and the filtrate concentrated in vacuo. The resulting crude material was triturated from MeCN and filtered to afford compound i19 as a white solid (24.68 g): $^1$H NMR (400 MHz, CDCl$_3$) δ 7.79 (s, 1H), 7.58 (d, J 6.0 Hz, 6H), 7.40-7.15 (m, 24H), 6.79 (s, 1H), 6.72 (s, 1H), 5.59 (dd, J 9.5, 5.2 Hz, 1H), 5.19 (d, J=5.2 Hz, 1H), 4.70 (s, 1H), 4.30 (d, J 9.5 Hz, 1H), 4.06 (s, 2H), 1.30-1.03 (m, 21H), 0.94 (s, 3H), 0.80 (d, J=7.0 Hz, 3H); LCMS (Method C) Rt 4.83 mins; m/z 995.3 (M+H$^+$).

Step 3:

Preparation of (2R,3R,4R,5R)-2-(hydroxymethyl)-5-(6-(tritylamino)-9H-purin-9-yl)-4-(trityloxy)tetra-hydrofuran-3-ol (i20): To a solution of compound i19 (24.7 g, 24.84 mmol) in THF (100 mL) at rt was added TBAF (1.0 M solution in THF, 49.7 mL, 49.7 mmol) dropwise. The resulting mixture was stirred at rt for 4 h after which time the reaction was concentrated in vacuo to give an oil. The crude material was then triturated from MeOH and filtered to afford compound i20 as a white solid (18.47 g): $^1$H NMR (400 MHz, DMSO-d$_6$) δ 8.30 (s, 1H), 7.69 (s, 1H), 7.56 (s, 1H), 7.44-7.36 (m, 6H), 7.32 (t, J 7.6 Hz, 6H), 7.27-7.16 (m, 9H), 7.12-6.96 (m, 9H), 6.05 (d, J 7.3 Hz, 1H), 5.47 (s, 1H), 5.01 (s, 1H), 4.79 (d, J 11.9 Hz, 1H), 4.02-3.78 (m, 1H), 3.43 (d, J 14.7 Hz, 1H), 3.28 (s, 1H), 3.15 (d, J 4.7 Hz, 1H); HRMS (Method E) calculated for C$_{48}$H$_{42}$N$_5$O$_4$ requires m/z 752.3237 found 752.3240 (M+H$^+$).

Step 4:

Preparation of (2R,3R,4R,5R)-5-(6-(tritylamino)-9H-purin-9-yl)-4-(trityloxy)-2-((trityloxy)methyl) tetrahydrofuran-3-ol (i21): To a solution of compound i20 (18.05 g, 24.01 mmol) in DCM (200 mL) at rt was added 2,6-di-tert-butylpyridine (6.47 mL, 28.8 mmol) followed by silver triflate (7.40 g, 28.8 mmol) and the resulting mixture was sonicated to dissolve most of the silver triflate and then the mixture cooled to 0° C. Triphenylmethyl chloride (8.03 g, 28.8 mmol) was added portion wise and the solution turned a dark brown color and a precipitate was observed; after 5 min the reaction was allowed to warm to rt. The reaction was allowed to stir for 4 h after which time the mixture was filtered through Celite™ and washed with DCM. The filtrate was washed with sat. aq. NaHCO$_3$ solution, brine, dried (Na$_2$SO$_4$), the drying agent then filtered off and the filtrate concentrated in vacuo to give a white solid. The resulting crude material was purified by chromatography on silica gel (isocratic elution 10% EtOAc/DCM) to afford compound i21 as a white solid (16 g): $^1$H NMR (400 MHz, CDCl$_3$) δ 7.95 (s, 1H), 7.91 (s, 1H), 7.48-7.38 (m, 6H), 7.38-7.14 (m, 35H), 7.09 (t, J 7.7 Hz, 6H), 7.03 (s, 1H), 6.35 (d, J 7.4 Hz, 1H), 5.17 (s, 1H), 4.07 (s, 1H), 3.28 (d, J 14.0 Hz, 1H), 3.02 (d, J 13.8 Hz, 1H), 2.86 (d, J 4.5 Hz, 1H); LCMS (Method C) Rt 4.20 mins; m/z 995.2 (M+H$^+$).

Step 5:

Preparation of 9-((2R,3S,4S,5R)-4-fluoro-3-(trityloxy)-5-((trityloxy)methyl)tetrahydrofuran-2-yl)-N-trityl-9H-purin-6-amine (i22): To a solution of compound i21 (11.51 g, 11.58 mmol) in CHCl$_3$ (75 mL) at 0° C. was added pyridine (14.05 mL, 174 mmol) followed by dropwise addition of DAST (8.05 mL, 57.9 mmol). After 5 min the mixture was allowed to warm to rt and stirred at that temperature for 15 h after which time the reaction was quenched by addition of sat. aq. NaHCO$_3$ solution and diluted with DCM. The phases were separated and the organic phase was further washed with sat. aq. NaHCO$_3$ followed by brine. The combined organic layers were dried (Na$_2$SO$_4$) the drying agent then filtered off and the filtrate concentrated in vacuo to give a yellow oil. The resulting crude material was purified by chromatography on silica gel (gradient elution 0-10% EtOAc/CH$_2$Cl$_2$) to afford compound i22 (5.02 g): $^1$H NMR (400 MHz, DMSO-d$_6$) δ 7.92 (d, J 15.4 Hz, 2H), 7.47-7.00 (m, 47H), 6.16 (s, 1H), 4.69 (d, J 20.4 Hz, 1H), 4.32 (dt, J 30.3, 7.3 Hz, 1H), 4.15 (d, J 50.7 Hz, 1H), 3.28-3.18 (m, 1H), 3.17-3.08 (m, 1H); $^{19}$F NMR (376 MHz, DMSO-d$_6$) δ −197.98; LCMS (Method E) Rt 3.21 mins; m/z 996.4 (M+H$^+$).

Step 6:

Preparation of (2R,3S,4R,5R)-2-(6-amino-9H-purin-9-yl)-4-fluoro-5-(hydroxymethyl)tetrahydrofuran-3-ol (i23): To a solution of compound i22 (10.3 g, 10.34 mmol) in DCM (20 mL) at 0° C. was added trifluoroacetic acid (11.95 mL, 155 mmol) dropwise. After 10 min the reaction was allowed to warm to rt and allowed to stir for 16 h after which time water was added (15 mL) and the aqueous layer was washed with DCM (3×50 mL). The aqueous layer was separated and then lyophilized to give a clear oil which was purified by chromatography on silica gel (gradient elution 0-10% MeOH/DCM) to afford compound i23 (2.57 g): $^1$H NMR (400 MHz, DMSO-d$_6$) δ 8.19 (s, 1H), 8.12 (s, 1H), 7.46 (s, 2H), 6.29 (s, 1H), 5.95 (s, 1H), 5.09 (d, J 52.0 Hz, 1H), 5.05 (br s, 1H), 4.75 (d, J 15.7 Hz, 1H), 4.41-4.23 (m, 1H), 3.87-3.61 (m, 2H); $^{19}$F NMR (376 MHz, DMSO-d$_6$) δ −200.82; LCMS (Method C) Rt 0.49 mins; m/z 270.1 (M+H$^+$).

Step 7:

Preparation of N-(9-((2R,3S,4R,5R)-4-fluoro-3-hydroxy-5-(hydroxymethyl)tetrahydrofuran-2-yl)-9H-purin-6-yl)benzamide (i24): To a solution of compound i23 (2.62, 6.84 mmol) in pyridine (25 mL) at 0° C. was added chlorotrimethylsilane (4.37 mL, 34.2 mmol) dropwise. After 5 min the reaction was allowed to warm to rt and stirred for 10 min. Benzoyl chloride (3.97 mL, 34.2 mmol) was then added and the reaction was allowed to stir at rt for 4 h, upon completion the mixture was cooled to 0° C. and quenched by addition of water (3.0 mL). Concentrated ammonia (28% aq. NH$_4$OH solution, 6.0 mL) was then added and the mixture was allowed to warm to rt and stirred for 30 min after which time the mixture was concentrated in vacuo. The resulting material was diluted further with water and extracted with EtOAc with the organic layer then being dried (Na$_2$SO$_4$) and the drying agent filtered off; the filtrate was concentrated in vacuo to give an oil. The resulting crude material was purified by chromatography on silica gel (gradient elution 0-10% MeOH/DCM) to afford compound i24 (2.68 g): $^1$H NMR (400 MHz, DMSO-d$_6$) δ 11.22 (s, 1H), 8.78 (s, 1H), 8.43 (s, 1H), 8.02-8.08 (m, 2H), 7.61-7.69 (m, 1H), 7.52-7.59 (m, 2H), 6.38 (d, J 4.6 Hz, 1H), 6.11 (d, J 2.3 Hz, 1H), 5.03-5.23 (m, 2H), 4.81-4.88 (m, 1H), 4.30-4.46 (m, 1H), 3.69-3.87 (m, 2H); $^{19}$F NMR (376 MHz, DMSO-d$_6$) δ −200.62; LCMS (Method G) Rt 1.49 mins; m/z 374.1 (M+H$^+$).

Step 8:

Preparation of N-(9-((2R,3S,4R,5R)-5-((bis(4-methoxyphenyl)(phenyl)methoxy)methyl)-4-fluoro-3-hydroxytetrahydrofuran-2-yl)-9H-purin-6-yl)benzamide (i25): To a solution compound i24 (812 mg, 2.18 mmol) in pyridine (3.0 mL) at rt was added DMTCl (1.35 g, 3.91 mmol). The mixture was stirred for 20 h after which time the reaction was quenched by addition of MeOH and concentrated in vacuo to give an oil. The resulting crude material was purified by chromatography on silica gel (gradient elution 0-10% MeOH/DCM) to afford compound i25 as a white solid (1.07 g): $^1$H NMR (400 MHz, DMSO-d$_6$) δ 11.23 (s, 1H), 8.78 (s, 1H), 8.24 (s, 1H), 8.00-8.08 (m, 2H), 7.61-7.69 (m, 1H), 7.52-7.59 (m, 2H), 7.39-7.44 (m, 2H), 7.13-7.33 (m, 8H), 6.86 (dd, J 8.8, 8.1 Hz, 4H), 6.43 (d, J 4.8 Hz, 1H), 6.14 (d, J=2.3 Hz, 1H), 5.11-5.30 (m, 1H), 4.84-4.94 (m, 1H), 4.52-4.67 (m, 1H), 3.73 (d, J=2.3 Hz, 6H); $^{19}$F NMR (376 MHz, DMSO-d$_6$) δ −199.41; LCMS (Method C) Rt 1.86 mins; m/z 676.2 (M+H$^+$).

Example 2: Synthesis of 3'3'-RR-(2'O,4'C-LNA-A)(2'O,4'C-LNA-A) (5a) and 3'3'-RS-(2'04'C-LNA-A)(2'O,4'C-LNA-A) (5b)

(2R,3R,3aS,5R,7aR,9S,10R,10aS,12R,14aR)-2,9-bis(6-amino-9H-purin-9-yl)-5,12-dimercaptotetrahydro-2H,7H,9H,14H-3,14a: 10,7a-bis(epoxymethano)difuro[3,2-d:3',2'-j][1,3,7,9]tetraoxa[2,8]diphosphacyclododecine 5,12-dioxide (5a), also referred to as 3'3'-RR-(2'O,4'C-LNA-A)(2'O,4'C-LNA-A), or dithio-(Rp,Rp)-cyclic-[2'O,4'C-LNA-A(3',5') p-2'O,4'C-LNA-A(3',5')p]; and (2R,3R,3 aS,5R,7aR,9S,10R,10aS,12S,14aR)-2,9-bis(6-amino-9H-purin-9-yl)-5,12-dimercaptotetrahydro-2H,7H,9H,14H-3,14a: 10,7a-bis(epoxymethano)difuro[3,2-d:3',2'-j][1,3,7,9]tetraoxa[2,8]diphosphacyclododecine 5,12-dioxide (5b), also referred to as 3'3'-RS-(2'O,4'C-LNA-A)(2'O,4' C-LNA-A), or dithio-(Rp,Sp)-cyclic-[2'O,4'C-LNA-A(3',5')p-2'O,4'C-LNA-A(3',5')p], were prepared according to the following Scheme 2:

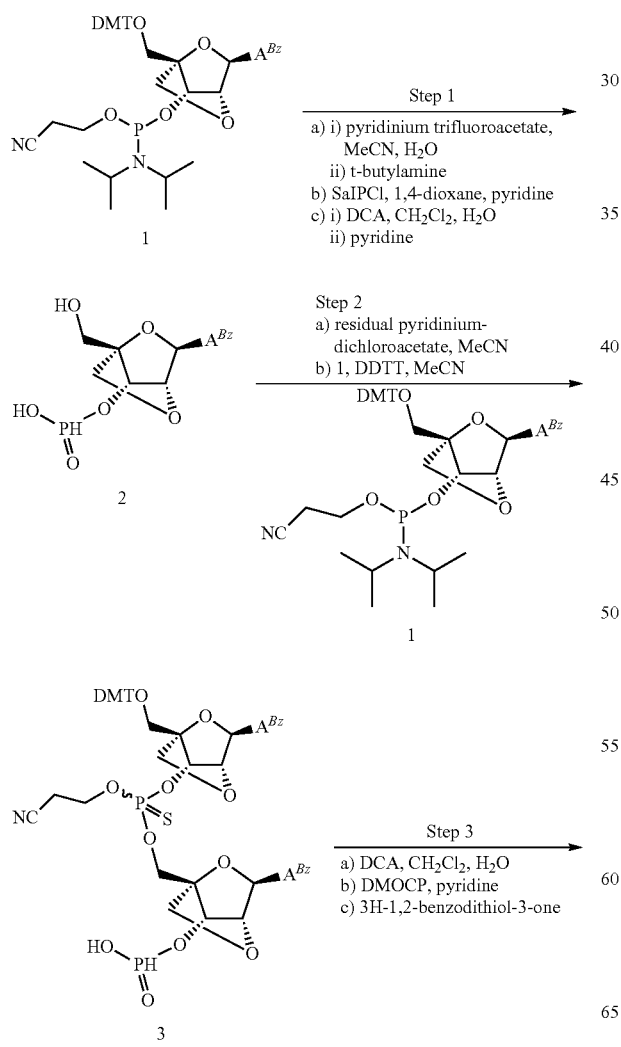

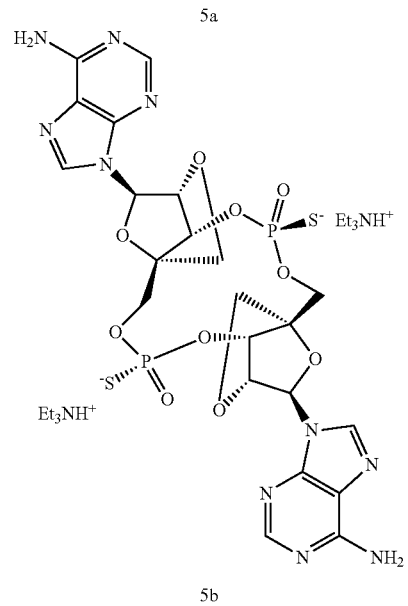

Step 1:

Preparation of (1S,3R,4R,7S)-3-(6-benzamido-9H-purin-9-yl)-1-(hydroxymethyl)-2,5-dioxabicyclo[2.2.1]heptan-7-yl hydrogen phosphonate (2): To a solution of (1R,3R,4R,7S)-3-(6-benzamido-9H-purin-9-yl)-1-((bis(4-methoxyphenyl)(phenyl)methoxy)methyl)-2,5-dioxabicyclo[2.2.1]heptan-7-yl (2-cyanoethyl) diisopropylphosphoramidite (1, 1.0 g, 1.2 mmol, Exiqon, Woburn, Mass.) in MeCN (10 mL) and H$_2$O (0.05 mL) was added pyridinium trifluoroacetate (270 g, 1.5 mmol). After 25 min, to the stirring reaction mixture at rt was added tert-butyl amine (5.0 mL). After 15 min, the reaction solution was concentrated in vacuo and water was removed as an azeotrope after concentration with MeCN (3×15 mL) to obtain a white foam. To a solution of the white foam in 1,4-dioxane (13 mL) was added a solution of SalPCl (226 mg, 1.0 mmol), in 1,4-dioxane (5 mL). After 7 min, to the cloudy white mixture was added pyridine (3 mL). After 1 h, to the cloudy reaction mixture was introduced water (2 mL). After 5 min, the mixture was poured into a 1N NaHCO$_3$ solution (100 mL). The solution was extracted with EtOAc (3×100 mL) and the organic layer was condensed to dryness in vacuo. The residue was dissolved in DCM (10 mL) to give a white mixture. To this solution was added water (150 µL) and 9% (v/v) solution of DCA in DCM (10 mL). After 10 min of stirring at rt, to the orange solution was charged pyridine (1.5 mL). The resulting clear solution was concentrated in vacuo and water was removed as an azeotrope after concentration with MeCN (3×20 mL). On the last evaporation, the resulting cloudy slurry of compound 2 was left in MeCN (20 mL).

Step 2:

Preparation of (1R,3R,4R,7S)-3-(6-benzamido-9H-purin-9-yl)-1-((((((1R,3R,4R,7S)-3-(6-benzamido-9H-purin-9-yl)-1-((bis(4-methoxyphenyl)(phenyl)methoxy)methyl)-2,5-dioxabicyclo[2.2.1]heptan-7-yl)oxy)(2-cyanoethoxy)phosphorothioyl)oxy)methyl)-2,5-dioxabicyclo[2.2.1]heptan-7-yl hydrogen phosphonate (3): A solution of compound 1 (1.0 g, 1.2 mmol, Exiqon) in MeCN (10 mL) was dried through concentration in vacuo. This process was repeated two more times to remove water as an azeotrope. On the last azeotrope, to the solution of compound 1 in MeCN (10 mL) was introduced ten 3A molecular sieves and the solution was stored under an atmosphere of nitrogen. To a stirred mixture of compound 2 with residual pyridinium dichloroacetate in MeCN (20 mL) was added the solution of compound 1 in MeCN (10 mL). After 40 min, to the stirred mixture was added DDTT (263 mg, 1.3 mmol). After 70 min, the yellow solution was concentrated in vacuo to give compound 3 as a yellow paste.

Step 3:

Preparation of N,N'-(((2S,3R,3aS,7aR,9R,10R,10aS,12R,14aR)-5-(2-cyanoethoxy)-12-mercapto-12-oxido-5-sulfido-tetrahydro-2H,7H,9H,14H-3,14a:10,7a-bis(epoxymethano)difuro[3,2-d:3',2'-j][1,3,7,9]tetraoxa[2,8]diphosphacyclododecine-2,9-diyl)bis(9H-purine-9,6-diyl))dibenzamide (4): To a solution of compound 3 in DCM (30 mL) was added water (180 µL) and 8.5% (v/v) solution of DCA in DCM (20 mL). After stirring for 15 min at rt, to the red-orange solution was introduced pyridine (10 mL). The resulting yellow solution was concentrated in vacuo until approximately 10 mL of the yellow mixture remained. To the yellow mixture was introduced pyridine (30 mL) and the mixture was concentrated in vacuo until approximately 10 mL of the yellow mixture remained. To the yellow mixture was added pyridine (30 mL) and the mixture was concentrated in vacuo until approximately 10 mL of the yellow mixture remained. To the stirred yellow mixture in pyridine (50 mL) was added DMOCP (631 mg, 3.4 mmol). After 15 min, to the brownish yellow solution was added water (750 µL), followed immediately by the introduction of 3H-1,2-benzodithiol-3-one (304 mg, 1.8 mmol). After 30 min, the brownish yellow solution was poured into a 1N aqueous NaHCO$_3$ solution (250 mL). After 15 min, the biphasic mixture was extracted with EtOAc (200 mL). After separation, the aqueous layer was back extracted with EtOAc (2×150 mL). The organic extracts were combined and concentrated in vacuo. To the concentrated yellow oil was added toluene (20 mL) and the mixture was evaporated in vacuo to remove residual pyridine. This procedure was repeated again with toluene (30 mL). The resulting oil was purified by silica gel chromatography (0% to 50% MeOH in DCM) to provide a mixture of compound 4 (604 mg, 52% yield) as beige solid.

Step 4:

Preparation of 3'3'-RR-(2'O,4'C-LNA-A)(2'O,4'C-LNA-A) (5a) and 3'3'-RS-(2'O,4'C-LNA-A)(2'O,4'C-LNA-A) (5b): To a stirred solution of compound 4 (472 mg, 0.5 mmol) in EtOH (5.0 mL) was added AMA (6.5 mL) and the yellow solution was heated at 50° C. After 2 h, the yellow solution was allowed to cool and concentrated in vacuo. The yellow residue in 10 mM TEAA (3 mL) was purified by reverse phase silica gel chromatography (0% to 25% MeCN in 10 mM aqueous TEAA) to obtain compound 5a (92 mg, 27% yield) as a white TEAH$^+$ salt after lyophilization. LCMS-ESI: 712.95 [M–H]$^-$ (calculated for C$_{22}$H$_{24}$N$_{10}$O$_{10}$P$_2$S$_2$: 714.56); Rt: 1.06 min by UPLC (20 mM NH$_4$OAc, 2% to 80% MeCN). $^1$H NMR (400 MHz, 45° C., D$_2$O) δ 8.45 (d, J=4.4 Hz, 2H), 8.30 (d, J=5.6 Hz, 2H), 6.36 (d, J=4.4 Hz, 2H), 5.12 (s, 4H), 4.63 (d, J=12.4 Hz, 2H), 4.34-4.24 (m, 6H), 3.33 (q, J=7.2 Hz, 12H), 2.09 (m, 1H), 1.40 (t, J=5.2 Hz, 18H). $^{31}$P NMR (45° C., D$_2$O) δ 54.57.

The Rp,Sp isomer was also isolated after purification in the reverse phase chromatography step, to provide compound 5b (35 mg, 10% yield) as the TEAH$^+$ salt after lyophilization. LCMS-ESI: 712.95 [M–H]$^-$ (calculated for C$_{22}$H$_{24}$N$_{10}$O$_{10}$P$_2$S$_2$: 714.56); Rt: 1.01 min by UPLC (20 mM NH$_4$OAc, 2% to 80% MeCN). $^1$H NMR (400 MHz, 45° C., D$_2$O) δ 8.58 (s, 1H), 8.46 (s, 1H), 8.31 (s, 1H), 8.27 (s, 1H), 6.38 (s, 2H), 5.32 (s, 1H), 5.11 (s, 1H), 5.07 (d, J=10.4 Hz, 2H), 4.62 (d, J=11.2 Hz, 1H), 4.53 (d, J=11.2 Hz, 1H), 4.41-4.31 (m, 4H), 4.24 (t, J=16.4 Hz, 1H), 3.33 (q, J=7.2 Hz, 10H), 1.41 (t, J=7.2 Hz, 15H). $^{31}$P NMR (45° C., D$_2$O) δ 55.33, 54.48.

The substantially pure compound 5a (2'3'-RR-(2'O,4'C-LNA-A)(2'O,4'C-LNA-A)) was co-crystalized with wild type STING protein, and the x-ray structure of this compound bound to STING confirmed the stereochemistry as depicted above in Scheme 2, compound 5a. The corresponding stereoisomer having RS configuration on the phosphorus linkers was separated as compound 5b, with a shorter retention time (1.01 min vs 1.06 min for the RR isomer 5a). While additional compounds below have not yet been co-crystalized, experience with these compounds indicates that the Rp, Rp isomer consistently has a longer retention time than the corresponding Rp, Sp isomer, Sp, Rp isomer or Sp, Sp isomer. The identity of the Rp, Rp isomers in the following examples is further verified as having improved biological activity (e.g. binding to STING, induction of IFNβ) compared to the Rp, Sp isomer, Sp, Rp isomer or Sp, Sp isomer.

The compound N,N'-(((2R,3R,3aS,5R,7aR,9R,10R,10aS,12R,14aR)-5,12-dimercapto-5,12-dioxidotetrahydro-2H,7H,9H,14H-3,14a:10,7a-bis(epoxymethano)difuro[3,2-d:3',2'-j][1,3,7,9]tetraoxa[2,8]diphosphacyclododecine-2,9-diyl)bis(9H-purine-9,6-diyl)dibenzamide (4a), also referred to as 3'3'-RR-(2'O,4'C-LNA-BzA)(2'O,4'C-LNA-BzA), was prepared from compound 4 as follows:

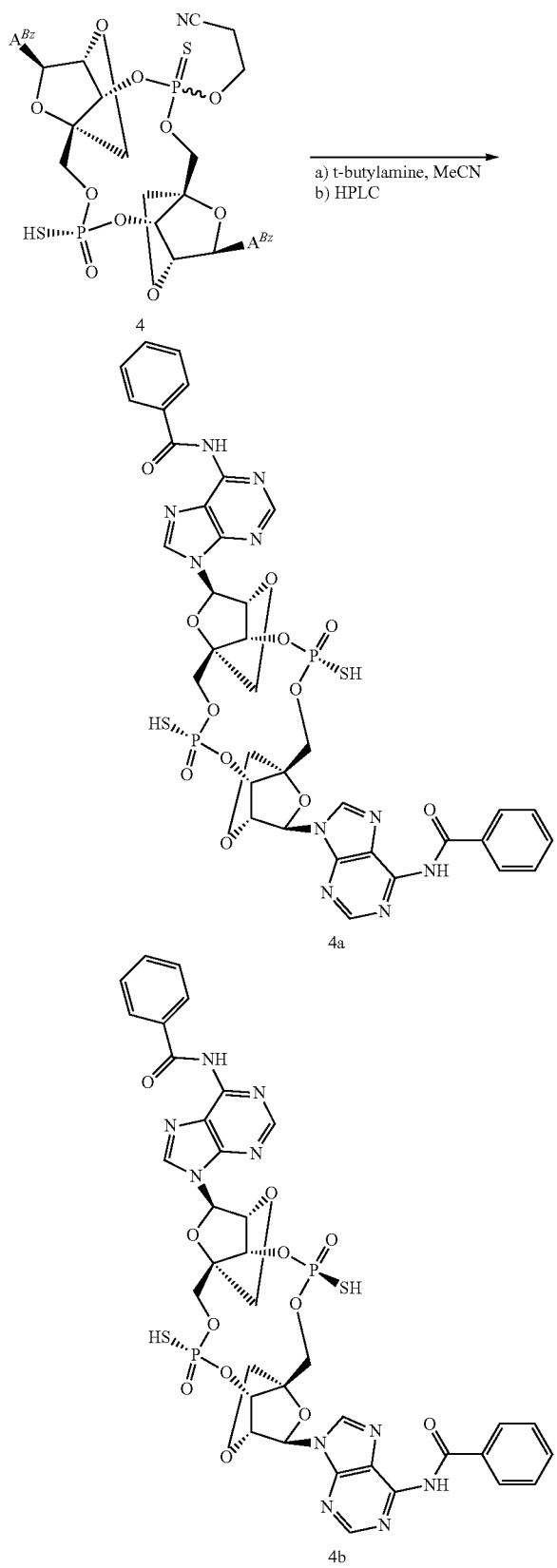

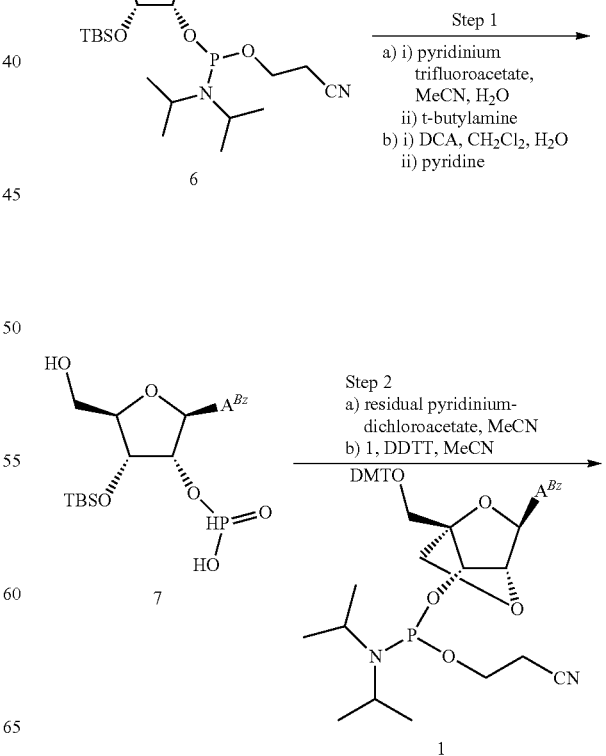

vacuo. The beige residue in 10 mM TEAA (3 mL) was purified by reverse phase silica gel chromatography (0% to 20% MeCN in 10 mM aqueous TEAA) to obtain compound 4a (27.8 mg, 51% yield) as a white bis-TEAH+ salt after lyophilization. LCMS-ESI: 922.78 [M−H]− (calculated for $C_{36}H_{32}N_{10}O_{12}P_2S_2$: 921.00); Rt: 1.40 min by UPLC condition (2% to 80% MeCN in 20 mM NH$_4$OAc). $^1$H NMR (400 MHz, 45° C., D$_2$O) δ 8.84 (s, 2H), 8.65 (s, 2H), 8.024 (d, J=8.0 Hz, 4H), 7.74 (t, J=7.6 Hz, 2H), 7.57 (t, J=7.6 Hz, 2H), 6.47 (s, 2H), 5.18 (d, J=9.2 Hz, 2H), 5.12 (s, 2H), 4.62 (d, J=11.6 Hz, 2H), 4.35-4.31 (m, 4H), 4.26 (d, J=8.4 Hz, 2H), 3.32 (q, J=14.8, 7.2 Hz, 14H), 2.09 (m, 1H), 1.41 (t, J=7.2 Hz, 20H). $^{31}$P NMR (45° C., D$_2$O) δ 54.87. The RS isomer 3'3'-RS-(2'O,4'C-LNA-BzA)(2'O,4'C-LNA-BzA) 4b was also isolated in the chromatography step.

Example 3: Synthesis of 2'3'-RR-(A)(2'O,4'C-LNA-A) (10a), 2'3'-RS-(A)(2'O,4'C-LNA-A) (10b), 2'3'-SR-(A)(2'O,4'C-LNA-A) (10c) and 2'3'-SS-(A)(2'O,4'C-LNA-A) (10d)

2'3'-RR-(A)(2'O,4'C-LNA-A) (10a), also referred to as dithio-(Rp,Rp)-cyclic-[A(2',5')p-2'O,4'C-LNA-A(3',5')p]; 2'3'-RS-(A)(2'O,4'C-LNA-A) (10b), also referred to as dithio-(Rp,Sp)-cyclic-[A(2',5')p-2'O,4'C-LNA-A(3',5')p]; 2'3'-SR-(A)(2'O,4'C-LNA-A) (10c), also referred to as dithio-(Sp,Rp)-cyclic-[A(2',5')p-2'O,4'C-LNA-A(3',5')p]; and 2'3'-SS-(A)(2'O,4'C-LNA-A) (10d), also referred to as dithio-(Sp,Sp)-cyclic-[A(2',5')p-2'O,4'-C-LNA-A(3',5')p] were prepared according to the following Scheme 3:

To a stirred solution of compound 4 (57.39 mg, 0.06 mmol) in MeCN (1.5 mL) was added tert-butylamine (0.3 mL). After 2 h, the white, cloudy mixture was concentrated in -continued
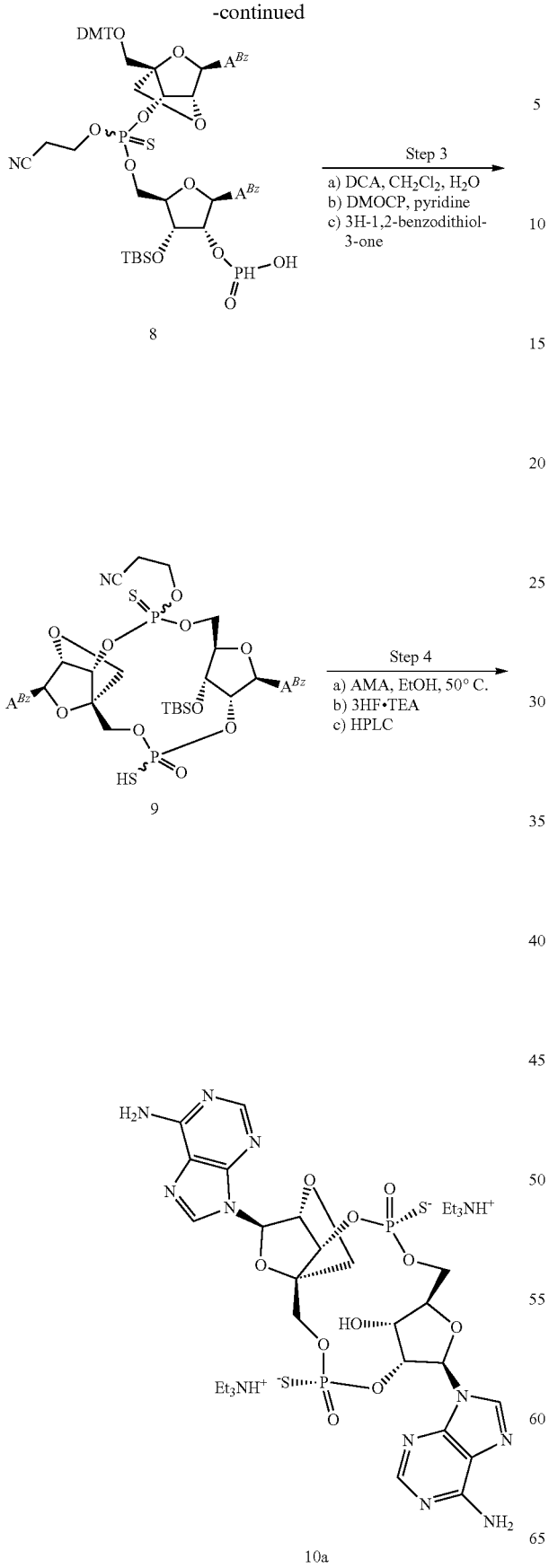
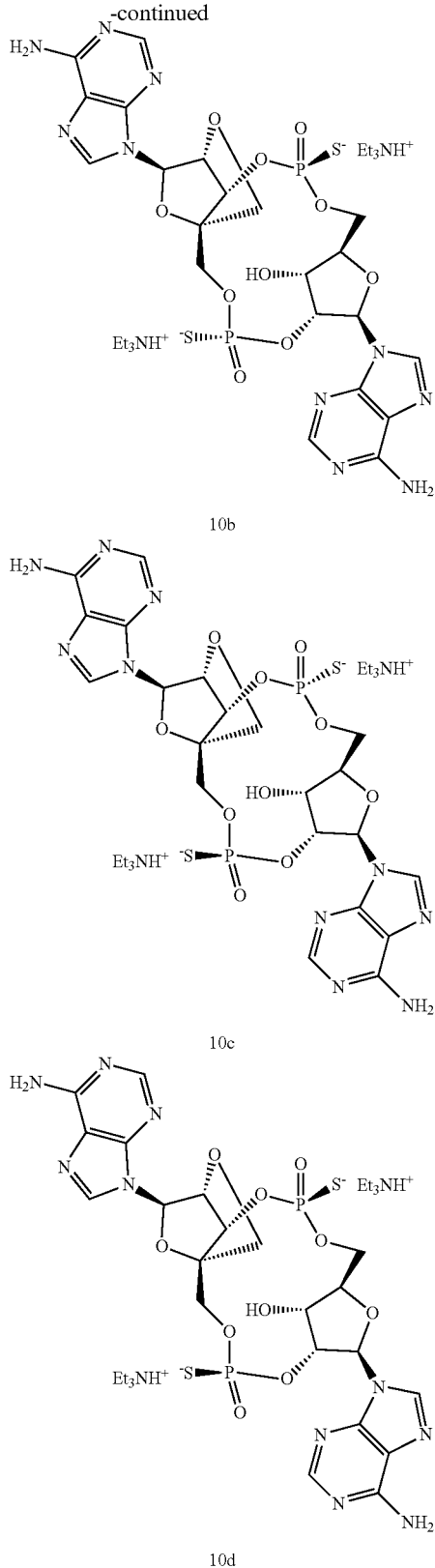
Step 1:
Preparation of (2R,3R,4R,5R)-2-(6-benzamido-9H-purin-9-yl)-4-((tert-butyldimethylsilyl)oxy)-5-(hydroxymethyl) tetrahydrofuran-3-yl hydrogen phosphonate (7): To a solution of (2R,3R,4R,5R)-2-(6-benzamido-9H-purin-9-yl)-5-((bis(4-methoxyphenyl)(phenyl)methoxy)methyl)-4-((tert-butyldimethylsilyl)oxy)tetrahydrofuran-3-yl (2-cyanoethyl) diisopropylphosphoramidite (6, 1.0 g, 1.0 mmol, Chem-Genes, Wilmington, Mass.) in MeCN (8 mL) and $H_2O$ (50 µL) was added pyridinium trifluoroacetate (0.27 g, 1.4 mmol). After 15 min, to the stirring reaction mixture at rt was added tert-butyl amine (5.0 mL, 47.6 mmol). After 15 min, the reaction solution was concentrated in vacuo and water was removed as an azeotrope after concentration in vacuo with MeCN (3×15 mL) to obtain a colorless foam. The colorless foam was dissolved in DCM (13 mL) to give a colorless solution. To this solution was added water (150 µL) and 8% (v/v) solution of DCA in DCM (10 mL). After 10 min of stirring at rt, the red solution was charged with pyridine (1.5 mL). The resulting clear solution was concentrated in vacuo and water was removed as an azeotrope after concentration in vacuo with MeCN (3×20 mL). On the last evaporation, the resulting peach slurry of compound 7 was left in MeCN (25 mL).

Step 2:

Preparation of (2R,3R,4R,5R)-2-(6-benzamido-9H-purin-9-yl)-5-((((((1R,3R,4R,7S)-3-(6-benzamido-9H-purin-9-yl)-1-((bis(4-methoxyphenyl)(phenyl)methoxy)methyl)-2,5-dioxabicyclo[2.2.1]heptan-7-yl)oxy)(2-cyanoethoxy) phosphorothioyl)oxy)methyl)-4-((tert-butyldimethylsilyl) oxy)tetrahydrofuran-3-yl hydrogen phosphonate (8): A solution of compound 1 (1.0 g, 1.14 mmol, Exiqon) in MeCN (25 mL) was dried through concentration in vacuo. This process was repeated two more times to remove water as an azeotrope. On the last azeotrope, to the solution of compound 1 in MeCN (10 mL) was introduced ten 3A molecular sieves and the solution was stored under an atmosphere of nitrogen. To a stirred mixture of compound 7 with residual pyridinium dichloroacetate in MeCN (25 mL) was added the solution of compound 1 in MeCN (10 mL). After 1 h, to the stirred mixture was added DDTT (280 mg, 1.4 mmol). After 2 h, the yellow mixture was concentrated in vacuo to give compound 8 as a yellow paste.

Step 3:

Preparation of Protected-dithio-2'3'-(A)(2'O,4'C-LNA-A) (9): To a solution of compound 8 in DCM (30 mL) was added water (180 µL) and 15% (v/v) solution of DCA in DCM (20 mL). After 10 min at rt, to the red solution was introduced pyridine (10 mL). The resulting yellow solution was concentrated in vacuo until approximately 20 mL of the yellow mixture remained. Addition of pyridine (30 mL) and concentration in vacuo to 10 mL was done twice, leaving a yellow mixture of approximately 10 mL. The stirred yellow mixture was brought to 50 mL with pyridine and DMOCP (629 mg, 3.4 mmol) was added. After 20 min, to the brownish yellow solution was added water (750 µL), followed immediately by the introduction of 3H-1,2-benzodithiol-3-one (299 mg, 1.8 mmol). After 45 min, the brownish yellow solution was poured into a 1N aqueous $NaHCO_3$ solution (250 mL). After 30 min, the biphasic mixture was extracted with EtOAc (200 mL). After separation, the aqueous layer was back extracted with EtOAc (1×200 mL, 1×150 mL). The organic extracts were combined and concentrated in vacuo. To the concentrated yellow oil was added toluene (75 mL) and the mixture was evaporated in vacuo to remove residual pyridine. This procedure was repeated twice with toluene (75 mL). The resulting oil was purified by silica gel chromatography (0% to 60% MeOH in DCM) to provide a mixture of compound 9 (733 mg, 68% yield) as a yellow paste.

Step 4:

Preparation of 2'3'-RR-(A)(2'O,4'C-LNA-A) (10a), 2'3'-RS-(A)(2'O,4'C-LNA-A) (10b), 2'3'-SR-(A)(2'O,4'C-LNA-A) (10c) and 2'3'-SS-(A)(2'O,4'C-LNA-A) (10d): To a stirred solution of compound 9 (600 mg, 0.56 mmol) in EtOH (19 mL) was added AMA (13.5 mL) and the yellow solution was heated at 50° C. After 2 h, the clear solution was allowed to cool and concentrated in vacuo. To the residual solid (363 mg, 0.44 mmol) was introduced triethylamine trihydrofluoride (4.3 mL) and the yellow solution was heated to 40° C. After 3 h, the yellow solution was allowed to cool to rt. This yellow solution was slowly added to a cooled solution of 1M TEAB (24 mL) and TEA (4.3 mL). The yellow mixture was allowed to stir for 1 h. The clear paste residue was purified by reverse phase silica gel chromatography (0% to 50% MeCN in 10 mM aqueous TEAA) to obtain compound 10a (14 mg, 5% yield) as a white bis-TEAH$^+$ salt after lyophilization. LCMS-ESI: 701.75 [M–H]$^-$ (calculated for $C_{21}H_{24}N_{10}O_{10}P_2S_2$: 702.53); Rt: 6.602 min by LCMS conditions (20 mM $NH_4OAc$, 2% to 50%). $^1H$ NMR (400 MHz, 45° C., $D_2O$) δ 8.61 (s, 1H), 8.42 (m, 3H), 6.46 (d, J=5.2 Hz, 1H), 6.42 (s, 1H), 5.60 (br s, 1H), 5.43 (s, 1H), 5.4 (s, 1H), 5.00 (s, 1H), 4.63-4.60 (m, 1H), 4.87-4.47 (m, 2H), 4.41-4.38 (m, 2H), 3.41 (d, J=5.2 Hz, 10H), 1.50 (s, 15H). $^{31}P$ NMR (45° C., $D_2O$) δ 55.46, 53.69.

The isomer 2'3'-RS-(A)(2'O,4'C-LNA-A) 10b was also isolated after purification in the reverse phase chromatography step as the TEAH$^+$ salt after lyophilization (20 mg, 6%). LCMS-ESI: 701.75 [M–H]$^-$ (calculated for $C_{21}H_{24}N_{10}O_{10}P_2S_2$: 702.53); Rt: 6.198 min by LCMS conditions (20 mM $NH_4OAc$, 2% to 50%). $^1H$ NMR. (400 MHz, 45° C., $D_2O$) δ 8.75 (s, 1H), 8.50-8.46 (m, 3H), 6.53-6.51 (m, 1H), 6.43 (d, J=6 Hz, 1H), 5.53-5.50 (m, 2H), 5.28 (s, 1H), 4.40-4.36 (m, 4H), 3.41 (q, J=6 Hz, 24H), 1.49 (t, J=6 Hz, 36H). $^{31}P$ NMR (45° C., $D_2O$) δ 57.52, 55.43.

The isomer 2'3'-SR-(A)(2'O,4'C-LNA-A) 10c was also isolated after purification in the reverse phase chromatography step as the bis-TEAH$^+$ salt after lyophilization (27 mg, 9%). LCMS-ESI: 701.75 [M–H]$^-$ (calculated for $C_{21}H_{24}N_{10}O_{10}P_2S_2$: 702.53); Rt: 6.064 min by LCMS conditions (20 mM $NH_4OAc$, 2% to 50. $^1H$ NMR. (400 MHz, 45° C., $D_2O$) δ 8.77 (s, 1H), 8.59 (s, 1H), 8.48 (s, 1H), 8.45 (s, 1H), 6.49 (d, J=8 Hz, 1H), 6.42 (s, 1H), 5.67 (br s, 1H), 5.47 (s, 1H), 5.36 (d, J=6 Hz, 1H), 5.01 (s, 1H), 4.72-4.59 (m, 7H), 3.41 (q, J=7.2 Hz, 13H), 1.49 (t, J=6.4 Hz, 20H). $^{31}P$ NMR (45° C., $D_2O$) δ 54.79, 53.33.

The isomer 2'3'-SS-(A)(2'O,4'C-LNA-A) 10d was also isolated after purification in the reverse phase chromatography step as the bis-TEAH$^+$ salt after lyophilization (6.0 mg, 2%). LCMS-ESI: 701.75 [M–H]$^-$ (calculated for $C_{21}H_{24}N_{10}O_{10}P_2S_2$: 702.53); Rt: 5.757 min by LCMS conditions (20 mM $NH_4OAc$, 2% to 50%). $^1H$ NMR. (400 MHz, 45° C., $D_2O$) δ 8.84 (s, 1H), 8.66 (s, 1H), 8.46 (s, 1H), 8.42 (s, 1H), 6.49 (d, J=8 Hz, 1H), 6.41 (s, 1H), 5.68-5.64 (m, 1H), 5.37 (s, 2H), 4.90 (br s, 1H), 4.55 (d, J=22 Hz, 1H), 4.49-4.47 (m, 2H), 4.37-4.34 (m, 2H), 3.39 (q, J=6.8 Hz, 10H), 1.47 (t, J=7.2 Hz, 15H). $^{31}P$ NMR (45° C., $D_2O$) δ 57.34, 55.20.

The compounds 2'3'-RR-(3'-OTBS-A)(2'O,4'C-LNA-A) (11a); 2'3'-RS-(3'-OTBS-A)(2'O,4'C-LNA-A) (11b); and 2'3'-SS-(3'-OTBS-A)(2'O,4'C-LNA-A) (11c), were prepared from the compound 9 in Step 4 a) of Scheme 3 as follows:

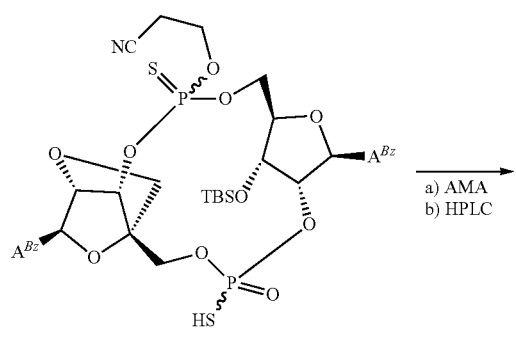

9

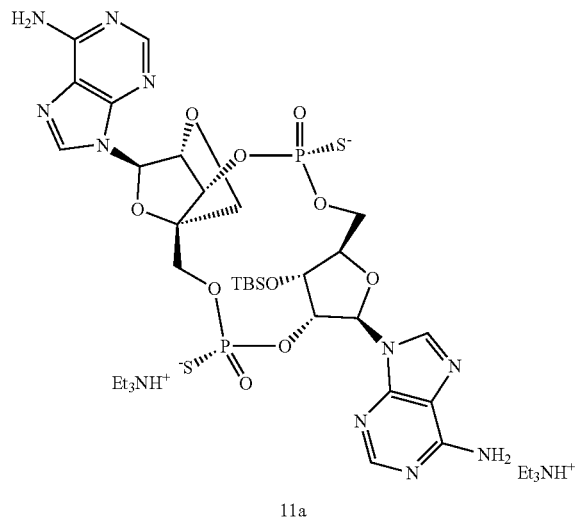

11a

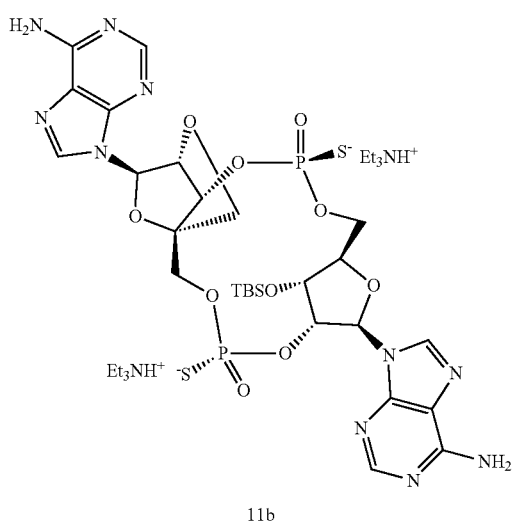

11b

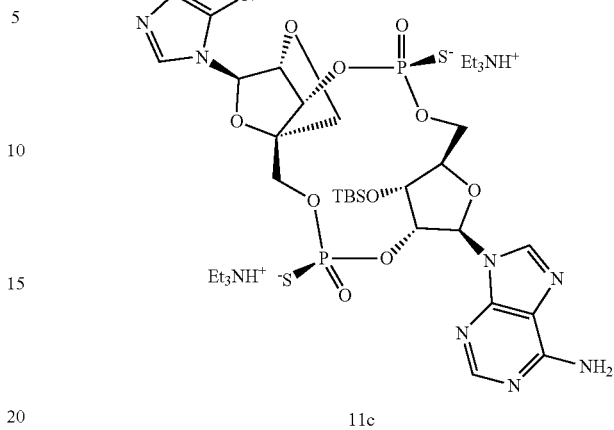

11c

To a stirred solution of compound 9 (600 mg, 0.56 mmol) in EtOH (19 mL) was added AMA (13.5 mL) and the yellow solution was heated at 50° C. After 2 h, the clear solution was allowed to cool and concentrated in vacuo. A portion of the residual intermediate was purified by reverse phase silica gel chromatography (0% to 50% MeCN in 10 mM aqueous TEAA) to obtain compound 11a (6.4 mg, 6% yield) as a white bis-TEAH+ salt after lyophilization. LCMS-ESI: 815.75 [M−H]− (calculated for $C_{27}H_{36}N_{10}O_{10}P_2S_2Si$: 816.80); Rt: 8.66 min by LCMS conditions (20 mM NH$_4$OAc, 2% to 50%). $^1$H NMR (400 MHz, 45° C., D$_2$O) δ 8.61 (s, 1H), 8.45-8.43- (m, 3H), 6.51 (d, J=8 Hz, 1H), 6.43 (s, 1H), 5.60 (br s, 1H), 5.43 (s, 1H), 5.4 (s, 1H), 5.39-5.38 (m, 1H), 4.93-4.92 (m, 1H), 4.63-4.60 (m, 1H), 4.70-4.46 (m, 2H), 4.48-4.41 (m, 4H), 3.42 (q, J=7.0 Hz, 11H), 2.1 (s, 0.5H), 1.49 (t, J=7.0 Hz, 17H), 1.20 (s, 9H), 0.49 (s, 6H). $^{31}$P NMR (45° C., D$_2$O) δ 55.94, 54.37.

2'3'-RS-(3'-OTBS-A)(2'O,4'C-LNA-A) 11b was also isolated by HPLC to provide 11.4 mg (11% yield) as the bis-TEAH+ salt after lyophilization. LCMS-ESI: 815.75 [M−H]− (calculated for $C_{27}H_{36}N_{10}O_{10}P_2S_2Si$: 816.80); Rt: 8.05 min by LCMS conditions (20 mM NH$_4$OAc, 2% to 50%). $^1$H NMR. (400 MHz, 45° C., D$_2$O) δ 8.73 (s, 1H), 8.50-8.46 (m, 3H), 6.56-6.54 (d, J=8.0 Hz, 1H), 6.43 (s, 1H), 5.55 (s, 2H), 5.27 (s, 1H), 4.54 (d, J=8.0 Hz, 1H), 4.39-4.33 (m, 3H), 3.41 (q, J=7.6 Hz, 12H), 2.15 (s, 0.5), 1.51 (t, J=7 Hz, 18H), 1.20 (s, 9H), 0.47 (s, 6H). $^{31}$P NMR (45° C., D$_2$O) δ 57.31, 55.66.

2'3'-SS-(3'-OTBS-A)(2'O,4'C-LNA-A) 11e was also isolated by HPLC to provide 2.38 mg (2% yield) as the bis-TEAH+ salt after lyophilization. LCMS-ESI: 815.75 [M−H]− (calculated for $C_{27}H_{36}N_{10}O_{10}P_2S_2Si$: 816.80); Rt: 7.46 min by LCMS conditions (20 mM NH$_4$OAc, 2% to 50%). $^1$H NMR (400 MHz, 45° C., D$_2$O) δ 8.82 (s, 1H), 8.70 (s, 1H), 8.48 (s, 1H), 8.44 (s, 1H), 6.53 (d, J=8.8 Hz, 1H), 6.43 (s, 1H), 5.40-5.37 (m, 2H), 4.57-4.48 (m, 6H), 4.39-4.31 (m, 4H), 4.39-4.33 (m, 3H), 3.41 (q, J=7.2 Hz, 17H), 1.50 (t, J=7.2 Hz, 25H), 1.20 (s, 9H), 1.51-1.23 (m, 5H) 0.47 (s, 6H). $^{31}$P NMR (45° C., D$_2$O) δ 57.30, 55.01.

The compounds 2'3'-RR-(BzA)(2'O,4'C-LNA-BzA) (11d); 2'3'-RS-(BzA)(2'O,4'C-LNA-BzA) (11e); and 2'3'-SR-(BzA)(2'O,4'C-LNA-BzA) (11f) were prepared from the compound 9 from Step 3 of Scheme 3 as follows:

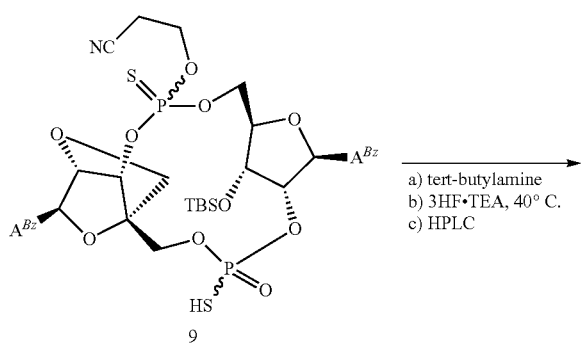
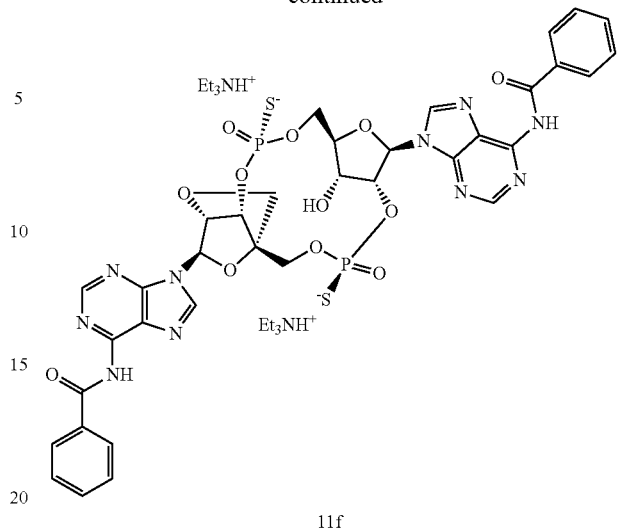
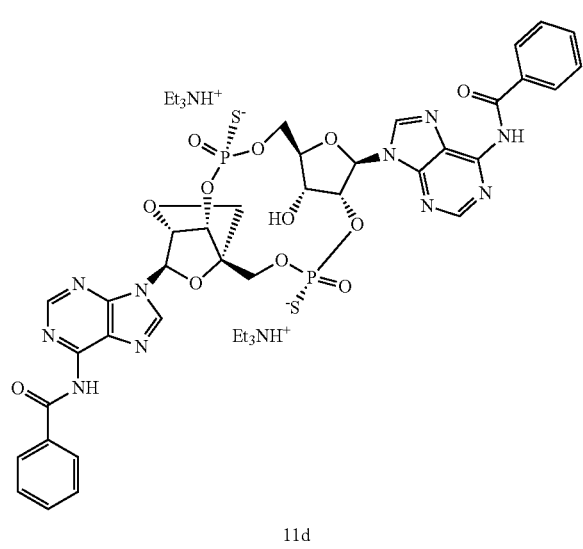
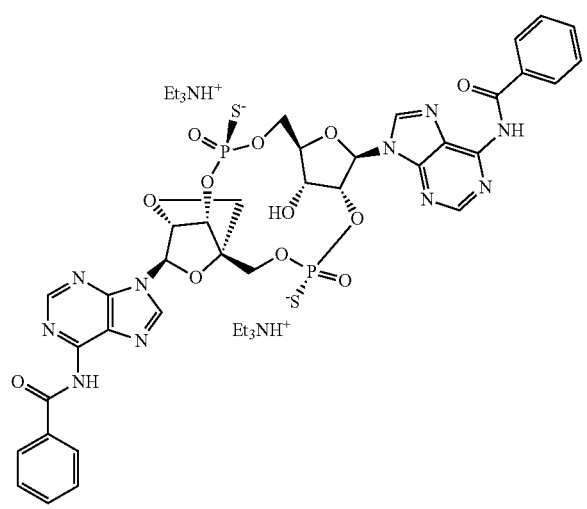

To a stirred solution of compound 9 (114.59 mg, 0.11 mmol) in MeCN (5 mL) was added tert-butylamine (1 mL). After 3 h, the yellow solution was condensed in vacuo to dryness. To the residual solid was introduced triethylamine trihydrofluoride (1 mL) and the yellow solution was heated to 40° C. After 2.5 h, the yellow solution was allowed to cool to rt. This yellow solution was slowly added to a cooled solution of 1M TEAB (8 mL) and TEA (1 mL). The yellow mixture was allowed to stir for 1 h. The solution was purified by reverse phase silica gel chromatography (0% to 50% MeCN in 10 mM aqueous TEAA) to obtain compounds 11d, 11e and 11f. The compound 11d (5 mg, 5% yield) was isolated as a white bis-TEAH$^+$ salt after lyophilization. LCMS-ESI: 909.70 [M–H]$^-$ (calculated for $C_{35}H_{32}N_{10}O_{12}P_2S_2$: 910.77); Rt: 9.70 min by LCMS conditions (MeCN in 20 mM NH$_4$OAc, 2% to 50%). $^1$H NMR (400 MHz, 45° C., D$_2$O) 68.86 (s, 1H), 8.84 (s, 1H), 8.73 (s, 1H), 8.73 (s, 1H), 8.05 (pseudo triplet, J=8 Hz, 4H), 7.75 (m, 2H), 7.59 (dd, J=8 Hz, 4H), 6.51 (d, J=8 Hz, 1H), 6.48 (s, 1H), 5.79-5.74 (m, 1H), 5.57 (s, 1H), 5.34 (d, J=6.8 Hz, 1H), 4.97 (s, 1H), 4.56-4.31 (m, 6H), 3.34 (q, J=8.0 Hz, 11H), 1.43 (t, J=8.0 Hz, 17H). $^{31}$P NMR (45° C., D$_2$O) δ 54.77, 53.02.

The Rp,Sp isomer was also isolated after purification in the reverse phase chromatography step, to provide compound 11e (6.46, 6% yield) as the bis-TEAH$^+$ salt after lyophilization. LCMS-ESI: 909.70 [M–H]$^-$ (calculated for $C_{35}H_{32}N_{10}O_{12}P_2S_2$: 910.77); Rt: 9.87 min by LCMS conditions (MeCN in 20 mM NH$_4$OAc, 2% to 50%). $^1$H NMR (400 MHz, 45° C., D$_2$O) δ 8.95 (s, 1H), 8.90 (s, 1H), 8.81 (s, 1H), 8.75 (s, 1H), 8.07 (dd, J=20, 8 Hz, 4H), 7.77 (m, 3H), 7.69-7.60 (m, 5H), 6.57 (d, J=8 Hz, 1H), 6.49 (s, 1H), 5.76-5.73 (m, 2H), 5.50 (s, 1H), 5.30 (d, J=5.6 Hz, 1H), 4.88 (d, J=3.2 Hz, 1H), 4.63-4.30 (m, 9H), 3.34 (q, J=8.0 Hz, 10H), 1.43 (t, J=8.0 Hz, 16H). $^{31}$P NMR (45° C., D$_2$O) δ 56.73, 55.21.

Example 4: Synthesis of Synthesis of 2'3'-RR-(3'F-G)(2'O,4'C-LNA-A) (15a), 2'3'-RS-(3'F-G)(2'O,4'C-LNA-A) (15b), 2'3'-SR-(3'F-G)(2'O,4'C-LNA-A) (15c) and 2'3'-SS-(3'F-G)(2'O,4'C-LNA-A) (15d)

2'3'-RR-(3'F-G)(2'O,4'C-LNA-A) (15a), also referred to as dithio-(Rp,Rp)-cyclic-[3'F-G(2',5')p-2'O,4'C-LNA-A(3', 5')p]; 2'3'-RS-(3'F-G)(2'O,4'C-LNA-A) (15b), also referred to as dithio-(Rp,Sp)-cyclic-[3'F-G(2',5')p-2'O,4'C-LNA-A (3',5')p]; 2'3'-SR-(3'F-G)(2'O,4'C-LNA-A) (15c), also referred to as dithio-(Sp,Rp)-cyclic-[3'F-G(2',5')p-2'O,4'C-LNA-A(3',5')p]; and 2'3'-SS-(3'F-G)(2'O,4'C-LNA-A) (15d), also referred to as dithio-(Sp,Sp)-cyclic-[3'F-G(2',5')p-2'O,4'C-LNA-A(3',5')p] were prepared according to the following Scheme 4:
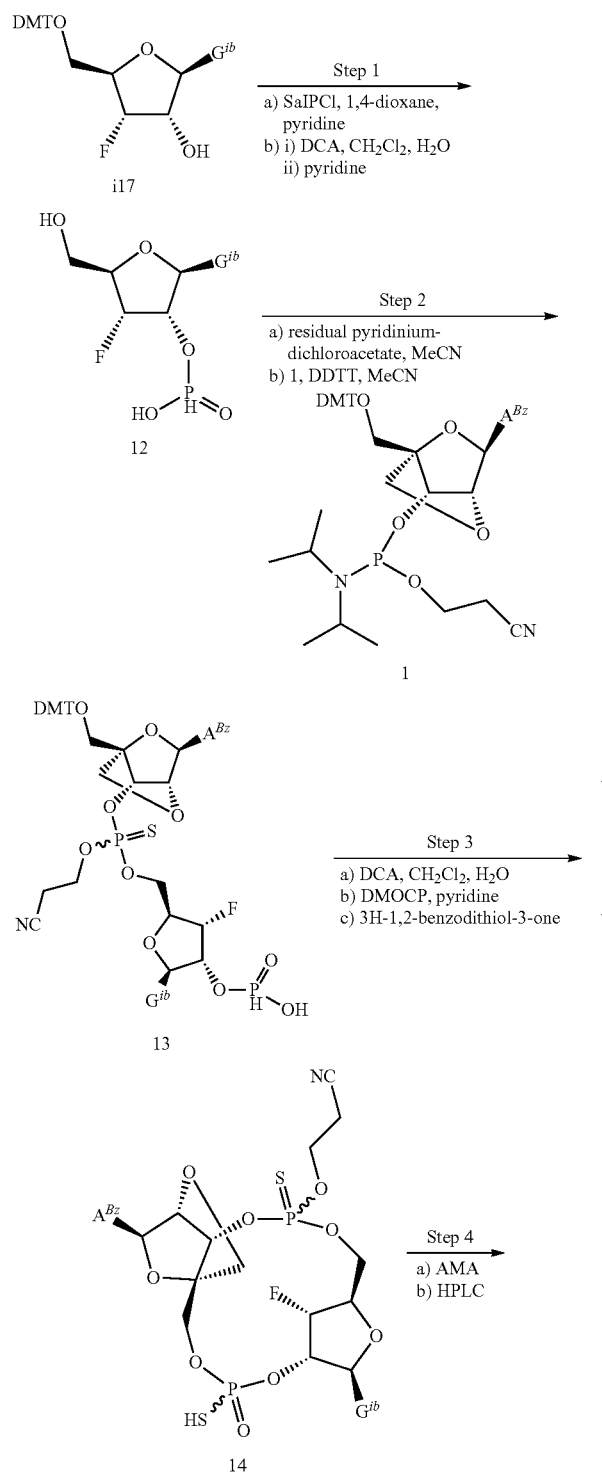
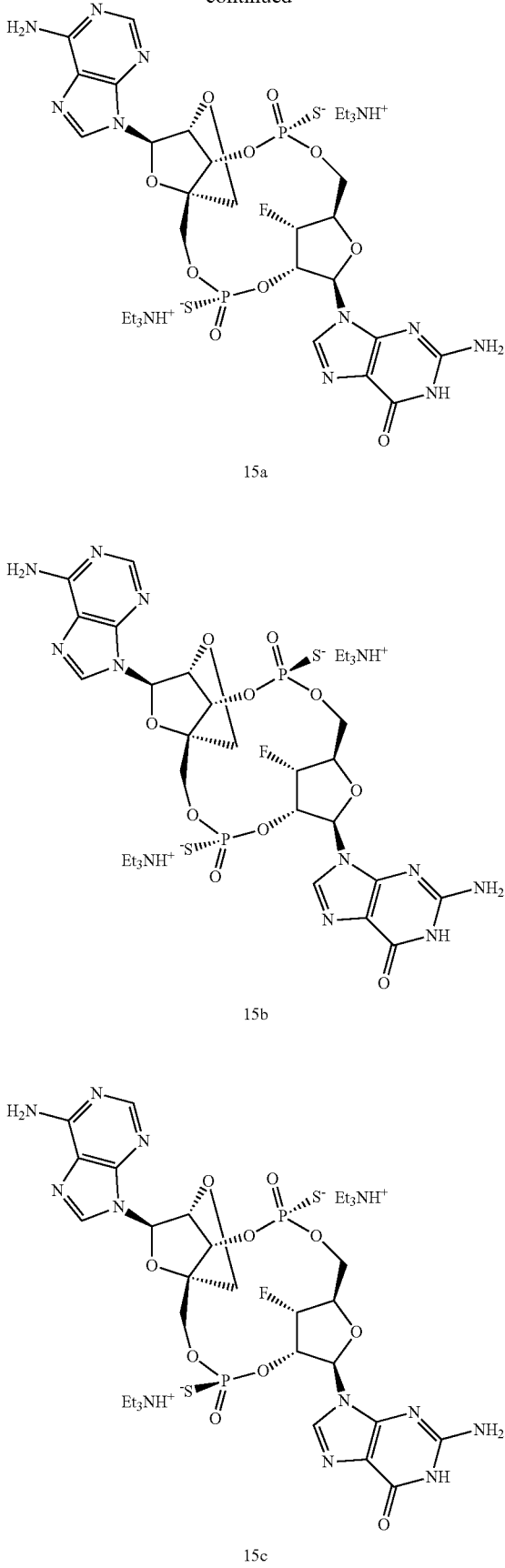

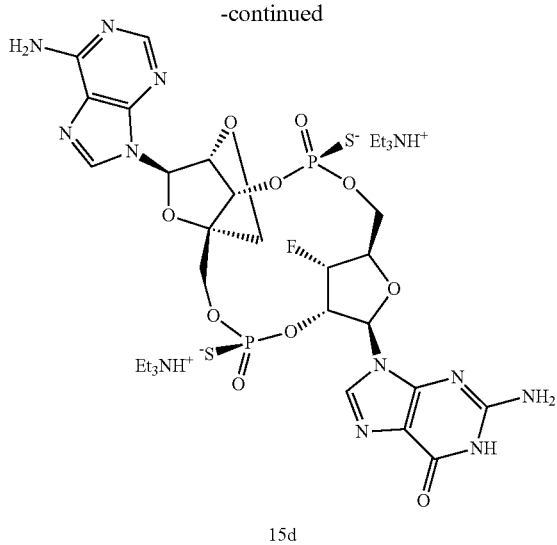

15d

Step 1:
Preparation of (2R,3S,4R,5R)-4-fluoro-5-(hydroxymethyl)-2-(2-isobutyramido-6-oxo-1,6-dihydro-9H-purin-9-yl)tetrahydrofuran-3-yl hydrogen phosphonate (12): To a solution of N-(9-((2R,3S,4S,5R)-5-((bis(4-methoxyphenyl)(phenyl)methoxy)methyl)-4-fluoro-3-hydroxytetrahydrofuran-2-yl)-6-oxo-6,9-dihydro-1H-purin-2-yl)isobutyramide (i17, 806 mg, 1.2 mmol, see Example 1) in 1,4-dioxane (12 mL) and pyridine (5 mL) was added a solution of SalPCl (327 mg, 1.6 mmol) in 1,4-dioxane (5 mL). After 100 min, to the stirred reaction mixture at rt was introduced water (1.9 mL), and after 25 min, the resulting mixture was poured into a 1N aqueous $NaHCO_3$ solution (80 mL). This aqueous mixture was extracted with EtOAc (2×50 mL), followed by DCM (2×50 mL), and the layers were partitioned. The EtOAc and DCM extracts were combined and concentrated to dryness in vacuo. The residue was purified by normal phase silica gel chromatography (1% to 50%, 0.5% pyridine in DCM) to obtain an intermediate compound (500 mg, 0.69 mmol, 56% yield) as a clear oil. The colorless oil was dissolved in DCM (15 mL) to give a colorless solution. To this solution was added water (150 μL) and an 11% (v/v) solution of DCA in DCM (15 mL). After 10 min of stirring at rt, to the red solution was charged pyridine (3.5 mL). The resulting white mixture was concentrated in vacuo and water was removed as an azeotrope after concentration with MeCN (30 mL). This azeotrope process was repeated two more times with MeCN (30 mL). On the last evaporation, the resulting white slurry of compound 12 was left in MeCN (20 mL).

Step 2:
Preparation of (2S,3R,4S,5S)-5-((((((1R,3R,4R,7S)-3-(6-benzamido-9H-purin-9-yl)-1-((bis(4-methoxyphenyl)(phenyl)methoxy)methyl)-2,5-dioxabicyclo[2.2.1]heptan-7-yl)oxy)(2-cyanoethoxy)phosphorothioyl)oxy)methyl)-4-fluoro-2-(2-isobutyramido-6-oxo-1,6-dihydro-9H-purin-9-yl)tetrahydrofuran-3-yl hydrogen phosphonate (13): A solution of compound 1 (1.0 g, 1.14 mmol, Exiqon) in MeCN (20 mL) was dried through concentration in vacuo. This process was repeated two more times to remove water as an azeotrope. On the last azeotrope, to the solution of compound 1 in MeCN (10 mL) was introduced ten 3A molecular sieves and the solution was stored under an atmosphere of nitrogen. To a stirred mixture of compound 12 with residual pyridinium dichloroacetate in MeCN (20 mL) was added the solution of compound 1 in MeCN (10 mL). After 1 h, to the stirred mixture was added DDTT (228 mg, 1.1 mmol). After 1 h, the yellow mixture was concentrated in vacuo to give compound 13 as a yellow paste.

Step 3:
Preparation of Protected-dithio-2'3'-(3'F-G)(2'O,4'C-LNA-A) (14): To a solution of compound 13 in DCM (30 mL) was added water (180 μL) and a 15% (v/v) solution of DCA in DCM (20 mL). After 10 min at rt, to the red solution was introduced pyridine (10 mL). The resulting yellow solution was concentrated in vacuo until approximately 20 mL of the yellow mixture remained. To the yellow mixture was introduced pyridine (20 mL) and the mixture was concentrated in vacuo until approximately 10 mL of the yellow mixture remained. Addition of pyridine (first 20 mL, then 30 mL) and concentration in vacuo to 10 mL was done twice, leaving a yellow mixture of approximately 10 mL. The stirred yellow mixture was brought to 40 mL with pyridine and DMOCP (383 mg, 2.1 mmol) was added. After 10 min, to the brownish yellow solution was added water (0.7 mL), followed immediately by the introduction of 3H-1,2-benzodithiol-3-one (175 mg, 1.0 mmol). After 1 h, the brownish yellow solution was poured into a 1N aqueous $NaHCO_3$ solution (200 mL). After 10 min, the biphasic mixture was extracted with EtOAc (150 mL). After separation, the aqueous layer was back extracted with EtOAc (150 mL) and DCM (150 mL). The organic extracts were combined and concentrated in vacuo. To the concentrated yellow oil was added toluene (75 mL) and the mixture was evaporated in vacuo to remove residual pyridine. This procedure was repeated twice with toluene (75 mL). The resulting oil was purified by silica gel chromatography (0% to 65% MeOH in DCM) to provide compound 14 (604 mg, 92.5% yield) as a yellow paste.

Step 4:
Preparation of 2'3'-SR-(3'F-G)(2'O,4'C-LNA-A) (15c) and 2'3'-SS-(3'F-G)(2'O,4'C-LNA-A) (15d): To a stirred solution of a mixture of compound 14 (550 mg, 0.58 mmol) in EtOH (19 mL) was added AMA (13.5 mL) and the yellow solution was heated at 50° C. After 2 h, the clear solution was allowed to cool and concentrated in vacuo. The clear paste residue was purified by reverse phase silica gel chromatography (0% to 50% MeCN in 10 mM aqueous TEAA) to obtain compound 15c (26.7 mg, 22% yield) as a white $TEAH^+$ salt after lyophilization. The isomer 2'3'-SS-(3'F-G)(2'O,4'C-LNA-A) 15d was also isolated after purification in the reverse phase chromatography step as a white $TEAH^+$ salt after lyophilization (24.4 mg, 8%).

The overall reaction was repeated on a larger scale, and all four isomers, including compounds 15a and 15b were similarly isolated by HPLC from the last step. The isomer 2'3'-RR-(3'F-G)(2'O,4'C-LNA-A) 15a was isolated as a white $TEAH^+$ salt after lyophilization (60.8 mg, 2.9%). LCMS-ESI: 719.50 $[M-H]^-$ (calculated for $C_{21}H_{23}FN_{10}O_{10}P_2S_2$: 720.54); Rt: 5.946 min by LCMS conditions (20 mM $NH_4OAc$, 2% to 80%). $^1H$ NMR (400 MHz, 45° C., $D_2O$) δ 8.18 (s, 1H), 7.90 (s, 1H), 7.81 (s, 1H), 6.07 (s, 1H), 5.98 (d, J=8.0 Hz, 1H), 5.86-5.79 (m, 2H), 5.61 (d, J=56 Hz, 1H), 5.10 (s, 1H), 4.92 (s, 1H), 4.59 (s, 1H), 4.42-4.13 (m, 6H), 3.99 (d, J=8.0 Hz, 1H), 3.11 (q, J=8 Hz, 8H), 1.83 (s, 0.6H), 1.19 (t, J=8 Hz, 12H). $^{19}F$ NMR (400 MHz, 45° C., $D_2O$) δ −198.07 (s). $^{31}P$ NMR (45° C., $D_2O$) δ 55.25, 52.31.

The isomer 2'3'-RS-(3'F-G)(2'O,4'C-LNA-A) 15b was isolated as a white $TEAH^+$ salt after lyophilization (61 mg, 2.9%). LCMS-ESI: 719.55 $[M-H]^-$ (calculated for $C_{21}H_{23}FN_{10}O_{10}P_2S_2$: 720.54); Rt: 5.606 min by LCMS conditions (20 mM $NH_4OAc$, 2% to 80%). $^1H$ NMR (400 MHz, 45° C., $D_2O$) δ 8.17 (s, 1H), 8.09 (s, 1H), 7.86 (s, 1H), 6.08 (s, 1H), 6.00 (d, J=12.0 Hz, 1H), 5.74-5.67 (m, 2H), 5.54 (d, J=52 Hz, 1H), 5.27 (s, 1H), 4.88 (s, 1H), 4.61 (s, 1H), 4.36-4.30 (m, 2H), 4.14-4.12 (m, 3H), 4.01 (d, J=8.0 Hz, 1H), 3.10 (q, J=8 Hz, 10H), 1.52-1.46 (t, J=8 Hz, 15). $^{19}F$ NMR (400 MHz, 45° C., $D_2O$) δ −199.63 (s). $^{31}P$ NMR (45° C., $D_2O$) δ 53.50, 53.15.

The isomer 2'3'-SR-(3'F-G)(2'O,4'C-LNA-A) 15c was isolated as a white $TEAH^+$ salt after lyophilization (63.4 mg, 3.1%). LCMS-ESI: 719.70 [M−H]$^−$ (calculated for $C_{21}H_{23}FN_{10}O_{10}P_2S_2$: 720.54); Rt: 5.573 min by LCMS conditions (20 mM $NH_4OAc$, 2% to 80%). $^1H$ NMR (400 MHz, 45° C., $D_2O$) δ 8.18 (s, 1H), 8.05 (s, 1H), 7.82 (s, 1H), 6.08 (s, 1H), 6.01 (d, J=8.0 Hz, 1H), 5.92-5.86 (m, 1H), 5.54 (d, J=52 Hz, 1H), 5.06 (d, J=4 Hz, 1H), 4.95 (s, 1H), 4.65 (s, 1H), 4.59 (s, 1H), 4.40-4.13 (m, 6H), 4.01 (d, J=8.0 Hz, 1H), 3.10 (q, J=8 Hz, 17H), 1.52-1.46 (t, J=8 Hz, 26H). $^{19}F$ NMR (400 MHz, 45° C., $D_2O$) δ −198.60 (s). $^{31}P$ NMR (45° C., $D_2O$) δ 55.38, 54.62.

The isomer 2'3'-SS-(3'F-G)(2'O,4'C-LNA-A) 15d was isolated as a white $TEAH^+$ salt after lyophilization (28.3 mg, 1.4%). LCMS-ESI: 719.50 [M−H]$^−$ (calculated for $C_{21}H_{23}FN_{10}O_{10}P_2S_2$: 720.54); Rt: 5.393 min by LCMS conditions (20 mM $NH_4OAc$, 2% to 80%). $^1H$ NMR (400 MHz, $D_2O$) δ 8.23 (s, 1H), 8.18 (s, 1H), 7.90 (s, 1H), 6.10 (s, 1H), 6.03 (d, J=8.0 Hz, 1H), 5.78-5.71 (m, 1H), 5.43 (d, J=52 Hz, 2H), 5.27 (s, 1H), 4.89 (s, 1H), 4.61 (s, 1H), 4.46 (m, 2H), 4.33 (d, J=12.0 Hz, 2H), 4.15 (d, J=8.0 Hz, 3H), 4.01 (d, J=8.0 Hz, 1H), 3.11 (q, J=8 Hz, 12H), 1.19 (t, J=8 Hz, 18H).). $^{19}F$ NMR (400 MHz, 45° C., $D_2O$) δ −199.83 (s). $^{31}P$ NMR (45° C., $D_2O$) δ 56.21, 53.88.

Example 5: Synthesis of 2'3'-RR-(3'H-A)(2'O,4'C-LNA-A) (21a) and 2'3'-RS-(3'H-A)(2'O,4'C-LNA-A) (21b)

2'3'-RR-(3'H-A)(2'O,4'C-LNA-A) (21a), also referred to as dithio-(Rp,Rp)-cyclic-[3'H-A(2',5')p-2'O,4'C-LNA-A(3',5')p]; and 2'3'-RS-(3'H-A)(2'O,4'C-LNA-A) (21b), also referred to as dithio-(Rp,Sp)-cyclic-[3'H-A(2',5')p-2'O,4'C-LNA-A(3',5')p], were prepared according to the following Scheme 5:

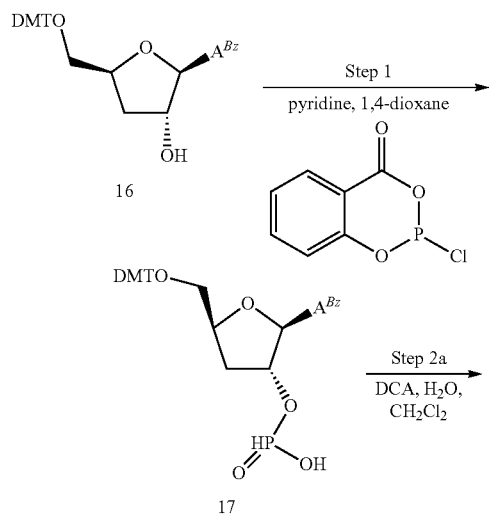

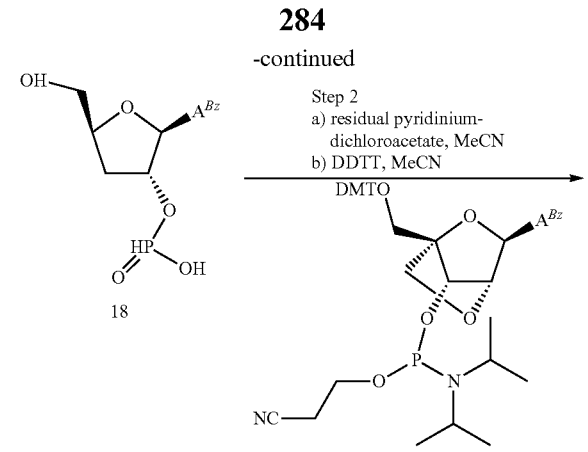

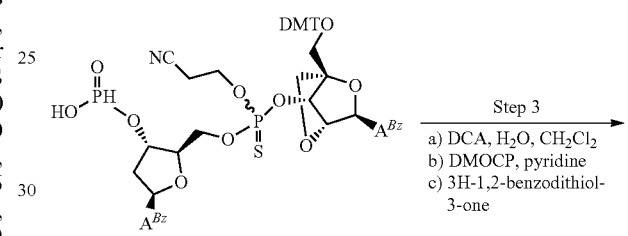

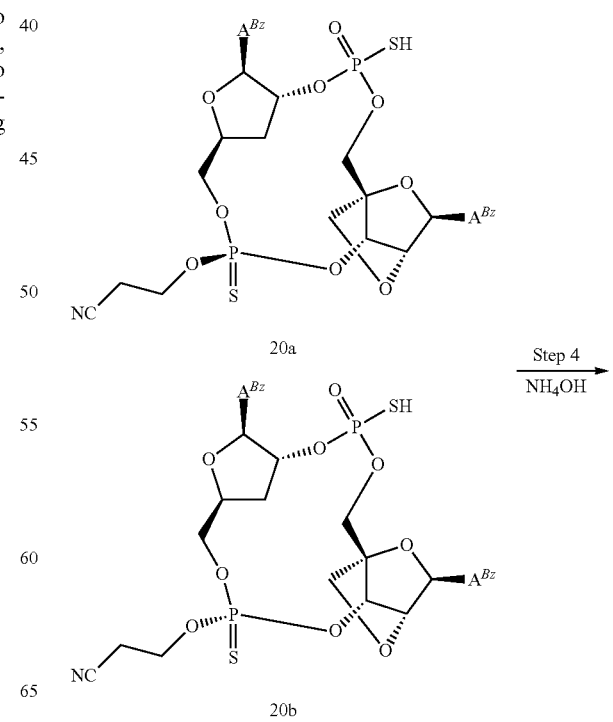

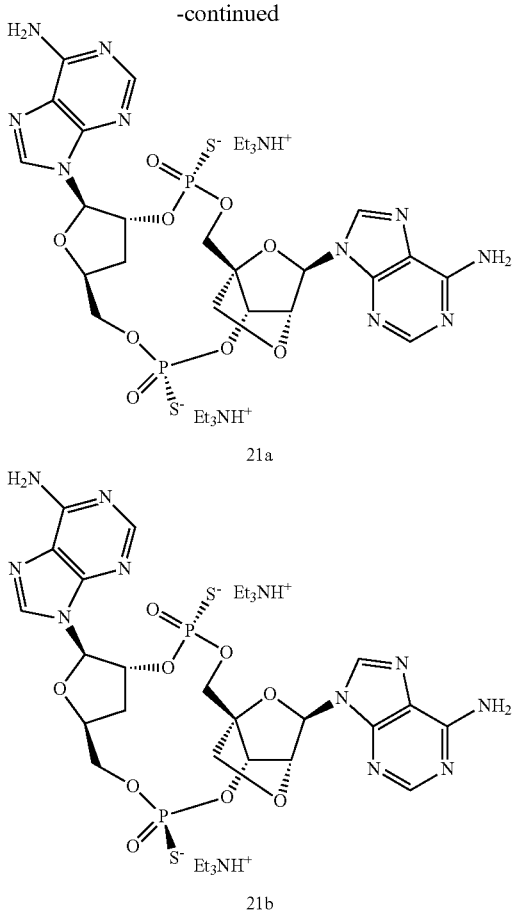

21a

21b

Step 1:

Preparation of (2R,3R,5S)-2-(6-benzamido-9H-purin-9-yl)-5-((bis(4-methoxyphenyl)(phenyl)methoxy)methyl)tetrahydrofuran-3-yl hydrogen phosphonate (17): To a solution of N-(9-((2R,3R,5S)-5-((bis(4-methoxyphenyl)(phenyl)methoxy)methyl)-3-hydroxytetrahydrofuran-2-yl)-9H-purin-6-yl)benzamide (16, 1.0 g, 1.5 mmole, 1 eq, Berry and Associates, Dexter, Mich.) in dioxane (12 mL) was added pyridine (3.2 mL, 40 mmole, 26 eq) followed by SalPCl (370 mg, 1.8 mmole, 1.2 eq). The reaction mixture is stirred for 1 h, then quenched with 10 mL of water followed by saturated NaHCO$_3$ solution (50 mL). The reaction mixture was extracted with EtOAc (3×50 mL), the combined organic layers were dried with Na$_2$SO$_4$, filtered and concentrated in vacuo. Purification by SiO$_2$ MPLC (DCM, MeOH and pyridine) gave 1.1 g of compound 17.

Step 2:

Preparation of (2R,3R,5R)-5-(6-benzamido-9H-purin-9-yl)-2-((((((1R,3R,4R,7R)-3-(6-benzamido-9H-purin-9-yl)-1-((bis(4-methoxyphenyl)(phenyl)methoxy)methyl)-2,5-dioxabicyclo[2.2.1]heptan-7-yl)oxy)(2-cyanoethoxy)phosphorothioyl)oxy)methyl)tetrahydrofuran-3-yl hydrogen phosphonate (19): Compound 1 (1.5 g, 1.6 mmole, 1.1 eq, Exiqon) was co-evaporated with anhydrous MeCN (3×20 mL) leaving 12 mL of MeCN. (Step 2a) To a solution of compound 17 (1.5 mmole, 1 eq) in DCM (20 mL) was added water (0.27 mL, 15 mmole, 10 eq) followed by 40 mL of 6% DCA in DCM solution. The reaction mixture was stirred for 20 min, then quenched with pyridine (4 mL, 50 mmole, 34 eq) and concentrated in vacuo to provide (2R,3R,5R)-2-(6-benzamido-9H-purin-9-yl)-5-(hydroxymethyl)tetrahydrofuran-3-yl hydrogen phosphonate (18). The crude mixture of compound 18 was co-evaporated with anhydrous MeCN (3×15 mL) leaving 4 mL of MeCN. The solution of compound 1 (1.5 g, Exiqon) in anhydrous MeCN (12 mL) was added to the solution of compound 18 in MeCN and stirred for 20 min. After the addition of DDTT (0.34 g, 1.6 mmole, 1.1 eq), the reaction mixture was stirred for 1 h then concentrated in vacuo to give 7.5 g of crude compound 19.

Step 3:

Preparation of Protected-dithio-2'3'-(3' H-A)(2'O,4'C-LNA-A) (20a, 20b): To a solution of crude compound 19 (7.5 g, 1.5 mmole, 1 eq) in DCM (37 mL) was added water (0.27 mL) followed by 74 mL of a 6% DCA in DCM solution. The reaction mixture was stirred for 30 min, then quenched with pyridine (30 mL). The mixture was condensed in vacuo to remove the DCM, then co-evaporated with anhydrous pyridine (30 mL) leaving 15 mL. DMOCP (0.82 g, 4.5 mmole, 3 eq) was added and stirred for 15 min followed by water (0.80 mL, 45 mmole, 30 eq) and immediately after with 3H-1,2-benzodithiol-3-one (0.38 g, 2.2 mmole, 1.5 eq). The reaction was allowed to proceed for 15 min and was poured into a saturated solution of NaHCO$_3$ (100 mL) then extracted with EtOAc (3×100 mL). The combined organic layers were concentrated in vacuo to give crude mixture of diastereomer compounds 20a and 20b. Prep MPLC-SiO$_2$ (100% DCM to 50% DCM/MeOH) gave 132 mg of compound 20a enriched in the RR diastereomer (LCMS) and 100 mg of 20b enriched in the RS diastereomers (LCMS).

Step 4:

Preparation of 2'3'-RR-(3'H-A)(2'O,4'C-LNA-A) (21a) and 2'3'-RS-(3'H-A)(2'O,4'C-LNA-A) (21b): To a solution of compound 20a (70 mg, 0.074 mmole, 1 eq) in MeOH (1.5 mL) was added concentrated NH$_4$OH (1.5 mL). The mixture was capped and stirred for 3 h at 50° C. The mixture was cooled to rt and concentrated in vacuo to give 60 mg of crude compound 21a. The reaction was purified using a prep-MPLC-C18 (100% 10 mM TEAA to 50% MeCN/10 mM TEAA) to give 19 mg of compound 21a (>95% pure) as the bis-TEAH$^+$ salt. LCMS-ESI: 685.80 [M−H]$^-$ (calculated for C$_{21}$H$_{24}$N$_{10}$O$_9$P$_2$S$_2$: 686.06); Rt: 7.2 min (2% to 50% MeCN in 20 mM NH$_4$OAc aqueous solution). $^1$H NMR. (400 MHz, 25° C., D$_2$O) δ 8.21 (s, 1H), 8.17 (s, 1H), 8.14 (s, 2H), 6.13 (s, 1H), 6.10 (d, J=4.0 Hz, 1H), 5.24-5.22 (m, 1H), 5.01 (s, 1H), 4.84 (d, J=4.4 Hz, 1H), 4.37-4.33 (m, 1H), 4.13-4.09 (m, 2H), 4.02-3.92 (m, 2H), 3.10 (q, J=7.2 Hz, 12H), 2.74-2.71 (m, 1H), 2.42-2.37 (m, 1H), 1.18 (t, J=7.6 Hz, 18H). $^{31}$P NMR (25° C., D$_2$O) δ 56.34, 53.89.

To a solution of compound 20b (100 mg, 0.11 mmole, 1 eq) in MeOH (1.5 mL) was added concentrated NH$_4$OH (1.5 mL). The mixture was capped and stirred for 3 h at 50° C. The mixture was cooled to rt and concentrated in vacuo to give 60 mg of crude compound 21b. The reaction was purified using a prep-MPLC-C18 (100% 10 mM TEAA to 50% MeCN/10 mM TEAA) to give 7 mg of compound 21b (>95% pure) as the bis-TEAH$^+$ salt. LCMS-ESI: 685.80 [M−H]$^-$ (calculated for C$_{21}$H$_{24}$N$_{10}$O$_9$P$_2$S$_2$: 686.06); R$_t$: 6.4 min (2% to 50% MeCN in 20 mM NH$_4$OAc aqueous solution). $^1$H NMR. (400 MHz, 25° C., D$_2$O) δ 8.44 (s, 1H), 8.42 (s, 1H), 8.24 (s, 1H), 8.22 (s, 1H), 6.21 (s, 1H), 6.15 (d, J=5.2 Hz, 1H), 5.39-5.36 (m, 1H), 5.32 (s, 1H), 5.03 (d, J=6.4 Hz, 1H), 4.73-4.69 (m, 1H), 4.43-4.33 (m, 2H), 4.24-4.16 (m, 4H), 3.19 (q, J=7.2 Hz, 12H), 1.27 (t, J=7.6 Hz, 18H). $^{31}$P NMR (25° C., D$_2$O) δ 54.68, 53.43.

The compounds 2'3'-RR-(3'H-BzA)(2'O,4'C-LNA-BzA) (22a) and 2'3'-RS-(3'H-BzA)(2'O,4'C-LNA-BzA) (22b) were prepared from the compounds 20a and 20b, respectively, from Step 3 of Scheme 4 as follows:

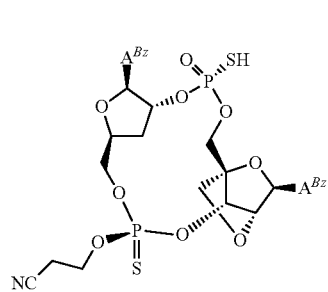

20a

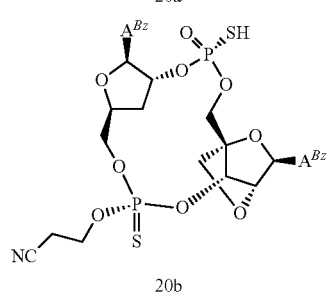

20b a) t-BuNH₂
b) HPLC

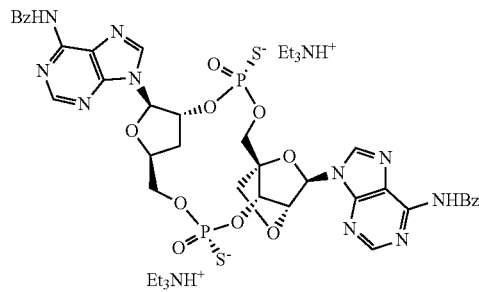

22a

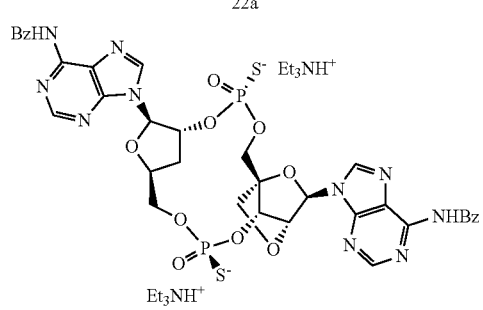

22b

To a solution of 20a (25 mg, 0.026 mmol, 1 eq) in MeCN (1 mL) was added tert-BuNH₂ (140 µL, 1.2 mmol, 48 eq). The reaction mixture was stirred for 15 min then concentrated in vacuo. The residue was taken up in anhydrous MeCN and co-evaporated to dryness twice. The reaction was purified using a prep-MPLC-C18 (10% to 50% MeCN/10 mM TEAA) to give 8 mg of compound 22a (>95% pure) as the bis-TEAH⁺ salt. LCMS-ESI: 895.8 [M+H]⁺ (calculated for $C_{35}H_{32}N_{10}O_{11}P_2S_2$: 894.12); $R_t$: 7.5 min (2% to 80% MeCN in 20 mM NH₄OAc aqueous solution). ¹H NMR. (400 MHz, 25° C., MeOD) δ 8.75 (s, 1H), 8.73 (s, 1H) 8.72 (s, 1H) 8.57 (s, 1H), 8.10 (d, J=7.2 Hz, 4H), 7.67 (t, J=8.0 Hz, 2H), 7.56 (t, J=7.2 Hz, 4H) 6.34 (d, J=2 Hz, 1H), 6.26 (s, 1H), 5.42-5.38 (m, 1H), 5.14 (s, 1H), 4.78 (d, J=4.0 Hz, 1H), 4.55-4.49 (m, 1H), 4.23 (d, J=7.6 Hz, 1H), 4.19-4.13 (m, 1H), 3.95-3.93 (m, 2H), 3.15 (q, J=7.6 Hz, 12H), 1.27 (t, J=7.6 Hz, 18H). ³¹P NMR (25° C., MeOD) δ 58.9, 55.7.

To a solution of 20b (26 mg, 0.027 mmol, 1 eq) in MeCN (1 mL) was added tert-BuNH₂ (140 µL, 1.2 mmol, 48 eq). The reaction mixture was stirred for 15 min then concentrated in vacuo. The residue was taken up in anhydrous MeCN and co-evaporated to dryness twice. The reaction was purified using a prep-MPLC-C18 (10% to 50% MeCN/10 mM TEAA) to give 8.1 mg of compound 22b (>95% pure) as the bis-TEAH⁺ salt. LCMS-ESI: 895.7 [M+H]⁺ (calculated for $C_{35}H_{32}N_{10}O_{11}P_2S_2$: 894.12); $R_t$: 7.43 min (2% to 80% MeCN in 20 mM NH₄OAc aqueous solution). ¹H NMR. (400 MHz, 25° C., MeOD) δ 8.92 (s, 1H), 8.75 (s, 1H), 8.73 (s, 1H), 8.71 (s, 1H), 8.10 (d, J=7.6 Hz, 4H), 7.65 (t, J=7.6 Hz, 2H), 7.55 (t, J=7.6 Hz, 4H), 6.34-6.26 (m, 2H), 5.5 (m, 1H), 5.37 (s, 1H), 5.05 (d, J=5.2 Hz, 1H), 4.64 (m, 1H), 4.44-4.3 (m, 2H), 4.30-4.10 (m, 4H), 4.02-3.98 (d, J=8, 1H), 3.08-3.07 (m, 12H), 1.27 (t, J=6.8 Hz, 18H).

Example 6: Synthesis of 2'3'-RR-(3'F-A)(2'O,4'C-LNA-A) (27a) and 2'3'-RS-(3'F-A)(2'O,4'C-LNA-A) (27b)

2'3'-RR-(3'F-A)(2'O,4'C-LNA-A) (27a), also referred to as dithio-(Rp,Rp)-cyclic-[3'F-A(2',5')p-2'O,4'C-LNA-A(3',5')p]; and 2'3'-RS-(3'F-A)(2'O,4'C-LNA-A) (27b), also referred to as dithio-(Rp,Sp)-cyclic-[3'F-A(2',5')p-2'O,4'C-LNA-A(3',5')p] were prepared according to the following Scheme 6:

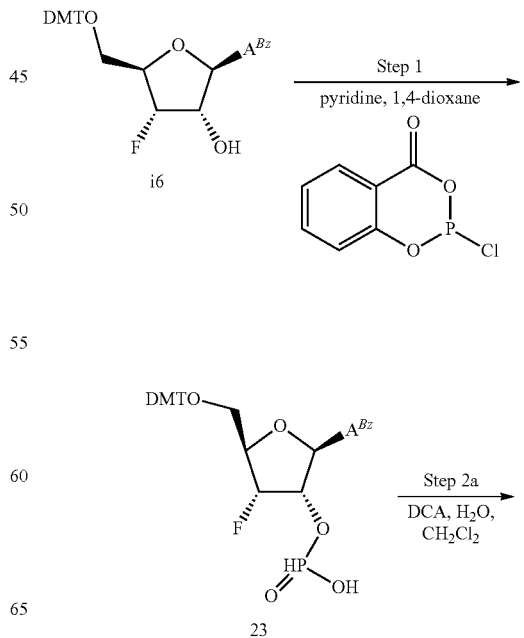

289
-continued

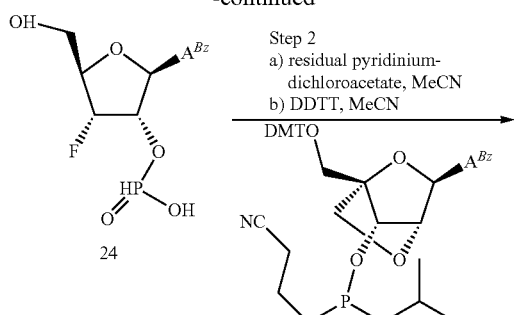

Step 2
a) residual pyridinium-dichloroacetate, MeCN
b) DDTT, MeCN

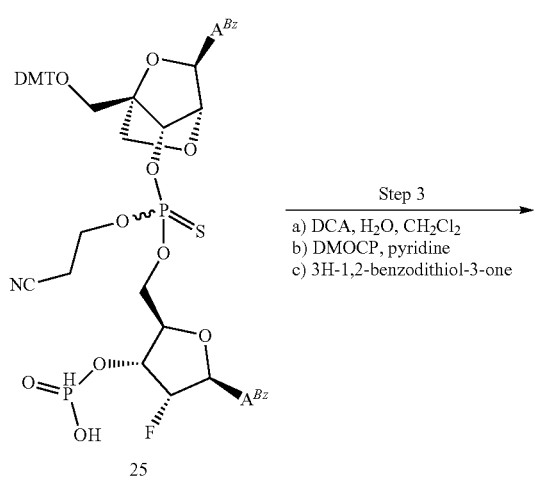

Step 3
a) DCA, H₂O, CH₂Cl₂
b) DMOCP, pyridine
c) 3H-1,2-benzodithiol-3-one

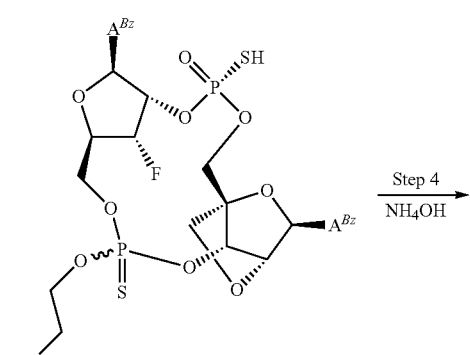

Step 4
NH₄OH

290
-continued

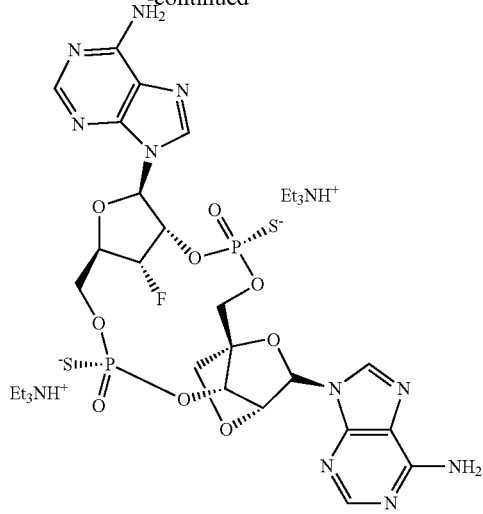

27a

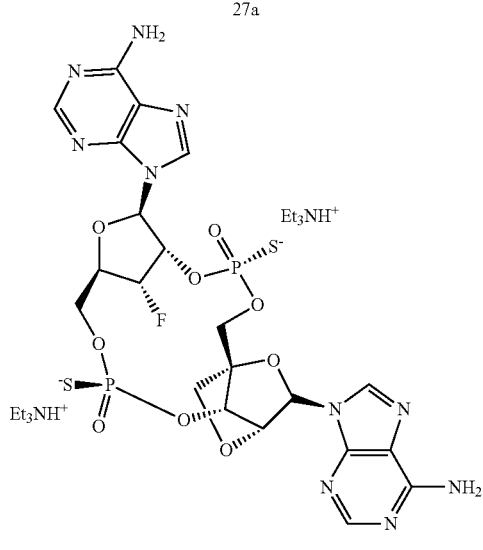

27b

Step 1:
Preparation of (2R,3S,4R,5R)-2-(6-benzamido-9H-purin-9-yl)-5-((bis(4-methoxyphenyl)(phenyl)methoxy)methyl)-4-fluorotetrahydrofuran-3-yl hydrogen phosphonate (23): To a solution of N-(9-((2R,3S,4S,5R)-5-((bis(4-methoxyphenyl)(phenyl)methoxy)methyl)-4-fluoro-3-hydroxytetrahydrofuran-2-yl)-9H-purin-6-yl)benzamide (i6, 1.1 g, 1.6 mmole, 1 eq, see Example 1) in dioxane (12.1 mL) was added pyridine (3.6 mL) followed by a solution of SalPCl (0.39 g, 1.9 mmole, 1.2 eq) in dioxane (6.6 mL). The reaction mixture was stirred for 2 h then quenched with 2.9 mL of water followed by 85 mL of a saturated NaHCO₃ solution. After extraction with EtOAc (55 mL) and DCM (55 mL), the organic layers were combined and concentrated in vacuo. The above conditions were repeated twice more giving 1.74 g of crude material, which was purified on Prep MPLC-SiO₂ (100% DCM to 50% 99.5:0.5 MeOH:pyridine in DCM) to give 1.04 g of compound 23.

Step 2:
Preparation of (2R,3S,4R,5R)-2-(6-benzamido-9H-purin-9-yl)-5-((((((1R,3R,4R,7S)-3-(6-benzamido-9H-purin-9- yl)-1-((bis(4-methoxyphenyl)(phenyl)methoxy)methyl)-2,5-dioxabicyclo[2.2.1]heptan-7-yl)oxy)(2-cyanoethoxy) phosphorothioyl)oxy)methyl)-4-fluorotetrahydrofuran-3-yl phosphonate (25): Compound 1 (1.0 g, 1.13 mmole, 1 eq, Exiqon) was co-evaporated with anhydrous MeCN (3×5 mL) leaving 3 mL of MeCN. (Step 2a) To a solution of compound 23 in DCM (1.04 g, 13.8 mL) was added water (0.207 mL) followed by 13.8 mL of a 6% DCA in DCM solution. The reaction was stirred for 10 minutes then quenched with pyridine (1.9 mL) and concentrated in vacuo to give (2R,3S,4R,5R)-2-(6-benzamido-9H-purin-9-yl)-4-fluoro-5-(hydroxymethyl)tetrahydrofuran-3-yl hydrogen phosphonate (24). The crude mixture of 24 was concentrated with anhydrous pyridine (2×2 mL) to remove the DCA, then co-evaporated with anhydrous MeCN (3×10 mL) leaving 5 mL of MeCN. The solution of compound 1 in 3 mL of anhydrous MeCN was added and the reaction stirred for 45 min. After the addition of DDTT (0.31 g), the reaction mixture was stirred for 90 min and concentrated in vacuo to give compound 25.

Step 3:

Preparation of Protected-dithio-2'3'-(3'F-A)(2'O,4'C-LNA-A) (26): To a solution of compound 25 in DCM (from step 2, 18 mL) was added water (0.203 mL) followed by 18 mL of a 6% DCA in DCM solution. The reaction mixture was stirred for 10 min and quenched with pyridine (12 mL). The mixture was concentrated in vacuo to remove the DCM, then co-evaporated with anhydrous pyridine (2×30 mL) leaving 20 mL. Anhydrous pyridine (50 mL) was added followed by DMOCP (0.77 g) and stirred for 15 min. Water (0.723 mL), immediately followed by 3H-1,2-benzodithiol-3-one (0.29 g), was added to the reaction. The reaction was allowed to proceed for 10 min, then was diluted with a 3% solution of NaHCO$_3$(170 mL) and extracted with EtOAc (2×200 mL). The combined organic layers were concentrated to give 8.02 g of material, which was purified on Prep MPLC-SiO$_2$ (100% DCM to 35% DCM/MeOH) to give 140 mg of compound 26 as a mixture of diastereomers.

Step 4:

Preparation of 2'3'-RR-(3'F-A)(2'O,4'C-LNA-A) (27a) and 2'3'-RS-(3'F-A)(2'O,4'C-LNA-A) (27b): To a solution of compound 26 (140 mg, 0.15 mmole, 1 eq) in MeOH (2.3 mL) was added concentrated NH$_4$OH (2.3 mL). The mixture was capped and heated to 50° C. for 3 h. The mixture was then cooled to rt, concentrated in vacuo to remove MeOH, and lyophilized to give 36 mg of the desired compounds as a mixture of diastereomers, which was purified using Prep MPLC-C18 (100% 10 mM TEAA to 25% MeCN/10 mM TEAA) to give 6.4 mg of compound 27a (>95% pure by LCMS) and 8.4 mg compound 27b (>95% pure) as the TEAH$^+$ salt.

Compound 27a: LCMS-ESI: 703.7. [M−H]$^−$ (Calculated for C$_{21}$H$_{23}$FN$_{10}$O$_9$P$_2$S$_2$: 704.54); $^1$H NMR (400 MHz, 25° C., D$_2$O) δ 8.22 (s, 1H), 8.06 (d, J=4.0, 1H), 8.03 (s, 1H), 6.15 (d, J=8.8, 1H), 6.08 (s, 1H), 5.6-5.46 (m, 1H), 5.37-5.30 (m, 1H), 5.23 (d, J=5.6, 1H), 5.04 (s, 1H), 4.56-4.50 (m, 1H), 4.30-4.26 (m, 2H), 4.15-4.10 (m, 4H). $^{19}$F NMR (400 MHz, 25° C., D$_2$O) δ −197.9-198.2, $^{31}$P NMR (25° C., D$_2$O) δ 55.2; 54.3.

Compound 27b: LCMS-ESI: 703.7. [M−H]$^−$ (Calculated for C$_{21}$H$_{23}$FN$_{10}$O$_9$P$_2$S$_2$: 704.54); $^1$H NMR (400 MHz, 25° C., D$_2$O) δ 8.39 (s, 1H), 8.29 (s, 1H), 8.17 (s, 1H), 6.25 (d, J=8.8, 1H), 6.19 (d, J=6.8, 1H), 5.74 (d, J=3.2, 1H), 5.61-5.47 (m, 1H), 5.27 (s, 1H), 5.20 (d, J=7.2, 1H), 4.29-4.22 (m, 4H), 4.14 (d, J=8.8, 2H). $^{19}$F NMR (400 MHz, 25° C., D$_2$O) δ −198.3-198.6, $^{31}$P NMR (25° C., D$_2$O) δ 54.5; 53.9.

Example 7: Synthesis of 3'3'-RR-(A)(2'O,4'C-LNA-G) (33a), 3'3'-RS-(A)(2'O,4'C-LNA-G) (33b), 3'3'-SR-(A)(2'O,4'C-LNA-G) (33c), and 3'3'-SS-(A) (2'O,4'C-LNA-G) (33d)

2-amino-9-((2R,3R,3aS,5R,7aR,9R,10R,10aS,12R,14aR)-9-(6-amino-9H-purin-9-yl)-10-hydroxy-5,12-dimercapto-5,12-dioxidohexahydro-2H,7H,14H-3,14a-(epoxymethano)difuro[3,2-d:3',2'-j][1,3,7,9]tetraoxa[2,8]diphosphacyclododecin-2-yl)-1,9-dihydro-6H-purin-6-one (33a), also referred to as 3'3'-RR-(A)(2'O,4'C-LNA-G), or dithio-(Rp, Rp)-cyclic-[A(3',5') p-2'O,4' C-LNA-G(3',5')p]; 2-amino-9-((2R,3R,3 aS,5S,7aR,9R,10R,10aS,12R,14aR)-9-(6-amino-9H-purin-9-yl)-10-hydroxy-5,12-dimercapto-5,12-dioxidohexahydro-2H,7H,14H-3,14a-(epoxymethano)difuro[3,2-d:3',2'-j][1,3,7,9]tetraoxa[2,8]diphosphacyclododecin-2-yl)-1,9-dihydro-6H-purin-6-one (33b), also referred to as 3'3'-RS-(A)(2'O,4'C-LNA-G), or dithio-(Rp,Sp)-cyclic-[A(3',5') p-2'O,4' C-LNA-G(3',5')p]; 2-amino-9-((2R,3R,3 aS,5R,7aR,9R,10R,10aS,12S,14aR)-9-(6-amino-9H-purin-9-yl)-10-hydroxy-5,12-dimercapto-5,12-dioxidohexahydro-2H,7H,14H-3,14a-(epoxymethano)difuro[3,2-d:3',2'-j][1,3,7,9]tetraoxa[2,8]diphosphacyclododecin-2-yl)-1,9-dihydro-6H-purin-6-one (33c), also referred to as 3'3'-SR-(A)(2'O,4'C-LNA-G), or dithio-(Sp,Rp)-cyclic-[A(3',5') p-2'O,4' C-LNA-G(3',5')p]; and 2-amino-9-((2R,3R,3 aS,5S,7aR,9R,10R,10aS,12S,14aR)-9-(6-amino-9H-purin-9-yl)-10-hydroxy-5,12-dimercapto-5,12-dioxidohexahydro-2H,7H,14H-3,14a-(epoxymethano)difuro[3,2-d:3',2'-j][1,3,7,9]tetraoxa[2,8]diphosphacyclododecin-2-yl)-1,9-dihydro-6H-purin-6-one (33d), also referred to as 3'3'-SS-(A)(2'O,4'C-LNA-G), or dithio-(Sp,Sp)-cyclic-[A(3',5')p-2'O,4'C-LNA-G(3',5')p], were prepared according to the following Scheme 7:

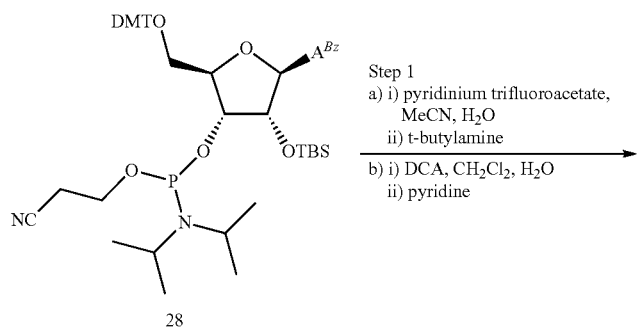

-continued
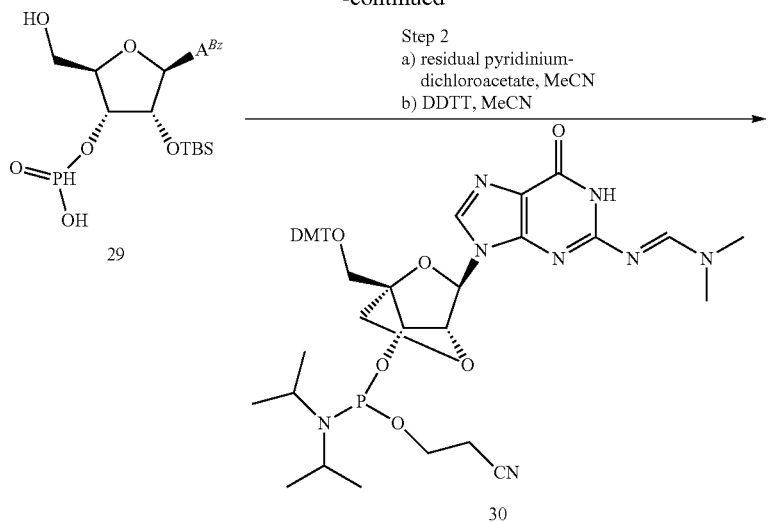
Step 2
a) residual pyridinium-dichloroacetate, MeCN
b) DDTT, MeCN
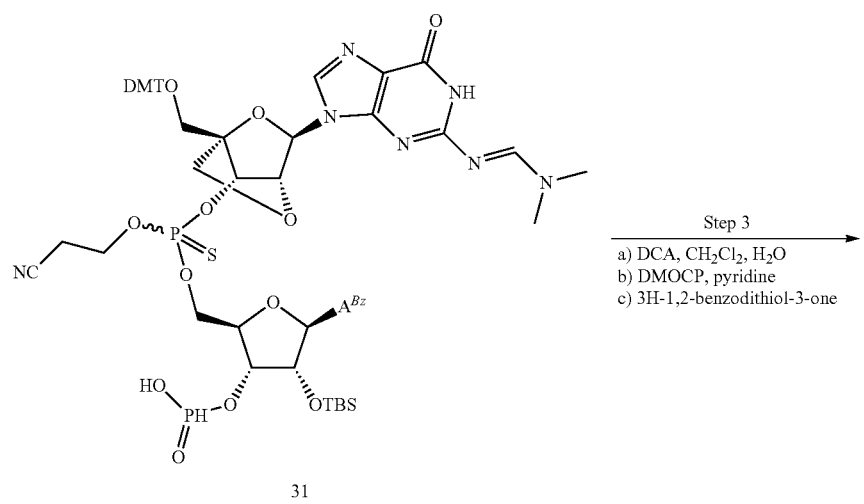
Step 3
a) DCA, CH$_2$Cl$_2$, H$_2$O
b) DMOCP, pyridine
c) 3H-1,2-benzodithiol-3-one
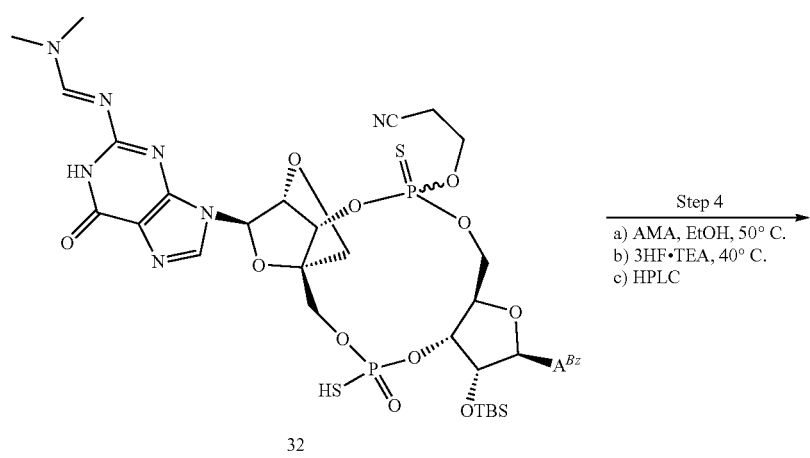
Step 4
a) AMA, EtOH, 50° C.
b) 3HF·TEA, 40° C.
c) HPLC -continued
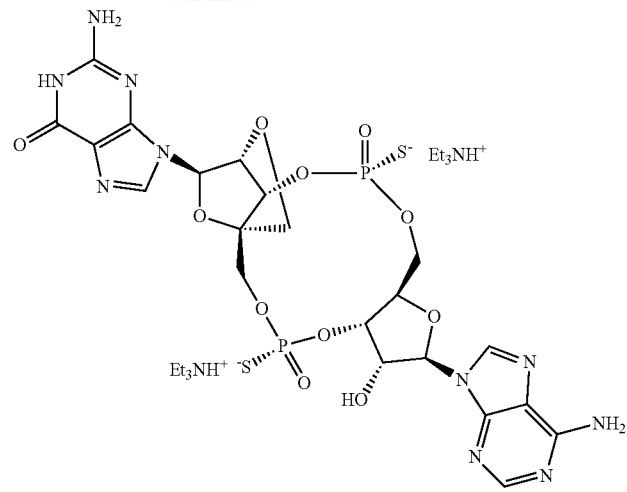
33a
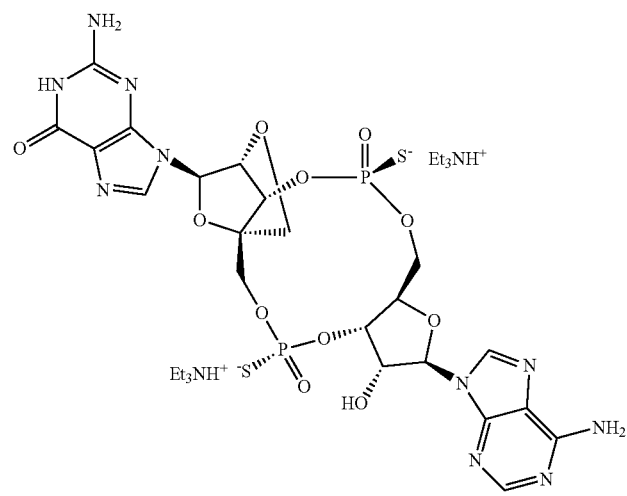
33b
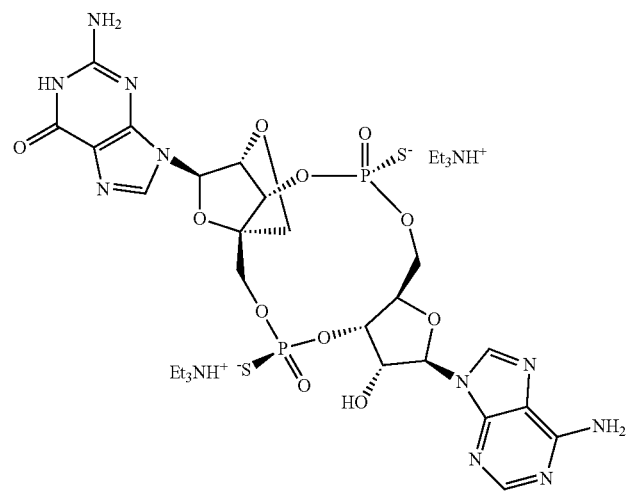
33c

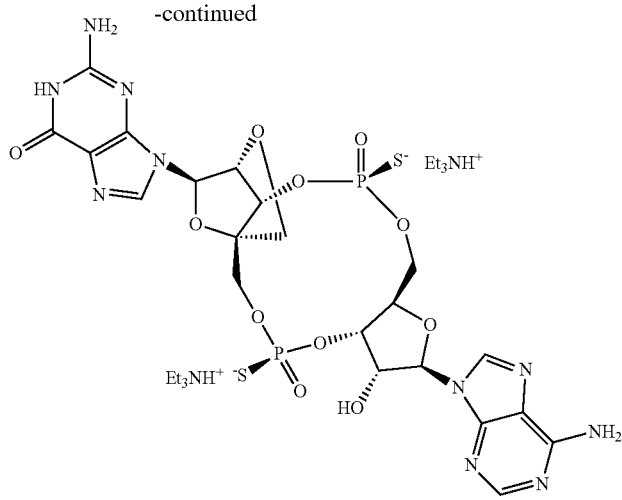

33d

Preparation of (2R,3R,4R,5R)-5-(6-benzamido-9H-purin-9-yl)-4-((tert-butyldimethylsilyl)oxy)-2-(hydroxymethyl) tetrahydrofuran-3-yl hydrogen phosphonate (29): To a solution of (2R,3R,4R,5R)-5-(6-benzamido-9H-purin-9-yl)-2-((bis(4-methoxyphenyl)(phenyl)methoxy)methyl)-4-((tert-butyldimethylsilyl)oxy)tetrahydrofuran-3-yl (2-cyanoethyl) diisopropylphosphoramidite (28, 0.99 g, 1.0 mmol, Chem-Genes) in MeCN (14 mL) and H₂O (100 µL) was added pyridinium trifluoroacetate (0.29 g, 1.5 mmol). After fifteen min, tert-butyl amine (5.0 mL, 47.6 mmol) was added with stirring at rt. After fifteen min, the reaction solution was concentrated in vacuo and water was removed as an azeotrope after concentration with MeCN (3×15 mL) to obtain a colorless foam. The colorless foam was dissolved in DCM (15 mL) to give a colorless solution. To this solution was added water (165 µL) and 9% (v/v) solution of DCA in DCM (10 mL). After ten min of stirring at rt, to the red solution was charged pyridine (1.5 mL). The resulting clear solution was concentrated in vacuo and water was removed as an azeotrope after concentration with MeCN (3×20 mL) to obtain a mixture of oil and solid. On the last evaporation, the resulting peach slurry of compound 29 was left in MeCN (25 mL).

Step 2:

Preparation of (2R,3R,4R,5R)-5-(6-benzamido-9H-purin-9-yl)-2-((((((1R,3R,4R,7S)-1-((bis(4-methoxyphenyl)(phenyl)methoxy)methyl)-3-(2-(((E)-(dimethylamino)methylene)amino)-6-oxo-1,6-dihydro-9H-purin-9-yl)-2,5-dioxabicyclo[2.2.1]heptan-7-yl)oxy)(2-cyanoethoxy)phosphorothioyl)oxy)methyl)-4-((tert-butyldimethylsilyl)oxy)tetrahydrofuran-3-yl hydrogen phosphonate (31): To a solution of (1R,3R,4R,7S)-1-((bis(4-methoxyphenyl)(phenyl)methoxy)methyl)-3-(2-(((E)-(dimethylamino)methylene)amino)-6-oxo-1,6-dihydro-9H-purin-9-yl)-2,5-dioxabicyclo[2.2.1]heptan-7-yl (2-cyanoethyl) diisopropylphosphoramidite (30, 1.0 g, 1.17 mmol, Exiqon, Woburn, Mass.) in MeCN (20 mL) was dried through concentration in vacuo. This process was repeated two more times to remove water as an azeotrope. On the last azeotrope, to the solution of compound 30 in MeCN (10 mL) was introduced ten 3A molecular sieves and the solution was stored under an atmosphere of nitrogen. To a stirred mixture of compound 29 with residual pyridin-1-ium dichloroacetate in MeCN (25 mL) was added the solution of compound 30 in MeCN (10 mL). After one h, to the stirred mixture was added DDTT (249 mg, 1.2 mmol). After one h, the yellow mixture was concentrated in vacuo to give compound 31 as a yellow paste.

Step 3:

Preparation of N-(9-((2S,3R,3aS,7aR,9R,10R,10aR,14aR)-10-((tert-butyldimethylsilyl)oxy)-5-(2-cyanoethoxy)-2-(2-(((E)-(dimethylamino)methylene)amino)-6-oxo-1,6-dihydro-9H-purin-9-yl)-12-mercapto-12-oxido-5-sulfidohexahydro-2H,7H,14H-3,14a-(epoxymethano)difuro[3,2-d:3',2'-j][1,3,7,9]tetraoxa[2,8]diphosphacyclododecin-9-yl)-9H-purin-6-yl)benzamide (32): To a solution of compound 31 in DCM (20 mL) was added water (180 µL) and 10% (v/v) solution of DCA in DCM (20 mL). After 10 min at rt, to the red solution was introduced pyridine (71 mL). The resulting yellow solution was concentrated in vacuo until approximately 20 mL of the yellow mixture remained. To the yellow mixture was introduced pyridine (17 mL) and the mixture was concentrated in vacuo until approximately 5 mL of the yellow mixture remained. To the yellow mixture was added pyridine (20 mL) and the mixture was concentrated in vacuo until approximately 5 mL of the yellow mixture remained. To the remaining mixture was added 35 mL of pyridine. To the stirred yellow mixture in pyridine (40 mL) was added DMOCP (598 mg, 3.2 mmol). After 20 min, to the brownish yellow solution was added water (700 µL), followed immediately by the introduction of 3H-1,2-benzodithiol-3-one (271 mg, 1.6 mmol). After 45 min, the brownish yellow solution was poured into a 1N aqueous NaHCO₃ solution (200 mL). After 30 min, the biphasic mixture was extracted with EtOAc (200 mL). After separation, the aqueous layer was back extracted with EtOAc (2×150 mL), and DCM (1×150 mL). The organic extracts were combined and concentrated in vacuo. The resulting oil was purified by silica gel chromatography (0% to 60% MeOH in DCM) to provide different fractions of compound 32 and impurities (921 mg, 88% yield) as a yellow paste.

Step 4:

Preparation of 3'3'-RR-(A)(2'O,4'C-LNA-G) (33a): To stirred solutions of each fraction of compound 32 (921 mg, 0.88 mmol) in EtOH (7.5 mL) were added aqueous NH₄OH and methyl amine (15 mL) and each yellow solution was heated at 50° C. After 2 h, the clear solution was allowed to cool and concentrated in vacuo. To the residual was added water and lyophilized. To the residual solid (551 mg, 0.6 mmol) was introduced triethylamine trihydrofluoride (6.5 mL) and the yellow solution was heated to 40° C. After 3 h, the yellow solution was allowed to cool to rt. This yellow solution was slowly added to a cooled solution of 1M TEAB (22.5 mL) and TEA (5.5 mL). The yellow mixture was allowed to stir for one h. The clear paste residue was purified by reverse phase silica gel chromatography (0% to 100% MeCN in 10 mM aqueous TEAA) to isolate compounds 33a, 33b, 33c and 33d. The compound 33a (35 mg, 10% yield) was obtained as a white TEAH$^+$ salt after lyophilization. LCMS-ESI: 717.80 [M–H]$^-$ (calculated for $C_{21}H_{24}N_{10}O_{11}P_2S_2$: 718.55); R$_t$: 6.89 min by LCMS conditions (MeCN in 20 mM NH$_4$OAc, 2% to 50%). $^1$H NMR. (400 MHz, 45° C., D$_2$O) δ 8.33 (s, 1H), 8.13 (s, 1H), 7.81 (s, 1H), 6.10 (s, 1H), 5.93 (s, 1H), 4.99 (d, J=8 Hz, 1H), 4.89 (m, 1H), 4.65 (s, 1H), 4.40-4.34 (m, 2H), 4.07-4.02 (m, 2H), 3.95 (d, J=8 Hz, 1H), 3.10 (q, J=8 Hz, 8H), 1.83 (s, 1H), 1.18 (t, J=8 Hz, 11H). $^{31}$P NMR (45° C., D$_2$O) δ 54.73, 54.49.

The Rp,Sp isomer was also isolated after purification in the reverse phase chromatography step, to provide compound 33b (45 mg, 13%) as the bis-TEAH$^+$ salt after lyophilization. LCMS-ESI: 717.80 [M–H]$^-$ (calculated for $C_{21}H_{24}N_{10}O_{11}P_2S_2$: 718.55); R$_t$: 6.02 min by LCMS conditions (MeCN in 20 mM NH$_4$OAc, 2% to 50%). $^1$H NMR. (400 MHz, 45° C., D$_2$O) δ 8.48 (s, 1H), 8.13 (s, 1H), 7.97 (s, 1H), 6.11 (s, 1H), 5.94 (s, 1H), 4.96 (s, 1H), 4.91-4.85 (m, 2H), 4.61 (d, J=4 Hz, 1H) 4.38-4.28 (m, 3H), 4.09-3.96 (m, 3H), 3.08 (q, J=8 Hz, 14H), 1.84 (s, 1H), 1.16 (t, J=8 Hz, 20H). $^{31}$P NMR (45° C., D$_2$O) δ 55.93, 54.61.

The Sp,Sp isomer was also isolated after purification in the reverse phase chromatography step, to provide compound 33d (10.3 mg, 3%) as the bis-TEAH$^+$ salt after lyophilization. LCMS-ESI: 717.80 [M–H]$^-$ (calculated for $C_{21}H_{24}N_{10}O_{11}P_2S_2$: 718.55); R$_t$: 5.49 min by LCMS conditions (MeCN in 20 mM NH$_4$OAc, 2% to 50%). $^1$H NMR. (400 MHz, 45° C., D$_2$O) δ 8.41 (s, 1H), 8.07 (s, 1H), 8.05 (s, 1H), 6.06 (s, 1H), 5.83 (s, 1H), 4.91 (s, 1H), 4.84-4.77 (m, 3H), 4.35-4.33 (m, 1H), 4.24 (m, 2H), 4.07-4.01 (m, 3H), 3.99-3.91 (m, 1H), 3.04 (q, J=8 Hz, 16H), 1.80 (s, 2H), 1.11 (t, J=7.2 Hz, 24H). $^{31}$P NMR (45° C., D$_2$O) δ 56.0, 54.98.

Example 8: Synthesis of 2'3'-RR-(3'βF-A)(2'O, 4'LNA-A) (37a), 2'3'-RS-(3'βF-A)(2'O,4'LNA-A) (37b), 2'3'-SR-(3'βF-A)(2'O,4'LNA-A) (37c), and 2'3'-SS-(3'βF-A)(2'O,4'LNA-A) (37d)

2'3'-RR-(3'βF-A)(2'O,4'LNA-A) (37a) also referred to as dithio-(R$_P$,R$_P$)-cyclic-[3'βF-A(2',5')p-2'O,4'C-LNA-A(3',5')p]; 2'3'-RS-(3'βF-A)(2'O,4'LNA-A) (37b) also referred to as dithio-(R$_P$,S$_P$)-cyclic-[3'βF-A(2',5')p-2'O,4'C-LNA-A(3',5')p]; 2'3'-SR-(3'βF-A)(2'O,4'LNA-A) (37c) also referred to as dithio-(Sp,Rp)-cyclic-[3'βF-A(2',5')p-2'O,4'C-LNA-A(3',5')p], and 2'3'-SS-(3'βF-A)(2'O,4'LNA-A) (37d) also referred to as dithio-(S$_P$,S$_P$)-cyclic-[3'βF-A(2',5')p-2'O,4'C-LNA-A(3',5')p], were prepared according to the following Scheme 8:

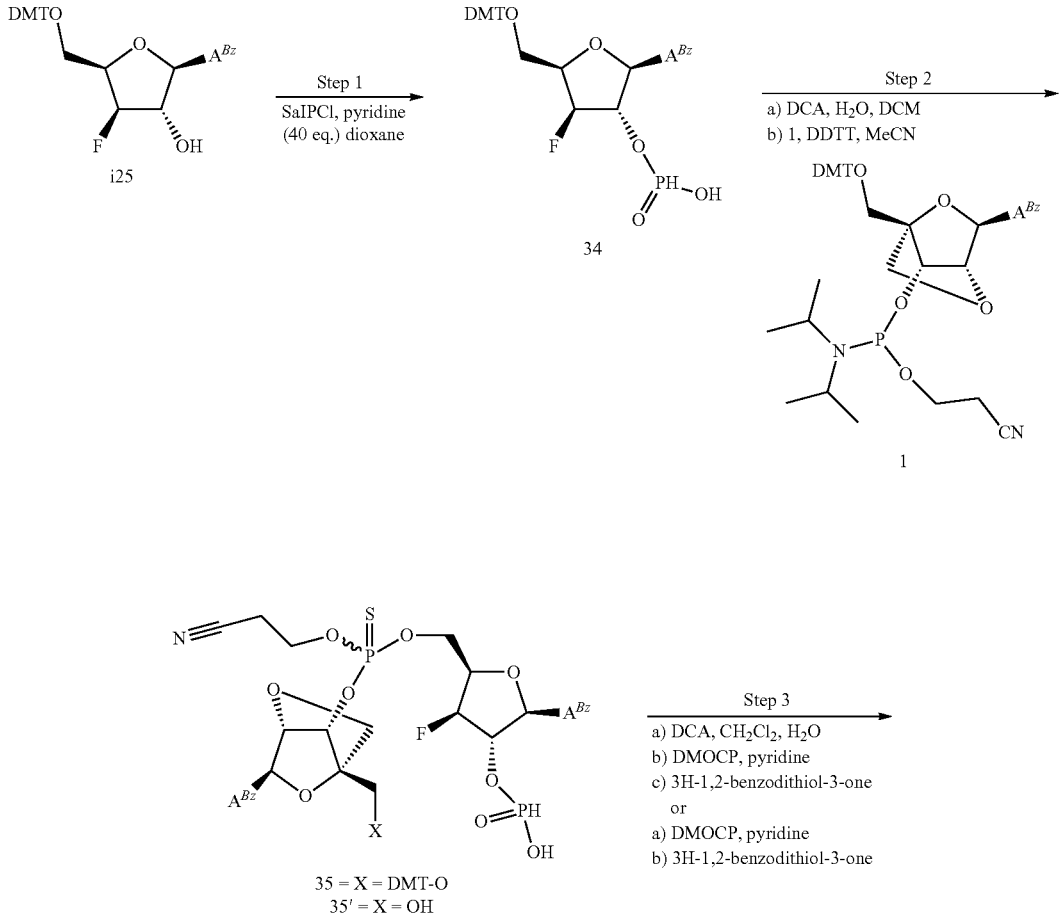

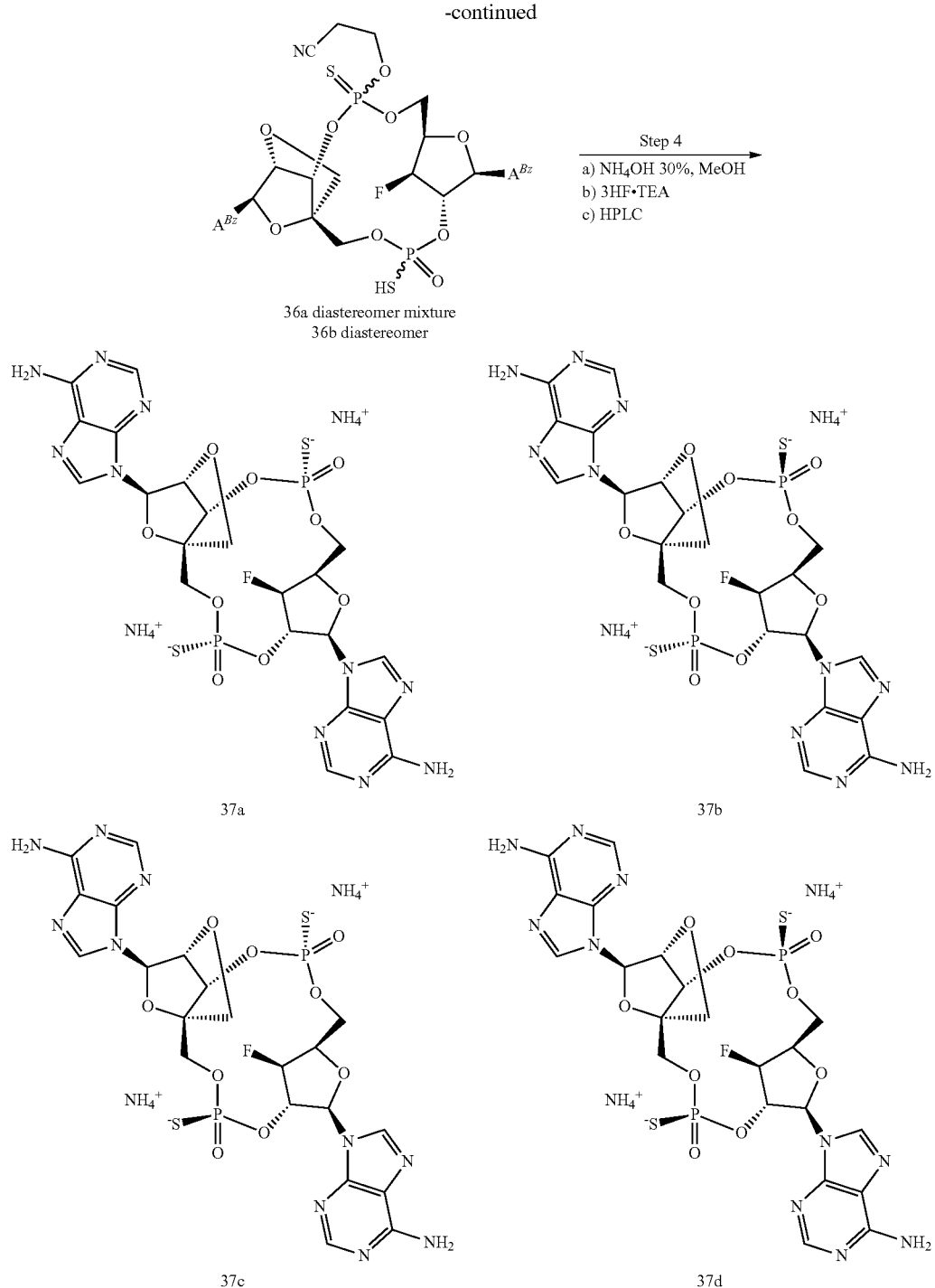

36a diastereomer mixture
36b diastereomer

Step 4
a) NH₄OH 30%, MeOH
b) 3HF·TEA
c) HPLC

37a

37b

37c

37d

Step 1:

Preparation of (2R,3S,4S,5R)-2-(6-benzamido-9H-purin-9-yl)-5-((bis(4-methoxyphenyl)(phenyl)methoxy)methyl)-4-fluorotetrahydrofuran-3-yl hydrogen phosphonate (34): To a solution of compound i25 (2.0 g, 3.0 mmol, per Example 1, Scheme 1C) in a mixture of anhydrous dioxane (10 mL) and pyridine (12 mL) was added dropwise a solution of SalPCl (780 mg, 3.90 mmol, Sigma Aldrich) in dioxane (5 mL). After 5 h of stirring, water (3.0 mL) was added and the reaction mixture was poured into a 1N aqueous NaHCO₃, then extracted with EtOAc (×3). The combined organic layers were dried (Na₂SO₄), filtered, the solvent removed in vacuo and the resulting oil purified by chromatography on silica gel (gradient elution 0% to 30% MeOH/DCM) to provide unreacted starting material (270 mg) and compound 34 as a white solid (1.67 g): $^1$H NMR (400 MHz, DMSO-$d_6$) δ 11.21 (s, 1H), 8.76 (s, 1H), 8.26 (s, 1H), 8.10-7.93 (m, 2H), 7.72-7.61 (m, 1H), 7.61-7.50 (m, 2H), 7.50-7.34 (m, 3H), 7.35-7.15 (m, 7H), 6.94-6.73 (m, 4H), 6.25 (d, J=2.3 Hz, 1H), 5.98 (s, 1H), 5.40 (ddd, J=51.2, 3.3, 1.4 Hz, 1H), 5.23 (ddd, J=16.0, 9.7, 2.2 Hz, 1H), 4.65-4.44 (m, 1H), 3.72 (d, J=2.8 Hz, 6H), 3.44-3.30 (m, 2H overlapped with H₂O); $^{19}$F NMR (376 MHz, DMSO) δ −199.22; $^{31}$P NMR (162 MHz, DMSO) δ 0.14; LCMS (Method C) $R_t$: 2.20 min; m/z 740.3 [M+H]$^+$.

Step 2:

Preparation of (2R,3S,4S,5R)-2-(6-benzamido-9H-purin-9-yl)-5-((((((1R,3R,4R,7S)-3-(6-benzamido-9H-purin-9-yl)-1-((bis(4-methoxyphenyl)(phenyl)methoxy)methyl)-2,5-dioxabicyclo[2.2.1]heptan-7-yl)oxy)(2-cyanoethoxy)phosphorothioyl)oxy)methyl)-4-fluorotetrahydrofuran-3-yl hydrogen phosphonate (35): To a cooled 0° C. solution of compound 34 (810 mg, 1.1 mmol) in DCM (15 mL) was added water (0.17 mL) followed by dropwise addition of a solution of v/v 12% of DCA in DCM (5.0 mL). After completion of the addition the ice bath was removed and the red solution was stirred at rt. After 1 h the reaction mixture was quenched with the addition of pyridine (1.5 mL) and then the solvents were removed in vacuo. The resulting oil was azeotroped in vacuo using MeCN (3×50 mL) to give crude (2R,3S,4S,5R)-2-(6-benzamido-9H-purin-9-yl)-4-fluoro-5-(hydroxymethyl)tetrahydrofuran-3-yl hydrogen phosphonate (474 mg, 1.08 mmol, crude): LCMS (Method B) $R_t$: 0.58 min; m/z 438.1 [M+H]$^+$. Compound 1 (1.15 g, 1.3 mmol, Exiqon) was dried by azeotroping in vacuo with MeCN (3×75 mL) before dissolution in anhydrous MeCN (5 mL) and addition to a stirred solution of the above formed crude phosphonate (474 mg, 1.08 mmol) in MeCN (5 mL). The resultant reaction mixture was stirred at rt for 1 h. Analysis of an aliquot indicated expected intermediates: LCMS (Method B) $R_t$: 3.63 min and 3.65 min; m/z 1222.5 [M+H]$^+$. DDTT (289 mg, 1.4 mmol, 1.3 eq) was subsequently added and after 45 min the reaction mixture was concentrated in vacuo to give compound 35 as a crude mixture. The crude mixture was purified by chromatography on silica gel (gradient elution 0% to 20% MeOH/DCM with 0.15% of triethylamine) to give compound 35 (440 mg, 0.35 mmol), LCMS (Method B) $R_t$: 3.64 min and 3.71 min; m/z 1254.5 and 1254.4 [M+H]$^+$; and compound 35' (240 mg, 0.25 mmol), having the DMT protecting group removed, LCMS (Method B) $R_t$: 1.96 min and 2.02 min; m/z 952.3 and 952.4 [M+H]$^+$.

Step 3:

Preparation of protected-dithio-2'3'-(3'βF-A)(2'O,4'LNA-A) (36a/36b): Starting with compound 35', to a solution of compound 35' (240 mg, 0.25 mmol) in 40 mL of dry pyridine was added DMOCP (93 mg, 0.5 mmol) and the reaction mixture stirred for 1 h at rt. Distilled water (70 µL) was added, followed immediately by the addition of 3H-1,2-benzodithiol-3-one (84 mg, 0.5 mmol) and the reaction mixture stirred overnight. The reaction mixture was quenched by addition to a solution of 1N aq. NaHCO$_3$, stirred for 15 min, then extracted with EtOAc (×3). The combined organic layers were dried (Na$_2$SO$_4$), filtered and the filtrate solvent removed in vacuo. The residue was treated with toluene (2×20 mL) then MeCN (2×25 mL) to remove the excess pyridine until the oily mixture became a white gummy precipitate. The white precipitate was filtered off and washed with MeCN. The combined filtrates were evaporated in vacuo to yield an oil which was further triturated with DCM to give a precipitate of the crude desired cyclized products as a mixture of diastereoisomers: LCMS (Method B) $R_t$: 2.35 min and 2.58 min; m/z 966.2 and 966.4 [M+H]$^+$. Alternatively starting with compound 35, to a 0° C. cooled solution of compound 35 (500 mg, 0.4 mmol) in DCM (10 mL) was added water (50 µL) followed by v/v 12% DCA in DCM solution (2 mL). The ice bath was removed once addition was complete, and the reaction mixture stirred for 1 h before it was quenched with pyridine (1 mL). The mixture was concentrated in vacuo to remove the solvent, then azeotroped in vacuo with MeCN (2×10 mL), then anhydrous pyridine (2×30 mL). The later solution was reduced to 20 mL, then diluted with additional pyridine (20 mL) to a total volume of ~50 mL, before DMOCP (221 mg, 1.2 mmol) was added. The reaction mixture was stirred for 1 h before water (120 µL) was added, which was immediately followed by addition of 3H-1,2-benzodithiol-3-one (101 mg, 0.60 mmol). The reaction was stirred for 2 h before it was partitioned between 1N NaHCO$_3$ (100 mL) and EtOAc, and extracted with EtOAc (3×20 mL). The combined organic layers were concentrated in vacuo to give a viscous amber oil. This was azeotroped in vacuo with MeCN (4×100 mL) and the resulting material was triturated with MeCN to give a light beige solid which was triturated again with DCM to yield the desired cyclized product mixture. This material was combined with previously obtained crude cyclized product and purified by chromatography on silica gel (gradient elution 0% to 20% MeOH/DCM) to give compound mixture 36a (50 mg), LCMS (Method B) $R_t$: 2.31 min; m/z 966.3 [M+H]$^+$; and compound 36b (10 mg), $^{19}$F NMR (376 MHz, DMSO-d$_6$) δ −200.53; $^{31}$P NMR (162 MHz, DMSO-d$_6$) δ 64.70, 51.11; LCMS (Method B) $R_t$: 2.53 min; m/z 966.3 [M+H]$^+$.

Step 4:

Preparation of 2'3'-RR-(3'βF-A)(2'O,4'LNA-A) (37a); 2'3'-RS-(3'βF-A)(2'O,4'LNA-A), (37b); and 2'3'-SR-(3'βF-A)(2'O,4'LNA-A) (37c) ammonium salts: To a solution of compound mixture 36a (50 mg, 0.06 mmol) in EtOH (2 mL) was added AMA (ChemGenes, 1.2 mL) and the reaction mixture heated to 50° C. for 5 h. The mixture was then cooled to rt, concentrated in vacuo to remove the solvent, and purified using C18 reverse phase ISCO flash column with a C18Aq RediSepR$_f$ Gold cartridge 15.5 gm (eluting with a gradient 0-60% MeCN/15 mM of ammonium formate in water) to give 3 diastereoisomers: Compound 37a (white solid, 2.4 mg) $^1$H NMR (400 MHz, DMSO-d$_6$) δ 8.23 (d, J=10.7 Hz, 2H), 8.14 (d, J=9.2 Hz, 1H), 8.05 (s, 1H), 7.20 (d, J=2.9 Hz, 2H), 7.07 (d, J=3.0 Hz, 2H), 6.95 (d, J=3.0 Hz, 2H), 6.12 (s, 1H), 5.93 (s, 1H), 5.62 (d, J=50.4 Hz, 1H), 4.93 (d, J=7.4 Hz, 2H), 4.73 (d, J=12.7 Hz, 1H), 4.58-4.20 (m, 2H), 4.11-3.84 (m, 2H), 3.72 (dd, J=29.5, 10.0 Hz, 2H); $^{19}$F NMR (376 MHz, DMSO) δ −202.49; $^{31}$P NMR (162 MHz, DMSO) δ 56.07, 52.46; HRMS calculated for C$_{21}$H$_{24}$FN$_{10}$O$_9$P$_2$S$_2$: 705.0623 [M+H]$^+$ found 705.0624.

Compound 37b (white solid, 0.9 mg) $^1$H NMR (400 MHz, DMSO-d$_6$) δ 8.33 (d, J=2.2 Hz, 1H), 8.26 (dd, J=9.2, 2.3 Hz, 2H), 8.08 (d, J=2.6 Hz, 1H), 7.99-7.66 (m, 3H), 7.23 (d, J=9.1 Hz, 1H), 7.10 (d, J=9.1 Hz, 1H), 6.98 (d, J=9.3 Hz, 1H), 6.19 (s, 1H), 5.95 (d, J=7.7 Hz, 1H), 5.79-5.56 (m, 1H), 4.94 (dd, J=9.9, 4.2 Hz, 1H), 4.88 (s, 1H), 4.73 (t, J=12.0 Hz, 1H), 4.55-4.36 (m, 1H), 4.31 (d, J=4.3 Hz, 1H), 4.18 (dd, J=11.8, 2.9 Hz, 1H), 4.09-3.85 (m, 3H), 3.85-3.69 (m, 3H). $^{19}$F NMR (376 MHz, DMSO-d$_6$) δ −203.38; 31P NMR (162 MHz, DMSO) δ 55.85, 51.06; HRMS calculated for C$_{21}$H$_{24}$FN$_{10}$O$_9$P$_2$S$_2$: 705.0623 [M+H]$^+$ found 705.0619.

Compound 37c (white solid, 1.6 mg) $^1$H NMR (400 MHz, DMSO-$d_6$) δ 8.23 (d, J=10.7 Hz, 2H), 8.14 (d, J=9.2 Hz, 1H), 8.05 (s, 1H), 7.20 (d, J=2.9 Hz, 2H), 7.07 (d, J=3.0 Hz, 2H), 6.95 (d, J=3.0 Hz, 2H), 6.12 (s, 1H), 5.93 (s, 1H), 5.62 (d, J=50.4 Hz, 1H), 4.93 (d, J=7.4 Hz, 2H), 4.73 (d, J=12.7 Hz, 1H), 4.58-4.20 (m, 2H), 4.11-3.84 (m, 2H), 3.72 (dd, J=29.5, 10.0 Hz, 2H); $^{19}$F NMR (376 MHz, DMSO-$d_6$) δ −201.39; $^{31}$P NMR (162 MHz, DMSO) δ 52.63, 51.92; HRMS calculated for $C_{21}H_{24}FN_{10}O_9P_2S_2$: 705.0623 [M+H]$^+$ found 705.0624.

Preparation of 2'3'-SS-(3'βF-A)(LNA-A) compound (37d) ammonium salt: To a solution of compound 36b (10 mg, 10 mmol) in EtOH (1 mL) was added AMA (200 mL) and the reaction mixture heated to 50° C. for 5 h. The mixture was then cooled to rt, concentrated in vacuo to remove EtOH, and purified using $C_{18}$ reverse phase ISCO flash column with a $C_{18}$Aq RediSepR$_f$ Gold cartridge 15.5 gm (eluting with a gradient 0-60% MeCN/15 mM of ammonium formate in water) to give compound 37d (1.1 mg) $^1$H NMR (400 MHz, DMSO-$d_6$) δ 8.39 (s, 1H), 8.18 (d, J=11.9 Hz, 2H), 8.00 (s, 1H), 7.57-7.35 (m, 5H), 7.26 (s, 2H), 7.13 (s, 2H), 7.01 (s, 2H), 6.17 (s, 1H), 5.93 (s, 1H), 5.70 (d, J=49.7 Hz, 1H), 5.26 (s, 1H), 4.88 (dd, J=10.0, 4.1 Hz, 1H), 4.54-4.38 (m, 3H), 4.27-3.98 (m, 2H), 3.97-3.69 (m, 3H); $^{19}$F NMR (376 MHz, DMSO) δ −202.72; $^{31}$P NMR (162 MHz, DMSO) δ 51.76, 51.11; HRMS calculated for $C_{21}H_{24}FN_{10}O_9P_2S_2$: 705.0623 [M+H]$^+$ found 705.0655.

Example 9: Synthesis of 3'3'-RR-(G)(2'O,4'C-LNA-A) (45a) and 3'3'-RS-(G)(2'O,4'C-LNA-A) (45b)

2-amino-9-((2R,3R,3aS,5R,7aR,9R,10R,10aS,12R,14aR)-2-(6-amino-9H-purin-9-yl)-10-hydroxy-5,12-dimercapto-5,12-dioxidohexahydro-2H,7H,14H-3,14a-(epoxymethano)difuro[3,2-d:3',2'-j][1,3,7,9]tetraoxa[2,8]diphosphacyclododecin-9-yl)-1,9-dihydro-6H-purin-6-one (45a), also referred to as 3'3'-RR-(G)(2'O,4'C-LNA-A) or dithio-(Rp,Rp)-cyclic-[G(3',5')p-2'O,4'C-LNA-A(3',5')p] and 2-amino-9-((2R,3R,3aS,5S,7aR,9R,10R,10aS,12R,14aR)-2-(6-amino-9H-purin-9-yl)-10-hydroxy-5,12-dimercapto-5,12-dioxidohexahydro-2H,7H,14H-3,14a-(epoxymethano)difuro[3,2-d:3',2'-j][1,3,7,9]tetraoxa[2,8]diphosphacyclododecin-9-yl)-1,9-dihydro-6H-purin-6-one (45b), also referred to as 3'3'-RS-(G)(2'O,4'C-LNA-A) or dithio-(Rp,Sp)-cyclic-[G(3',5')p-2'O,4'C-LNA-A(3',5')p], were prepared according to the following Scheme 9:

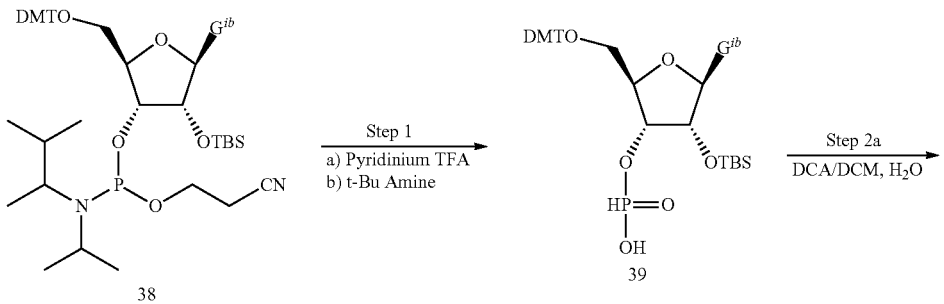

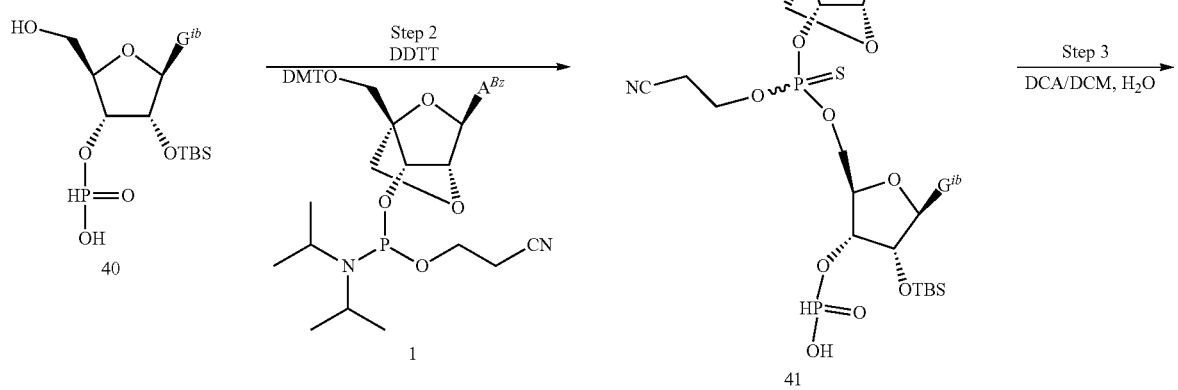

307 308

-continued

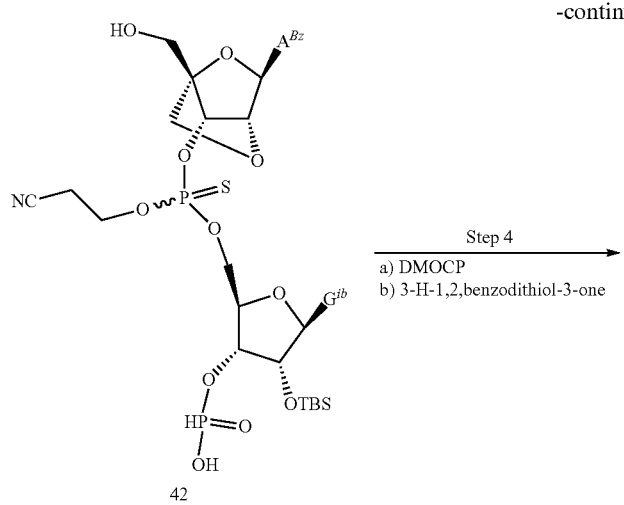

42

Step 4
a) DMOCP
b) 3-H-1,2,benzodithiol-3-one

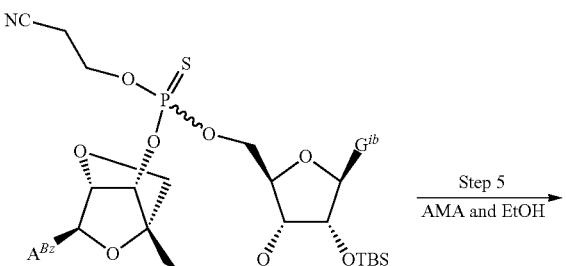

43

Step 5
AMA and EtOH

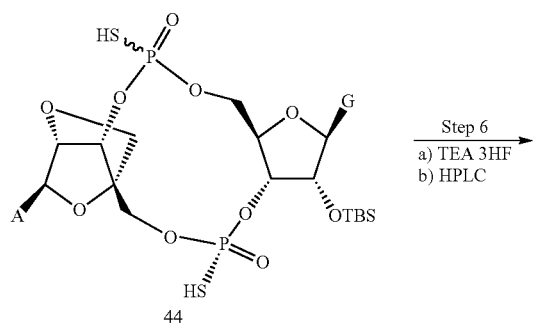

44

Step 6
a) TEA 3HF
b) HPLC

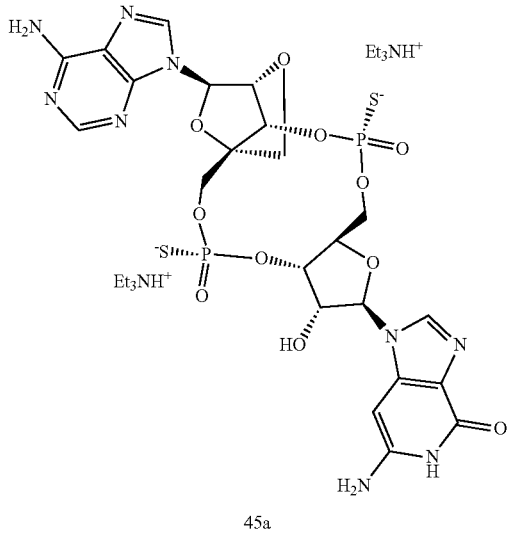

45a

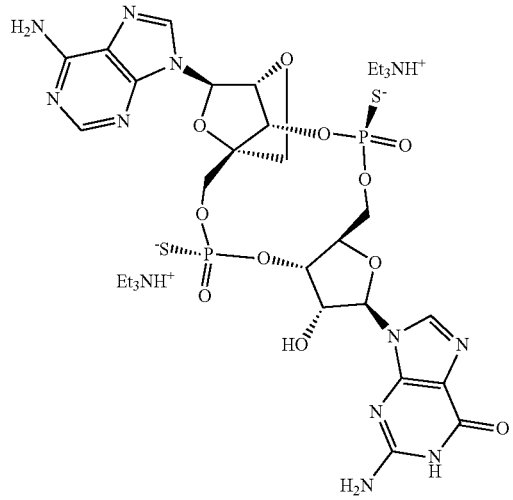

45b

Step 1:

Preparation of (2R,3R,4R,5R)-2-((bis(4-methoxyphenyl)(phenyl)methoxy)methyl)-4-((tert-butyldimethylsilyl)oxy)-5-(2-isobutyramido-6-oxo-1,6-dihydro-9H-purin-9-yl)tetrahydrofuran-3-yl phosphonate (39): To a solution of compound 38 (1.1 g, 1.13 mmole, 1 eq, ChemGenes) in MeCN (5.8 mL) was added water (0.040 mL) followed by pyridinium trifluoroacetate (0.26 g, 1.36 mmole, 1.2 eq). The reaction was stirred for 5 min and tert-Butyl amine (5.75 mL, 54.7 mmole, 48 eq) was added. After 10 min of stirring the reaction was concentrated in vacuo to give crude compound 39 used in the next step.

Step 2:

Preparation of (2R,3R,4R,5R)-2-(((((1R,3R,4R,7S)-3-(6-benzamido-9H-purin-9-yl)-1-((bis(4-methoxyphenyl)(phenyl)methoxy)methyl)-2,5-dioxabicyclo[2.2.1]heptan-7-yl)oxy)(2-cyanoethoxy)phosphorothioyl)oxy)methyl)-4-((tert-butyldimethylsilyl)oxy)-5-(2-isobutyramido-6-oxo-1,6-dihydro-9H-purin-9-yl)tetrahydrofuran-3-ylphosphonate (40): Compound 1 (1.0 g, 1.13 mmole, 1 eq, Exiqon) was coevaporated in vacuo with anhydrous MeCN (3×5 mL) leaving 3 mL of MeCN. To a solution of compound 39 in DCM (13.8 mL) was added water (0.207 mL) followed by 13.8 mL of a 6% DCA in DCM solution. The reaction was stirred for 10 min, then quenched with pyridine (1.9 mL) and concentrated in vacuo to give compound 40. The crude compound 40 was concentrated in vacuo with anhydrous pyridine (2×2 mL) to remove the DCA, then coevaporated in vacuo with anhydrous MeCN (3×10 mL) leaving 5 mL of MeCN. The solution of compound 1 (1.0 g) in anhydrous MeCN (3 mL) was added to compound 40 and stirred for 45 min. After the addition of DDTT (0.31 g), the reaction mixture was stirred for 90 min, then concentrated in vacuo to give compound 41.

Step 3:
Preparation of (2R,3R,4R,5R)-2-(((((1S,3R,4R,7S)-3-(6-benzamido-9H-purin-9-yl)-1-(hydroxymethyl)-2,5-dioxabicyclo[2.2.1]heptan-7-yl)oxy)(2-cyanoethoxy)phosphorothioyl)oxy)methyl)-4-((tert-butyldimethylsilyl)oxy)-5-(2-isobutyramido-6-oxo-1,6-dihydro-9H-purin-9-yl)tetrahydrofuran-3-yl hydrogen phosphonate (42): To a solution of compound 41 in DCM (18 mL) was added water (0.203 mL) followed by 18 mL of a 6% DCA in DCM solution. The reaction mixture was stirred for 10 min, then quenched with pyridine (12 mL). The mixture was concentrated in vacuo to remove the DCM, then coevaporated in vacuo with anhydrous pyridine (2×30 mL) leaving 20 mL of crude compound 42 for use in the next step.

Step 4:
Preparation of N-(9-((2R,3R,3aS,7aR,9R,10R,10aR,14aR)-10-((tert-butyldimethylsilyl)oxy)-5-(2-cyanoethoxy)-9-(2-isobutyramido-6-oxo-1,6-dihydro-9H-purin-9-yl)-12-mercapto-12-oxido-5-sulfidohexahydro-2H,7H,14H-3,14a-(epoxymethano)difuro[3,2-d:3',2'-j][1,3,7,9]tetraoxa[2,8]diphosphacyclododecin-2-yl)-9H-purin-6-yl)benzamide (43): Anhydrous pyridine (50 mL) was added to the solution of compound 42, followed by DMOCP (0.77 g) and the reaction was stirred for 15 min. Water (0.723 mL) was added, immediately followed by 3H-1,2-benzodithiol-3-one (0.29 g). The reaction was allowed to proceed for 10 min and was diluted with a 3% solution of NaHCO$_3$(170 mL) and extracted with EtOAc (2×200 mL). The combined organic layers were concentrated to give 8.02 g of crude compound 43. Prep MPLC-SiO$_2$ (100% DCM to 70% DCM/MeOH) gave 240 mg of 43 as a mixture of diastereomers.

Step 5:
Preparation of 2-amino-9-((2R,3R,3aS,7aR,9R,10R,10aR,14aR)-2-(6-amino-9H-purin-9-yl)-10-((tert-butyldimethylsilyl)oxy)-5,12-dimercapto-5,12-dioxidohexahydro-2H,7H,14H-3,14a-(epoxymethano)difuro[3,2-d:3',2'-j][1,3,7,9]tetraoxa[2,8]diphosphacyclododecin-9-yl)-1,9-dihydro-6H-purin-6-one (44): To a solution of compound mixture 43 (108 mg, 0.10 mmole, 1 eq) in EtOH (1.2 mL) was added AMA (2 mL). The mixture was capped and heated to 50° C. for 90 min. The mixture was then cooled to rt and concentrated in vacuo to give crude compound 44 as a mixture of diastereomers used in the next step.

Step 6:
Preparation of 3'3'-RR-(G)(2'O,4'C-LNA-A) (45a) and 3'3'-RS-(G)(2'O,4'C-LNA-A) (45b): To the crude mixture of compound 44 was added TEA 3HF (1.1 mL). The reaction was heated to 50° C. for 2 h. The mixture was poured into a solution of TEA and TEAB with stirring, then desalted and purified using a prep MPLC-C18 column (100% 10 mM TEAA to 30% MeCN/10 mM TEAA) to give 38 mg of a mixture of diastereomers. The crude mixture was then purified via prep HPLC (6-24% MeCN/10 mM TEAA) to give 2 mg of compound 45b (>95% purity by LCMS) and 9 mg of compound 45a (>95% pure). LCMS-ESI: 717.7. [M−H]$^-$ (Calculated for $C_{21}H_{24}FN_{10}O_{11}P_2S_2$).

Compound 45a: $^1$H NMR (400 MHz, 25° C., D$_2$O) δ 8.19 (s, 1H), 8.13 (s, 1H), 7.90 (s, 1H), 6.11 (s, 1H), 5.88 (d, J=2.0, 1H), 4.94-4.90 (m, 1H), 4.87 (s, J=8.8, 1H), 4.75-4.66 (m, 3H), 4.43-4.38 (m, 1H), 4.32-4.30 (m, 2H), 4.09-3.99 (m, 4.3H). $^{31}$P NMR (25° C., D$_2$O) δ 54.9.

Compound 45b: $^1$H NMR (400 MHz, 25° C., D$_2$O) δ 8.36 (s, 1H), 8.15 (s, 1H), 8.02 (s, 1H), 6.11 (s, 1H), 5.89 (d, J=2.0, 1H), 4.98 (s, 1H), 4.93-4.91 (m, 1H), 4.85 (s, J=11.2, 1H), 4.76-4.65 (m, 1H), 4.41-4.37 (m, 1H), 4.30 (d, J=8.0, 1H), 4.24-4.21 (m, 1H), 4.08-4.01 (m, 4.3H). $^{31}$P NMR (25° C., D$_2$O) δ 56.2; 54.6.

Example 10: In Vitro Binding Analysis of LNA-CDN Compounds with Purified STING Protein DNA encoding amino acids 140-379 (amino acid numbering corresponding to Swiss Prot Q86WV6) was amplified from plasmids containing the full length sequence of human STING alleles via polymerase chain reaction with the following primers: forward TACTTCCAATCCAATGCAGCCCCAGCTGAGATCTCTG (SEQ ID NO: 9) and reverse TTATCCACTTCCAATGTTATTATTATCAAGAGAAATCCGTGCGGAG (SEQ ID NO: 10). STING variant alleles were assigned according to $Y_1$, et al, (2013), PLoS One, 8(10), e77846 (DOI: 10.1371/journal.pone.0077846. PCR products were cloned into bacterial expression vector encoding a N-terminal hexa-histidine affinity tag (6×HIS) followed by a small ubiquitin-like modifier (SUMO) solubility sequence (Butt, et al, (2005) Protein expression and purification 43.1, 1-9) and tobacco etch virus protease cleavage site (TEV) using ligation independent cloning (Aslanidis, et al, (1990) Nucleic acids research, 18.20, 6069-6074).

Plasmids encoding 6×HIS-SUMO-TEV-STING amino acids 140-379 were transformed into Rosetta2 (DE3) *E. coli* cells (EMD Millipore) for protein expression. Cells were grown in lysogeny broth at 37° C. until a 600 nM absorbance of 0.6 was reached. Cells were then transferred to 18° C. and protein expression was induced overnight by the addition of isopropyl β-D-1-thiogalactopyranoside to the media at a concentration of 0.25 mM. Cells were harvested by centrifugation at 6,000 times gravity for 10 minutes. Cell pellets were re-suspended on ice in a buffer containing 50 mM Tris hydrochloride (Tris-HCl) pH 7.5, 500 mM sodium chloride (NaCl), 20 mM imidazole, 10% glycerol, 1 mM tris(2-carboxyethyl)phosphine hydrochloride (TCEP) and protease inhibitor tablet (Pierce) (Buffer A). Cells were lysed using an S-450D sonifier (Emmerson industrial) on ice. Cell lysate was centrifuged at 15,000 times gravity for 30 minutes at 4° C. Soluble material was applied to nickel-nitrilotriacetic acid (Ni-NTA) coupled Sepharose CL-6B (Qiagen) for 1 hour with gentle rocking at 4° C. After transfer to a gravity flow poly-prep column (Bio-Rad), resin was washed extensively in buffer A. Protein was eluted from the column in a buffer containing 20 mM Tris-HCl pH 7.5, 150 mM NaCl, 300 mM imidazole, 10% glycerol and 0.5 mM TCEP. To remove the 6×HIS-SUMO tag eluted protein was mixed with TEV protease (Sigma) at a ratio of 1:250 (w:w) and dialyzed overnight against a buffer containing 20 mM Tris-HCl pH 7.5, 150 mM NaCl, 5 mM imidazole, 10% glycerol and 0.5 mM TCEP. TEV protease and 6×HIS-SUMO tags were depleted by the addition of Ni-NTA resin (Qiagen) to the sample, purified STING amino acids 140-379 was collected by removal of the resin using a poly-prep column. STING AA140-379 was concentrated with a 10,000 Dalton molecular weight cutoff centrifuge concentrator (EMD Millipore) to a final concentration of approximately 10 mg/ml. Protein was aliquoted, flash frozen in liquid nitrogen and stored at −80° C. until use.

Differential scanning fluorometry (DSF) is a technique that measures the ability of ligands to bind to and stabilize purified proteins (Niesen, et al, (2007) Nature protocols 2.9, 2212-2221). The protein is heated in the presence of a dye that binds to and fluoresces in hydrophobic environments. The protein is thermally denatured by heating resulting in increased dye binding to the unfolded protein and fluorescence. The temperature midpoint ($T_m$) of a proteins denaturation is established by calculating the half maximal value of the denaturation curve. The temperature midpoint of the protein in the presence of a ligand is directly related to the affinity of the ligand for the protein and therefore its ability to stabilize the protein at higher temperatures.

DSF was performed in a 20 µL reaction comprising 20 mM Tris-HCl pH 7.5, 150 mM NaCl, 1:500 dilution of SYPRO Orange (Life Technologies), 1 mg/ml purified STING AA140-379 protein and ligand at a concentration of 1 mM. Each of wild type hSTING, HAQ allele hSTING and REF allele hSTING were used with each of the reference compounds and compounds of the invention as listed in Table 4. Samples were placed in hard shell PCR plate (Bio-Rad). The fluorescence as a function of temperature was recorded in a CFX 96 real time PCR machine (Bio-Rad) reading on the HEX channel, excitation 450-490, emission 560-580 nm. The temperature gradient was from 15-80° C. ramping 0.5° C. per 15 seconds and recording every 0.5° C. After subtraction of the background signal from a sample lacking protein and ligand. The midpoint temperature ($T_m$) was calculated by fitting the curves of the fluorescence as a function of temperature to a Boltzmann sigmoidal function (Graph Pad Prism). The change in thermal stability of STING AA140-379 in the presence of ligand ($T_m$ Shift) was calculated by subtracting the $T_m$ (Protein and Ligand) from $T_m$ (Protein alone).

TABLE 4

$T_m$ shifts in hSTING WT, HAQ allele and REF allele

| Example no. Compound no. Compound name | hSTING $T_m$ Shift (° C.) | | |
|---|---|---|---|
| | WT | HAQ | REF |
| Reference Compound 2'3'-(G)(A) | 16.1 | 26.8 | 7.0 |
| Reference Compound 2'3'-RR-(A)(A) | 11.2 | 18.5 | 7.3 |
| Reference Compound 2'3'-RR-(G)(A) | 20.5 | 34.1 | 12.6 |
| Example 2 Compound 5a 3'3'-RR-(2'O,4'C-LNA-A)(2'O,4'C-LNA-A) | 16.8 | 27.6 | 10.6 |
| Example 2 Compound 5b 3'3'-RS-(2'O,4'C-LNA-A)(2'O,4'C-LNA-A) | 11.3 | 18.3 | 8.7 |
| Example 2 Compound 4a 3'3'-RR-(2'O,4'C-LNA-BzA)(2'O,4'C-LNA-BzA) | 4.3 | 5.6 | 4.4 |
| Example 3 Compound 10a 2'3'-RR-(A)(2'O,4'C-LNA-A) | 10.4 | 16.1 | 7.5 |
| Example 3 Compound 10b 2'3'-RS-(A)(2'O,4'C-LNA-A) | 8.7 | 13.9 | 7.4 |
| Example 3 Compound 10c 2'3'-SR-(A)(2'O,4'C-LNA-A) | 6.5 | 10.4 | 5.0 |
| Example 3 Compound 10d 2'3'-SS-(A)(2'O,4'C-LNA-A) | 4.1 | 5.0 | 3.2 |
| Example 3 Compound 11a 2'3'-RR-(3'-OTBS-A)(2'O,4'C-LNA-A) | 7.0 | 11.6 | 5.4 |
| Example 3 Compound 11b 2'3'-RS-(3'-OTBS-A)(2'O,4'C-LNA-A) | −1.8 | 3.3 | −1.5 |
| Example 3 Compound 11d 2'3'-RR-(BzA)(2'O,4 'C-LNA-BzA) | 2.5 | 3.7 | 2.4 |
| Example 3 Compound 11e 2'3'-RS-(BzA)(2'O,4'C-LNA-BzA) | 1.1 | 1.5 | 1.2 |
| Example 3 Compound 11f 2'3'-SR-(BzA)(2'O,4'C-LNA-BzA) | 6.6 | 7.5 | 6.5 |
| Example 4 Compound 15a 2'3'-RR-(3'F-G)(2'O,4'C-LNA-A) | 20.5 | 33.6 | 12.1 |
| Example 4 Compound 15b 2'3'-RS-(3'F-G)(2'O,4'C-LNA-A) | 12.1 | 19.2 | 8.4 |
| Example 4 Compound 15c 2'3'-SR-(3'F-G)(2'O,4'C-LNA-A) | 13.5 | 21.2 | 8.6 |
| Example 4 Compound 15d 2'3'-SS-(3'F-G)(2'O,4'C-LNA-A) | 7.5 | 11.6 | 6.1 |
| Example 5 Compound 21a 2'3'-RR-(3'H-A)(2'O,4'C-LNA-A) | 9.5 | 16.2 | 6.2 |
| Example 5 Compound 21b 2'3'-RS-(3'H-A)(2'O,4'C-LNA-A) | 5.0 | 10.0 | 4.2 |
| Example 5 Compound 22a 2'3'-RR-(3'H-BzA)(2'O,4'C-LNA-BzA) | 0.6 | 2.2 | 0.6 |
| Example 5 Compound 22b 2'3'-RS-(3'H-BzA)(2'O,4'C-LNA-BzA) | 4.6 | 5.9 | 4.6 |
| Example 6 Compound 27a 2'3'-RR-(3'F-A)(2'O,4'C-LNA-A) | 11.8 | 18.2 | 10.2 |
| Example 6 Compound 27b 2'3'-RS-(3'F-A)(2'O,4'C-LNA-A) | 8.2 | 13.2 | 7.1 |
| Example 7 Compound 33a 3'3'-RR-(A)(2'O,4'C-LNA-G) | 18.36 | 29.6 | 11.9 |
| Example 7 Compound 33b 3'3'-RS-(A)(2'O,4'C-LNA-G) | 13.2 | 19.3 | 9.3 |
| Example 8 Compound 37a 2'3'-RR-(3'βF-A)(2'O,4'LNA-A) | 4.7 | 11.2 | 2.1 |
| Example 8 Compound 37b 2'3'-RS-(3'βF-A)(2'O,4'LNA-A) | 1.8 | 6.8 | 0.5 |
| Example 8 Compound 37c 2'3'-SR-(3'βF-A)(2'O,4'LNA-A) | 1.2 | 5.7 | 0.8 |
| Example 8 Compound 37d 2'3'-SS-(3'βF-A)(2'O,4'LNA-A) | −0.3 | 2.4 | −0.3 |
| Example 9 Compound 45a 3'3'-RR-(G)(2'O,4'C-LNA-A) | 20.3 | 34.0 | 13.1 |
| Example 9 Compound 45b 3'3'-RS-(G)(2'O,4'C-LNA-A) | 9.4 | 14.7 | 7.4 |

The LNA-CDN compounds bind to WT, HAQ and REF alleles of STING, with several of the compounds (5a, 5b, 15a, 15b, 15c, 27a, 33a, 33b and 45a) having a $T_m$ shift that is comparable to or greater than that of the reference compound 2'3'-RR-(A)(A) for all three alleles, with greater $T_m$ shift than both 2'3'-RR-(A)(A) and 2'3'-(G)(A) for the REF allele. Compounds 5a, 15a, 33a and 45a demonstrated a greater $T_m$ shift than the natural ligand 2'3'-(G)(A) for all three alleles.

Example 11: Induction of Type I Interferon by LNA-CDN Compounds in hPBMCs

The induction of type I interferon was measured in human primary blood mononuclear cells (hPBMCs) to evaluate the potency of the LNA-CDN compounds as described herein. hPBMCs from three unique donors were used: one donor was homozygous for the wild type (WT) STING allele ($STING^{WT/WT}$), one donor was homozygous for the so-called reference (REF) (R232H) STING allele ($STING^{REF/REF}$), and the third donor was homozygous for the HAQ (R71H, G230A, R293Q) STING allele ($STING^{HAQ/HAQ}$). The STING genotype of these donors was determined by PCR amplification and sequencing: genomic DNA was isolated from hPBMCs using Quick Extract DNA Extraction Solution (Epicentre) and was used to amplify regions of exon 3, 6, and 7 of the human STING gene. Primers for amplification and sequencing were: hSTING exon3F GCT- GAGACAGGAGCTTTGG (SEQ ID NO: 11), hSTING exon3R AGCCAGAGAGGTTCAAGGA (SEQ ID NO: 12), hSTING exon6F GGCCAATGACCTGGGTCTCA (SEQ ID NO: 13), hSTING exon6R CACCCAGAATAGCATCCAGC (SEQ ID NO: 14), hSTING exon7F TCAGAGTTGGGTATCAGAGGC (SEQ ID NO: 15), hSTING exon7R ATCTGGTGTGCTGGGAAGAGG (SEQ ID NO: 16). STING variant alleles were assigned according to $Y_1$, et al., 2013, PLoS One, 8(10), e77846 (DOI: 10.1371/journal.pone.0077846).

Figure 1B:
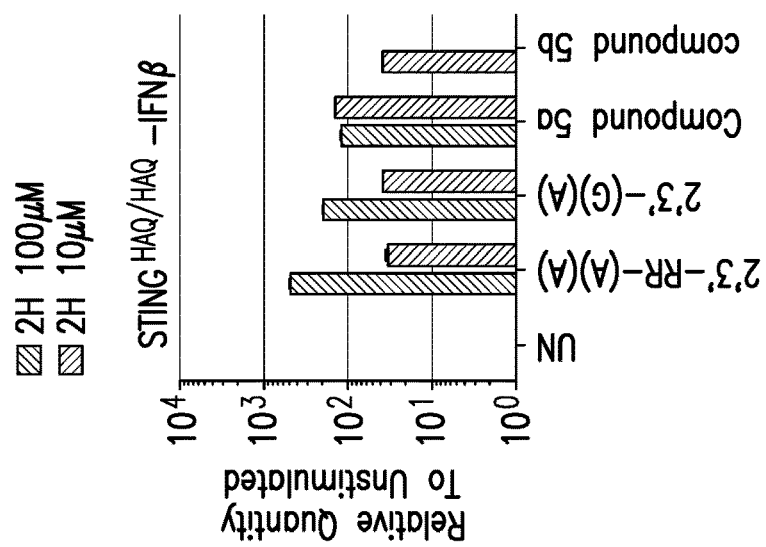
Figure 1A:
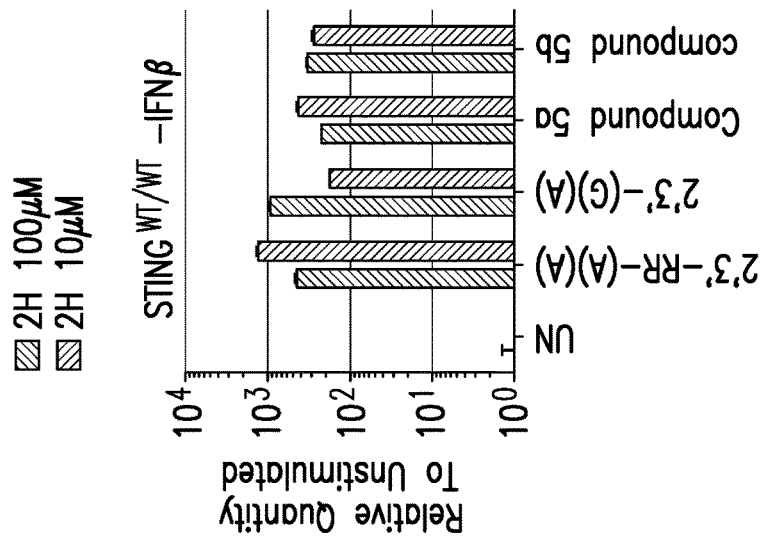
Figure 2C:
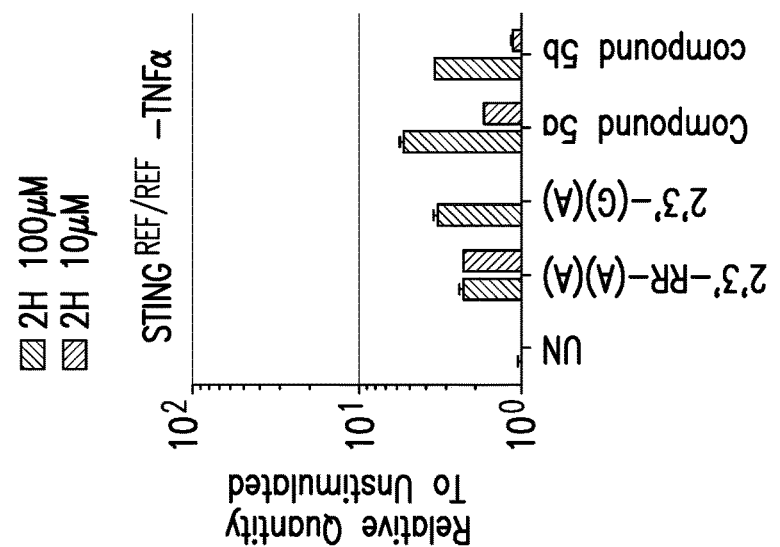
FIG. 2A-C depicts relative expression of TNFα by $STING^{WT/WT}$ (2A), $STING^{HAQ/HAQ}$ (2B), and $STING^{REF/REF}$ (2C) in human PBMCs at 2 hours following stimulation with 10 μM or 100 μM of LNA-CDN Compounds 5a and 5b.
Figure 2B:
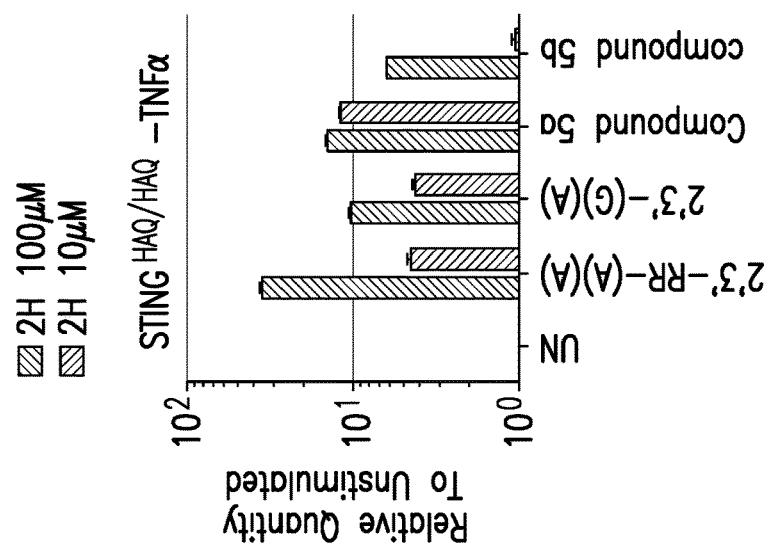
Figure 2A:
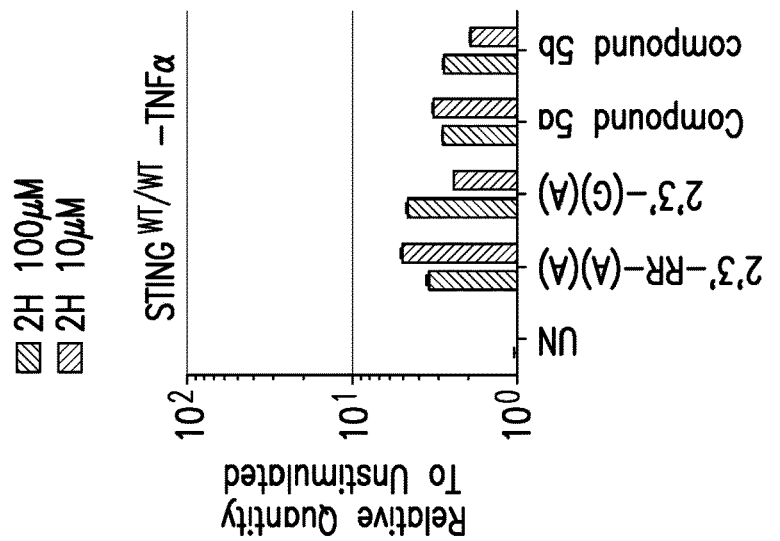
Figure 3C:
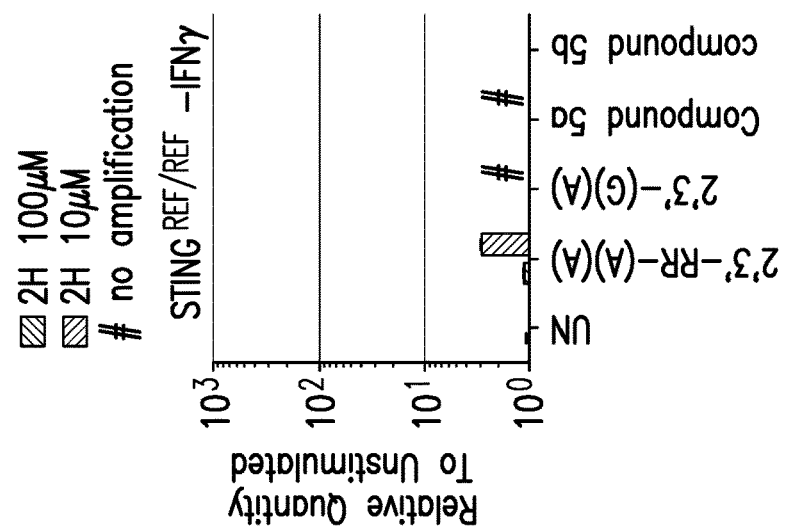
FIG. 3A-C depicts relative expression of IFNγ by $STING^{WT/WT}$ (3A), $STING^{HAQ/HAQ}$ (3B), and $STING^{REF/REF}$ (3C) in human PBMCs at 2 hours following stimulation with 10 μM or 100 μM of LNA-CDN Compounds 5a and 5b.
Figure 3B:
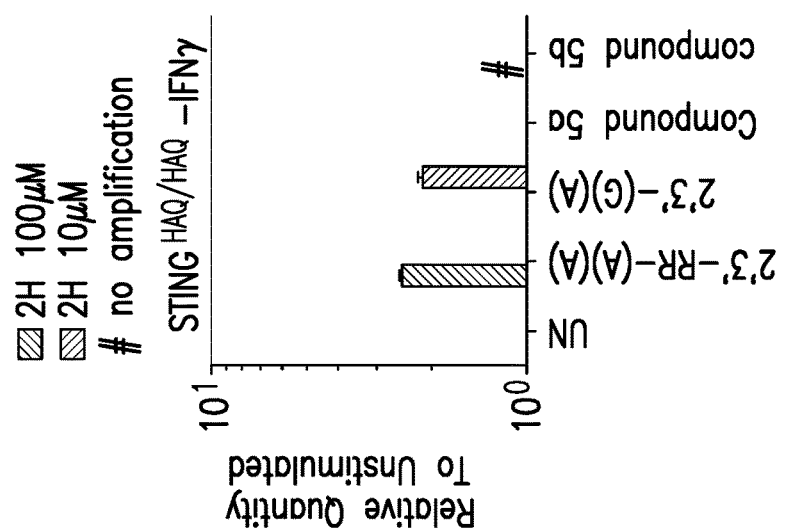
Figure 3A:
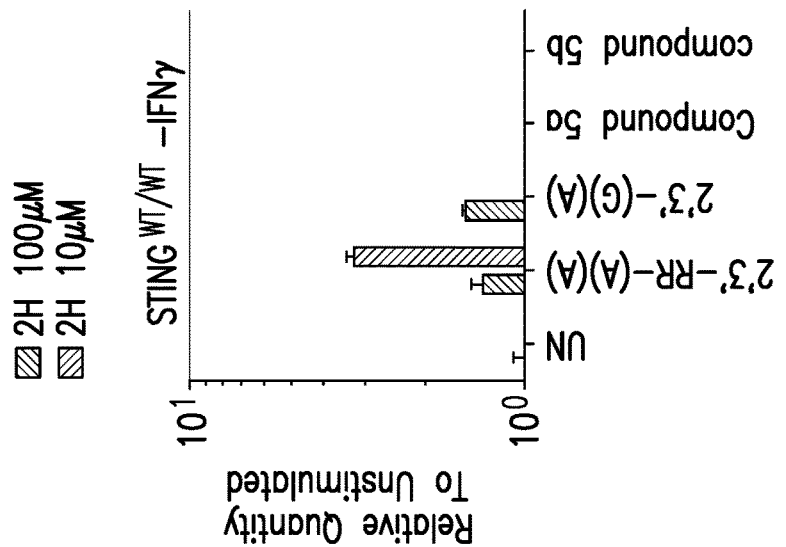
Figure 5A:
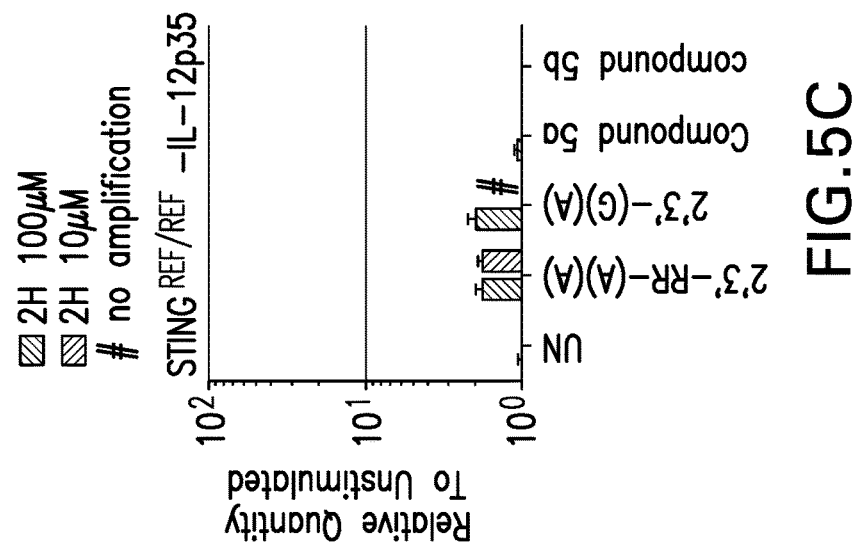
FIG. 5A-C depicts relative expression of IL-12p35 by $STING^{WT/WT}$ (5A), $STING^{HAQ/HAQ}$ (5B), and $STING^{REF/REF}$ (5C) in human PBMCs at 2 hours following stimulation with 10 μM or 100 μM of LNA-CDN Compounds 5a and 5b.
Figure 5B:
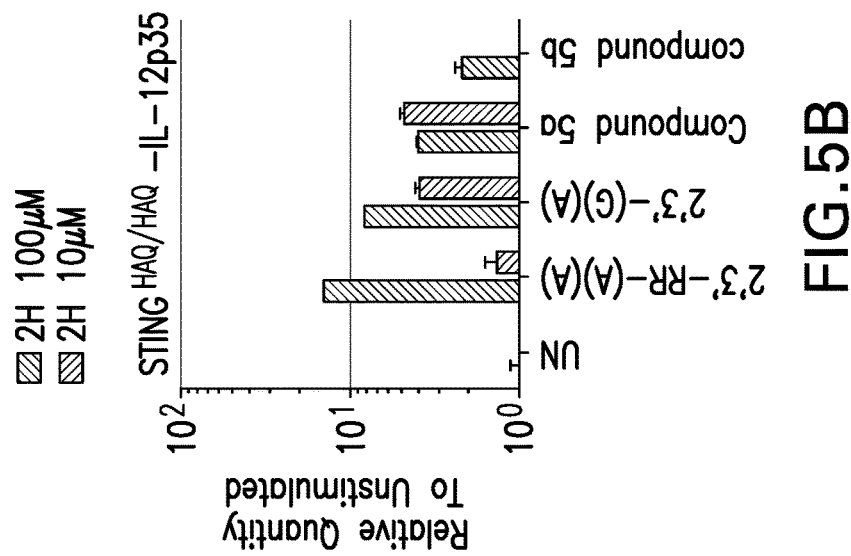
Figure 5C:
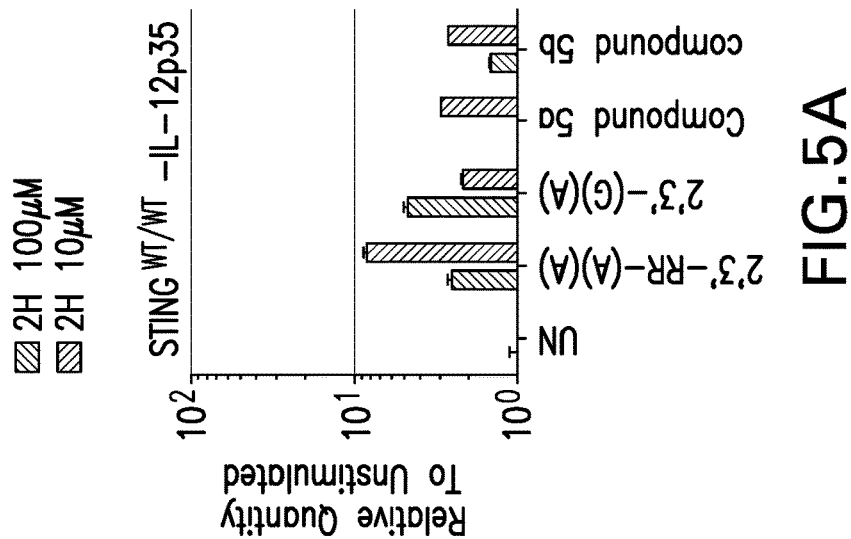
Figure 6C:
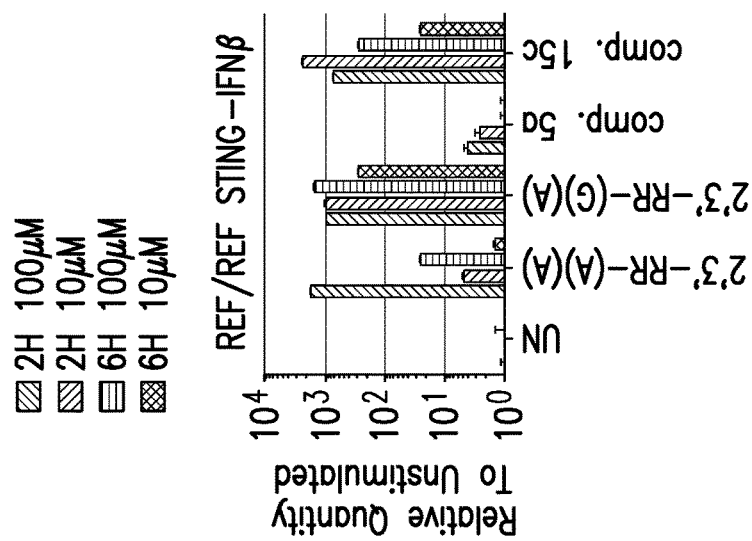
Figure 6B:
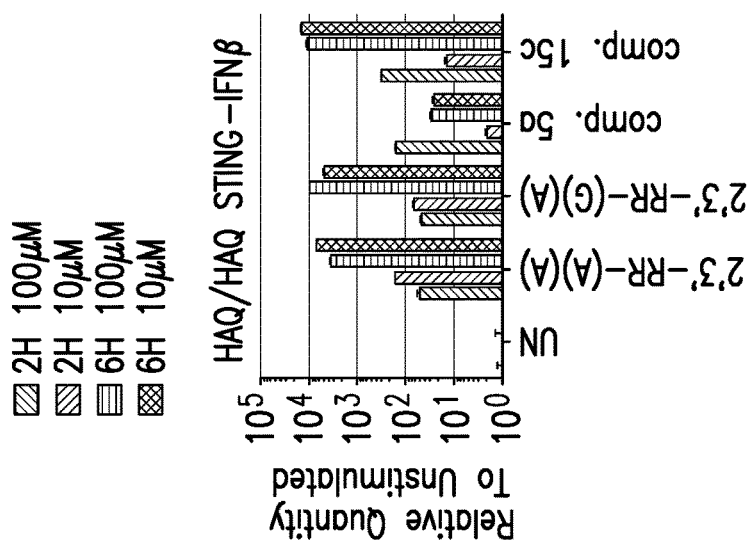
Figure 6A:
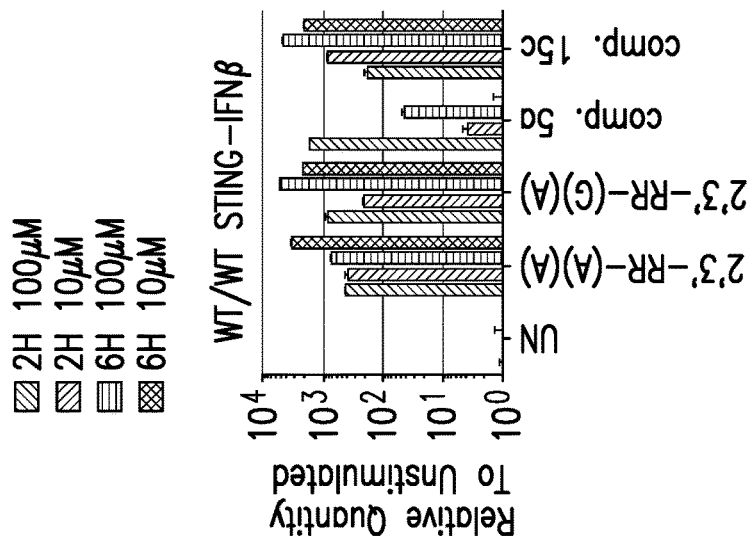
Figure 7C:
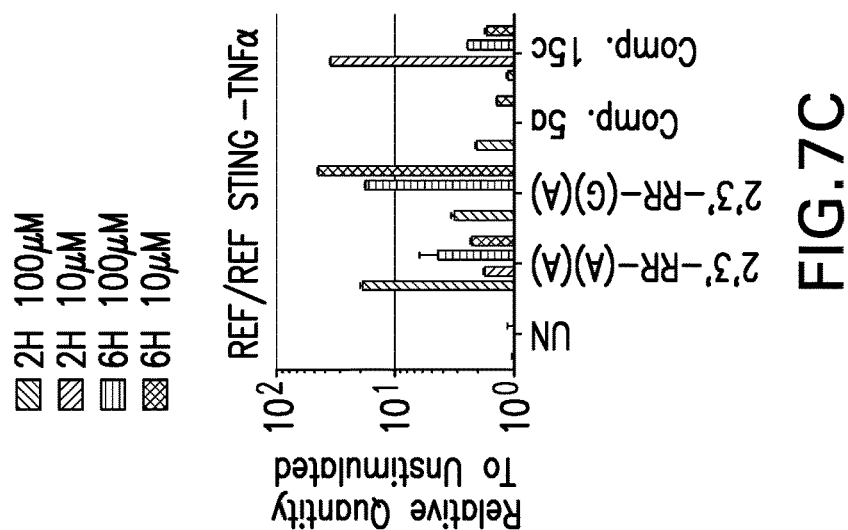
Figure 7B:
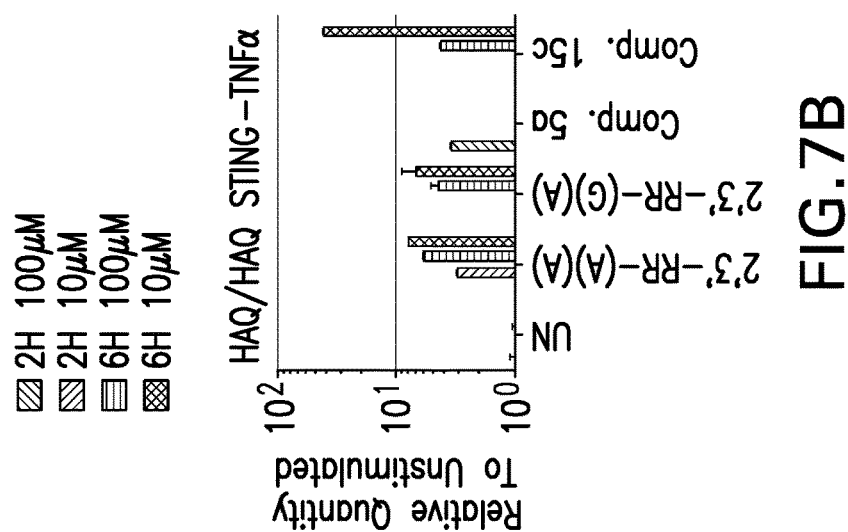
Figure 7A:
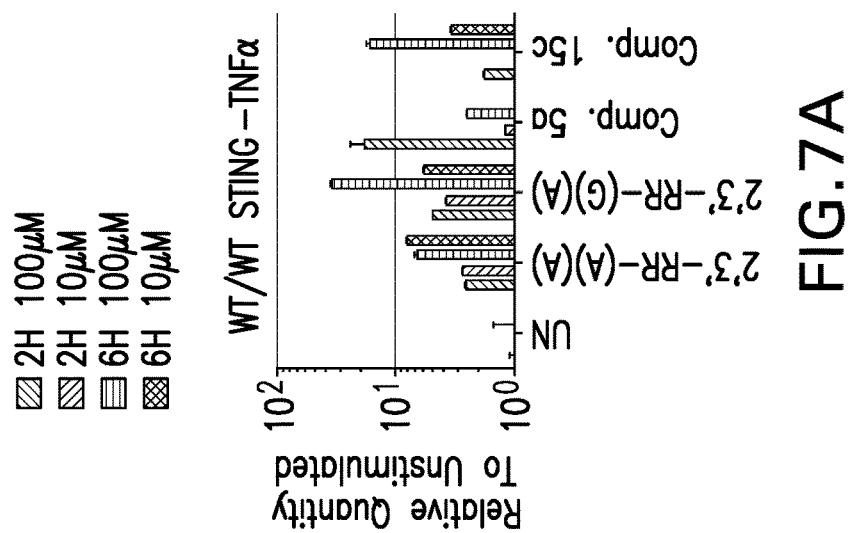
Figures 8A, 8B, 8C:
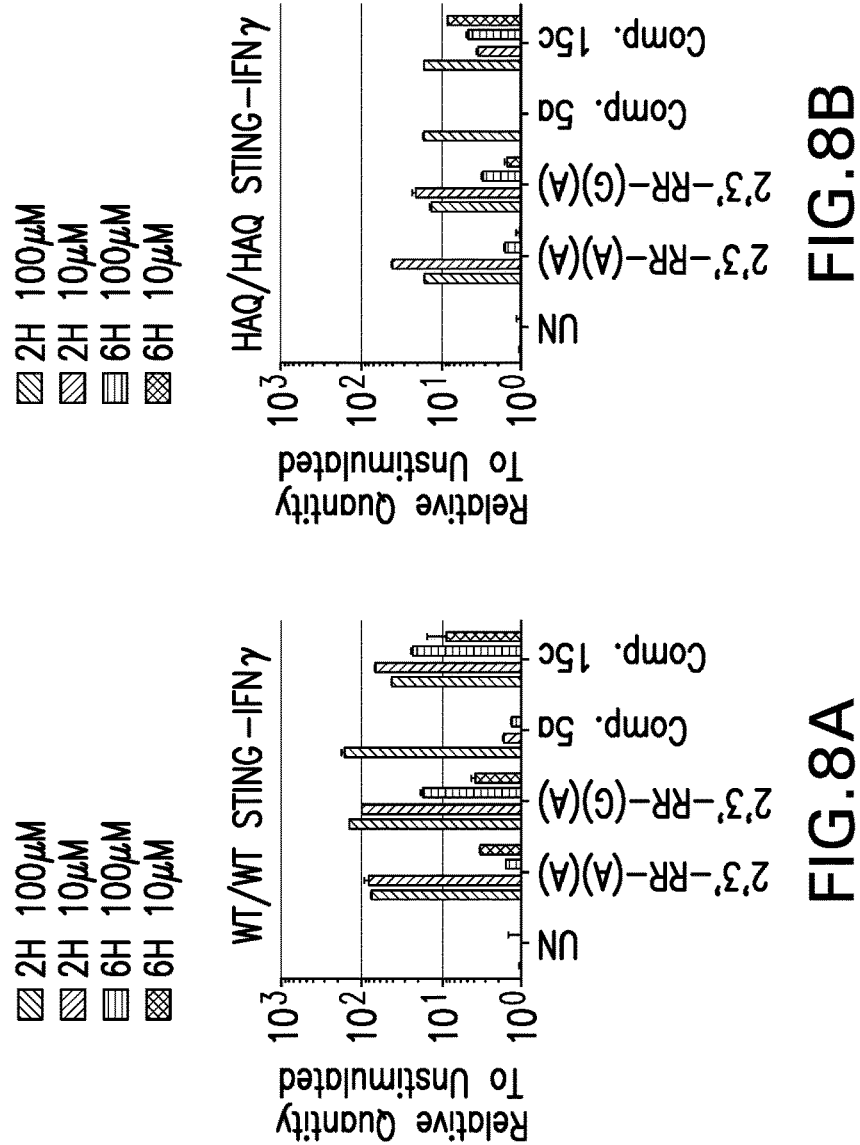
Figure 9C:
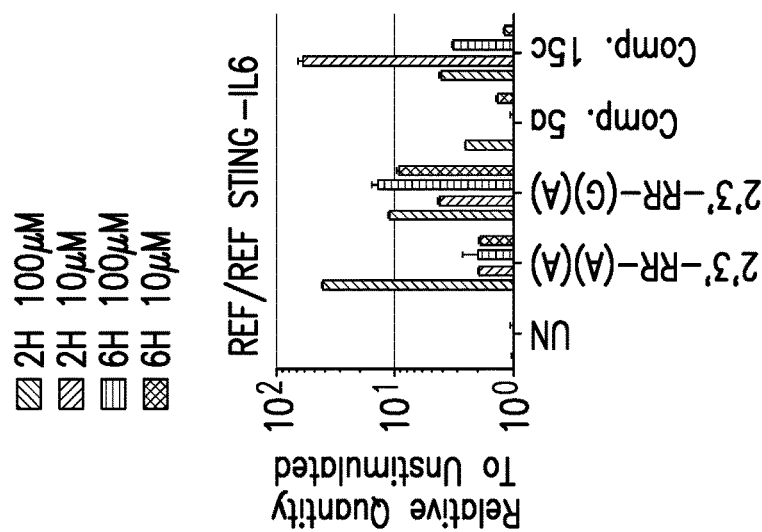
Figure 9B:
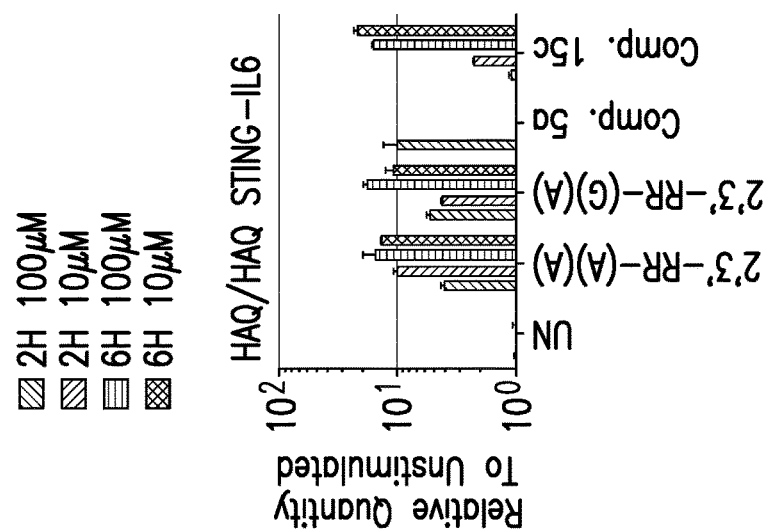
Figure 9A:
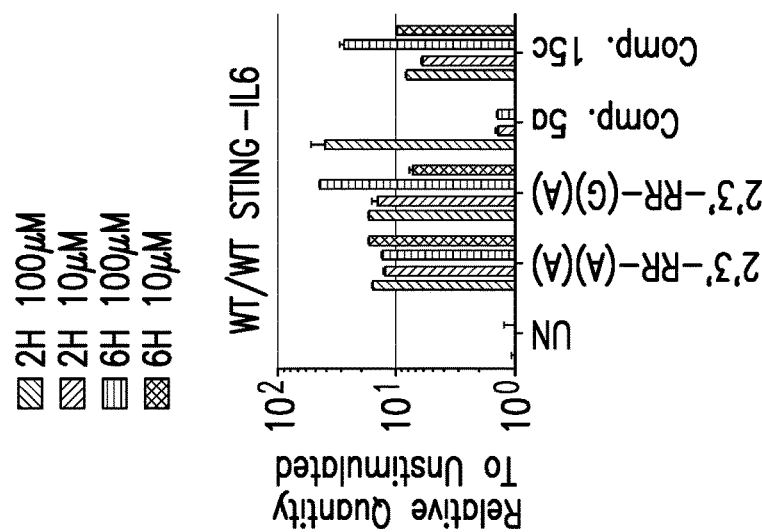
Figure 10C:
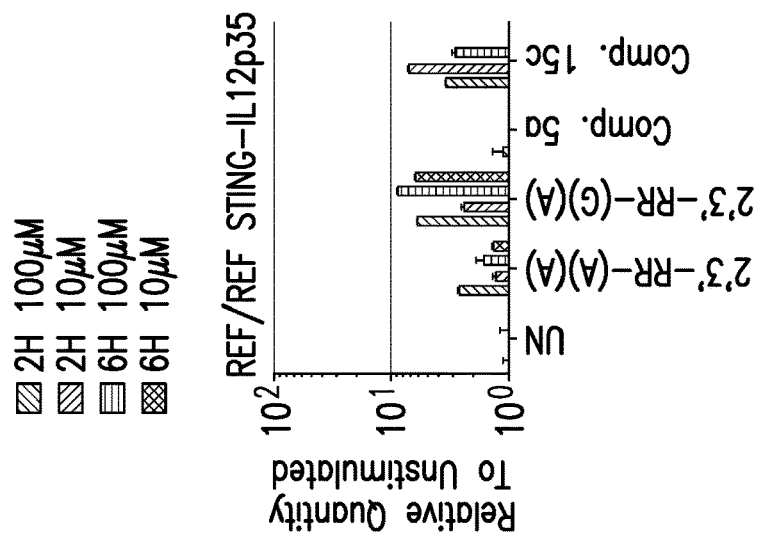
Figure 10B:
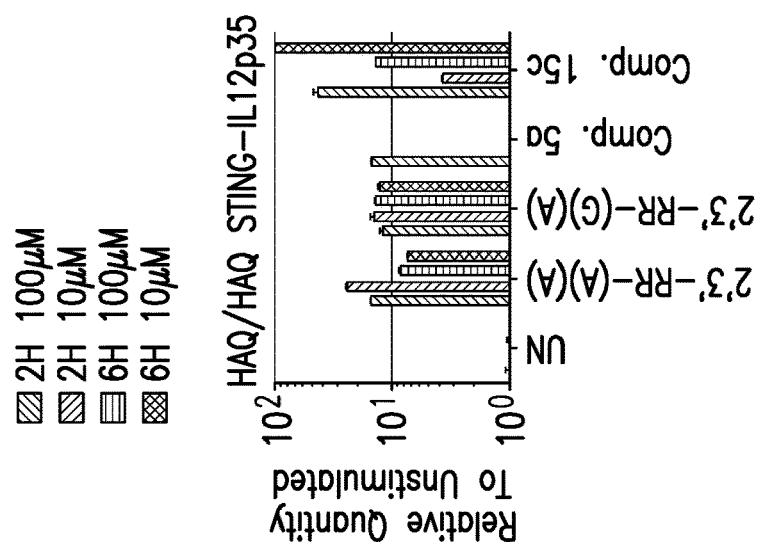
Figure 10A:
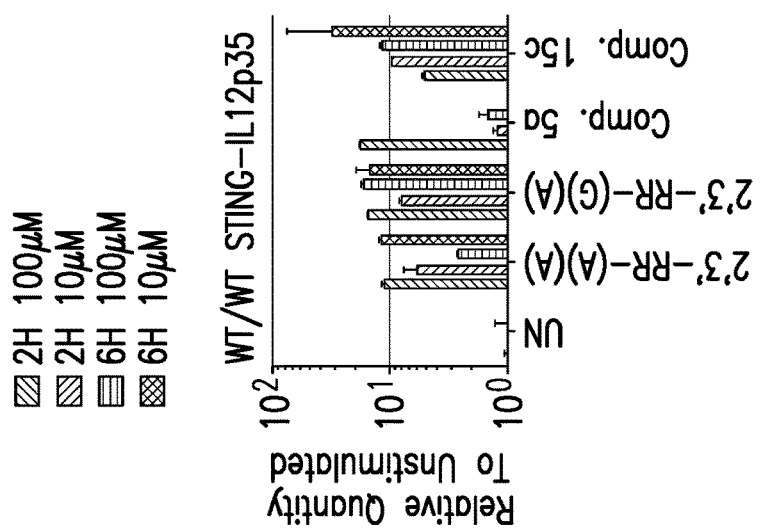
Figure 11A:
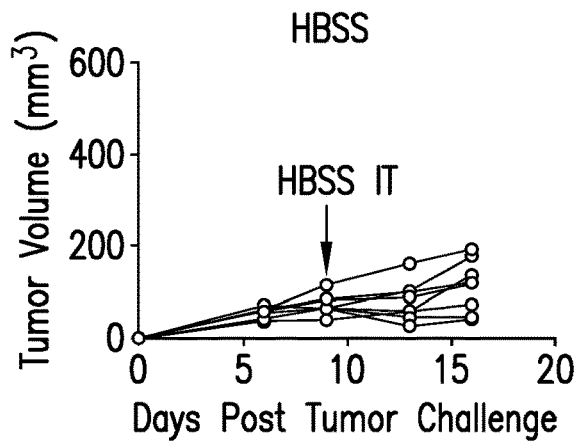
FIG. 11A-F depicts the tumor volume in a B16.SIY melanoma mouse model, following intra-tumoral injection of HBSS vehicle (11A), reference compound 2'3'-RR-(A)(A) at 1 μg (11B) and LNA-CDN Compound 5a at 0.1 μg (11C), 1 μg (11D), 10 μg (11E), or 100 μg (11F).
Figure 11B:
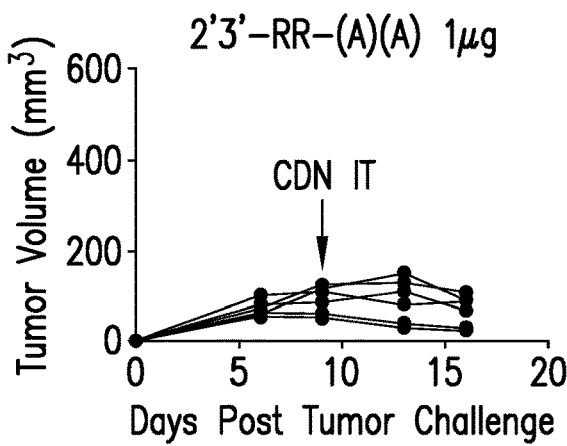
Figure 11C:
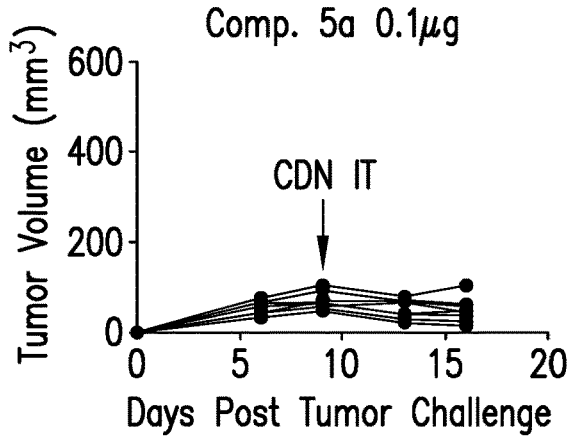
Figure 11D:
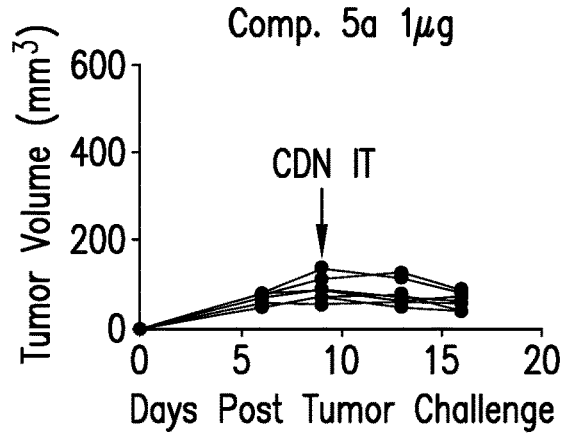
Figure 11E:
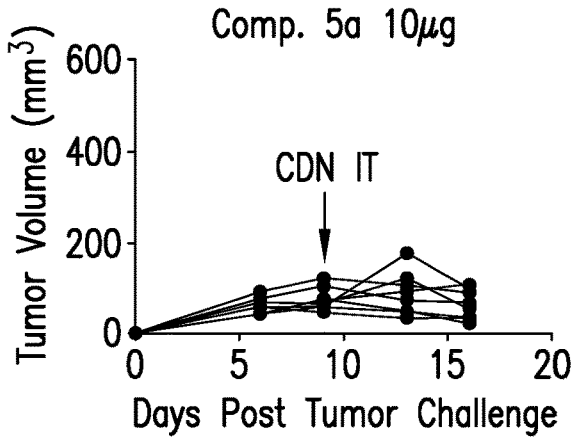
Figure 11F:
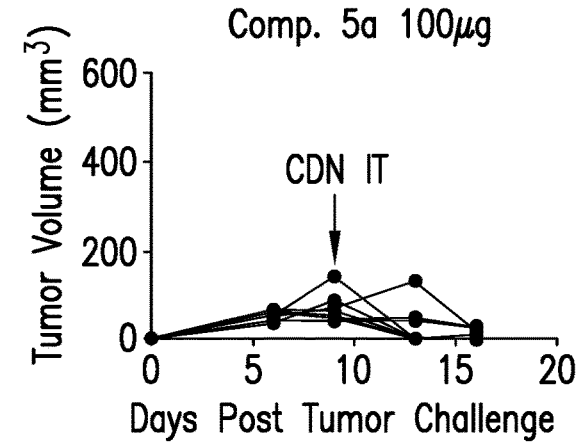
Figure 12A:
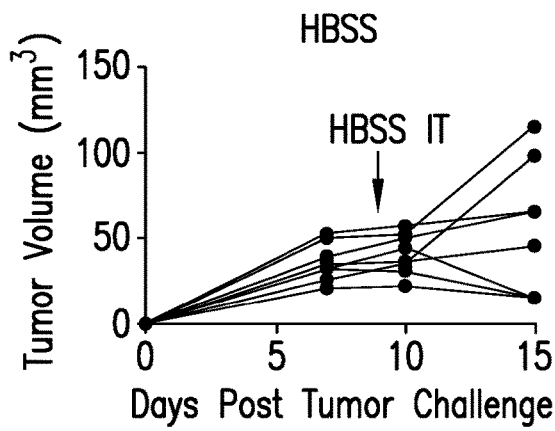
FIG. 12A-F depicts the tumor volume in a B16.SIY melanoma mouse model, following intra-tumoral injection of HBSS vehicle (12A), reference compound 2'3'-RR-(A)(A) at 1 μg (12B) and LNA-CDN Compound 10c at 0.1 μg (12C), 1 μg (12D), 10 μg (12E), or 100 μg (12F).
Figure 12B:
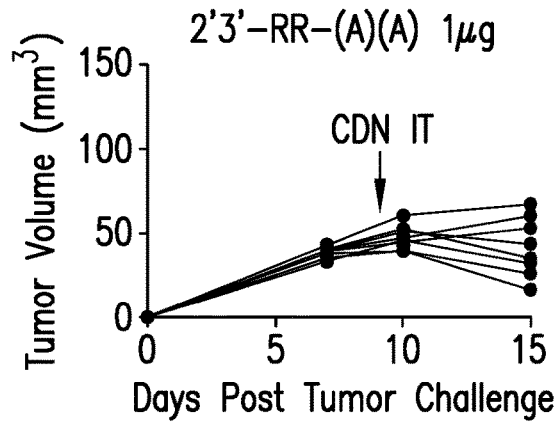
Figure 12C:
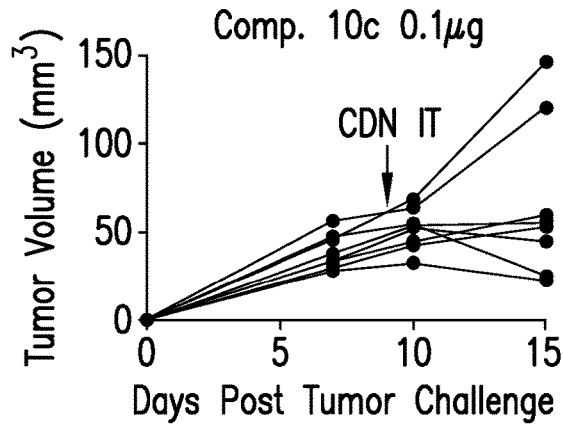
Figure 12D:
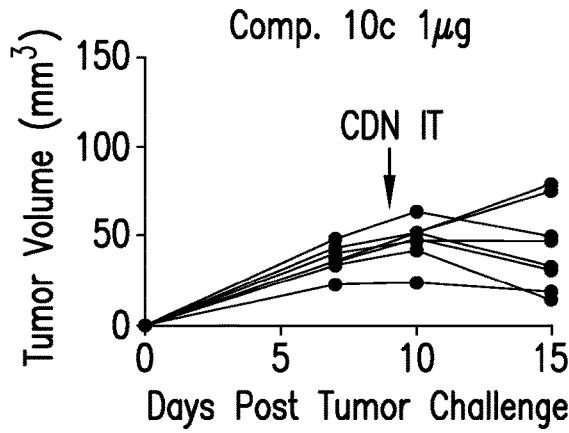
Figure 12E:
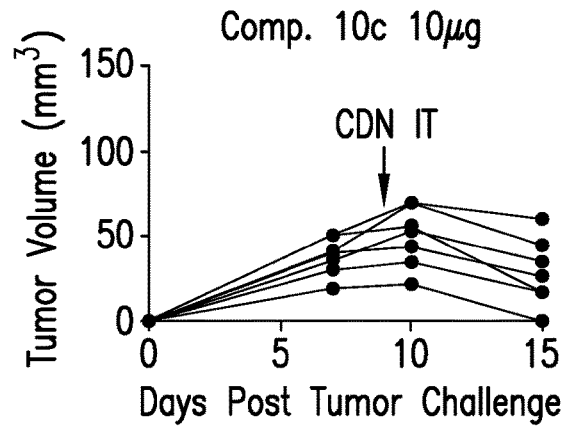
Figure 12F:
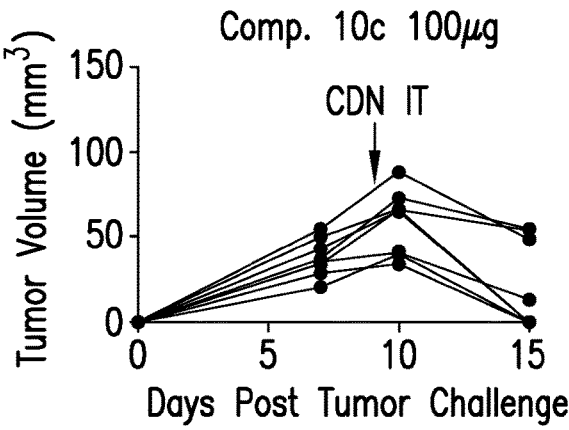
Figure 13A:
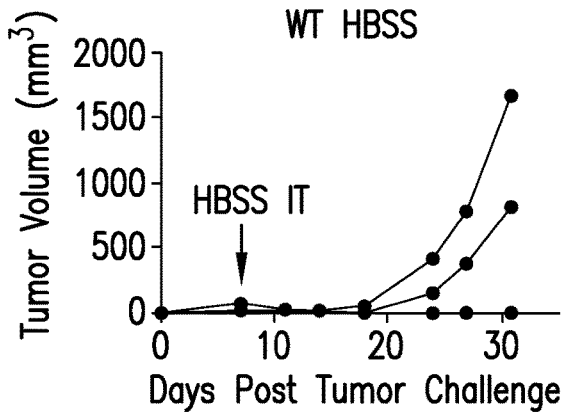
FIG. 13A-D depicts the tumor volume in a B16.SIY melanoma mouse model, using WT or STING-deficient Goldenticket (GT) mice, following intra-tumoral injection of HBSS vehicle into WT (13A) or GT (13C); or 100 μg of LNA-CDN Compound 15c into WT (13B) or GT (13D).
Figure 13B:
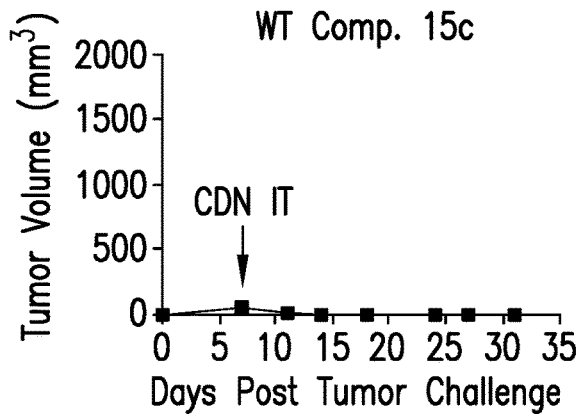
Figure 13C:
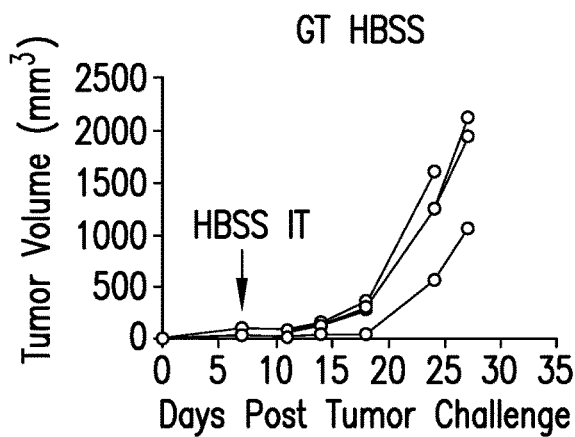
Figure 13D:
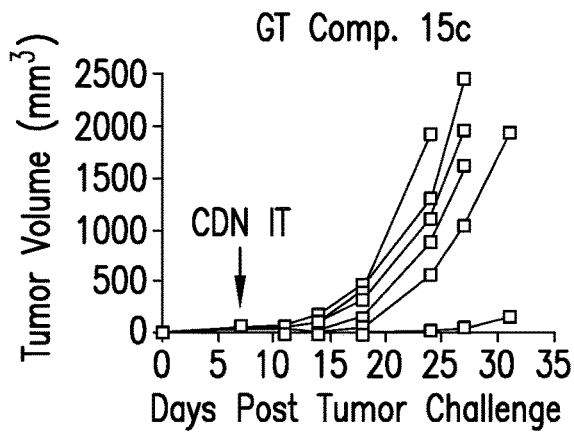
Figure 14A:
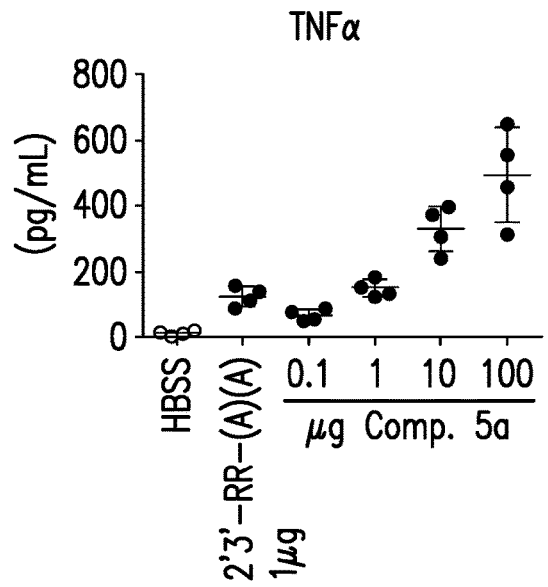
FIG. 14A-D depicts serum concentrations of pro-inflammatory cytokines TNF-α (14A), IFN-γ (14B), IL-6 (14C), and MCP-1 (14D) in a B16.SIY melanoma mouse model, 6 hours post intra-tumoral injection of HBSS vehicle control, reference compound 2'3'-RR-(A)(A) at 1 μg, or LNA-CDN Compound 5a at 0.1 μg, 1 μg, 10 μg or 100 μg.
Figure 14B:
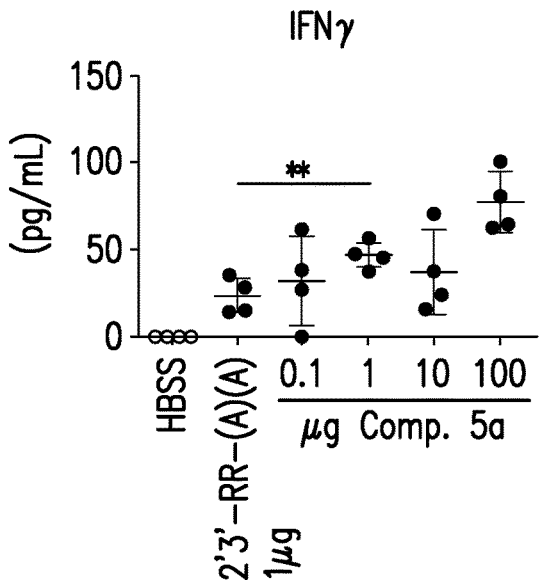
Figure 14C:
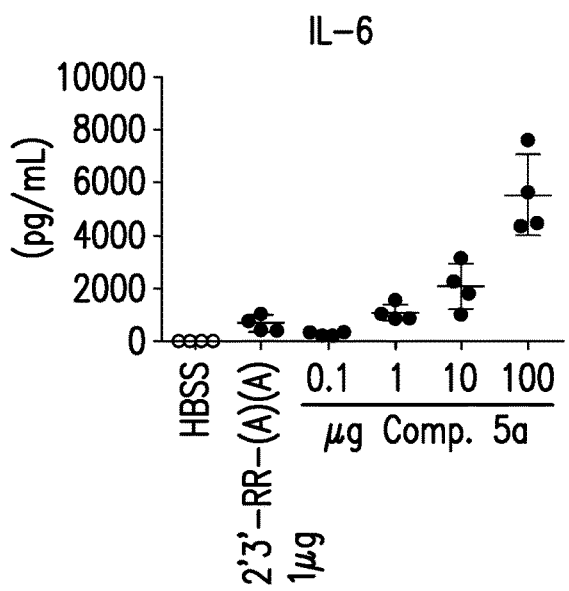
Figure 14D:
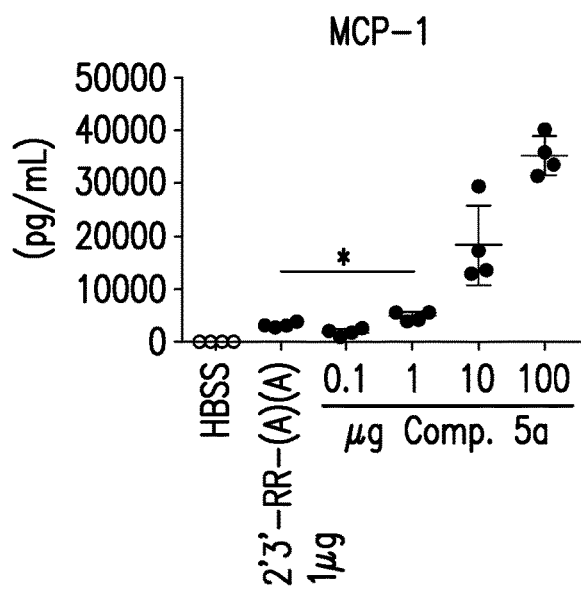
Figure 15A:
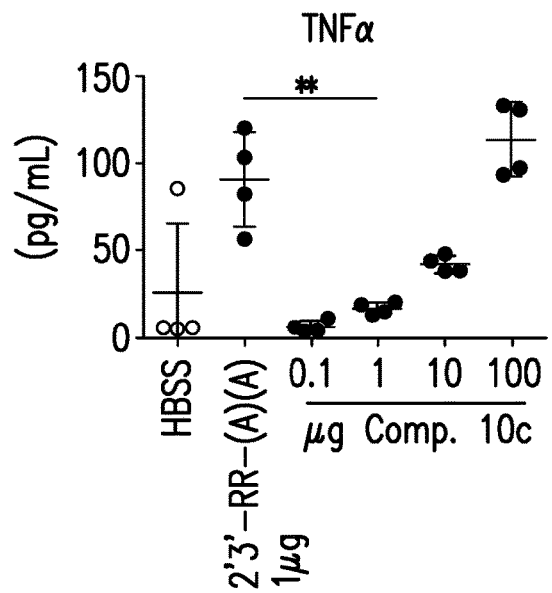
FIG. 15A-D depicts serum concentrations of pro-inflammatory cytokines TNF-α (15A), IFN-γ (15B), IL-6 (15C), and MCP-1 (15D) in a B16.SIY melanoma mouse model, 6 hours post intra-tumoral injection of HBSS vehicle control, reference compound 2'3'-RR-(A)(A) at 1 μg, or LNA-CDN Compound 10c at 0.1 μg, 1 μg, 10 μg or 100 μg.
Figure 15B:
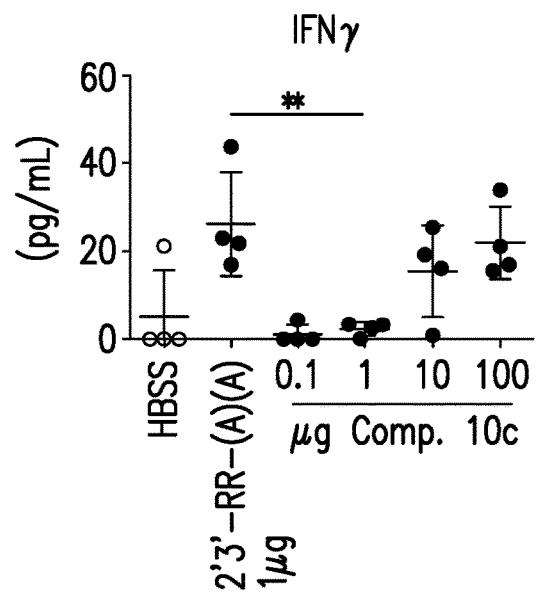
Figure 15C:
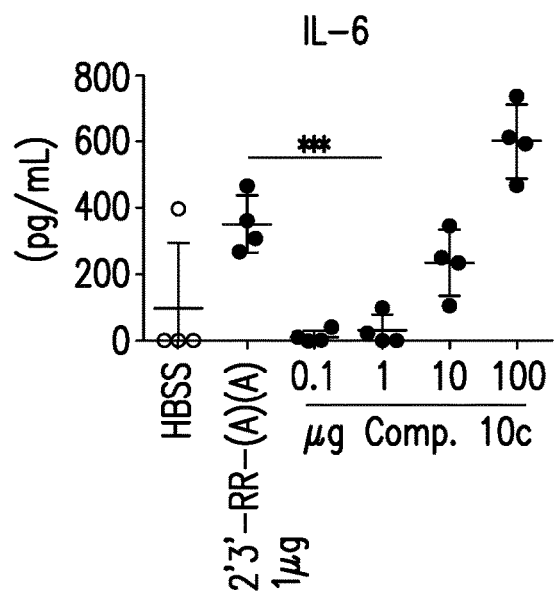
Figure 15D:
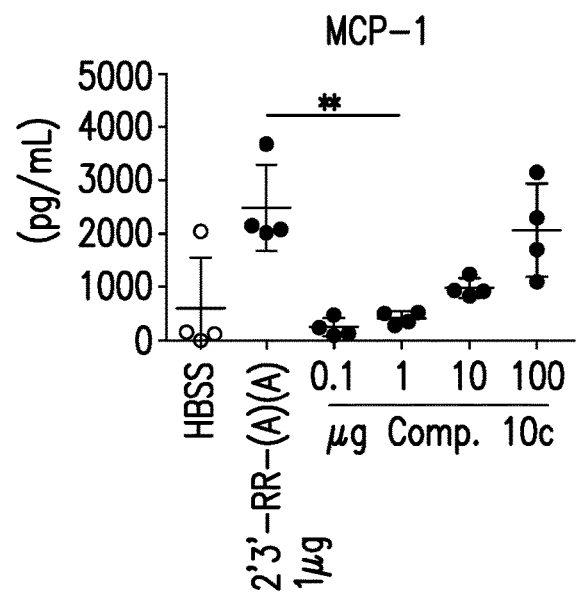

Cryopreserved hPBMCs were thawed and $10^6$ cells were either left untreated or treated with 10 μM or 100 μM of reference compounds 2'3'-RR-(A)(A) or 2'3'-(G)(A) (known activators of STING) and with the LNA-CDNs 3'3'-RR-(2'O,4'C-LNA-A) (2'O,4'C-LNA-A) (Compound 5a, Example 2) and 3'3'-RS-(2'O,4'C-LNA-A)(2'O,4'C-LNA-A) (Compound 5b, Example 2) in RMPI media supplemented with 10% fetal bovine serum and 1% Penicillin/Streptomycin. After 2 hours stimulation, cells were harvested by centrifugation and washed once in phosphate-buffered saline. Cellular RNA was isolated using the Aurum Total RNA 96 Kit normalized by concentration across samples, and cDNA was synthesized using the iScript cDNA Synthesis Kit. Gene expression was assessed by real-time qRT-PCR using PrimePCR probe assays and the CFX96 gene cycler (all reagents and equipment from BioRad). IFNβ expression was expressed relative to untreated cells. Target genes included type I interferon (IFNβ), Th1-associated cytokines (IFNγ, IL-12p35) and NF-kB dependent inflammatory cytokines (TNFα, IL-6). Results for these samples are shown in FIGS. 1A-C(IFNβ), 2A-C(TNFα), 3A-C(IFNγ), 4A-C(IL-6), and 5A-C(IL-12p35). Additional samples were assayed with 10 μM or 100 μM of reference compounds 2'3'-RR-(A)(A) or 2'3'-RR-(G)(A) and LNA-CDNs 3'3'-RR-(2'O,4'C-LNA-A)(2'O,4'C-LNA-A) (Compound 5a, Example 2) and 2'3'-SR-(3'F-G)(2'O,4'C-LNA-A) (Compound 15c, Example 4), sampled after 2 or 6 hours of stimulation. Results for these samples are shown in FIGS. 6A-C(IFNβ), 7A-C (TNFα), 8A-C(IFNγ), 9A-C(IL-6), and 10A-C(IL-12p35). In each Figure, A is WT, B is HAQ and C is REF STING alleles. These results demonstrate the LNA-CDN Compounds are potent STING activators, and that the Rp,Rp isomer of Compound 5a generally shows greater activation of cytokines than the Rp,Sp isomer of Compound 5b. Further, Compound 15c more broadly activates all human alleles than Compound 5a, with Compound 15c potently inducing activation of the most refractory human STING allele (REF/REF).

Example 12: LNA-CDN Compounds Potently Activate Human STING Signaling in THP1 Cells To determine the relative level of type I interferon induced in human cells by each of the LNA-CDN as a signature of adjuvant potency, 100,000 THP1-Dual cells (a human monocyte cell line containing the hSTING HAQ allele transfected with an IRF-3 inducible secreted luciferase reporter gene (Invivogen) which express secreted luciferase under the control of a promoter comprised of five IFN-stimulated response elements) were activated with 30 ng/ml phorbol 12-myristate 13-acetate overnight in a 96-well dish. Cells were washed with fresh media and incubated for 30 min at 37° C. with 5% $CO_2$ with compounds in 3-fold titration steps from 2,000 to 0.0338 μM in PB buffer (50 mM 4-(2-hydroxyethyl)-1-piperazineethanesulfonic acid, 100 mM KCl, 3 mM $MgCl_2$, 0.1 mM dithiothreitol, 85 mM sucrose, 1 mM ATP, 0.1 mM GTP and 0.2% bovine serum albumin). After 30 minutes, cells were washed and fresh RPMI media containing 10% FBS was added, and cells were incubated at 37° C. with 5% $CO_2$ Cell culture supernatants from each sample were collected after overnight incubation, and 10 μL of the cell culture supernatants was added to 50 μL QUANTI-Luc reagent (Invivogen). Type I interferon activation was determined by measuring secreted luciferase levels on a SpectraMax M3 spectrophotometer (Molecular Devices). The EC50 value was determined from the dose-response curve for the 10 concentrations from the serial dilution of the reference compounds and compounds of the invention tested in this assay as listed in Table 5, showing the results without digitonin.

TABLE 5

| EC50 without digitonin in THP1 cells (HAQ allele). | |
| --- | --- |
| Example/Compound Compound name | EC50 (μM) |
| Reference Compound 2'3'-(G)(A) | 252.5 |
| Reference Compound 2'3'-RR-(A)(A) | 41.5 |
| Reference Compound 2'3'-RR-(G)(A) | 28.6 |
| Example 2 Compound 5a 3'3'-RR-(2'O,4'C-LNA-A)(2'O,4'C-LNA-A) | 41.6 |
| Example 2 Compound 5b 3'3'-RS-(2'O,4'C-LNA-A)(2'O,4'C-LNA-A) | 19.3 |
| Example 2 Compound 4a 3'3'-RR-(2'O,4'C-LNA-BzA)(2'O,4'C-LNA-BzA) | 340.9 |
| Example 3 Compound 10a 2'3'-RR-(A)(2'O,4'C-LNA-A) | 24.3 |
| Example 3 Compound 10b 2'3'-RS-(A)(2'O,4'C-LNA-A) | 110.1 |
| Example 3 Compound 10c 2'3'-SR-(A)(2'O,4'C-LNA-A) | >150 |
| Example 3 Compound 10d 2'3'-SS-(A)(2'O,4'C-LNA-A) | >150 |
| Example 4 Compound 15a 2'3'-RR-(3'F-G)(2'O,4'C-LNA-A) | 45.1 |
| Example 4 Compound 15b 2'3'-RS-(3'F-G)(2'O,4'C-LNA-A) | 23.4 |
| Example 4 Compound 15c 2'3'-SR-(3'F-G)(2'O,4'C-LNA-A) | 9.5 |
| Example 4 Compound 15d 2'3'-SS-(3'F-G)(2'O,4'C-LNA-A) | >200 |
| Example 5 Compound 21a 2'3'-RR-(3'H-A)(2'O,4'C-LNA-A) | 26.9 |
| Example 5 Compound 21b 2'3'-RS-(3'H-A)(2'O,4'C-LNA-A) | 77.3 |
| Example 6 Compound 27a 2'3'-RR-(3'F-A)(2'O,4'C-LNA-A) | 10.0 |
| Example 6 Compound 27b 2'3'-RS-(3'F-A)(2'O,4'C-LNA-A) | 81.0 |
| Example 7 Compound 33a 3'3'-RR-(A)(2'O,4'C-LNA-G) | 30.2 |
| Example 7 Compound 33b 3'3'-RS-(A)(2'O,4'C-LNA-G) | 38.0 |
| Example 8 Compound 37a 2'3'-RR-(3'βF-A)(2'O,4'LNA-A) | 61.2 |
| Example 8 Compound 37b 2'3'-RS-(3'βF-A)(2'O,4'LNA-A) | >150 |
| Example 8 Compound 37c 2'3'-SR-(3'βF-A)(2'O,4'LNA-A) | >150 |
| Example 8 Compound 37d 2'3'-SS-(3'βF-A)(2'O,4'LNA-A) | >150 |
| Example 9 Compound 45a 3'3'-RR-(G)(2'O,4'C-LNA-A) | 5.8 |
| Example 9 Compound 45b 3'3'-RS-(G)(2'O,4'C-LNA-A) | 60.0 |

The LNA-CDN compounds are very active STING agonists as shown in the THP-1 assay, with several compounds having an EC50 of less than that of the reference compound 2'3'-RR-(A)(A), and compounds 5b, 15c, 27a and 45a having an EC50 of less than 20 μM.

Example 13: Anti-Tumor Efficacy of LNA-CDN Compounds

To assess the ability of the LNA-CDN molecules to promote anti-tumor immunity in aggressive murine tumor models, 6-8 week old female C57BL/6 mice (8 mice per group) were implanted with B16.SIY melanoma tumor cells ($1\times10^6$ cells in 100 μL PBS). Mice were treated with 3'3'-RR-(2'O,4'C-LNA-A)(2'O,4'C-LNA-A) (Compound 5a, Example 2) or 2'3'-SR-(A)(2'O,4'C-LNA-A) (Compound 10c, Example 3), both at 0.1, 1, 10 and 100 μg in a total volume of 40 μL HBSS, and compared to 2'3'-RR-(A)(A) as a reference compound (1 μg in a total volume of 40 μL HBSS) or HBSS vehicle control. Treatments began when tumors reached a volume of approximately 100 mm$^3$, on day 9 post tumor implantation. The compounds were administered by a single subcutaneous injection into the center of the tumor (IT) using a 27 gauge needle. Tumors were measured twice weekly.

As shown in FIGS. 11A-F and 12A-F, in the aggressive B16-SIY melanoma model, the LNA-CDN Compounds 5a and 10c induced potent tumor inhibition as compared to HBSS, in a dose-dependent manner, with both compounds demonstrating comparable tumor efficacy as compared to the reference compound 2'3'-RR-(A)(A) at the 1 μg dose, with Compound 5a eliciting complete tumor regression at the 100 μg dose. These data demonstrate the potent anti-tumor effects of these LNA-CDN compounds in an aggressive murine tumor model.

Example 14: Anti-Tumor Efficacy of LNA-CDN Compounds is STING-Dependent

To assess the ability of the LNA-CDN molecules to promote STING-dependent anti-tumor immunity in an aggressive murine tumor model, 6-8 week old female C57BL/6 (WT) mice or STING-deficient Goldenticket (GT) mice were implanted with B16.SIY melanoma cells ($1\times10^6$ cells in 100 μL PBS). Treatments began when tumors reached a volume of approximately 100 mm$^3$, on day 7 post tumor implantation. Mice were treated with 2'3'-SR-(3'F-G)(2'O,4'C-LNA-A) (Compound 15c, Example 4), at 100 μg in a total volume of 40 μL HBSS (6 mice per group), and compared to HBSS vehicle control (4 mice per group). The compounds were administered by a single subcutaneous injection into the center of the tumor (IT) using a 27-gauge needle. Tumors were measured twice weekly.

As shown in FIGS. 13A-D, in the aggressive B16.SIY melanoma model, the LNA-CDN Compound 15c induces complete tumor rejection in the WT mice, as compared to HBSS vehicle control, while having no anti-tumor effect in the STING-deficient GT mice, similar to HBSS. Further, it was observed that all surviving mice in the WT group treated with Compound 15c presented with patches of vitiligo and alopecia, indicative of a strong CD8$^+$ T cell response against endogenous melanocyte and keratinocyte differentiation antigens, which was not evident in the GT mice treated with Compound 15c (data not shown). These data demonstrate the profound anti-tumor immunity of this LNA-CDN compound in an aggressive murine tumor model.

Example 15: Systemic Pro-Inflammatory Cytokines Induced by LNA-CDN Compounds To assess the relative induction of systemic serum cytokines by the LNA-CDN compounds as a measure of safety and tolerability, mice from Example 13 were bled six hours post-IT injection and their serum was assessed by Mouse Inflammation Cytometric Bead Array (CBA, BD Biosciences). As shown in FIGS. 14A-D (Comp. 5a) and 15A-D (Comp. 10c), concentrations of pro-inflammatory cytokines TNF-α (A), IFN-γ (B), IL-6 (C), and MCP-1 (D) at the 1 μg dose were comparable between 2'3'-RR-(A)(A) and the LNA-CDN Compounds 5a and 10c, with Compound 10c demonstrating significantly lower systemic cytokines than 2'3'-RR-(A)(A) (* $P<0.05$,  $P<0.01$, * $P<0.001$, student's t-test). These data demonstrate a comparable safety profile for Compound 5a, as compared to reference compound 2'3'-RR-(A)(A), and a superior safety profile for Compound 10c.

Example 16: T Cell Mediated Anti-Tumor Immunity Induced by LNA-CDN Compounds To demonstrate that the anti-tumor effect is mediated by adaptive T cell immune responses, mice from Example 13 were euthanized on day 7 post IT injection and spleens were harvested and splenocytes prepared. Splenocytes ($2\times10^5$) were (A) stimulated overnight in an IFNγ ELISPOT assay with media alone or with 1 μM SIYRYYGL (SIY) (SEQ ID NO: 17) peptide. IFN-γ ELISPOT plates were developed and quantified using a CTL plate reader and ImmunoSpot software; or (B) pre-incubated with anti-CD16/32 monoclonal antibody to block potential nonspecific binding, and labeled with PE-MHC class I pentamer (Proimmune) consisting of murine H-2Kb complexed to SIYRYYGL (SIY) (SEQ ID NO: 17) peptide, anti-TCRβ-AF700 (H57-597), anti-CD8-Pacific Blue (53-6.7), anti-CD4-Pacific Orange (RM4-5) (all antibodies from BioLegend) and the Fixable Viability Dye eFluor 450 (eBioscience). Stained cells were analyzed using FACS Versa cytometer with FACSDiva software (BD). Data analysis was conducted with FlowJo software (Tree Star).

Figure 16A:
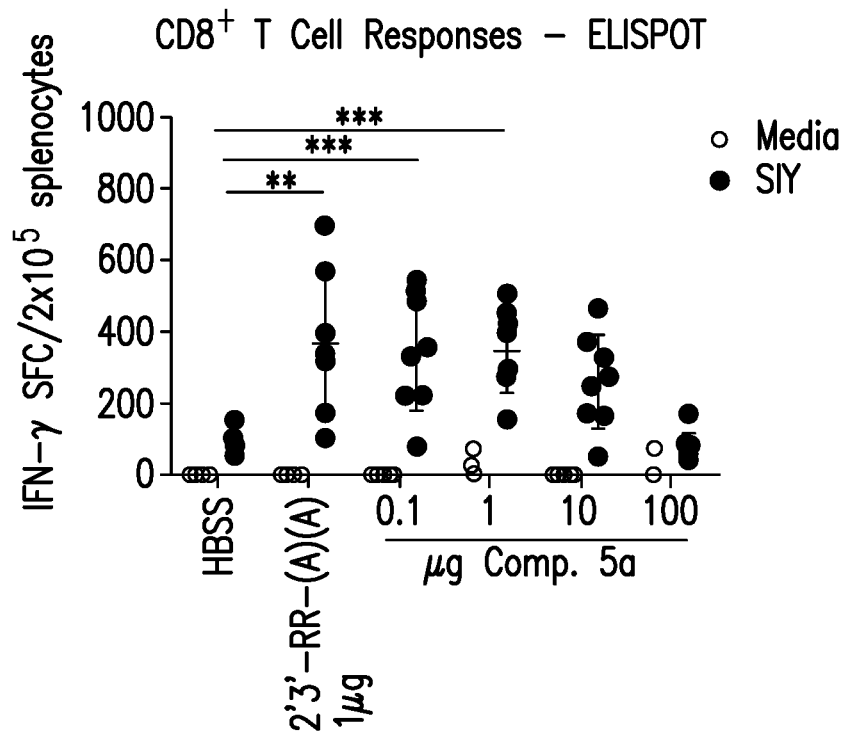
FIG. 16A-B depicts SIY+ CD8+ T-cells in splenocytes in a B16.SIY melanoma mouse model, measured in an IFNγ ELISPOT assay 7 days post intra-tumoral injection of HBSS vehicle control, reference compound 2'3'-RR-(A)(A) at 1 μg, or LNA-CDN Compound 5a (16A) or LNA-CDN Compound 10c (16B) at 0.1 μg, 1 μg, 10 μg or 100 μg.
Figure 16B:
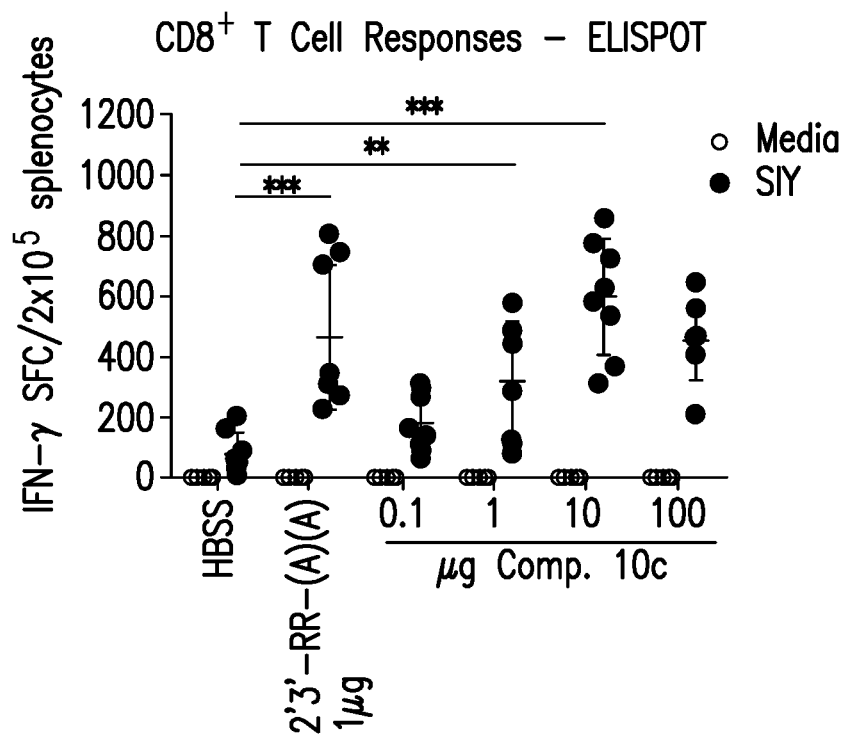
Figure 17A:
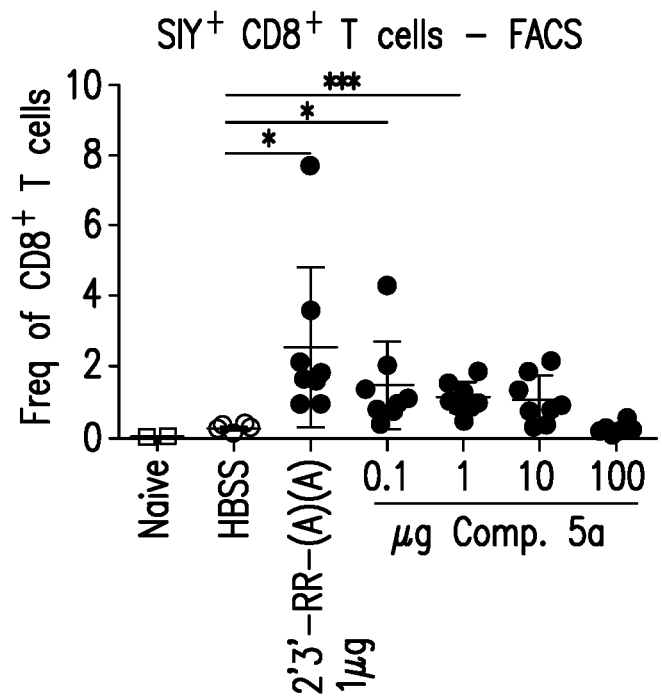
FIG. 17A-B depicts SIY+ CD8+ T-cells in splenocytes in a B16.SIY melanoma mouse model, measured in a FACS assay 7 days post intra-tumoral injection of HBSS vehicle control, reference compound 2'3'-RR-(A)(A) at 1 μg, or LNA-CDN Compound 5a (17A) or LNA-CDN Compound 10c (17B) at 0.1 μg, 1 μg, 10 μg or 100 μg.
Figure 17B:
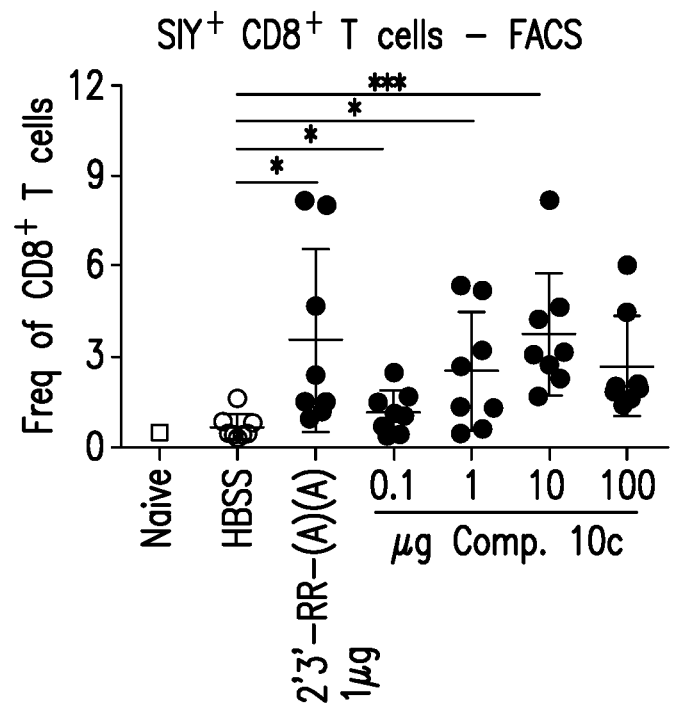

As shown in FIG. 16A, Compound 5a elicits significantly higher T cell production of IFNγ in response to SIY peptide stimulation at the 0.1, 1 and 10 μg doses, as compared to HBSS, and comparable T cell responses at 1 μg to the reference compound 2'3'-RR-(A)(A) (* $P<0.05$,  $P<0.01$, * $P<0.001$, student's t-test). As shown in FIG. 16B, Compound 10c demonstrates comparable responses at the 1 μg dose compared to the reference compound 2'3'-RR-(A)(A), and significantly higher responses at all doses tested compared to HBSS, demonstrating an even broader range of efficacy than Compound 5a. To further confirm that these responses were due to SIY-specific CD8$^+$ T cells, flow cytometry analysis was conducted using an SIY pentamer and antibodies specific to CD8$^+$ T cells. As shown in FIGS. 17A and B (A-Comp. 5a, B-Comp. 10c), similar trends in SIY-specific CD8$^+$ T cell frequencies were observed for both compounds, demonstrating the ability of these LNA-CDN compounds to elicit functional T cell-mediated anti-tumor immunity, in an antigen-specific manner. Further, Compound 10c demonstrated a broader range of dose responses, significantly improving the therapeutic window for inducing anti-tumor immunity.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

It is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

While the invention has been described and exemplified in sufficient detail for those skilled in this art to make and use it, various alternatives, modifications, and improvements should be apparent without departing from the spirit and scope of the invention. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

We claim:
1. A compound having the structure selected from the group consisting of Formula Ib, Formula Ic, and Formula Id:

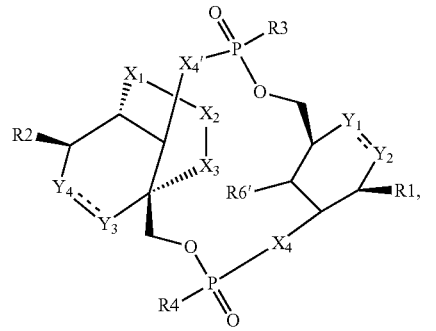

Formula Ia

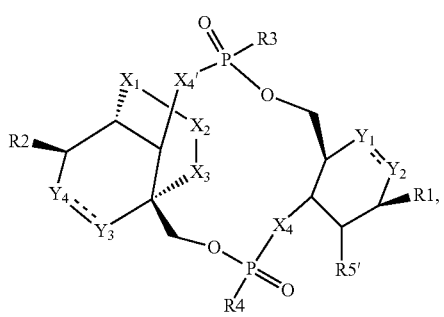

Formula Ib

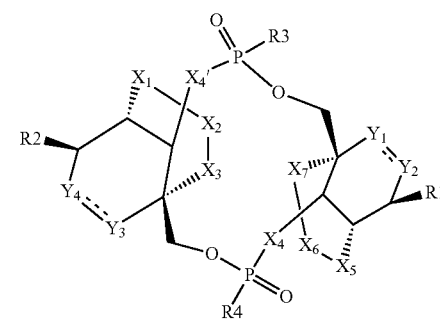

Formula Ic and

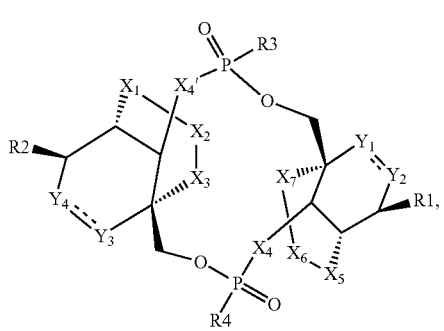

Formula Id or a prodrug, pharmaceutically acceptable salt, pharmaceutically acceptable solvate or pharmaceutically acceptable hydrate thereof, wherein:

R1 and R2 are independently a pyrimidine or purine nucleic acid base or analog or derivative thereof;

R3 and R4 are independently —OH, —OR$^a$, —SH or —SR$^a$;

$Y_1$ is —O—, —S— or —CRR— and $Y_2$ is absent, wherein each R is independently —H or —C$_{1-6}$alkyl, or the two R together with the carbon to which they are attached form a 3-6 membered heterocycloalkyl or C$_{3-6}$cycloalkyl spirocyclic ring; or $Y_1$ is —O—, —CH$_2$— or —CH= and $Y_2$ is —CH$_2$— or =CH—, selected to provide —Y$_1$-Y$_2$— as —O—CH$_2$—, —CH$_2$—CH$_2$— or —CH=CH—;

$Y_3$ is —O—, —S— or —CRR— and $Y_4$ is absent, wherein each R is independently —H or —C$_{1-6}$alkyl, or the two R together with the carbon to which they are attached form a 3-6 membered heterocycloalkyl or C$_{3-6}$cycloalkyl spirocyclic ring; or $Y_3$ is —O—, —CH$_2$— or —CH= and $Y_4$ is —CH$_2$— or =CH—, selected to provide —Y$_3$-Y$_4$— as —O—CH$_2$—, —CH$_2$—CH$_2$— or —CH=CH—;

$X_1$, $X_2$, and $X_3$ are all present, $X_1$ and $X_2$ are —C(R$^b$R$^c$)—, —N(R$^d$), —O— or —S(=O)$_2$—, and $X_3$ is —C(R$^b$R$^c$)— or —O—, selected to provide —X$_1$-X$_2$-X$_3$— as —C(R$^b$R$^c$)—C(R$^b$R$^c$)—C(R$^b$R$^c$)—, —C(R$^b$R$^c$)—N(R$^d$)—C(R$^b$R$^c$)—, —C(R$^b$R$^c$)—O—C(R$^b$R$^c$)—, —C(R$^b$R$^c$)—C(R$^b$R$^c$)—O—, —O—C(R$^b$R$^c$)—C(R$^b$R$^c$)—, —O—N(R$^d$)—C(R$^b$R$^c$)—, —S(=O)$_2$—N(R$^d$)—C(R$^b$R$^c$)—, —N(R$^d$)—C(R$^b$R$^c$)—C(R$^b$R$^c$)—, —N(R$^d$)—O—C(R$^b$R$^c$)— or —N(R$^d$)—S(=O)$_2$—C(R$^b$R$^c$)—; or $X_2$ is absent, $X_1$ and $X_3$ are both present, $X_1$ is —C(R$^b$R$^c$)—, —N(R$^d$) or —O— and $X_3$ is —C(R$^b$R$^c$)— or —S(=O)$_2$—, selected to provide —X$_1$-X$_3$— as —C(R$^b$R$^c$)—C(R$^b$R$^c$)—, —O—C(R$^b$R$^c$)—, —N(R$^d$)—C(R$^b$R$^c$)— or —N(R$^d$)—S(=O)$_2$—;

$X_4'$ is —O— or —NH—;

$X_4$ is —O— or —NH—;

R5' is selected from the group consisting of —H, —OH, halogen and —OR$^e$;

for Formula Ic, $X_5$ and $X_6$ are —C(R$^b$R$^c$)—, —N(R$^d$), —O— or —S(=O)$_2$—, and $X_7$ is —C(R$^b$R$^c$)— or —O—, selected to provide —X$_5$-X$_6$-X$_7$— as —C(R$^b$R$^c$)—C(R$^b$R$^c$)—C(R$^b$R$^c$)—, —C(R$^b$R$^c$)—N(R$^d$)—C(R$^b$R$^c$)—, —C(R$^b$R$^c$)—O—C(R$^b$R$^c$)—, —C(R$^b$R$^c$)—C(R$^b$R$^c$)—O—, —O—C(R$^b$R$^c$)—C(R$^b$R$^c$)—, —O—N(R$^d$)—C(R$^b$R$^c$)—, —S(=O)$_2$—N(R$^d$)—C(R$^b$R$^c$)—, —N(R$^d$)—C(R$^b$R$^c$)—C(R$^b$R$^c$)—, —N(R$^d$)—O—C(R$^b$R$^c$)— or —N(R$^d$)—S(=O)$_2$—C(R$^b$R$^c$)—;

for Formula Id, $X_5$ is —C(R$^b$R$^c$)—, —N(R$^d$) or —O— and $X_7$ is —C(R$^b$R$^c$)— or —S(=O)$_2$—, selected to provide —X$_5$-X$_7$— as —C(R$^b$R$^c$)—C(R$^b$R$^c$)—, —O—C(R$^b$R$^c$)—, —N(R$^d$)—C(R$^b$R$^c$)— or —N(R$^d$)—S(=O)$_2$—;

R$^a$ at each occurrence is independently selected from the group consisting of alkyl, alkenyl, alkynyl, heteroalkyl, carbocyclyl, heterocyclyl, aryl, heteroaryl and —C(=O)R$^f$; wherein alkyl, alkenyl, alkynyl or heteroalkyl are optionally independently substituted with one or more —R$^m$, and carbocyclyl, heterocyclyl, aryl or heteroaryl are optionally independently substituted with one or more —Re;

R$^b$ and R$^c$, at each occurrence, are independently selected from the group consisting of —H, halogen, alkyl, alkenyl, alkynyl, heteroalkyl, carbocyclyl, heterocyclyl, aryl, heteroaryl, —R' and -L$_1$-R$^g$; or R$^b$ and R$^c$ together on a carbon are =O, =CR$^h$R$^h$, =N—OR$^i$, =N—R$^i$, or =N—NR$^i$R$^i$; or R$^b$ and R$^c$ together with the carbon to which they are attached form a C$_{3-6}$cycloalkyl or 3 to 6 membered heterocycloalkyl spirocyclic ring; wherein alkyl, alkenyl, alkynyl or heteroalkyl are optionally independently substituted with one or more —$R^m$, and carbocyclyl, heterocyclyl, aryl or heteroaryl are optionally independently substituted with one or more —$R^n$;

$R^d$ at each occurrence is independently selected from the group consisting of —H, alkyl, alkenyl, alkynyl, heteroalkyl, carbocyclyl, heterocyclyl, aryl, heteroaryl, —R" and -$L_2$-$R^j$; wherein alkyl, alkenyl, alkynyl or heteroalkyl are optionally independently substituted with one or more —$R^m$, and carbocyclyl, heterocyclyl, aryl or heteroaryl are optionally independently substituted with one or more —$R^n$; or $R^d$ is a suitable nitrogen protecting group;

$R^e$ is selected from the group consisting of alkyl, alkenyl, alkynyl, heteroalkyl, carbocyclyl, heterocyclyl, aryl, heteroaryl and —C(=O)$R^f$; wherein alkyl, alkenyl, alkynyl or heteroalkyl are optionally independently substituted with one or more —$R^m$, and carbocyclyl, heterocyclyl, aryl or heteroaryl are optionally independently substituted with one or more —$R^n$; or $R^e$ is a suitable oxygen protecting group;

$R^f$ at each occurrence is independently selected from the group consisting of alkyl, alkenyl, alkynyl, heteroalkyl, carbocyclyl, heterocyclyl, aryl, and heteroaryl; wherein alkyl, alkenyl, alkynyl or heteroalkyl are optionally independently substituted with one or more —$R^m$, and carbocyclyl, heterocyclyl, aryl or heteroaryl are optionally independently substituted with one or more —$R^n$;

R' at each occurrence is selected from the group consisting of —CN, —$NO_2$, —OH, —SH, —$NH_2$, —C(=W)—WH, —C(=W)—$NH_2$, —C(=W)—NH—WH, —C=N—OH, —C(=NH)—$NH_2$, —W—C(=W)—WH, —W—C(=W)—$NH_2$, —S(=O)$_2$—$NH_2$, —S(=O)$_2$—NH—W—, —NH—$NH_2$, —NH—WH, —NH—C(=W)—WH, —NH—C(=W)—$NH_2$, —NH—S(=O)$_2$—$NH_2$, and —NH—C(=NH)—$NH_2$;

R" at each occurrence is selected from the group consisting of —OH, —SH, —$NH_2$, —C(=W)—WH, —C(=W)—$NH_2$, —C(=NH)—$NH_2$, and —S(=O)$_2$—$NH_2$;

$L_1$ is selected from the group consisting of —O—, —S—, —S(=O)—, —S(=O)$_2$—, —C(=W)—, —C(=W)—W—, —C(=W)—$NR^k$—, —C(=W)—$NR^k$—W—, —C(=$NR^k$)$NR^k$—, —C($NR^kR^k$)=N—, —W—C(=W)—, —W—C(=W)—$NR^k$—, —S(=O)$_2$—$NR^k$—, —S(=O)$_2$—$NR^k$—W—, —$NR^k$—, —N=$CR^h$—, —$NR^k$—W—, —$NR^k$—$NR^k$—, —$NR^k$—C(=$NR^k$)$NR^k$—, —$NR^k$—C($NR^kR^k$)=N—, —$NR^k$—C(=W)—, —$NR^k$—C(=W)—W—, —$NR^k$—C(=W)—$NR^k$—, —$NR^k$—S(=O)$_2$—$NR^k$— and —$NR^k$—S(=O)$_2$—;

$L_2$ is selected from the group consisting of —O—, —S—, —$NR^k$—, —C(=W)—, —C(=W)—W—, —C(=W)—$NR^k$—, —C(=$NR^k$)$NR^k$—, —C($NR^kR^k$)=N—, —S(=O)$_2$—$NR^k$—, and —S(=O)$_2$—;

$R^g$ and $R^j$, at each occurrence, are independently selected from the group consisting of alkyl, alkenyl, alkynyl, heteroalkyl, carbocyclyl, heterocyclyl, aryl and heteroaryl; wherein alkyl, alkenyl, alkynyl or heteroalkyl are optionally independently substituted with one or more —$R^m$, and carbocyclyl, heterocyclyl, aryl or heteroaryl are optionally independently substituted with one or more —Re;

$R^h$ at each occurrence is independently selected from the group consisting of —H, halogen, alkyl, alkenyl, alkynyl, heteroalkyl, carbocyclyl, heterocyclyl, aryl and heteroaryl; wherein alkyl, alkenyl, alkynyl or heteroalkyl are optionally independently substituted with one or more —$R^m$, and carbocyclyl, heterocyclyl, aryl or heteroaryl are optionally independently substituted with one or more —Re;

$R^i$ and $R^k$, at each occurrence, are independently selected from the group consisting of —H, alkyl, alkenyl, alkynyl, heteroalkyl, carbocyclyl, heterocyclyl, aryl and heteroaryl; wherein alkyl, alkenyl, alkynyl or heteroalkyl are optionally independently substituted with one or more —$R^m$, and carbocyclyl, heterocyclyl, aryl or heteroaryl are optionally independently substituted with one or more —Re;

$R^m$ at each occurrence is independently selected from the group consisting of =O, halogen, carbocyclyl, heterocyclyl, aryl, heteroaryl, —R' and -$L_3$-$R^o$, when substituted on an available carbon atom, and carbocyclyl, heterocyclyl, aryl, heteroaryl, —R" and -$L_4$-R", when substituted on an available nitrogen atom; wherein carbocyclyl, heterocyclyl, aryl and heteroaryl are optionally independently substituted with one or more —$R^n$;

$R^n$ at each occurrence is independently selected from the group consisting of =O, halogen, alkyl, alkenyl, alkynyl, heteroalkyl, carbocyclyl, heterocyclyl, aryl, heteroaryl, —R' and -$L_3$-$R^o$, when substituted on an available carbon atom, and alkyl, alkenyl, alkynyl, heteroalkyl, carbocyclyl, heterocyclyl, aryl, heteroaryl, —R" and -$L_4$-R", when substituted on an available nitrogen atom;

$L_3$ is selected from the group consisting of —O—, —S—, —S(=O)—, —S(=O)$_2$—, —C(=W)—, —C(=W)—W—, —C(=W)—$NR^q$—, —C(=W)—$NR^q$—W—, —C=N—O—, —C(=$NR^q$)$NR^q$—, —C($NR^qR^q$)=N—, —W—C(=W)—, —W—C(=W)—W—, —W—C(=W)—$NR^q$—, —S(=O)$_2$—$NR^q$—, —S(=O)$_2$—$NR^q$—W—, —$NR^q$—, —N=$CR^r$—, —$NR^q$—W—, —$NR^q$—$NR^q$—, —$NR^q$—C(=$NR^q$)$NR^q$—, —$NR^q$—C($NR^qR^q$)=N—, —$NR^q$—C(=W)—, —$NR^q$—C(=W)—W—, —$NR^q$—C(=W)—$NR^q$—, —$NR^q$—S(=O)$_2$—$NR^q$—, and —$NR^q$—S(=O)$_2$—;

$L_4$ is selected from the group consisting of —O—, —S—, —$NR^q$—, —C(=W)—, —C(=W)—W—, —C(=W)—$NR^q$—, —C(=NW)$NR^q$—, —C($NR^qR^q$)=N—, —S(=O)$_2$—$NR^q$—, and —S(=O)$_2$—;

each W is independently O or S;

$R^o$ and $R^p$, at each occurrence, are independently selected from the group consisting of alkyl, alkenyl, alkynyl, heteroalkyl, carbocyclyl, heterocyclyl, aryl and heteroaryl; wherein alkyl, alkenyl, alkynyl and heteroalkyl, are optionally independently substituted with one or more —$R^s$; carbocyclyl or heterocyclyl are optionally independently substituted with one or more —$R^t$; and aryl or heteroaryl are optionally independently substituted with one or more —$R^u$;

$R^q$ at each occurrence is independently selected from the group consisting of —H, alkyl, alkenyl, alkynyl, heteroalkyl, carbocyclyl, heterocyclyl, aryl and heteroaryl; wherein alkyl, alkenyl, alkynyl and heteroalkyl, are optionally independently substituted with one or more —$R^s$; carbocyclyl or heterocyclyl are optionally independently substituted with one or more —$R^t$; and aryl or heteroaryl are optionally independently substituted with one or more —$R^u$;

$R^r$ at each occurrence is independently selected from the group consisting of —H, halogen, alkyl, alkenyl, alkynyl, heteroalkyl, carbocyclyl, heterocyclyl, aryl and heteroaryl; wherein alkyl, alkenyl, alkynyl and heteroalkyl, are optionally independently substituted with one or more —R$^s$; carbocyclyl or heterocyclyl are optionally independently substituted with one or more —R$^t$; and aryl or heteroaryl are optionally independently substituted with one or more —R$^u$;

R$^s$ at each occurrence is independently selected from the group consisting of halogen, =O, —OH, —SH, —NH$_2$, —CN, C$_{1-6}$alkoxy, C$_{1-6}$alkylthio, C$_{1-6}$alkylsulfinyl, C$_{1-6}$ alkylsulfonyl, C$_{1-6}$alkylamino, C$_{1-6}$dialkylamino, and N-linked-heterocycloalkyl; wherein C$_{1-6}$alkyl, alone or as part of C$_{1-6}$alkoxy, C$_{1-6}$alkylthio, C$_{1-6}$alkylsulfinyl, C$_{1-6}$alkylsulfonyl, C$_{1-6}$alkylamino, or C$_{1-6}$dialkylamino, is optionally substituted with one or more substituents independently selected from the group consisting of —OH, —SH, —NH$_2$, halogen, C$_{1-6}$alkoxy, C$_{1-6}$haloalkoxy, C$_{1-6}$alkylthio, C$_{1-6}$haloalkylthio, C$_{1-6}$alkylsulfinyl, C$_{1-6}$haloalkylsulfinyl, C$_{1-6}$alkylsulfonyl, C$_{1-6}$haloalkylsulfonyl, C$_{1-6}$ alkylamino, C$_{1-6}$dialkylamino and N-linked-heterocycloalkyl;

R$^t$ at each occurrence is independently selected from the group consisting of halogen, =O, —OH, —SH, —NH$_2$, —CN, C$_{1-6}$alkyl, C$_{2-6}$alkenyl, C$_{2-6}$alkynyl, C$_{1-6}$alkoxy, C$_{1-6}$alkylthio, C$_{1-6}$ alkylsulfinyl, C$_{1-6}$alkylsulfonyl, C$_{1-6}$ alkylamino, C$_{1-6}$dialkylamino and N-linked-heterocycloalkyl; wherein C$_{2-6}$alkenyl, C$_{2-6}$alkynyl, and C$_{1-6}$alkyl, alone or as part of C$_{1-6}$alkoxy, C$_{1-6}$alkylthio, C$_{1-6}$alkylsulfinyl, C$_{1-6}$alkylsulfonyl, C$_{1-6}$alkylamino, or C$_{1-6}$dialkylamino, is optionally substituted with one or more substituents independently selected from the group consisting of —OH, —SH, —NH$_2$, halogen, C$_{1-6}$alkoxy, C$_{1-6}$haloalkoxy, C$_{1-6}$alkylthio, C$_{1-6}$haloalkylthio, C$_{1-6}$alkylsulfinyl, C$_{1-6}$haloalkylsulfinyl, C$_{1-6}$alkylsulfonyl, C$_{1-6}$haloalkylsulfonyl, C$_{1-6}$alkylamino, C$_{1-6}$dialkylamino and N-linked-heterocycloalkyl; and R$^u$ at each occurrence is independently selected from the group consisting of halogen, —OH, —SH, —NH$_2$, —CN, —NO$_2$, C$_{1-6}$alkyl, C$_{2-6}$alkenyl, C$_{2-6}$alkynyl, C$_{1-6}$alkoxy, C$_{1-6}$alkylthio, C$_{1-6}$alkylsulfinyl, C$_{1-6}$alkylsulfonyl, C$_{1-6}$alkylamino, C$_{1-6}$dialkylamino, and N-linked-heterocycloalkyl; wherein C$_{2-6}$alkenyl, C$_{2-6}$alkynyl, and C$_{1-6}$alkyl, alone or as part of C$_{1-6}$alkoxy, C$_{1-6}$alkylthio, C$_{1-6}$alkylsulfinyl, C$_{1-6}$alkylsulfonyl, C$_{1-6}$alkylamino, or C$_{1-6}$dialkylamino, is optionally substituted with one or more substituents independently selected from the group consisting of —OH, —SH, —NH$_2$, halogen, C$_{1-6}$alkoxy, C$_{1-6}$haloalkoxy, C$_{1-6}$alkylthio, C$_{1-6}$haloalkylthio, C$_{1-6}$alkylsulfinyl, C$_{1-6}$haloalkylsulfinyl, C$_{1-6}$alkylsulfonyl, C$_{1-6}$haloalkylsulfonyl, C$_{1-6}$alkylamino, C$_{1-6}$dialkylamino and N-linked-heterocycloalkyl.

2. The compound according to claim 1, wherein R1 and R2 are independently selected from the group consisting of:

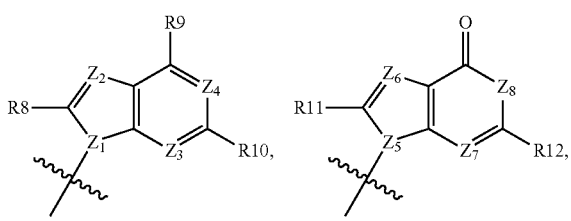

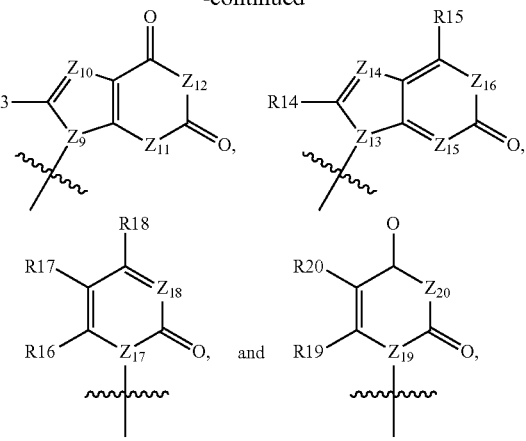

wherein:

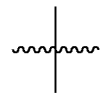

indicates the bond of R1 or R2 to the ring as shown in Formula Ib, Formula Ic or Formula Id;

$Z_1$, $Z_5$, $Z_9$, $Z_{13}$, $Z_{17}$ and $Z_{19}$ are independently

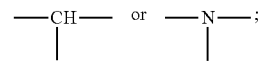

$Z_8$, $Z_{11}$, $Z_{12}$, $Z_{16}$ and $Z_{20}$ are independently —CR$^v$R$^w$—, —O— or —NR$^x$—;

$Z_2$, $Z_3$, $Z_4$, $Z_6$, $Z_7$, $Z_{10}$, $Z_{14}$, $Z_{15}$ and $Z_{18}$ are independently =CR$^v$— or =N—;

R$^v$ and R$^w$, at each occurrence, are independently selected from the group consisting of —H, halogen, alkyl, alkenyl, alkynyl, heteroalkyl, carbocyclyl, heterocyclyl, aryl, heteroaryl, —R' and -L$_1$-R$^g$; or R$^v$ and R$^w$ together are =O, =CR$^h$R$^h$, =N—OR$^i$, =N—R$^i$, or =N—NR$^i$R$^i$; wherein alkyl, alkenyl, alkynyl or heteroalkyl are optionally independently substituted with one or more —R$^m$, and carbocyclyl, heterocyclyl, aryl or heteroaryl are optionally independently substituted with one or more —Rn;

each RX is independently selected from the group consisting of —H, alkyl, alkenyl, alkynyl, heteroalkyl, carbocyclyl, heterocyclyl, aryl, heteroaryl, —R'' and -L$_2$-R$^3$; wherein alkyl, alkenyl, alkynyl or heteroalkyl are optionally independently substituted with one or more —R$^m$, and carbocyclyl, heterocyclyl, aryl or heteroaryl are optionally independently substituted with one or more —Rn;

R8, R9, R10, R11, R12, R13, R14, R15, R16, R17, R18, R19 and R20 are independently selected from the group consisting of —H, halogen, alkyl, alkenyl, alkynyl, heteroalkyl, carbocyclyl, heterocyclyl, aryl, heteroaryl, —R' and -L$_1$-R$^g$; wherein alkyl, alkenyl, alkynyl or heteroalkyl are optionally independently substituted with one or more —R$^m$, and carbocyclyl, heterocyclyl, aryl or heteroaryl are optionally independently substituted with one or more —R$^n$;

$R^{g'}$ is $R^g$ or a suitable nitrogen protecting group when $L_1$ is —NH—; and $R^l$, $R^n$, $R^g$, $R^h$, $R^i$, $R^j$, $R^m$, $R^n$, $L_1$ and $L_2$ are as defined in claim 1.

3. The compound according to claim 1, wherein R5' is —H, —OH or —F.

4. The compound according to claim 3, wherein R1 and R2 are independently

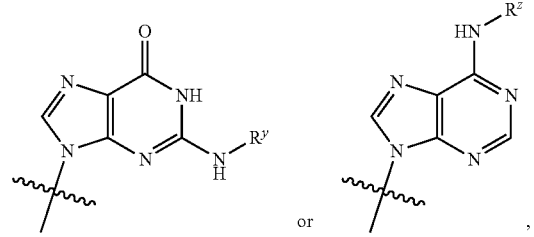

or

, wherein

indicates the bond of R1 or R2 to the ring of Formula Ib, Formula Ic, or Formula Id, and wherein $R^y$ and $R^z$ are independently —H, —C(=O)—$C_{1-6}$ alkyl, —C(=O)-phenyl or other suitable nitrogen protecting group.

5. The compound according to claim 4, wherein R3 and R4 are —SH.

6. The compound according to claim 5, wherein —$X_1$-$X_2$-$X_3$— or —$X_1$-$X_3$—, and when present —$X_5$-$X_6$-$X_7$— or —$X_5$-$X_7$—, are independently —O—C($R^{b'}R^{c'}$)—, where $R^{b'}$, $R^{c'}$ at each occurrence are —H.

7. The compound according to claim 1, wherein the compound is a compound of Formula IIb or Formula IIc:

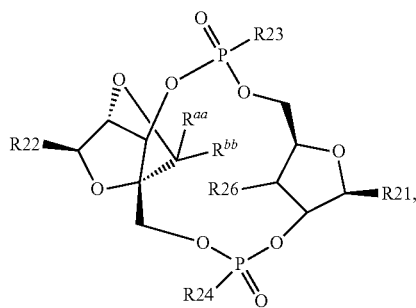

Formula IIa

Formula IIb

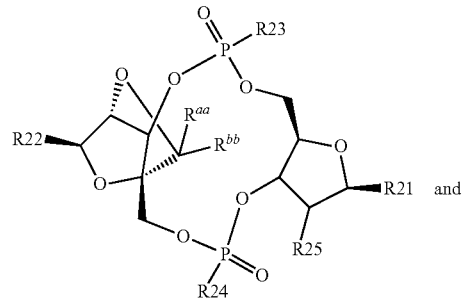

and

Formula IIc

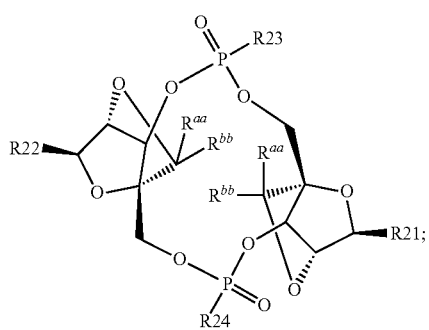

;

or a prodrug, pharmaceutically acceptable salt, pharmaceutically acceptable solvate or pharmaceutically acceptable hydrate thereof, wherein:

R21 and R22 are independently selected from the group consisting of:

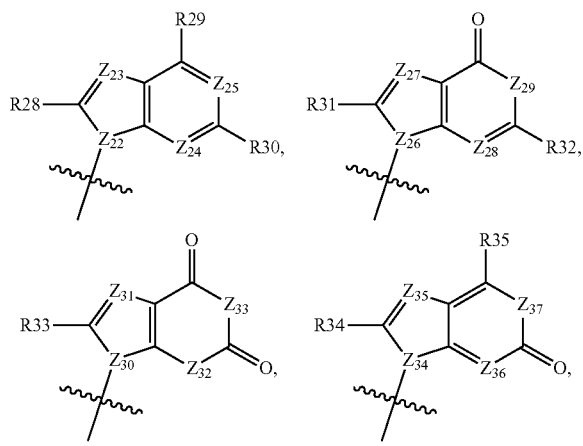

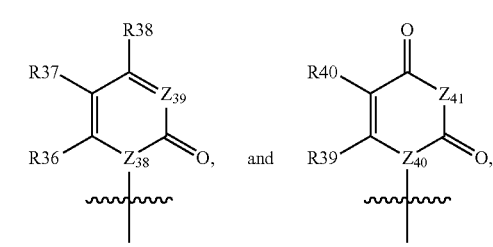

and wherein

indicates the bond of R21 or R22 to the ring as shown in Formula IIb or Formula IIc;

R23 and R24 are independently —OH, —SH or —SR$^{cc}$;

R25 is selected from the group consisting of —H, —OH, halogen and —OR$^{dd}$;

R$^{aa}$ and R$^{bb}$, at each occurrence, are independently selected from the group consisting of —H, halogen, alkyl, alkenyl, alkynyl, heteroalkyl, carbocyclyl, heterocyclyl, aryl, heteroaryl, —R' and -L$_5$-R$^{ee}$; or R$^{aa}$ and R$^{bb}$ together on a carbon are =O, =C$^{ff}$R$^{ff}$, =N—OR$^{gg}$, =N—R$^{gg}$, or =N—NR$^{gg}$R$^{gg}$; or R$^{aa}$ and R$^{bb}$ together with the carbon to which they are attached form a C$_{3-6}$cycloalkyl or 3 to 6 membered heterocycloalkyl spirocyclic ring; wherein alkyl, alkenyl, alkynyl or heteroalkyl are optionally independently substituted with one or more —R$^{jj}$, and carbocyclyl, heterocyclyl, aryl or heteroaryl are optionally independently substituted with one or more —R$^{kk}$;

R$^{cc}$ at each occurrence are independently selected from the group consisting of alkyl, alkenyl, alkynyl, heteroalkyl, carbocyclyl, heterocyclyl, aryl, heteroaryl and —C(=O)R$^{hh}$; wherein alkyl, alkenyl, alkynyl or heteroalkyl are optionally independently substituted with one or more —R$^{jj}$, and carbocyclyl, heterocyclyl, aryl or heteroaryl are optionally independently substituted with one or more —R$^{kk}$;

R$^{dd}$ is selected from the group consisting of alkyl, alkenyl, alkynyl, heteroalkyl, carbocyclyl, heterocyclyl, aryl, heteroaryl and —C(=O)R$^{hh}$; wherein alkyl, alkenyl, alkynyl or heteroalkyl are optionally independently substituted with one or more —R$^{jj}$, and carbocyclyl, heterocyclyl, aryl or heteroaryl are optionally independently substituted with one or more —R$^{kk}$; or R$^{dd}$ is a suitable oxygen protecting group;

R$^{ee}$ at each occurrence is independently selected from the group consisting of alkyl, alkenyl, alkynyl, heteroalkyl, carbocyclyl, heterocyclyl, aryl and heteroaryl; wherein alkyl, alkenyl, alkynyl or heteroalkyl are optionally independently substituted with one or more —R$^{jj}$, and carbocyclyl, heterocyclyl, aryl or heteroaryl are optionally independently substituted with one or more —R$^{kk}$;

R$^{ff}$ at each occurrence is independently selected from the group consisting of —H, halogen, alkyl, alkenyl, alkynyl, heteroalkyl, carbocyclyl, heterocyclyl, aryl and heteroaryl; wherein alkyl, alkenyl, alkynyl or heteroalkyl are optionally independently substituted with one or more —R$^{jj}$, and carbocyclyl, heterocyclyl, aryl or heteroaryl are optionally independently substituted with one or more —R$^{kk}$;

R$^{gg}$ at each occurrence is independently selected from the group consisting of —H, alkyl, alkenyl, alkynyl, heteroalkyl, carbocyclyl, heterocyclyl, aryl and heteroaryl; wherein alkyl, alkenyl, alkynyl or heteroalkyl are optionally independently substituted with one or more —R$^{jj}$, and carbocyclyl, heterocyclyl, aryl or heteroaryl are optionally independently substituted with one or more —R$^{kk}$;

R$^{hh}$ at each occurrence is independently selected from the group consisting of alkyl, alkenyl, alkynyl, heteroalkyl, carbocyclyl, heterocyclyl, aryl, and heteroaryl; wherein alkyl, alkenyl, alkynyl or heteroalkyl are optionally independently substituted with one or more —R$^{jj}$, and carbocyclyl, heterocyclyl, aryl or heteroaryl are optionally independently substituted with one or more —R$^{kk}$;

R' at each occurrence is selected from the group consisting of —CN, —NO$_2$, —OH, —SH, —NH$_2$, —C(=W)—WH, —C(=W)—NH$_2$, —C(=W)—NH—WH, —C=N—OH, —C(=NH)—NH$_2$, —W—C(=W)—WH, —W—C(=W)—NH$_2$, —S(=O)$_2$—NH$_2$, —S(=O)$_2$—NH—W—, —NH—NH$_2$, —NH—WH, —NH—C(=W)—WH, —NH—C(=W)—NH$_2$, —NH—S(=O)$_2$—NH$_2$, and —NH—C(=NH)—NH$_2$;

L$_5$ is selected from the group consisting of —O—, —S—, —S(=O)—, —S(=O)$_2$—, —C(=W)—, —C(=W)—W—, —C(=W)—NR$^{ii}$—, —C(=W)—NR$^{ii}$—W—, —C=N—O—, —C(=NR$^{ii}$)NR$^{ii}$—, —C(NR$^{ii}$R$^{ii}$)=N—, —W—C(=W)—, —W—C(=W)—W—, —W—C(=W)—NR$^{ii}$—, —S(=O)$_2$—NR$^{ii}$—, —S(=O)$_2$—NR$^{ii}$—W—, —NR$^{ii}$—, —N=CR$^{ff}$—, —NR$^{ii}$—W—, —NR$^{ii}$—NR$^{ii}$—, —NR$^{ii}$—C(=NR$^{ii}$)NR$^{ii}$—, —NR$^{ii}$—C(NR$^{ii}$R$^{ii}$)=N—, —NR$^{ii}$—C(=W)—, —NR$^{ii}$—C(=W)—W—, —NR$^{ii}$—C(=W)—NR$^{ii}$—, —NR$^{ii}$—S(=O)$_2$—NR$^{ii}$— and —NR$^{ii}$—S(=O)$_2$—;

R$^{ii}$ at each occurrence is independently selected from the group consisting of —H, alkyl, alkenyl, alkynyl, heteroalkyl, carbocyclyl, heterocyclyl, aryl and heteroaryl; wherein alkyl, alkenyl, alkynyl or heteroalkyl are optionally independently substituted with one or more —R$^{jj}$, and carbocyclyl, heterocyclyl, aryl or heteroaryl are optionally independently substituted with one or more —R$^{kk}$;

R$^{jj}$ at each occurrence is independently selected from the group consisting of =O, halogen, carbocyclyl, heterocyclyl, aryl, heteroaryl, —R' and -L$_6$-R", when substituted on an available carbon atom, and carbocyclyl, heterocyclyl, aryl, heteroaryl, —R" and -L$_7$-R'", when substituted on an available nitrogen atom; wherein carbocyclyl, heterocyclyl, aryl and heteroaryl are optionally independently substituted with one or more —R$^{kk}$;

R$^{kk}$ at each occurrence is independently selected from the group consisting of =O, halogen, alkyl, alkenyl, alkynyl, heteroalkyl, carbocyclyl, heterocyclyl, aryl, heteroaryl, —R' and -L$_6$-R'", when substituted on an available carbon atom, and alkyl, alkenyl, alkynyl, heteroalkyl, carbocyclyl, heterocyclyl, aryl, heteroaryl, —R" and -L$_7$-R'"', when substituted on an available nitrogen atom;

R" at each occurrence is selected from the group consisting of —OH, —SH, —NH$_2$, —C(=W)—WH, —C(=W)—NH$_2$, —C(=NH)—NH$_2$, and —S(=O)$_2$—NH$_2$;

L$_6$ is selected from the group consisting of —O—, —S—, —S(=O)—, —S(=O)$_2$—, —C(=W)—, —C(=W)—W—, —C(=W)—NR$^{oo}$—, —C(=W)—NR$^{oo}$—W—, —C=N—O—, —C(=NR$^{oo}$)NR$^{oo}$—, —C(NR$^{oo}$R$^{oo}$)=N—, —W—C(=W)—, —W—C(=W)—W—, —W—C(=W)—NR$^{oo}$—, —S(=O)$_2$—NR$^{oo}$—, —S(=O)$_2$—NR$^{oo}$—W—, —NR$^{oo}$—, —N=CR$^{pp}$—, —NR$^{oo}$—W—, —NR$^{oo}$—NR$^{oo}$—, —NR$^{oo}$—C(=NR$^{oo}$)NR$^{oo}$—, —NR$^{oo}$—C(NR$^{oo}$R$^{oo}$)=N—, —NR$^{oo}$—C(=W)—, —NR$^{oo}$—C(=W)—W—, —NR$^{oo}$—C(=W)—NR$^{oo}$—, —NR$^{oo}$—S(=O)$_2$—NR$^{oo}$—, and —NR$^{oo}$—S(=O)$_2$—;

$L_7$ is selected from the group consisting of —O—, —S—, —NR$^{oo}$—, —C(=W)—, —C(=W)—W—, —C(=W)—NR$^{oo}$—, —C(=NR$^{oo}$)NR$^{oo}$—, —C(NR$^{oo}$R$^{oo}$)=N—, —S(=O)$_2$—NR$^{oo}$—, and —S(=O)$_2$—;

each W is independently O or S;

$R^{mm}$ n and $R^{nn}$, at each occurrence, are independently selected from the group consisting of alkyl, alkenyl, alkynyl, heteroalkyl, carbocyclyl, heterocyclyl, aryl and heteroaryl; wherein alkyl, alkenyl, alkynyl and heteroalkyl, are optionally independently substituted with one or more —R$^{qq}$; carbocyclyl or heterocyclyl are optionally independently substituted with one or more —R$^{rr}$; and aryl or heteroaryl are optionally independently substituted with one or more —R$^{ss}$;

$R^{oo}$ at each occurrence is independently selected from the group consisting of —H, alkyl, alkenyl, alkynyl, heteroalkyl, carbocyclyl, heterocyclyl, aryl and heteroaryl; wherein alkyl, alkenyl, alkynyl and heteroalkyl, are optionally independently substituted with one or more —R$^{qq}$; carbocyclyl or heterocyclyl are optionally independently substituted with one or more —R$^{rr}$; and aryl or heteroaryl are optionally independently substituted with one or more —R$^{ss}$;

$R^{pp}$ at each occurrence is independently selected from the group consisting of —H, halogen, alkyl, alkenyl, alkynyl, heteroalkyl, carbocyclyl, heterocyclyl, aryl and heteroaryl; wherein alkyl, alkenyl, alkynyl and heteroalkyl, are optionally independently substituted with one or more —R$^{qq}$; carbocyclyl or heterocyclyl are optionally independently substituted with one or more —R$^{rr}$; and aryl or heteroaryl are optionally independently substituted with one or more —R$^{ss}$;

$R^{qq}$ at each occurrence is independently selected from the group consisting of halogen, =O, —OH, —SH, —NH$_2$, —CN, $C_{1-6}$alkoxy, $C_{1-6}$alkylthio, $C_{1-6}$alkylsulfinyl, $C_{1-6}$alkylsulfonyl, $C_{1-6}$alkylamino, $C_{1-6}$dialkylamino, and N-linked-heterocycloalkyl; wherein $C_{1-6}$alkyl, alone or as part of $C_{1-6}$alkoxy, $C_{1-6}$alkylthio, $C_{1-6}$alkylsulfinyl, $C_{1-6}$alkylsulfonyl, $C_{1-6}$alkylamino, or $C_{1-6}$dialkylamino, is optionally substituted with one or more substituents independently selected from the group consisting of —OH, —SH, —NH$_2$, halogen, $C_{1-6}$alkoxy, $C_{1-6}$haloalkoxy, $C_{1-6}$alkylthio, $C_{1-6}$haloalkylthio, $C_{1-6}$alkylsulfinyl, $C_{1-6}$haloalkylsulfinyl, $C_{1-6}$alkylsulfonyl, $C_{1-6}$haloalkylsulfonyl, $C_{1-6}$alkylamino, $C_{1-6}$dialkylamino and N-linked-heterocycloalkyl;

$R^{rr}$ at each occurrence is independently selected from the group consisting of halogen, =O, —OH, —SH, —NH$_2$, —CN, $C_{1-6}$alkyl, $C_{2-6}$alkenyl, $C_{2-6}$alkynyl, $C_{1-6}$alkoxy, $C_{1-6}$alkylthio, $C_{1-6}$alkylsulfinyl, $C_{1-6}$alkylsulfonyl, $C_{1-6}$alkylamino, $C_{1-6}$dialkylamino and N-linked-heterocycloalkyl; wherein $C_{2-6}$alkenyl, $C_{2-6}$alkynyl, and $C_{1-6}$alkyl, alone or as part of $C_{1-6}$alkoxy, $C_{1-6}$alkylthio, $C_{1-6}$alkylsulfinyl, $C_{1-6}$alkylsulfonyl, $C_{1-6}$alkylamino, or $C_{1-6}$dialkylamino, is optionally substituted with one or more substituents independently selected from the group consisting of —OH, —SH, —NH$_2$, halogen, $C_{1-6}$alkoxy, $C_{1-6}$haloalkoxy, $C_{1-6}$alkylthio, $C_{1-6}$haloalkylthio, $C_{1-6}$alkylsulfinyl, $C_{1-6}$haloalkylsulfinyl, $C_{1-6}$alkylsulfonyl, $C_{1-6}$haloalkylsulfonyl, $C_{1-6}$alkylamino, $C_{1-6}$dialkylamino and N-linked-heterocycloalkyl; and $R^{ss}$ at each occurrence is independently selected from the group consisting of halogen, —OH, —SH, —NH$_2$, —CN, —NO$_2$, $C_{1-6}$alkyl, $C_{2-6}$alkenyl, $C_{2-6}$alkynyl, $C_{1-6}$alkoxy, $C_{1-6}$alkylthio, $C_{1-6}$alkylsulfinyl, $C_{1-6}$alkylsulfonyl, $C_{1-6}$alkylamino, $C_{1-6}$dialkylamino, and N-linked-heterocycloalkyl; wherein $C_{2-6}$alkenyl, $C_{2-6}$alkynyl, and $C_{1-6}$alkyl, alone or as part of $C_{1-6}$alkoxy, $C_{1-6}$alkylthio, $C_{1-6}$alkylsulfinyl, $C_{1-6}$alkylsulfonyl, $C_{1-6}$alkylamino, or $C_{1-6}$dialkylamino, is optionally substituted with one or more substituents independently selected from the group consisting of —OH, —SH, —NH$_2$, halogen, $C_{1-6}$alkoxy, $C_{1-6}$haloalkoxy, $C_{1-6}$alkylthio, $C_{1-6}$haloalkylthio, $C_{1-6}$alkylsulfinyl, $C_{1-6}$haloalkylsulfinyl, $C_{1-6}$alkylsulfonyl, $C_{1-6}$haloalkylsulfonyl, $C_{1-6}$alkylamino, $C_{1-6}$dialkylamino and N-linked-heterocycloalkyl;

$Z_{22}$, $Z_{26}$, $Z_{30}$, $Z_{34}$, $Z_{38}$ and $Z_{40}$ are independently

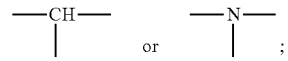

$Z_{29}$, $Z_{32}$, $Z_{33}$, $Z_{37}$ and $Z_{41}$ are independently —CR$^{tt}$R$^{uu}$—, —O— or —NR$^{vv}$—;

$Z_{23}$, $Z_{24}$, $Z_{25}$, $Z_{27}$, $Z_{28}$, $Z_{31}$, $Z_{35}$, $Z_{36}$ and $Z_{39}$ are independently =CR$^{tt}$— or =N—;

$R^{tt}$ and $R^{uu}$, at each occurrence, are independently selected from the group consisting of —H, halogen, alkyl, alkenyl, alkynyl, heteroalkyl, carbocyclyl, heterocyclyl, aryl, heteroaryl, —R' and -L$_5$-R$^{ee}$; or R$^{tt}$ and R$^{uu}$ together are =O, =C$^{ff}$R$^{ff}$, =N—OR$^{gg}$, =N—R$^{gg}$, or =N—NR$^{gg}$R$^{gg}$;

wherein alkyl, alkenyl, alkynyl or heteroalkyl are optionally independently substituted with one or more —R$^{jj}$, and carbocyclyl, heterocyclyl, aryl or heteroaryl are optionally independently substituted with one or more —R$^{kk}$;

each R$^{vv}$ is independently selected from the group consisting of —H, alkyl, alkenyl, alkynyl, heteroalkyl, carbocyclyl, heterocyclyl, aryl, heteroaryl, —R" and -L$_8$-R$^{ww}$; wherein alkyl, alkenyl, alkynyl or heteroalkyl are optionally independently substituted with one or more —R$^{jj}$, and carbocyclyl, heterocyclyl, aryl or heteroaryl are optionally independently substituted with one or more —R$^{kk}$;

$L_8$ is selected from the group consisting of —O—, —S—, —C(=W)—, —C(=W)—W—, —C(=W)—NR$^{xx}$—, —C(=NR$^{xx}$)NR$^{xx}$—, —C(NR$^{xx}$R$^{xx}$)=N—, —S(=O)$_2$—NR$^{xx}$—, and —S(=O)$_2$—;

R$^{ww}$ at each occurrence is independently selected from the group consisting of alkyl, alkenyl, alkynyl, heteroalkyl, carbocyclyl, heterocyclyl, aryl and heteroaryl; wherein alkyl, alkenyl, alkynyl or heteroalkyl are optionally independently substituted with one or more —R$^{jj}$, and carbocyclyl, heterocyclyl, aryl or heteroaryl are optionally independently substituted with one or more —R$^{kk}$;

R$^{xx}$ at each occurrence is independently selected from the group consisting of —H, alkyl, alkenyl, alkynyl, heteroalkyl, carbocyclyl, heterocyclyl, aryl and heteroaryl; wherein alkyl, alkenyl, alkynyl or heteroalkyl are optionally independently substituted with one or more —R$^{jj}$, and carbocyclyl, heterocyclyl, aryl or heteroaryl are optionally independently substituted with one or more —R$^{kk}$;

R28, R29, R30, R31, R32, R33, R34, R35, R36, R37, R38, R39 and R40 are independently selected from the group consisting of —H, halogen, alkyl, alkenyl, alkynyl, heteroalkyl, carbocyclyl, heterocyclyl, aryl, heteroaryl, —R' and -L$_5$-R$^{ee'}$; wherein alkyl, alkenyl, alkynyl or heteroalkyl are optionally independently substituted with one or more —$R^{jj}$, and carbocyclyl, heterocyclyl, aryl or heteroaryl are optionally independently substituted with one or more —$R^{kk}$, wherein $R^{ee'}$ is $R^{ee}$ or a suitable nitrogen protecting group when $L_s$ is —NH—.

8. The compound according to claim 7, wherein R21 and R22 are independently

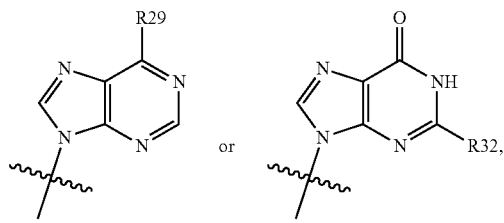

wherein R29 and R32 are independently —$NH_2$ or —NH—$C_{1-6}$alkyl, wherein —$NH_2$ is optionally substituted with a suitable nitrogen protecting group.

9. The compound according to claim 8, wherein R25 is —H, —OH, —OTBS or —F, R3 and R4 are —SH, and $R^{aa}$ and $R^{bb}$ at each occurrence are —H.

10. The compound according to claim 1, wherein the compound is a compound of Formula IIIb or Formula IIIc:

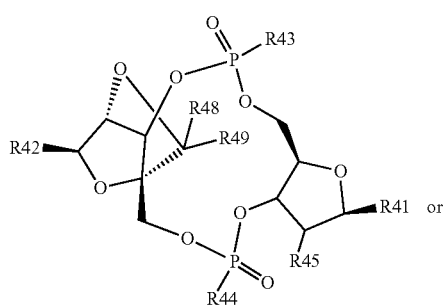

Formula IIIb

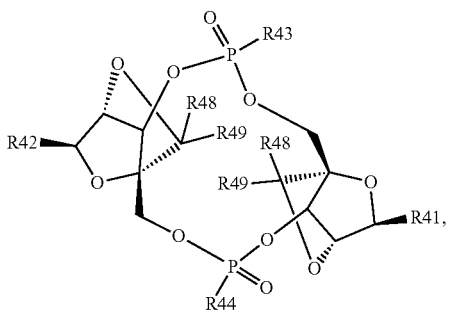

Formula IIIc or a prodrug, pharmaceutically acceptable salt, pharmaceutically acceptable solvate or pharmaceutically acceptable hydrate thereof, wherein:

R43 and R44 are independently selected from the group consisting of —OH, —SH, —O—$C_{1-14}$alkyl, —S—$C_{1-14}$alkyl, —O—(C=O)—$C_{1-14}$alkyl and —S—C(=O)—$C_{1-14}$alkyl;

R45 is selected from the group consisting of —H, —OH optionally substituted with a suitable oxygen protecting group, halogen, —O—$C_{1-14}$alkyl and —O—(C=O)—$C_{1-14}$alkyl;

R48 and R49 at each occurrence are independently —H or —$C_{1-6}$alkyl, wherein alkyl is optionally substituted with 1, 2 or 3 —F or with —$C_{1-6}$alkoxy; or R48 and R49 on the same carbon together form a $C_{3-6}$cycloalkyl spirocyclic ring;

and

R41 and R42 are independently

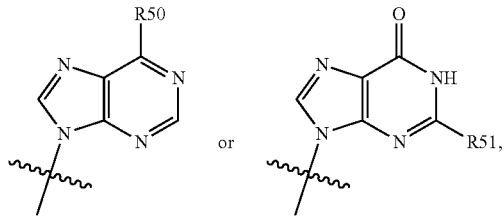

wherein

indicates the bond of R41 or R42 to the ring as shown in Formula IIIb or Formula IIIc, and wherein R50 and R51 are independently —$NH_2$ or —NH—$C_{1-6}$alkyl, wherein —$NH_2$ is optionally substituted with a suitable nitrogen protecting group.

11. The compound according to claim 10, wherein R45 is —H, —OH, —OTBS or —F.

12. The compound according to claim 11, wherein R50 and R51 are both —$NH_2$, and wherein R43 and R44 are —SH.

13. The compound according to claim 1, wherein the compound is a compound of Formula IVb or Formula IVc:

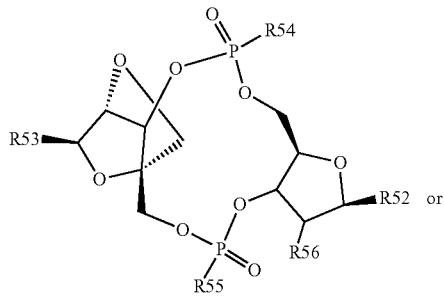

Formula IVb

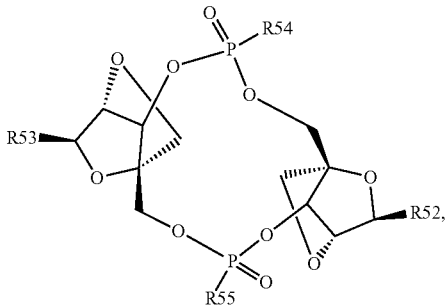

Formula IVc or a prodrug, pharmaceutically acceptable salt, pharmaceutically acceptable solvate or pharmaceutically acceptable hydrate thereof, wherein:

R54 and R55 are independently —OH or —SH;

R52 and R53 are independently

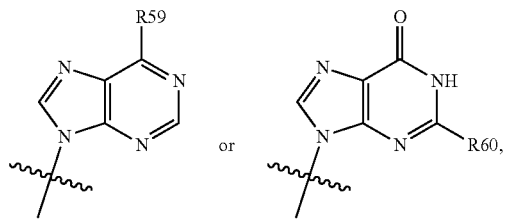

wherein

indicates the bond of R52 or R53 to the ring as shown in Formula IVb or Formula IVc, and wherein R59 and R60 are independently —NH$_2$ optionally substituted with a suitable nitrogen protecting group.

14. The compound according to claim 13, wherein the compound is selected from the group consisting of a compound of Formula IVb-1, a compound of Formula IVb-2, a compound of Formula IVb-3, a compound of Formula IVb-4, a compound of Formula IVc-1, a compound of Formula IVc-2, a compound of Formula IVc-3, and a compound of Formula IVc-4:

Formula IVb-1

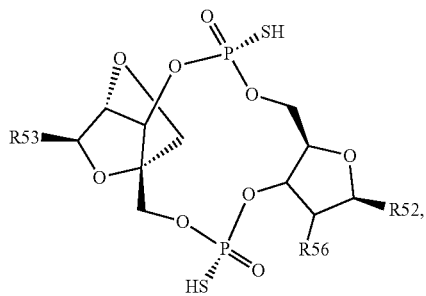

Formula IVb-2

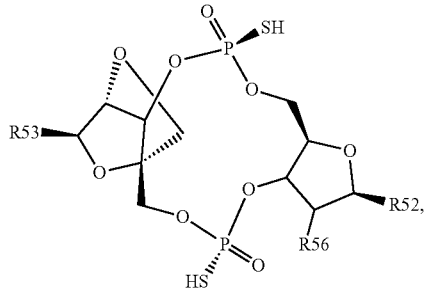

Formula IVb-3

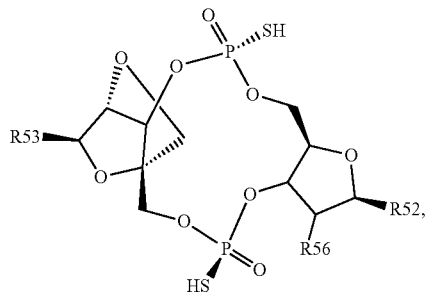

Formula IVb-4

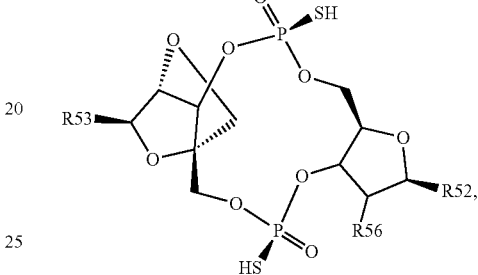

Formula IVc-1

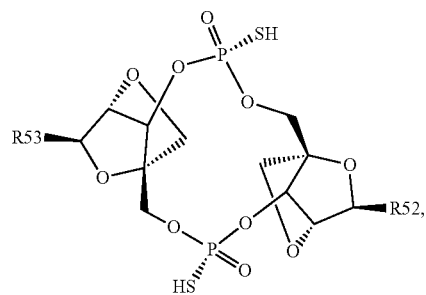

Formula IVc-2

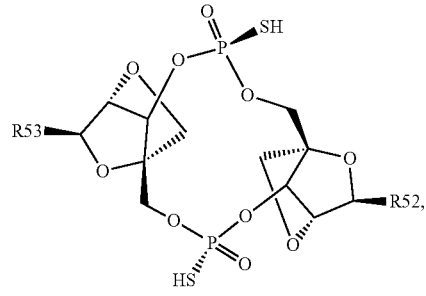

Formula IVc-3

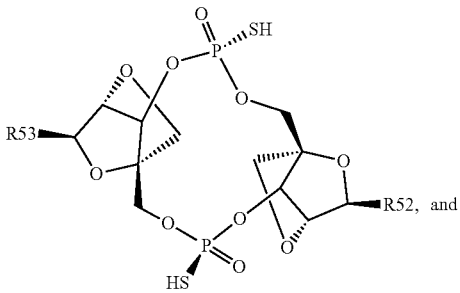

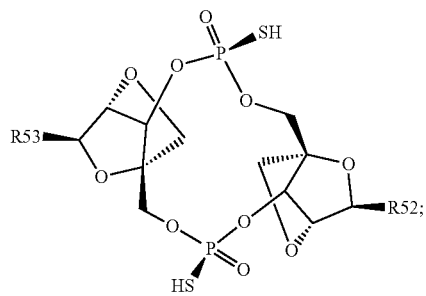
Formula IVc-4
or a prodrug, pharmaceutically acceptable salt, pharmaceutically acceptable solvate or pharmaceutically acceptable hydrate thereof, wherein R52 and R53 are as defined in claims 13 and R56 is —H, —OH, —OTBS or —F.
15. The compound according to claim 1, selected from the group consisting of:
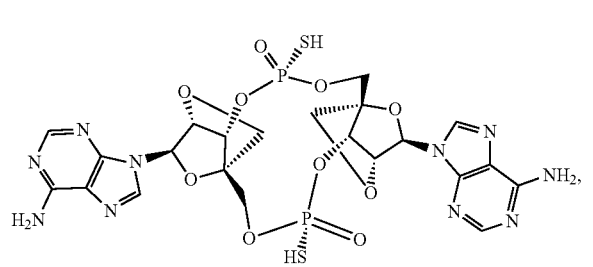
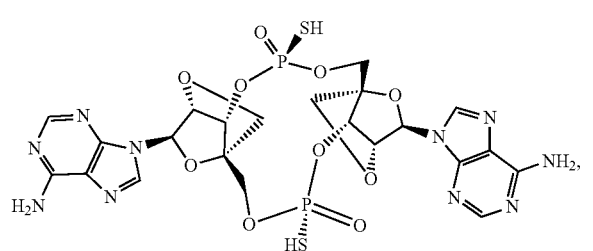
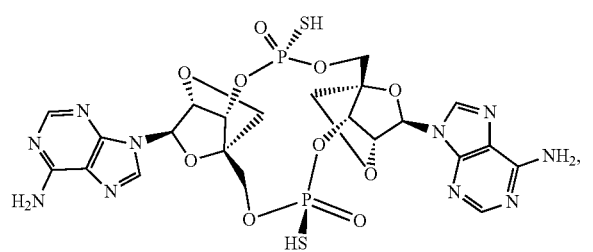
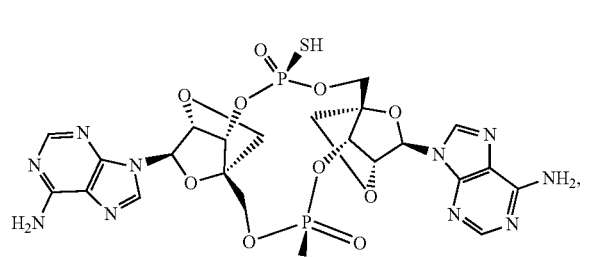
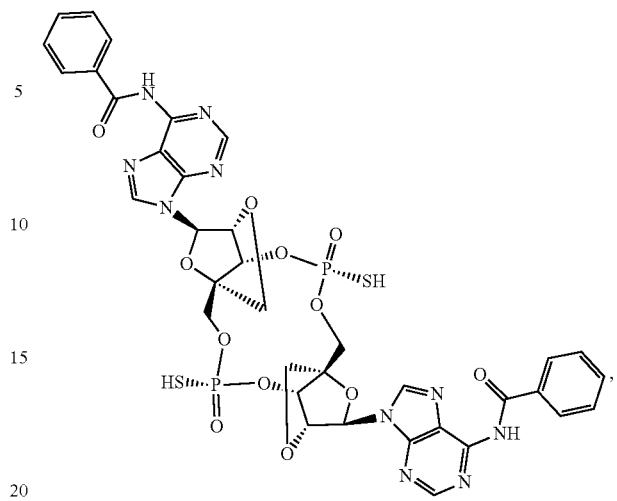
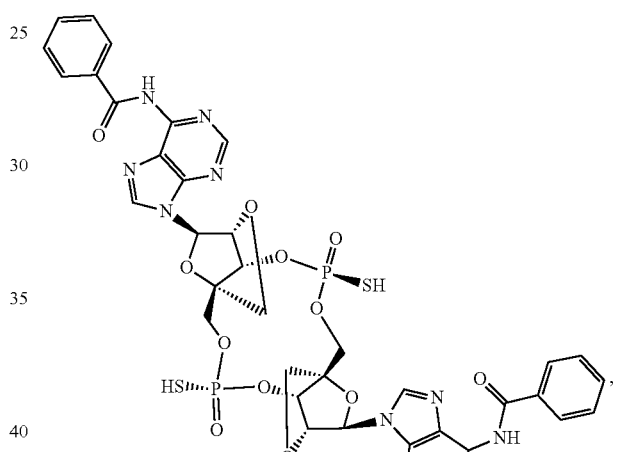
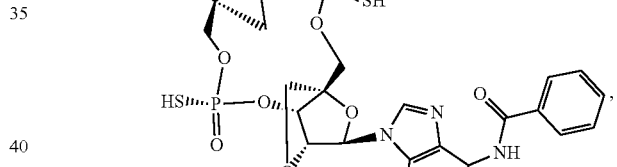
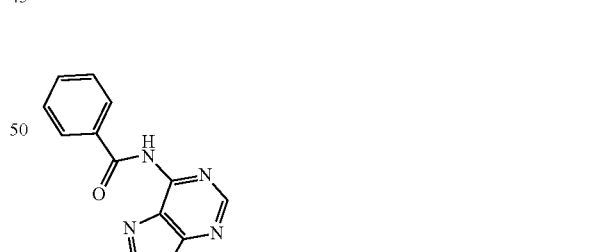
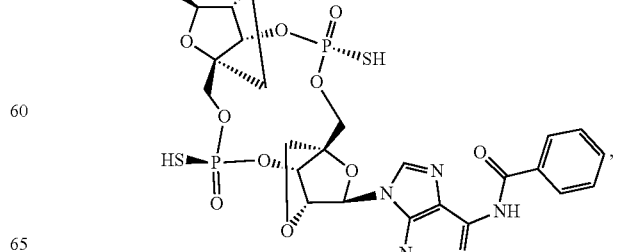

349
-continued

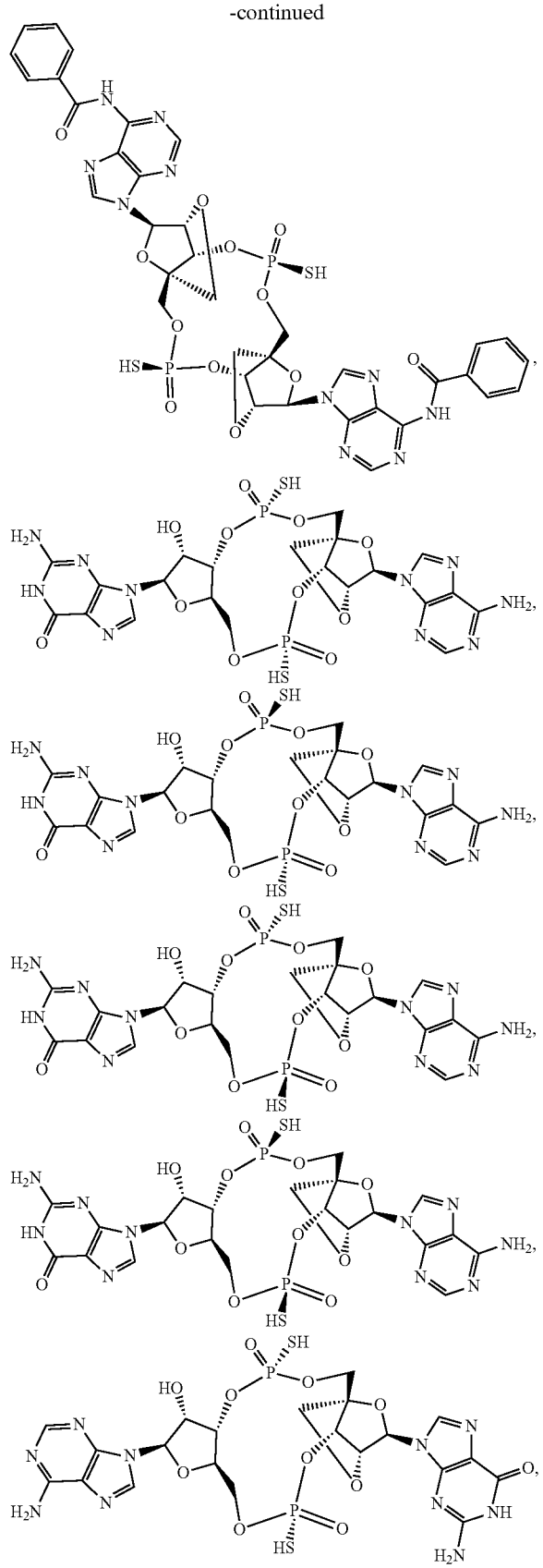

350
-continued

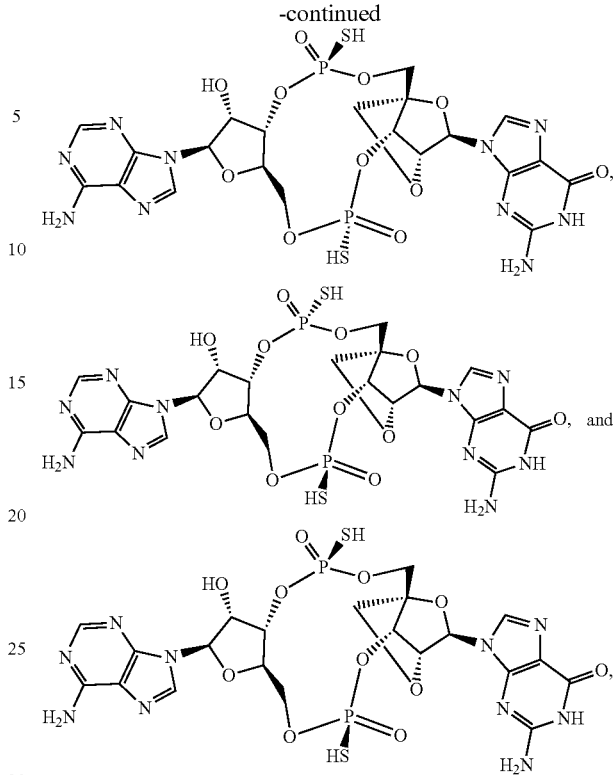

or a prodrug, pharmaceutically acceptable salt, pharmaceutically acceptable solvate or pharmaceutically acceptable hydrate thereof.

16. A composition comprising one or more compounds according to claim 1 and a pharmaceutically acceptable excipient.

17. A method for treating an individual suffering from cancer, comprising:
    administering to the individual in need thereof an effective amount of the compound according to claim 1.

18. The method according to claim 17, wherein the cancer is selected from the group consisting of a colorectal cancer, an aero-digestive squamous cancer, a lung cancer, a brain cancer, a liver cancer, a stomach cancer, a bladder cancer, a thyroid cancer, an adrenal cancer, a gastrointestinal cancer, an oropharyngeal cancer, an esophageal cancer, a head and neck cancer, an ovarian cancer, a uterine cancer, a cervical cancer, an endometrial cancer, a breast cancer, a melanoma, a prostate cancer, a pancreatic carcinoma, a renal carcinoma, a sarcoma, a leukemia, a Merkel-cell carcinoma, a lymphoma and a multiple myeloma.

19. The method according to claim 17, wherein the administration is intra-tumoral, peri-tumoral, or directly into the tumor-draining lymph node(s).

20. The method according to claim 19, wherein the method further comprises administering one or more additional cancer therapies to the individual, wherein the one or more additional cancer therapies comprises administering one or more checkpoint inhibitors to the individual.

* * * * *

```
                          SEQUENCE LISTING

<160> NUMBER OF SEQ ID NOS: 17

<210> SEQ ID NO 1
<211> LENGTH: 440
<212> TYPE: PRT
<213> ORGANISM: Artificial Sequence
<220> FEATURE:
<223> OTHER INFORMATION: Synthetic: heavy chain amino acid sequence of
      nivolumab

<400> SEQUENCE: 1

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160
```

Ser Gly Val His Thr Phe Pro Ala Val Leu Gln Ser Gly Leu Tyr
            165                 170                 175

Ser Leu Ser Ser Val Val Thr Val Pro Ser Ser Ser Leu Gly Thr Lys
        180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
            245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
            325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
            405                 410                 415

Ser Cys Ser Val Met His Glu Ala Leu His Asn His Tyr Thr Gln Lys
            420                 425                 430

Ser Leu Ser Leu Ser Leu Gly Lys
        435                 440

<210> SEQ ID NO 2
<211> LENGTH: 214
<212> TYPE: PRT
<213> ORGANISM: Artificial Sequence
<220> FEATURE:
<223> OTHER INFORMATION: Synthetic: light chain amino acid sequence of
      nivolumab

<400> SEQUENCE: 2

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 447
<212> TYPE: PRT
<213> ORGANISM: Artificial Sequence
<220> FEATURE:
<223> OTHER INFORMATION: Synthetic: heavy chain amino acid sequences of
      pembrolizumab

<400> SEQUENCE: 3

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro

```
                210                 215                 220
Pro Cys Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 4
<211> LENGTH: 218
<212> TYPE: PRT
<213> ORGANISM: Artificial Sequence
<220> FEATURE:
<223> OTHER INFORMATION: Synthetic: light chain amino acid sequences of
      pembrolizumab

<400> SEQUENCE: 4

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
                20                  25                  30

Gly Tyr Ser Tyr Leu His Trp Tyr Gln Gln Lys Pro Gly Gln Ala Pro
            35                  40                  45

Arg Leu Leu Ile Tyr Leu Ala Ser Tyr Leu Glu Ser Gly Val Pro Ala
        50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125
```

```
Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 5
<211> LENGTH: 118
<212> TYPE: PRT
<213> ORGANISM: Artificial Sequence
<220> FEATURE:
<223> OTHER INFORMATION: Synthetic: heavy chain amino acid sequence of
      MSB0010718C

<400> SEQUENCE: 5

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Ile Lys Leu Gly Thr Val Thr Thr Val Asp Tyr Trp Gly Gln Gly Thr
            100                 105                 110

Leu Val Thr Val Ser Ser
        115

<210> SEQ ID NO 6
<211> LENGTH: 110
<212> TYPE: PRT
<213> ORGANISM: Artificial Sequence
<220> FEATURE:
<223> OTHER INFORMATION: Synthetic: light chain amino acid sequence of
      MSB0010718C

<400> SEQUENCE: 6

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45
```

```
Met Ile Tyr Asp Val Ser Asn Arg Pro Ser Gly Val Ser Asn Arg Phe
 50                  55                  60
Ser Gly Ser Lys Ser Gly Asn Thr Ala Ser Leu Thr Ile Ser Gly Leu
 65                  70                  75                  80
Gln Ala Glu Asp Glu Ala Asp Tyr Tyr Cys Ser Ser Tyr Thr Ser Ser
                 85                  90                  95
Ser Thr Arg Val Phe Gly Thr Gly Thr Lys Val Thr Val Leu
            100                 105                 110
```

<210> SEQ ID NO 7

<400> SEQUENCE: 7

000

<210> SEQ ID NO 8

<400> SEQUENCE: 8

000

<210> SEQ ID NO 9
<211> LENGTH: 37
<212> TYPE: DNA
<213> ORGANISM: Artificial Sequence
<220> FEATURE:
<223> OTHER INFORMATION: Synthetic: forward primer

<400> SEQUENCE: 9
tacttccaat ccaatgcagc cccagctgag atctctg                           37

<210> SEQ ID NO 10
<211> LENGTH: 46
<212> TYPE: DNA
<213> ORGANISM: Artificial Sequence
<220> FEATURE:
<223> OTHER INFORMATION: Synthetic: reverse primer

<400> SEQUENCE: 10
ttatccactt ccaatgttat tattatcaag agaaatccgt gcggag                 46

<210> SEQ ID NO 11
<211> LENGTH: 19
<212> TYPE: DNA
<213> ORGANISM: Artificial Sequence
<220> FEATURE:
<223> OTHER INFORMATION: Synthetic: hSTING exon3F

<400> SEQUENCE: 11
gctgagacag gagctttgg                                               19

<210> SEQ ID NO 12
<211> LENGTH: 19
<212> TYPE: DNA
<213> ORGANISM: Artificial Sequence
<220> FEATURE:
<223> OTHER INFORMATION: Synthetic: hSTING exon3R

<400> SEQUENCE: 12
agccagagag gttcaagga					19

<210> SEQ ID NO 13
<211> LENGTH: 20
<212> TYPE: DNA
<213> ORGANISM: Artificial Sequence
<220> FEATURE:
<223> OTHER INFORMATION: Synthetic: hSTING exon6F

<400> SEQUENCE: 13
ggccaatgac ctgggtctca					20

<210> SEQ ID NO 14
<211> LENGTH: 20
<212> TYPE: DNA
<213> ORGANISM: Artificial Sequence
<220> FEATURE:
<223> OTHER INFORMATION: Synthetic: hSTING exon6R

<400> SEQUENCE: 14
cacccagaat agcatccagc					20

<210> SEQ ID NO 15
<211> LENGTH: 21
<212> TYPE: DNA
<213> ORGANISM: Artificial Sequence
<220> FEATURE:
<223> OTHER INFORMATION: Synthetic: hSTING exon7F

<400> SEQUENCE: 15
tcagagttgg gtatcagagg c					21

<210> SEQ ID NO 16
<211> LENGTH: 21
<212> TYPE: DNA
<213> ORGANISM: Artificial Sequence
<220> FEATURE:
<223> OTHER INFORMATION: Synthetic: hSTING exon7R

<400> SEQUENCE: 16
atctggtgtg ctgggaagag g					21

<210> SEQ ID NO 17
<211> LENGTH: 8
<212> TYPE: PRT
<213> ORGANISM: Artificial Sequence
<220> FEATURE:
<223> OTHER INFORMATION: Synthetic

<400> SEQUENCE: 17

Ser Ile Tyr Arg Tyr Tyr Gly Leu
1               5